US010781427B2

(12) United States Patent
Barouch et al.

(10) Patent No.: US 10,781,427 B2
(45) Date of Patent: Sep. 22, 2020

(54) RECOMBINANT ADENOVIRUSES AND USE THEREOF

(71) Applicants: Beth Israel Deaconess Medical Center, Inc., Boston, MA (US); Washington University, St. Louis, MO (US)

(72) Inventors: Dan H. Barouch, Newton, MA (US); Herbert Virgin, IV, St. Louis, MO (US); Peter Abbink, Winthrop, MA (US)

(73) Assignees: Beth Israel Deaconess Medical Center, Inc., Boston, MA (US); Washington University, St. Louis, MO (US)

( * ) Notice: Subject to any disclaimer, the term of this patent is extended or adjusted under 35 U.S.C. 154(b) by 0 days.

(21) Appl. No.: 16/159,336

(22) Filed: Oct. 12, 2018

(65) Prior Publication Data

US 2019/0136205 A1 May 9, 2019

Related U.S. Application Data

(63) Continuation of application No. 14/443,299, filed as application No. PCT/US2013/070353 on Nov. 15, 2013, now Pat. No. 10,106,781.

(Continued)

(51) Int. Cl.
*C12N 15/00* (2006.01)
*C12N 7/00* (2006.01)
(Continued)

(52) U.S. Cl.
CPC ................ *C12N 7/00* (2013.01); *A61K 39/00* (2013.01); *A61K 39/12* (2013.01);
(Continued)

(58) Field of Classification Search
None
See application file for complete search history.

(56) References Cited

U.S. PATENT DOCUMENTS 4,695,623 A 9/1987 Stabinsky
7,247,472 B2 7/2007 Wilson et al.
(Continued)

FOREIGN PATENT DOCUMENTS

CN 1578678 A 2/2005
EP 1944043 A1 7/2008
(Continued)

OTHER PUBLICATIONS

Finkbeiner et al., "Metagenomic analysis of Human Diarrhea: Viral Detection and Discovery," PLOS Pathogens 4(2): e1000011 (Year: 2008).*

(Continued)

*Primary Examiner* — M Franco G Salvoza
(74) *Attorney, Agent, or Firm* — Clark & Elbing LLP

(57) ABSTRACT

The present invention relates to recombinant adenoviruses and vectors thereof. In particular, the adenoviruses are novel simian adenoviruses having a low seroprevalence and high immunogenicity relative to other adenoviruses and vectors thereof. The invention also provides methods for production of the adenoviruses and for the treatment of diseases by administering the adenoviral vector(s) to a subject (e.g., a human).

29 Claims, 25 Drawing Sheets

Specification includes a Sequence Listing.

Related U.S. Application Data

(60) Provisional application No. 61/727,455, filed on Nov. 16, 2012.

(51) Int. Cl.
*C12N 15/74* (2006.01)
*A61K 39/23* (2006.01)
*A61K 39/12* (2006.01)
*A61K 39/00* (2006.01)

(52) U.S. Cl.
CPC ................ *A61K 2039/5256* (2013.01); *A61K 2039/5258* (2013.01); *C12N 2710/10042* (2013.01); *C12N 2710/10321* (2013.01); *C12N 2710/10343* (2013.01); *C12N 2740/15034* (2013.01)

(56) References Cited

U.S. PATENT DOCUMENTS

| | | | |
|---|---|---|---|
| 2004/0136963 A1 | 7/2004 | Wilson et al. |
| 2005/0232900 A1 | 10/2005 | Vogels et al. |
| 2010/0034774 A1 | 2/2010 | Vogels et al. |
| 2011/0000480 A1 | 1/2011 | Turner et al. |
| 2011/0306090 A1 | 12/2011 | Francky et al. |
| 2012/0027788 A1 | 2/2012 | Colloca et al. |
| 2012/0076812 A1 | 3/2012 | Barouch et al. |
| 2014/0348791 A1 | 11/2014 | Barouch et al. |

FOREIGN PATENT DOCUMENTS

| | | |
|---|---|---|
| WO | WO-97/00326 A1 | 1/1997 |
| WO | WO-00/70071 A1 | 11/2000 |
| WO | WO-01/02607 A1 | 1/2001 |
| WO | WO-02/22080 A2 | 3/2002 |
| WO | WO-02/40665 A2 | 5/2002 |
| WO | WO-2003046124 A2 | 6/2003 |
| WO | WO-2007/104792 A2 | 9/2007 |
| WO | WO-2011/057248 A2 | 5/2011 |
| WO | WO-2011/057254 A2 | 5/2011 |
| WO | WO-2011/129468 A1 | 10/2011 |
| WO | WO-2012/021730 A2 | 2/2012 |

OTHER PUBLICATIONS

Abbink et al., "Comparative seroprevalence and immunogenicity of six rare serotype recombinant adenovirus vaccine vectors from subgroups B and D," J Virol. 81(9):4654-63 (2007).

Abbink et al., "Development of Novel Simian Adenovirus Based Vaccine Vectors." Poster, 2013. <http://epostersonline.s3.amazonaws.com>. Retrieved on Apr. 16, 2014 (1 page).

Bangari and Mittal, "Development of nonhuman adenoviruses as vaccine vectors," Vaccine 24(7):849-62 (2006) (21 pages).

Barouch et al., "Immunogenicity of recombinant adenovirus serotype 35 vaccine in the presence of pre-existing anti-Ad5 immunity," J Immunol. 172(10):6290-7 (2004) (9 pages).

Barouch et al., "International seroepidemiology of adenovirus serotypes 5, 26, 35, and 48 in pediatric and adult populations," Vaccine. 29(32):5203-9 (2011) (14 pages).

Communication Pursuant to 94(3) EPC for European Patent Application No. 13854932.4, dated Sep. 28, 2017 (8 pages).

Communication Pursuant to Rules 70(2) and 70a(2)EPC for International Patent Application No. PCT/US 13/70353, dated Jul. 5, 2016 (1 page).

EMBOSS Needle, "Pairwise Sequence Alignment (PROTEIN)," http://www.ebi.ac.uk/Tools/psa/emboss_needle/, retrieved Aug. 18, 2017 (40 pages).

Extended European Search Report for European Patent Application No. 13854932.4, dated Jun. 17, 2016 (8 pages).

Geisbert et al., "Recombinant adenovirus serotype 26 (Ad26) and Ad35 vaccine vectors bypass immunity to Ad5 and protect nonhuman primates against ebolavirus challenge," J Virol. 85(9):4222-33 (2011).

GenBank Accession No. AF326321.1. Retrieved on Apr. 16, 2014 (3 pages).

GenBank Accession No. AY771780.1. Retrieved on Apr. 16, 2014 (15 pages).

GenBank Accession No. AZ111781.1. Retrieved on Jul. 13, 2016 (2 pages).

GenBank Accession No. JA453575.1. Retrieved on Jul. 13, 2016 (8 pages).

GenBank Accession No. AY771780. Retrieved Oct. 24, 2017 (17 pages).

Handley et al., "Pathogenic simian immunodeficiency virus infection is associated with expansion of the enteric virome," Cell. 151(2):253-66 (2012).

Hayes, "Zika virus outside Africa," Emerg Infect Dis. 15(9):1347-50 (2009).

Holterman et al., "Novel replication-incompetent vector derived from adenovirus type 11 (Ad11) for vaccination and gene therapy: low seroprevalence and non-cross-reactivity with Ads," J Virol. 78(23):13207-15 (2004).

International Preliminary Report on Patentability for International Patent Application No. PCT/US2013/070353, dated May 19, 2015 (8 pages).

International Search Report and Written Opinion for International Patent Application No. PCT/US13/70353, dated May 12, 2014 (17 pages).

Kovacs et al., "Complete genome sequence of simian adenovirus 1: an Old World monkey adenovirus with two fiber genes," Journal of General Virology. 86(6):1681-6 (2005).

Lemckert et al., "Immunogenicity of heterologous prime-boost regimens involving recombinant adenovirus serotype 11 (Ad11) and Ad35 vaccine vectors in the presence of anti-ad5 immunity," J Virol. 79(15):9694-701 (2005).

Letvin et al., "Prospects for vaccine protection against HIV-1 infection and AIDS," Annu Rev Immunol. 20:73-99 (2002).

Liu et al., "Modulation of DNA vaccine-elicited CD8+ T-lymphocyte epitope immunodominance hierarchies," J Virol. 80(24):11991-7 (2006).

Notice of Reasons for Rejection for Japanese Patent Application No. 2015-542833, dated Sep. 5, 2017 (20 pages).

Office Action for Chinese Patent Application No. 201380068078.0, dated Apr. 4, 2018 (5 pages).

Ostapchuk et al., "Pseudopackaging of adenovirus type 5 genomes into capsids containing the hexon proteins of adenovirus serotypes B, D, or E," J Virol. 75(1):45-51 (2001).

Search Report for Singaporean Application No. 11201503864T, dated Feb. 29, 2016 (3 pages).

Shiver et al., "Recent advances in the development of HIV-1 vaccines using replication-incompetent adenovirus vectors," Annu Rev Med. 55:355-72 (2004).

Shiver et al., "Replication-incompetent adenoviral vaccine vector elicits effective anti-immunodeficiency-virus immunity," Nature. 415(6869):331-5 (2002).

Sprangers et al., "Quantifying adenovirus-neutralizing antibodies by luciferase transgene detection: addressing preexisting immunity to vaccine and gene therapy vectors," J Clin Microbiol. 41(11):5046-52 (2003).

Sumida et al., "Neutralizing antibodies to adenovirus serotype 5 vaccine vectors are directed primarily against the adenovirus hexon protein," J Immunol. 174(11):7179-85 (2005).

Tripp et al., "Development of a Zika vaccine," Expert Rev Vaccines. 15(9):1083-5 (2016).

Vogels et al., "Replication-deficient human adenovirus type 35 vectors for gene transfer and vaccination: efficient human cell infection and bypass of preexisting adenovirus immunity," J Virol. 77(15):8263-71 (2003).

Wodrich et al., "Switch from capsid protein import to adenovirus assembly by cleavage of nuclear transport signals," EMBO J. 22(23):6245-55 (2003).

Written Opinion for Singaporean Application No. 11201503864T, dated Apr. 1, 2016 (6 pages).

(56) References Cited

OTHER PUBLICATIONS

Office Action for Japanese Patent Application No. 2015-542833, dated Aug. 7, 2018 (8 pages).
Dicks et al., "A novel chimpanzee adenovirus vector with low human seroprevalence: improved systems for vector derivation and comparative immunogenicity," PLoS One 7(7):e40385 (2012) (12 pages).
Office Action for Israeli Patent Application No. 238847, dated May 27, 2019 (7 pages).
Examination Report for Australian Patent Application No. 2018229561, dated Jun. 21, 2019 (4 pages).
Examination Review Report for Singapore Patent Application No. 11201503864T, dated Apr. 22, 2019 (4 pages).
First Examination Report for New Zealand Patent Application No. 708144, dated Mar. 13, 2019 (5 pages).
Office Action for Japanese Patent Application No. 2018-038380, dated Mar. 12, 2019 (28 pages).
Extended European Search Report for European Patent Application No. 19179450.2, dated Oct. 9, 2019 (7 pages).
GenBank Accession No. AZI11781.1. Retrieved Jan. 7, 2020 (2 Pages).
"Sequence alignment results, EMBOSS Needle/Pairwise Sequence Alignment/EMBLE-EBI website," <https://www.ebi.ac.uk/Tools/psa/emboss_needle/nucleotide.html>, retrieved on Feb. 15, 2019 (10 pages).
Abbink et al., "Construction and Evaluation of Novel Rhesus Monkey Adenovirus Vaccine Vectors," J Virol. 89(3):1512-22 (2015) (11 pages).
EMBOSS Needle, "Pairwise Sequence Alignment (NUCLEOTIDE)," www.ebi.ac.uk/Tools/psa/emboss_needle/nucleotide.html, retrieved Feb. 28, 2019 (10 pages).
Foy et al., "Probable Non-Vector-borne Transmission of Zika Virus, Colorado, USA," Emerg Infect Dis. 17(5):880-2 (2011) (7 pages).
Kubo, "The Task of Isolating and Identifying Human Pathogenic Viruses," Seikatsu Eisei. 50(5):381-6 (2006) (English language abstract included).
Kuno et al., "Full-length sequencing and genomic characterization of Bagaza, Kedougou, and Zika viruses," Arch Virol. 152(4):687-96 (2007).
Larocca et al., "Vaccine protection against Zika virus from Brazil," Nature. 536(7617):474-8 (2016) (15 pages).
Office Action for Japanese Patent Application No. 2018-038380, dated Mar. 10, 2020 (16 pages).
Poland et al., "Development of vaccines against Zika virus," Lancet Infect Dis. 18(7):e211-e219 (2018) (9 pages).
Communication pursuant to Article 94(3) EPC for European Application No. 1979450.2, dated May 13, 2020 (5 pages).
Kass-Eisler et al., "Circumventing the immune response to adenovirus-mediated gene therapy," Gene Ther. 3(2):154-62 (1996) (10 pages).
Kass-Eisler et al., "The Impact of Developmental Stage, Route of Administration and the Immune System on Adenovirus-Mediated Gene Transfer," Gene Ther. 1(6):395-402 (1994).
Office Action for Japanese Patent Application No. 2015-542833, dated Apr. 22, 2020 (4 pages).
Setoguchi et al., "Intraperitoneal In Vivo Gene Therapy to Deliver alpha1-Antitrypsin to the Systemic Circulation," Am J Respir Cell Mol Biol. 10(4):369-77 (1994).
Yei et al., "Adenovirus-mediated Gene Transfer for Cystic Fibrosis: Quantitative Evaluation of Repeated in Vivo Vector Administration to the Lung," Gene Ther. 1(3):192-200 (1994).
Zabner et al., "Safety and efficacy of repetitive adenovirus-mediated transfer of CFTR cDNA to airway epithelia of primates and cotton rats," Nat Genet. 6(1):75-83 (1994).

* cited by examiner

RECOMBINANT ADENOVIRUSES AND USE THEREOF

STATEMENT AS TO FEDERALLY FUNDED RESEARCH

This invention was made with government support under Grant Nos. AI078526, AI096040, and OD011170, awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Dec. 24, 2019, is named 01948-219003_Sequence_Listing_12_24_19_ST25 and is 600,226 bytes in size.

BACKGROUND OF THE INVENTION

Recombinant adenoviral vectors have been used in the development of vaccines. To date, approximately 55 different adenovirus serotypes have been identified. The subgroup C adenoviruses have been most extensively studied for applications such as vaccination and gene therapy. Adenovirus serotypes 2 and 5 (Ad2 and Ad5), in particular, are widely used in the field. Importantly, Ad5 vector-based vaccines have been shown to elicit potent and protective immune responses in a variety of animal models. Moreover, large-scale clinical trials for HIV vaccination using Ad5-based recombinant vectors are ongoing (see, e.g., WO 01/02607; WO 02/22080; Shiver et al., *Nature.* 415:331-335, 2002; Letvin et al., *Annu. Rev. Immunol.* 20:73-99, 2002; and Shiver and Emini, *Annu. Rev. Med.* 55:355, 2004).

The usefulness of recombinant Ad5 vector-based vaccines for HIV and other pathogens, however, may be limited due to high pre-existing anti-Ad5 immunity in human populations. The presence of anti-Ad5 immunity has been correlated with a reduction in the immunogenicity of Ad5-based vaccines in studies in mice and rhesus monkeys. Early data from phase-1 clinical trials show that this problem may also occur in humans. Although both Ad5-specific neutralizing antibodies (NAbs) and $CD8^+$ T lymphocytes contribute to anti-Ad5 immunity, the Ad5-specific NAbs appear to play the primary role in this process (Sumida et al., *J. Virol.,* 174:7179-7185, 2004).

Accordingly, there is an unmet need in the field for alternative adenoviral vectors that have low seroprevalence and potent immunogenicity.

SUMMARY OF THE INVENTION

The entire genomes of three novel simian adenoviruses (sAds), sAd4287, sAd4310A, and sAd4312, have been identified and their entire genomes determined. These adenoviruses exhibit both surprisingly low seroprevalence and potent immunogenicity, which suggests that these viruses may be useful as novel vaccine vector candidates. In a first aspect, this invention features isolated polynucleotides including a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 1-3, or its complement. SEQ ID NOs: 1, 2, and 3 are the full-length genome sequence of wild-type sAd4287, sAd4310A, and sAd4312, respectively. The isolated polynucleotides of the invention may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, or 35000 or more contiguous or non-contiguous nucleotides of a reference polynucleotide molecule (e.g., SEQ ID NOs: 1-3).

In some embodiments, the isolated polynucleotides of the invention include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 4-12, or its complement. SEQ NOs: 4-12 feature the nucleotide sequences encoding the fiber-1, fiber-2, and hexon proteins of wild-type sAd4287, sAd4310A, and sAd4312. Accordingly, in some embodiments, the nucleotide sequence encoding all or a portion of the fiber-1 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-1 protein of wild-type sAd4287, sAd4310A, or sAd4312, which corresponds to SEQ ID NO: 4, 5, and 6, respectively. In some embodiments, the nucleotide sequence encoding all or a portion of the fiber-2 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-2 protein of wild-type sAd4287, sAd4310A, or sAd4312, which corresponds to SEQ ID NO: 7, 8, and 9, respectively. In some embodiments, the nucleotide sequence encoding all or a portion of the hexon protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the hexon protein of wild-type sAd4287, sAd4, 310A, or sAd4312, which corresponds to SEQ ID NO: 10, 11, and 12, respectively. In some embodiments, the nucleotide sequence can be at least 90% identical (e.g., at least 91%, 92%, 93%, or 94% identical), at least 95% identical (e.g., at least 96%, 97%, 98%, or 99% identical), or 100% identical to all or a portion of one or more hexon protein hypervariable regions (HVRs) (e.g., HVR1 (nt 403 to nt 489), HVR2 (nt 520 to nt 537), HVR3 (nt 592 to nt 618), HVR4 (nt 706 to nt 744), HVR5 (nt 763 to 786), HVR6 (nt 856 to nt 874), and/or HVR7 (nt 1201 to nt 1296) of sAd4287 hexon protein (SEQ ID NO: 10); HVR1 (nt 403 to nt 477), HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12)).

In some embodiments, the one or more nucleotide sequences encoding one or more hexon protein hypervariable regions (HVRs) of the invention have been substituted with that of another virus (e.g., HVR1 (nt 403 to nt 489), HVR2 (nt 520 to nt 537), HVR3 (nt 592 to nt 618), HVR4 (nt 706 to nt 744). HVR5 (nt 763 to 786), HVR6 (nt 856 to nt 874), and/or HVR7 (nt 1201 to nt 1296) of sAd4287 hexon protein (SEQ ID NO: 10); HVR1 (nt 403 to nt 477). HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12)) substituted with the corresponding HVR sequences of one or more other viruses, e.g., an adenovirus, e.g., an adenovirus that has a lower seroprevalence compared to that of Ad5, such as subgroup B (Ad11, Ad34, Ad35, and Ad50) and subgroup D (Ad15, Ad24, Ad26, Ad48, and Ad49) adenoviruses as well as simian adenoviruses (e.g., Pan9, also known as AdC68)). In other embodiments, the nucleotide sequence includes an adenoviral vector backbone of Ad5, Ad11, Ad15, Ad24, Ad26, Ad34, Ad48, Ad49, Ad50, or Pan9/AdC68 having a substitution of all or a portion of one or more of the above hexon HVRs of sAd4287, sAd4310A, and/or sAd4312.

In some embodiments, the isolated polynucleotides of the invention include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of SEQ ID NOs: 13-18, or its complement. SEQ ID NOs: 13-18 feature the nucleotide sequences encoding the knob domain of the fiber-1 and fiber-2 proteins of wild-type sAd4287, sAd4310A, and sAd4312. In some embodiments, the nucleotide sequence encoding all or a portion of the knob domain of fiber-1 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-1 protein of wild-type sAd4287, sAd4310A, or sAd4312, which corresponds to SEQ ID NO: 13, 14, and 15, respectively. In some embodiments, the nucleotide sequence encoding all or a portion of the knob domain of fiber-2 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-2 protein of wild-type sAd4287, sAd4310A, or sAd4312, which corresponds to SEQ ID NO: 16, 17, and 18, respectively. In some embodiments, one or more nucleotide sequences encoding a knob domain of a fiber protein (e.g., a fiber-1 or fiber-2 protein) of the invention (SEQ ID NOs: 13-18) have been substituted with that of another virus.

In a second aspect, the invention features recombinant vectors including an isolated polynucleotide of the invention, the recombinant vectors including a nucleotide sequence that is at least 90% identical (e.g., at least 91%, 92%, 93%, or 94% identical), at least 95% identical (e.g., at least 96%. 97%, 98%, or 99% identical), or 100% identical to all or a portion of any one of SEQ ID NOs: 34-51. In some embodiments, the vector is an sAd4297 adenoviral vector including all or a portion of any one of SEQ ID NOs: 34-39. In some embodiments, the vector is an sAd4310A adenoviral vector including all or a portion of any one of SEQ ID NOs: 40-45. In some embodiments, the vector is an sAd4312 adenoviral vector including all or a portion of any one of SEQ ID NOs: 46-51. In other embodiments, more than one (e.g., 2, 3, or 4) of the vectors described by SEQ ID NOs: 34-51 may be used to establish a plasmid system for the generation of a recombinant adenovirus of the invention.

In an embodiment of the first or second aspect of the invention, the isolated polynucleotides and/or recombinant vectors are used to generate recombinant adenoviruses wherein all or a portion of the adenoviruses is derived from any one of SEQ ID NOs: 1-3. In some embodiments, the recombinant adenovirus includes an isolated polynucleotide including a deletion in or of the E1 region (e.g., nt 474 to nt 3085 of sAd4287 (SEQ ID NO: 1); nt 474 to nt 3088 of sAd4310A (SEQ ID NO: 2); and nt 487 to nt 3100 of sAd4312 (SEQ ID NO: 3)). A recombinant adenoviral vector that includes this deletion is rendered replication-defective. In some embodiments, the replication-defective virus may also include a deletion in or of the E3 region (e.g., nt 25973 to nt 28596 of sAd4287 (SEQ ID NO: 1); nt 25915 to nt 28496 of sAd4310A (SEQ ID NO: 2); and nt 25947 to nt 28561 of sAd4312 (SEQ ID NO: 3)) and/or E4 region (e.g., nt 31852 to nt 34752 of sAd4287 (SEQ ID NO: 1); nt 31750 to nt 34048 of sAd4310A (SEQ ID NO: 2); and nt 31818 to nt 34116 of sAd4312 (SEQ ID NO: 3)). In other embodiments, the recombinant adenovirus includes one or more of the E1, E3, and/or E4 regions and is replication-competent.

According to a preferred embodiment, the recombinant adenovirus further includes a heterologous nucleotide sequence encoding an antigenic or therapeutic gene product of interest, or fragment thereof. In some embodiments, the antigenic gene product, or fragment thereof, includes a bacterial, viral, parasitic, or fungal protein, or fragment thereof.

The bacterial protein, or fragment thereof, may be from *Mycobacterium tuberculosis, Mycobacterium Bovis, Mycobacterium africanum, Mycobacterium microti, Mycobacterium leprae, Pseudomonas aeruginosa, Salmonella typhimurium, Escherichia coil, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani*, or *Bacillus anthracis*. Examples of preferred gene products, or fragments thereof, from *Mycobacterium* strains include 10.4, 85A, 85E, 85C, CFP-10, Rv3871, and ESAT-6 gene products or fragments thereof.

The viral protein, or fragment thereof, may be from a virus of the Retroviridae family, which includes the human immunodeficiency virus (HIV; e.g., types 1 and 2), and human T-lymphotropic virus Types I and II (HTLV-1 and HTLV-2, respectively); Flaviviridae family (e.g., a member of the *Flavivirus, Pestivirus*, and *Hepacivirus* genera), which includes the hepatitis C virus (HCV), Yellow fever virus, tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey island virus, Dakar bat virus, Montana myotis leukoencephalitis virus, Phnom Penh bat virus, Rio Bravo virus, Tamana bat virus, and the Cell fusing agent virus; Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Cliveros virus, Paraná virus, Pichinde virus, Pirital virus, Sabiá virus, Tacaribe virus, Tamiami virus, Whitewater Arroyo virus, Chapare virus, and Lujo virus; Bunyaviridae family (e.g., a member of the *Hantavirus, Nairovirus, Orthobunyavirus*, and *Phlebovirus* genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus; Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); Togaviridae family (e.g., a member of the *Alphavirus* genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barman Forest virus, O'nyong'nyong virus, and the chikungunya virus; Poxviridae family (e.g., a member of the *Orthopoxvirus* genus), which includes the smallpox virus, monkeypox virus, and vaccinia virus; Herpesviridae family; which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); Orthomyxoviridae family, which includes the influenza virus (A, B, and C), such as the H5N1 avian influenza virus or H1N1 swine flu; Coronaviridae family, which includes the severe acute respiratory syndrome (SARS) virus; Rhabdoviridae family, which includes the rabies virus and vesicular stomatitis virus (VSV); Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; Picornaviridae family, which includes the poliovirus, human enterovirus (A, B, C, and D), hepatitis A virus, and the coxsackievirus; Hepadnaviridae family, which includes the hepatitis B virus; Papillomaviridae family, which includes the human papiliomavirus; Parvoviridae family, which includes the adeno-associated virus; Astroviridae family, which includes the astrovirus; Polyomaviridae family, which includes the JC virus, BK virus, and SV40 virus; Calciviridae family, which includes the Norwalk virus; or Reoviridae family, which includes the rotavirus. In a preferred embodiment, the viral protein, or fragment thereof, is from human immunodeficiency virus (HIV), human papiliomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, or Marburg virus. In a most preferred embodiment, the viral protein, or fragment thereof, from HIV is Gag, Pol, Env, Nef, Tat, Rev, Vif, Vpr, or Vpu.

The parasitic protein, or fragment thereof, may be from *Toxoplasma gondii, Plasmodium falciparum, Plasmodium vivax, Plasmodium ovale, Plasmodium malariae, Trypanosome* spp., or *Legionella* spp. Examples of particularly preferred parasitic proteins that may be cloned into the vectors of the present invention include those from *Plasmodium falciparum*, such as the circumsparozoite (CS) protein and Liver Specific Antigens 1 or 3 (SA-1 or LSA-3).

The fungal protein, or fragment thereof, may be from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*. Examples of fungal gene products, or fragments thereof, include any cell wall mannoprotein (e.g., Afmp1 of *Aspergillus fumigatus*) or surface-expressed glycoprotein (e.g., SOWgp of *Coccidioides immitis*).

The therapeutic gene products, or fragments thereof, may be interferon (IFN) proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and/or colony stimulating factors, or fragments thereof.

A third aspect of the invention features a method of treating a subject (e.g., a human) having a disease (e.g., HIV or cancer) by administering a recombinant sAd adenovirus vector of the second aspect of the invention to the subject. In a preferred embodiment, the recombinant sAd adenovirus of the invention includes an antigenic gene product, or fragment thereof, that promotes an immune response against an infective agent in a subject at risk of exposure to, or exposed to, the infective agent. In some embodiments, the infective agent is a bacterium, a virus, a parasite, or a fungus, such as those described above. In one non-limiting example, the administration of a sAd adenovirus of the invention expressing an HIV Gag protein, or fragment thereof, to an HIV-positive subject or a subject with acquired immune deficiency syndrome (AIDS) can stimulate an immune response in the subject against HIV, thereby treating the subject. In another embodiment, the recombinant sAd adenovirus of the invention includes a therapeutic gene product, or fragment thereof, such as an interferon (IFN) protein, or fragment thereof, that provides therapy to a subject having a disease caused by a non-infective agent, such as cancer, by stimulating a favorable immune response in the subject against neoplasia and/or by providing gene therapy, thereby treating the subject. Other non-limiting examples of diseases that may be treated include any human health disease, such as tuberculosis, leprosy, typhoid fever, pneumonia, meningitis, staphylococcal scalded skin syndrome (SSSS), Ritter's, disease, tularemia (rabbit fever), brucellosis, Glanders disease, bubonic plague, septicemic plague, pneumonic plague, diphtheria, pertussis (whooping cough), tetanus, anthrax, hepatitis, smallpox, monkeypox, measles, mumps, rubella, chicken pox, polio, rabies, Japanese encephalitis, herpes, mononucleosis, influenza, Ebola virus disease, hemorrhagic fever, yellow fever, Marburg virus disease, toxoplasmosis, malaria, trypanosomiasis, legionellosis, aspergillosis, blastomycosis, candidiasis (thrush), coccidioidomycosis, cryptococcosis, histoplasmosis, paracoccidioidomycosis, sporotrichosis, or sinus-orbital zygomycosis. Treatment of these diseases may be by administration of a recombinant sAd vector of the invention that encodes or expresses on its surface an immune response-stimulating antigen from the selected infective agent.

In some embodiments, the recombinant adenovirus or adenoviral vector is administered Intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions. In one preferred embodiment, the recombinant adenovirus or adenoviral vector is administered as a pharmaceutical composition that includes a pharmaceutically acceptable carrier, diluent, or excipients, and may optionally include an adjuvant. In some embodiments, the subject is administered at least one dose (e.g., 1, 2, 3, 4, 5, 6, 7, 8, 9, 10, or more doses) of the composition. In other embodiments, the subject is administered at least two doses (e.g., 2, 3, 4, 5, 6, 7, 8, 9, 10, or more doses) of the composition. In yet another embodiment, the pharmaceutical composition is administered to the subject as a prime boost or in a prime boost regimen. The subject can be administered at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{14}$ vp/dose. The pharmaceutical composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, 20 years or longer post-diagnosis or post-exposure or to the infective agent. When treating disease (e.g., AIDS or cancer), the pharmaceutical compositions of the invention may be administered to the subject either before the occurrence of symptoms or a definitive diagnosis or after diagnosis or symptoms become evident. The pharmaceutical composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In a fourth aspect, the invention features a method of producing a recombinant adenovirus of the invention that includes culturing a cell in a suitable medium; transfecting the cell with an isolated polynucleotide of the first aspect of the invention or a recombinant vector of the second aspect of the invention; allowing replication of the polynucleotide or vector in the cell; and harvesting the produced recombinant adenovirus from the medium and/or cell. In some embodiments, the cell is a bacterial, plant, or mammalian cell. In a preferred embodiment, the mammalian cell is a PER.55K cell or a Chinese hamster ovary (CHO) cell.

Definitions

By "adenovirus" is meant a medium-sized (90-100 nm), nonenveloped icoshedral virus that includes a capsid and a double-stranded linear DNA genome. The adenovirus can be a naturally occurring, but isolated, adenovirus (e.g., sAd4287, sAd4310A, or sAd4312) or a recombinant adenovirus (e.g., replication-defective or replication competent sAd4287, sAd4310A, or sAd4312, or a chimeric variant thereof).

As used herein, by "administering" is meant a method of giving a dosage of a pharmaceutical composition (e.g., a recombinant adenovirus of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraocularly, orally, topically, locally, by inhalation, by injection, by infusion, by continuous infusion, by localized perfusion bathing target cells directly, by catheter, by lavage, by gavage, in cremes, or in lipid compositions. The preferred method of administration can vary depending on various factors (e.g., the components of the composition being administered and the severity of the condition being treated).

Throughout this specification and claims, the word "comprise," or variations such as "comprises" or "comprising," will be understood to imply the inclusion of a stated integer or group of integers but not the exclusion of any other integer or group of integers.

By "deletion" of an adenoviral genomic region is meant the partial or complete removal, the disruption (e.g., by an insertion mutation), or the functional inactivation (e.g., by a missense mutation) of a specified genomic region (e.g., the E1, E2, E3, and/or E4 region), or any specific open-reading frame within the specified region.

By "gene product" is meant to include mRNAs or other nucleic acids (e.g., microRNAs) transcribed from a gene as well as polypeptides translated from those mRNAs. In some embodiments, the gene product is from a virus (e.g., HIV) and many include, for example, any one or more of the viral proteins, or fragments thereof, described in, for example, pending U.S. Pub. No, 2012/0076812. In some embodiments, the gene product is a therapeutic gene product, including, but not limited to, interferon proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and colony stimulating factors.

By "heterologous nucleic acid molecule" is meant any exogenous nucleic acid molecule that can be incorporated into, for example, an adenovirus of the invention, or polynucleotide or vector thereof, for subsequent expression of a gene product of interest, or fragment thereof, encoded by the heterologous nucleic acid molecule. In a preferred embodiment, the heterologous nucleic acid molecule encodes an antigenic or therapeutic gene product, or fragment thereof, that is a bacterial, viral, parasitic, or fungal protein, or fragment thereof (e.g., a nucleic acid molecule encoding one or more HIV or SIV Gag, Pol, Env, Net, Tat, Rev, Vif, Vpr, or Vpu gene products, or fragments thereof). The heterologous nucleic acid molecule is one that is not normally associated with the other nucleic acid molecules found in the wild-type adenovirus.

By "isolated" is meant separated, recovered, or purified from a component of its natural environment.

By "pharmaceutical composition" is meant any composition that contains a therapeutically or biologically active agent, such as a recombinant adenoviral vector of the invention, preferably including a heterologous nucleotide sequence encoding an antigenic or therapeutic gene product of interest, or fragment thereof, that is suitable for administration to a subject and that treats a disease (e.g., cancer or AIDS) or reduces or ameliorates one or more symptoms of the disease. For the purposes of this invention, pharmaceutical compositions include vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* ($21^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "portion" or "fragment" is meant a part of a whole. A portion may comprise at least 10%, 20%, 30%, 40%, 50%, 60%, 70%, 80%, 90%, or 95% of the entire length of an polynucleotide or polypeptide sequence region. For polynucleotides, for example, a portion may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000 or more contiguous nucleotides of a reference polynucleotide molecule. For polypeptides, for example, a portion may include at least 5, 6, 7, 8, 9, 10, 11, 12, 13, 14, 15, 16, 17, 18, 19, 20, 25, 50, 75, 90, 100, 125, 150, 175, 200, 225, 250, 275, 300, or 350 or more contiguous amino acids of a reference polypeptide molecule.

By "promotes an immune response" is meant eliciting a humoral response (e.g., the production of antibodies) or a cellular response (e.g., the activation of T cells, macrophages, neutrophils, and natural killer cells) directed against, for example, one or more infective agents (e.g., a bacterium, virus, parasite, fungus, or combination thereof) or protein targets in a subject to which the pharmaceutical composition (e.g., a vaccine) has been administered.

By "recombinant" with respect to a vector or virus, is meant a vector or virus that has been manipulated in vitro, such as a vector or virus that includes a heterologous nucleotide sequence (e.g., a sequence encoding an antigenic or therapeutic gene product) or a vector or virus bearing an alteration, disruption, or deletion in a viral E1, E3, and/or E4 region relative to a wild-type viral E1, E3, and/or E4 region.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," wherein the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

A "subject" is a vertebrate, such as a mammal (e.g., primates and humans). Mammals also include, but are not limited to, farm animals (such as cows), sport animals (e.g., horses), pets (such as cats, and dogs), mice, and rats. A subject to be treated according to the methods described herein (e.g., a subject having a disease such as cancer and/or a disease caused by an infective agent, e.g., a bacterium, virus, fungus, or parasite) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been subjected to standard tests or may have been identified, without examination, as one at high risk due to the presence of one or more risk factors (e.g., exposure to a biological agent, such as a virus).

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "vaccine," as used herein, is defined as material used to provoke an immune response and may confer immunity after administration of the vaccine to a subject.

By "vector" is meant a composition that includes one or more genes (non-structural or structural), or fragments thereof, from a viral species, such as an adenoviral species (e.g., sAd4287, sAd4310A, or sAd4312), that may be used to transmit one or more heterologous genes from a viral or non-viral source to a host or subject. The nucleic acid material of the viral vector may be encapsulated, e.g., in a lipid membrane or by structural proteins (e.g., capsid proteins), that may include one or more viral polypeptides (e.g., a glycoprotein). The viral vector can be used to infect cells of a subject, which, in turn, promotes the translation of the heterologous gene(s) of the viral vector into a protein product.

The term "virus," as used herein, is defined as an infectious agent that is unable to grow or reproduce outside a host cell and that infects mammals (e.g., humans) or birds.

Other features and advantages of the invention will be apparent from the following Detailed Description, the drawings, and the claims.

DETAILED DESCRIPTION

Figure 1:
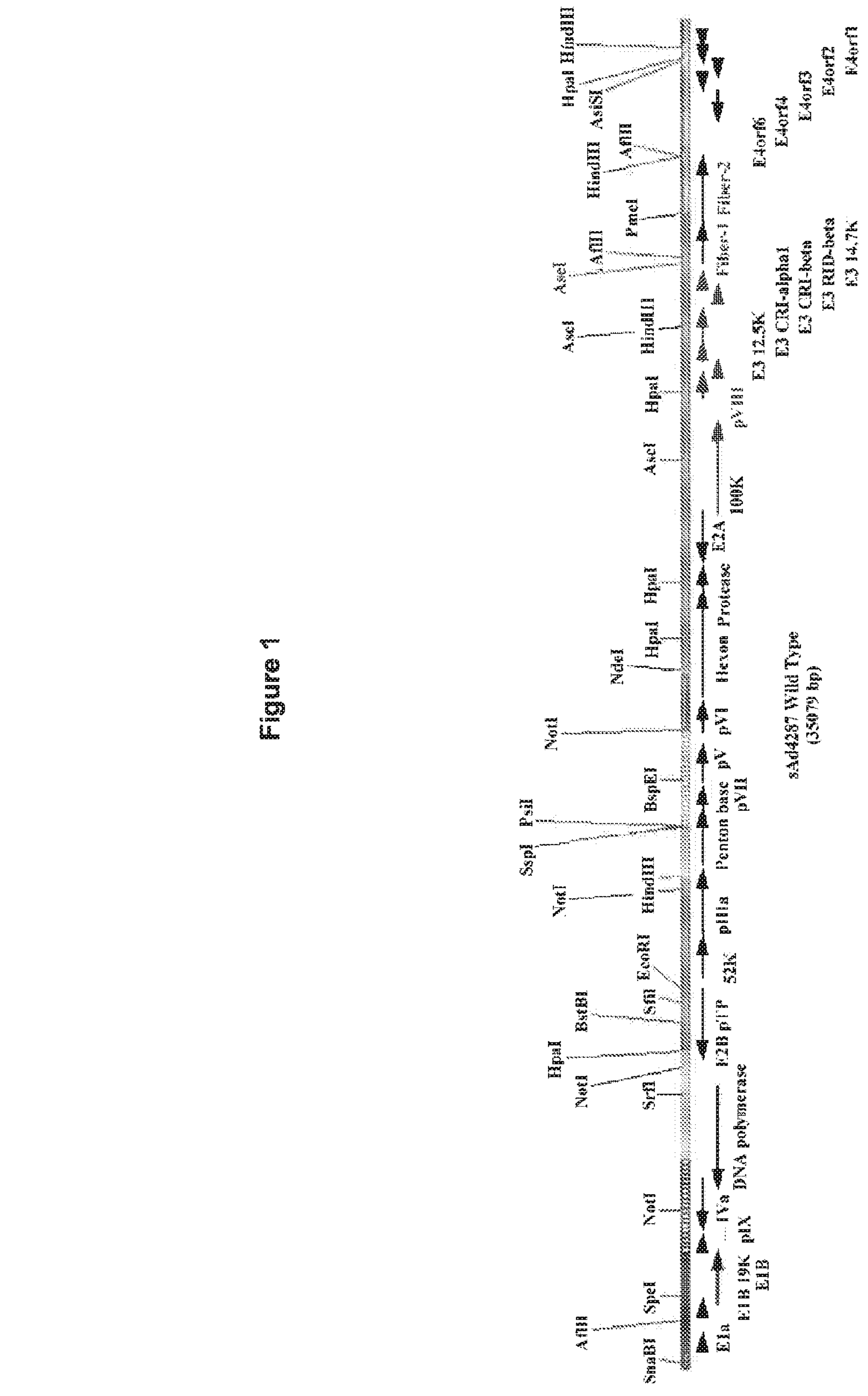
FIG. 1 is a schematic map of the genomic organization of sAd4287.

We have previously identified a variety of novel viruses, including several novel adenoviruses, from rhesus monkeys as part of a metagenomics study (Handley et al. *Cell,* 151(2):253-266, 2012). In the present invention, we isolated, amplified, and purified three novel simian adenoviruses (sAds), sAd4287, sAd4310 #13-1 (sAd4310A), and sAd4312. The three skis were obtained from the rhesus monkey metagenomics study described above. These viruses are entirely novel and their full sequences have never previously peen reported. As these viruses have not yet been officially "named," they do not yet have an official adenovirus number. Accordingly, the nomenclature used throughout represents our internal laboratory designation.

The complete genome sequence of the novel sAds as well as the vector systems we generated for each of the viruses is described in detail below. We generated recombinant sAd4287, sAd4310A, and sAd4312 vectors expressing a variety of transgenes, including luciferase and SIV Gag. In addition, we demonstrated that these vectors (i) have extremely and surprisingly low seroprevalence in human populations and (ii) exhibit potent immunogenicity in mice.

This combination of low baseline anti-vector immunity and potent immunogenicity suggests that these novel adenoviral vectors can be useful in the generation of vaccines against diseases, such as cancer and those caused by an infective agent.

Polynucleotides of the Invention

As a first aspect, the invention provides polynucleotide sequences related to the three novel sAds (sAd4287, sAd4310A, and sAd4312). The isolated polynucleotides may include a nucleotide sequence that is at least 90% identical (e.g., at least 91%, 92%, 93%, or 94% identical), at least 95% identical (e.g., at least 96%, 97%, 98%, or 99% identical), or 100% identical to all or a portion of any one of the full-length genome sequence of wild-type sAd4287 (SEQ ID NO: 1), sAd4310A (SEQ ID NO: 2), or sAd4312 (SEQ ID NO: 3), or their complement. The isolated polynucleotides of the invention may include at least 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35000 or more contiguous or non-contiguous nucleotides of SEQ ID NOs: 1-3.

In some embodiments, the polynucleotides of the invention may be used as primers that are between 10-100 nucleotides in length, more particularly between 10-30 nucleotides in length (e.g., 10, 11, 12, 13, 14, 15, 16, 17, 18, 19, 20, 21, 22, 23, 24, 25, 26, 27, 28, 29, or 30 nucleotides in length), and can be at least 90% identical (e.g., at least 91%, 92%, 93%, or 94% identical), at least 95% identical (e.g., at least 96%, 97%, 98%, or 99% identical), or 100% identical to any one of SEQ ID NOs: 52-123.

In some embodiments, the polynucleotides of the invention include all or a portion of the nucleotide sequence encoding the fiber-1, fiber-2; and/or hexon protein of wild-type sAd4287, sAd4310A, and/or sAd4312. In some embodiments, the nucleotide sequence encoding all or a portion of the fiber-1 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-1 protein of wild-type sAd4287, sAd4310A, or sAd4312, which corresponds to SEQ ID NO: 4, 5, and 6, respectively. The polypeptide sequences of the fiber-1 protein of wild-type sAd4287, sAd4310A, and sAd4312 correspond to SEQ ID NOs: 19, 20, and 21, respectively. In some embodiments, the nucleotide sequence encoding all or a portion of the fiber-2 protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the fiber-2 protein of wild-type sAd4287, sAd4310A, or sAd4312, which corresponds to SEQ ID NO: 7, 8, and 9, respectively. The polypeptide sequences of the fiber-2 protein of wild-type sAd4287, sAd4310A, and sAd4312 correspond to SEQ ID NOs: 22, 23, and 24, respectively. In some embodiments, the nucleotide sequence encoding all or a portion of the hexon protein can be at least 90% identical (e.g., at least 91%, 92%, 93%, or 94% identical), at least 95% identical (e.g., at least 96%, 97%, 98%, or 99% identical), or 100% identical to the nucleotide sequence encoding the hexon protein of wild-type sAd4287, sAd4310A, or sAd4312, which corresponds to SEQ ID NO: 10, 11, and 12, respectively. The polypeptide sequences of the hexon protein of wild-type sAd4287, sAd4310A, and sAd4312 correspond to SEQ ID NOs: 25, 26, and 27, respectively.

In other embodiments, the polynucleotides of the invention include all or a portion of the nucleotide sequence encoding the knob domain of fiber-1 of wild-type sAd4287, sAd4310A, and/or sAd4312. In some embodiments, the nucleotide sequence encoding all or a portion of the knob domain of fiber-1 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-1 protein of wild-type sAd4287, sAd4310A, or sAd4312, which corresponds to SEQ ID NO: 13, 14, or 15, respectively. The polypeptide sequences of the knob domain of the fiber-1 protein of wild-type sAd4287, sAd4310A, and sAd4312 correspond to SEQ ID NOs: 28, 29, and 30, respectively. In some embodiments, the nucleotide sequence encoding all or a portion of the knob domain of fiber-2 can be at least 90% identical (e.g., at least 91%, 92%, 93%, or 94% identical), at least 95% identical (e.g., at least 96%, 97%, 98%, or 99% identical), or 100% identical to the nucleotide sequence encoding the knob domain of the fiber-2 protein of wild-type sAd4287, sAd4310A, or sAd4312, which corresponds to SEQ ID NO: 16, 17, and 18, respectively. The polypeptide sequences of the knob domain of the fiber-2 protein of wild-type sAd4287, sAd4310A, and sAd4312 correspond to SEQ ID NOs: 31, 32, and 33, respectively.

In other embodiments, the polynucleotides of the invention include all or a portion of one or more of the nucleotide sequences encoding the fiber-1, fiber-2, hexon, fiber-1 knob, and/or fiber-2 knob proteins of sAd4287, sAd4310A, and/or sAd4312 and nucleotide sequence from one or more adenoviral vectors including Ad11, Ad15, Ad24, Ad26, Ad34, Ad35, Ad48, Ad49, Ad50, and/or Pan9 (also known as AdC68) directed to the generation of chimeric adenoviral vectors, as discussed below. In other embodiments, the polynucleotides of the invention include all or a portion of one or more of the nucleotide sequences encoding the fiber-1, fiber-2, hexon, fiber-1 knob, and/or fiber-2 knob proteins of sAd4287, sAd4310A, and/or sAd4312 and nucleotide sequence that can be at least 90% identical (e.g., at least 91%, 92%, 93%, or 94% identical), at least 95% identical (e.g., at least 96%, 97%, 98%, or 99% identical), or 100% identical to nucleotide sequence from one or more adenoviral vectors including Ad11, Ad15, Ad24, Ad26, Ad34, Ad35, Ad48, Ad49, Ad50, and/or Pan9 (also known as AdC68). In other embodiments, the polynucleotides of the invention include nucleotide sequence from one or more adenoviral vectors including Ad5, Ad11, Ad15, Ad24, Ad26, Ad34, Ad35, Ad48, Ad49, Ad50, and/or Pan9 (also known as AdC68) and all or a portion of one or more of a nucleotide sequence that can be at least 90% identical (e.g., at least 91%, 92%, 93%, or 94% identical), at least 95% identical (e.g., at least 96%, 97%, 98%, or 99% identical), or 100% identical to all or a portion of one or more of the nucleotide sequences encoding the fiber-1, fiber-2, hexon, fiber-1 knob, and/or fiber-2 knob proteins of sAd4287, sAd4310A, and/or sAd4312.

Vectors of the Invention

The present invention also features recombinant vectors including any one or more of the polynucleotides described above. In some embodiments, one vector of the invention can be used in conjunction with one or more other vectors (e.g., 1, 2, 3, or more vectors) of the invention as a vector system, which can be used to generate recombinant replication-defective sAds (rdsAds) or replication-competent sAds (rcsAds) of the invention. Accordingly, the invention features novel adenovirus vector systems for each of the three novel sAds (sAd4287, sAd4310A, and sAd4312) described herein. Such vector systems to generate replication-defective adenoviruses are known in the art and have been applied to generate replication competent adenovirus-free batches based of, for example, Ad5, Ad11, Ad35 and Ad49 (see, e.g., WO 97/00326, WO 00/70071; WO 02/40665; U.S. Pub. No. 2005/0232900, all incorporated herein by reference). However, the vectors and vector systems of the present invention, applied towards the sAds sAd4287, sAd4310A, and sAd4312 are novel.

Figure 7:
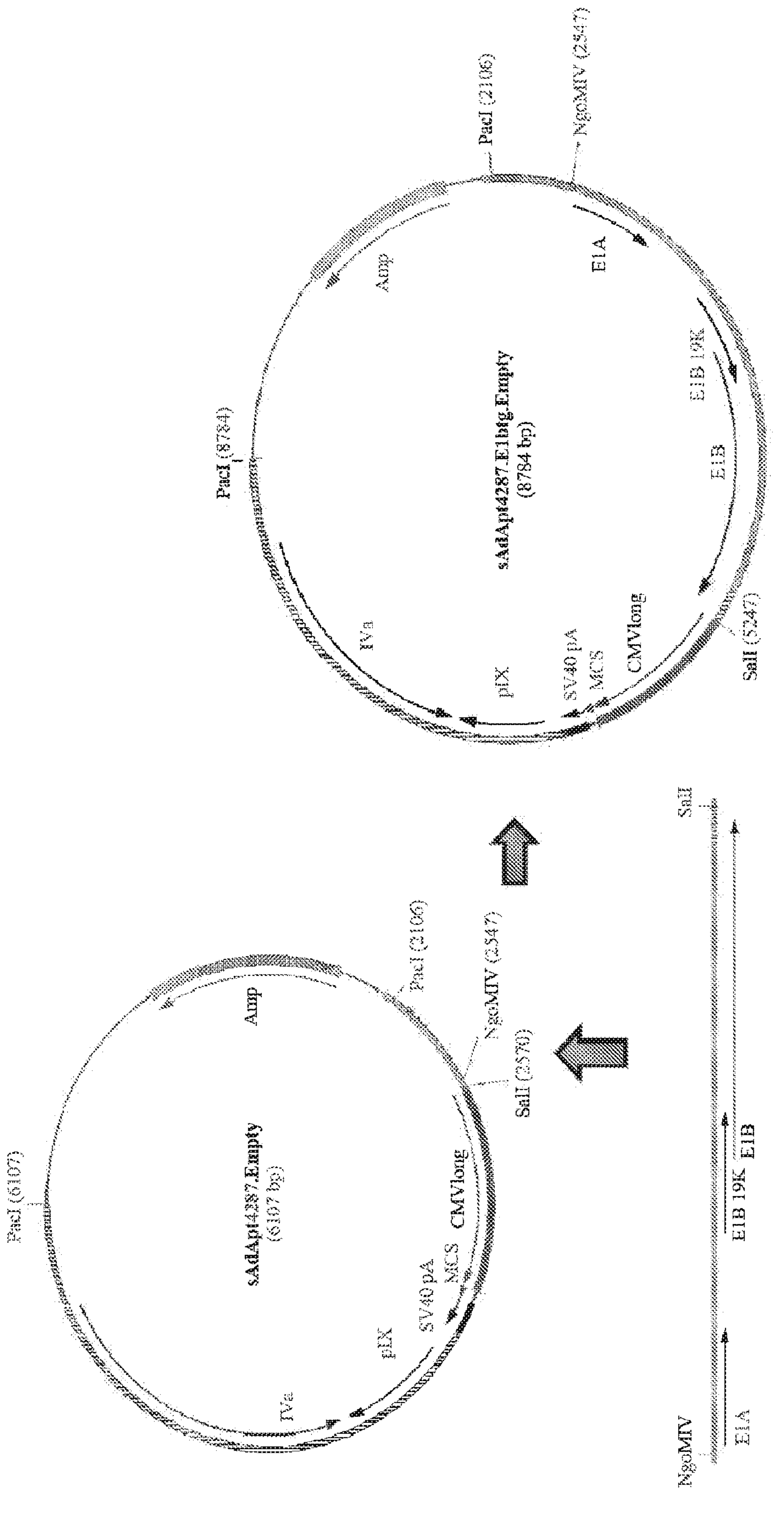
FIG. 7 illustrates the cloning strategy used to obtain plasmid sAdApt4287.E1btg.Empty and a schematic map of sAdApt4287.E1btg.Empty relative to that of its parental plasmid sAdApt4287.Empty.
Figure 14:
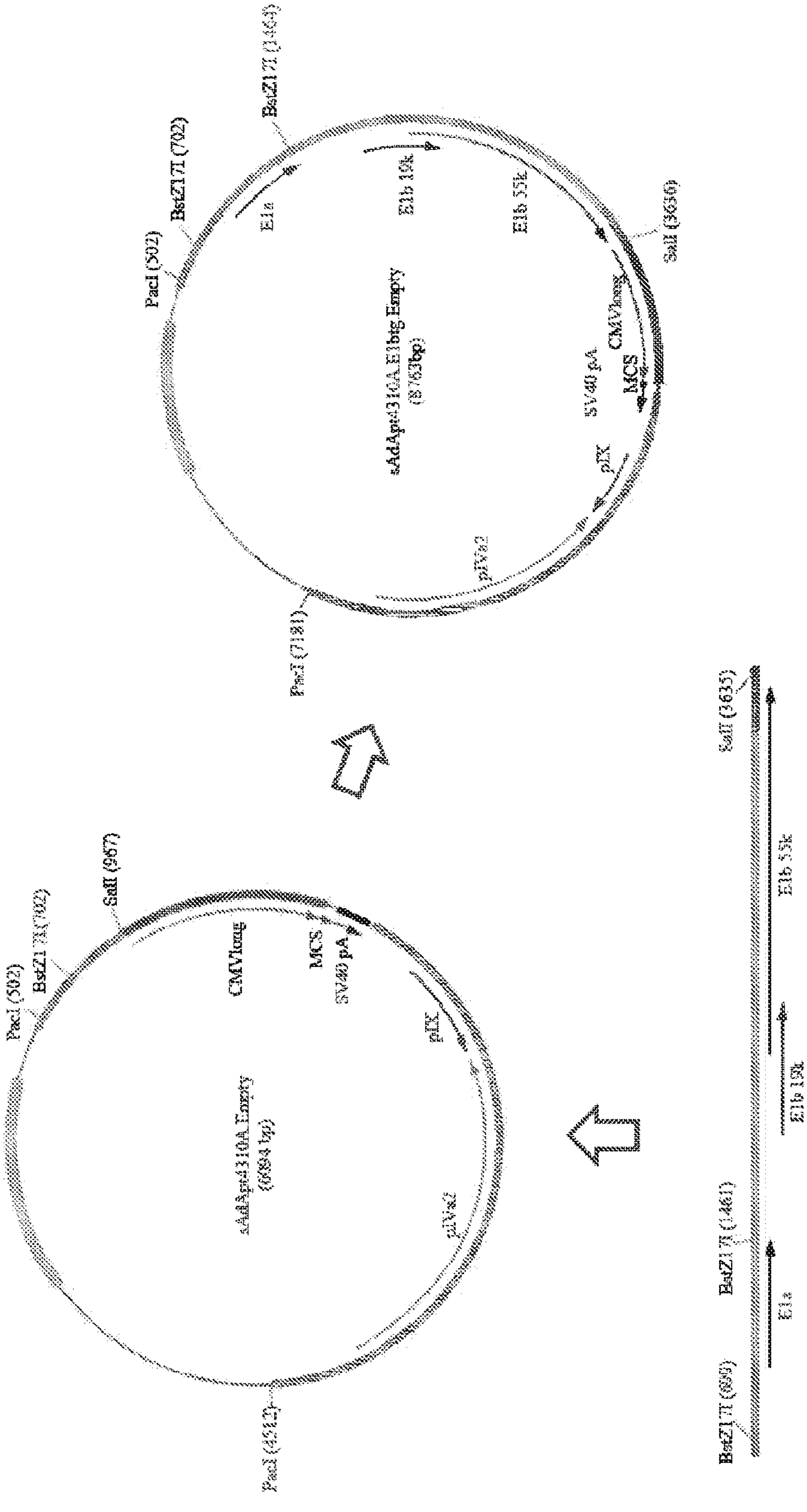
FIG. 14 illustrates the cloning strategy used to obtain plasmid sAdApt4310A.E1btg.Empty and a schematic map of sAdApt4310A.E1btg.Empty relative to that of its parental plasmid sAdApt4310A.Empty.
Figure 21:
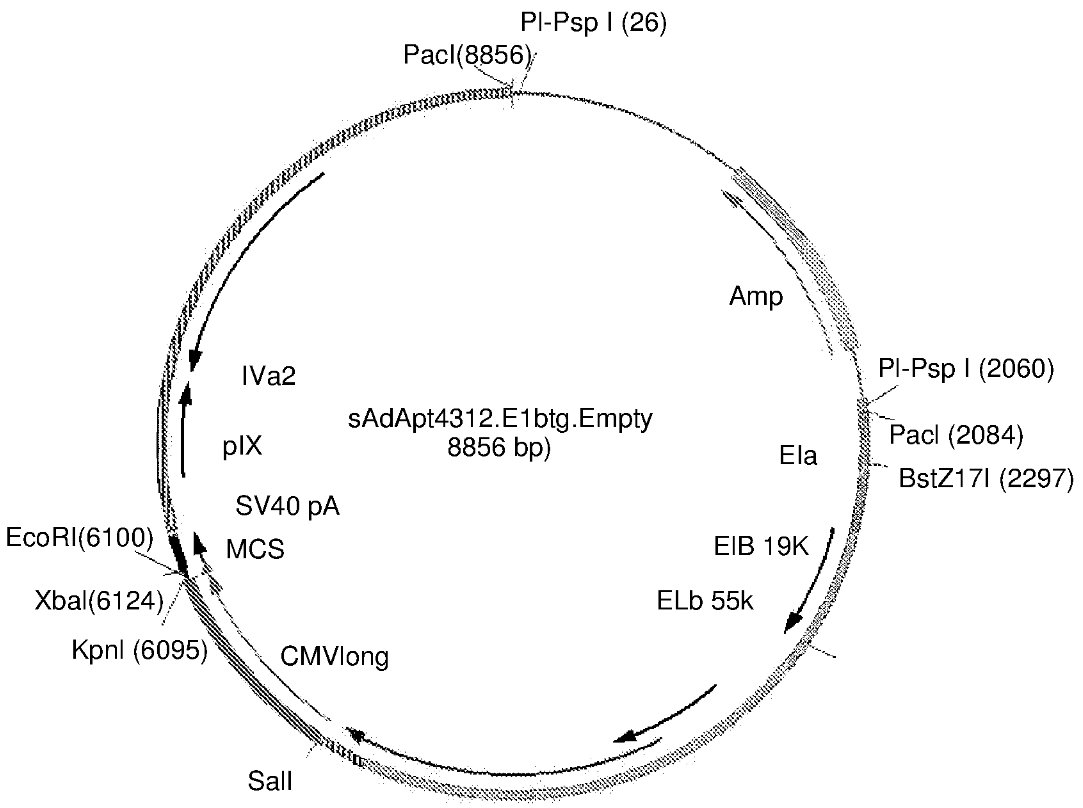
FIG. 21 is a schematic map of plasmid sAdApt4312.E1btg.Empty.

In some embodiments, the vectors of the invention can contain the E1 region (e.g., nt 474 to nt 3065 of sAd4287 (SEQ ID NO: 1); nt 474 to nt 3088 of sAd4310A (SEQ ID NO: 2); and nt 487 to nt 3100 of sAd4312 (SEQ ID NO: 3)) of the specific sAd (e.g., sAd4287, sAd4310A, and sAd4312) for the purposes of producing replication-competent sAd (rcsAd). Such vectors are exemplified, for example, in the .E1btg.Empty vectors of the invention (see, e.g., FIGS. 7, 14, and 21, which depict the .E1btg.Empty vectors of the invention for each of the three novel adenoviruses).

Figure 2:
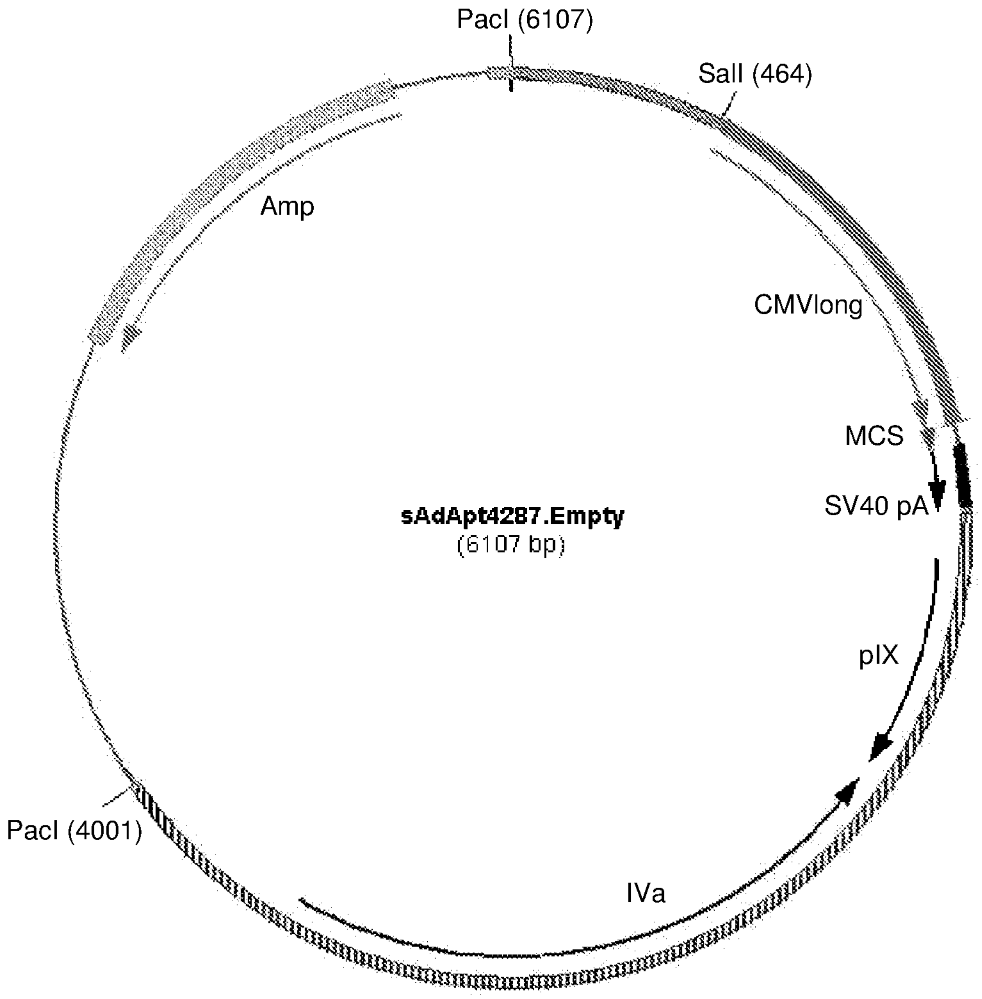
FIG. 2 is a schematic map of plasmid sAdApt4287.Empty.
Figure 3:
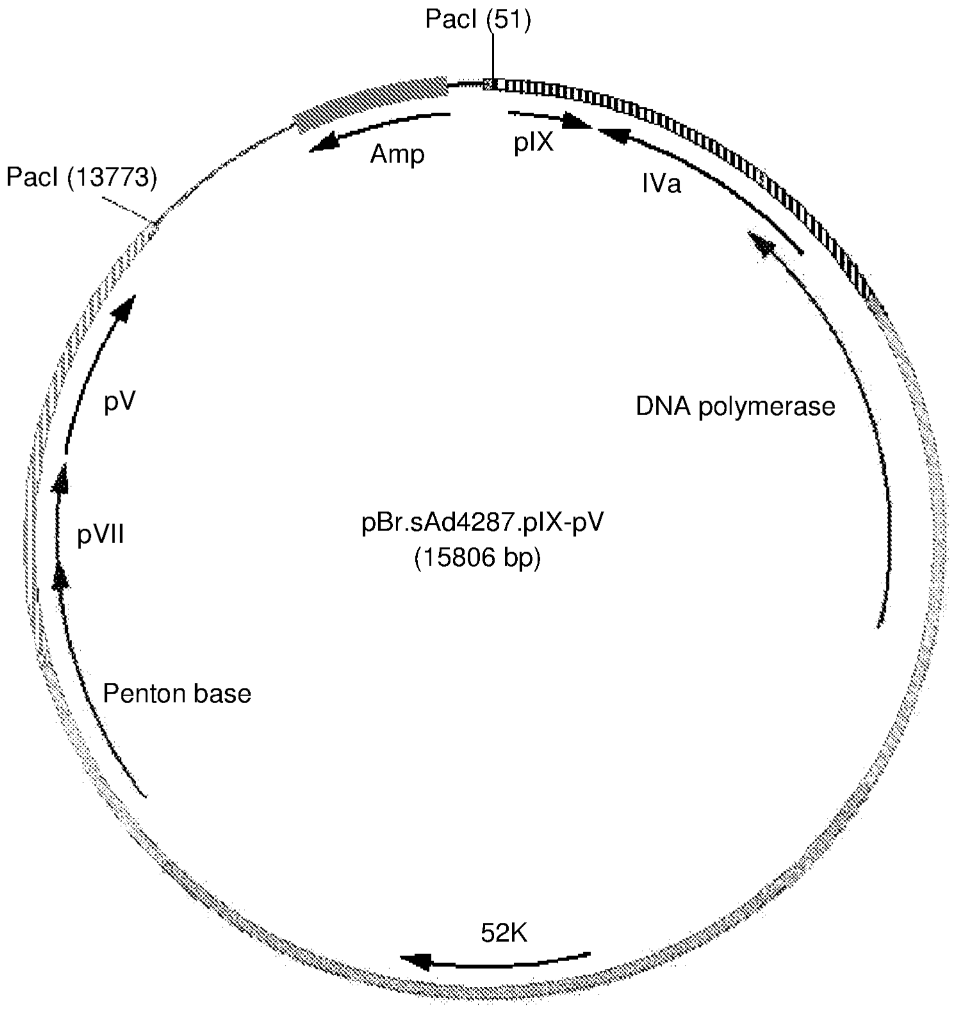
FIG. 3 is a schematic map of plasmid pBr/sAd4287.pIX-pV.
Figure 9:
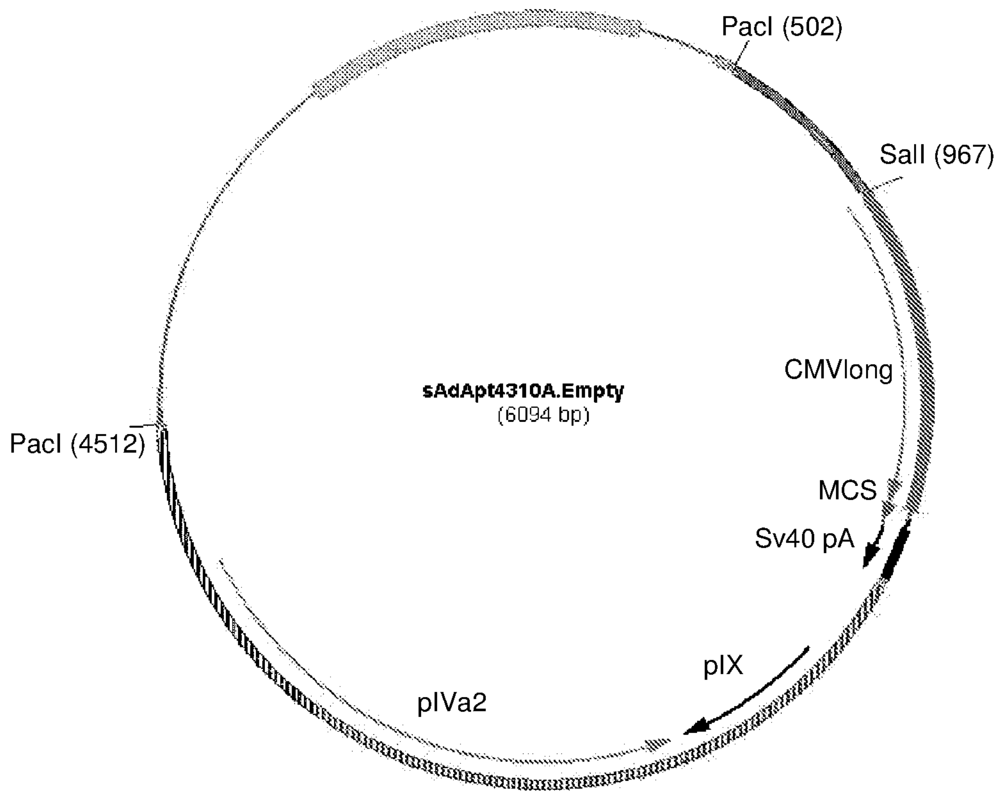
FIG. 9 is a schematic map of plasmid sAdApt4310A.Empty.
Figure 16:
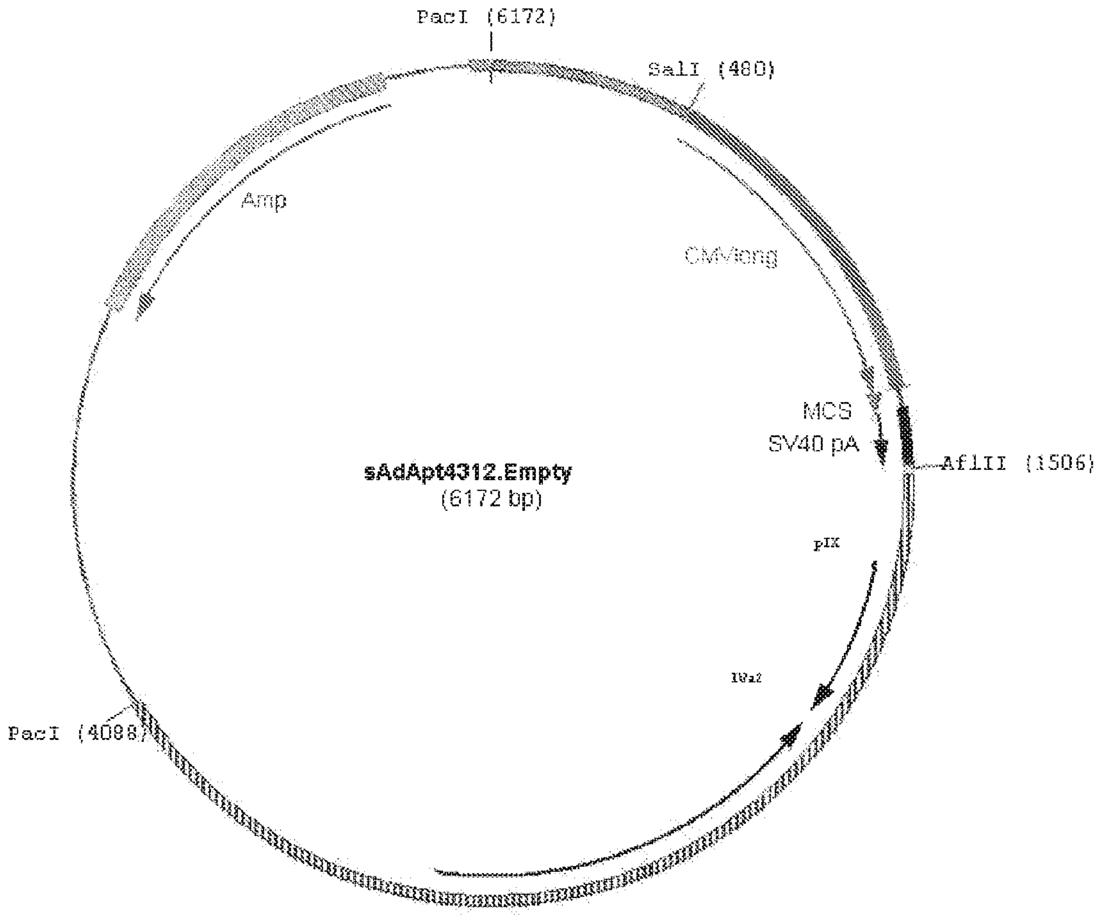
FIG. 16 is a schematic map of plasmid sAdApt4312.Empty.

In some embodiments, the vectors of the invention can contain the left-end sAd sequences and an expression/transgene cassette (see, e.g., FIG. 3, depicting the pBr/sAd4287.pIX-pV vector that includes the left part of the sAd4287 genome from approximately pIX to pV). In some embodiments, the expression cassette of the vector replaces or disrupts the E1 region of the specific adenovirus. In preferred embodiments, the expression cassette includes a promoter (e.g., a CMV promoter, e.g., a CMVlong promoter) that stimulates expression of a transgene, and optionally a poly-adenylation signal (e.g., a heterologous nucleotide sequence encoding an antigenic gene product of interest, e.g., a bacterial, viral, parasitic, fungal, or therapeutic protein, or fragment thereof) (see, e.g., FIGS. 2, 9, and 16, depicting .Empty vectors of the invention for each of the three novel adenoviruses). The E1 region can be deleted (either partially or completely), disrupted, or rendered inactive, by one or more mutations.

Figure 10:
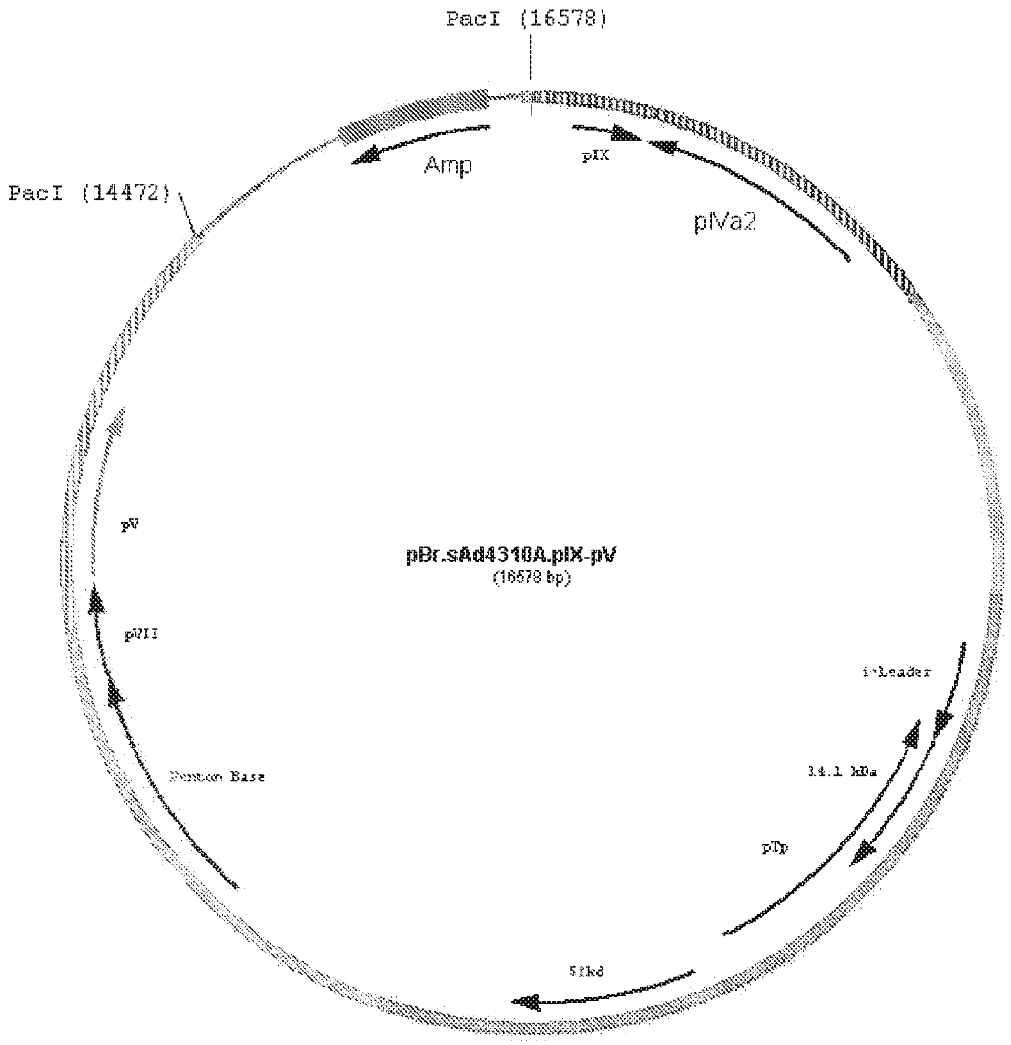
FIG. 10 is a schematic map of plasmid pBr/sAd4310A.pIX-pV.
Figure 17:
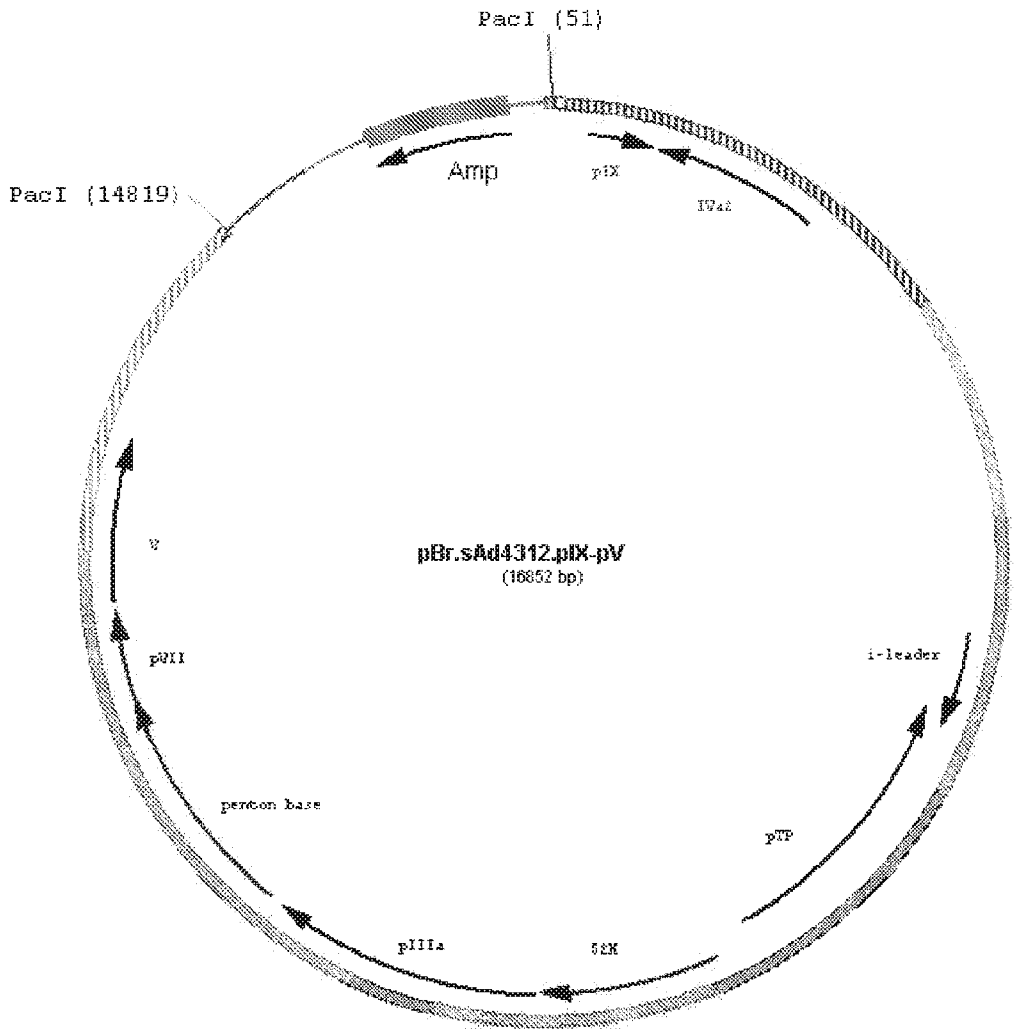
FIG. 17 is a schematic map of plasmid pBr/sAd4312.pIX-pV.

In some embodiments, the vectors of the invention can contain the left part of the sAd sequences (see, e.g., FIG. 3, depicting the pBr/sAd4287.pIX-pV vector that includes the left part of the sAd4287 genome from approximately pIX to pV), which includes the penton base and 52 K coding regions of the sAd (see, e.g., FIGS. 3, 10, and 17, depicting the .pIX-pV vectors of the invention for each of the three novel adenoviruses).

Figure 4:
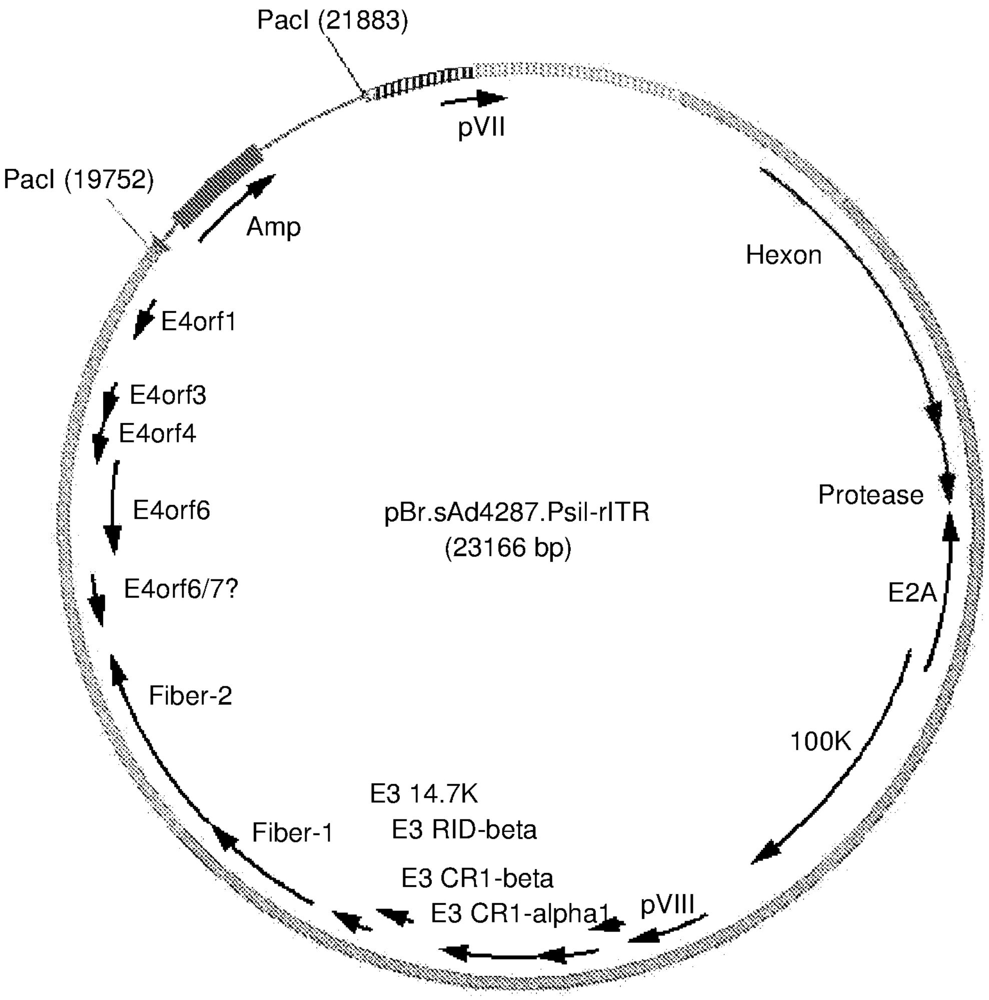
FIG. 4 is a schematic map of plasmid pBr/sAd4287.PsiI-rITR.
Figure 5:
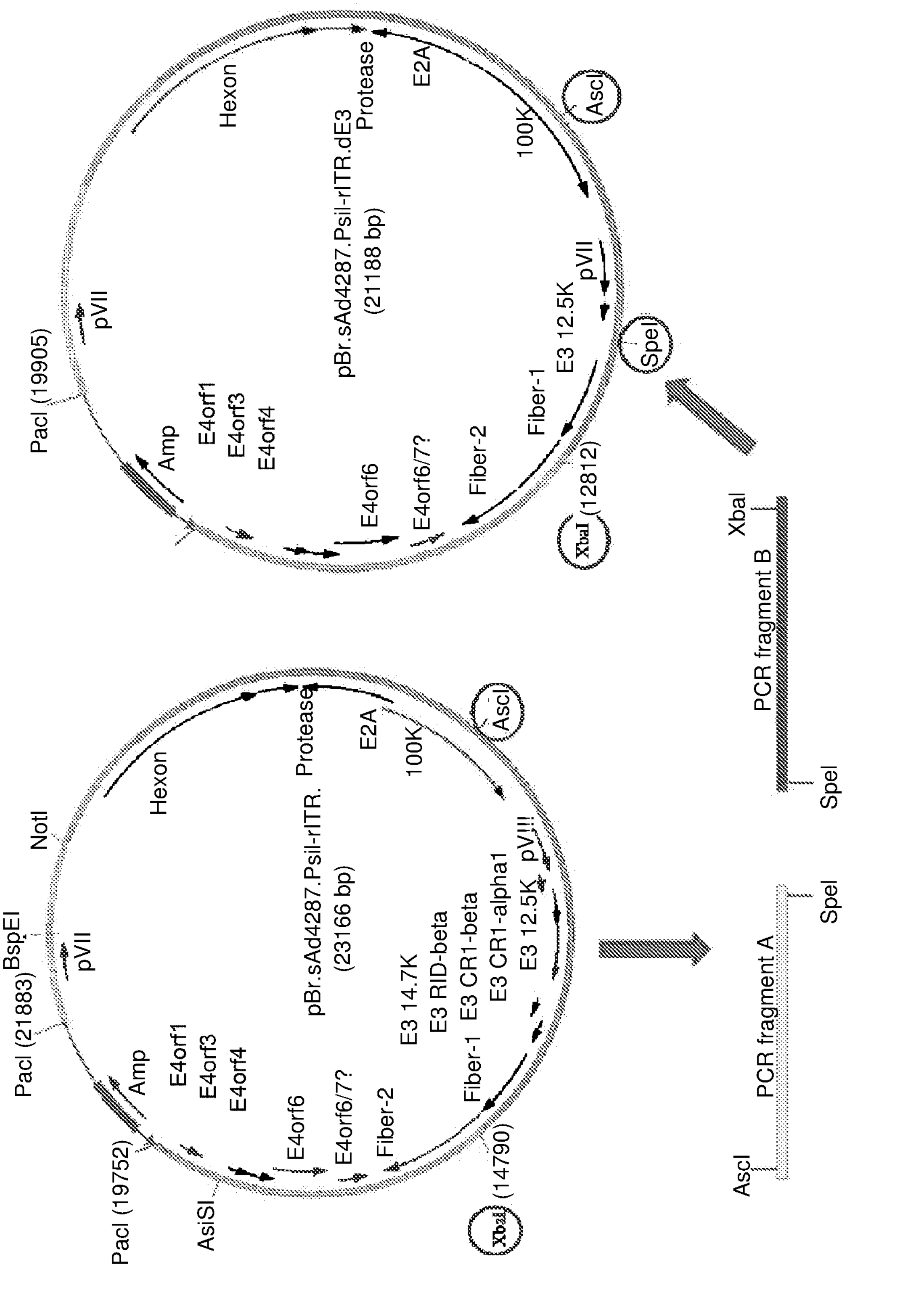
FIG. 5 illustrates the cloning strategy used to obtain plasmid pBr/sAd4287.PsiI-rITR.dE3 and a schematic map of pBr/sAd42.87.PsiI-rITR.dE3 relative to that of its parental plasmid pBr/sAd4287.PsiI-rITR.
Figure 6:
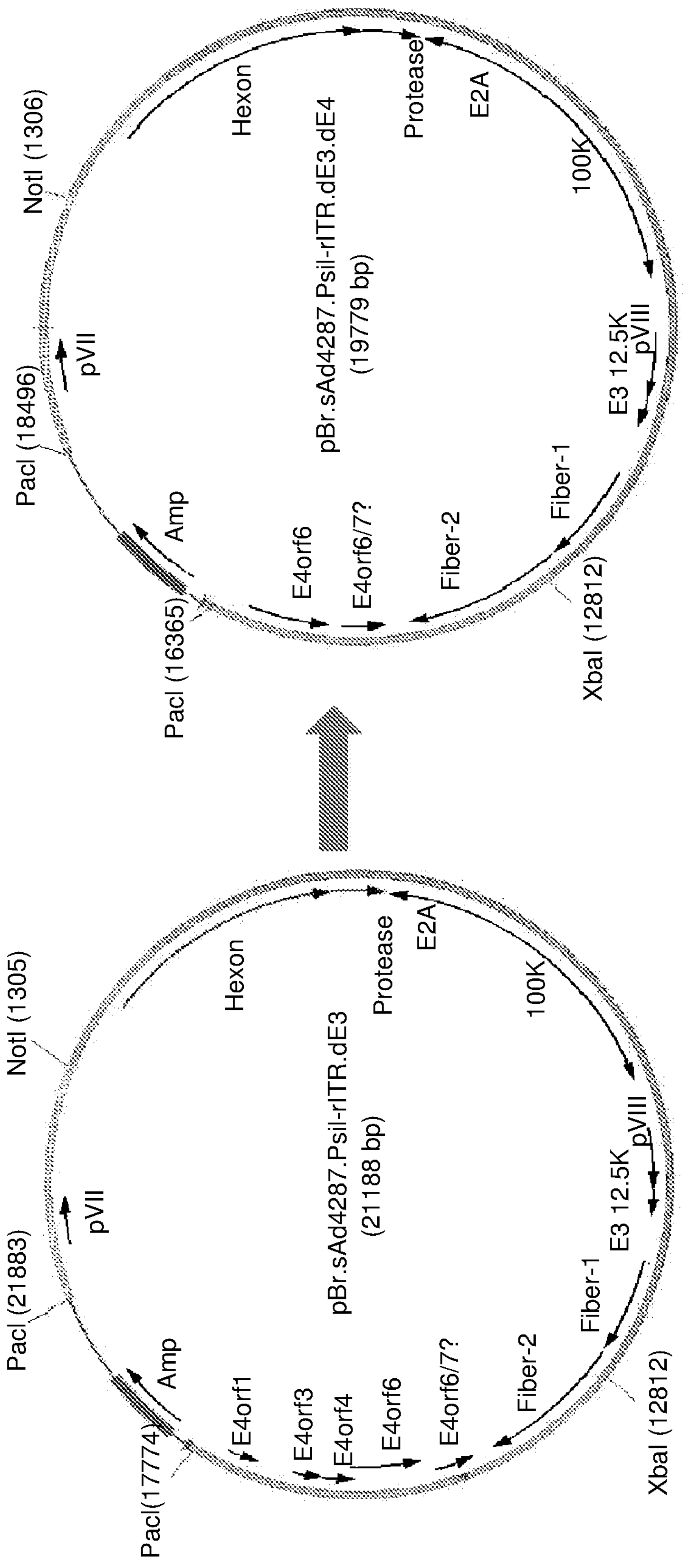
FIG. 6 shows a schematic map of plasmid pBr/sAd4287.PsiI-rITR.dE3.dE4 relative to that of its parental plasmid pBr/sAd4287.PsiI-rITR.dE3.
Figure 11:
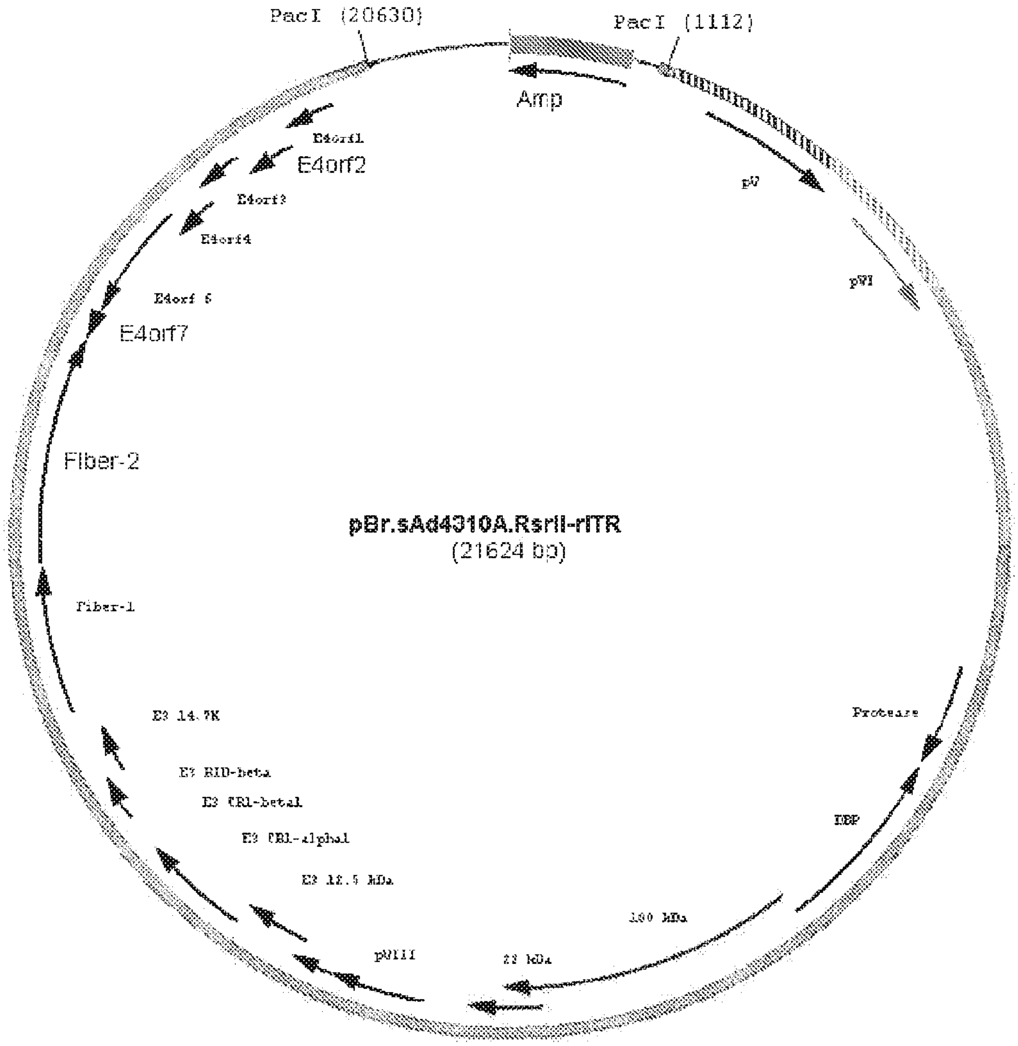
FIG. 11 is a schematic map of plasmid pBr/sAd4310A.RsrII-rITR.
Figure 12:
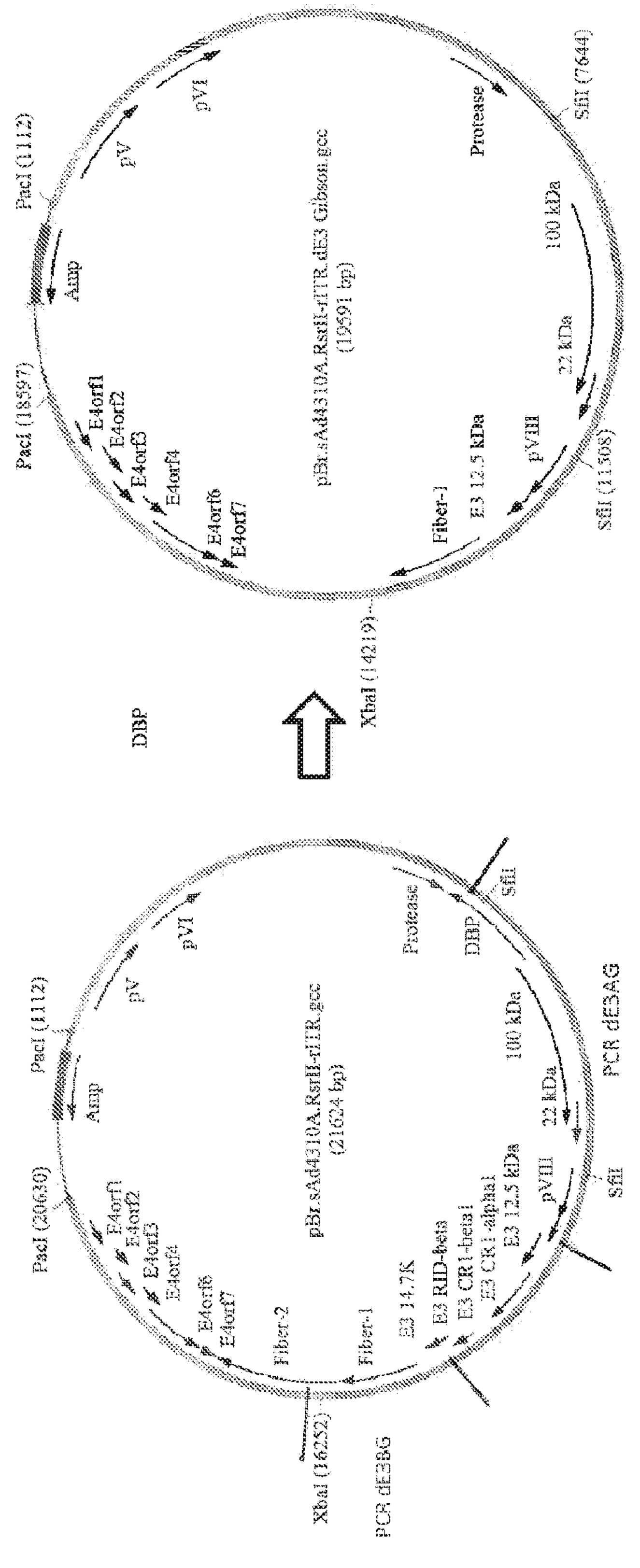
FIG. 12 shows a schematic map of pBr/sAd4310A.RsrII-rITR.dE3 relative to that of its parental plasmid pBr/sAd4310A.RsrII-rITR.
Figure 13:
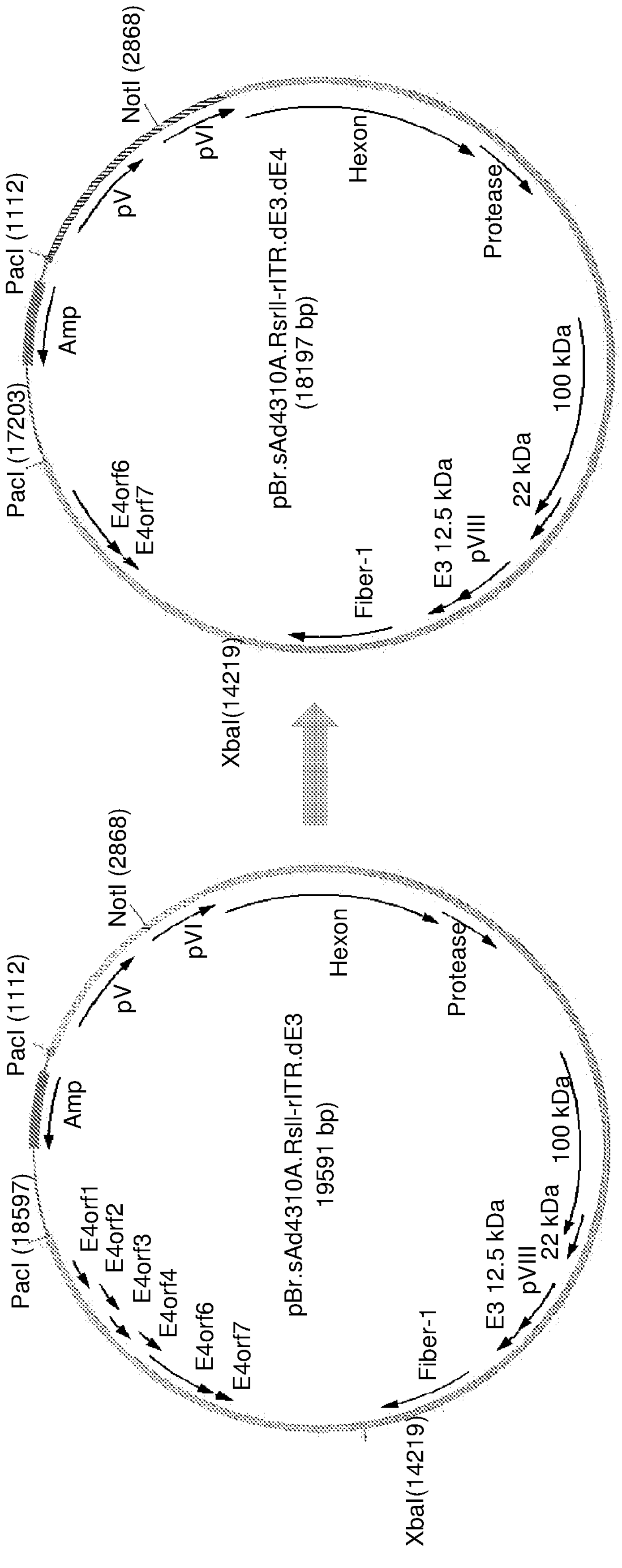
FIG. 13 shows a schematic map of plasmid pBr/sAd4310A.RsrII-rITR.dE3.dE4 relative to that of its parental plasmid pBr/sAd4310A.RsrII-rITR.dE3.
Figure 18:
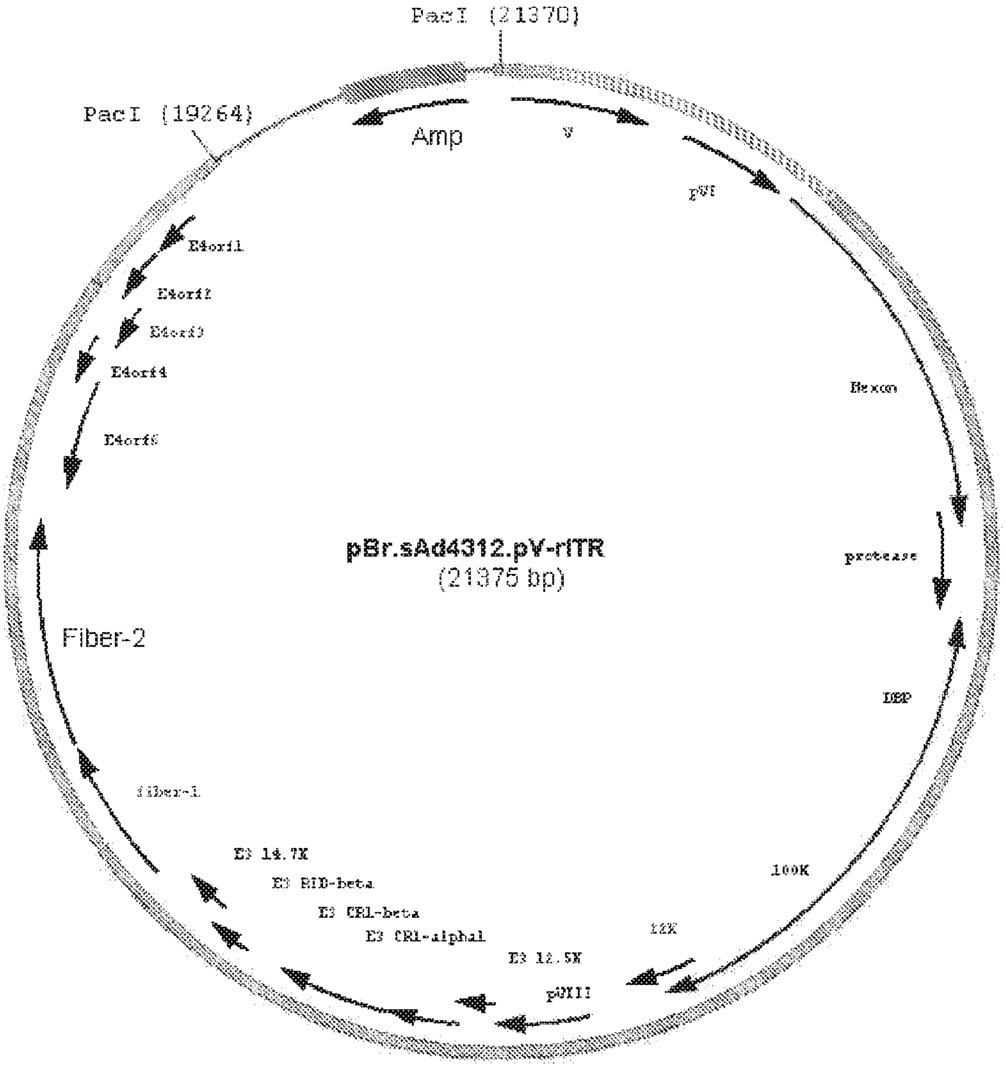
FIG. 18 is a schematic map of plasmid pBr/sAd4312.pV-rITR.
Figure 19:
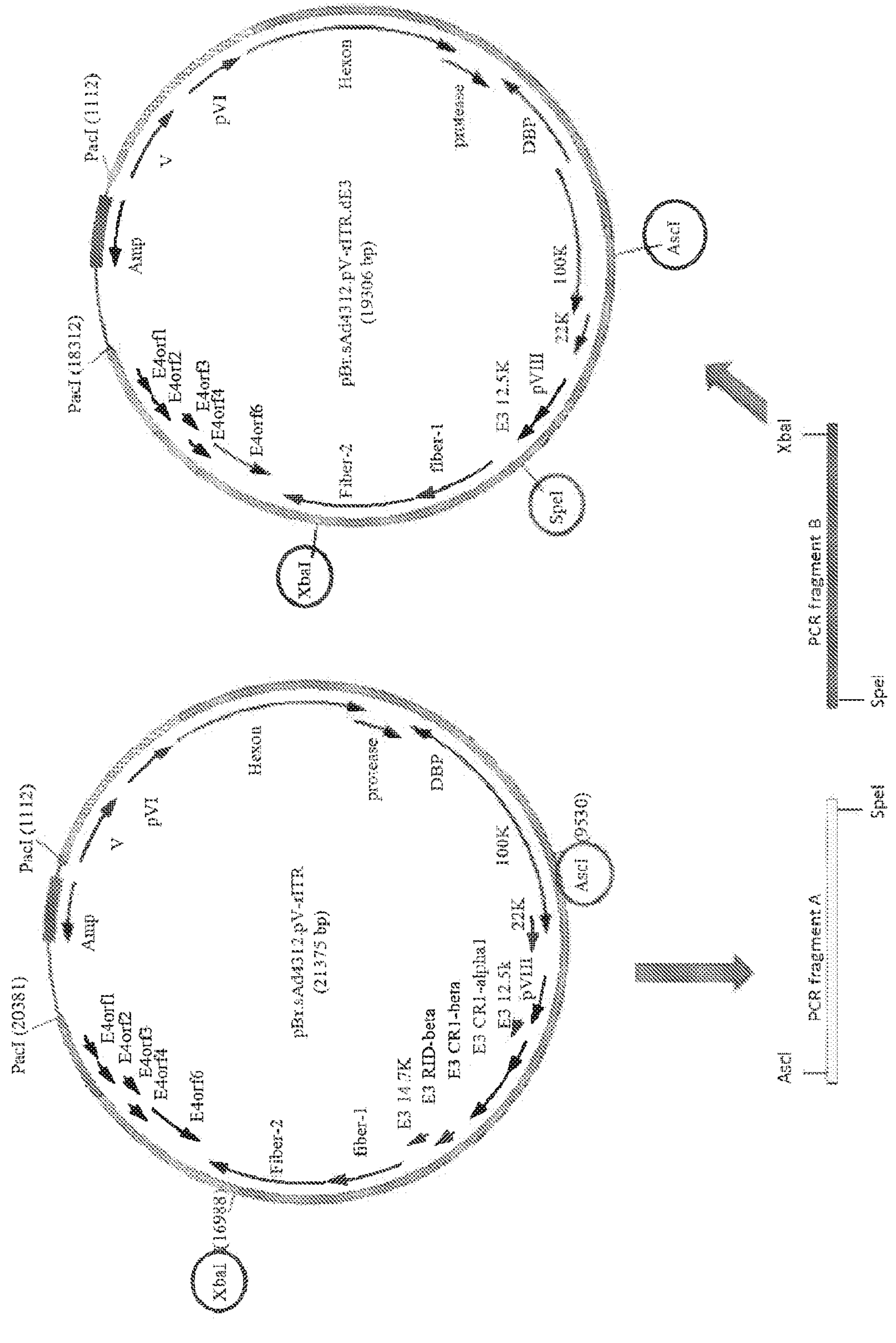
FIG. 19 illustrates the cloning strategy used to obtain plasmid pBr/sAd4312.pV-rITR.dE3 and a schematic map of pBr/sAd4312.pV-rITR.dE3 relative to that of its parental plasmid pBr/sAd4312.pV-rITR.
Figure 20:
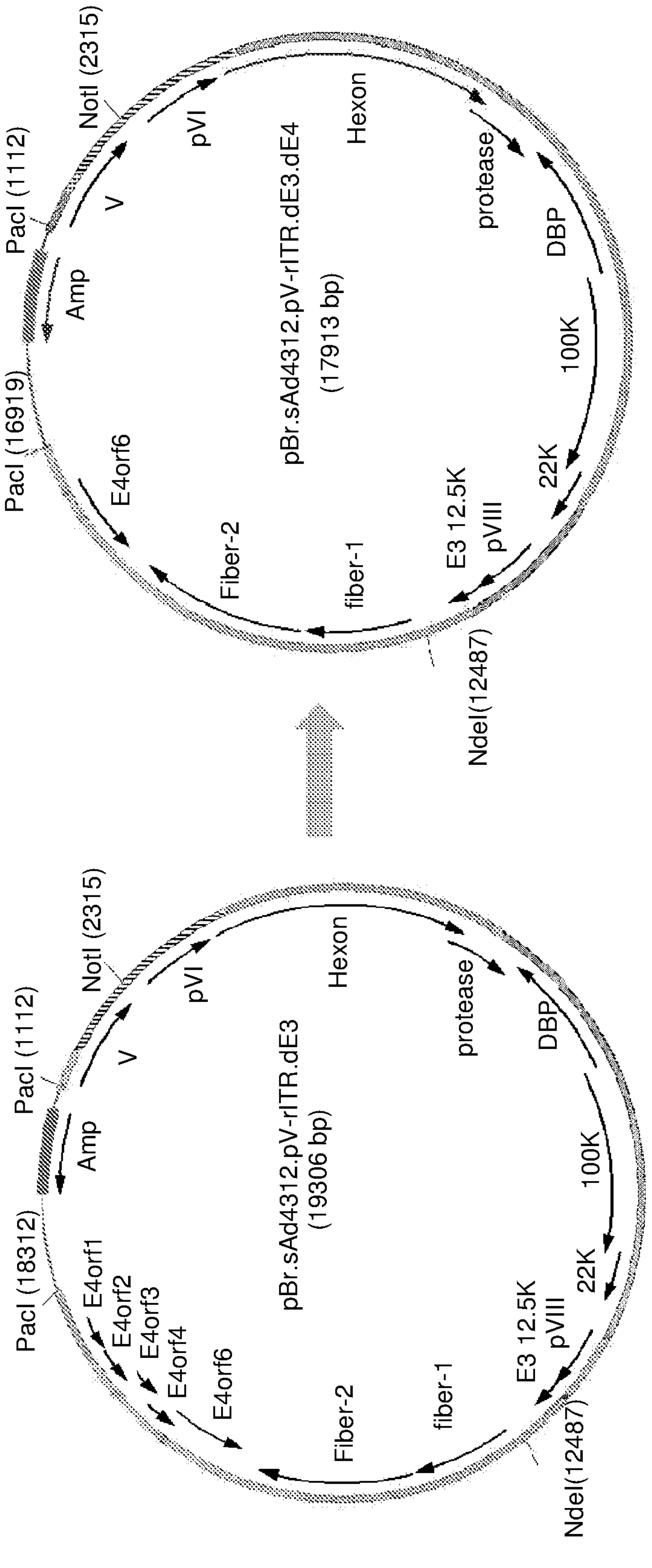
FIG. 20 shows a schematic map of plasmid pBr/sAd4312.pV-rITR.dE3.dE4 relative to that of its parental plasmid pBr/sAd4312.pV-rITR.dE3.

In other embodiments, the vectors of the invention can contain the right part of the sAd sequences (see, e.g., FIG. 4, depicting the pBr/sAd4287,PsiI.rITR vector that includes the right part of the sAd4287 genome from approximately pVII to the right ITR (rITR)) (see, e.g., FIGS. 4, 11, and 18, depicting the .pV-rITR vectors of the invention for each of the three novel adenoviruses). In some embodiments, these vectors may further have a deleted, disrupted, or mutated E3 (e.g., nt 25973 to nt 28596 of sAd4287 (SEQ ID NO: 1); nt 25915 to nt 28496 of sAd4310A (SEQ ID NO: 2): and nt 25947 to nt 28561 of sAd4312 (SEQ ID NO: 3); see FIGS. 5, 12, and 19, depicting the .dE3 vectors of the invention for each of the three novel adenoviruses) and/or E4 region (e.g., nt 31652 to nt 34752 of sAd4267 (SEQ ID NO: 1); nt 31750 to nt 34048 of sAd4310A (SEQ ID NO: 2); and nt 31818 to nt 34116 of sAd4312 (SEQ ID NO: 3); see FIGS. 6, 13, and 20, depicting the .dE3.dE4 vectors of the invention for each of the three novel adenoviruses), which are not required for replication and packaging of the adenoviral particle. Deletion of the E3 region is generally preferred if large transgene sequences are to be incorporated into the vector since the genome size which can be packaged into a functional particle is limited to approximately 105% of the wild type size. Although not applied herein, it is to be understood that other modifications may be introduced in the adenoviral genome, such as deletion of the E2A region, or most if not all of the entire E4 region. In some embodiments, a cell transfected with a vector of the invention can complement these deficiencies by delivering the functionality of the missing regions. The E2A region can be provided by, for instance, a temperature sensitive E2A mutant, or by delivering the E4 functions. Cells that can be used to complement a deficiency of an adenoviral gene (e.g., a E1, E3, and/or E4 deletion) of a vector of the invention include, for example, PER.55K, PER.C6®, and 293 cells. All such systems are known in the art and such modifications of the adenoviral genomes are within the scope of the present invention, which in principal relates to the three novel sAd4287, sAd4310A, and sAd4312 genomic sequences, and the use thereof. As described above, any one vector of the invention can be used in conjunction with one or more other vectors of the invention. In some embodiments, vectors are used which encode both left and right sides of the sAd genome in order to generate a given sAd of the invention.

The present invention also features vectors for the generation of chimeric adenoviruses which include a portion of the sAd4287, sAd4310A, or sAd4312 genome as well as a portion of the genome of one or more other viruses. In some embodiments, the chimeric adenoviral vectors of the invention may include a substitution of all or a portion of the hexon and/or fiber protein. In some embodiments, the portion of the hexon protein substituted with that of another virus is one or more of the hexon protein hypervariable regions (HVRs), for example, HVR1 (nt 403 to nt 489), HVR2 (nt 520 to nt 537), HVR3 (nt 592 to nt 618), HVR4 (nt 706 to nt 744), HVR5 (nt 763 to 786), HVR6 (nt 856 to nt 874), and/or HVR7 nt 1201 to nt 1296) of sAd4287 hexon protein (SEQ ID NO: 10); HVR1 (nt 403 to nt 477), HVR2 (nt 505 to nt 516), HVR3 (nt 571 to nt 591), HVR4 (nt 679 to nt 690), HVR5 (nt 709 to 735), HVR6 (nt 805 to nt 816), and/or HVR7 (nt 1144 to nt 1236) of sAd4310A hexon protein (SEQ ID NO: 11); or HVR1 (nt 403 to nt 474), HVR2 (nt 505 to nt 522), HVR3 (nt 577 to nt 597), HVR4 (nt 685 to nt 726), HVR5 (nt 748 to 777), HVR6 (nt 847 to nt 864), and/or HVR7 (nt 1192 to nt 1284) of sAd4312 hexon protein (SEQ ID NO: 12). In some embodiments, the portion of the fiber protein substituted with that of another virus is the fiber knob domain. In some embodiments, the substituted regions are replaced with a region derived from an adenovirus that has a lower seroprevalence compared to that of Ad5, such as subgroup B (Ad11, Ad34, Ad35, and Ad50) and subgroup D (Ad15, Ad24, Ad26, Ad48, and Ad49) adenoviruses as well as simian adenoviruses (e.g., Pan9, also known as AdC68). In some embodiments, an adenoviral vector backbone of Ad5, Ad11, Ad15, Ad24, Ad26, Ad34, Ad48, Ad49, Ad50, or Pan9/AdC68 includes a substitution of all or a portion of one or more of the above hexon HVRs of sAd4287, sAd4310A, and/or sAd4312.

Adenoviruses of the Invention

As discussed above, a recombinant adenovirus of the invention derived, at least in part, from sAd4287, sAd4310A, and/or sAd4312 can be generated using the above-described vectors of the invention. These adenoviruses may be rcsAds or rdsAds. rdsAds will include a deleted, disrupted, or mutational inactivation of the E1 region, and may further include a deletion, disruption, or mutational inactivation of the E2, E3, and/or E4 regions. In some embodiments, the adenovirus of the invention may include an antigenic or therapeutic gene product, or fragment thereof, including a bacterial, viral, parasitic, or fungal protein, or fragment thereof. In a preferred embodiment, the antigenic gene product, or fragment thereof, when expressed in a host, or host cells, is capable of eliciting a strong immune response. In some embodiments, the bacterial protein, or fragment thereof, may be derived from *Mycobacterium tuberculosis, Mycobacterium bovis, Mycobacterium africanum, Mycobacterium microti, Mycobacterium leprae, Pseudomonas aeruginosa, Salmonella typhimurium, Escherichia coil, Klebsiella pneumoniae, Streptococcus pneumoniae, Staphylococcus aureus, Francisella tularensis, Brucella, Burkholderia mallei, Yersinia pestis, Corynebacterium Neisseria meningitidis, Bordetella pertussis, Clostridium tetani*, or *Bacillus anthracis*. In some embodiments, the viral protein, or fragment thereof, may be derived from a virus of a viral family selected from the group consisting of *Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae*, and *Reoviridae*. In some embodiments, the virus is human immunodeficiency virus (HIV), human papillomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, or Marburg virus. In some embodiments, the parasitic protein, or fragment thereof, is from *Toxoplasma gondii, Plasmodium falciparum, Plasmodium vivax, Plasmodium ovale, Plasmodium malariae, Trypanosome* spp., or *Legionella* spp. In some embodiments, the fungal protein, or fragment thereof, is from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*. In some embodiments, the therapeutic gene products may be interferon (IFN) proteins, Factor VIII, Factor IX, erythropoietin, alpha-1 antitrypsin, calcitonin, glucocerebrosidase, growth hormone, low density lipoprotein (LDL), receptor IL-2 receptor and its antagonists, insulin, globin, immunoglobulins, catalytic antibodies, the interleukins, insulin-like growth factors, superoxide dismutase, immune responder modifiers, parathyroid hormone and interferon, nerve growth factors, tissue plasminogen activators, and/or colony stimulating factors (see, e.g., U.S. Pat. No. 6,054,288, incorporated by reference herein). In some embodiments, the IFN protein has an amino acid sequence substantially identical (e.g., at least 70%, 75%, 80%, 85%, 90%, 95%, 96%, 97%, 98%, 99%, or even 100% identical) to the sequence of a human IFN-α (e.g., IFN-α-1α, IFN-α-1b, IFN-α-2α, IFN-α-2b, and consensus IFN-α (conIFN-α); FIG. 1), a human IFN-β (e.g., IFN-β-1a and IFN-β-1b), a human IFN-γ), or an IFN-τ or a polypeptide that demonstrates the same or similar biological activity to an interferon (e.g., at least 50%, 60%, 70%, 75%, 80%, 85%, 90%, 95%, or 100% of the activity of a human IFN-α, a human IFN-β, a human IFN-γ, an IFN-τ, or a conIFN-α (see, e.g., U.S. Pat. No. 4,695,623 and U.S. Pub. No. 2011/0000480, incorporated by reference herein, for examples of specific IFN sequences).

Non-limiting examples of bacterial gene products, or fragments thereof, include 10.4, 85A, 85B, 86C, CFP-10, Rv3871, and ESAT-6 gene products, or fragments thereof, of *Mycobacterium*, O, H, and K antigens, or fragments thereof, of *E. coli*; and protective antigen (PA), or fragments thereof, of *Bacillus anthracis*. Non-limiting examples of viral gene products, or fragments thereof, include Gag, Pol, Nef, Tat, Rev, Vif, Vpr, or Vpu, or fragments thereof, of HIV and other retroviruses (see, e.g., U.S. Pub. No. 2012/0076812, incorporated by reference herein); 9D antigen, or fragments thereof, of HSV; Env, or fragments thereof, of all envelope protein-containing viruses. Non-limiting examples of parasitic gene products, or fragments thereof, include circumsporozoite (CS) protein, gamete surface proteins Pfs230 and Pfs48/45, and Liver Specific Antigens 1 or 3 (LSA-1 or LSA-3), or fragments thereof, of *Plasmodium falciparum*. Non-limiting examples of fungal gene products, or fragments thereof, include any cell wall mannoprotein (e.g., Afmp1 of *Aspergillus fumigatus*) or surface-expressed glycoprotein (e.g., SOWgp of *Coccidioides immitis*).

Methods of Prophylaxis or Treatment Using Compositions of the Invention

The pharmaceutical compositions of the invention can be used as vaccines for treating a subject (e.g., a human) with a disease (e.g., cancer or a disease caused by an infective agent, e.g., AIDS). In particular, the compositions of the invention car be used to treat (pre- or post-exposure) infection by bacteria, including *Mycobacterium tuberculosis, Mycobacterium bovis, Mycobacterium africanum, Mycobacterium microti, Mycobacterium leprae, Pseudomonas aeruginosa, Salmonella typhimurium, Escherichia coli, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani*, or *Bacillus anthracis*; viruses of a viral family selected from the group consisting of *Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae*, and *Reoviridae*; parasites, including *Toxoplasma gondii, Plasmodium falciparum, Plasmodium vivax, Plasmodium ovale, Plasmodium malariae, Trypanosoma* spp., or *Legionella* spp.; and fungi, including *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*.

Accordingly, in other non-limiting embodiments, the pharmaceutical compositions of the invention can be used to treat a subject (e.g., a human) with acquired immune deficiency syndrome (AIDS), cancer, tuberculosis, leprosy, typhoid fever, pneumonia, meningitis, staphylococcal scalded skin syndrome (SSSS), Ritter's disease, tularemia (rabbit fever), brucellosis, Glanders disease, bubonic plague, septicemic plague, pneumonic plague, diphtheria, pertussis (whooping cough), tetanus, anthrax, hepatitis, smallpox, monkeypox, measles, mumps, rubella, chicken pox, polio, rabies, Japanese encephalitis, herpes, mononucleosis, influenza, Ebola virus disease, hemorrhagic fever, yellow fever, Marburg virus disease, toxoplasmosis, malaria, trypanosomiasis, legionellosis, aspergillosis, blastomycosis, candidiasis (thrush), coccidioidomycosis, cryptococcosis, histoplasmosis, paracoccidioidomycosis, sporotrichosis, or sinus-orbital zygomycosis.

Pharmaceutical Formulation and Administration of the Compositions of the Invention Administration The pharmaceutical compositions of the invention can be administered to a subject (e.g., a human), pre- or post-exposure to an infective agent (e.g., bacteria, viruses, parasites, fungi) or pre- or post-diagnosis of a disease of a disease without an etiology traceable to an infective, agent (e.g., cancer), to treat, prevent, ameliorate, inhibit the progression of, or reduce the severity of one or more symptoms of the disease in the subject. For example, the compositions of the invention can be administered to a subject to treat having AIDS. Examples of symptoms of diseases caused by a viral infection, such as AIDS, that can be treated using the compositions of the invention include, for example, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, for example, a physician during a physical examination or by other tests and methods known in the art.

The compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in cremes, or in lipid compositions.

The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-exposure prophylaxis or after a subject has been diagnosed with a disease having a disease without an etiology traceable to an infective agent (e.g., cancer) or a subject exposed to an infective agent, such as a bacterium, virus, parasite, or fungus. The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis or post-exposure to the infective agent.

When treating disease (e.g., AIDS or cancer), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the recombinant replication-defective sAd vector containing a heterologous nucleic acid encoding an antigenic gene product, or fragment thereof, (e.g., an sAd4287, sAd4310A, or sAd4312 HIV Gag delivery vector) and, if desired, one or more immunomodulatory agents, such as in a sealed package of tablets or capsules, or in a suitable dry powder inhaler (DPI) capable of administering one or more doses.

Dosages

The dose of the compositions of the invention (e.g., the number of antigenic gene product-encoding recombinant sAd vectors) or the number of treatments using the compositions of the invention may be increased or decreased based on the severity of, occurrence of, or progression of, the disease in the subject (e.g., based on the severity of one or more symptoms of, e.g., viral infection or cancer).

The pharmaceutical compositions of the invention can be administered in a therapeutically effective amount that provides an immunogenic and/or protective effect against an infective agent or target protein for a disease caused by a non-infective agent. For example, the subject can be administered at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{11}$ vp/dose.

Viral particles include nucleic acid molecules encoding an antigenic gene product or fragment thereof (e.g., viral structural and non-structural proteins) and are surrounded by a protective coat (a protein-based capsid with hexon and fiber proteins, which may be derived from a single sAd of the invention or a chimeric variant thereof). Viral particle number can be measured based on, for example, lysis of vector particles, followed by measurement of the absorbance at 260 nm (see, e.g., Steel, Curr. Opin. Biotech., 1999).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of the antigenic or therapeutic gene product, or fragment thereof (e.g., a level of an antigenic gene product that elicits an immune response without undue adverse physiological effects in the host caused by the antigenic gene product).

In addition, single or multiple administrations of the compositions of the present invention may be given (pre- or post-exposure and/or pre- or post-diagnosis) to a subject (e.g., one administration or administration two or more times). For example, subjects who are particularly susceptible to, for example, viral infection may require multiple treatments to establish and/or maintain protection against the virus. Levels of induced immunity provided by the pharmaceutical compositions described herein can be monitored by, for example, measuring amounts of neutralizing secretory and serum antibodies. The dosages may then be adjusted or repeated as necessary to trigger the desired level of immune response. For example, the immune response triggered by a single administration (prime) of a composition of the invention may not sufficiently potent and/or persistent to provide effective protection. Accordingly, in some embodiments, repeated administration (boost), such that a prime boost regimen is established, can significantly enhance humoral and cellular responses to the antigen of the composition.

Alternatively, the efficacy of treatment can be determined by monitoring the level of the antigenic or therapeutic gene product, or fragment thereof, expressed in a subject (e.g., a human) following administration of the compositions of the invention. For example, the blood or lymph of a subject can be tested for antigenic or therapeutic gene product, or fragment thereof, using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of the compositions of the invention may achieve protection, pre exposure or pre-diagnosis. In addition, a single dose administered post-exposure or post-diagnosis can function as a treatment according to the present invention.

A single dose of the compositions of the invention can also be used to achieve therapy in subjects being treated for a disease. Multiple doses (e.g., 2, 3, 4, 5, or more doses) can also be administered, in necessary, to these subjects.

Carriers, Excipients, Diluents

The compositions of the invention include sAd5 vectors containing a heterologous nucleic acid molecule encoding an antigenic or therapeutic gene product, or fragment thereof. Therapeutic formulations of the compositions of the invention are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

EXAMPLES

The following examples are to illustrate the invention. They are not meant to limit the invention in any way.

The practice of this invention may employ, unless otherwise indicated, conventional techniques of molecular biology, cell biology, and recombinant DNA, which are within the skill of the person skilled in the art (see, e.g., Green and Sambrook. *Molecular Cloning: A Laboratory Manuel,* $4^{th}$ edition, 2012; Ausubel, et al. *Current Protocols in Molecular Biology,* 1987; *Methods in Enzymology*. Academic Press, Inc.; and MacPherson et al. *PCR2: A Practical Approach,* 1995).

Example 1. Sequence of Simian Adenovirus sAd4287

The total genome sequence of simian adenovirus sAd4287 was determined following the isolation, amplification, and purification of the novel virus obtained from the rhesus monkey metagenomics study of Handley et al. (*Cell.* 151(2):253-266, 2012). The obtained sequence of the sAd4287 genome (35079 nucleotides (nt)) is given as SEQ ID NO: 1. A schematic genome structure of sAd4287 is depicted in FIG. 1. Using the full genomic sequence in an NCBI web-based BLAST search, the most closely related virus to sAd4287 was identified as simian adenovirus 1 (sAd1) ATCC VR-195 (query coverage: 93%; maximum identity: 98%). NCBI web-based BLAST searches were also performed to assess homology of three major capsid proteins of sAd4287 (fiber-1, fiber-2, and hexon proteins). The most closely related protein to sAd4287 fiber-1 was identified as sAd1 fiber-1 (query coverage: 100%; maximum identity: 74%). The most closely related protein to sAd4287 fiber-2 was identified as sAd7 long fiber (query coverage: 100%; maximum identity: 97%). The most closely related protein to sAd4287 hexon was identified as sAd1 hexon (query coverage: 100%; maximum identity: 93%).

Example 2. Generation of Recombinant sAd4287 Viruses

Here, the construction of an sAd4287 plasmid-based system to generate recombinant sAd4287 vectors in a safe and efficient manner is described. The plasmid system consists of a first plasmid, referred to as an adapter plasmid, which contains sAd4287 nucleotides 1 to 460 including the left inverted terminal repeat (lITR) and packaging signal, an expression cassette and an sAd4287 fragment corresponding to nucleotides 2966 to 5466. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al, *J. Virol.* 81(9): 4654-4663, 2007), albeit now generated to comprise the sAd4287-derived sequences instead of the Ad26-derived sequences. Furthermore, the system consists of other plasmids together constituting sAd4287 sequences between nucleotide 2966 and 35079 that may be deleted for E1 region (nt 474 to nt 3085 of SEQ ID NO: 1), E3 region (nt 25973 to nt 28596 of SEQ ID NO: 1), and/or E4 region (nt 31852 to nt 34752 of SEQ ID NO: 1) sequences.

Generation of Adapter Plasmid sAdApt4287.Empty

Plasmids that were used for harboring the sAd4287 sequences were prepared. Primers (sAd4287.1A.fwd and sAd4287.1A.rev, SEQ ID NOs: 52 and 53, respectively) were designed to obtain the first 460 nucleotides of sAd4287 by PCR, with PacI and SalI at the 5'- and 3'-end of the resulting PCR product, respectively. A second set of primers (sAd4287.1B.fwd and sAd4287.1B.rev, SEQ ID NOs: 54 and 55, respectively) was designed to obtain pIX (nt 2966) through 2.5 kb upstream (nt 5466), with AflII and PacI designed on the 5'- and 3'-end, respectively. A third set of PCR primers (sAd4287.TGC.fwd and sAd4287.TGC.rev, SEQ ID NOs: 56 and 57, respectively) were designed to obtain the transgene cassette from AdApter plasmid pAdApt26.Empty (Abbink, et al. *J. Virol.* 81(9): 4654-4663, 2007) from start of the CMV to end of the polyA with a SalI and AflII site designed on the 5'- and 3'-end, respectively. These three PCR fragments were ligated together with the pAdApt bacterial backbone obtained by PacI digestion from pAdApt26 in a 4-point ligation, resulting in sAdApt4287.Empty (SEQ ID NO: 34). A schematic map of sAdApt4287.Empty is depicted in FIG. 2. This adapter plasmid contains left-end sAd4287 sequences (1-460 and 2966-5466) with the E1 region replaced by an expression/transgene cassette including the CMV promoter.

Generation of pBr/sAd4287.pIX-pV

To enable cloning of an sAd4287 HpaI-HindIII restriction fragment, which encompasses the 52K protein of sAd4287, a new plasmid was generated by inserting two PCR fragments in a pBr backbone. For this, primers (SEQ ID NOs: 58 and 59) were designed to obtain a PCR fragment from start of pIX over the HpaI site in wild-type sAd4287 (nt 2966 to nt 8311) with a PacI and a SbfI designed on the 5'- and 3'-end, respectively. A second PCR fragment was generated from HindIII (nt 12761) to the end of PCR (nt 16679), with a SbfI and PacI site designed on the 5'- and 3'-end, respectively. The second PCR fragment was generated using a second primer set (SEQ ID NOs: 60 and 61). These PCR fragments were ligated (PacI-SbfI-PacI) into a pBr backbone, obtained from pBr/Ad26.SfiI (see, e.g., WO 2007/104792) by PacI digestion, resulting in the pBr/sAd4287.pIX-pV shuttle vector. Finally, the sAd4287 HpaI-HindIII restriction fragment obtained from the sAd4287 wild-type genome was ligated into the pBr/sAd4287.pIX-pV shuttle vector digested with HpaI-HindIII, resulting in the complete pBr/sAd4287.pIX-pV plasmid (SEQ ID NO: 35). A schematic map of pBr/sAd4287.pIX-pV is depicted in FIG. 3.

Generation of pBr/sAd4287.PsiI-rITR pBr/sAd4287.PsiI-rITR contains sAd4287 sequences from the PsiI site at nucleotide 14053 to the end of the right inverted terminal repeat (rITR). To enable cloning of this sequence first a new plasmid was generated by inserting two PCR fragments in a pBr backbone. The two PCR fragments were generated such that they could be ligated together and cloned into a pBr-based backbone using the PacI restriction site. Primers were designed to obtain a PCR fragment from before PsiI site at nt 14053 to ~4 kb upstream over the NdeI site (nt 18186) at nt 18234, with a PacI and a SbfI site designed on the 5'- and 3'-end, respectively. A second set of primers was designed to obtain a PCR fragment from before PmeI site at nt30022 until the end of rITR at nt35079, with an SbfI and PacI site designed at the 5'- and 3'-end, respectively. The sequences of the primers used to generate these two PCR fragments is set forth in SEQ ID NOs: 62-65. These PCR fragments were ligated into a pBr backbone obtained from pBr/Ad26.SfiI by PacI-SbfI digestion, resulting in the pBr/sAd4287.PsiI-rITR shuttle vector. Finally, the NotI-AsiSI fragment (nt 16639-nt 34032) was obtained from the wild-type sAd4287 genome and ligated into the pBr/sAd4287.PsiI.rITR shuttle vector, resulting in the complete pBr/sAd4287.PsiI-rITR plasmid (SEQ ID NO: 36). A schematic map of pBr/sAd4287.PsiI-rITR is depicted in FIG. 4.

Generation of pBr/sAd4287.PsiI-rITR.dE3 pBr/sAd4287.PsiI-rITR was modified to delete part of the E3 region, which spans approximately nt 25973 to nt 28596 of sAd4287, and which is not required for replication and packaging of the adenoviral particle. To create the pBr/sAd4287.PsiI-rITR.dE3, two PCR fragments were generated. The first PCR fragment contained the pVIII from AscI to 140 bp after the polyA of pVIII (nt 8291-11192). The forward primer (SEQ ID NO: 66) was directed against the ApaLI in 100K and the reverse primer (SEQ ID NO: 67) has a SpeI site designed in it. The second PCR contains the Fiber region starting 100 bp before the polyA of the E3 region until the unique XbaI restriction site in the Fiber-2 region (nt 13177-14824). The forward primer, directed 100 bp in front of the polyA of E3, will have a SpeI site designed in it (SEQ ID NO: 68). The reverse primer was directed to the XbaI site (SEQ ID NO: 69). These two PCR fragments were ligated into pBr/sAd4287.PsiI-rITR with a 3-point ligation, with AscI-SpeI-XbaI, to generate pBr/sAd4287.PsiI-rITR.dE3 (SEQ ID NO: 37). FIG. 5 depicts a schematic map of pBr/sAd4287.PsiI-rITR.dE3 as well as an overview of the cloning strategy set forth above to generate the E3-deleted plasmid.

Generation of pBr/sAd4287.PsiI-rITR.dE3.dE4 pBr/sAd4287.PsiI-rITR.dE3 was modified to delete part of the E4 region, which spans approximately nt 31852 to nt 34752 of sAd4287, and specifically E4orf1-E4orf4. The modified plasmid, pBr/sAd4287.PsiI-rITR.dE3.dE4 (SEQ ID NO: 38), resulted in an enlarged cloning capacity with a 1409 bp gain of space. To create the pBr/sAd4287.PsiI-rITR.dE3.dE4, two PCR products were generated. The first PCR fragment starts at the XbaI site until the start of E4orf6. The sequences of the forward and reverse primers used to generate this first PCR fragment are set forth in SEQ ID NOs: 72 and 73, respectively. The second PCR fragment starts directly in front of the E4orf1 until the NotI site. The sequences of the forward and reverse primers used to operate this second PCR fragment are set forth in SEQ ID NOs: 74 and 75, respectively. These PCR fragments have 30-bp overlaps with flanking regions at the XbaI and Not I site and a 15-bp overlap with each other (30 bp total). The PCR fragments were assembled into pBr/sAd4287.PsiI-rITR.dE3 digested with XbaI and NotI by Gibson Assembly (New England BioLabs), resulting in pBr/sAd4287.PsiI-rITR.dE3.dE4. FIG. 6 depicts a schematic map of pBr/sAd4287.PsiI-rITR.dE3.dE4 relative to pBr/sAd4287.PsiI-rITR.dE3.

Generation of sAdApt4287.E1btg.Empty

To clone the E1 region of sAd4287 (approximately nt 474 to nt 3085 of SEQ ID NO: 1) into sAdApt4257.Empty for the purposes of producing replication-competent sAd4287 (rcsAd4287), a PCR fragment was generated from the wild-type sAd4287 with the forward primer (SEQ ID NO: 70) starting ~30 bp before the NgoMIV site in the lITR region until ~10 bp after the polyA of the E1 region (nt 218 to nt 3137). The reverse primer (SEQ ID NO: 71) has a ~30 bp overlap with the start of the CMV promoter in the sAdApt4287.Empty and includes the SalI restriction site. This PCR fragment was cloned into sAdApt4257.Empty, digested with NgoMIV and SalI, with Gibson Assembly (New England BioLabs), resulting in sAdApt4287.E1btg.Empty (SEQ ID NO: 39). A schematic map of sAdApt4287.E1btg.Empty and the cloning strategy described above is depicted in FIG. 7.

Example 3. Sequence of Simian Adenovirus sAd4310 #13-1 (sAd4310A)

Figure 8:
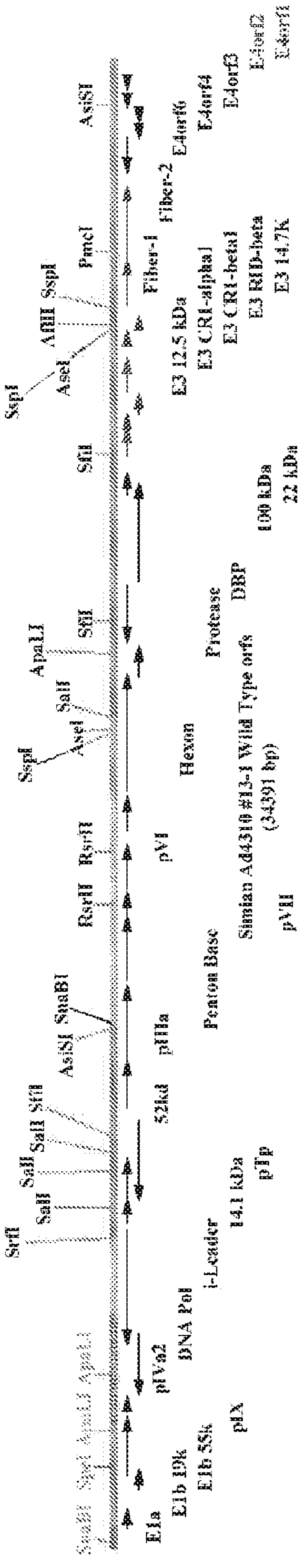
FIG. 8 is a schematic map of the genomic organization of sAd4310 #13-1 (sAd4310A).

The total genome sequence of simian adenovirus sAd4310 #13-1 (sAd4310A) was determined as described above for sAd4287. The obtained sequence of the sAd4310A genome (34391 nucleotides) is given as SEQ ID NO: 2. A schematic map of the genome structure of sAd4310A is depicted in FIG. 8. Using the full genomic sequence in an NCBI web-based BLAST search, the most closely related virus to sAd4310A was identified as simian adenovirus 1 (sAd1) ATCC VR-195 (query coverage: 97%; maximum identity: 98%). NCBI web-based BLAST searches were also performed to assess homology of three major capsid proteins of sAd4310A (fiber-1, fiber-2, and hexon proteins). The most closely related protein to sAd4310A fiber-1 was identified as sAd1 fiber-1 (query coverage: 100%; maximum identity: 99%). The most closely related protein to sAd4310A fiber-2 was identified as sAd1 fiber-2 (query coverage: 100%; maximum identity: 99%). The most closely related protein to sAd4310A hexon was identified as human Ad31 hexon (query coverage: 100%; maximum identity: 87%).

Example 4. Generation of Recombinant sAd4310A Viruses

Here, the construction of an sAd4310A plasmid-based system to generate recombinant sAd4310A vectors in a safe and efficient manner is described. The plasmid system consists of a first plasmid, referred to as an adapter plasmid, which contains sAd4310A nucleotides 1 to 461 including the left inverted terminal repeat (lITR) and packaging signal, an expression cassette and an sAd4310A fragment corresponding to nucleotides 2903 to 5410. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al. *J. Virol.* 81(9): 4654-4663, 2007), albeit now generated to comprise the sAd4310A-derived sequences instead of the Ad26-derived sequences. Furthermore, the system consists of other plasmids together constituting sAd4310A sequences between nucleotide 2903 and 34391 that may be deleted for E1 region (nt 474 to nt 3088 of SEQ ID NO: 2), E3 region (nt 25915 to nt 28496 of SEC) ID NO: 2), and/or E4 region (nt 31750 to nt 34048 of SEQ ID NO: 2) sequences.

Generation of Adapter Plasmid sAdApt4310A.Empty

Plasmids that were used for harboring the sAd4310A sequences were prepared. Primers (sAd4310A.1A.fwd and sAd4310A.1A.rev, SEQ ID NOs: 76 and 77, respectively) were designed to obtain the first 461 nucleotides of sAd4310A by PCR, with PacI and SalI at the 5'- and 3'-end of the resulting PCR product, respectively. A second set of primers (sAd4310A.1B.fwd and sAd4310A.1B.rev, SEQ ID NOs: 78 and 79, respectively) was designed to obtain pIX (nt 2903) through approximately 2.5 kb upstream (nt 5410), with AflII and PacI designed on the 5'- and 3'-end, respectively. A third set of PCR primers (sAd4310A.TGC.fwd and sAd4310A.TGC.rev, SEQ ID NOs: 80 and 81, respectively) were designed to obtain the transgene cassette from AdApter plasmid pAdApt26.Empty (Abbink, et al. *J. Virol.* 81(9): 4654-4663, 2007) from start of the CMV to end of the polyA with a SalI and AflII site designed on the 5'- and 3'-end, respectively. These three PCR fragments were ligated together with the pAdApt bacterial backbone obtained by PacI digestion from pAdApt26 in a 4-point ligation, resulting in sAdApt4310A.Empty (SEQ ID NO: 40). A schematic map of sAdApt4310A.Empty is depicted in FIG. 9. This adapter plasmid contains left-end sAd4310A sequences (1-451 and 2903-5410) with the E1 region replaced by an expression/transgene cassette including the CMV promoter.

Generation of pBr/sAd4310A.pIX-pV

To enable cloning of an sAd4310A SrfI-SnaBI restriction fragment, which encompasses the 52K protein of sAd4310A, a new plasmid was generated by inserting two PCR fragments in a pBr backbone. For this, primers (SEQ ID NOs: 82 and 83) were designed to obtain a PCR fragment from start of pIX over the SrfI site in wild-type sAd4310A (nt 2903 to nt 7224) with a PacI and a SbfI designed on the 5'- and 3'-end, respectively. A second PCR fragment was generated tram SnaBI (nt 12098) in pIIIa to pVI (nt 17365), with a SbfI and PacI site designed on the 5'- and 3'-end, respectively. The second PCR fragment was generated using a second primer set (SEQ ID NOs: 84 and 85). These PCR fragments were ligated (PacI-SbfI-PacI) into a pBr backbone, obtained from pBr/Ad26.SfiI (see, e.g., WO 2007/104792) by PacI digestion, resulting in the pBr/sAd4310A.pIX-pV shuttle vector. Finally, the sAd4310A SrfI-SnaBI restriction fragment obtained from the sAd4310A wild-type genome was ligated into the pBr/sAd4310A.pIX-pV shuttle vector digested with SrfI-SnaBI, resulting in the complete pBr/sAd4310A.pIX-pV plasmid (SEQ ID NO: 41). A schematic map of pBr/sAd4310A.pIX-pV is depicted in FIG. 10.

Generation of pBr/sAd4310A.RSrII-rITR pBr/sAd431 0A.RsrII-rITR contains sAd431 0A sequences from the RsrII site at nucleotide 14882 to the end of the right inverted terminal repeat (rITR) at nucleotide 34391. To enable cloning of this sequence first a new plasmid was generated by inserting two PCR fragments in a pBr backbone. The two PCR fragments were generated such that they could be ligated together and cloned into a pBr-based backbone using the Paci restriction site. Primers (sAd431 0A.3A.fwd and sAd431 0A.3A.rev, SEQ ID NOs: 86 and 87, respectively) were designed to obtain a PCR fragment from the RsrII site at nt 14882 to 4.5 kb upstream over the Sal I site (nt 19189) to nt 19224, with a Paci and a SbfI site designed on the 5' and 3'-end, respectively. A second set of primers (sAd431 0A.3B.fwd and sAd431 0A.3B.rev, SEQ ID NOs: 88 and 89, respectively) was designed to obtain a PCR fragment from before the PmeI site at nt 29829 until the end of the rITR at nt 34391, with an SbfI and Paci site designed at the 5'- and 3'-end, respectively. These PCR fragments were ligated into a TOPO® vector using the commercially available ZERO BLUNT® TOPO® PCR Cloning Kit (Invitrogen). The two PCR fragments were digested as PCR fragments or from the TOPO® clone with Paci and SbfI and subsequently ligated into a pBr backbone obtained from pBr/Ad26.SfiI digested with Paci. Finally, SalI-XbaI fragment (nt 19190-nt 30014) was obtained from the wild-type sAd431 0A genome and ligated into the pBr/sAd431 0A.RsrII.rITR shuttle vector, resulting in the complete pBr/sAd431 0A.RsrII-rITR plasmid (SEQ ID NO: 42). A schematic map of pBr/sAd431 0A.RsrII-rITR is depicted in FIG. 11.

Generation of pBr/sAd4310A.RsrII-rITR.dE3 pBr/sAd4310A.RsrII-rITR was modified to delete part of the E3 region, which spans approximately nt 25915 to nt 28496 of sAd4310A, and which is not required for replication and packaging of the adenoviral particle. To create the pBr/sAd4310A.RsrII-rITR.dE3 with Gibson Assembly, two PCR fragments were generated. The first PCR fragment (dE3AG) contained from approximately 50 bp before the SfiI site at nt 7644 to 140 bp after the polyA of pVIII. The forward primer and reverse primer have sequences set forth in SEQ ID NOs: 90 and 91, respectively, wherein the reverse primer was designed to have an approximately 25-bp overlap with the second PCR fragment. The second PCR fragment (dE3BG) starts at nt 14641 (approximately 100 bp before the polyA of the E3 region) until approximately 50 bp after the XbaI site at nt 16252. The forward primer and reverse primer for the second PCR have sequences set forth in SEQ ID NOs: 92 and 93, respectively, wherein the forward primer was designed to have an approximately 25-bp overlap with the first PCR fragment. The two PCR fragments were assembled with Gibson Assembly, with the pBr/sAd4310A.RsrII.rITR digested with SfiI and XbaI. The resulting plasmid, pBr/sAd4310A.RsrII.rITR.dE3 (SEQ ID NO: 43), is depicted in FIG. 12, along with the parental plasmid, pDr/sAd4310A.RsrII.rITR.

Generation of pBr/sAd4310A.RsrII-rITR.dE3.dE4 pBr/sAd4310A.RsrII-rITR.dE3 was modified to delete part of the E4 region, which spans approximately nt 31750 to nt 34048 of sAd4310A, and specifically E4orf1-E4orf4. The modified plasmid, pBr/sAd4310A.RsrII-rITR.CE3.dE4 (SEQ ID NO: 44), resulted in an enlarged cloning capacity with a 1394 bp pain of space. To create the pBr/sAd4310A.RsrII-rITR.dE3.dE4 plasmid, two PCR products were generated. The first PCR fragment starts at the XbaI site until the start of E4orf6. The sequences of the forward and reverse primers used to generate this first PCR fragment are set forth in SEQ ID NOs: 96 and 97, respectively. The second PCR fragment starts directly in front of the E4orf1 until the NotI site. The sequences of the forward and reverse primers used to generate this second PCR fragment are set forth in SEQ ID NOs: 98 and 99, respectively. These PCR fragments have 30-bp overlaps with flanking regions at the XbaI and Not I site and a 15-bp overlap with each other (30 bp total). The PCR fragments were assembled by Gibson Assembly (New England BioLabs) into pBr/sAd4310A.RsrII-rITR.dE3 digested with XbaI and NotI, resulting in pBr/sAd4310A.RsrII-rITR.dE3.dE4 (SEQ ID NO: 44). FIG. 13 depicts a schematic map of pBr/sAd4310A.RsrII-rITR.dE3.dE4 relative to the parental plasmid pBr/sAd4310A.RsrII-rITR.dE3.

Generation of sAdApt4310A.E1btg.Empty

To clone the E1 region of sAd4310A (nt 474 to nt 3088 of SEQ ID NO: 2) into sAdApt4310A.Empty for the purposes of producing replication-competent sAd4310A (rcsAd4310A), a PCR fragment was generated from the wild-type sAd4310A with the forward primer (SEQ ID NO: 94) starting ~40 bp before the BstZ17I site in the lITR region ~10 bp after the polyA of the E1 region (nt 150 to nt 3131). The reverse primer (SEQ ID NO: 95) has a ~30 bp overlap with the start of the CMV promoter in the sAdApt4310A.Empty and includes the SalI restriction site. This PCR fragment was cloned into sAdApt4310A.Empty, digested with BstZ17I and SalI, with Gibson Assembly (New England BioLabs), resulting in sAdApt4310A.E1btg.Empty (SEQ ID NO: 45). A schematic map of sAdApt4310A.E1btg.Empty and the cloning strategy described above is depicted in FIG. 14.

Example 5. Sequence of Simian Adenovirus sAd4312

Figure 15:
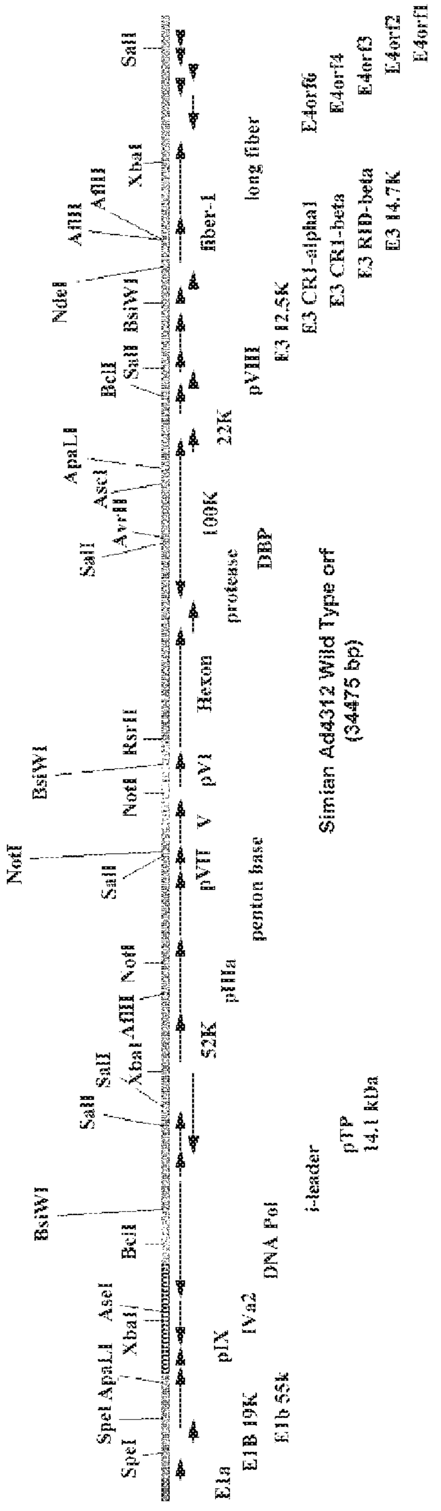
FIG. 15 is a schematic map of the genomic organization of sAd4312.

The total genome sequence of simian adenovirus sAd4312 was determined as described above for sAd4287 and sAd4310A. The obtained sequence of the sAd4312 genome (34475 nucleotides) is given as SEQ ID NO: 3. A schematic map of the genome structure of sAd4312 is depicted in FIG. 15. Using the full genomic sequence in an NCBI web-based BLAST search, the most closely related virus to sAd4312 was identified as simian adenovirus 1 (sAd1) ATCC VR-195 (query coverage: 90%; maximum identity: 98%). NCBI web-based BLAST searches were also performed to assess homology of three major capsid proteins of sAd4312 (fiber-1, fiber-2, and hexon proteins). The most closely related protein to sAd4312 fiber-1 was identified as human Ad52 fiber-1 (query coverage: 100%; maximum identity: 99%). The most closely related protein to sAd4312 fiber-2 was identified as sAd7 lone fiber (query coverage: 99%; maximum identity: 73%). The most closely related protein to sAd4312 hexon was identified as human Ad40 hexon (query coverage: 100%; maximum identity: 89%).

Example 6. Generation of Recombinant sAd4312 Viruses

Here, the construction of an sAd4312 plasmid-based system to generate recombinant sAd4312 vectors in a safe and efficient manner is described. The plasmid system consists of a first plasmid, referred to as an adapter plasmid, which contains sAd4312 nucleotides 1 to 472 including the left inverted terminal repeat (lITR) and packaging signal, an expression cassette and an sAd4312 fragment corresponding to nucleotides 2939 to 5510. The expression cassette comprises the human CMV promoter, a multiple cloning site (MCS), and the SV40 polyadenylation signal (polyA) as previously described (see, e.g., WO 00/70071). The adapter plasmid is based on pAdApt26.Empty (Abbink, et al. *J. Virol.* 81(9): 4654-4663, 2007), albeit now generated to comprise the sAd4312-derived sequences instead of the Ad26-derived sequences. Furthermore, the system consists of other plasmids together constituting sAd4312 sequences between nucleotide 2939 and 344475 that may be deleted for E1 region (nt 487 to nt 3100 of SEQ ID NO: 3), E3 region (nt 25947 to nt 28561 SEQ ID NO: 3), and/or E4 region (nt 31818 to nt 34116 SEQ ID NO: 3) sequences.

Generation of Adapter Plasmid sAdApt4312.Empty

Plasmids that were used for harboring the sAd4312 sequences were prepared. Primers (sAd4312.1A.fwd and sAd4312.1A.rev, SEQ ID NOs: 100 and 101, respectively) were designed to obtain the first 472 nucleotides of sAd4312 by PCR, with PacI and SalI at the 5'- and 3'-end of the resulting PCR product, respectively. A second set of primers (sAd4312.1B.fwd and sAd4312.1B.rev, SEQ ID NOs: 102 and 103, respectively) was designed to obtain pIX (nt 2939) through approximately 2.5 kb upstream (nt 5510), with AflII and PacI designed on the 5- and 3'-end, respectively. A third set of PCR primers (sAd4312.TGC.fwd and sAd4312.TGC.rev, SEQ ID NOs: 104 and 105, respectively) were designed to obtain the transgene cassette from AdApter plasmid pAdApt26.Empty (Abbink, et al. *J. Virol.* 81(9): 4654-4663, 2007) from start of the PCR to end of the polyA with a SalI and AflII site designed on the 5- and 3'-end, respectively. These three PCR fragments were ligated together with the pAdApt bacterial backbone obtained by PacI digestion from pAdApt26 in a 4-point ligation, resulting in sAdApt4312.Empty (SEQ ID NO: 46). A schematic map of sAdApt4312.Empty is depicted in FIG. 16. This adapter plasmid contains left-end sAd4312 sequences (1-472 and 2939-5510) with the E1 region replaced by an expression/transgene cassette including the CMV promoter.

Generation of pBr/sAd4312.pIX-pV

To enable cloning of an sAd4312 BsiWI-BsiWI restriction fragment, a new plasmid was generated by inserting two PCR fragments in a pBr backbone. For this, primers (SEQ ID NOs: 106 and 107) were designed to obtain a PCR fragment from start of pIX over the BsiWI site in wild-type sAd4312 (nt 2939 to nt 6791) with a Paci and a NdeI designed on the 5'- and 3'-end, respectively. A second PCR fragment was generated from pV (nt 15564) to the RsrII site at the end of pVI (nt 17698), with a NdeI and Paci site designed on the 5'- and 3'-end, respectively. The second PCR fragment was generated using a second primer set (SEQ ID NOs: 108 and 109). These PCR fragments were cloned into a TOPO® vector using the commercially available ZERO BLUNT® TOPO® PCR Cloning Kit (Invitrogen), resulting in the pBr/sAd4312.pIX-pV shuttle vector. Finally, the sAd4312 BsiWI-BsiWI restriction fragment obtained from the sAd4312 wild-type genome was ligated into the pBr/sAd4312.pIX-pV shuttle vector digested with BsiWI and screened for orientation, resulting in the complete pBr/sAd4312.pIX-pV plasmid (SEQ ID NO: 47). A schematic map of pBr/sAd4312.pIX-pV is depicted in FIG. 17.

Generation of pBr/sAd4312.pV-rITR pBr/sAd4312.pV-rITR contains sAd4312 sequences from the start of pV at nucleotide 15215 to the end of the right inverted terminal repeat (rITR) at nucleotide 34475. To enable cloning of this sequence first a new plasmid was generated by inserting two PCR fragments in a pBr backbone. The two PCR fragments were generated such that they could be ligated together and cloned into a pBr-based backbone using the Paci restriction site. Primers (sAd4312.3A.fwd and sAd4312.3A.rev, SEQ ID NOs: 110 and 111, respectively) were designed to obtain a PCR fragment from the start of pV at nt 15215 to 2.5 kb upstream over the RsrII site to nt 17698, with a Paci and a SbfI site designed on the 5'- and 3'end, respectively. A second set of primers (sAd4312.3B.fwd and sAd4312.3B.rev, SEQ ID NOs: 112 and 113, respectively) was designed to obtain a PCR fragment from before the XbaI site at nt 31015 until the end of the rITR at nt 34475, with an SbfI and Paci site designed at the 5'- and 3'-end, respectively. These PCR fragments were ligated into a TOPO® vector using the commercially available ZERO BLUNT® TOPO® PCR Cloning Kit (Invitrogen). The two PCR fragments were digested from the TOPO® clones with SbfI and Paci and subsequently ligated into a pBr backbone obtained from pBr/Ad26.SfiI digested with Paci, resulting in the pBr/sAd4312.pV-rITR shuttle vector. Finally, the NotI-XbaI fragment (nt 16412-nt 31083) was obtained from the wild-type sAd4312 genome and ligated into the pBr/sAd4312.pV-rITR shuttle vector, resulting in the complete pBr/sAd4312.pV-rITR plasmid (SEQ ID NO: 48). A schematic 1 o map of pBr/sAd4312.pV-rITR is depicted in FIG. 18.

Generation of pBr/sAd4312.pV-rITR.dE3 pBr/sAd4312.pV-rITR was modified to delete part of the E3 region, which spans approximately nt 487 to nt 3100 of sAd4312, and which is not required for replication and packaging of the adenoviral particle. To create the pBr/sAd4312.pV-rITR.dE3, two PCR fragments were generated. The first PCR fragment contains the pVIII from AscI to 140 bp after the polyA of pVIII (nt 9859 to nt 12302). The forward primer (sAd4312.dE3A.fwd, SEQ ID NO: 114) is directed against the AscI in 100K, and the reverse primer (sAd4312.dE3A.rev, SEQ ID NO: 115) has a SpeI site designed in it.

The second PCR contains the fiber region starting 100 bp before the polyA of the E3 region until the unique restriction site, XbaI, in the fiber-2 region (nt 14378 to nt 17020). The forward primer (sAd4312.dE3B.fwd, SEQ ID NO: 116), directed 100 bp in front of the polyA of E3, has a SpeI site designed in it. The reverse primer (sAd4312.dE3B.fwd, SEQ ID NO: 117) is directed to the XbaI site. These two PCR fragments were ligated into pBr/sAd4312.pV-rITR with a 3-point ligation, with AscI-SpeI-XbaI. The resulting plasmid, pBr/sAd4312.pV-rITR.dE3 (SEQ ID NO: 49), is depicted in FIG. 19, along with the parental plasmid, pBr/sAd4312.pV-rITR.

Generation of pBr/sAd4312.pV-rITR.dE3.dE4 pBr/sAd4312/pV-rITR.dE3 was modified to delete part of the E4 region, which spans approximately nt 25947 to nt 28561 of sAd4312, and specifically E4orf1-E4orf4. The modified plasmid, pBr/sAd4312.pV-rITR.dE3.dE4 (SEQ ID NO: 50), resulted in an enlarged cloning capacity with a 1393 bp gain of space. To create the pBr/sAd4312.pV-rITR.dE3.dE4 plasmid, two PCR products were generated. The first PCR fragment starts at the NdeI site until the start of E4orf6. The sequences of the forward and reverse primers used to generate this first PCR fragment are set forth in SEQ ID NOs: 120 and 121, respectively. The second PCR fragment starts directly in front of the E4orf1 until the NotI site. The sequences of the forward and reverse primers used to generate this second PCR fragment are set forth in SEQ ID NOs: 122 and 123, respectively. These PCR fragments have 30-bp overlaps with flanking regions at the NdeI and NotI site and a 15-bp overlap with each other (30 bp total). The PCR fragments were assembled into pBr/sAd4312.pV-rITR.dE3 digested with XbaI and NotI, resulting in pBr/sAd4312.pV-rITR.dE3.dE4 (SEQ ID NO: 50). FIG. 20 depicts a schematic map of pBr/sAd4312.pV-rITR.dE3.dE4 and that of the parental plasmid, pBr/sAd4312.pV-rITR.dE3.

Generation of sAdApt4312.E1btg.Empty

To clone the E1 region of sAd4312 (nt 487 to 3100 SEQ ID NO: 3) into sAdApt4312.Empty for the purposes of producing replication-competent sAd4312 (rcsAd4312), a PCR fragment was generated from the wild-type sAd4312 which included the complete E1 region of sAd4312. The forward primer (SEQ ID NO: 118) is directed to ~40 bp in front of the first BstZ17I site in the lITR region. The reverse primer (SEQ ID NO: 119) has a ~30 bp overlap with the start of the CMV promoter in the sAdApt4312.Empty. The generated PCR fragment was cloned into sAdApt4312.Empty, digested with BstZ17I and SalI, with Gibson Assembly (New England BioLabs), resulting in sAdApt4312.E1btg.Empty (SEQ ID NO: 51). In this cloning step, only the AdApt plasmid was digested; the PCR product was not digested with restriction enzymes. A schematic map of sAdApt4312.E1btg.Empty and the cloning strategy described above is depicted in FIG. 21.

Figures 22A, 22B, 22C:
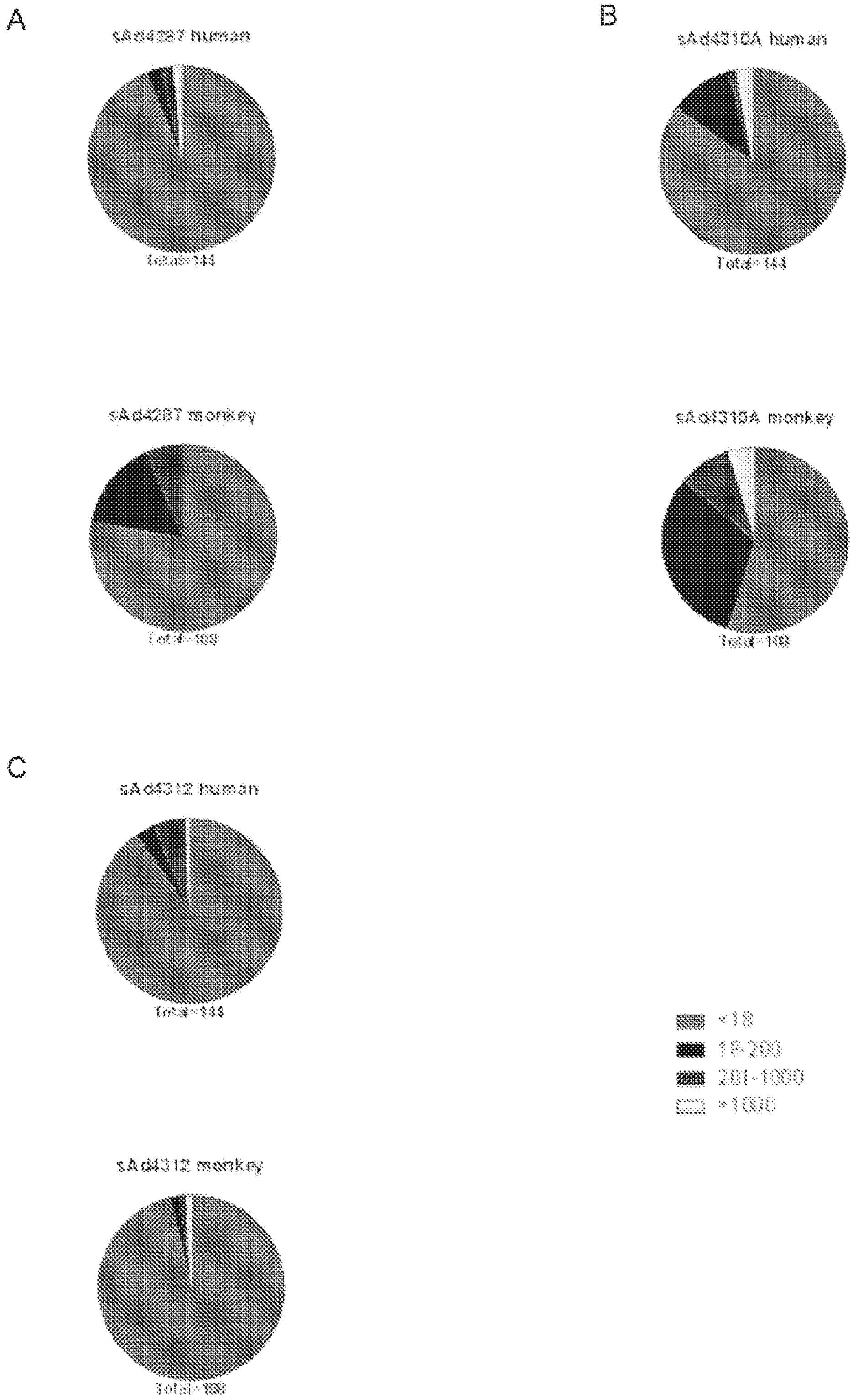
FIG. 22A is a pie chart showing the relative sAd4287-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high, and >1000=high), as assessed by luciferase-based virus neutralization assays, is shown.
FIG. 22B is a pie chart showing the relative sAd4310A-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high and >1000=high), as assessed by luciferase-based virus neutralization assays, is shown.
FIG. 22C is a pie chart showing the relative sAd4312-specific neutralizing antibody (NAb) responses in sub-Saharan humans (n=144; top) and rhesus monkeys (n=108; bottom). The relative number of individuals that fall within each of the four NAb titer categories (<18=negative, 18-200=low, 201-1000=high, and >1000=high), as assessed by luciferase-based virus neutralization assays, is shown.

Example 7. Seroprevalence of sAd4287, sAd4310A, and sAd4312 in sub-Saharan Humans and Rhesus Monkeys We next evaluated sAd4287, sAd4310A, and sAd4312 titers in 144 sub-Saharan humans and 108 rhesus monkeys (FIGS. 22A-22C). Adenovirus-specific neutralizing antibody (NAb) titers were determined by luciferase-based virus neutralization assays as previously described (Sprangers et al. *J. Clin. Microbiol.* 41: 5046-5052, 2003; Barouch et al. *Vaccine.* 29: 5203-5209, 2011). Titers of <18 are regarded as negative by this assay, 18-200 is low, 201-1000 is high, and >1000 is considered very high. It is suspected that titers >200 will likely be suppressive, according to data known in the art. Representative pie charts summarizing the relative number of individuals (humans or monkeys) that fall within each of the four titer categories are depicted for each of the three adenoviruses tested (see FIGS. 22A-22C).

The results of the seroprevalence studies clearly indicate that the majority of both sub-Saharan humans and rhesus monkeys tested exhibited negative (<18) or low (18-200) NAb titers for each of the three adenoviruses tested (sAd4287, sAd4310A, and sAd4312). These seroprevalence studies indicate that the sAd4287, sAd4310A, and sAd4312 vectors have extremely and surprisingly low seroprevalence in human populations (e.g., sub-Saharan human populations) and monkey populations (e.g., rhesus monkey populations). The extremely low seroprevalence of the sAd vectors of the invention are in marked contrast to the relatively high seroprevalence of Ad5 in human populations. Accordingly, these studies indicate a distinct advantage of using a vaccine comprising all or a portion of a recombinant sAd4287, sAd4310A, and sAd4312, as the neutralizing activities in the majority of both humans and monkeys alike are unlikely to hamper the efficacy of the vaccine.

Example 8. Determination of Cellular Responses to Recombinant Adenoviruses of the Invention in Mice We next studied whether recombinant replication-defective adenoviruses based on simian adenoviruses of the invention (e.g., sAd4287 or sAd4310A) were able to elicit a significant immune response in vivo. For this, vectors were generated that all contained the SIVmac239 Gag insert from Simian Immunodeficiency Virus (SIV). Recombinant DNA, such as the required adapter plasmids, and the recombinant viruses were generated generally as described (Lemckert et al. *J. Virol.* 79:9694-9701, 2005).

Figure 23A:
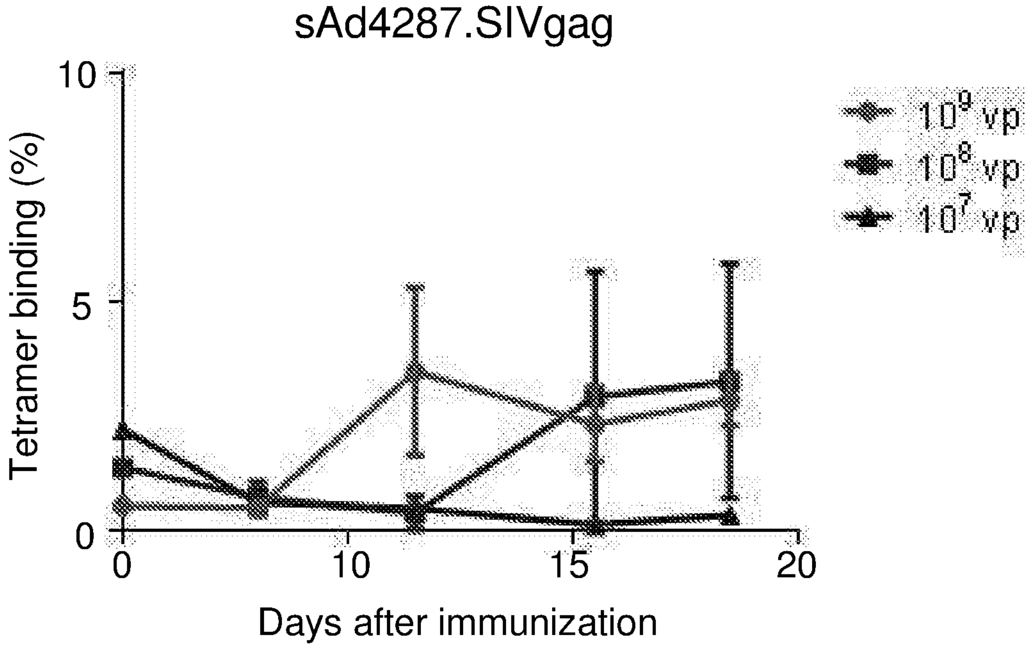
FIG. 23A is a graph showing the cellular responses induced by sAd4287 vectors bearing SIVmac239 Gag in C57BL/6 mice immunized with $10^7$, $10^8$, and $10^9$ viral particles (vp) of the vector, as assessed by measuring the $CD8^+$ T cell response via $D^b$/AL11 tetramer binding assays at days 0, 7, 14, 21, and 28 post-immunization.
Figure 23B:
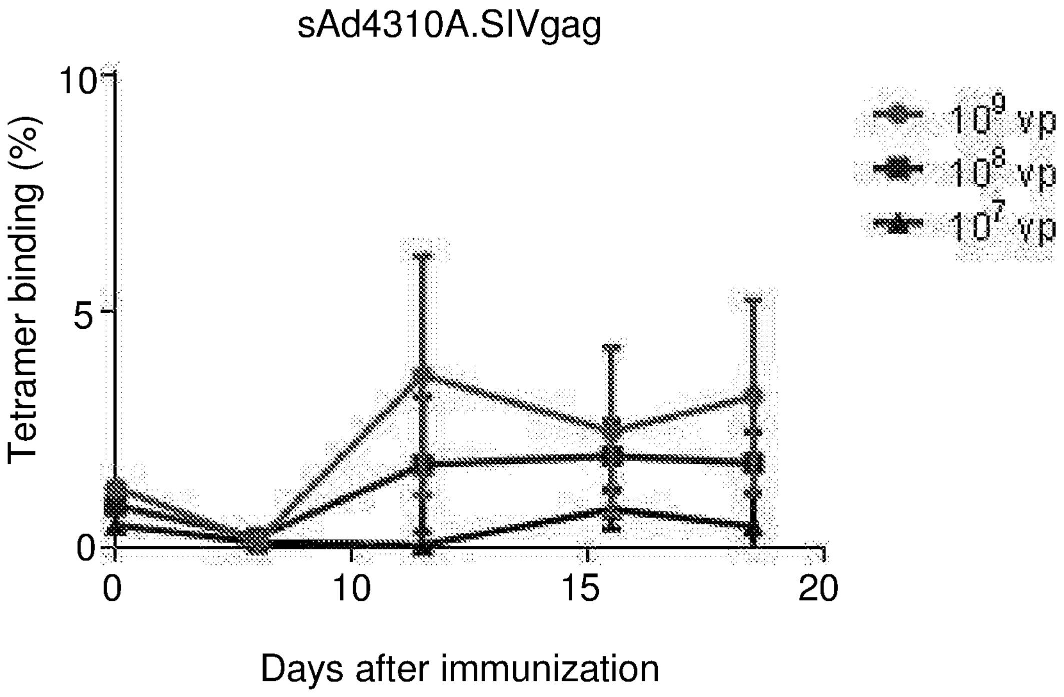
FIG. 23B is a graph showing the cellular responses induced by sAd4310A vectors bearing SIVmac239 Gag in C57BL/6 mice immunized with $10^7$, $10^8$, and $10^9$ viral particles (vp) of the vector, as assessed by measuring the $CD8^+$ T cell response via $D^b$/AL11 tetramer binding assays at days 0, 7, 14, 21, and 28 post-immunization.

C57BL/6 mice were injected intramuscularly with different amounts of viral vectors: $10^7$, $10^8$, and $10^9$ viral particles (vp). All vaccination procedures and cellular immune responses were performed and measured by assessing the $CD8^+$ T cell response via $D^b$/AL11 tetramer binding assays as previously described (Barouch et al. *J. Immunol.* 172: 6290-6297, 2004). Tetrameric H-2Db complexes folded around the immunodominant SIV Gag AL11 epitope (AAVKNWMTQTL; SEQ ID NO: 124) (Liu et al., J. Viral. 80: 11991-11997, 2006) were prepared and SIV Gag-specific $CD8^+$ T lymphocyte responses were measured on days 0, 7, 14, 21, and 28 post-immunization. For immunogenicity experiments with sAd4287 and sAd4310A, the results are shown in FIGS. 23A and 23B. From these results, it can be concluded that the adenoviral vectors of the invention exhibit potent immunogenicity in mice, especially with $10^8$ or $10^9$ vp doses.

Figures 24A, 24B, 24C:
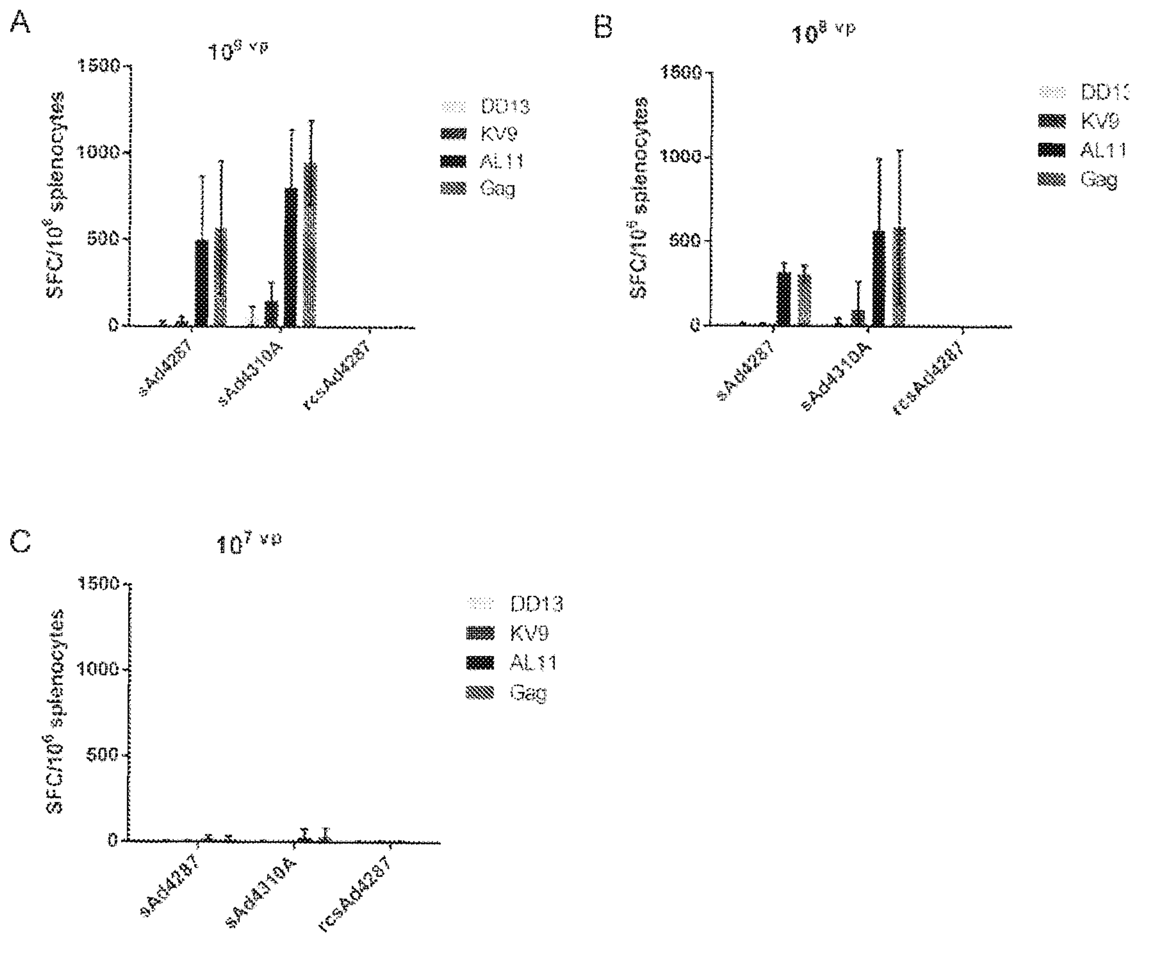
FIG. 24A is a graph showing the cellular responses induced by sAd4287, sAd4310A, and replication-competent sAd4287 (rcsAd4287) at $10^9$ vp as determined by IFN-γ ELISPOT assays using splenocytes from C57BL/6 mice on day 28 post-immunization. IFN-γ ELISPOT responses were measured to overlapping Gag peptides (Gag), the dominant $CD8^+$ T cell epitope AL11, the sub-dominant $CD8^+$ epitope KV9, and the $CD4^+$ T cell epitope DD13.
FIG. 24B is a graph showing the cellular responses induced by sAd4287, sAd4310A, and rcsAd4287 at $10^8$ vp as determined by IFN-γ ELISPOT assays using splenocytes from C57BL/6 mice on day 28 post-immunization. IFN-γ ELISPOT responses were measured to Gag, the dominant $CD8^+$ T cell epitope AL11, the sub-dominant $CD8^+$ T epitope KV9, and the $CD4^+$ T cell epitope DD13.
FIG. 24C is a graph showing the cellular responses induced by sAd4287, sAd4310A, and rcsAd4287 at $10^7$ vp as determined by IFN-γ ELISPOT assays using splenocytes from C57BL/6 mice on day 28 post-immunization. IFN-γ ELISPOT responses were measured to Gag, the dominant $CD8^+$ T cell epitope AL11, the sub-dominant $CD8^+$ T epitope KV9, and the $CD4^+$ T cell epitope DD13.

To evaluate functional responses, splenocytes from day 28 were utilized in IFN-γ ELISPOT assays. IFN-γ ELISPOT responses were measured to overlapping Gag peptides (Gag), the dominant CD8+ T cell epitope AL11 (AAVKNWMTQTL; SEQ ID NO: 124), the sub-dominant $CD8^+$ T epitope KV9 (KSLYNTVCV; SEQ ID NO: 125), and the CO4+ T cell epitope DD13 (DRFYKSLRAEQTD; SEQ ID NO: 126) (Liu et al., J. Virol. 80: 11991-11997, 2006) at $10^7$, $10^8$, and $10^9$ vp of viral vectors (sAd4287, sAd431 0A, and rcsAd4287). As depicted in FIGS. 24A-24C, the IFN-γ ELISPOT responses increased with increasing amounts of vp, and both Gag and AL11 responses were elevated relative to the responses to KV9 or DD13 epitopes. In addition, these functional responses were elicited only when replication-defective adenoviruses of the invention were used (e.g., sAd4287 and sAd4310A), but not when replication-competent adenoviruses of the invention were used (e.g., rcsAd4287). Collectively, the studies of cellular responses to the recombinant adenoviral vectors of the invention clearly indicate potent immunogenicity in mice.

The combination of low baseline anti-vector immunity (low seroprevalence), potent immunogenicity, and novel biology suggests that the novel adenoviral vectors of the invention can be useful as novel vaccine candidates against human or veterinary pathogens, including, but not limited to, HIV, SIV, cancer, malaria, and tuberculosis, in addition to utility in gene therapy and/or diagnostics.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

What is claimed is:

1. A recombinant adenovirus comprising a nucleotide sequence having at least 90% sequence identity over the entire sequence of any one of SEQ ID NOs: 10 and 12, or a complementary sequence to a nucleotide sequence having at least 90% sequence identity over the entire sequence of any one of SEQ ID NOs: 10 and 12;

wherein said recombinant adenovirus comprises a deletion in or of an E1 region, an E3 region, and/or an E4 region, said deletion rendering said recombinant adenovirus a replication-defective virus.

2. The recombinant adenovirus of claim 1, wherein said nucleotide sequence further comprises all or a portion of any one of SEQ ID NOs: 4, 6, 7, 9, 13, 15, 16, and 18, or a complementary sequence to all or a portion of any one of SEQ ID NOs: 4, 6, 7, 9, 13, 15, 16, and 18.

3. The recombinant adenovirus of claim 1, further comprising a nucleotide sequence having at least 90% sequence identity to the sequence of any one of SEQ ID NOs: 1 and 3 or a complementary sequence to a nucleotide sequence having at least 90% sequence identity over the entire sequence of any one of SEQ ID NOs: 1 and 3.

4. The recombinant adenovirus of claim 2, wherein said nucleotide sequence comprises the nucleotide sequence of any one of SEQ ID NOs: 34-39 and 46-51.

5. The recombinant adenovirus of claim 1, further comprising a heterologous nucleotide sequence encoding an antigenic or therapeutic gene product of interest, or fragment thereof, wherein said antigenic gene product, or fragment thereof, comprises a bacterial, viral, parasitic, or fungal protein, or fragment thereof.

6. The recombinant adenovirus of claim 5, wherein:

(i) said bacterial protein, or fragment thereof, is from *Mycobacterium tuberculosis, Mycobacterium bovis, Mycobacterium africanum, Mycobacterium microti, Mycobacterium leprae, Pseudomonas aeruginosa, Salmonella typhimurium, Escherichia coli, Klebsiella pneumoniae, Streptococcus pneumoniae, Staphylococcus aureus, Francisella tularensis, Brucella, Burkholderia mallei, Yersinia pestis, Corynebacterium diphtheria, Neisseria meningitidis, Bordetella pertussis, Clostridium tetani*, or *Bacillus anthracis;*

(ii) said parasitic protein, or fragment thereof, is from *Toxoplasma gondii, Plasmodium falciparum, Plasmodium vivax, Plasmodium ovale, Plasmodium malariae, Trypanosoma* spp., or *Legionella* spp; or (iii) said fungal protein, or fragment thereof, is from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus.*

7. The recombinant adenovirus of claim 5, wherein said viral protein, or fragment thereof, is from a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae, and Reoviridae, or said viral protein, or fragment thereof, is from human immunodeficiency virus (HIV), human papillomavirus (HPV), hepatitis A virus (Hep A), hepatitis B virus (HBV), hepatitis C virus (HCV), Variola major, Variola minor, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, Zika virus, or Marburg virus.

8. The recombinant adenovirus of claim 7, wherein said viral protein, or fragment thereof, from HIV is Gag, Pol, Env, Nef, Tat, Rev, Vif, Vpr, or Vpu.

9. A method of treating a subject having a disease, said method comprising administering the recombinant adenovirus of claim 5 to said subject.

10. The method of claim 9, wherein said recombinant adenovirus comprises an antigenic gene product, or fragment thereof, that promotes an immune response in said subject against an infective agent, wherein said infective agent is a bacterium, a virus, a parasite, or a fungus.

11. The method of claim 9, wherein:

(a) said subject is human;

(b) said adenovirus is administered intramuscularly; and/or (c) said adenovirus is administered as a pharmaceutical composition comprising a pharmaceutically acceptable carrier.

12. The method of claim 11, wherein:

(i) said subject is administered at least one dose of said pharmaceutical composition;

(ii) said subject is administered at least two doses of said pharmaceutical composition;

(iii) said pharmaceutical composition is administered to said subject as a prime boost.

13. A method of producing a recombinant adenovirus comprising transfecting a cell with: (a) an isolated polynucleotide comprising a nucleotide sequence having at least 90% sequence identity over the entire sequence of any one of SEQ ID NOs: 10 and 12, or a complementary sequence to a nucleotide sequence having at least 90% sequence identity over the entire sequence of any one of SEQ ID NOs: 10 and 12 or (b) a recombinant vector comprising said polynucleotide; culturing said cell in a suitable medium to allow replication of said polynucleotide or vector in said cell; and harvesting produced recombinant adenovirus from said medium and/or said cell.

14. The method of claim 13, wherein said cell is a bacterial, plant, or mammalian cell, wherein optionally said mammalian cell is a PER.55K cell or a Chinese hamster ovary (CHO) cell.

15. The recombinant adenovirus of claim 5, wherein the viral gene product is an envelope glycoprotein or fragment thereof.

16. A method of inducing an immune response against a flavivirus in a subject comprising administering the recombinant adenovirus of claim 5 to said subject, wherein the antigenic gene product, or fragment thereof, is a viral gene product from the flavivirus.

17. The method of claim 16, wherein the viral gene product is an envelope glycoprotein or fragment thereof.

18. The method of claim 16, wherein the subject is a human.

19. The method of claim 16, wherein the adenovirus is administered intramuscularly.

20. The method of claim 16, wherein the adenovirus is administered as a pharmaceutical composition comprising a pharmaceutically acceptable carrier.

21. The method of claim 20, wherein the subject is administered at least one or two doses of the pharmaceutical composition, optionally wherein the pharmaceutical composition is administered to the subject as a prime boost.

22. A method of inducing an immune response against a retrovirus in a subject comprising administering the recombinant adenovirus of claim 5 to the subject, wherein the antigenic gene product, or fragment thereof, is a viral gene product from the retrovirus.

23. The method of claim 22, wherein the retrovirus is human immunodeficiency virus (HIV).

24. The method of claim 22, wherein the subject is a human.

25. The method of claim 22, wherein the viral gene product is an envelope glycoprotein or fragment thereof.

26. The method of claim 25, wherein the viral gene product is a protein or fragment thereof from HIV.

27. The method of claim 22, wherein the recombinant adenovirus is administered intramuscularly.

28. The method of claim 22, wherein the recombinant adenovirus is administered as a pharmaceutical composition comprising a pharmaceutically acceptable carrier.

29. The method of claim 28, wherein the subject is administered at least one or two doses of the pharmaceutical composition, optionally wherein the pharmaceutical composition is administered to the subject as a prime boost.

* * * * *

SEQUENCE LISTING

<160> NUMBER OF SEQ ID NOS: 126

<210> SEQ ID NO 1
<211> LENGTH: 35079
<212> TYPE: DNA
<213> ORGANISM: Simian Adenovirus 4287 (sAd4287) Wild Type

<400> SEQUENCE: 1

```
catcatcaat aatatacctt attctggaaa cgtgccaata tgataatgag cggggaggag      60
cgaggcgggg ccggggtgac gtgcggtgac gcggggtgac gcggggtggc gcgagggcgg     120
ggcgggagtg gggaggcgct tagtttttac gtatgcggaa ggaggtttta taccggaagt     180
tgggtaattt gggcgtatat ttgtaagttt tgtgtaattt ggcgcgaaaa ccgggtaatg     240
aggaagttga ggttaatatg tactttttat gactgggcgg aatttctgct gatcagcagt     300
gaactttggg cgctgacggg gaggtttcgc tacgtggcag taccacgaga aggctcaaag     360
gtcccattta ttgtactcct cagcgttttc gctgggtatt taaacgctgt cagatcatca     420
agaggccact cttgagtgcc ggcgagtaga gttttctcct ccgcgctgcc gcgatgaggc     480
tggttcccga gatgtacggt gttttctgca gcgagacggc ccggaactca gatgagctgc     540
ttaatacaga tctgctggat gttcccaact cgcctgtggc ttcgcctccg tcgcttcatg     600
atcttttcga tgtggaagtg gatccaccgc aagatcccaa cgaggacgcg gtaaacagta     660
tgttccctga atgtctgttt gaggcggctg aggagggttc tcacagcagt gaagagagca     720
gacggggaga ggaactggac ttgaaatgct acgaggaatg tctgccttct agcgattctg     780
aaacggaaca gacaggggga gacggctgtg agtcggcaat gaaaaatgaa cttgtattag     840
actgtccaga acatcctggt catggctgcc gtgcctgtgc ttttcataga aatgccagcg     900
gaaatcctga gactctatgt gctctgtgtt atctgcgcct taccagcgat tttgtataca     960
gtaagtaaag tgttttcatt ggcgtacggt aggggattcg ttgaagtgct ttgtgactta    1020
ttatgtgtca ttatttctag gtgacgtgtc cgacgtggaa ggggaaggag atagatcagg    1080
ggctgctaat tctccttgca ctttgggggc tgtggttcca gctggcatta ttaaacccgt    1140
ggcggtcaga gtctcaggca gacggtgcgc agttgaaaaa attgaagact tgctgcagga    1200
agaacagacg caacctttgg acctgtccat gaaacgccct aagctgactt aagtgtgttt    1260
attgtatgca ataaaagtgt tgatctttga actgtgttta tgtgttgggt gtgtctgtgg    1320
gtatataagc aggtggatgg gaagtgagag cacagctgct tcagatggat ctgctaggag    1380
acctaagaga atttggcgtg gttcggcgct tgttggagtt ggcctctgac agaacttcca    1440
agttttggag gttttgtttt ggctcaacgc ttagcaacgt gctatatagg gtcaagaagg    1500
agcaggagac gcagtttgct aggctgttgg ccgatactcc tggagttttt gtggctctgg    1560
atctaggcca tcactctctt ttccaagaga aaattatcaa aaacctaact tttacgtctc    1620
ctggccgcac ggttgcttcc gctgccttta ttacctatat tttggatcaa tggagcaaca    1680
gcggcagcca cctgtcgtgg gagtacatgc tggattacat gtcgatggcg ctgtggaggg    1740
ccatgctgcg gaggagggtt tgcatttact tgcgggcgca gcctccgcgg ctgggccgag    1800
tggaggagga ggacgagccg ggagagatgg agaacctgag ggccgggctg gaccctccaa    1860
```

-continued

```
cggaggacta ggtgctgagg atgatcctga agaggggact agtgggggag ctaggaaaaa   1920
gcaaaaaact gagcctgaac ctagaaactt tttgaatgag ttgactgtaa gcctgatgaa   1980
tcggcagcgt cctgagacgg tgttttgggc tgagttggag gatgagttca agaaggggga   2040
attgaacctc ttgtacaagt atgggtttga gcagttgaaa actcactggt tggagccgtg   2100
ggaggacatg gaaatggctc tagacacctt tgctaaagtg gctctgcggc cggataaagt   2160
ttacactatt cgccgcactg ttaatataaa aaagagtgtt tatgttatcg gtcatggagc   2220
tctggtgcag gtgcagaccc cagaccgggt ggctttcaat tgcggcatgc agagtttggg   2280
ccccggggtg ataggtttga atggagttac atttcaaaat gtcaggttta ctggtgatga   2340
ttttaatggc tctgtgtttg tgactagcac ccagctaacc ctccacggtg tttacttttt   2400
taactttaac aatacatgtg tggagtcatg gggtagggtg tctctgaggg gctgcagttt   2460
tcatggttgc tggaaggcgg tggtgggaag aattaaaagt gtcatgtctg tgaagaaatg   2520
catatttgaa cgctgtgtga tagctctagc agtagagggg tacggacgga tcaggaataa   2580
cgccgcatct gagaatggat gtttttcttt gctgaaaggt acggccagcg ttaagcataa   2640
tatgatttgc ggcagcggcc tgtgcccctc gcagctctta acttgcgcag atggaaactg   2700
tcacaccttg cgcaccgtgc acatagtgtc ccactcgcgc cgcacctggc caacatttga   2760
gcacaatatg ctcatgcgtt gcgccgttca cctaggtgct agacgcggcg tgtttatgcc   2820
ttatcaatgt aactttagtc atactaagat tttgctggaa actgattcct tccctcgagt   2880
atgtttcaat ggggtgtttg acatgtcaat ggaacttttt aaagtgataa gatatgatga   2940
aaccaagtct cgttgtcgct catgtgaatg cggagctaat catttgaggt tgtatcctgt   3000
aaccctgaac gtcaccgagg agctgaggac ggaccaccac atgctgtctt gcctgcgtac   3060
cgactatgaa tccagtgatg aggagtgagg tgaggggcgg agccacaaag ggtataaagg   3120
ggcatgaagg gtggacgcgg tgtttcaaaa tgagcgggac gacggacggc aatgcgtttg   3180
agggggagt gttcagccca tatctgacat ctcgtcttcc ttcctgggca ggagtgcgtc   3240
agaatgtagt gggctccacc gtggacggac ggccggtcgc cctgcaaat tccgccaccc   3300
tcacctatgc caccgtggga tcatcgttgg acactgccgc ggcagctgcc gcttctgctg   3360
ccgcttctac tgctcgcggc atggcggctg attttggact atataaccaa ctggccactg   3420
cagctgtggc gtctcggtct ctggttcaag aagatgccct gaatgtgatc ttgactcgcc   3480
tggagatcat gtcacgtcgc ctggacgaac tggctgcgca gatatcccaa gctaaccccg   3540
ataccgcttc agaatcttaa ataaagacaa acaaatttgt tgaaaagtaa aatggcttta   3600
tttgtttttt ttggctcggt aggctcgggt ccacctgtct cggtcgttaa ggactttgtg   3660
tatgttttcc aaaacacggt acagatgggc ttggatgttc aagtacatgg gcatgaggcc   3720
atctttgggg tggagatagg accactgaag agcgtcatgt tccggggtgg tattgtaaat   3780
cacccagtcg tagcagggtt tttgagcgtg gaactggaat atgtccttca ggagcaggct   3840
aatggccaag ggcagcccct tagtgtaggt gtttacaaag cggttgagct gggagggatg   3900
catgcggggg gagatgatat gcatcttggc ttggattttg aggttagcta tgttaccacc   3960
caggtctctg cgggggttca tgttatgaag gaccaccagc acggtgtagc cggtgcactt   4020
ggggaacttg tcatgcagtt tggaggggaa ggcgtggaag aatttagata ccccccttgtg   4080
ccccccctagg ttttccatgc actcatccat aataatggca atgggacccc tggcggccgc   4140
tttagcaaac acgttttggg ggttggaaac atcatagttt tgctctagag tgagctcatc   4200
ataggccatc tttacaaagc ggggtaggag ggtgcccgac tgggggatga tagttccatc   4260
```

-continued

```
tgggcctgga gcgtagttgc cctcacagat ctgcatctcc caggccttaa tttccgaggg   4320
ggggatcatg tccacctggg gggcgataaa gaacacggtt tctggcgggg gattgatgag   4380
ctgggtggaa agcaagttac gcaatagctg ggatttgccg caaccggtgg ggccgtagat   4440
gaccccgatg acgggttgca gctggtagtt cagagaggaa cagctgccgt cggggcgcag   4500
gagggggcc acatcgttca tcatgcttct gacatgttta ttttcactca ctaagttttg   4560
caagagcctc tccccaccca gggataagag ttcttccagg ctgttgaagt gtttcagcgg   4620
tttcaggccg tcggccatgg gcatcttttc aagcgactga cgaagcaagt acagtcggtc   4680
ccagagctcg gtgacgtgct ctatggaatc tcgatccagc agacttcttg gttgcggggg   4740
ttgggccgac tttcgctgta gggcaccagc cggtgggcgt ccagggccgc gagggttctg   4800
tccttccagg gtctcagcgt tcgggtgagg gtggtctcgg tgacggtgaa gggatgagcc   4860
ccgggctggg cgcttgcgag ggtgcgcttc aggctcatcc tgctggtgct gaagcgggcg   4920
tcgtctccct gtgagtcggc cagatagcaa cgaagcatga ggtcgtagct gagggactcg   4980
gccgcgtgtc ccttggcgcg cagctttccc ttggaaacgt gctgacattt ggtgcagtgc   5040
agacacttga gggcgtagag ttttggggcc aggaagaccg actcgggcga gtaggcgtcg   5100
gctccgcact gagcgcagac ggtctcgcac tccaccagcc acgtgagctc gggtttagcg   5160
ggatcaaaaa ccaagttgcc tccatttttt ttgatgcgtt tcttaccttg cgtctccatg   5220
agtctgtgtc ccgcttccgt gacaaaaagg ctgtcggtgt ccccgtagac cgacttgagg   5280
gggcgatctt ccaaaggtgt tccgaggtct tccgcgtaca ggaactggga ccactccgag   5340
acaaaggctc gggtccaggc taacacgaag gaggcgatct gcgaggggta tctgtcgttt   5400
tcaatgaggg ggtccacctt ttccagggtg tgcagacaca ggtcgtcctc ctccgcgtcc   5460
acgaaggtga ttggcttgta agtgtaggtc acgtgacccg cacccccca aggggtataa   5520
aagggggcgt gcccactctc cccgtcactt tcttccgcat cgctgtggac cagagccagc   5580
tgttcgggtg agtaggccct ctcaaaagcc ggcatgattt cggcgctcaa gttgtcagtt   5640
tctacaaacg aggtggattt gatattcacg tgccccgcgg cgatgctttt gatggtggag   5700
gggtccatct gatcagaaaa cacgatcttt ttattgtcaa gtttggtggc gaaagacccg   5760
tagagggcgt tggaaagcaa cttggcgatg gagcgcaggg tctgattttt ctcccgatcg   5820
gccctctcct tggcagcgat gttgagttgc acgtactcgc gagccacgca ccgccactcg   5880
gggaacacgg cggtgcgctc gtcgggcagg atgcgcacgt gccagccgcg gttgtgcagg   5940
gtgatgaggt ccacgctggt ggccacctcc ccgcggaggg gctcgttggt ccaacacaat   6000
cgcccccctt ttctggagca gaacggaggc aggggatcta gcaagttggc gggcgggggg   6060
tcggcgtcga tggtaaatat gccgggtagc agaattttat taaaataatc gatttcggtg   6120
tccgtgtctt gcaacgcgtc ttcccacttc ttcaccgcca gggccctttc gtagggattc   6180
aggggcggtc cccagggcat ggggtgggtc agggccgagg cgtacatgcc gcagatgtcg   6240
tacacgtaca ggggctccct caacaccccg atgtaagtgg ggtaacagcg ccccccgcgg   6300
atgctggctc gcacgtagtc gtacatctcg tgagagggag ccatgagccc gtctcccaag   6360
tgggtcttgt ggggtttctc ggcccggtag aggatctgcc tgaagatggc gtgggagttg   6420
gaagagatgg tggggcgttg gaagacatta aagttggctc cgggcagtcc cacggagtct   6480
tggatgaact gggcgtagga ttcccggagc ttgtccacca gggctgcggt taccagcacg   6540
tcgagagcgc agtagtccaa cgtctcgcgg accaggttgt aggccgtctc ttgttttttc   6600
```

-continued tcccacagtt cgcgattgag gaggtattcc tcgcggtctt tccagtactc ttcggcggga 6660
aatccttttt cgtccgctcg gtaagaacct aacatgtaaa attcgttcac ggctttgtat 6720
ggacaacagc ctttttctac cggcagggcg tacgcttgag cggcctttct gagagaggtg 6780
tgggtgaggg cgaaggtgtc ccgcaccatc actttcaggt actgatgttt gaagtccgtg 6840
tcgtcgcagg caccctgttc ccacagcgtg aagtcggtgc gctttttctg cctgggattg 6900
gggagggcga atgtgacgtc gttaaaaagg attttcccgg agcggggcat gaagttgcga 6960
gagatcctga agggtccggg cacgtccgag cggttgttga tgacttgtgc cgccaggacg 7020
atctcgtcga agccgttgat gttgtggccc acgatgtaaa gttcgataaa gcgcggctgt 7080
cccttgaggg ccggcgcttt tttcaactcc tcgtaggtga gacagtccgg cgaggagaga 7140
cccagctccg cccgggccca gtcggagagc tgagggttag ccgcgaggaa agagctccat 7200
aggtcaaggg ctagcagagt ttgcaagcgg tcgcggaact cgcgaaactt tttccccacg 7260
gccattttct ccggcgtcac cacgtagaaa gtgcaggggc ggtcgttcca gacgtcccat 7320
cggagctcta gggccagctc gcaggcttgg cgaacgaggg tctcctcgcc cgagacgtgc 7380
atgaccagca tgaagggtac caactgtttc ccgaacgagc ccatccatgt gtaggtttct 7440
acgtcgtagg tgacaaagag ccgctgggcg cgcgcgtggg agccgatcgg gaagaagctg 7500
atctcctgcc accagttgga ggaatgggtg ttgatgtggt gaaagtagaa gtcccgccgg 7560
cgcacagagc attcgtgctg atgtttgtaa aagcgaccgc agtagtcgca gcgctgcacg 7620
ctctgtatct cctgaatgag atgcgctttt cgcccgcgca ccagaaaccg gagggggaag 7680
ttgagacggg gggcttgtgg ggcggcatcc cattcgcctt ggcggtggga gtctgcgtct 7740
gcgtcctcct tctctgggtg gacgacggtg gggacgacaa cgccccgggt gccgcaagtc 7800
cagatctccg ccacggaggg gcgcaggcgc tgcaggaggg gacgcagctg cccgctgtcc 7860
agggagtcga gggcggccgc gctgaggtcg gcgggaagcg tttgcaagtt cactttcaga 7920
agaccggtaa gagcgtgagc caggtgcaga tggtacttga tttccagggg ggtgttggaa 7980
gaggcgtcca cggcgtagag gaggccgtgt ccgcgcgggg ccaccaccgt gccccgagga 8040
ggttttatct caatcgtcga gggcgagcgc cggggggtag aggcggctct gcgccggggg 8100
gcagcggagg cagcggcacg ttttcgtgag gatttggcag cggttgatga cgagcccgga 8160
gactgctggc gtgggcgacg acgcggcggt tgaggtcctg gatgtgccgt ctctgcgtga 8220
agaccaccgg cccccgggtc ctgaacctga aagagagttc cacagaatca atgtctgcat 8280
cgttaacggc ggcctgcctg aggatctcct gtacgtcgcc cgagttgtct tgataggcga 8340
tctcggccat gaactgctcc acttcttcct cgcggaggtc gccgtggccc gctcgctcca 8400
cggtggcggc caggtcgttg gagatgcgac gcatgagttg agagaaggcg ttgaggccgt 8460
tctcgttcca cacgcggctg tacaccacgt tgccgaagga gtcgcgcgct cgcatgacca 8520
cctgggccac gttgagttcc acgtggcggg cgaagacggc gtagtttctg aggcgctgga 8580
agaggtagtt gagcgtggtg gcgatgtgct cgcagacgaa gaagtacatg atccagcgcc 8640
gcagggtcat ctcgttgatg tctccgatgg cttcgagacg ctccatggcc tcgtagaagt 8700
cgacggcgaa gttgaaaaat tgggagttgc gggcggccac cgtgagttct tcttgcagga 8760
ggcggatgag atcggcgacc gtgtcgcgca cctcctgctc gaaagcgccc cgaggcgcct 8820
ctgcttcttc ctccggctcc tcctcttcca ggggcacggg ttcctccggc agctctgcga 8880
cggggacggg gcggcgacgt cgtcgtctga ccggcaggcg gtccacgaag cgctcgatca 8940
tttcgccgcg ccggcgacgc atggtctcgg tgacggcgcg tccgttttcg cgaggtcgca 9000

-continued

```
gttcgaagac gccgccgcgc agagcgcccc cgtgcaggga gggtaagtgg ttagggccgt   9060
cgggcaggga cacggcgctg acgatgcatt ttatcaattg ctgcgtaggc actccgtgca   9120
gggatctgag aacgtcgagg tcgacgggat ccgagaactt ctctaagaaa gcgtctatcc   9180
aatcgcagtc gcaaggtaag ctgaggacag tgggtcgctg gggggcgtcc gcgggcagtt   9240
gggaggtgat gctgctgatg atgtaattaa agtaggcggt cttcaggcgg cggatggtgg   9300
cgaggaggac cacgtctttg ggcccggcct gttgaatgcg caggcgctcg gccatgcccc   9360
aggcctcgct ctgacagcga cgcaggtctt tgtagtagtc ttgcatcagt ctctccaccg   9420
gaacctctgc ttctcccctg tctgccatgc gagtcgagcc gaacccccgc aggggctgca   9480
gcaacgctag gtcggccacg accctttcgg ccagcacggc ctgttgaatc tgcgtgaggg   9540
tggtctggaa gtcgtccagg tccacgaagc ggtgataggc cccgtgttg atggtgtagg   9600
tgcagttggc catgacggac cagttgacga cttgcatacc gggttgggtg atctccgtgt   9660
acttgaggcg cgagtaggcg cgggactcga acacgtagtc gttgcatgtg cgcaccagat   9720
actggtagcc gaccaggaag tgaggaggcg gctctcggta caggggccag ccgacggtgg   9780
cgggggcgcc gggggacagg tcgtccagca tgaggcgatg gtagtggtag atgtagcggg   9840
agagccaggt gatgccggcc gaggtggtcg cggccctggt gaattcccgg acgcggttcc   9900
agatgttgcg caggggacgg aagcgttcca tggtgggcac gctctgcccc gtgaggcggg   9960
cgcagtcctg tacgctctag atggaaaaaa gacagggcgg tcatcgactc ccttccgtag  10020
cttgggggt aaagtcgcaa gggtgcggcg gcggggaacc ccggttcgag accggccgga  10080
tccgccgctc ccgatgcgcc tggccccgca tccacgacgt ccgcgccgag acccagccgc  10140
gacgctctgc cccaatacgg aggggagtct tttggtgttt tttcgtagat gcatccggtg  10200
ctgcggcaga tgcgacctca gacgcccacc accaccgccg cggcggcagt aaacctgagc  10260
ggaggcggtg acagggaggt ggaggagctg gctttagacc tggaagaggg agaggggctg  10320
gcccggctgg gagcgccgtc cccagagaga caccctaggg ttcagctcgt gagggacgcc  10380
aggcaggctt ttgtgccgaa gcagaacctg tttagggacc gcagcggtca ggaggcggag  10440
gagatgcgcg attgcaggtt tcgggcgggt agagagctga gggcgggctt cgatcgcgag  10500
cggctcctga gggcggagga tttcgagccc gacgagcgtt ctggggtgag cccggcccgc  10560
gctcacgtct cggcggccaa cctggtgagc gcgtacgagc agacggtgaa cgaggagcgc  10620
aacttccaaa agagctttaa caatcacgtg aggaccctga tcgcgaggga ggaggtgacc  10680
atcgggctga tgcatctgtg ggacttcgtg gaggcctacg tgcagaaccc ggccagcaaa  10740
cctctgacgg cccagctgtt cctgatcgtg cagcacagcc gcgacaacga gacgttccgc  10800
gacgccatgt tgaacatcgc ggagcccgag ggtcgctggc tcttggatct gattaacatc  10860
ctgcagagca tcgtggtgca ggagaggggt ctgagtttag cggacaaggt ggcggccatt  10920
aactattcga tgcagagcct ggggaagttc tacgctcgca agatctacaa gagcccttac  10980
gtgcccatag acaaggaggt gaagatagac agcttttaca tgcgcatggc gctaaaggtg  11040
ctgacgctga gcgacgacct cggcgtgtac cgtaacgaca agatccacaa ggcggtgagc  11100
gccagccgcc ggcgggagct gagcgacagg gagctgatgc acagcctgca gagggcgctg  11160
gcgggcgccg gggacgagga gcgtgaggct tactttgaca tgggagccga tctgcagtgg  11220
cgtcccagcg cgcgcgcctt ggaggcggcg ggttatcccg acgaggagga tcgggacgat  11280
ttggaggagg caggcgagta cgaggacgaa gcctgaccgg gcaggtgttg ttttagatgc  11340
```

-continued agcggccggc ggacggggcc accgcggatc ccgcactttt ggcatccatg cagagtcaac 11400
cttcgggcgt gaccgcctcc gatgactggg cggcggccat ggaccgcatc atggcgctga 11460
ccacccgcaa ccccgaggct tttaggcagc aaccccaggc caaccgtttt tcggccatct 11520
tggaagcggt ggtgccctcc cgcaccaacc ccacacacga gaaagtcctg actatcgtga 11580
acgccctggt agacagcaag gccatccgcc gcgacgaggc gggcttgatt tacaacgctc 11640
tgctggaacg ggtggcgcgc tacaacagca ctaacgttca gaccaatctg gatcgcctca 11700
ccaccgacgt gaaggaggcg ctggctcaga aggagcggtt tctgagggac agcaatctgg 11760
gctctctggt ggcactcaac gccttcctga gcacgcagcc ggccaacgtg ccccgcgggc 11820
aggaggacta cgtgagcttc atcagcgctc tgaggctgct ggtgtccgag gtgccccaga 11880
gcgaggtgta tcagtctggg ccggattact tcttccagac gtcccgacag ggcttgcaaa 11940
cggtgaacct gactcaggcc tttaaaaact tgcaaggcat gtggggcgtt aaggccccgg 12000
tgggcgatcg agccaccatc tccagtctgc tgacccccaa cactcgcctg ctgctgctct 12060
tgatcgcgcc gttcaccaac agtagcacta tcagccgtga ctcgtacctg ggtcatctca 12120
tcactttgta ccgcgaggcc atcggtcagg ctcagattga cgagcataca tatcaggaga 12180
tcactaacgt gagccgggcc ctgggtcagg aagataccgg cagcctggaa gccacgttga 12240
actttttgct aaccaaccgg aggcaaaaaa taccctccca gtttacgtta agcgccgagg 12300
aggagaggat tctgcgatac gtgcagcagt ccgtgagtct gtacttgatg cgggagggcg 12360
ccaccgcttc cacggcttta gacatgacgg ctcggaacat ggaaccgtcc ttttactccg 12420
cccaccggcc gttcattaac cgtctgatgg actacttcca tcgcgcggcc gccatgaacg 12480
gggagtattt taccaatgcc atcctgaatc cgcattggat gcccccgtcc ggcttctaca 12540
ccggcgagtt tgacctgccc gaagccgacg acggctttct ttgggacgac gtgtccgaca 12600
gcattttcac gccgggcaat cgccgattcc agaagaagga gggcggagac gagctccccc 12660
tctccagcgt ggaggcggcc tctaggggag agagtccctt tcccagtctg tcttccgcca 12720
gcagtggtcg ggtaacgcgc ccgcggttgc cgggggagag cgactacctg aacgacccct 12780
tgctgcggcc ggctaggaag aaaaatttcc ccaacaacgg ggtggaaagc ttggtggata 12840
aaatgaatcg ttggaagacc tacgcccagg agcagcggga gtgggaggac agtcagccgc 12900
gaccgctggt tccgccgcac tggcgtcgtc agagagaaga cccggacgac tccgcagacg 12960
atagtagcgt gttggacctg ggagggagcg gagccaaccc ctttgctcac ttgcaaccca 13020
aggggcgttc gagccgcctc tactaataaa aaagaagcgg aaacttacca gagccatggc 13080
cacagcgtgt gtgctttctt cctctctttc ttcctcggcg cggcagaatg agaagagcgg 13140
tgagagtcac gccggcggcg tatgagggtc cgcccccttc ttacgaaagc gtgatgggat 13200
cagcgaacgt gccggccacg ctggaggcgc cttacgttcc tcccagatac ctgggaccta 13260
cggagggcag aaacagcatc cgttactccg agctggcacc cctgtacgat accaccaagg 13320
tgtacctggt ggacaacaag tcggcggaca tcgcctccct gaattatcaa aacgatcaca 13380
gcaactttct gactaccgtg gtgcagaaca atgacttcac ccccgacgga ggcgggcacgc 13440
agaccattaa ctttgacgag cgttcccgct ggggcggtca gctgaaaacc atcctgcaca 13500
ccaacatgcc caacatcaac gagttcatgt ccaccaacaa gttcagggct aagctgatgg 13560
tagaaaaaag taatgcggaa actcggcagc cccgatacga gtggttcgag tttaccattc 13620
cagagggcaa ctattccgaa actatgacta tcgatctcat gaataacgcg atcgtggaca 13680
attacctgca agtggggaga cagaacgggg tgctggaaag cgatatcggc gtgaaattcg 13740

-continued

```
ataccagaaa cttccgactg ggtgggatc ccgtgaccaa gctggtgatg ccaggcgtgt  13800
acaccaacga ggcttttcac cccgacatcg tgctgctgcc ggggtgcggt gtggacttca  13860
ctcagagccg tttgagtaac ctgttaggaa ttagaaagcg ccgccccttc caagagggct  13920
ttcaaatcat gtatgaggac ctggagggag gtaatatacc cgccttactg gacgtgtcga  13980
agtacgaagc tagcatacaa cgcgccaaag cggagggtag agagattcgg ggagacacct  14040
ttgcggtagc tccccaggac ctggaaatag tgcctttaac taaagacagc aaagacagaa  14100
gctacaatat tataaacaac acgacggaca ccctgtatcg gagctggttt ctggcttaca  14160
actacggaga ccccgagaaa ggagtgagat catggaccat actcaccacc acggacgtga  14220
cctgtggctc gcagcaagtg tactggtccc tgccggatat gatgcaagac ccggtcacct  14280
tccgcccctc cacccaagtc agcaacttcc cggtggtggg caccgagctg ctgcccgtcc  14340
atgccaagag cttctacaac gagcaggccg tctactcgca acttattcgc cagtccaccg  14400
cgcttaccca cgtgttcaat cgctttcccg agaaccagat tctggtgcgc cctcccgctc  14460
ctaccattac caccgtcagt gaaaacgttc ccgccctcac agatcacgga accctgccgc  14520
tgcgcagcag tatcagtgga gttcagcgcg tgaccatcac cgacgccaga cgtcgaacct  14580
gcccctacgt ttacaaagcg cttggcgtgg tggctcctaa agttctttct agtcgcacct  14640
tctaaaaaca tgtccatcct catctctccc gataacaaca ccggctgggg actgggctcc  14700
ggcaagatgt acggcggagc caaaaggcgc tccagtcagc acccagttcg agttcggggc  14760
cacttccgcg ctccttgggg agcttacaag cgaggactct cgggtcgaac ggctgtagac  14820
gataccatag atgccgtgat tgccgacgcc cgccggtaca accccggacc ggtcgctagc  14880
gccgcctcca ccgtggattc cgtgatcgac agcgtggtag ccggcgctcg ggcctatgct  14940
cgccgcaaga ggcggctgca tcggagacgt cgccccaccg ccgccatgct ggcagccaga  15000
gccgtgctga gacgggcccg gagggtaggc aggagggcta tgcgccgcgc tgccgccaac  15060
gccgccgccg ggagggcccg ccgacaggct gcccgccagg ctgctgccgc catcgctagc  15120
atggccagac ccaggagagg gaacgtgtac tgggtgcgcg attctgtgac gggagtccga  15180
gtgccggtgc gcagccgacc tccccgaagt tagaagatcc aagctgcgaa gacggcggta  15240
ctgagtctcc ctgttgttat cagcccaaca tgagcaagcg caagtttaaa gaagaactgc  15300
tgcagacgct ggtgcctgag atctatggcc ctccggacgt gaagcctgac attaagcccc  15360
gcgatatcaa gcgtgttaaa aagcgggaaa agaaagagga actcgcggtg gtagacgatg  15420
gcggagtgga atttattagg agtttcgccc cgcggcgcag ggttcaatgg aaagggcgac  15480
gggtacaacg cgttttgagg ccgggcaccg cggtagtttt taccccggga gagcggtcgg  15540
ccgttagggg ttttaaaagg cagtacgacg aggtgtacgg cgacgaggac atattggaac  15600
aggcggctca acagatcgga gaatttgcct atggaaagcg ctcgcgtcgc gaagacctgg  15660
ccatcgcctt agacagcggc aaccccacgc ccagcctcaa acccgtgacg ctgcagcagg  15720
tgcttcccgt gagcgccagc acggacagca agaggggaat aaaaagagaa atggaagatc  15780
tgcagcctac catccagctc atggttccta aacggcagag gctggaagag gtcctggaga  15840
agatgaaagt ggaccccagc atagagccgg acgttaaagt caggccgatc aaagaagtgg  15900
cccctggact cggggtgcag acggtggata tccagatccc cgtcacgtca gcttcgaccg  15960
ccgtggaagc catggaaacg caaaccgaaa cccccgccgt ggttggtacc aaagaagtgg  16020
cgttgcaaac cgacccctgg tacgaatttg ccgccccccg gcgtcagagg cgacccgctc  16080
```

-continued

```
gttacggccc cgccaacgcc atcatgccag aatatgcgct gcatccgtct atcctgccca  16140
cccccggcta ccggggagtg acgtatcgcc cgtcaggaac ccgccgccga acccgtcgcc  16200
gccgccgctc ccgtcgcgct ctggcccccg tgtcggtgcg ccgcgtaaca cgccggggaa  16260
agacagtcac cattcccaac ccgcgctacc accctagcat cctttaatga ctctgccgtt  16320
ttgcagatgg ctctgacttg ccgcgtgcgc cttcccgttc cgcactatcg aggaagatct  16380
cgtcgtagga gaggcatggc gggcagtggt cgccggcggg ctttgcgcag gcgcatgaaa  16440
ggcggaattt tacccgcttt gatacccata atcgccgccg ccatcggtgc catacccggc  16500
gtcgcttcag tggccttgca agcagctcgt aataaataaa cgaaggcttt tgcacttatg  16560
tcctggtcct gactatttta tgcagaaaga gcatggaaga catcaatttt acgtcgctgg  16620
ctccgcggca cggctcgcgg ccgctcatgg gcacctggaa cgacatcggc accagtcagc  16680
tcaacggggg cgctttcaat tgggggagcc tttggagcgg cattaaaaac tttggctcca  16740
cgattaaatc ctacggcagc aaagcctgga acagtagtgc tggtcagatg ctccgagata  16800
aactgaagga caccaacttc caagaaaaag tggtcaatgg ggtggtgacc ggcatccacg  16860
gtgcggtaga tctcgccaac caagcggtgc agaaagagat tgacaggcgt ttggaaaact  16920
cgcgggtgcc gccgcagagg ggggatgagg tggaggtcga ggaagtagaa gtagaggaaa  16980
agctgccccc gctggagaaa gttcccggtg cacctccgag gccgcagaag cggcccaggc  17040
cagaactaga agaaactctg gtgacggaga gcaaggagcc tccctcgtac gagcaagcct  17100
tgaaagaggg cgcctctcca ccctcctacc cgatgactaa gccgatcgca cccatggctc  17160
gaccggtgta cggcaaggat tacaagcccg tcacgctaga gctgccccca ccgcccccctt  17220
cgcgtccgac ggtgcctccg ctgcctgccc cgtcggcggg tcccgagtct gcaccatccg  17280
ctgtgcctct gccagccgcc cgtcccgtgg ccgtggccac tgccaggaac cccagaggcc  17340
agagaggagc caactggcaa agcacgctga acagcatcgt gggcctgggg gtgaaaagcc  17400
tgaaacgccg ccgttgctat tattaaaaag tgtagctaaa aaatttcccg ttgtatacgc  17460
ctcctatgtt accgccagag acgcgtgact gtcgccgcga gcgccgcttc caagatggcc  17520
accccatcga tgatgccgca gtggtcttac atgcacatcg ccggccagga cgcctcggag  17580
tacctgagtc ccggcctcgt gcagtttgcc cgcgccaccg acacctactt cagcttggga  17640
aacaagttta gaaaccccac cgtggccccc acccacgatg tgaccacgga ccgctcgcag  17700
aggctgaccc tgcgctttgt gcccgtagac cgggaggaca ccgcgtactc ttacaaagtg  17760
cgctacacgc tggccgtagg ggacaaccga gtgctggaca tggccagcac ctactttgac  17820
atccgggggg tgctggatcg gggtcccagc ttcaagccct actccggcac cgcttacaac  17880
tccctggctc ccaagggcgc ccccaatcct gcagaatggg ccgataccaa cgacagcaac  17940
aaactgaaag tgaggggtca ggcgcctttt gtcagtactt acggttctgc tacggcgctt  18000
acaaaagatg ggatacaggt gggagtggat acttccgaag catctcaggc tgtttatgcc  18060
gacagaagtt accagccaga accccaaatt ggagagacag agtggaacag cgaagtgggt  18120
aatgacgaca gagtggcggg aagggtgcta aagaaaacaa ctcccatgtt cccttgttac  18180
ggttcatatg ccaagcccac caacgaaaaa ggcggacaag caatacagcc caccgccggc  18240
aacggcgata atcaggctgt agagttacaa ttctttgcca ctactagcac tcccactgcg  18300
ccaaaggcag tattgtacgc ggaggacgtg gccattgaag ctccagatac tcacttagtg  18360
tttaagccaa cagtagtcgc gggaactaca agttcggaag ctctgctaac ccaacaagcc  18420
gcacctaacc gcccaaacta cattgccttt agagataact ttattggtct catgtactac  18480
```

-continued

```
aattcaaccg ggaatatggg agtactggcc ggacaagcat ctcagctcaa tgcagtggtt  18540
gatcttcagg acagaaacac cgaactgtca tatcagctaa tgctggatgc tctgggagat  18600
cgcagtcggt acttttctat gtggaatcaa gctgtagata gctatgatcc agatgtaaga  18660
attgtagaaa accacggtgt ggaagacgaa ctgcctaatt attgcttccc actaggcggg  18720
atggtagtaa cggacactta caaagccata aaggtaaatg gaagcggatg gacggctaat  18780
actgacgttt tcagcgagag agtagaaata ggctcaggta acctgtttgc catggaaatt  18840
aacttgcaag ctaatctgtg gcgcagtttc ttgtattcca acataggact gtacctcccg  18900
gactctttaa aattaacccc tgacaacatc acgctccctg agaacaaaaa tacctaccag  18960
tatatgaacg gtcgcgtaac accacccggg ctcgtggaca cctacgttaa cgtgggtgcg  19020
cgctggtccc ccgatgttat ggacagcatt aaccctttta accaccaccg caacgccggg  19080
ctccgctacc gttccatgct cctgggaaac ggacgctacg tacccttcca cattcaggtg  19140
ccccagaaat tctttgcaat taaaaacctg ctgctgctcc ccggttccta tacctacgag  19200
tggaatttcc gcaaggacgt gaacatgatt ttgcaaagct cgctgggtaa cgacctgcga  19260
gttgacgggg ccagcatacg cttcgacagc atcaacctgt atgctaactt tttccccatg  19320
gcccacaaca cggcctccac cctggaagcc atgctgcgca acgacaccaa tgaccagtcc  19380
ttcaacgact acctgtgcgc ggccaacatg ctgtatccca tccccgccaa cgccaccagc  19440
gtgcccatct ccatcccgtc tcgcaactgg gccgccttta ggggttggag tttcacccgc  19500
ctcaaaacca aggaaacccc ctcgctgggc tctggcttcg acccctactt cgtctactca  19560
ggctccattc cctacctgga cggcactttc tatcttaacc acactttcaa aaaggtgtct  19620
atcatgttcg attcctcggt cagctggccc ggcaacgacc gcctgctgac gcccaacgag  19680
ttcgaaatca agcgttcggt ggacggtgaa gggtacaacg tggcccagag caacatgacc  19740
aaggactggt tcctggttca aatgctcagc cattacaaca tcggttacca gggcttctat  19800
gtgcccgaga actacaagga ccgcatgtac tccttcttta ggaacttcca acccatgagt  19860
cgccaagtcg tggactcagt ggcttacagg gactactacc aggacgttaa gctcccctac  19920
cagcacaaca actcagggtt cgtgggctac atgggtccca ccatgcgaga ggggcaggcc  19980
tacccggcca actatcctta tcccctaatc ggagagactg ctgtacccag cctgacgcag  20040
aaaaagttcc tctgcgaccg ggtgatgtgg aggataccct tctctagcaa cttcatgtct  20100
atgggctccc tcaccgacct ggggcagaac atgctgtacg ccaactccgc tcacgccttg  20160
gacatgacct ttgaggtgga tcccatggat gagcccacgc ttctctatgt tctgtttgaa  20220
gtcttcgacg tggtgcgcat ccaccagccg caccgcggcg tcatcgaggc cgtctacctg  20280
cgcacacctt tctctgccgg taacgccacc acctaaagaa gccgatgggc tccagcgaac  20340
aggagctgca ggccattgtt cgcgacctgg gctgcgggcc ctactttttg ggcaccttcg  20400
acaagcggtt ccccggcttc atgtcccctc acaagccggc ctgtgccatc gttaacacgg  20460
ccggacggga aaccgggggg gtccactggc tcgccttcgc ctggaacccg cgtaaccgca  20520
cctgctacct gttcgaccct tttggtttct ccgacgaaag gctgaagcag atctaccagt  20580
tcgagtacga ggggctcctc cagcgcagcg ctctggcctc cacgcccgac cactgcgtca  20640
ccctggaaaa gtccacccag acggtccagg ggcccctctc ggccgcctgc gggctcttct  20700
gttgcatgtt tttgcacgcc ttcgtgcact ggcctcacac ccccatggat cacaacccca  20760
ccatggatct gctcaccgga gtgcccaaca gcatgcttca cagcccccag gtcgccccca  20820
```

-continued ccctgcgccg taaccaggaa cacctgtatc gctttctggg gaaacactct gcctatttcc 20880
gccgccatcg gcagcgcatc gaacaggcca cggccttcga aagcatgagc caaagagtgt 20940
aatcaataaa aaccattttt atttgacatg atacgcgctt ctggcgtttt tattaaaaat 21000
cgaagggttc gagggagggg tcctcgtgcc cgctggggag ggacacgttg cgatactgga 21060
atcgggcgct ccaacgaaac tcggggatca ccagtcgcgg caggggcacg tcttccaggt 21120
tctgcttcca aaactgtcgc accagctgca gggctcccat cacgtcgggc gccgatatct 21180
tgaagtcgca gttagggccg gagctcccgc ggctgttccg gaacacgggg ttggcacact 21240
ggaacaccat cacgctgggg ttgtgaatac tagccagggc cgtcggatcg gtcacctccg 21300
acgcatccag atcctcggcg ttgctcaggg cgaacggggt cagcttgcac atctgccgcc 21360
cgatctgggg caccaggtcg ggtttgttga ggcaatcgca gcgcagaggg atcaggatgc 21420
gtcgctgccc gcgttgcatg atagggtaac tcgccgccag gaactcctcc atctgacgga 21480
aggccatctg ggccttaacg ccctcggtga aaaacagccc acaggacttg ctagaaaata 21540
cgttattgcc gcagttaatg tcttccgcgc agcagcgtgc atcttcgttc ttcagctgaa 21600
ccacgttacg cccccagcgg ttctggacca ccttggcttt cgtaggatgc tccttcagcg 21660
cccgctgccc gttctcgctg gtcacatcca tttccaccac gtgctccttg cagaccatct 21720
ccactccgtg gaagcaaaac aggacgccct cctgccgggt attgcgatgc tcccaaacgg 21780
cacacccggt gggctcccag ctcttgtgtt ttaccccccgc gtaggcttcc atgtaagcca 21840
tgaggaatct gcccatcagc tcggtgaagg tcttctgatt ggtgaaggtt agcggcaggc 21900
cgcggtgctc ctcgttcaac caagtttgac agatcttgcg gtacaccgtt ccctggtcgg 21960
gcagaaactt aaaagccgct ctgctgtcgt tgtccacgtg gaacttctcc attaacatca 22020
tcatggtttc catacccttc tcccacgctg acaccagcgg tttgctgtcg gggttcttca 22080
ccaacacggc ggtagagggg ccctcgccgg ccccgacgtc cttcatggtc attctttgaa 22140
actccacgga gccgtccgcg cgacgtactc tgcgcaccgg agggtagctg aagcccacct 22200
ccaccacggt gccttcgccc tcgctgtcgg aaacgatctc cggggatggc ggcggtgcgg 22260
gtgtcgcctt gcgagccttc ttcttgggag ggagctgagg cgcctcctgc tcgcgctcgg 22320
ggctcatctc ccgcaagtag gggggttatgg agctgcctgc ttggttctga cggttggcca 22380
ttgtatccta ggcagaaaga catggagctt atgcgcgagg aaactttaac cgccccgtcc 22440
cccgtcagcg acgaagatgt catcgtcgaa caggacccgg gctacgttac gccgcccgag 22500
gatctggagg ggcctgaccg gcgcgacgct agtgagcggc aggaaaatga gaaagaggag 22560
gcctgctacc tcctggaagg cgacgttttg ctaaagcatt tcgccaggca gagcaccata 22620
gttaaggagg ccttgcaaga ccgctccgag gtgcccttgg acgtcgccgc gctctcccag 22680
gcctacgagg cgaacctttt ctcgcctcga gtgcctccga agagacagcc caacggcacc 22740
tgcgagccca acccgcgact caacttctac cccgtgttcg ccgtaccaga ggcgctggcc 22800
acctatcaca ttttttttcaa aaaccaacgc atccccctat cgtgccgggc caaccgcacc 22860
gcggccgata ggaatctcag gcttaaaaac ggagccaaca tacctgatat cacgtcgctg 22920
gaggaagtgc ccaagatttt cgagggtctg ggtcgagatg agaagcgggc ggcgaacgct 22980
ctgcagaaag aacagaaaga gagtcagaac gtgctggtgg agctggaggg ggacaacgcg 23040
cgtctggccg tcctcaaacg ctgcatagaa gtctcccact tcgcctaccc cgccctcaac 23100
ttgccaccca aagttatgaa atcggtcatg gatcagctgc tcatcaagag agctgagccc 23160
ctggatcccg accaccccga ggcggaaaac tcagaggacg gaaagcccgt cgtcagcgac 23220

```
gaggagctcg agcggtggct ggaaaccagg gacccccaac agttgcaaga gaggcgcaag  23280
atgatgatgg cggccgtgct ggtcaccgtg gagctggaat gcctgcaacg gtttttcagc  23340
gacgtggaga cgctacgcaa aatcggggaa tccctgcact acaccttccg ccagggctac  23400
gtccgccagg cctgcaagat ctccaacgtg gagctcagca acctggtctc ctacatgggc  23460
atcctccacg agaaccggct ggggcagagc gtgctgcact gcaccttgca aggcgaggcg  23520
cggcgggact acgtgcgaga ctgcatctac ctcttcctca ccctcacctg gcagaccgcc  23580
atgggcgtct ggcagcagtg cttggaagag agaaacctca aagagctaga caaactcctc  23640
tgccgccagc ggcgcgccct gtggtccggt ttcagcgagc gcacggtcgc cagcgctctg  23700
gcggacatca tcttcccgga gcgcctgatg aaaaccttgc aaaacggcct gccggatttc  23760
atcagtcaaa gcattttgca aaacttccgc tcttttgtcc tggaacgctc cgggatcttg  23820
cccgccatga gctgcgcgct accttctgac tttgtccccc tctcctaccg cgagtgccct  23880
cccccactgt ggagccactg ctacctcttc caactggcca actttctggc ctaccactcc  23940
gacctcatgg aagacgtaag cggagagggt ttactggagt gccactgccg ctgcaacctg  24000
tgcacccccc acagatcgct ggcctgcaac accgagctac tcagcgaaac ccaggtcata  24060
ggtaccttcg agatccaggg gccccagcag caagagggtg cttccggctt gaagctcact  24120
ccggcgctgt ggacctcggc ttacttacgc aaatttgtag ccgaggacta ccacgcccac  24180
aaaattcagt tttacgaaga ccaatctcaa ccaccgaaag ccccccctcac ggcctgcgtc  24240
atcacccaga gcaagatcct ggcccaattg caatccatca accaagcgcg ccgcgatttc  24300
cttttgaaaa agggtcgggg ggtgtatctg gacccccaga ccggcgagga actcaacccg  24360
tccacactct ccgtcgaagc agccccccg agacatgccg cccaagggaa ccgccaagca  24420
gctgatcgct cggcagagag cgaagaagca agagctgctc cagcagcagg tggaggacga  24480
ggaagagatg tgggacagcc aggcagagga ggtgtcagag gacgaggagg agatggaaag  24540
ctgggacagc ctagacgagg aggaggacga gctttcagag gaagaggcga ccgaagaaaa  24600
accacctgca tccagcgcgc cttctctgag ccgacagccg aagccccggc ccccgacgcc  24660
cccggccggc tcactcaaag ccagccgtag gtgggacgcc accgaatctc cagcggcagc  24720
ggcaacggca gcgggtaagg ccaaacgcga gcggcggggg tattgctcct ggcgggccca  24780
caaaagcagt attgtgaact gcttgcaaca ctgcggggga aacatctcct ttgcccgacg  24840
ctacctcctc ttccatcacg gtgtggcctt ccctcgcaac gttctctatt attaccgtca  24900
tctctacagc ccctacgaaa cgctcggaga aaaaagctaa ggcctcctcc gccgcgagga  24960
aaaactccgc cgccgctgcc gccgccaagg atccaccggc caccgaggag ctgagaaagc  25020
gcatctttcc cactctgtat gctatctttc agcaaagccg cgggcagcac cctcagcgcg  25080
aactgaaaat aaaaaaccgc tccttccgct cgctcacccg cagctgtctg taccacaaga  25140
gagaagacca gctgcagcgc accctggacg acgccgaagc actgttcagc aaatactgct  25200
cagcgtctct taaagactaa aagacccgcg ctttttcccc ctcggccgcc aaaacccacg  25260
tcatcgccag catgagcaag gagattccca ccccctacat gtggagctat cagccccaga  25320
tgggcctggc cgcgggggcc gcccaggact actccagcaa gatgaactgg ctcagcgccg  25380
gcccccacat gatctcacga gttaacggca tccgagccca ccgaaaccag attctcttag  25440
aacaggcggc aatcaccgcc acaccccggc gccaactcaa cccgcctagt tggcccgccg  25500
cccaggtgta tcaggaaaat ccccgcccga ccacagtcct cctgccacgc gacgcggagg  25560
```

-continued

```
ccgaagtcct catgactaac tctggggtac aattagcggg cgggtccagg tacgccaggt  25620
acagaggtcg ggccgctcct tactctcccg ggagtataaa gagggtgatc attcgaggcc  25680
gaggtatcca gctcaacgac gagacggtga gctcctcaac cggtctcaga cctgacggag  25740
tcttccagct cggaggagcg ggccgctctt ccttcaccac tcgccaggcc tacctgaccc  25800
tgcagagctc ttcctcgcag ccgcgctccg ggggaatcgg cactctccag ttcgtggaag  25860
agttcgttcc ctccgtctac ttcaacccct tctccggctc gcctggacgc tacccggacg  25920
ccttcattcc caactttgac gcagtgagtg aatccgtgga cggctacgac tgatgacaga  25980
tggtgcggcc gtgagagctc ggctgcgaca tctgcatcac tgccgtcagc ctcgctgcta  26040
cgctcgggag gcgatcgtct tcagctactt tgagctgccg gacgagcacc ctcagggtcc  26100
ggctcacggg ttgaaactcg agatcgagaa cgcgctcgag tctcgcctca tcgacacctt  26160
caccgcccga cctctcctgg tagaaatcga acgcgggatc actaccatca ccctgttctg  26220
catctgcccc acgcccggat tacatgaaga tctgtgctgt catctttgcg ctcagtttaa  26280
taaaaactga actttttgcc gcaccttcaa cgccacgcgt cgtttctcca aaagttgtcg  26340
acagctcttc agtcagaggt atacgagaaa ctgtttattt ttacaactct actacttttc  26400
tcacccttaa ctgctcctgc actaacgaac taattcagtg gttcgcgaac ggctcactct  26460
gccaagtctt ttttaattct gctgttcttc ctgagtttgg ctcctttgcg tgtggaaatt  26520
ctacccccctc caccttaacc attgcggcgc ccttttcgga aatccagtat ttttgtattg  26580
gggcgggagg taaaccgggt tgtattcacc gcttgtttgt aaagccattt gttgcttcaa  26640
ttcccattaa cacttcactt tcctctaata catacttacc taccttacat tctactcacc  26700
cctcctggca acctcttatt ggcctcacgg cttttatttc cgttgtttta ctaaacttta  26760
taattcttaa caaactttct taaacatgct tgccattttg cttctgctcg ttactttaac  26820
gtccgcagat taccacaatg taattgtacg agaaaacagt ttacaaaacc catcacaggt  26880
atatgttaaa gcaggctcta acttaacttt acaatccttc tattcgcctt accctgagga  26940
catgccacgt gttacttggt acttagaagt ttttgattcg ctatttgaaa ggcatacgat  27000
tcctccattt tttacaggcg ttatactttg tgacatttct ggtgacatac agcatgtgtg  27060
gaaccattgg cctttacaat ttaattgcat aaataaaagc ttacatatta ttaatctcaa  27120
accaagtgat gaaggccttt acaatgtgaa ggttttaaag gacagcattc agcataatac  27180
atactttcga gtgcatgtag taagttttcc aagacctgaa tgtaacatca ccactacata  27240
tctttcagat gactactgcc ttattaacat tgattgctct caattaccat accctgctaa  27300
ggtctattat aatggcaatg aaagtaagct gcattactac ttatctgaac gcggtggcca  27360
gccaaacctt ccaaattact ttactgttgg gtatcgatat agagatctcc gacaaaatta  27420
tacagttgaa tatccattta atgaactatg tacagagata attgctcttg aaacagggtc  27480
tgattttatg ccaattttta tagttaccct agtggtgagc attatagtta ttgtgatggg  27540
catcacatat cttatttatc actgtaggac tttaaagacc aaaaccaaaa ccaaaaccaa  27600
gcctcctgaa atccgtttgc tttaattttt tccagaatgg tagctgcttt cttcattttt  27660
ctctgtatac caatcatctg cgcctccaca acttttgccg ctgtttccca cctggaacca  27720
gactgtctac cacctttttgt tgtatacctg atactgactt ttgtggtctg tacagccatt  27780
accagcatag cctgcttttt tgtaacaatt ttccaagccg ccgattatct ctacgtacgg  27840
tttgcttatt ttagacatca ccccgagtat cggaatcaaa acgtagcttc tttactttgt  27900
ctagcatgat tcgcctattt atactgcaca ctctgtttac cctcgcaaaa tgtcattgcc  27960
```

```
cttttaccaa accttggtcc ttttacacct gttacgatgt actgcccgaa acccctattg  28020
cctggcttta cgtagccaca gcggttttag tttttgtagc aacctgcatt ggcgttaaac  28080
tgtacttcta cttaaaaatt ggatggcttc atcccccaga agatttaccc cgatatcctc  28140
ttgttaataa ctttcaacag cctctgccgc ctcctgatcc tcttccgcga gctccctccg  28200
ttgttagcta ctttcaactc accggtggag atgactgact ctcaggacat tgatattagt  28260
gtggaaagaa tagccgctca gcgtcagcga gaaactcggg tgctggagta ctttgaacta  28320
cagcagctta aagagtccca ctggtgtgag aaaggagtgc tgtgtcatgt taagcaggca  28380
gccctttctt acgatgtcag ccttcaggga catgaactgt cttacacttt gccttcgcaa  28440
aaacaaacct tctgcaccat gatgggctct acctccatca caatcaccca acaaaccgga  28500
cctgttgagg gagctatcct gtgtcactgt cacgcgcctg attgtatgcc caaactaatt  28560
agaactctct gtgccttagg tgatatattt aaaatgtaag tcagtatcaa taaacttacc  28620
ttaaatttga cagcagtttt ttggtaacat cattcagcag caccacttta ccctcttccc  28680
aactctcgta tgggacgtga tggtgggcgg caaacttcct ccaaacccta aaacaaatat  28740
taatatccac ttccttgtcc ttacccacaa ttttcatctt ttcatagatg aaaagaacca  28800
gagttgatga agacttcaac cccgtctacc cttatgactc cacatccact cctgcggtcc  28860
cctttatatc ccccccgttt gtaaacagcg atggtcttca ggaaaaccct cctggagtct  28920
taagtttacg aatagctaaa cccttgtatt ttgacatgga aaggaaacta gcgctttcac  28980
ttggaagagg attggcaatt acctccaccg gacagctaga aagcacacag agcgtgcaaa  29040
ccacccctcc attagttgtc aacaacagca acacgcttgt cctgcgttat tcctccccgt  29100
taggcttatc gggtgacaat ttaatactaa attgctccga tcctctccgc gtagtaaaca  29160
acagcctgac attcagctac ctatctccac ttcgttttga aggtggcagt cttacattca  29220
attacacatc tcccccttaaa ctgttgaaca gcagccttgc gatcggaata aattccaaca  29280
aaggtctcgg caatgacagc gatgaacttt ctgtcaaact aacatcagat ctaaagttta  29340
acaacgatgg aaaaatagct tttggtatac aaagcctgtg taccaccccc acagccgcct  29400
ctaactgtac cgtttttacc aacggtgatt ctttactctg tttatgttta accaaatgtg  29460
gagctcacgt gttaggaagt gtgagtttaa ccggaatgca aggaaccata acagccatga  29520
cacagaacta cattagtatt caatttctat ttgacaacaa tggtgcgttg acttcatcac  29580
cgctcctcaa caacaacact tggggtatac ggcaaaacga cacttcgtcc gctaaccccg  29640
cctacaatgc tcttgcattt atgcctaaca gcactgtata tgtaagaggt caaagtggtg  29700
agcccagaaa taactattac acccaaacat accttagggg aaacgttaaa aagccaatta  29760
tccttaccgt tacctacaac tcggctgctt caggttattc actaactttt aaatgggatg  29820
ctgtagtaac agaaaaattt gccactccaa catcttcttt ttgctatatt acagaacaat  29880
aaattcctat taccccacca attcgttttt ttcagatgaa acgggccaga gttgatgaag  29940
acttcaaccc agtgtaccct tatgaccccc catacgctcc cgttatgccc ttcattactc  30000
caccttttac ctcctcggat gggttgcagg aaaaaccact tggagtgtta agtttaaact  30060
acaaggatcc cattactaca caaaatggat ctctcacgtt gaaaatagga aacggcctca  30120
ctctagacaa ccagggacaa ttaacatcaa ctgctgggga agtagagcct ccgctcacta  30180
atgctaacaa caaacttgca ctagcctata gcgaaccatt agcagtaaaa agcaaccgct  30240
taactttatc acacaccgcc ccccttgtcg ttgctaataa ttctttagcg ttgcaagttt  30300
```

-continued

```
cagaacctat ttttataaat gacgatgaca agctagccct gcagacagcc gccccccttg  30360
taactaacgc tggcaccctt cgcttacaga gcgccgcccc tttaggattg gttgaaaata  30420
ctcttagact gctgttttct aaacccttgt atttgcaaaa tgattttctt gcattaggca  30480
ttgaacgccc cctggctata gcagccgcag gtactctagc actacaactc actcctccat  30540
taaagactaa cgatgacggg ctgacactat ccacagtcga gccattaact gtaaaaaacg  30600
gaaacttagg cttgcaaata tctcgccctt tggttgttca aaacagcagc ctttcgcttg  30660
ctattacccc cccgctgcgt ctatttaaca gcgaccccgt tcttggtttg ggctttactt  30720
ttcccctagc cgtgacagac aacctactct ccttaaacat gggagacggt gttaaactaa  30780
cctataataa actaacagcc aatttgggta gggatttaca atttgaaaac ggtgccattg  30840
ccgtaacgct tactgccgaa tcacctttgc aatacactaa caaacttcaa ctgaatattg  30900
gagctggcct tcgttacaat ggagccagca gaaaactaga tgtaaacatt aaccaaaata  30960
agggcttaac ttgggacaac gatgcagtta ttcccaaatt aggatcaggt ttacaattcg  31020
accctaatgg taacatcgct gttatccctg aaaccgtaaa gccgcaaacg ttatggacaa  31080
ctgcagatcc atcgcctaac tgctcagtgt accaggactt ggacgccagg ctgtggctcg  31140
ctcttgttaa aagtggtgac atggttcatg gaagcattgc tctaaaagcc ctaaaaggaa  31200
cgttgctaaa tcctacagca agctacatct ccattgtgat atatttttac agcaacggag  31260
tcaggcgtac caactatccc acgtttgaca acgaaggcac cttagctaac agcgctacct  31320
ggggataccg agaggggcaa tctgctaaca ctaatgtaac caatgccact gaatttatgc  31380
ccagctcaac caggtacccc gtgaataaag gagacaatat tcagaatcaa tctttttcat  31440
acacctgtat caaaggagat ttcgctatgc ctgtcccgtt ccgtgtaaca tataatcatg  31500
ccctggaagg atactccctt aagttcacct ggcgcgttgt agccaaccaa gcttttgata  31560
ttccttgctg ttccttttca tacatcacag aataaaccac tttttaaaat ttttcttttt  31620
attttacacg cacagtaagg cttcctcccc ccttccattt gacagcatac accagcctct  31680
cccccttcat ggcagtaaac tgctgcgagc cagtccggta tttgggagtt aaaatccaaa  31740
cagtctcttt ggtgatgaaa cgtcgatccg tgatggacac aaatccctgg ggcaggtttt  31800
ccagcgtttc ggtaaaaaac tgcacaccgc cctacaaaac aaacaggttc aggctctcca  31860
tgggttatct ccccgatcaa actcagacag ggtaaaggtg cggtgatgtt ccactaaacc  31920
acgcaggtgg cgctgtctga acctctcggt gcgactcctg tgaggctggt aagaagttag  31980
attgtccagt agcctcacag catggatgat cagtttacgt gtacgtctgg cgcaacagcg  32040
catctgaatc tcactgagat tccggcaaga atcgcacacc atcacaatca ggttgttcat  32100
gatcccatag ctgaacacgc tccagccaaa gctcattcgc tccaacagcg ccaccgcgtg  32160
tccgtccaac cttactttaa cataaatcag gtgtctgccg cgtacaaaca tactacccgc  32220
atacagaact tcccggggca aacccctgtt caccacctgc ctgtaccagg gaaacctcac  32280
atttatcagg gagccataga tagccatttt aaaccaatta gctaacaccg ccccaccagc  32340
tctacactga agagaaccgg gagagttaca atgacagtga ataatccatc tctcataacc  32400
cctgatggtc tgatggaaat ccagcacacc gccctacaaa acaaacaggt tcaggctctc  32460
catgggttat ctccccgatc aaactcagac agggtaaagg tgcggtgatg ttccactaaa  32520
ccacgcaggt ggcgctgtct gaacctctcg gtgcgactcc tgtgaggctg gtaagaagtt  32580
agattgtcca gtagcctcac agcatggatg atcagtttac gtgtacgtct ggcgcaacag  32640
cgcatctgaa tctcactgag attccggcaa gaatcgcaca ccatcacaat caggttgttc  32700
```

```
atgatcccat agctgaacac gctccagcca aagctcattc gctccaacag cgccaccgcg  32760
tgtccgtcca accttacttt aacataaatc aggtgtctgc cgcgtacaaa catactaccc  32820
gcatacagaa cttcccgggg caaacccctg ttcaccacct gcctgtacca gggaaacctc  32880
acatttatca gggagccata gatagccatt ttaaaccaat tagctaacac cgccccacca  32940
gctctacact gaagagaacc gggagagtta caatgacagt gaataatcca tctctcataa  33000
cccctgatgg tctgatggaa atccagatct aacgtggcac agcagataca cactctcata  33060
tacattttca tcacatggtt ttcccaggcc gttaaaatac aatcccaata cacgggccac  33120
tcctgcagta caataaagct aatacaagat ggtatactcc tcacctcact aacattgtgc  33180
atgttcatat tttcacattc taagtaccga gagttctcct ctacaacagc actgctgcgg  33240
tcctcacaag gtggtagctg gtgacgatcg taaggagcca gtctgcaacg ataccgtctg  33300
tcgcgctgca tcgtagacca gagaccgacg cacctcctgg tacttgtggt agcagaacca  33360
cgtccgctgc caacaggtat ccacgtaacg ccggtccctg cgtcgcgcgc gctctgttct  33420
caatgcaaaa tgcagccact cttgtaatcc acacagatcc ctctcggcct ccgggaggat  33480
acacacttca aacctacaaa tgtctcggta cagttccaaa cacgaagtga gggcgagttc  33540
caaccaagac aggcaggctg gtctatcccg acacactgga ggtggaggaa gacacggaag  33600
aggcatgtta ttccaagcga ttcaccaacg ggtcgaaatg aagatcccga agatgacaac  33660
ggtcgcctcc ggagccctga tggaatttaa cagccaaatc aaacattatg cgattttcca  33720
ggctatcgat cgcggcctcc aaaagagcct ggacccgcac ttccacaaac accagcaaag  33780
caaaagcgtt attatcaaac tcttcgatca tcaagctgca agactgtaca atgcccaagt  33840
aattttcatt tctccactcg cgaatgatgt cgcggcaaat agtctgaagg ttcatgccgt  33900
gcatattaaa aagctccgaa agggcgccct ctatagccat gcgtagacac accatcatga  33960
ctgcaagata tcgggctcct gagacacctg cagcagattt aacagaccca ggtcaggttg  34020
ctctccgcga tcgcgaatct ccatccgcaa ggtcatttgc aaataattaa atagatctgc  34080
gccgactaaa tctgttaact ccgcgttagg aactaaatca ggtgtggcta cgcagcacaa  34140
aagttccagg gatggcgcca aactcactag aaccgctccc gagtagcaaa actgatgaat  34200
gggagtaaca cagtgtaaaa tgttcagcca aaaatcacta agccgctcct ttaaaaagtc  34260
cagtacttct atattcagtt cgtgcaagta ctgaagcaac tgtgtgggaa tatgcacaac  34320
aaaaaaaata gggcggctca gatacatgtt gacctaaaat aaaaagaatc attaaactaa  34380
agaagcttgg cgaacggtgg gataaatgac acgttccagc agcaggcaag caaccggctg  34440
tccccgggaa ccgcggtaaa attcatccga atgattaaaa agaacaacag aaacttccca  34500
ccatgtactc ggttggatct cctgagcaca gagcaatacc cccctcacat tcatatccgc  34560
cacagaaaaa aagcgtccca gatacccagc gggaatatcc aacgacagct gcaaagacag  34620
caaaacaatc cctctgggag caatcacaaa atcctccggt gaaaaaagca catacatatt  34680
agaataaccc tgctgctggg gcaaaaaggc ccgtcgtccc agcaaatgca cataaatatg  34740
ttcatcagcc attgccccgt cttaccgcgt aaacagccac gaaaaattcg agctaaaatc  34800
cacccaacag cctatagcta tatatacact ccgcccaatg acgctaatac cgcaccaccc  34860
accgccaaag ttcacccaca cccacgaaac ccgcgaaaat ccagcgccgt cagcacttcc  34920
gcaatttcag tctcacaacg tcacttccgc gcgccttttc acattcccac acccgcccac  34980
aaaccccgcg tcaccgcccg tcaccccggc cccgcctcgc tcctccccgc tcattatcat  35040
```

-continued

```
attggcacgt ttccagaata aggtatatta ttgatgatg                    35079

<210> SEQ ID NO 2
<211> LENGTH: 34391
<212> TYPE: DNA
<213> ORGANISM: Simian Adenovirus 4310A (sAd4310A) Wild Type

<400> SEQUENCE: 2

catcatcaat aatatacctt attctggaaa cgtgccaata tgataatgag cggggaggag     60

cgaggcgggg ccggggtgac gtgcggtgac gcggggtgac gcggggtggc gcgagggcgg    120

ggcgggtgtg cggaggcgct tagtttttac gtatgcggaa ggaggtttta taccggaagt    180

tgggtaattt gggcgtatac ttgtaagttt tgtgtagttt ggcgcgaaaa ccgggtaatg    240

aggaagttga ggttaatatg tactttttat gactgggcgg aatttctgct gatcagcagt    300

gaactttggg cgctgacggg gaggtttcgc tacgtggcag taccacgaga aggctcaaag    360

gtcccattta ttgtactcct cagcgttttc gctgggtatt taaacgctgt cagatcatca    420

agaggccact cttgagtgcc ggcgagtaga gttttctcct ccgcgctgcc gcgatgaggc    480

tggttcccga gatgtacggt gttttctgca gcgagacggc ccggaactca gatgagctgc    540

tgaattcaga cctgctggaa atttcgaatt cgcctgtgct tttgccgccg tcacttcacg    600

acctgtttga tgtggaagtg gaccctccgg aagatcccaa cgaggacgcg gtaaatacta    660

tgtttccaga atgtctgttt gaggcggctg aggagggttc ttacagcggt gaagacggcg    720

ggcagggaga ggaagtggac ctgaagtgct acgaggaatg tctaccttct agcgattctg    780

aaacggaaca gacaggggga gatggctgtg ctgaacctgt tgtgaaaaat gaacttgtat    840

tagactgtcc tgataatcct ggtcacggtt gccgcgcctg tgattttcat agaaatgcca    900

gtggaaatcc tgagactcta tgtgctctgt gttacctgcg ccttaccagc cattgtgtat    960

acagtaagta gaaacttttt cgctttgtgc atgctggtgg gatttttaaa gtgcgttggg   1020

cttattgttg cgtaatgttt tacaggcgac gtgtctgacg cggaagggga tggagataga   1080

tcaggctctg ctggttctcc ttgcactttg gggctgtgg ttccagatgg cattattaaa   1140

cccgtggcgg taagagtttc aggcagacgg tgtgcggtcg aaaaaattga agacttgctg   1200

caggaggaac agatgcaacc tttggacctg tccctgaaac gccctaagct gacctaagag   1260

tgtttattgt atgcaataaa aagtgttgat ctttgaactg tgtttatgtg ttgggtgtgt   1320

ctgtgggtat ataagcaggt ggatgggaag tgagagcaca gctgcttcag atggatctgc   1380

taggagacct gagggaattt ggcgtggttc ggcgcttgct ggagttggcc tctgacagaa   1440

cttccaagtt ttggaggttt tgttttggct caacgcttag caacgtgcta tatagggtca   1500

agaaggagca ggagacgcag tttgctaggc tgttggccga tactcctgga gtttttgtgg   1560

ctctggatct aggccatcac tctcttttcc aagagaaaat tatcaaaaac ttaactttta   1620

cgtctcctgg tcgcacggtt gcttccgctg cctttattac ctatattttg gatcaatgga   1680

gcaacagcgg cagtcacctg tcgtgggagt acatgctgga ttacatgtcg atggcgctgt   1740

ggagggccat gctgcggagg agggtttgca tttacttgcg ggcgcagcct ccgcggctgg   1800

accgagtgga ggaggaggac gagccggggg agaccgagaa cctgagggcc gggctggacc   1860

ctccaacgga ggactaggtg ctgaggatga tcccgaagag gggactagtg gggctaggaa   1920

gaagcaaaag actgagtctg aacctcgaaa ctttttgaat gagttgactg tgagtttgat   1980

gaatcgtcag cgtccggaga caattttctg gtctgaattg gaggaggaat tcaggagggg   2040

ggaactgaac ctgctataca agtatgggtt tgaacagttg aaaactcact ggttggagcc   2100
```

gtgggaggat tttgaaaccg ccttggacac ttttgctaaa gtggctctgc gaccggataa 2160
ggtttacact atccgccgca ctgttaacat aaagaagagt gtttatgtta taggccatgg 2220
agctctggtg caggtgcaaa ccgccgaccg ggtggccttt agttgcggca tgcaaaatct 2280
gggccccggg gtgataggct taaatggtgt aacatttcac aatgtaaggt ttactggtga 2340
aagttttaac ggctctgtgt ttgcaaataa cacacagctg acgctccacg gcgtttactt 2400
ttttaacttt aataacacat gtgtggagtc gtggggcagg gtgtctttga ggggctgctg 2460
ttttcacggc tgctggaagg cggtggtggg aagacttaaa agtgtaacat ctgtaaaaaa 2520
atgcgtgttt gagcgctgtg tgttggcttt aaccgtggag ggctgtggac gcattaggaa 2580
taatgcagcg tctgagaatg gatgtttcct tttgctaaaa ggcacggcta gcgttaagca 2640
taacatgata tgcggcagcg gtttgtaccc ttcgcagctg ttaacttgcg cggatggaaa 2700
ctgtcagacc ctgcgcaccg tgcacatagc gtcccaccag cgacgcgcct ggccaacatt 2760
cgagcacaat atgcttatgc gctgtgccgt tcacctgggc cctaggcgag gcgtgtttgt 2820
gccttaccag tgtaacttta gccataccaa gtttttacta gaacctgaca ccttctctcg 2880
agtgtgtttc aacggggttt ttgacatgtc aatggaactg tttaaagtga taagatatga 2940
tgaatccaag tctcgttgtc gcccatgtga atgcggagct aatcatttga ggttgtatcc 3000
tgtaactctg aacgtcaccg aggagctgag aacggaccac cacatgctgt cttgcctgcg 3060
cactgactat gaatccagcg acgaggagtg aggtgagggg cggagccaaa cgggtataaa 3120
ggggcgtgag ggtcggtgc ggtgtttcaa aatgagcggg acgacggacg gcaatgcgtt 3180
tgagggggga gtgttcagcc catatctgac atctcgtctt ccttcctggg caggagtgcg 3240
tcagaatgta gtgggatcca ccgtggacgg acgaccggtg gctcctgcaa attccgccac 3300
cctcacctat gccaccgtgg gatcatcgtt ggacactgcc gcggcagctg ccgcttctgc 3360
tgccgcttct actgctcgcg gcatggcggc tgattttgga ctgtataacc aactggccac 3420
tgcagctgtg gcgtctcggt ccctggttca agaagatgcc ctgaatgtga ttctgactcg 3480
cctggagatc atgtcacgcc gcctggacga actggctgcg cagatatcct caactaaccc 3540
cgataccact tcagaacctt aaataaagac aaacaaattt gttgaaaagt aaaatggctt 3600
tatttgtttt tttggctcgg taggctcggg tccacctgtc ccggtcgtta aggaccttgt 3660
gtatgttttc caagacccgg tacagatggg cttggatgtt caagtacatg ggcatgaggc 3720
catctcgggg gtggagatag gaccattgca gagcgtcatg ctccggggtg gtgttgtaaa 3780
taacccagtc gtagcagggt ttctgagcgt ggaactggaa gatgtccttt aggagcaggc 3840
tgatggccaa gggcagcccc ttagtgtagg tgttaacaaa gcggttaagc tgggagggat 3900
gcatgcgggg ggagatgata tgcatcttgg cttgaatttt gaggttagct atgttaccac 3960
ctaggtccct gcgggggttc atgttatgaa ggaccaccag cacggtgtag ccggtgcact 4020
tggggaactt gtcatgcagt ttggagggga aggcgtggaa gaatttagag acccccttgt 4080
ggcctcctag gttttccatg cactcatcca taatgatggc aatgggaccc ctggcggccg 4140
ctttggcaaa cacgttttgg gggttggaaa catcatagtt ttgctctaga gtgagctcat 4200
cataggccat cttaacaaag cggggtagga gggtgcccga ctgggggatg atagttccat 4260
ctgggcctgg ggcgtagttg ccctcacaaa tctgcatttc ccaggcctta atttccgagg 4320
ggggtatcat gtccacctgg ggggcgataa agaacacggt ttctggcggg ggattgatga 4380
gctgggtgga aagcaagtta cgcaacagtt gggatttgcc gcaaccggtg ggaccgtaga 4440

```
tgaccccgat gacgggttgc agctggtagt tgagagagga acagctgccg tcggggcgca   4500
ggaggggggc tacatcgttc atcatgcttc tgacatgttt attttcactc actaagtttt   4560
gcaagagcct ctccccaccc aggataaga gttcttccag gctgttgaag tgtttcagcg   4620
gtttcaggcc gtctgccatg ggcatctttt caagcgactg acgaagcaag tacagtcggt   4680
cccagagctc ggtgacgtgc tctatggaat ctcgatccag cagacttctt ggttgcgggg   4740
gttgggccga ctttcgctgt agggcaccag ccggtgggcg tccagggccg cgagggttct   4800
gtccttccag ggtctcagcg ttcgggtgag ggtggtctcg gtgacggtga agggatgagc   4860
cccgggctgg gcgcttgcga gggtgcgctt caggctcatc ctgctggtgc tgaagcgggc   4920
gtcgtctccc tgtgagtcgg ccagatagca acgaagcatg aggtcgtagc tgagggactc   4980
ggccgcgtgt cccttggcgc gcagctttcc cttggaaacg tgctgacatt tggtgcagtg   5040
cagacacttg agggcgtaga gtttgggggc caggaagacc gactcggacg agtaggcgtc   5100
ggctccgcac tgagcgcaga cggtctcgca ctccaccagc cacgtgagct cgggtttagc   5160
gggatcaaaa accaagttgc ctccattttt tttgatgcgt ttcttacctt gcgtctccat   5220
gagtctgtgt cccgcttccg tgacaaaaag gctgtcggtg tccccgtaga ccgacttgag   5280
ggggcgatct tccaaaggtg ttccgagatc ttccgcgtac aggaactggg accactccga   5340
gacaaaggct cgggtccagg ctaacacgaa ggaggcgatc tgcgaggggt atctgtcgtt   5400
ttcaatgagg gggtccacct tttccagggt gtgcagacac aggtcgtcct cctccgcgtc   5460
cacgaaggtg attggcttgt aagtgtaggt cacgtgaccc gcaccccccc aaggggtata   5520
aaagggggcg tgcccactct ccccgtcact ttcttccgca tcgctgtgga ccagagccag   5580
ctgttcgggt gagtaggccc tctcaaaagc cggcatgatt tcggcgctca agttgtcagt   5640
ttctacaaac gaggaggatt tgatattcac gtgccccgcg gcgatgcttt tgatggtgga   5700
ggggtccatc tgatcagaaa acacgatctt tttattgtca agtttggtgg cgaaagaccc   5760
gtagagggcg ttggaaagca acttggcgat ggagcgcagg gtctgatttt tctcccgatc   5820
ggccctctcc ttggcggcga tgttgagttg cacgtactcg cgagccacgc accgccactc   5880
ggggaacacg gcggtgcgct cgtcgggcag gatgcgcacg tgccagccgc ggttgtgcag   5940
ggtgatgagg tccacgctgg tggccacctc cccgcggagg ggctcgttgg tccaacacaa   6000
tcgccccct tttctggagc agaacggagg caggggatct agcaagttgg cgggcggggg   6060
gtcggcgtcg atggtaaata tgccgggtag cagaatttta ttaaaataat cgatttcggt   6120
gtccgtgtct tgcaacgcgt cttcccactt cttcaccgcc agggcccttt cgtagggatt   6180
taggggcggt ccccagggca tggggtgggt cagggccgag gcgtacatgc cgcagatgtc   6240
gtacacgtac aggggctccc tcaacacccc gatgtaagtg ggtaacagc gcccccgcg   6300
gatgctggct cgcacgtagt cgtacatctc gtgagaggga gccatgagcc cgtctcccaa   6360
gtgggtcttg tggggtttct cggcccggta gaggatctgc ctgaagatgg cgtgggagtt   6420
ggaagagatg gtggggcgtt ggaagacgtt aaagttggct ccgggcagtc ccacggagtc   6480
ttggatgaat tgggcgtagg attcccggag cttgtccacc agggctgcgg ttaccagcac   6540
gtcgagagcg cagtagtcca acgtctcgcg gaccaggttg taggccgtct cttgtttttt   6600
ctcccacagt tcgcggttga ggaggtattc ctcgcggtct ttccagtact cttcggcggg   6660
aaatcctttt tcgtccgctc ggtaagaacc taacatgtaa aattcgttca cggctttgta   6720
tggacaacag ccttttttcta ccggcagggc gtacgcttga gcggcctttc tgagagaggt   6780
gtgggtgagg gcgaaggtgt cccgcaccat cactttcagg tactgatgtt tgaagtccgt   6840
```

```
gtcgtcgcag gcaccctgtt cccacagcgt gaagtcggtg cgctttttct gcctgggatt   6900
ggggagggcg aaggtgacgt cgttaaagag gattttcccg gcgcggggca tgaagttgcg   6960
agagatcctg aagggtccgg gcacgtccga gcggttgttg atgacttgcg ccgccaggac   7020
gatctcatcg aagccgttga tgttgtggcc cacgatgtaa agttcgataa agcgcggctg   7080
tcccttgagg gccggcgctt ttttcaactc ctcgtaggtg agacagtccg gcgaggacag   7140
acccagctca gcccgggccc agtcggagag ttgaggatta gccgcgagga aggaactcca   7200
tagatccaag gccaggagag tttgcaagcg gtcgcggaac tcgcggaact ttttgcccac   7260
ggccattttc tccggcgtta ccacgtaaaa ggtgtcgggg cggttgttcc agacgtccca   7320
tcggagctct agggccagct cgcaggcttg gcgaacgagg gtctcctcgc ccgagacgtg   7380
catgaccagc atgaagggta ccaactgttt cccgaacgag cccatccatg tgtaggtttc   7440
tacgtcgtag gtgacaaaga gccgctgggt gcgcgcgtgg gagccgatcg ggaagaagct   7500
gatctcctgc caccagctgg aggaatgggt gttgatgtgg tgaaagtaga agtcccgccg   7560
gcgcacagag cattcgtgct gatgtttgta aaagcgaccg cagtagtcgc agcgttgcac   7620
gctctgtatc tcctgaatga gatgcgcttt tcgcccgcgc accagaaacc ggagggggaa   7680
gttgagactg gggcttggtg gggcggcatc cccttcgcct tggcggtggg agtctgcgtc   7740
tgcgcccttc ttctctgggt ggacgacggt ggggacgacg acgccccggg tgccgcaagt   7800
ccagatctcc gccacggagg ggcgcaggcg ctgcaggagg gggcgcagct gcccgctgtc   7860
cagggagtcg agggcggccg cgctgaggtc gacgggaagc gtttgcaagt tcactttcag   7920
aagaccggta agagcgtgag ccaggtgcag atggtacttg atttccaggg gggtgttgga   7980
agaggcgtcc acggcgtaga ggaggccgtg tccgcgcggg gtcaccaccg tgccccgagg   8040
aggttttatc tcactcgtcg agggcgagcg ccgggtggta gaggcggctc tgcgccgggg   8100
ggcagcggag gcagaggcac gttttcgtga ggattcggca gcggttgatg acgagcccgg   8160
agactgctgg cgtgggcgac gacgcggcgg ttgaggtcct ggatgtgctg tctctgcgtg   8220
aagaccaccg gtccccgggt cctgaacctg aaagagagtt ccacagaatc aatgtctgca   8280
tcgttaacgg cggcctgcct gaggatctcc tgtacgtcgc ccgagttgtc ttgataggcg   8340
atctcggcca tgaactgctc cacttcttcc tcgcggaggt cgccgtggcc cgctcgctcc   8400
acggtggcgg ccaggtcgtt ggagatgcga cgcatgagtt gagagaaggc gttgaggccg   8460
ttctcgttcc acacgcggct gtacaccacg tttccgaagg agtcgcgcgc tcgcatgacc   8520
acctgggcca cgttgagttc cacgtggcgg gcgaagacgg cgtagtttct gaggcgctgg   8580
aagaggtagt tgagcgtggt ggcgatgtgc tcgcagacga agaagtacat gatccagcgc   8640
cgcagggtca tctcgttgat gtctccgatg gcttcgagac gctccatggc ctcgtagaag   8700
tcgacggcga agttgaaaaa ttgggagttg cgggcggcca ccgtgagttc ttcttgcagg   8760
aggcggatga gatcggcgac cgtgtcgcgc acctcctgct cgaaagcgcc ccgaggcgcc   8820
tctgcttctt cctccggctc ctcctcttcc aggggcacgg gttcctccgg cagctctgcg   8880
acggggacgg ggcggcgacg tcgtcgtctg accggcaggc ggtccacgaa gcgctcgatc   8940
atttcgccgc gccggcgacg catggtctcg gtgacggcgc gtccgttttc gcgaggtcgc   9000
agttcgaaga cgccgccgcg cagagcgccc ccgtgcaggg agggtaagtg gttagggccg   9060
tcgggcaggg acacggcgct gacgatgcat tttatcaatt gctgcgtagg cactccgtgc   9120
agggatctga gaacgtcgag gtcgacggga tccgagaact tctctaggaa agcgtctatc   9180
```

-continued

```
caatcgcaat cgcaaggtaa gctgaggacg gtgggccgct ggggggcgtc cgcgggcagt   9240
tgggaggtga tgctgctgat gatgtaatta aagtaggcgg tcttcaggcg gcggatggtg   9300
gcgaggagga ccacgtcttt gggcccggcc tgttgaatgc gcaggcgctc ggccatgccc   9360
caggcctcgc tctgacagcg acgcaggtct ttgtagtagt cttgcatcag tctctccacc   9420
ggaacctctg cttctcccct gtctgccatg cgagtcgagc cgaagccccg caggggctgc   9480
agcaacgcta ggtcggccac gaccctctcg gccagcacgg cctgttgaat ctgcgtgagg   9540
gtggtctgga agtcgtccag gtccacgaag cggtgatagg cccccgtgtt gatggtgtag   9600
gtgcagttgg ccataacgga ccagttgacg acttgcatgc cgggttgggt gatctccgtg   9660
tacttgaggc gcgagtaggc gcgggactcg aacacgtagt cgttgcatgt gcgcaccaga   9720
tactggtagc cgaccaggaa gtgaggaggc ggttctcggt acaggggcca gccgacggtg   9780
gcgggggcgc cgggggacag gtcgtccagc atgaggcggt ggtagtggta gatgtagcgg   9840
gagagccagg tgatgccggc cgaggtggtc gcggccctgg tgaattcgcg gacgcggttc   9900
cagatgttgc gcaggggggcg aaagcgctcc atggtgggca cgctctgccc cgtgaggcgg   9960
gcgcaatctt gtacgctcta gatggaaaaa agacagggcg gtcatcgact cccttccgta  10020
gctcgggggg taaagtcgca agggtgcggc ggcggggaac cccggttcga gaccggccgg  10080
atccgccgct cccgatgcgc ctggccccgc atccacgacg tccgcgccga gacccagccg  10140
cgacgctccg ccccaatacg gaggggagtc ttttggtgtt ttttcgtaga tgcatccggt  10200
gctgcggcag atgcgacctc agacgcccac caccaccgcc gcggcggcag taaacctgag  10260
cggaggcggt gacagggagg aggaggagct ggctttagac ctggaagagg gagaggggtt  10320
ggcccggctg ggagcgccgt ccccagagag acaccctagg gttcagctcg tgagggacgc  10380
caggcaggct tttgtgccga agcagaacct gtttagggac cgcagcggtc aggaggcgga  10440
ggagatgcgc gattgcaggt ttcgcgcggg cagagagctg agggcgggct tcgatcgcga  10500
gcggctcctg agggcggagg atttcgagcc cgacgagcgt tctggggtga gcccggcccg  10560
cgctcacgtc tcggcggcca acctggtgag cgcgtacgag cagacggtga acgaggagcg  10620
caacttccaa aagagcttta acaatcacgt gaggaccctg atcgcgaggg aggaggtgac  10680
catcgggctg atgcatctgt gggacttcgt ggaggcctac gtgcagaacc cggccagcaa  10740
acctctgacg gcccagctgt tcctgatcgt gcagcacagc cgcgacaacg agacgttccg  10800
cgacgccatg ttgaacatcg cggagcccga gggtcgctgg ctcttggatc tgattaacat  10860
cctgcagagc atcgtggtgc aggagagggg gctgagttta gcggacaagg tggcggccat  10920
taactattcg atgcagagcc tggggaagtt ctacgctcgc aagatctaca agagccctta  10980
cgtgcccata gacaaggagg tgaagataga cagcttttac atgcgcatgg cgctgaaggt  11040
gctgacgctg agcgacgatc tcggcgtgta ccgtaacgac aagatccaca aggcggtgag  11100
cgccagccgc cggcgggagc tgagcgacag ggagctgatg cacagcctgc agagggcgct  11160
ggcgggcgcc ggggacgagg agcgcgaggc ttacttcgac atgggagccg atctgcagtg  11220
gcgtcccagc gcgcgcgcct tggaggcggc gggctacccc gacgaggagg accgggatga  11280
tttggaggag gcaggcgagt acgaggacga agcctgaccg ggcaggtgtt gttttagatg  11340
cagcggccgg cggacggggc caccgcggat cccgcacttt tggcatccat gcagagtcaa  11400
ccttcgggcg tgaccgcctc cgatgactgg gcggcggcca tggaccgcat catggcgctg  11460
accacccgca accccgaggc ttttaggcag caaccccagg ccaaccgttt ttcggccata  11520
ttggaagcgg tggtaccgtc gcgcaccaac cccacacacg agaaagtcct gactatcgtg  11580
```

aacgccctgg tagacagcaa agctatccgc cgcgacgagg cggggctgat ctacaacgct 11640
ctgttggaac gggtggcgcg ctacaacagc actaacttgc agaccaatct ggatcgcctc 11700
accacggacg tgaaggaggc gctggctcag aaggagcggt ttctgaggga tagcaatctg 11760
ggttctctgg tggcactgaa cgcctttctg agcacgcagc cggccaacgt gccccgcggg 11820
caggaggatt acgtgagctt catcagcgct ctgagactgc tggtgtccga ggtgccccag 11880
agcgaggtgt accagtctgg gccggattac tttttcaga cgtcccgaca gggcttgcaa 11940
acggtgaacc tgactcaggc ctttaaaaac ttgcaaggta tgtggggcgt caaggccccg 12000
gtgggcgatc gcgccactat ctccagtctg ctgaccccca acactcgcct gctgctgctc 12060
ttgatcgcac cgttcaccaa cagtagcact atcagccgtg actcgtacct gggtcatctc 12120
atcactctgt accgcgaggc catcggccag gctcagatcg acgagcatac gtatcaggag 12180
atcactaacg tgagccgggc cctgggtcag gaagataccg gcagcctgga agccacgttg 12240
aactttttgc taaccaaccg gaggcaaaaa ataccctccc agttcacgtt aagcgccgag 12300
gaggagagga ttctgcgata cgtgcagcag tccgtgagcc tgtacttgat gcgcgagggc 12360
gccaccgctt ccacggcttt agacatgacg gctcggaaca tggaaccgtc cttttactcc 12420
gcccaccggc cgttcattaa ccgtctgatg gactacttcc atcgtgcggc cgccatgaac 12480
ggggagtact tcaccaatgc catcctgaat ccgcattgga tgcccccgtc cggcttctac 12540
accggggagt ttgacctgcc cgaagccgac gacggctttc tgtgggacga cgtgtccgat 12600
agcattttca cgccggggaa tcgccgattc cagaagaagg agggcggaga cgagctcccc 12660
ctctccagcg tggaggctgc ctctagggga gagagcccct ttcccagtct gtcttccgcc 12720
agtagcggtc gggtaacgcg cccgcggttg ccgggggaga gcgactacct gaacgacccc 12780
ttgctgcgac cggctagaaa gaaaaatttc cccaacaacg gggtggaaag cttggtggat 12840
aaaatgaatc gttggaagac ctacgcccag gagcagcggg agtgggagga cagtcagccg 12900
cgaccgctgg ttccgccgca ctggcgtcgc cagagagaag acccggacga ctccgcagac 12960
gatagtagcg tgttggacct gggagggagc ggagccaacc cctttgctca cttgcaaccc 13020
aaggggcgtt cgagtcgcct ctactaataa aaaagacgcg gaaacttacc agagccatgg 13080
ccacagcgtg tgtcctttct tcctctcttt cttcctcggc gcggcagaat gagaagagcg 13140
gtgagagtca cgccggcggc gtatgagggt ccgcccccctt cttacgaaag cgtgatggga 13200
tcagcgaacg tgccggccac gctggaggcg ccttacgttc ctcccagata cctgggacct 13260
accgagggca gaaacagcat ccgttactcc gagctggcgc ccctgtacga taccaccaag 13320
gtgtacctgg tggacaacaa gtcggcggac atcgcctccc tgaattacca aaacgaccac 13380
agcaactttc tgaccaccgt ggtgcagaac aatgacttca ccccgacgga ggcgggcacg 13440
cagaccatta actttgacga gcgttcccgc tggggcggtc agctgaaaac catcctgcac 13500
accaacatgc ccaacatcaa cgagttcatg tccaccaaca agttcagggc caggctgatg 13560
gttaaaaagg tagaaaacca gcctcccgag tacgaatggt ttgagttcac catccccgag 13620
ggcaactatt ccgagactat gactatcgat ctgatgaaca atgcgatcgt ggacaattac 13680
ctgcaagtgg ggaggcagaa cggggtattg gaaagcgata tcggtgtgaa atttgatacc 13740
agaaacttcc gactggggtg ggatcccgtg accaagctgg taatgccagg cgtgtacacc 13800
aacgaggctt ttcaccccga catcgtgctg ctgccggggt gcggcgtgga tttcactcag 13860
agccgcttga gtaacctgtt aggaatcagg aagcgccgtc ccttccagga gggctttcag 13920

-continued atcatgtatg aggacctgga gggaggtaac attcccgctc tactagatgt gacaaagtac 13980
gaacaaagtg tacagcgagc caaggcggaa gggcgagaga ttcgcggaga cacttttgcc 14040
gtgtctcccc aggatttggt tatagagccg ttagagcatg acagcaaaaa tcgtagttac 14100
aatcttttgc ccaacaaaac cgacacggcc tatcgcagct ggtttttggc ttacaactac 14160
ggagaccccg agaaaggagt gagatcatgg accatactca ccaccacgga cgtgacctgc 14220
ggctcgcagc aagtgtactg gtccctgccg gatatgatgc aagacccggt caccttccgc 14280
ccctccaccc aagtcagcaa cttcccggtg gtgggcaccg agctgctgcc cgtccatgcc 14340
aagagcttct acaacgagca ggccgtctac tcgcaactca ttcgccagtc caccgcgctt 14400
acccacgtgt tcaatcgttt tcccgagaac cagattctgg tgcgccctcc cgctcctacc 14460
attaccaccg tcagtgaaaa cgttcccgcc ctcacagatc acggaaccct accgctgcgc 14520
agcagtatca gtggagttca gcgcgtgacc atcaccgacg ccagacgtcg aacctgcccc 14580
tacgtttaca aagcgctcgg cgtggtggcc cctaaagttc tctctagtcg caccttttaa 14640
acatgtccat tctcatctct cccgataaca acaccggctg gggattgggc tccggcaaga 14700
tgtacggcgg ggctaagcga cgctccagtc agcatcccgt tcgcgttcgg ggtcacttcc 14760
gcgctccctg gggagcttac aagcgaggac tctctggccg aacggctgta gacgatacca 14820
tagatgccgt gattgccgac gcccgccggt acaaccccgg accggtcgct agcgccgcct 14880
ccaccgtgga ttccgtgatc gacagcgtgg tggccagcgc cagggcctat gctcgccgca 14940
agaggcggct gcatcggaaa cgtcgcccca ccgccgccat gctagcagcc agggccgtgc 15000
tgaggcgggc ccggagggta ggcaggaggg ctatgcgccg cgctgccgcc aacgccgccg 15060
ggagggcccg cagacaagcc gcccgccagg ccgccgctgc catcgctagc atggccagac 15120
ccaggagagg gaacgtgtac tgggtgcgcg attctgtaac gggagtccga gtgccggtgc 15180
gcagccgacc tccccgaagt tagaagatcc aagctgcgaa gacggcggta ctgagtctcc 15240
ctgttgttat tagcccaaca tgagcaagcg caagtttaaa gaagaactgc tgcagacgct 15300
ggtgcctgag atctatggcc ctccggacgt gaagcctgac attaagcccc gcgatatcaa 15360
gcgtgttaaa aagcgggaaa aaaaagagga acttgcggcg gtagacgatg gcggtgtaga 15420
atttattagg agtttcgccc cacggcgcag ggttcaatgg aaagggcggc gtgtacaacg 15480
cgttctgagg ccgggcaccg cggtagtttt taccccggga gagcggtcgg ccgttagggg 15540
tttcaagcgg cagtacgatg aggtgtacgg cgacgaagac atactggaac aggcggctca 15600
gcagattgga gaattcgctt atggcaaacg ttctcggcgc gaagacctgg ccatcgcctt 15660
ggacagcggc aatcccacac ccagcctcaa acccgtgacg ctgcaacagg tgcttcccgt 15720
gagcgccagt actgacagca aaagggggat taaaagagag atggaagagc tgcaacccac 15780
catccaactt atggtcccta aacgacagag gttggaagag gtcctggaga agatgaaagt 15840
ggaccccagc atagagccgg atgtgaaagt gaggcctatt aaggaagtgg cccccggtct 15900
tggggtgcaa acggtggaca ttcaaatccc cgtcacgtcc gcttcaacag cggtggaagc 15960
catggaaacg caaacggaag cccccgccgt cacggtcggt accagggaag tggcgttgca 16020
aacggaaccc tggtacgaat acgccacccc taggcgtcag aggcggtccg cccgttacgg 16080
acccgtcaac gccatcatgc ccgagtacgc gctacatccg tctatccggc ccactcccgg 16140
ctaccgggga gtgacgtatc gcccgtcagg aactcgccgc cgttaccgtc gccgccgtcg 16200
ctctcgccgc gctctggccc cagtgtcggt gcggcgcgtg acccgccagg ggaaaacagt 16260
caccatcccc aacccgcgct accaccctag cattctttaa tgactctgcc gttttgcaga 16320

```
tggctctgac ttgccgcgtg cgccttcccg ttctgcacta tcgaggaaga tctcgtcgta  16380
ggagaggcat ggcgggcagt ggtcgccggc gggctttgcg caggcgcatg aaaggcggaa  16440
ttttacccgc cctaatacct ataatcgccg ccgccatagg cgccataccc ggcgtcgctt  16500
cagtggcctt gcaagcagct cgtaataaat aaacgaaggc ttttgcactt atgtcctggt  16560
cctgactatt ttatgcagaa aaagcatgga agacatcaat tttacgtcgc tggctccgcg  16620
gcaaggctcg cggccgctca tgggcacctg gaacgacatc ggcaccagtc agctcaacgg  16680
gggcgctttc aattgggggga gcctttggag cggcattaaa aactttggct ccacgattaa  16740
atcctacggc agcaaagcct ggaacagtag tgctggtcaa atgctccgag ataaactgaa  16800
ggacaccaac ttccaagaga aagtggtcaa cggggtggtg accggcatac acggcgcggt  16860
agatcttgcc aaccaagcgg tgcagaaaga gattgacagg cgattggaaa actcgcgggt  16920
gccgccgcag agaggggatg aggtggaggt cgaggaagta gaagtagagg aaaagctgcc  16980
ccccttggag aaagttcccg gtgcgattcc aaggccgcag aagcggccaa ggccagaact  17040
agaagaaact ctggtgacgg agagcaagga gcctccctcg tacgagcaag ccttaaaaga  17100
gggcgcttca ccctacccga tgaccaaacc gatcgcgcct atggctcggc cggtgtacgg  17160
gaaggactac aaacctgtca cgctagaact tcctccgcca ctcccttcgc gtcctacggt  17220
gcctcccatg ccagcgccgt cggccggtcc cgtgtctgca ccttccgcag cgcctctgcc  17280
agccgcccgc ccagtggccg tggccactgc cagaaacccc agaggccaga gaggagccaa  17340
ctggcaaaac acgctgaaca gcatcgtggg cctgggagtt aaaagcctga aacgccgccg  17400
ttgctattat taaaaaagtg tagctaaaaa atctcccgtt gtatacgcct cctatgttac  17460
cgccagagac gtgtgactgt cgtcgcgagc agcgctttca agatggccac cccatcgatg  17520
atgccgcagt ggtcttacat gcacatcgcc gggcaggacg cctcggagta tctgagcccc  17580
ggtcttgtgc agtttgcccg cgccaccgac acctacttca gcttgggaaa caagtttaga  17640
aatcccaccg tggcccccac gcacgatgtg accacggatc gttcgcagag gctgactctg  17700
cgctttgtac cggtagaccg tgaggatact gcctattctt acaaagttcg gtatacgtta  17760
gccgtaggag acaacagggt gctggacatg gccagtactt actttgacat ccgcggtgtt  17820
cttgaccgcg gtccaagctt taaaccgtat accggaacgg catacaatgc cttggctcca  17880
aagggcgctc caaatgcttg ccagtggaca acgaccaacg ggggcaataa aacgaacact  17940
tttgcccaag cccctttaat aggcacggct attgacggaa ccaacggact gcagattggg  18000
caagataatg gacaagctgt ttatgctgac aaaacctttc aacccgaacc acaagtggga  18060
gaatctcagt ggaatactaa tccaaccaca aacgcagcag gacgcgtgtt aaaaaacaact  18120
actcgcatgc tgccttgcta tggttctttt gcaaggccca ccaatgagaa agggggtcaa  18180
gcttcaggag acgttacctt ccaatttttc gacactgcct cggacaatgg caacaaccct  18240
aaggtggtgc tatatggaga agacgtcaac attgaatcgc ctgacacaca cttaatctac  18300
aaacccaccg ctgacaacac aaactctgaa aacctttttgg gtcaacaggc cgctccaaac  18360
agagccaatt acattgcctt tcgggacaac ttcattggac taatgtacta taattcaaca  18420
ggaaacatgg gagtgttggc agggcaggct tcccaactaa atgctgtggt agacttgcaa  18480
gacagaaaca ctgagctttc ctaccaactc atgttagatg caataggaga ccggagtcgt  18540
tacttttcaa tgtggaacca agcagtggac agctatgatc cagatgtgcg aattattgaa  18600
aatcatggcg ttgaggacga actgccaaat tactgcttcc ctcttaacgc tcaaggaatt  18660
```

-continued gctaacacct ataaaggcgt taagaaaaac aacggcaatt gggcgaaaga cgacgcagta 18720
gtagaaacta acgaaattgg cataggaaat gtttttgcca tggagataaa tttaactgct 18780
aacttgtggc gaaactttct gtattccaat attgctttgt acctgccaga ctcctacaag 18840
tattcaccgg gaaacataac cttacccgaa aacaaaaaca gttacaatta cattaatggt 18900
cgagtaacag ctcctggtct ggtagacacc tttgtaaaca ttggcgcgcg atggtctccc 18960
gaccccatgg acaacgtgaa tccttttaat caccatcgca atgctggtct gcgttatcgc 19020
tccatgcttc taggcaacgg ccgctacgtg cccttccaca ttcaggtgcc tcaaaaattc 19080
tttgccatta agaacctgct tctgctgcct gggtcctaca cctacgagtg gaacttcaga 19140
aaagatgtaa acatgatctt gcagagcacg ctgggcaacg acctccgtgt cgacggggcc 19200
agcgtcagat tcgacagcat taacctctac gctaatttct tccccatggc acataacacc 19260
gcttccaccc tggaggctat gttacgcaac gacaccaacg accagtcctt taatgactac 19320
ctctgcgcgg ccaacatgct ataccccatt cctgccaatg ccaccagtgt gcccatctcc 19380
atcccctctc gcaactgggc agctttcaga gggtggagtt tcacccgcct caaaacaaaa 19440
gaaacccccct cgctgggttc cggatttgat ccatactttg tttactcagg ctccattccc 19500
tacctggatg gtaccttcta cctgaaccac accttcaaaa aggtgtctat tatgttcgac 19560
tcttctgtga gctggcccgg caacgaccgc ctgctgaccc ctaatgagtt tgaaattaag 19620
cgctcggtgg acggagaagg atacaatgta gcccagagca acatgaccaa agactggttc 19680
ttaattcaaa tgctcagcca ctacaacatt ggttaccaag ggttttacgt gcccgaggct 19740
tacaaagaca gaatgtactc ctttttttaga aacttccaac ctatgagtag acaggtagtg 19800
gatgcagatc ggtatgaaca atacaaaaaa gtcaccgttg agtatcaaca taataattct 19860
ggttttgtgg gatacatggg acccaccatg agggaagggc aggcttatcc agcgaattac 19920
ccttatcctc ttattggaga caccgccgtg cccagcctga cccagaaaaa gttcctctgt 19980
gaccgcacca tgtggagaat cccctctct agcaacttca tgtctatggg ggccctcacc 20040
gacctggggc agaacatgct gtacgccaat tccgctcacg ccttggatat gacctttgag 20100
gtggaccccca tggatgagcc cacgcttctc tatgttctgt ttgaagtctt cgacgtggtg 20160
cgcatccacc agccgcaccg cggcgtcatc gaggccgtct acctgcgcac acctttctct 20220
gccggtaacg ccaccacata agaagcaaat gggctccagc gaacaggagc tgcgggccat 20280
tattcgcgac ctgggctgcg gaccctactt tttgggcacc ttcgacaagc gtttccccgg 20340
attcatgtcc ccccagaagc cggcctgtgc catagtcaac acggccgggc gggagaccgg 20400
gggggttcac tggctcgcct tcgcctggaa cccgcgcaac cgcacctgct acctgttcga 20460
cccttttggt ttttccgacg aaaggctgaa gcaaatctac cagttcgaat acgaaggact 20520
cctcaagcgc agcgctctgg cctccacgcc cgaccactgc gtcaccctgg aaaaatccac 20580
ccaaacggtg caggggcccc tctcggccgc ctgcgggctt ttctgttgca tgtttttgca 20640
cgccttcgtg cactggcctc acaaccccat ggagcgcaac cccaccatgg atctgctcac 20700
cggagtgccc aacagcatgc ttcacagccc ccaggtcgcc cccaccctgc gccgtaacca 20760
ggaacacctg tatcgctttc tggggaaaca ctctgcctat ttccgccgcc accggcagcg 20820
catcgagcag gccacggcct ttgaaagcat gagccaaaga gtgtaatcaa taaaaaccat 20880
ttttatttaa catgatacgc gcttctggcg tttttattaa aaatcgaacg gttcgaggga 20940
ggggtcctcg tgcccgctgg gaagggacac gttgcggtac tggaaacggg cgctccaacg 21000
aaactcgggg atcaccagcc gcggcagggg cacgtcttct aggttctgct tccagaactg 21060
ccgcaccagc tgcagggctc ccatgacgtc gggcgccgag atcttgaagt cgcagttagg 21120
gccggagccc ccgcggctgt tgcggaacac ggggttggca cactggaaca ccagcacgct 21180
ggggttgtaa atactggcca gggccgttgg gtcggtcacc tccgacgcat ccagatcctc 21240
ggcattgctc agggcgaacg gagtcagctt gcacatctgc cgtccgatct ggggcaccag 21300
gtcgggtttg ttgaggcaat cgcagcgcag agggattagg atgcgacgct gcccgcgttg 21360
catgataggg taactcgccg ccaggaactc ctccatctga cggaaggcca tctgggcctt 21420
ggtaccctcg gtgaaaaata gcccacagga cttgctagaa aatacgttat tgccgcagtt 21480
gatgtcttcc gcgcagcagc gtgcatcttc gttcttcagc tgaaccacgt tacgccccca 21540
gcggttctgg accaccttgg ctttcgtagg atgctccttc aacgcccgct gaccgttctc 21600
gctggtcaca tccatttcca ccacgtgctc cttgcagacc atctccactc cgtggaagca 21660
gaacaggacg ccctcctgct gggtattgcg atgctcccaa acggcacatc cggtgggctc 21720
ccagctcttg cgtttcaccc ccgcgtatgc ttccatgtaa gccatgagga atctgcccat 21780
cagctcggtg aaggtcttct ggttggtgaa ggttagcggc aggccgcggt gctcctcgtt 21840
caaccaagtt tgacagattt tgcggtacac ggctccctgg tcgggcagaa acttaaaagc 21900
cgctctgctc tcgttgtcca cgtggaactt ctccatcaac atcgtcatga cttccatgcc 21960
cttctcccac gccgtcacca acggttcggt cccggggttc ttcaccaaca cggcggtgga 22020
ggggccctcg ccggccccga cgtccttcat ggtcattctt tggaactcca cggtgccgtc 22080
cgcgcggcgt actctgcgca tcggagggta gctgaagccc acctccacca cggtgccttc 22140
gccctcgctg tcggaaacga tctccgggga tggcggcggc gcgggtgtcg ccttgcgagc 22200
cttcttcttg ggagggagcg gaggcacctc ctgctcgcgc tcggggctca tctcccgcaa 22260
gtagggggta atggagcttc cgggttggtt ctgacggttg gccattgtat cctaggcaga 22320
aagacatgga tcttatgcgc gaggaaactt taaccgcccc gtcccccgtc agcgacgaag 22380
aggtcatcgt cgaacaggac ccgggctacg ttacgccgcc cgaggatctg gagtccccct 22440
tagacgaccg acgcgacgct agtgagcggc aggaaaatga gaaagaggag gaggagggct 22500
gctacctcct ggaaggcgac gtcttgctaa agcatttcgc caggcagagc accatactca 22560
aggaggcctt gcaagaccgc tccgaggtgc ccttggacgt cgccgcgctc tcccaggcct 22620
acgaggcgaa ccttttctcg ccccgagtgc ctccgaagag acagcccaac ggcacctgcg 22680
agcccaaccc gcgactcaac ttctaccccg tgttcgccgt gcccgaggcg ctggccacct 22740
accacatctt tttcaaaaac cagcgcattc ccctttcctg ccgggccaac cgcaccgcag 22800
ccgataggaa gctaacactc agaaacggag ccagcatacc tgatatcacg tcactggagg 22860
aagtgcctaa gatcttcgag ggtctgggtc gagatgagaa gcgggcggcg aacgctctgc 22920
agaaagaaca gaaagagagt cagaacgtgc tggtggagct ggagggggac aacgcgcgtc 22980
tggccgtcct caaacgctgc atagaagtct cccacttcgc ctaccccgcc ctcaacttgc 23040
cacccaaagt tatgaaatcg gtcatggatc agctgctcat caagagagct gagcccctgg 23100
atcccgacca ccccgaggcg gaaaactcag aggacggaaa gcccgtcgtc agcgacgagg 23160
agctcgagcg gtggctggaa accggggacc cccaacagtt gcaagagagg cgcaagatga 23220
tgatggcggc cgtgctggtc accgtggagc tggaatgcct gcaacggttt ttcagcgacg 23280
tggagacgct acgcaaaatc ggggagtccc tgcactacac cttccgccag ggctacgtcc 23340
gccaggcctg caagatctcc aacgtggagc tcagcaacct ggtctcctac atgggcatcc 23400

-continued

```
tccacgagaa ccggctgggg cagagcgtgc tgcactgcac cttgcaaggc gaggcgcggc  23460
gggactacgt ccgcgactgc atctacctct tcctcaccct cacctggcag accgccatgg  23520
gcgtctggca gcagtgcttg gaagagagaa acctcaaaga gctagacaaa ctcctctgcc  23580
gccagcggcg ggccctctgg accggtttca gcgagcgcac ggtcgcctgc gccctggcag  23640
acattatctt cccggagcgc ctgatgaaaa ccttgcagaa cggcctgccg gattttatca  23700
gtcaaagtat tttgcaaaac ttccgctcct tcgttctgga gcgctccggg atcttgcccg  23760
ccatgagctg cgcgctgcct tctgactttg tcccccttc ctaccgcgag tgtcctcccc  23820
ccctgtggag ccactgctac ctcttccaac tggccaactt tctggcctac cactccgacc  23880
tcatggaaga cgtgagcgga gaggggctgc tcgagtgcca ctgccgctgc aacctctgca  23940
ccccccacag atcgctggcc tgcaacaccg agctgctcag cgaaacccag gtcataggta  24000
ccttcgagat ccaggggccc cagcagcaag agggtgcttc cggcttgaag ctcactccgg  24060
cgctgtggac ctcggcttac ttacgcaaat ttgtagccga ggactaccac gcccacaaaa  24120
ttcagttcta tgaagaccaa tctcgaccac ccaaagcccc cctcacggcc tgcgtcatca  24180
ctcagagcaa aatcctggcc caattgcaat ccatcaacca agcgcgccga gatttccttt  24240
tgaaaaaggg tcggggggtg tacctagacc cccagaccgg cgaggaactc aacccgtcca  24300
cactctccgt cgaagcagcc cccccgagac atgccgccca agggaaccgc caagcagctg  24360
atcgctcggc agagagcgaa gaagcaagag ctgctccagc agcagcagca ggtggaggac  24420
gaggaagagc tgtgggacag ccaggcagag gaggtgtcag aggacgagga ggagatggaa  24480
agctgggaca gcctagacga ggaggaggac gagctttcag aggaagaggc gaccgaagaa  24540
aaaccacctg catccagcgc gccttctctg agccgacagc cgaagccccg gcccccgacg  24600
cccccggccg gctcactcaa agccagccgt aggtgggacg ccaccggatc tccagcggca  24660
gcggcaacgg cagcgggtaa ggccaaacgc gagcggcggg ggtattgctc ctggcgggcc  24720
cacaaaagca gtatcgtgaa ctgcttgcaa cactgcgggg gaaacatctc ctttgcccga  24780
cgctacctcc tcttccatca cggtgtggcc ttccctcgca acgttctcta ttattaccgt  24840
catctctaca gcccctacga aacgctcgga gaaaaaagct aaggcctcct ctgccgcgag  24900
gaaaaactcc gccgccgctg ccgccgccaa ggatccgccg gccaccgagg agctgagaaa  24960
gcgcatcttt cccactctgt atgctatctt tcagcaaagc cgcgggcagc accctcagcg  25020
cgaactgaaa ataaaaaacc gctccttccg ctcactcacc cgcagctgtc tgtaccacaa  25080
gagagaagac cagctgcagc gcaccctgga cgacgccgaa gcactgttca gcaaatactg  25140
ctcagcgtct cttaaagact aaaagacccg cgctttttcc ccctcgggcg ccaaaaccca  25200
cgtcattgcc agcatgagca aggagattcc cacccttac atgtggagct atcagcccca  25260
gatgggcctg gccgcggggg ccgcccagga ctactccagc aagatgaact ggctcagcgc  25320
cggcccccac atgatctcac gagttaacgg catccgagcc caccgaaacc agatcctctt  25380
agaacaggcg gcaatcaccg ccacaccccg gcgccaactc aacccgccca gttggcccgc  25440
cgcccaggtg tatcaggaaa ctccccgccc gaccacagtc ctcctgccac gcgacgcgga  25500
ggccgaagtc ctcatgacta actctggggt acaattagcg ggcgggtcca ggtacgccag  25560
gtacagaggt cgggccgctc cttactctcc cgggagtata aagagggtga tcattcgagg  25620
ccgaggtatc cagctcaacg acgaggcggt gagctcctca accggtctca gacctgacgg  25680
agtcttccag ctcggaggag cgggccgctc ttccttcacc actcgccagg cctacctgac  25740
cctgcagagc tcttcctcgc agccgcgctc cgggggaatc ggcactctcc agttcgtgga  25800
```

agagttcgtc ccctccgtct acttcaaccc gttttccggc tcacctggac gctacccgga 25860
cgccttcatt cccaactttg acgcagtgag tgaatccgtg gacggctacg actgatgaca 25920
gatggtgcgg ccgtgagagc tcggctgcga catctgcatc actgccgcca gcctcgctgc 25980
tacgctcggg aggcgatcgt gttcagctac tttgagctgc cggacgagca ccctcagggg 26040
ccggctcacg ggttgaaact cgagatcgag aacgcgctcg agtctcgcct catcgacgcc 26100
ttcaccgccc ggcctctcct ggtagaaacc gaacgcggga tcactaccat caccctgttc 26160
tgcatctgcc ccacgcccgg attacatgaa gatctgtgtt gtcatctttg cgctcagttt 26220
aataaaaact gaactgtttg ccgcaccttc aacgccatct gtgatttcta caacaaaaag 26280
ttcttctggc aaaggtacac aaactgtatt ttattctaat tctacctcat ctattgtgct 26340
gaactgcgcc tgcactaacg aacttatcca gtggattgca aacggtagtg tgtgcaagta 26400
cttttggggg aacgagatag ttagtagaaa taacagcctt tgcaagcact gcaactcctc 26460
cacactaatc ctttatcccc catttgttac tggatggtat atgtgcgttg gctccggttt 26520
aaatcctagt tgctttcata agtggtttct acaaaaagag acccttccca acaattctgt 26580
ttcttttttc accctgtcct actgctgttc tccctctggt tactctttca aacctctaat 26640
tggtatttta gctttgatac tgataatctt tattaacttt ataataatta acaacttaca 26700
gtaaacatgc ttgttatcct cctgctcgcc acatttttcg ctctctctca cgccagaaca 26760
agtattgttg gcgcaggtta caatgcaact cttcaatctg cttacatgcc agattccgac 26820
cagataccoc atattacgtg gtacttacaa acctccaaac ctaattcttc attttatgaa 26880
ggaaacaaac tctgcgatga ctccgacaac aggacgcaca catttcccca cccttcacta 26940
caattcgaat gcgtaaacaa aagcttgaag ctttacaact taaagccttc agattctggc 27000
ttgtatcatg ctgtagttga aaaaagtaat ttagaagtcc acagtgatta cattgaattg 27060
atggttgtgg acctgccacc tccaaaatgt gaggtttcct cctcttacct tgaagttcaa 27120
ggcgtggatg cctactgcct catacacatt aactgcagca actctaaata tccagctaga 27180
atttactata atggacagga aagtaatctt ttttattatt taacaacaag cgctggtaac 27240
ggtaaacagt tacctgatta ttttactgct gttgttgaat tttccaccta cagagaaacg 27300
tatgccaagc ggccttacaa tttctcatac ccgtttaacg acctttgcaa tgaaatacaa 27360
gcgctcgaaa ctggaactga ttttactcca attttcattg ctgccattgt tgtgagctta 27420
attaccatta ttgtcagcct agcattttac tgcttttgca agcccaaaaa acctaagttt 27480
gaaaaactta aactaaaacc tgtcattcaa caagtgtgat tttgttttcc agcatggtag 27540
ctgcatttct acttctcctc tgtctaccca tcattttcgt ctcttcaact ttcgccgcag 27600
tttcccacct ggaaccagag tgcctaccgc cttttgacgt gtatctgatt ctcacctttg 27660
tttgttgtat atccatttgc agtatagcct gctttttttat aacaatcttt caagccgccg 27720
actatcttta cgtgcgaatt gcttacttta gacaccatcc tgaatacaga aatcaaaacg 27780
ttgcctcctt actttgtttg gcatgattaa gctattgcta atacttaatt atttacccct 27840
aatcaactgt aattgtccat tcaccaaacc ctggtcattc tacacctgtt atgataaaat 27900
ccccgacact cctgttgctt ggctttacgc agccaccgcc gctttggtat ttgtatctac 27960
ttgccttgga gtaaaattgt attttattct acacactggg tggctacatc ccagagaaga 28020
tttacctaga catcctcttg taaacgcttt tcaattacag cctctgcctc ctcctgatct 28080
tcttcctcga gctccctcta ttgtgagcta ctttcaactc accggtggag atgactgact 28140

-continued

```
ctcaggacat taatattagt gtggaaagaa tagctgctca gcgtcagcga gaaacgcgag  28200
tgttggaata cctggaacta caacagctta aggagtccca ctggtgtgag aaaggagtgc  28260
tgtgtcatgt taagcaggca gccctttcct acgatgtcag cgttcaggga catgaactgt  28320
cttacacttt gcctttgcag aaacaaacct tctgcaccat gatgggctct acctccatca  28380
caatcaccca acaagccggg cctgtagagg gggctatcct ctgtcactgt cacgcacctg  28440
attgcatgtc caaactaatc aaaactctct gtgctttagg tgatattttt aaaatgtaaa  28500
tcataataaa cttaccttaa atttgacaac aattttctgg tgacatcatt cagcagcacc  28560
actttaccct cttcccagct ctcgtatggg atgcgatagt gggtggcaaa cttcctccaa  28620
accctaaaag aaatattggt atccacttcc ttgtcctcac ccacaatttt catcttttca  28680
tagatgaaaa gaaccagagt tgatgaagac ttcaaccccg tctaccccta tgacaccaca  28740
accactcctg cagttccctt tatatcaccc ccctttgtaa acagcgatgg tcttcaggaa  28800
aaccccccag gtgttttaag tctgcgaata gctaaacccc tatatttcga catggagaga  28860
aaactagccc tttcacttgg aagagggttg acaattaccg ccgccggaca attagaaagt  28920
acgcagagcg tacaaaccaa cccaccgttg ataattacca acaacaacac actgacccta  28980
cgtcattctc ccccttaaa cctaactgac aatagcttag tgctaggcta ctcgagtccg  29040
ctccgcgtca cagacaacaa acttacattt aacttcacat caccactccg ttatgaaaat  29100
gaaaacctta cttttaacta tacagagcct cttaaactta taaataacag ccttgccatt  29160
gacatcaatt cctcaaaagg ccttagtagc gtcggaggct cactagctgt aaacctgagt  29220
tcagacttaa agtttgacag caacggatcc atagcttttg gcatacaaac cctgtggacc  29280
gctccgacct cgactggcaa ctgcaccgtc tacagcgagg gcgattccct acttagtctc  29340
tgtttaacca aatgcggagc tcacgtctta ggaagtgtaa gtttaaccgg tttaacagga  29400
accataaccc aaatgactga tatttctgtc accattcaat ttacatttga caacaatggt  29460
aagctactaa gctctccgct tataaacaac gcctttagta ttcgacagaa tgacagtacg  29520
gcctcaaacc ctacctacaa cgccctggcg tttatgccta acagtaccat atatgcaaga  29580
gggggaggtg gtgaaccacg aaacaactac tacgtccaaa cgtatcttag gggaaatgtt  29640
caaaaaccaa tcattcttac tgtaacctac aactcagccg ccacaggata ttccttatct  29700
tttaagtgga ctgctcttgc acgtgaaaag tttgcaaccc caacaacttc gttttgctac  29760
attacagaac aataaaaccg tgtaccccac cgtttcgttt ttttcagatg aaacgggcga  29820
gagttgatga agacttcaac ccagtgtacc cttatgaccc ccacatgct cccgttatgc  29880
ccttcattac tccacctttt acctcctcgg atgggttgca ggaaaaacca cttggagtgt  29940
taagtttaaa ctacagagat cccattacta cgcaaaatgg gtctcttaca gttaaactag  30000
gaaacggcct cactctagac aaccagggac aactaacatc aaccgctggg gaagtagaac  30060
ctccactcac taacgctaac aacaaacttg cactggtcta tagcgatcct ttagcagtaa  30120
agcgcaacag cctaacctta tcgcacaccg ctccccttgt tattgctgat aactctttag  30180
cattgcaagt ttcagagcct atttttataa atgacaagga caaactagcc ctgcaaacag  30240
ccgcgcccct tgtaactaac gctggcaccc ttcgcttaca aagcgccgcc cctttaggca  30300
ttgcagacca aaccctaaaa ctcctgttta ccaacccttt gtacttgcag aataactttc  30360
tcacgttagc cattgaacga ccccttgcca ttaccaatag tggaaagctg gctctacagc  30420
tctccccacc gctacaaaca gcagacacag gcttgacttt gcaaaccaac gtgccattaa  30480
ctgtaagcaa cgggacccta ggcttagcca taaagcgccc acttattgtt caggacaaca  30540
```

```
acttgttttt ggacttcaga gctcccctgc gtcttttcaa cagcgacccc gtactagggc  30600
ttaactttta cacccctctt gcagtgcgcg atgaggcgct cactgttaac acaggccgcg  30660
gcctcacagt gagttacgat ggtttaattt taaatcttgg taaggatctt cgctttgaca  30720
acaacaccgt ttctgtcgct cttagtgctg ctttgccttt acaatacact gatcagcttc  30780
gccttaacgt gggcgctggg ctgcgttaca atccagtgag taaaaaattg gacgtgaacc  30840
ccaatcaaaa caagggttta acctgggaaa atgactacct cattgtaaag ctaggaaatg  30900
gattaggttt tgatggcaat ggaaacatag ctgtttctcc tcaagttaca tcgcctgaca  30960
ccttatggac cactgccgat ccatccccca attgttccat ctacactgat ttagatgcca  31020
aaatgtggct ctcgttggta aaacaagggg gtgtggttca cggttctgtt gctttaaaag  31080
cattgaaagg aaccctattg agtcctacgg aaagtgccat tgttattata ctacattttg  31140
acaattatgg agtgcgaatt ctcaattatc ccactttggg cactcaaggc acgttgggaa  31200
ataatgcaac ttggggttat aggcagggag aatctgcaga cactaatgta ctcaatgcac  31260
tagcatttat gcccagttca aaaaggtacc caagagggcg tggaagcgaa gttcagaatc  31320
aaactgtggg ctacacttgt atacagggtg acctttctat gcccgtaccg taccaaatac  31380
agtacaacta tggaccaact ggctactcct ttaaatttat ttggagaact gtttcaagac  31440
aaccatttga catcccatgc tgtttttct cttacattac ggaagaataa aacaactttt  31500
ccttttatt ttcttttat tttacacgca cagtaaggct tcctccaccc ttccatttga  31560
cagcatacac cagcctctcc cccttcatgg cagtaaactg ctgcgagcca gtccggtatt  31620
tgggagttaa gatccaaaca gtctctttgg taatcagatg tcgatccgtg atggacacaa  31680
atccctgggg caggttctcc aacgtttcgg tgaaaaactg catgccgccc tacaaaacaa  31740
acaggttcag gctctccacg ggttatctcc ccgatcaaac tcagacaggg taaaggtgcg  31800
atgatgttcc actaaaccac gcaggtggcg ctgtctgaac ctctcggtgc gactcctgtg  31860
aggctggtaa gaagttagat tgtccagcag cctcacagca tggatcatca gtctacgagt  31920
gcgtctggcg cagcagcgca tctgaatctc actgagattc cggcaagaat cgcacaccat  31980
cacaatcagg ttgttcatga tcccatagct gaacacgctc cagccaaagc tcattcgctc  32040
caacagcgcc accgcgtgtc cgtccaacct tactttaaca taaatcaggt gtctgccgcg  32100
tacaaacatg ctacccgcat acagaacctc ccggggcagt cccctgttca ccacctgcct  32160
gtaccaggga aacctcacat ttatcaggga gccatagata gccatcttaa accaattagc  32220
taacaccgcc ccaccagctc tacactgaag agaaccggga gagttacaat gacagtgaat  32280
aatccatctc tcataacccc taatggtctg atggaaatcc agatctaacg tggcacagca  32340
gatacacact ttcatataca ttttcatcac atgtttttcc caggccgtta aaatacaatc  32400
ccaatacacg ggccactcct gcagtacaat aaagctaata caagatggta tactcctcac  32460
ctcactaaca ttgtgcatgt tcatattttc acattctaag taccgagagc tctcctctac  32520
aacagcactg ccgcggtcct cacaaggtgg tagctggtga caattgtagg gagccagtct  32580
gcagcgatac cgtctgtcgc gttgcatcgt agaccaggga ccgacgcact tcctcgtact  32640
tgtagtagca gaaccacgtc cgctgccagc acgtctccaa gtaacgccgg tccctgcgtc  32700
gctcacgctc cctcctcaac gcaaagtgca accactcttg taatccacac agatccctct  32760
cggcctccgg ggcgatgcac acctcaaacc tacagatgtc tcggtacagt tccaaacacg  32820
tagtgagggc gagttccaac caagacagac agcctgatct atcccgacac actggaggtg  32880
```

```
gaggaagaca cggaagaggc atgttattcc aagcgattca ccaacgggtc gaaatgaaga  32940
tcccgaagat gacaacggtc gcctccggag ccctgatgga atttaacagc cagatcaaac  33000
attatgcgat tttccaggct atcaatcgcg gcctccaaaa gagcctggac ccgcacttcc  33060
acaaacacca gcaaagcaaa agcgttatta tcaaactctt cgatcatcaa gctgcaggac  33120
tgtacaatgc ccaagtaatt ttcatttctc cactcgcgaa tgatgtcgcg gcaaatagtc  33180
tgaaggttca tgccgtgcat attaaaaagc tccgaaaggg cgccctctat agccatgcgt  33240
agacacacca tcatgactgc aagatatcgg gctcctgaga cacctgcagc agatttaaca  33300
gacccaggtc aggttgctct ccgcgatcgc gaatctccat ccgcaaggtc atttgcaaat  33360
aattaaatag atctgcgccg actaaatctg ttaactccgc gctaggaact aaatcaggtg  33420
tggctatgca gcacaaaagt tccagggatg gcgccaaact cactagaacc gctcccgagt  33480
agcaaaactg atgaatggga gtaacacagt gtaaaatgtt cagccaaaaa tcactaagct  33540
gctcctttaa aaagtccagt acttctatat tcagtccgtg caagtactga agcaactgtg  33600
cgggaatatg cacagcaaaa aaaatagggc ggctcagata catgttgacc taaaataaaa  33660
ataaacatta aactaaagaa gcttggcgaa cggtgggata tatgacacgc tccagcagca  33720
ggcaagcaac cggctgtccc cgggaaccgc ggtaaaattc atccgaatga ttaaaaagaa  33780
caacagaaac ttcccaccat gtactcggtt ggatctcctg agcacacagc aatacccccc  33840
tcacattcat atccgccaca gaaaaaaaac gtcccagata cccagtggga atatccaacg  33900
acagctgcaa agacagcaaa ataatccctc tgggagcaag cacaaaatcc tccggtgaaa  33960
aaagaacata catattagaa taaccctgtt gctggggcaa aaaggcccga cgtcccagca  34020
aatgcacata tatgtgttga tcagccattg ccccgtctta ccgcgtataa agccacgaaa  34080
aagtcgagct aaaatccacc caacagccta tagctatata tacactccgc ccaatgacgc  34140
taacaccgta ccacccacga ccaaagttca cccacaccca caaaacccgc gaaaatccag  34200
cgccgtcagc acttccgcaa tttcagtctc acaacgtcac ttccgcgcgc ctttttttcac  34260
tattcccaca cccgccctcg cgccaccccg cgtcaccccg cgtcaccgca cgtcaccccg  34320
gccccgcctc gctcctcccc gctcattatc atattggcac gtttccagaa taaggtatat  34380
tattgatgat g                                                      34391
```

<210> SEQ ID NO 3
<211> LENGTH: 34475
<212> TYPE: DNA
<213> ORGANISM: Simian Adenovirus 4312 (sAd4312) Wild Type

<400> SEQUENCE: 3

```
catcatcaat aatatacctt attctggaaa cgtgccaata tgataatgag tggggaggag     60
cgaggcgggg ccggggtggg gtgaggcggg gccggggtgg ggtgagggtg acgtcggggc    120
gggcggggcg gccgacgtgt gtggggaggc gcgtagtgtt tacgtatgcg gaaggaggtt    180
ttataccgga agatgggtaa tttgggcgta tacttgtaag ttttgtgtaa tttggcgcga    240
aaactgggta atgaggaagt tgaggttaat atgtactttt tatgactggg cggaatttct    300
gctgttcagc agtgaacttt gggcgctgac ggggaggttt cgctacgtgg cagtaccacg    360
agaaggctca aaggtcccat ttattgtact cctcagcgtt ttcgccgggt atttaaacgc    420
tgtcagatca tcaagaggcc actcttgagt gctggcgagt agagttttct cctccgcgct    480
gccacaatga ggctggtccc cgagatgttt ggtgtttttt gcgacgaggc ggcgcggaac    540
tcagatgacc tgctgaattc agatttgctg gaaattccca attcgcctgt ggcttcgcct    600
```

ccgtcacttc acgacctttt cgatgtggaa gtggatcctc cggcagatcc caacgaggac 660
gcggtaaata gtatgtttcc cgaatgtctg ttcgaggcgg ctgacgaggg tagcgacagc 720
ggtggagaga gtggacaggg tgaggaactg gacttaaaat gctacgagga atgcataccg 780
tctagcgatt ctgaaacgga acaaacaggg ggagatggct gcgctgagcc aactgagaaa 840
aatgaactta tattagactg tcctgaacat cctggtcatg gctgccgtgc ctgtgctttt 900
catagagatg ccagtggaaa tcctgaaact ctatgtgctc tgtgttacct gcgtcttacc 960
ggcaattttg tatacagtaa gtaggttttt tactttgtgt acggtaggga agtttttgta 1020
aagtgtgtta tgacttattg cttgtgtaat gttttacagg tgacgtgtct gatgtggagg 1080
agggagataa gtcagtccat actagttctc cttgcacttt gggggctgtg gttccagata 1140
atgttattaa acccgtggcg gtcagagtat caggcaggcg gtgtgcagtc gaaaaaattg 1200
aagacttgct gcaggaagag cagatgcaac ctttggacct gtccctcaaa cgccctaaga 1260
tgacctaagc ctgtttattg agtgcaataa aactgttgat ctttgaactg tgtttatgtg 1320
ttgggtgtgt ctgtggatat ataagcaggt ggatgggaag tgagagcaca tctgccttga 1380
tggatctgtt ggggaacttg cgggaatttg acgtggttcg tcgcttgctg gagttggcct 1440
ccgacaaaac ttccaggctt tggaggtttt ggtttggctc aacgcttagc agcgtagtgt 1500
acagggtcaa gaaggagcag gaggggcaat tttctaggct gttggctgat attcctggag 1560
tttttgtggc tctggattta ggccatcaca gtctttttca agagaaaatt gtcaaaagct 1620
taactttctc gtctcctggc cgcacggttg tttcagcagc ctttattacc tatattttgg 1680
atcaatggag cagcagcggc agccacctgt cgtgggatta catgctggat tacctggcaa 1740
tggccctgtg gagggccatg ctgcggagga gggtttgcat ttactcgcgg gcgcagcctc 1800
cgcggctgga tcgagtggtg gaggaggacg agccggacga gaccgagaac ctgagagccg 1860
gcctggaccc tccaatggaa gactaggtgc agaggataat cctgaagagg gaactagtgg 1920
gggtgctaga aaaaagcaaa aaaccgagac tgagcctaga aactttttga atgagctgac 1980
tgtgagtttg atgaatcgcc atcgtcccga gacaattttc tggtctgagt tggaggaaga 2040
gtttaggaag ggggatttga acctgctgta caagtatggg ttcgaacagt tgaagactca 2100
ctggttggag ccgtgggagg attttgaaac cgctctggac acttttgcta aagtggcttt 2160
gcggccggat aaagtttata ctatccgctg cactgttaat ataaggaaaa gtgtttatgt 2220
tataggccat ggagcactgg tgcaggtgga gaccgccgat cgggtggctt tcaactgcgg 2280
catgcagaat ctgggccctg ggtgataggg tgttaatggt gtcacgtttc agaacgtgag 2340
gttcgcgggt gaaagcttta gcggctccgt gtttgcaaat aacacacagc tcactctcca 2400
cggcgtttac ttttttaact ttaacaatac atgtgtggag tcgtggggca gggcgtcctt 2460
gaggggctgc acttttcacg gttgctggaa ggcggtggtg ggaagactga aaagtgtaac 2520
gtctgtgaaa aaatgcatat tcgagcggtg tgtgctagct gtaaccgtgg aagggcatgg 2580
acgcattaga aacaacgcag cgtctgagaa tgggtgtttt cttttactga aaggcacggc 2640
cagcgttaag cataacatga tctgtggcag tgggctgtac ccgtcgcagt tgttaacctg 2700
cgcggatgga aactgccaga cattgcgcac cgtgcacata gtgtctcacc cgcgtcgcca 2760
ctggccaacg tttgagcaca acttgcttat gcgttgtacg gtccatctgg ggcctagacg 2820
gggcatgttt gtgccttttc agtgtaactt tagccacact aagatcttac tagaagcaga 2880
tgccttcact cgagtgtgtt tcaatggggt gtttgacatg tcggtggaaa tttttaaagt 2940
gataagatat gatgaatcca agtctcgttg tcgcccctgt gaatgcggag ctaatcattt 3000
gaggttgtat cccgcgaccc tgaacgtaac cgaggagctg agggccgacc accacatgtt 3060
gtcctgcttg cgcaccgact atgagtccag cgacgaagag tgaggtgagg ggcggagcca 3120
caaagggtat aaagggtcag gatgggtggg cacaggtatt caaaatgagc gggacgacgg 3180
acggcaacgc gtttgagggg ggagtgttca gcccatatct gacatctcgt cttccttcct 3240
gggcaggagt gcgtcagaat gtagtgggct ccaccgtgga cggacggccg gtcgcccctg 3300
cgaattccgc cacccttacc tatgccaccg tgggatcacc gttggacact gccgcggcag 3360
ccgcagcttc tgctgccgct tctactgctc gcggtatggc ggctgacttt ggactttata 3420
accaactggc taccgcggct gtggcatctc gcactctggt tcaagaagat gccctgagcg 3480
tggttctgct tcgactggaa gatctgtctc gtcgcttgga tcagctggct gcgcagatat 3540
ccccacctaa ccccgatact actcaagaat cttaaataaa gacaaacaga tttgttgaaa 3600
ataaatggct ttatttgttt tttttggctc gataggctcg ggtccacctg tcccggtcgt 3660
taaggacttt gtgtatgctt tccaagaccc ggtacagatg ggcttggatg tttagataca 3720
tgggcatgag gccatcccgg gggtggagat aggaccattg cagagcgtca tgctccgggg 3780
tggtgttgta gatgacccag tcgtagcagg gtttttgggc gtggaactga aaaatgtcct 3840
tgagaagcag gctgatggcc aggggcagac ccttagtgta ggtgttcaca aagcggttga 3900
gctgggaggg atgcatgcgg ggagagatga tatgcatctt agcctggatt ttcaggttag 3960
ctatgttgcc ccccaggtcc cttcgagggt tcatattgtg gaggaccacc agaacggtgt 4020
agccggtaca cttgggaaac ttatcgtgca gtttggaggg gaaggcgtga aagaatttgg 4080
aaaccccttt gtgaccacct aagttttcca tgcactcgtc catgataatg gcgatgggcc 4140
ccttggcggc agctttagcg aacacgttgt gggggttgga aacatcatag ttttgctcta 4200
gagttagctc gtcataggcc atttttacga agcggggtag gagggtgcca gactgaggga 4260
cgatagttcc atctggcccc ggtgcgtaat taccctcgca gatctgcatc tcccaagctt 4320
taatttccga gggagggatc atgtccacct gggggcgat aaagaacacg gtttctggcg 4380
ggggattaat gagctgggtg gaaagcaggt tgcgcaagag ctgagacttg ccgcaaccgg 4440
tgggaccgta gatgaccccg atgacgggct gcagctggta gttgagagag gagcagctgc 4500
cgtcggggcg taggagggga gccacctcgt tcatcatgct tcttacatgt ttattttcac 4560
tgactaagct ttgcaagagc ctctccccac ccagggacaa gagttcttcc aggctgttga 4620
agtgtttcag cggtttcagg ccgtcggcca tgggcatctt ttcaagcgac tgacgaagca 4680
agtacagccg gtcccagagc tcggtgacgt gctctatgga atctcgatcc agcagacttc 4740
ttggttgcgg gggttgggcc gactttcgct gtagggtacg agccggtggg cgtccagggc 4800
cgcgagggtt ttgtccttcc agggtctcag cgtccgggtg agggtggtct cggtgacggt 4860
gaacggatga gccccgggct gggcgcttgc cagggtgcgc ttcaggctca tccggctggt 4920
gctgaagcgg gcgtcgtctc cctgggaatc ggccagatag caacggagca tgaggtcgta 4980
gctaagggat tcggccgcgt gtcccttggc gcgcagtttt cccttggaaa catgctggca 5040
tctggtgcag tgtaaacact tgagggcgta cagcttgggg gcgaggaaga cggactcggg 5100
cgagtaggcg tcggccccgc actcggcgca gacggtttca cactccacca gccacgtgag 5160
ctcgggtttg tcggggtcaa aaaccaggtt gcctccattt tttttgatgc gtttcttacc 5220
ttgcgtctcc atgagcctgt gacccgcttc ggtgacaaaa aggctgtctg tgtctccgta 5280
gaccgacttg agggggcgtt cttccaaggg cgtgccgcgg tcttctgcgt acaaaaactg 5340

```
ggaccactcc gaaacgaagg ccctggtcca cgctaacacg aaggatgcga tctgcgaggg   5400
gtatctgtcg ttctcaatga ggggatccac cttttccagg gtatgcagac acaggtcgtc   5460
ctcctccgcg tccacaaagg tgattggctt gtaagtgtag gtcacgtgac cggcgccccc   5520
cggaggggta taaaaggggg cgtgcccacc ctccccgtca ctttcttccg catcgctgtg   5580
gaccagagcc agctgttcgg gtgagtaggc cctctcaaag gccggcatga cttcggcact   5640
caagttgtca gtttctacaa acgaggagga tttgatgttc acgtgccccg cggcgatgct   5700
tttgatggtg gagtggtcca tctggtcaga aaacacgatc tttttgttgt caagtttggt   5760
ggcaaaagac ccatagaggg cgttggaaag caacttggcg atggagcgca gggtctgatt   5820
tttttcccga tcggcccttt ccttcgcggc gatgtttaat tgcacgtact cgcgggccac   5880
gcatcgccat tccgggaaca cggcggtgcg ctcgtcgggc aggatgcgca cgcgccagcc   5940
gcgattgtgc agggtgatca tgtccacgct ggtggccacc tcccccccgga ggggctcgtt   6000
ggtccaacac aatctccctc cttttctgga gcagaacgga gggaggggat ctaggaggtt   6060
ggcgtgcggg gggtcggcgt cgatggtgaa gatgccaggc aggagaactt tattaaagta   6120
atcgatctcg gtttccacgt cttgcaacgc ctcctcccat ctctttaccg ccagggccct   6180
ctcgtagggg ttcaggggcg ccccccaggg catggggtgg gtgagagccg aggcgtacat   6240
gccacagatg tcatagacgt agaggggctc ccgtaggacc ccgatgtaag tgggataaca   6300
gcgccccccg cggatgctgg cccgcacgta gtcgtacatc tcgtgagatg ggggccaggag   6360
accctctccc aagtgggtct tgtggggctt ctccgcccgg tagaggatct gcctgaagat   6420
ggcgtgggag ttggaagaga tggtgggccg ttggaagacg ttaaagttgg cccgcggcag   6480
ccccaccgag tcttcgatga actgggcgta ggattcctgg agtttgttca cgagggcggc   6540
ggtgaccagc acgtccaggg cgcagtaatc cagggtctcg cggaccaggt tgtaggagct   6600
ctcttgtttt ttctcccaca gttcgcggtt gaggaggtat tcctcgcggt ctttccagta   6660
ctcttcggcg ggaaatcctt tttcgtccgc tcggtaagaa cctaacatgt aaaactcgtt   6720
caccgctttg tatggacaac agcctttctc taccggcagg gcgtacgcct gagcggcctt   6780
tctgagagaa gtgtgggtga gggcgaaggt gtcccgcacc atgactttca ggtactgatg   6840
tttgaagtcc gtgtcgtcgc agcttccttg ttcccacagg ctgaagtcgg tgcgcttttt   6900
ctgcctcggg ttggggaggg cgaaagtgac atcgttaaac aagattttcc cggcgcgggg   6960
cataaagttg cgagagattc tgaagggccc tggcacgtcc gagcggttgt tgatgacctg   7020
cgccgccagg acgatctcgt cgaagccgtt gatgttatgc cccacgatgt acagttctat   7080
gaagcgcggc tgtcccttga gggcgggcgc ttttttcagt tcctcgtagg tgagggactc   7140
gggagaggcg agccccagct ccgcgcgggc ccagtcggcc agttgagggt tagccgcgag   7200
gaaggaattc cagagctccg aggccagaag agtttgcaag cgatcgcgaa actcgcggaa   7260
ctttttcccc acggccattt tttctggcgt gaccacgtag aaagtggcgg agcgatcgtt   7320
ccagacgtcc cacttgagct cccgggccag ctcgcaggcc tgacgcacga gagtttcctc   7380
gcccgagacg tgcatgacca acatgaaagg cactaactgt tttccgaacg cgcccatcca   7440
cgtgtaggtc tctacatcgt aggtgacaaa gagccgttgg gtgcgtgcgt gggagccgat   7500
cggaaagaag ctgatctcct gccaccagct ggaggaatgg gtgttgatgt ggtgaaagta   7560
gaagtcccgc cggcgcacag agcattcgtg ctggtgtttg taaaagcgac cgcagtagtc   7620
gcagcgctgc acgctctgta tttcttgaat gagatgcact tttcgcccgc gaaccagaaa   7680
```

```
tcggagggga aagttgagcc cgggggatgg tggagtcgcg tccccttcgc cttggcggtg   7740
ggcgtctgcg tctgcgtcct gtttttctgg gtggacgacg gtggggacga cgacgccccg   7800
ggttccgcaa gtccagattt cagcgacgga ggggcgcaga cgcagaagga gggggcgcag   7860
ttgcccgctg tccagagagt cgaggaaagc gacgctgagg tcagcgggga gcgtttgcaa   7920
attcactttc aagagaccgg taagagcgtg agccaggtgg agatgatact tgatttccag   7980
gggggtgttg gaagaggcgt ccacgccgta caagaggccg tgtccgcgcg gagccaccac   8040
ggttccccgc ggaggtttta tctcactcgc cgagggcgag cgccgggggg tagaggcggc   8100
tctgcgccgg gtggtagcgg aggcagaggc acgttttcgt gaggattcgg cagcggctga   8160
tgacgcgctc ggagactgct ggcgtgggcg acgacgcggc ggttgaggtc ctggatgtgc   8220
tgcctctgcg tgaagaccac cggtcccctg gtcctgaacc tgaaagagag ttccacagag   8280
tcaatgtctg catcgttaac ggccgcctgc ctgaggatct cctgcacgtc gcccgagttg   8340
tcttggtagg cgatctcggc catgaactgt tcgacttctt cttcgcggag gtcgccgtgg   8400
cccgcgcgtt ctacggtggc ggccaggtcg ttagagatgc gacgcatgag ctgggagaag   8460
gcgttgaggc cgttctcgtt ccacacgcgg ctgtacacca cgttaccgaa ggagtcgcgc   8520
gctcgcatga ccacctgcgc cacgttgagt tccacgtggc gggcgaagac ggcgtagttt   8580
ctgaggcgct ggaagaggta gttgagcgtg gtggcgatgt gctcgcagac gaagaagtac   8640
atgatccagc gcctcagagt ctgctcgttg atgtctccga tggcttcgag gcgttccatg   8700
gcctcgtaga agtcgacggc gaagttgaaa aattgggagt tgcgggcggc caccgtgagt   8760
tcttcttgca ggaggcggat gagatcggcg acggtgtcgc gcacctcctg ttcgaaagcg   8820
ccccgaggcg cctctgcttc ttcctccagc tcctcctctt ccaggggcac aggttcctcc   8880
ggcacctctg cggcggggac ggggcggcga cgtcgtcgtc tgaccggcag tcggtccacg   8940
aagcgttcga tcatttcacc gcgccggcga cgcatggtct cggtgacggc gcgtccgttt   9000
tcgcggggac gcagttcgaa gacgccgccg cgcagagcgc ccccgtgcag ggagggtaag   9060
tggttagggc cgtcgggcag agacacggcg ctgacgatgc attttatcaa ttgttgcgta   9120
ggcactccgt gcagggatct gagaacgtcg aggtcgacgg gatccgaaaa cttctctagg   9180
aaagcgtcta tccaatcgca atcgcaaggt aagctgagga cggtgggccg ctgggggggcg  9240
tccgcgggta gttgggaggt gatgctgctg atgatgtaat taaagtaggc ggttttcagg   9300
cggcggatgg tggcgaggag gaccacgtct ttgggcccgg cctgttgaat gcgcaggcgc   9360
tcggccatcc cccaggcctc gctctgacag cgacgcaggt ctttgtagta gtcttgcatc   9420
agtctctcca ccggaatctc tgcttctccc ctgtctgcca tgcgagtcga gccgtacccc   9480
cgcaagggct gcagcaacgc taggtctgcc actactcttt cggccagcac ggcctgttga   9540
atctgcgtga gggtggcctg gaagtcgtcc aggtccacga agcggtggta ggctcccgtg   9600
ttgatggtgt aggtgcagtt ggccatgacg gaccagttga cgacttggat gccgggttgg   9660
gtgatctccg tgtacttgag gcgcgagtag gccctggact cgaacacgta gtcgttgcat   9720
gcgcgcacca gatactggta gccgacgaga aagtgcggag gcggttcccg atacaggggc   9780
cagcccacgg tggcgggggc tccgggggcc aggtcttcca gcatgaggcg gtggtagtgg   9840
tacacgtatc gagagagcca ggtgatgccg gctgaggtgg tggcggccct ggtgaactcg   9900
cggacgcggt tccagatgtt gcgcaggggg cggaagcgtt ccatggtggg cacgctctgt   9960
cccgtcaggc gcgcgcaatc ctgtacgctc tagatggaga aaagacaggg cggtcatcga  10020
ctcccgtccg tagctgggag gtaaagtcgc aagggtgcgg cggcggggaa ccccggttcg  10080
```

agaccggctg gatccgccgt tcccgatgcg cctggccccg catccacgac gttcgcgccg 10140
agacccagcc gcggcacacc gccccaatac ggaggggagt cttttggtgt tttttcatag 10200
atgcatccgg tgctgcgaca gatgcgaccc cagacgccca ctgctactac cgccgcggcg 10260
gcagtaaacc tgagcggagg cggtgacagg gaggacgaag agctggcttt agacctggaa 10320
gagggagagg gtctggcgcg actgggcgcc ccctccccg agagacaccc cagggtccag 10380
ctcgtgaggg atgcgagaca ggcttttgta ccgcggcaga acctgtttag ggaccgcagc 10440
ggccaggagg cggaggagat gcgcgattgt cggtttcggg cgggcagaga gctgagggcg 10500
gggttcgacc gggagcggtt gctgcgggcg gaggatttcg aacccgacga gcggtcgggg 10560
gtgagtccgg cccgagccca cgtgtcggcc gccaacctgg tgagtgcgta tgagcagacg 10620
gtgaacgagg agcgtaactt tcaaaagagc tttaataatc acgttcggac cctcatcgcg 10680
agggaggagg tggccatcgg gctgatgcat ctgtgggact tcgtggaggc ctacgtgcag 10740
aacccggcga gcaagcccct gacggctcag ctgttcctga tcgtgcagca cagccgcgac 10800
aacgagacgt ttcgcgacgc catgctcaac atcgccgagc ccgagggccg ctggctcttg 10860
gatcttatca acatcttgca gagcatcgtg gttcaggaga ggggtctcag cttagcggac 10920
aaggtggcgg ccattaacta ctccatgcag agtctgggaa aattctacgc tcgcaagatc 10980
tacaagagcc cctacgtgcc catagacaag gaggtgaaga tagacagctt ttacatgcgc 11040
atggcgctga aggtgctgac gctgagcgac gatctcggcg tgtaccgtaa cgacaagatc 11100
cacaaggcgg tgagcgccag ccgccggcgg gagctgagcg atagggagct gatgcacagc 11160
ctgcagaggg cgctggcggg tgccggggac gaggagcgcg agacttactt cgatatggga 11220
gcggacttac agtggaaacc cagcgcccga gcgttggagg cggcgggcta ccgtggcgac 11280
gaggatcggg atgactttga ggaggcaggc gagtacgagg acgaagcctg accgggcagg 11340
tgttgtttta gatgcagcgt ccggcggacg gggccaccgt ggatcccgcg cttttggcat 11400
ccatgcagag tcaacctacg ggcgtgaccg cctccgatga ctgggcggcg gccatggacc 11460
gcatcatggc actgaccacc cgcaaccccg aggcttttag gcagcaaccc caggccaacc 11520
gtttttcggc catcttggaa gcggtagtgc cgtctcgcac taatccgacc cacgaaaagg 11580
ttttaactat cgtgaacgcg ctggtagaca gcaaggccat ccgccgcgac gaggcggggc 11640
tgatttacaa cgctctgctg gaacgcgtgg cgcgctacaa cagcactaac gtgcagacca 11700
atctggaccg cctcaccacg gacgtgaagg aagcgttggc tcagaaggag cggttcttaa 11760
gggacagcaa tctgggttct ctggtggcgc tgaacgcttt tctgagcacg cagccggcga 11820
acgtaccccg cgggcaggag gactacgtga gcttcatcag cgctctgaga ctgctcgttt 11880
ccgaggtgcc gcagagcgag gtgtaccagt cgggacctga ctacttcttc cagacgtccc 11940
gacagggctt gcaaacggtg aacctgactc aggcttttaa aaacttgcaa ggcatgtggg 12000
gcgtgaaggc gccggttggc gatcgcgcga ccatttccag cctgctgacc cccaacacga 12060
gactgctgtt gcttttaatc gccccgttca ccaacagcag caccatcagc cgcgactcgt 12120
acctgggcca tctcatcact ctgtaccgag aggccatagg tcaggctcag attgacgagc 12180
atacgtatca agagatcacc aatgtgagcc gagccctggg tcaggaagac accggcagtt 12240
tggaagccac gctaaacttt ctgctgacca atcggagaca aaagattccc tcgcagtaca 12300
cgttaagcgc cgaggaggag aggattctgc gctacgtgca gcagtccgtg agcctgtact 12360
tgatgcggga gggtgctacc gcttccacgg ccttggacat gacggctcga aacatggaac 12420

```
cgtcttttta ctcagcccac cgtccgttca tcaatcgcct gatggactac ttccatcgcg  12480
cggccgccat gaacggggag tatttcacca atgccatctt gaatccgcat tggatgcctc  12540
cgtccggttt ctacaccggg gagttcgacc tgcccgaggc cgacgacggc tttctgtggg  12600
acgatgtgtc cgacagcatt tttacgccag gtaacagtcg tttccataaa aaggaagggg  12660
gagacgaact tccccttcg agtgtggagg cggcctccag gggggagagc cccttttcca  12720
gcttgtcttc cgtgagtagc ggtcgggtga cgcgcccacg cttgccgggg gagagcgact  12780
acctaaacga ccctttgctg cgaccggcta aaaagaaaaa ttttcccaac aacggggtgg  12840
aaagcttggt ggataaaatg aatcgttgga agacctacgc tcaggagcag cgggagtggg  12900
aggacagtca gccccgaccg ctggtcccgc cgcactggcg ccgccagaga gaagacccgg  12960
acgactccgc agacgatagt agcgtgttgg acttgggagg gagcggagcc aacccctttg  13020
ctcacttgca acccaagggg cgcttgagtc gcctgtacta ataaaaagaa agcggaaacg  13080
taccagagcc atggccacag cgtgtgtcct ttcttcctct ctttcctcct cggcgcggca  13140
gaatgagaag agcggtgaga gtcacgccgg cggtgtatgc cgagggtccg ccccccttctt  13200
acgaaagcgt gatgggatca gcgaacgtgc cggccacgct ggaggcgcct tacgttcctc  13260
ccagatacct gggacctacc gagggcagaa acagcatccg ttactccgag ctggcccccc  13320
tgtacgatac caccaaggtg tacctggtgg acaacaagtc ggcggacatc gcctccctga  13380
attaccaaaa cgaccacagc aacttcctga ccaccgtggt gcagaacaat gacttcaccc  13440
cgacggaggc gggcacgcaa accattaact ttgacgagcg ttcccgctgg ggcggtcagc  13500
tgaaaaccat cctgcacacc aacatgccca acatcaacga gtttatgtcc accaacaagt  13560
ttagggccag gttgatggta gagaagacta gcggccagcc gcccaaatac gagtggttcg  13620
agttcaccat tcccgagggt aactactccg agaccatgac tatcgatctc atgaataacg  13680
cgatcgtgga caattacctg caagttggaa ggcaaaacgg ggtattggag agcgacatag  13740
gagtaaaatt tgataccagg aacttccgac tggggtggga tccggtgacc aagctggtga  13800
tgcctggcgt gtacaccaac gaggcttttc accccgatat cgtgctgctt ccggggtgcg  13860
gagtggactt tacgcagagc cgcttgagta acctgttagg aatcaggaag cgccgtccct  13920
ttcaggaggg ctttcagatt atgtatgagg acttggaggg aggtaatatt ccaggcctgc  13980
tagacgtgcc ggcctatgaa caaagcttac aacaggccca agaggaggga agagtcactc  14040
gcggagacac ctttgccacg gctcccaacg aggtagtgat taagccctta ttgaaagaca  14100
gtaaggatag aagttataat attataaccg acaccacgga cactttgtac cggagttggt  14160
ttctggctta caactacggg gaccccgaaa acggagtgag atcatggacc atactcacca  14220
ccacggacgt gacctgcggc tcgcagcaag tgtactggtc cctgccggat atgatgcaag  14280
acccagtcac cttccgcccc tccacccaag tcagcaactt tccggtggtg ggcactgagc  14340
tgttgcccgt tcacgccaag agcttctaca acgagcaggc tgtttattcg caactcattc  14400
gccagtctac cgcgcttacc cacgtattca accgtttccc cgagaaccag attctcgtgc  14460
gccctcccgc tcctaccatt accaccgtga gtgaaaacgt tcccgccctc acagatcacg  14520
gaaccctgcc gctgcgcagc agtatcagtg gagttcagcg cgtgaccatc accgacgcca  14580
gacgtcgaac ctgcccttac gtttacaaag cgctcggcgt agtggcccca aaagtgctct  14640
ctagtcgcac cttctaaaac atgtccattc tcatctctcc cgataacaac accggctggg  14700
gactgggctc cggcaagatg tatggcgggg cgaagcggcg ctccagtcag caccctgttc  14760
gcgttcgggg tcatttccgc gctccctggg gagcttacaa acgaggactc tcgggccgaa  14820
```

-continued cggcggtaga cgacaccatt gacgccgtca ttgccgatgc ccgccggtat aaccccggaa 14880
cggtcgctag cgccgcctcc accgtggatt ccgtgatcga cagcgtggtg gccggcgcca 14940
gggcctacgc tcgccgcaaa aggcggctgc accgcaggcg tcgacccacg gccgccatgc 15000
tggccgccag ggccgtgctg agacgggccc gcagggtagg caggagggcc atgcgccgcg 15060
cggccgccaa cgctgccgcc gggagggccc gcaggcaagc cgccagccgg gccgccgccg 15120
ccatcgctaa catggccaga cccaggagag ggaacgttta ctgggtgcgc gattctgtga 15180
cgggagtcag agtgccggtg cgcagccgac ctccccgaag ttagaagacc aaaggtgcga 15240
agacggcgta ctgagtctcc ctgttgttat cagcccaaca tgagcaagcg caagtttaaa 15300
gaagaactcc tgcagaccct ggctcctgaa atctatggcc ctccggacgt gaagcccgac 15360
attaagcccc gcgatatcaa gcgtgttaaa aagcgggaaa aaaaagagga actcgcggtg 15420
gtagacgatg gcggggtaga atttattaga agtttcgccc cgcgacgcag ggtgcagtgg 15480
aaagggcggc gcgtgcaacg cgttctcagg ccaggcaccg cggtagtttt tactccggga 15540
gagcggtcgg ctgtcagggg tttcaagcgg caatatgacg aggtgtacgg cgacgaagac 15600
atcctggaac aggcggctca gcagattgga gaattcgcct acggaaagcg gtctcgccgc 15660
gaagacctgg ccattgcctt ggacagtggc aaccccaccc ccagcctcaa acccgtcacg 15720
ctgcagcagg tgctccccgt gagcgcgagc acggagagca aaaggggaat caagagagag 15780
atggaagatc tgaagcccac catccaactt atggtcccta aacgacagaa gctggaggag 15840
gttctggaaa acatgaaagt ggaccccagc atagagccgg atgtaaaagt gaggcctatt 15900
aaggaagtgg ctccgggtct cggggtgcaa acggtggaca ttcagatccc agtcagatcc 15960
gcttcgaccg ccgtggaagc catggaaacg caaaccgaaa ctccggtcgc ggccggtacc 16020
agagaagtgg ctttgcaaac ggagccctgg tacgaataca ccgctcctcg gcgccagagg 16080
cggcgttacg gcccggcaaa tgccatcatg ccagagtatg cgctgcaccc gtctatccga 16140
cccacccccg gctaccgggg ggtaacgtat cgcccgtcgc caacccgacg ccgttatcgt 16200
cgccgccgcc gttctcgtcg cgctctggcg cccgtgtccg tgcgacgcgt aacgcgccgg 16260
ggaagaacag tcaccatccc taacccgcgc taccacccta gcattcttta atgactctgc 16320
cgttttgcag atggctctga cttgccgcgt gcgccttccc gttctgcact atcgaggaag 16380
atctcgtcgt aggagaggca tggcggggag cggccgccgt cgggctttac gcaggcgcat 16440
gaaaggcgga attttgcccg cactgattcc cataattgcc gccgccattg gggcgatacc 16500
cggcgttgct tcagtggcct tgcaagcagc tcgtaataaa taaacgaagg cttttcaact 16560
tatgacctgg tcctgactat tttatgcaga aaaagcatgg aagacatcaa ttttacgtcg 16620
ctggctccgc ggcaaggctc acgcccgctc atgggcacct ggaacgacat cggcagcagc 16680
cagctcaacg gggcgcttt caattggggg agcctttgga gcggcattaa aaactttggc 16740
tccgcgatta aatcctacgg cagcaaagcc tggaacagta gtactggtca gatgctccgg 16800
gataaactga aggacacaaa ctttcaagag aaagtggtca acggggtggt gaccggcatc 16860
cacggcgcgg tggatctcgc taatcaagcg gtgcaaaaag agatagacag acgatgggaa 16920
aactcgcggg tgcctccgca gagaggggac gaagtggagg tggaggaagt agaagtcgag 16980
gagaaactgc ccccgctaga gaaagttccc ggggcgccgc ccaggccaca gaagcgtccc 17040
cggccggatc tggaagaaac tttagtgacg gaaaccatcg aacctccctc gtacgaacaa 17100
gctttaaagg agggcgcctc tccttacccc atgactaagc ccatcgcgcc catggcgcgt 17160

-continued

```
ccggtgtacg gaaaagatca caagccagta acgttagagc tacccccacc acccccttcc  17220
cgtcctacgg tgcctccgtt acccgccccg tcggcaggtc ccagctctgc accatccgca  17280
gctcctgcac caaccgctcg cccggtggcc gtggcaaccg ccagagcccc cagaggatcc  17340
aactggcaaa gcacgctgaa cagcatcgtg ggcttgggag tgaaaaccct aaaacgccgc  17400
cgctgctatt attaaagagt gtagctaaaa atttcccgtt gtatacgcct cctatgttac  17460
cgccagagac gcgtgactgg tcgccgctcc gccgctttca agatggccac cccatcgatg  17520
atgccgcagt ggtcttacat gcacatcgcc ggccaggacg cctcggagta cctgagtccc  17580
ggcctggtgc agtttgcccg cgccaccgaa agctacttca gcttgggaaa caagtttaga  17640
aaccccaccg tggcccccac gcacgatgta accacggacc gctcgcagag gctgacactg  17700
cgcttcgtgc ccgtagaccg ggaggacacc gcgtactcct acaaagtgcg cttcaccctc  17760
gccgtagggg acaacagggt gctggacatg gccagcacgt actttgacat ccggggaatg  17820
ctggaccgag ggcccagctt taaaccctac tcgggaactg cctacaattc gctggcacct  17880
aagggcgctc ccaaccctag tcaatggact actaccaacg gagggaataa aacaaattca  17940
tttgcccaag catcctacat aggtcaaagc ctgtcgaaag acggggtgca agtagcagta  18000
gatacagccg ctgggggggc tgcagtatat gctgacaaaa cgtttcaacc agaaccccaa  18060
gtaggaatat cacaatggaa tgaaaatcct actacaaatg ctgcaggaag aattttaaag  18120
cctactaccg caatgcgtcc atgctacggt tcatacgctt accccaccaa cgaaaaaggt  18180
gggcaggtaa aaatcactga ccctaacaat gacaaaaccg gcgctaataa cgttagctta  18240
aatttttca acactgccgc tgacaatggg aataacaatc caaaagtagt actctacagc  18300
gaagatgtaa atttagaagg gccagatacc caccttgttt ttaagccaga tgtaactggc  18360
gacgcaacca gtgcagaaac cctgttaggt caacaagcag ctcccaatcg tccaaactac  18420
attgggttca gggacaactt tattggcctg atgtactaca attcaactgg aaacatggga  18480
gtgctagcag gtcaggcttc tcagctaaac gccgtagtgg atcttcaaga cagaaatacc  18540
gaattgtcat atcagctaat gcttgacgct ttgggtgaca gaagtcggta cttttctatg  18600
tggaatcaag cagtggacag ctacgatcct gacgttagaa tcatagaaaa tcatggagta  18660
gaagacgaac ttccaaatta ttgttttccg ttaaatggac aggggatttc gaatacatac  18720
aaaggtgtga aatataacac aaacacttgg acgcaagaca ctgatgtagt cacaaccaat  18780
gaaatttcca ttggcaacat tttgccatg gaaataaacc tggcggctaa cttgtggcgc  18840
agctttctgt actccaatgt cgccctgtac ttgccagatt cctacaaata cactcccgac  18900
aatattgaac ttcctacaaa caagaacagc tacggctaca ttaacggaag ggtaaccgcc  18960
cccactgcca tcgacactta cgttaacatc ggcgcccggt ggtctccgga ccccatggac  19020
aacgttaacc ctttcaacca ccaccgcaac gccggcttgc gataccgctc catgctgctg  19080
ggcaacggtc gctacgtacc cttccacatt caggtgcccc agaaattttt tgccattaaa  19140
aacctgcttc tgcttcccgg gtcctacacc tacgagtgga acttcaggaa agatgtaaac  19200
atgatcttgc agagcacctt gggcaacgac ctccgcgttg acggagctag cgtgaggttt  19260
gacagcatta acctctacgc taacttcttc cccatggccc acaacacggc ctccaccttg  19320
gaagccatgc tgcgcaacga caccaacgac cagtccttta atgattacct gtgcgcggcc  19380
aacatgctgt accccatccc cgccaatgcc accagcgtgc cgatctccat tccctcacgc  19440
aactgggccg ccttcagagg ttggagtttc actcgcctga aaaccaagga gacccccctcg  19500
ctgggctccg gtttcgaccc atactttgtt tactccggga gcattcccta cctggacgga  19560
```

```
actttctacc tgaaccacac cttcaaaaag gtgtctatta tgtttgactc ctccgtgagc  19620
tggcccggta acgaccgctt gctaaccccc aacgagttcg aaatcaaacg ctcggtggac  19680
ggagagggtt acaatgtagc ccagagcaac atgaccaaag actggttttt aattcaaatg  19740
ctaagccact ataacattgg ctaccaagga ttctacgtgc ctgaagccta caaggacaga  19800
atgtactcct tctttagaaa cttccaaccc atgagccgcc aggtagtaga cacggtaaac  19860
tatgctaact acaaggaagt aacaatgcca ttccagcaca acaactcagg cttcgtgggg  19920
tacatgggac ctaccatgag agaggggcag gcctacccgg ctaattatcc ctacccccta  19980
atcggagcca ctgccgtgcc cagcctgaca cagaaaaagt ttctctgcga tcgaacaatg  20040
tggaggattc ccttctctag caacttcatg tccatggggg ctctcaccga cctggggcag  20100
aacatgctgt acgctaactc cgctcacgcc ttggacatga cctttgaggt ggaccccatg  20160
gatgagccca cgcttctcta tgttctgttt gaagtcttcg acgtggtgcg cattcaccag  20220
ccgcaccgcg gcgtcatcga ggccgtctac ctgcgcacac ctttctctgc cggtaacgcc  20280
accacctaag aagctgatgg gctccagcga acaggagctg cgggccattg ttcgcgacct  20340
gggctgcggg ccctactttt tggcaccttt cgacaagcgc ttccccggct tcatgtcccc  20400
ccacaagccg gcctgcgcca tcgtcaacac ggccggacgc gagaccgggg gggttcactg  20460
gctcgccttt gcctggaacc cgcgtaacca cacctgctac ctgttcgacc cttttggttt  20520
ttctgacgaa aggcttaaac agatttacca gttcgagtac gaggggctcc ttaaacgcag  20580
cgctctggcc tccacgcccg accactgcgt caccctggag aagtccaccc aaacggttca  20640
gggtcccctc tcggcggcct gcggactctt ttgttgcatg tttttgcatg ctttcgtcca  20700
ctggccgaac acccccatgg accgcaaccc cactatggat ctgctcacgg gagtgcctaa  20760
cagcatgctt cacagccctc aggtcgcacc caccctgcgt cgcaatcagg aacagctgta  20820
tgcttttctg ggaaaacatt ctgcctactt tcgccgccac cggcagcgca tagaacaggc  20880
cacggccttt gaaagcatga gtcaaagagt gtaatcaata aaatcaactt ttattttaca  20940
tcacacgcgc ttctggcgtt ttcttaaaaa tcaaagggtt cgggggaggg gtcgtcgtgc  21000
ccgctgggca gggacacgtt gcgatactgg aagcgggggc tccagcggaa ctcggggatc  21060
gccagccggg gcagaggcac ttcttccagg ttctgcttcc aaaactgccg caccagctgg  21120
agggctccca ttacgtcggg cgccgagatc ttgaagtcgc agttggggcc cgagcttccg  21180
cggctgttgc gaaacacggg gttggcacac tggaacacca gcacgctcgg gtagttgata  21240
ctggccaggg ccgttgcgtc ggtcaccgcc gttacatcca gatcctccgc gttggtcagg  21300
gcgaagggag tcagcttgca catctgccgc ccgatgtggg gcacgccgtc atgcttgttg  21360
aggcagtcgc aacgcagggg aatcagaatg cgatgctggc cgcgttgcat ctgagggtag  21420
ttggcccgca agaacgcttc catctgacgg aaggccgtct gggctttcat tccctcggtg  21480
tagaaaagac cgcaggactt gctagaaaat acattattgc cgcaggtgac gtcttccgcg  21540
cagcagcggg cgtcttcgtt ctttagctgc accacgttgc gaccccaccg gttctgtacc  21600
accttggccc tcgtgggctg ctccttcagc gcccgctggc cgttttcgct ggtcacatcc  21660
atttccaaca cgtgctcctt acacaccatt tccactccgt ggaagcagaa caggacgccc  21720
tcctgctggg tattgcgatg ctcccacacg gcgcagcctg tggcctccca gctcttatgc  21780
ttcacccccg cgtagtttc catgtaagcc atcaggaatc tgcccatcat ctcggtaaag  21840
gttttctgac tggtgaaggt caaaggcaag ccgcggtgct cttcgttcag ccacgtttga  21900
```

-continued

```
cagatcttgc ggtacgtggc gccctgatcc ggcagaaact taaacgcccc cttgctctcg  21960
ttgtccacgt ggaacttttc catcagcatt agcataactt ccataccctt ctcccacgcc  22020
gtcaccagcg gtgtgctgtc ggggttcttc accaacatgg tagaagggcc ctcgccggcc  22080
ctgaagtcgc tcatactcat tttttgaaac tccacagtgc cgtccgcacg acggacccgg  22140
cgcatcggag ggtagctgaa gccaacctcc accagggtgc cttcgctctc gctgtcggag  22200
acgatctccg gggagggcgg cggcgcgggt gtcgacttgc gagccttctt cttgggagga  22260
agcggtggcg cctcttggtc gcgctcggga ctcatctccc tcaagtaggg ggtgatggag  22320
cttcctgctt ggttctgacg gttggccatt gtatcctagg cagaaacaca tggagcttat  22380
gcgcgaggaa actttaaccg ccccgtcccc cgtcaacgac gaagaggtca tcatcgaaca  22440
ggacccgggc tacgttactc cgcccgagga tctggagggg cctttagacg accggcgcga  22500
cgctagtgag cagcaggaaa atgagaaaga ggaagcctgc tacctcctgg aaggcgacgt  22560
gttgctaaaa catttcgcca ggcagagcac catagtgaag gaggctttgc aagaccgctc  22620
ggaggtgccc ttggacgtcg ccgcgctctc ccaggcctac gaggcgaacc tcttctcgcc  22680
ccgagtgcct ccgaagagac agcccaacgg cacctgcgag cccaacccgc gccttaactt  22740
ctaccccgtg ttcgccgtgc ccgaggcgct ggccacctac cacatttttt tcaagaacca  22800
gcgcatcccg ctctcgtgcc gggccaaccg caccgcggcc gatagaaagc tgagactcaa  22860
aaacggagct agcatacctg atatcacgtc cctggaggaa gtgcctaaga tcttcgaagg  22920
tctgggtcga gacgagaaac gggcggcaaa cgctctgcag aaagaacaga aggacagtca  22980
gaacgtgctg gtggaactgg agggggacaa tgcgcgtctg gccgttctca agcgctgcat  23040
agaagtttcc cacttcgcct accctgccct gaacctgccg cccaaagtca tgcgctcggt  23100
catggaccag ctgctcatca agagagctga gcccctgaac cccgagcacc ccgaggcgga  23160
gaactcggag gacggaaagc ccgtcgtcag cgacgaggag ctcgagcggt ggctggacag  23220
cacggacccc gagcagttgc aagagcggcg caaaatgatg atggcggccg tcctggtcac  23280
cgttgagctg gagtgcctgc agcggttttt tagcgacgtg gaaacgctgc gtaaaatcgg  23340
agagtccctg cactacacct tccgccaggg ctacgtccgc caggcctgca agatctccaa  23400
cgtggagctc agcaacctgg tctcctacat gggcatcctc cacgagaacc ggctgggaca  23460
gagcgtgctg cactgcacct tgcaaggcga ggcgcggcgg gactacgtgc gagactgcgt  23520
ctacctcttc ctcactctca cctggcagac cgccatggga gtgtggcagc agtgcttgga  23580
agacagaaac ctcaaagagc tagacaaact cctctgccgc cagcggcgcg ccctgtggtc  23640
cggtttcagc gagcgcacgg tcgccagcgc tctggcggac atcatcttcc cggagcgcct  23700
gatgaaaacc ttgcaaaacg gcctgccgga tttcatcagt caaagcattt tgcaaaactt  23760
ccgctctttt gtcctggaac gctccgggat attgcccgcc atgagctgcg cgctaccttc  23820
tgactttgtc cccctctcct accgcgagtg ccctccccca ctgtggagcc actgctacct  23880
cttccaactg gccaactttc tggcctacca ctccgacctc atggaagacg taagcggaga  23940
gggtttactg gagtgccact gccgctgcaa cctgtgcacc ccccacagat cgctggcctg  24000
caacaccgag ctactcagcg aaacccaggt cataggtacc ttcgagatcc aggggcccca  24060
gcagcaagag ggtgcttccg gcttgaagct cactccggcg ctgtggacct cggcttactt  24120
acgcaaattt gtagccgagg actaccacgc ccacaaaatt cagttttacg aagaccaatc  24180
tcgaccaccg aaagcccccc tcacggcctg cgtcatcacc cagagcaaga tcctggccca  24240
attgcaatcc atcaaccaag cgcgccgcga tttccttttg aaaaagggtc ggggggtgta  24300
```

cctggacccc cagaccggcg aggaactcaa cccgtccaca ctctccgtcg aagcagcccc 24360
cccgagacat gccgcccaag ggaaccgcca agcagctgat cgctcggcag agagcgaaga 24420
agcaagagct gctccagcag caggtggagg acgaggaaga gatgtgggac agccaggcag 24480
aggaggtgtc agaggacgag gaggagatgg aaagctggga cagcctagac gaggaggagg 24540
acgagctttc agaggaagag gcgaccgaag aaaaaccacc tgcatccagc gcgccttctc 24600
tgagccgaca gccgaagccc cggcccccga cgcccccggc cggctcactc aaagccagcc 24660
gtaggtggga cgccaccgaa tctccagcgg cagcggcaac ggcagcgggt aaggccaaac 24720
gcgagcggcg ggggtattgc tcctggcggg cccacaaaag cagtattgtg aactgcttgc 24780
aacactgcgg gggaaacatc tcctttgccc gacgctacct cctcttccat cacggtgtgg 24840
ccttccctcg caacgttctc tattattacc gtcatctcta cagcccctac gaaacgctcg 24900
gagaaaaaag ctaaggcctc ctccgccgcg aggaaaaact ccgccgccgc tgccgccgcc 24960
aaggatccac cggccaccga agagctgaga aagcgcatct ttcccactct gtatgctatc 25020
tttcagcaaa gccgcgggca gcaccctcag cgcgaactga aataaaaaaa ccgctccttc 25080
cgctcgctca cccgcagctg tctgtaccac aagagagaag accagctgca gcgcaccctg 25140
gacgacgccg aagcactgtt cagcaaatac tgctcagcgt ctcttaaaga ctaaaagacc 25200
cgcgcttttt ccccctcggc cgccaaaacc cacgtcatcg ccagcatgag caaggagatt 25260
cccacccccct acatgtggag ctatcagccc cagatgggcc tggccgcggg ggccgcccag 25320
gactactcca gcaagatgaa ctggctcagc gccggccccc acatgatctc acgagttaac 25380
ggcatccgag cccaccgaaa ccagattctc ttagaacagg cggcaatcac cgccacaccc 25440
cggcgccaac tcaacccgcc tagttggccc gccgcccagg tgtatcagga aaatccccgc 25500
ccgaccacag tcctcctgcc acgcgacgcg gaggccgaag tcctcatgac taactctggg 25560
gtacaattag cgggcgggtc caggtacgcc aggtacagag gtcgggccgc tccttactct 25620
cccgggagta taaagagggt gatcattcga ggccgaggta tccagctcaa cgacgagacg 25680
gtgagctcct caaccggtct cagacctgac ggagtcttcc agctcggagg agcaggccgc 25740
tcttccttca ccactcgcca ggcctacctg accctgcaga gctcttcctc gcagccgcgc 25800
tccgggggaa tcggcactct ccagttcgtg gaagagttcg ttccctccgt ctacttcaac 25860
cccttctccg gctcgcctgg acgctacccg gacgccttca ttcccaactt tgacgcagtg 25920
agtgaatccg tggacggcta cgactgatga cagatggtgc ggccgtgaga gctcggctgc 25980
gacatctgca tcactgccgt cagcctcgct gctacgctcg ggaggcgatc gtgttcagct 26040
actttgagct gccggacgag caccctcagg gtccggctca cgggttgaaa ctcgagatcg 26100
agaacgcgct cgagtctcgc ctcatcgaca ccttcaccgc ccgacctctc ctggtagaaa 26160
tccaacgggg gatcactacc atcaccctgt tctgcatctg ccccacgccc ggattacatg 26220
aagatctgtg ttgtcatctt tgcgctcagt ttaataaaaa ctgaactttt tgccgcacct 26280
tcaacgccac gcgttgtttc tccaacagtc gacgatagct cttcaattaa aggtacccga 26340
gaaactgttt attttgacaa ttctactact tctcttatcc ttaactgttc ttgcactaac 26400
gaactaattc agtggttcgc caacggttca ctctgcaaag ttttccttga ctctgcgata 26460
cttcccggat ttagcagctc tgcgtgtgat aattctaccc cctccacctt aaccatcaca 26520
aagccatttt cagaagtcca gtatttttgt attggagcgg ggggtaaacc gggctgtatt 26580
caccgcttct ttctggagac atttgttgct tcgattccca ttaacacttc actttcctct 26640
aatacatact taactacctt acattctact cacccctcct ggaaacctct tattggcctc 26700
acagctttta tttccgttgt tttactaaac tttataattc ttaacaaact ttcttaaaca 26760
tgcttgccat tttgcttctg ctcgttactt taacctccgc agattaccac aatgcaattg 26820
tacgagaaaa cagtttacaa aacccatcac aggtatatgt taaagcaggt tctaacttaa 26880
ctctacaatc cttctattcg ccttaccctg aggacatgcc acgtgtcacc tggtacttag 26940
aagtttttga ttcgctattt gaaagacata caattcctcc attttttaca ggcgttatac 27000
tttgtgacat ttctggtgac atacagcatg tgtggaacca ttggccttta caatttaatt 27060
gcataaataa aagcttacat attatcaatc tcaaaccaag tgatgaaggc ctttacaatg 27120
tgaaggtttt aaagggcagc attcagcata atacatactt tcgtgtgcat gtagtaagtt 27180
ttccaaaacc tgaatgtaac atcaccacta catatctttc agatgactac tgccttatta 27240
acattgattg ctctcaatta ccataccctg ctaaggtcta ttataatggc aatgaaagta 27300
agctgcatta ctacttatct gaacgcggtg gccaaccaaa ccttccaaat tactttactg 27360
ttgggtatcg atatagagat ctccgacaga attatacagt tgaatatcca tttaatgaac 27420
tctgtacaga tataattgct cttgaaacag ggtctgattt tacgccaatt tttatagtta 27480
ccctagtggt gagcattata gttattgtga tgggcatcac atatcttatt tatcactgta 27540
ggactttaaa aaccaaaacc aaaaccaagc ctcctgaaat ccgtctgctt taattttttc 27600
cagaatggta gctgctttct tcattctcct ctgtatacca atcatctgcg cctccacaac 27660
ttttgccgct gtttcccacc tggaaccaga ctgtctacca ccttttgttg tatacctaat 27720
actgactttt gtggtctgta cagccattac cagtatagcc tgctttttttg taacaatttt 27780
ccaagccgcc gattacctct acgtacggtt tgcttacttt agacatcacc ccgagtatcg 27840
gaatcaaaac gtagcctctc tgctttgttt agcatgattc gcatttttat actttgtaag 27900
ctctttacca ccacaatatg tcaatgccct tttaccaaac cctggtcctt ttacacttgt 27960
tataatgtat tacccgaaac cccattgcc tggctttacg tagccacagc ggctttagtt 28020
tttgtagcaa cctgcattgg cgttaaactg tacttttact taaaaattgg atggcttcat 28080
cccccagaag atttaccccg atatcctctt gttaataact ttcaacagcc tctaccgcct 28140
cctgatcttc cgcgagctcc ctccgttgtt agctactttc aactcaccgg tggagatgac 28200
tgacactcag gacattaaca ttactgtgga aagaatagct gctcagcgtc agcgagagac 28260
gcgggtgatg gagtacgtgg aactacagca gcttaaagag tcccactggt gtgaaaaagg 28320
agtgctttgc catgttaagc aagcagccct ttcttacgat gtcagcactc agggacatga 28380
actgtcctac actttgcctt tacagaaaca aaccttctgc accatgatgg gctctacctc 28440
cattacaatc agccaacaaa ccggacctgt cgagggggct atcctgtgtc actgtcacgc 28500
gcctgattgt atgcccaaac taatcagaac tctttgtgct ttaggtgata tatttaaaat 28560
atagatagta tcaataaact taccttaaat ttgacagcaa ttttttggta tcatcattca 28620
gcagcaccac tttaccctct tcccaactct catatgggat atgatggtgg gcggcaaact 28680
tcctccaaac cctgaaagaa atatcggtat ccacttcctt gtcctcaccc acaattttca 28740
tcttttcata gatgaaaaga acccgagttg atgaagactt caaccccgtc tacccttatg 28800
acaccacaac cactccagcc gttcctttca tatcaccccc gtttgtaaac agtgacggtc 28860
ttcaggaaaa cccccccgga gttttaagcc tgcgaatagc taaacccctg tattttgaca 28920
tggagagaaa actagccctt tcacttggaa gagggttaac aattaccgcg aacggacaat 28980
tagaaagcac ccagagcgtg cagactaacc cgccgttaac tgtcaccaat aacaacacac 29040

```
ttatcctacg ccactcctcc cctttaatcc taactgacaa taatttaacc gtaggcttct  29100
caagtcctct ccgtgttata gacaacaaac tgacattcac ttttacctca cctctccgtt  29160
atgaaaacga aacccttacc ttcaattaca cagagcccct tacacttatg aacagcaacc  29220
ttgcgcttaa cgtaaactcc tctaaaggcc ttagggttga cgggggctca ctaggtacaa  29280
acttaagtcc ggacttaagg tttaacagca gtggagccat agcttttggt atacaaaccc  29340
tatggacacc cccgacctca aatcctaact gcaccgttta caccgaaagc gattccttac  29400
ttagtctctg cttaactaaa tgcggagctc acgttttagg aagtgtaagc ttaaccgggg  29460
tagcaggtac catgataaac atggctgaaa cttcgcttgc tattgaattt acgtttgacg  29520
acactggaaa actacttcac tcaccacttg ttaacaccac ttttagcatt cgtcagggcg  29580
acagccccgc ctcaaatcct acctacaatg ctctagcatt tatgccaaac agtaccctct  29640
acgctagagg aggaagtggt gaaccccgaa acaattacta cgtccaaaca tacctcaggg  29700
gaaatgttca gagaccgatt accctcactg ttactttcaa ctcagccgcc acgggatatt  29760
ccttatcttt taagtggact gctgttgcac gtgaaaaatt tgcagctcct gcaacttcat  29820
tttgctacat taccgaacaa taaaaccctg tgttcccacc gtttcgtttt ttccagatga  29880
aacgggccag agttgatgaa gacttcaatc ccgtgtaccc ttacgatccc ccttacgccc  29940
ccattatgcc gtttattacc ccgccgttta catcttcaga tgggttacag gaaaaaccac  30000
ttggtgtttt aagtttaaaa tacaaggatc ctatcactac acaaaatggt tctctaaccc  30060
ttaaattagg aaacgggctg aacattaaca accagggcca acttacatca tctgctgggg  30120
aagtcgagcc tcccctcacc aatgctgaca acaagctggc cttagcctac agcgaccctc  30180
tgacattaaa aaacagccgt ctaacactgt ctcacaatgc ccccacttgca attaacaata  30240
attctctaag tttggaagta tcagagccta tatttataaa taacgacaac aaactgtctc  30300
tgaaagctga cgcccccctg acaaccagcg ctggaaccct ccgcctgcaa agcgctgctc  30360
cattaggact tgctgaacag acactaaagc tgctgttttc taaccctttg tacttgcgag  30420
gtgacttcct tacattagcc attgaacgcc cattggctgt aacagcagac gggctattat  30480
cacttgccct caaccctccg ctcacaacaa ctaacacagg cttagctctc tctaccgcgg  30540
ttccattaac tgttaccaac gggaacctta gcctaaacgt aaaacggccg tttattatac  30600
aggacggcag cctttacatg gattttagac cccactata tctgtttaac agcgagccac  30660
aacttggtgt taattttaat gcccctctaa ctgttagaga taacggccta gctataaaca  30720
ccggagacgg gctaacagta acgtataata aactaacatt aaacctcggt agagacttgc  30780
aatatgaaaa tggagctgca gctgttaagc taagtaccgc ccctcctcta cagtatacta  30840
ctcaactgca gctgaatttg ggagcgggct tacgtctagg tcctactagg aacttagacg  30900
tggccattaa ccacaataaa gggttagcgt gggaaaacaa tgaagtggtt actaaattag  30960
gacaaggcct ttactttgat tcctccggaa gcatagcttt atcgcctaca aaccccagac  31020
cagatacttt atggaccacg gccgatcctt cgccaaactg cactgtatat gaatcacttg  31080
actctagact gtggctagcg cttgttaaat gtgggggaat ggtacacggc agcatagccc  31140
tacaagctga aaaaggccaa ttgctgcgtc ctactgctag ttttatctcc atcgtaattt  31200
acttctacag tgatggggtc cgtcgcacca actaccctac aattggcaat gatgagggta  31260
ctctggccaa cagcgctact tggggctaca gacaagggca atctgcagac accaacgtca  31320
ccaatgctgt tgaattcatg cctagtttac acagatatcc tataaatcag ggagacaata  31380
```

```
ttaaaaacca aatgataact tacacttgca tacaaggcaa cgtgaacatg ccagtaccct  31440
tgaaaatcac gttcaatcat gctcttgaag gctactcctt aaagtttaca tggcgtgtgg  31500
tggctaatga aaagtttgat attccttgct gttcgttttc ttacattaca gaacaataaa  31560
acaacttttt tatttttcat ttcttttatt ttacacgcac agtaagactt cctcccccct  31620
tccatttaac agcgtacacc agcctttccc ccttcatggc ggtaaacttc tgtgagttag  31680
tccggtattt gggagttaaa atccaaacag gctctttggt gattaaacgt tgatccgtga  31740
tggacacaaa tccctgagac aggtcctcca acgttgcggt aaaaaactga acgccgccct  31800
acaaaacaaa cagttcaggc tctccacggg ttatcacccc gatcaaactc agacagagta  31860
aaggtgcggt gatgttccac aagaccgcgc aagtggcgct gtctaaagct ctcagtgcga  31920
cttctatgcg gctggtagga tgttacatta tccaacagcc tcacagcgcg gattattagt  31980
ctacgagtgc gcctggcgca gcagcgcatc tgaatttcag tcaagtcttg acaagaagcg  32040
cataccataa caatcaggtt gttcatgatc ccatagctaa acgcgctcca gccaaaactc  32100
attcgctcca acagcaccac cgcgtgtccg tcaagtctta cttttacata aacaaggtgt  32160
ctgccacgta catacatgct acccgcatac aaaacttccc ggggcaaacc tctattcacc  32220
acctgtctgt accagggaaa cctgatgttt atcagggaac catagatggc cattttaaac  32280
cagttagcca gcaccacccc gccagctcta cactgaaggg aaccgggaga gttacaatga  32340
cagtggatca tccacctctc gtaaccccta attacctgat taaaatccaa atctaacgtg  32400
gcacaacaga tacacactct cataaacatt ttcatgacat gtttttccca ggatgttaaa  32460
atacaatccc aatacacggg ccactcctgt aatacaataa agctaatgca tgatggaacg  32520
ctcctcacct cactaacatt gtgcatgttt acattttcac actctaagta ccgagtcctc  32580
tcctcaacag ccgcagtgtc gcgctcctca cacggtggta gctgatgaca attgtaaggg  32640
gccagtctgc agcgatatcg tctgtcgcgc tgcatcgtaa aacagggacc gtctcacttc  32700
ctcgtacttc caatagcaga accacgtccg ctgccagcag gtttccacga accgccgatc  32760
ccttcgtcgt tcacgctccc tcctcaacgc aaaatgcagc cactcctgca atccacacaa  32820
atccctctcg gcctccggag tcatgcacac ctcataccta tatatgtctc ggtacagttc  32880
caaacacgaa gtaagggcga gctccaacca acacaaacag gctgatttat cccgacacac  32940
tggaggtgga ggaagacacg gaagaggcat gttattccaa gcgatccggc aaaggatcaa  33000
agtgcagatc ccgaagatgg caacgctcgc ctccggagcc ctggtgaaat ttaacggcca  33060
aatcaaacat tatgcggttt tccaaactat caatcgccgc ctccaaaagg gcctgaaccc  33120
gcacttccac aatcaccagc aaagcaaaag cgtgattatc aaagtcttca atcatcagat  33180
ggcatgactg tacaatgccc aaataattct catttctcca ctcgcgaata gtgtcgcggc  33240
agatcgtctg aaggtccatg ccatgcatgt taaaaagctc ccagagggcg ccctctaccg  33300
acatgcgtag acacaccatc atgactgcaa aatatcaggc tcctgagaca cctgcagcag  33360
atttaacaga tcaaagtcag gttgctgtcc gcggtcacga atctccatgc gcaaagccat  33420
ttgcaaaaaa ttatataggt ctgtgccaac tagctctgtt aattccgcgt taggaagcaa  33480
atcaggtgag gctatgcagc acaaaagttg cagggaaggc gccaaactca gtaaaaccgc  33540
tccagaataa caaaattgat gaagcggagt cacacagtgt aaaatgtgca accaaaaatc  33600
attcagctgc tcttttaaat agtccagtac ttctatattc aatccgtgca agtactgaag  33660
caactgcgcg ggaacagtca cattaaaaaa aatggggcgg ctcaaataca tgtcgaccta  33720
aaataaaaat aatcattaaa ccagagaagc ttgacgaatg gaaggataaa atacacgctc  33780
```

cagcaaaagg caggcaaccg gctgtccccg agaaccgtaa aaaaattcat ccgaatgatt 33840
aaaaagaacc acagaaattt cccaccatgt actcggttgt aactcctgag cacacagcaa 33900
caccccccta acgttcatgt ccgccactga aaaaagacgt cccaaatacc caggtggaat 33960
gtcaagagac aactgcagag acagcaaaac aacccctctg ggagcgatca taaactcctc 34020
cggtgagaaa agcgcataca aattagaata accctgttgc tggggcaaaa tagcccggcg 34080
gcccagcaaa tggacataaa tatgttcagc agccatcgcc ccgtcttacc gcgtaaaaag 34140
ccagaaaaat ccagctaact acactctaca gcctattact atatatactc tcctcccact 34200
gacgctatac caccccgccc acgtccaaag ttcacccacg cccaaaaaac ccgcgaaaat 34260
ccagcgccgt cagcacttcc gcaattgtag tctctcaacg tcacttccgc gcgccttttc 34320
cctattccca cacacgcccg cggacttcgc cccgcccgcc ctcgcgccac cccgcgtcac 34380
cccgcgtcac cgcacgtcac cccggccccg cctcgctcct ccccactcat tatcatattg 34440
gcacgtttcc agaataaggt atattattga tgatg 34475

<210> SEQ ID NO 4
<211> LENGTH: 1092
<212> TYPE: DNA
<213> ORGANISM: Artificial Sequence
<220> FEATURE:
<223> OTHER INFORMATION: Synthetic oligonucleotide sAd4287 Fiber-1

<400> SEQUENCE: 4
atgaaaagaa ccagagttga tgaagacttc aaccccgtct acccttatga ctccacatcc 60
actcctgcgg tccccttttat atcccccccg tttgtaaaca gcgatggtct tcaggaaaac 120
cctcctggag tcttaagttt acgaatagct aaacccttgt attttgacat ggaaaggaaa 180
ctagcgcttt cacttggaag aggattggca attacctcca ccggacagct agaaagcaca 240
cagagcgtgc aaaccacccc tccattagtt gtcaacaaca gcaacacgct tgtcctgcgt 300
tattcctccc cgttaggctt atcgggtgac aatttaatac taaattgctc cgatcctctc 360
cgcgtagtaa acaacagcct gacattcagc tacctatctc cacttcgttt tgaaggtggc 420
agtcttacat tcaattacac atctcccctt aaactgttga acagcagcct tgcgatcgga 480
ataaattcca acaaaggtct cggcaatgac agcgatgaac tttctgtcaa actaacatca 540
gatctaaagt ttaacaacga tggaaaaata gcttttggta tacaaagcct gtgtaccacc 600
cccacagccg cctctaactg taccgttttt accaacggtg attctttact ctgtttatgt 660
ttaaccaaat gtggagctca cgtgttagga agtgtgagtt taaccggaat gcaaggaacc 720
ataacagcca tgacacagaa ctacattagt attcaatttc tatttgacaa caatggtgcg 780
ttgacttcat caccgctcct caacaacaac acttggggta tacggcaaaa cgacacttcg 840
tccgctaacc ccgcctacaa tgctcttgca tttatgccta acagcactgt atatgtaaga 900
ggtcaaagtg gtgagcccag aaataactat tacacccaaa catacettag gggaaacgtt 960 aaaaagccaa ttatccttac cgttacctac aactcggctg cttcaggtta ttcactaact 1020
tttaaatggg atgctgtagt aacagaaaaa tttgccactc caacatcttc tttttgctat 1080
attacagaac aa 1092

<210> SEQ ID NO 5
<211> LENGTH: 1089
<212> TYPE: DNA
<213> ORGANISM: Artificial Sequence
<220> FEATURE:

<223> OTHER INFORMATION: Synthetic oligonucleotide sAd4310A Fiber-1

<400> SEQUENCE: 5
atgaaaagaa ccagagttga tgaagacttc aaccccgtct accccctatga caccacaacc 60 actcctgcag ttccctttat atcacccccc tttgtaaaca gcgatggtct tcaggaaaac 120
cccccaggtg ttttaagtct gcgaatagct aaacccctat atttcgacat ggagagaaaa 180
ctagcccttt cacttggaag agggttgaca attaccgccg ccggacaatt agaaagtacg 240
cagagcgtac aaaccaaccc accgttgata attaccaaca acaacacact gaccctacgt 300
cattctcccc ccttaaacct aactgacaat agcttagtgc taggctactc gagtccgctc 360
cgcgtcacag acaacaaact tacatttaac ttcacatcac cactccgtta tgaaaatgaa 420
aaccttactt ttaactatac agagcctctt aaacttataa ataacagcct tgccattgac 480
atcaattcct caaaaggcct tagtagcgtc ggaggctcac tagctgtaaa cctgagttca 540
gacttaaagt ttgacagcaa cggatccata gcttttggca tacaaaccct gtggaccgct 600
ccgacctcga ctggcaactg caccgtctac agcgagggcg attccctact tagtctctgt 660
ttaaccaaat gcggagctca cgtcttagga agtgtaagtt taaccggttt aacaggaacc 720
ataacccaaa tgactgatat ttctgtcacc attcaattta catttgacaa caatggtaag 780
ctactaagct ctccgcttat aaacaacgcc tttagtattc gacagaatga cagtacggcc 840
tcaaacccta cctacaacgc cctggcgttt atgcctaaca gtaccatata tgcaagaggg 900
ggaggtggtg aaccacgaaa caactactac gtccaaacgt atcttagggg aaatgttcaa 960
aaaccaatca ttcttactgt aacctacaac tcagccgcca caggatattc cttatctttt 1020
aagtggactg ctcttgcacg tgaaaagttt gcaaccccaa caacttcgtt ttgctacatt 1080
acagaacaa 1089

<210> SEQ ID NO 6
<211> LENGTH: 1089
<212> TYPE: DNA
<213> ORGANISM: Artificial Sequence
<220> FEATURE:
<223> OTHER INFORMATION: Synthetic oligonucleotide sAd4312 Fiber-1

<400> SEQUENCE: 6
atgaaaagaa cccgagttga tgaagacttc aaccccgtct acccttatga caccacaacc 60
actccagccg ttcctttcat atcacccccg tttgtaaaca gtgacggtct tcaggaaaac 120
ccccccggag ttttaagcct gcgaatagct aaacccctgt attttgacat ggagagaaaa 180
ctagcccttt cacttggaag agggttaaca attaccgcga acggacaatt agaaagcacc 240
cagagcgtgc agactaaccc gccgttaact gtcaccaata acaacacact tatcctacgc 300
cactcctccc ctttaatcct aactgacaat aatttaaccg taggcttctc aagtcctctc 360
cgtgttatag acaacaaact gacattcact tttacctcac ctctccgtta tgaaaacgaa 420
acccttacct tcaattacac agagcccctt acacttatga acagcaacct tgcgcttaac 480
gtaaactcct ctaaaggcct tagggttgac gggggctcac taggtacaaa cttaagtccg 540
gacttaaggt ttaacagcag tggagccata gcttttggta tacaaaccct atggacaccc 600
ccgacctcaa atcctaactg caccgtttac accgaaagcg attccttact tagtctctgc 660
ttaactaaat gcggagctca cgttttagga agtgtaagct taaccggggt agcaggtacc 720
atgataaaca tggctgaaac ttcgcttgct attgaattta cgtttgacga cactggaaaa 780
ctacttcact caccacttgt taacaccact tttagcattc gtcagggcga cagccccgcc 840
tcaaatccta cctacaatgc tctagcattt atgccaaaca gtaccctcta cgctagagga 900
ggaagtggtg aaccccgaaa caattactac gtccaaacat acctcagggg aaatgttcag 960
agaccgatta ccctcactgt tactttcaac tcagccgcca cgggatattc cttatctttt 1020
aagtggactg ctgttgcacg tgaaaaattt gcagctcctg caacttcatt ttgctacatt 1080
accgaacaa 1089

<210> SEQ ID NO 7
<211> LENGTH: 1677
<212> TYPE: DNA
<213> ORGANISM: Artificial Sequence
<220> FEATURE:
<223> OTHER INFORMATION: Synthetic oligonucleotide sAd4287 Fiber-2

<400> SEQUENCE: 7
atgaaacggg ccagagttga tgaagacttc aacccagtgt acccttatga ccccccatac 60
gctcccgtta tgcccttcat tactccacct tttacctcct cggatgggtt gcaggaaaaa 120
ccacttggag tgttaagttt aaactacaag gatcccatta ctacacaaaa tggatctctc 180
acgttgaaaa taggaaacgg cctcactcta gacaaccagg gacaattaac atcaactgct 240
ggggaagtag agcctccgct cactaatgct aacaacaaac ttgcactagc ctatagcgaa 300
ccattagcag taaaaagcaa ccgcttaact ttatcacaca ccgccccccct tgtcgttgct 360 aataattctt tagcgttgca agtttcagaa cctattttta taaatgacga tgacaagcta 420
gccctgcaga cagccgcccc ccttgtaact aacgctggca cccttcgctt acagagcgcc 480 gccccttag gattggttga aaatactctt agactgctgt tttctaaacc cttgtatttg 540
caaaatgatt ttcttgcatt aggcattgaa cgccccctgg ctatagcagc cgcaggtact 600
ctagcactac aactcactcc tccattaaag actaacgatg acgggctgac actatccaca 660
gtcgagccat taactgtaaa aaacggaaac ttaggcttgc aaatatctcg ccctttggtt 720
gttcaaaaca gcagcctttc gcttgctatt acccccccgc tgcgtctatt taacagcgac 780
cccgttcttg gtttgggctt tacttttccc ctagccgtga cagacaacct actctcctta 840
aacatgggag acggtgttaa actaacctat aataaactaa cagccaattt gggtagggat 900
ttacaatttg aaaacggtgc cattgccgta acgcttactg ccgaatcacc tttgcaatac 960
actaacaaac ttcaactgaa tattggagct ggccttcgtt acaatggagc cagcagaaaa 1020
ctagatgtaa acattaacca aaataagggc ttaacttggg acaacgatgc agttattccc 1080
aaattaggat caggtttaca attcgaccct aatggtaaca tcgctgttat ccctgaaacc 1140
gtaaagccgc aaacgttatg gacaactgca gatccatcgc ctaactgctc agtgtaccag 1200
gacttggacg ccaggctgtg gctcgctctt gttaaaagtg gtgacatggt tcatggaagc 1260
attgctctaa aagccctaaa aggaacgttg ctaaatccta cagcaagcta catctccatt 1320
gtgatatatt tttacagcaa cggagtcagg cgtaccaact atcccacgtt tgacaacgaa 1380
ggcaccttag ctaacagcgc tacctgggga taccgagagg ggcaatctgc taacactaat 1440
gtaaccaatg ccactgaatt tatgcccagc tcaaccaggt accccgtgaa taaaggagac 1500
aatattcaga atcaatcttt ttcatacacc tgtatcaaag gagatttcgc tatgcctgtc 1560
ccgttccgtg taacatataa tcatgccctg gaaggatact cccttaagtt cacctggcgc 1620
gttgtagcca accaagcttt tgatattcct tgctgttcct tttcatacat cacagaa 1677

<210> SEQ ID NO 8

-continued

<211> LENGTH: 1680
<212> TYPE: DNA
<213> ORGANISM: Artificial Sequence
<220> FEATURE:
<223> OTHER INFORMATION: Synthetic oligonucleotide sAd4310A Fiber-2

<400> SEQUENCE: 8

```
atgaaacggg cgagagttga tgaagacttc aacccagtgt acccttatga ccccccacat     60

gctcccgtta tgcccttcat tactccacct tttacctcct cggatgggtt gcaggaaaaa    120

ccacttggag tgttaagttt aaactacaga gatcccatta ctacgcaaaa tgggtctctt    180

acagttaaac taggaaacgg cctcactcta gacaaccagg gacaactaac atcaaccgct    240

ggggaagtag aacctccact cactaacgct aacaacaaac ttgcactggt ctatagcgat    300

cctttagcag taaagcgcaa cagcctaacc ttatcgcaca ccgctcccct tgttattgct    360

gataactctt tagcattgca agtttcagag cctattttta taaatgacaa ggacaaacta    420

gccctgcaaa cagccgcgcc ccttgtaact aacgctggca cccttcgctt acaaagcgcc    480

gcccctttag gcattgcaga ccaaacccta aaactcctgt ttaccaaccc tttgtacttg    540

cagaataact ttctcacgtt agccattgaa cgaccccttg ccattaccaa tagtggaaag    600

ctggctctac agctctcccc accgctacaa acagcagaca caggcttgac tttgcaaacc    660

aacgtgccat taactgtaag caacgggacc ctaggcttag ccataaagcg cccacttatt    720

gttcaggaca acaacttgtt tttggacttc agagctcccc tgcgtctttt caacagcgac    780

cccgtactag ggcttaactt ttacacccct cttgcagtgc gcgatgaggc gctcactgtt    840

aacacaggcc gcggcctcac agtgagttac gatggtttaa ttttaaatct tggtaaggat    900

cttcgctttg acaacaacac cgtttctgtc gctcttagtg ctgctttgcc tttacaatac    960

actgatcagc ttcgccttaa cgtgggcgct gggctgcgtt acaatccagt gagtaaaaaa   1020

ttggacgtga accccaatca aaacaagggt ttaacctggg aaaatgacta cctcattgta   1080

aagctaggaa atggattagg ttttgatggc aatggaaaca tagctgtttc tcctcaagtt   1140

acatcgcctg acaccttatg gaccactgcc gatccatccc ccaattgttc catctacact   1200

gatttagatg ccaaaatgtg gctctcgttg gtaaaacaag gggtgtggt tcacggttct    1260

gttgctttaa aagcattgaa aggaacccta ttgagtccta cggaaagtgc cattgttatt   1320

atactacatt ttgacaatta tggagtgcga attctcaatt atcccacttt gggcactcaa   1380

ggcacgttgg gaaataatgc aacttggggt tataggcagg gagaatctgc agacactaat   1440

gtactcaatg cactagcatt tatgcccagt tcaaaaaggt acccaagagg gcgtggaagc   1500

gaagttcaga atcaaactgt gggctacact tgtatacagg gtgacctttc tatgcccgta   1560

ccgtaccaaa tacagtacaa ctatggacca actggctact cctttaaatt tatttggaga   1620

actgtttcaa gacaaccatt tgacatccca tgctgttttt tctcttacat tacggaagaa   1680
```

<210> SEQ ID NO 9
<211> LENGTH: 1680
<212> TYPE: DNA
<213> ORGANISM: Artificial Sequence
<220> FEATURE:
<223> OTHER INFORMATION: Synthetic oligonucleotide sAd4312 Fiber-2

<400> SEQUENCE: 9

```
atgaaacggg ccagagttga tgaagacttc aatcccgtgt acccttacga tccccccttac    60

gcccccatta tgccgtttat taccccgccg tttacatctt cagatgggtt acaggaaaaa    120

ccacttggtg ttttaagttt aaaatacaag gatcctatca ctacacaaaa tggttctcta    180
```

acccttaaat taggaaacgg gctgaacatt aacaaccagg gccaacttac atcatctgct 240
ggggaagtcg agcctcccct caccaatgct gacaacaagc tggccttagc ctacagcgac 300
cctctgacat taaaaaacag ccgtctaaca ctgtctcaca atgccccact tgcaattaac 360
aataattctc taagtttgga agtatcagag cctatattta taaataacga caacaaactg 420
tctctgaaag ctgacgcccc cctgacaacc agcgctggaa ccctccgcct gcaaagcgct 480
gctccattag gacttgctga acagacacta aagctgctgt tttctaaccc tttgtacttg 540
cgaggtgact tccttacatt agccattgaa cgcccattgg ctgtaacagc agacgggcta 600
ttatcacttg ccctcaaccc tccgctcaca acaactaaca caggcttagc tctctctacc 660
gcggttccat taactgttac caacgggaac cttagcctaa acgtaaaacg gccgtttatt 720
atacaggacg gcagccttta catggatttt agacccccac tatatctgtt taacagcgag 780
ccacaacttg gtgttaattt taatgcccct ctaactgtta gagataacgg cctagctata 840
aacaccggag acgggctaac agtaacgtat aataaactaa cattaaacct cggtagagac 900
ttgcaatatg aaaatggagc tgcagctgtt aagctaagta ccgcccctcc tctacagtat 960
actactcaac tgcagctgaa tttgggagcg ggcttacgtc taggtcctac taggaactta 1020
gacgtggcca ttaaccacaa taaagggtta gcgtgggaaa acaatgaagt ggttactaaa 1080
ttaggacaag gcctttactt tgattcctcc ggaagcatag ctttatcgcc tacaaacccc 1140
agaccagata ctttatggac cacggccgat ccttcgccaa actgcactgt atatgaatca 1200
cttgactcta gactgtggct agcgcttgtt aaatgtgggg gaatggtaca cggcagcata 1260
gccctacaag ctgaaaaagg ccaattgctg cgtcctactg ctagttttat ctccatcgta 1320
atttacttct acagtgatgg ggtccgtcgc accaactacc ctacaattgg caatgatgag 1380
ggtactctgg ccaacagcgc tacttggggc tacagacaag ggcaatctgc agacaccaac 1440
gtcaccaatg ctgttgaatt catgcctagt ttacacagat atcctataaa tcagggagac 1500
aatattaaaa accaaatgat aacttacact tgcatacaag gcaacgtgaa catgccagta 1560
cccttgaaaa tcacgttcaa tcatgctctt gaaggctact ccttaaagtt tacatggcgt 1620
gtggtggcta atgaaaagtt tgatattcct tgctgttcgt tttcttacat tacagaacaa 1680

<210> SEQ ID NO 10
<211> LENGTH: 2799
<212> TYPE: DNA
<213> ORGANISM: Artificial Sequence
<220> FEATURE:
<223> OTHER INFORMATION: Synthetic oligonucleotide sAd4287 Hexon

<400> SEQUENCE: 10
atggccaccc catcgatgat gccgcagtgg tcttacatgc acatcgccgg ccaggacgcc 60
tcggagtacc tgagtcccgg cctcgtgcag tttgcccgcg ccaccgacac ctacttcagc 120
ttgggaaaca agtttagaaa ccccaccgtg gcccccaccc acgatgtgac cacggaccgc 180
tcgcagaggc tgaccctgcg ctttgtgccc gtagaccggg aggacaccgc gtactcttac 240
aaagtgcgct acacgctggc cgtaggggac aaccgagtgc tggacatggc cagcacctac 300
tttgacatcc ggggggtgct ggatcggggt cccagcttca agccctactc cggcaccgct 360
tacaactccc tggctcccaa gggcgccccc aatcctgcag aatgggccga taccaacgac 420
agcaacaaac tgaaagtgag ggtcaggcg ccttttgtca gtacttacgg ttctgctacg 480
gcgcttacaa aagatgggat acaggtggga gtggatactt ccgaagcatc tcaggctgtt 540

```
tatgccgaca gaagttacca gccagaaccc caaattggag agacagagtg gaacagcgaa    600
gtgggtaatg acgacagagt ggcgggaagg gtgctaaaga aaacaactcc catgttccct    660
tgttacggtt catatgccaa gcccaccaac gaaaaaggcg gacaagcaat acagcccacc    720
gccggcaacg gcgataatca ggctgtagag ttacaattct ttgccactac tagcactccc    780
actgcgccaa aggcagtatt gtacgcggag gacgtggcca ttgaagctcc agatactcac    840
ttagtgttta agccaacagt agtcgcggga actacaagtt cggaagctct gctaacccaa    900
caagccgcac ctaaccgccc aaactacatt gcctttagag ataactttat tggtctcatg    960
tactacaatt caaccgggaa tatgggagta ctggccggac aagcatctca gctcaatgca   1020
gtggttgatc ttcaggacag aaacaccgaa ctgtcatatc agctaatgct ggatgctctg   1080
ggagatcgca gtcggtactt ttctatgtgg aatcaagctg tagatagcta tgatccagat   1140
gtaagaattg tagaaaacca cggtgtggaa gacgaactgc ctaattattg cttcccacta   1200
ggcgggatgg tagtaacgga cacttacaaa gccataaagg taaatggaag cggatggacg   1260
gctaatactg acgttttcag cgagagagta gaaataggct caggtaacct gtttgccatg   1320
gaaattaact tgcaagctaa tctgtggcgc agtttcttgt attccaacat aggactgtac   1380
ctcccggact ctttaaaatt aacccctgac aacatcacgc tccctgagaa caaaaatacc   1440
taccagtata tgaacggtcg cgtaacacca cccgggctcg tggacaccta cgttaacgtg   1500
ggtgcgcgct ggtcccccga tgttatggac agcattaacc cttttaacca ccaccgcaac   1560
gccgggctcc gctaccgttc catgctcctg ggaaacggac gctacgtacc cttccacatt   1620
caggtgcccc agaaattctt tgcaattaaa aacctgctgc tgctccccgg ttcctatacc   1680
tacgagtgga atttccgcaa ggacgtgaac atgattttgc aaagctcgct gggtaacgac   1740
ctgcgagttg acggggccag catacgcttc gacagcatca acctgtatgc taactttttc   1800
cccatggccc acaacacggc ctccaccctg gaagccatgc tgcgcaacga caccaatgac   1860
cagtccttca acgactacct gtgcgcggcc aacatgctgt atcccatccc cgccaacgcc   1920
accagcgtgc ccatctccat cccgtctcgc aactgggccg cctttagggg ttggagtttc   1980
acccgcctca aaaccaagga aaccccctcg ctgggctctg gcttcgaccc ctacttcgtc   2040
tactcaggct ccattcccta cctggacggc actttctatc ttaaccacac tttcaaaaag   2100
gtgtctatca tgttcgattc ctcggtcagc tggcccggca acgaccgcct gctgacgccc   2160
aacgagttcg aaatcaagcg ttcggtggac ggtgaagggt acaacgtggc ccagagcaac   2220
atgaccaagg actggttcct ggttcaaatg ctcagccatt acaacatcgg ttaccagggc   2280
ttctatgtgc ccgagaacta caaggaccgc atgtactcct tctttaggaa cttccaaccc   2340
atgagtcgcc aagtcgtgga ctcagtggct tacagggact actaccagga cgttaagctc   2400
ccctaccagc acaacaactc agggttcgtg ggctacatgg gtcccaccat gcgagagggg   2460
caggcctacc cggccaacta tccttatccc ctaatcggag agactgctgt acccagcctg   2520
acgcagaaaa agttcctctg cgaccgggtg atgtggagga taccettctc tagcaacttc   2580
atgtctatgg gctccctcac cgacctgggg cagaacatgc tgtacgccaa ctccgctcac   2640
gccttggaca tgacctttga ggtggatccc atggatgagc ccacgcttct ctatgttctg   2700
tttgaagtct tcgacgtggt gcgcatccac cagccgcacc gcggcgtcat cgaggccgtc   2760
tacctgcgca cacctttctc tgccggtaac gccaccacc                          2799
```

<210> SEQ ID NO 11
<211> LENGTH: 2736

```
<212> TYPE: DNA
<213> ORGANISM: Artificial Sequence
<220> FEATURE:
<223> OTHER INFORMATION: Synthetic oligonucleotide sAd4310A Hexon

<400> SEQUENCE: 11

atggccaccc catcgatgat gccgcagtgg tcttacatgc acatcgccgg gcaggacgcc      60

tcggagtatc tgagccccgg tcttgtgcag tttgcccgcg ccaccgacac ctacttcagc     120

ttgggaaaca agtttagaaa tcccaccgtg gcccccacgc acgatgtgac cacggatcgt     180

tcgcagaggc tgactctgcg ctttgtaccg gtagaccgtg aggatactgc ctattcttac     240

aaagttcggt atacgttagc cgtaggagac aacagggtgc tggacatggc cagtacttac     300

tttgacatcc gcggtgttct tgaccgcggt ccaagcttta aaccgtatac cggaacggca     360

tacaatgcct tggctccaaa gggcgctcca aatgcttgcc agtggacaac gaccaacggg     420

ggcaataaaa cgaacacttt tgcccaagcc cctttaatag gcacggctat tgacggaacc     480

aacggactgc agattgggca agataatgga caagctgttt atgctgacaa aacctttcaa     540

cccgaaccac aagtgggaga atctcagtgg aatactaatc caaccacaaa cgcagcagga     600

cgcgtgttaa aaacaactac tcgcatgctg ccttgctatg gttcttttgc aaggcccacc     660

aatgagaaag gggtcaagc ttcaggagac gttaccttcc aatttttcga cactgcctcg     720

gacaatggca acaaccctaa ggtggtgcta tatggagaag acgtcaacat tgaatcgcct     780

gacacacact taatctacaa acccaccgct gacaacacaa actctgaaaa ccttttgggt     840

caacaggccg ctccaaacag agccaattac attgcctttc gggacaactt cattggacta     900

atgtactata attcaacagg aaacatggga gtgttggcag ggcaggcttc ccaactaaat     960

gctgtggtag acttgcaaga cagaaacact gagctttcct accaactcat gttagatgca    1020

ataggagacc ggagtcgtta cttttcaatg tggaaccaag cagtggacag ctatgatcca    1080

gatgtgcgaa ttattgaaaa tcatggcgtt gaggacgaac tgccaaatta ctgcttccct    1140

cttaacgctc aaggaattgc taacacctat aaaggcgtta agaaaaacaa cggcaattgg    1200

gcgaaagacg acgcagtagt agaaactaac gaaattggca taggaaatgt ttttgccatg    1260

gagataaatt taactgctaa cttgtggcga aactttctgt attccaatat tgctttgtac    1320

ctgccagact cctacaagta ttcaccggga aacataacct tacccgaaaa caaaaacagt    1380

tacaattaca ttaatggtcg agtaacagct cctggtctgg tagacacctt tgtaaacatt    1440

ggcgcgcgat ggtctcccga ccccatggac aacgtgaatc cttttaatca ccatcgcaat    1500

gctggtctgc gttatcgctc catgcttcta ggcaacggcc gctacgtgcc cttccacatt    1560

caggtgcctc aaaaattctt tgccattaag aacctgcttc tgctgcctgg gtcctacacc    1620

tacgagtgga acttcagaaa agatgtaaac atgatcttgc agagcacgct gggcaacgac    1680

ctccgtgtcg acggggccag cgtcagattc gacagcatta acctctacgc taatttcttc    1740

cccatggcac ataacaccgc ttccaccctg gaggctatgt tacgcaacga caccaacgac    1800

cagtccttta atgactacct ctgcgcggcc aacatgctat accccattcc tgccaatgcc    1860

accagtgtgc ccatctccat cccctctcgc aactgggcag ctttcagagg gtggagtttc    1920

acccgcctca aaacaaaaga aaccccctcg ctgggttccg gatttgatcc atactttgtt    1980

tactcaggct ccattcccta cctggatggt accttctacc tgaaccacac cttcaaaaag    2040

gtgtctatta tgttcgactc ttctgtgagc tggcccggca acgaccgcct gctgacccct    2100

aatgagtttg aaattaagcg ctcggtggac ggagaaggat acaatgtagc ccagagcaac    2160
```

-continued

```
atgaccaaag actggttctt aattcaaatg ctcagccact acaacattgg ttaccaaggg   2220

ttttacgtgc ccgaggctta caaagacaga atgtactcct tttttagaaa cttccaacct   2280

atgagtagac aggtagtgga tgcagatcgg tatgaacaat acaaaaaagt caccgttgag   2340

tatcaacata ataattctgg ttttgtggga tacatgggac ccaccatgag ggaagggcag   2400

gcttatccag cgaattaccc ttatcctctt attggagaca ccgccgtgcc cagcctgacc   2460

cagaaaaagt tcctctgtga ccgcaccatg tggagaatcc ccttctctag caacttcatg   2520

tctatggggg ccctcaccga cctggggcag aacatgctgt acgccaattc cgctcacgcc   2580

ttggatatga cctttgaggt ggaccccatg gatgagccca cgcttctcta tgttctgttt   2640

gaagtcttcg acgtggtgcg catccaccag ccgcaccgcg gcgtcatcga ggccgtctac   2700

ctgcgcacac ctttctctgc cggtaacgcc accaca                             2736


<210> SEQ ID NO 12
<211> LENGTH: 2784
<212> TYPE: DNA
<213> ORGANISM: Artificial Sequence
<220> FEATURE:
<223> OTHER INFORMATION: Synthetic oligonucleotide sAd4312 Hexon

<400> SEQUENCE: 12

atggccaccc catcgatgat gccgcagtgg tcttacatgc acatcgccgg ccaggacgcc     60

tcggagtacc tgagtcccgg cctggtgcag tttgcccgcg ccaccgaaag ctacttcagc    120

ttgggaaaca agtttagaaa ccccaccgtg gcccccacgc acgatgtaac cacggaccgc    180

tcgcagaggc tgacactgcg cttcgtgccc gtagaccggg aggacaccgc gtactcctac    240

aaagtgcgct tcaccctcgc cgtaggggac aacagggtgc tggacatggc cagcacgtac    300

tttgacatcc ggggaatgct ggaccgaggg cccagcttta aaccctactc gggaactgcc    360

tacaattcgc tggcacctaa gggcgctccc aaccctagtc aatggactac taccaacgga    420

gggaataaaa caaattcatt tgcccaagca tcctacatag gtcaaagcct gtcgaaagac    480

ggggtgcaag tagcagtaga tacagccgct ggggggctg cagtatatgc tgacaaaacg     540

tttcaaccag aaccccaagt aggaatatca caatggaatg aaaatcctac tacaaatgct    600

gcaggaagaa ttttaaagcc tactaccgca atgcgtccat gctacggttc atacgcttac    660

cccaccaacg aaaaaggtgg gcaggtaaaa atcactgacc ctaacaatga caaaaccggc    720

gctaataacg ttagcttaaa ttttttcaac actgccgctg acaatgggaa taacaatcca    780

aaagtagtac tctacagcga agatgtaaat ttagaagggc cagataccca ccttgttttt    840

aagccagatg taactggcga cgcaaccagt gcagaaaccc tgttaggtca acaagcagct    900

cccaatcgtc caaactacat tgggttcagg gacaacttta ttggcctgat gtactacaat    960

tcaactggaa acatgggagt gctagcaggt caggcttctc agctaaacgc cgtagtggat   1020

cttcaagaca gaaataccga attgtcatat cagctaatgc ttgacgcttt gggtgacaga   1080

agtcggtact tttctatgtg gaatcaagca gtggacagct acgatcctga cgttagaatc   1140

atagaaaatc atggagtaga agacgaactt ccaaattatt gttttccgtt aaatggacag   1200

gggatttcga atacatacaa aggtgtgaaa tataacacaa acacttggac gcaagacact   1260

gatgtagtca caaccaatga aatttccatt ggcaacattt ttgccatgga aataaacctg   1320

gcggctaact tgtggcgcag ctttctgtac tccaatgtcg ccctgtactt gccagattcc   1380

tacaaataca ctcccgacaa tattgaactt cctacaaaca agaacagcta cggctacatt   1440

aacggaaggg taaccgcccc cactgccatc gacacttacg ttaacatcgg cgcccggtgg   1500
```

tctccggacc ccatggacaa cgttaaccct ttcaaccacc accgcaacgc cggcttgcga 1560
taccgctcca tgctgctggg caacggtcgc tacgtaccct tccacattca ggtgccccag 1620 aaatttttg ccattaaaaa cctgcttctg cttcccgggt cctacaccta cgagtggaac 1680
ttcaggaaag atgtaaacat gatcttgcag agcaccttgg gcaacgacct ccgcgttgac 1740
ggagctagcg tgaggtttga cagcattaac ctctacgcta acttcttccc catggcccac 1800
aacacggcct ccaccttgga agccatgctg cgcaacgaca ccaacgacca gtcctttaat 1860
gattacctgt gcgcggccaa catgctgtac cccatccccg ccaatgccac cagcgtgccg 1920
atctccattc cctcacgcaa ctgggccgcc ttcagaggtt ggagtttcac tcgcctgaaa 1980
accaaggaga ccccctcgct gggctccggt ttcgacccat actttgttta ctccgggagc 2040
attccctacc tggacggaac tttctacctg aaccacacct tcaaaaaggt gtctattatg 2100
tttgactcct ccgtgagctg gcccggtaac gaccgcttgc taacccccaa cgagttcgaa 2160
atcaaacgct cggtggacgg agagggttac aatgtagccc agagcaacat gaccaaagac 2220
tggtttttaa ttcaaatgct aagccactat aacattggct accaaggatt ctacgtgcct 2280
gaagcctaca aggacagaat gtactccttc tttagaaact tccaacccat gagccgccag 2340
gtagtagaca cggtaaacta tgctaactac aaggaagtaa caatgccatt ccagcacaac 2400
aactcaggct tcgtggggta catgggacct accatgagag aggggcaggc ctacccggct 2460
aattatccct accccctaat cggagccact gccgtgccca gcctgacaca gaaaaagttt 2520
ctctgcgatc gaacaatgtg gaggattccc ttctctagca acttcatgtc catgggggct 2580
ctcaccgacc tggggcagaa catgctgtac gctaactccg ctcacgcctt ggacatgacc 2640
tttgaggtgg accccatgga tgagcccacg cttctctatg ttctgtttga agtcttcgac 2700
gtggtgcgca ttcaccagcc gcaccgcggc gtcatcgagg ccgtctacct gcgcacacct 2760
ttctctgccg gtaacgccac cacc 2784

<210> SEQ ID NO 13
<211> LENGTH: 492
<212> TYPE: DNA
<213> ORGANISM: Artificial Sequence
<220> FEATURE:
<223> OTHER INFORMATION: Synthetic oligonucleotide sAd4287 Fiber-1 Knob

<400> SEQUENCE: 13
ctgtgtacca cccccacagc cgcctctaac tgtaccgttt ttaccaacgg tgattcttta 60
ctctgtttat gtttaaccaa atgtggagct cacgtgttag gaagtgtgag tttaaccgga 120
atgcaaggaa ccataacagc catgacacag aactacatta gtattcaatt tctatttgac 180
aacaatggtg cgttgacttc atcaccgctc ctcaacaaca acacttgggg tatacggcaa 240
aacgacactt cgtccgctaa ccccgcctac aatgctcttg catttatgcc taacagcact 300
gtatatgtaa gaggtcaaag tggtgagccc agaaataact attacaccca aacatacctt 360
aggggaaacg ttaaaaagcc aattatcctt accgttacct acaactcggc tgcttcaggt 420
tattcactaa cttttaaatg ggatgctgta gtaacagaaa aatttgccac tccaacatct 480
tctttttgct at 492

<210> SEQ ID NO 14
<211> LENGTH: 489
<212> TYPE: DNA
<213> ORGANISM: Artificial Sequence
<220> FEATURE:

-continued

<223> OTHER INFORMATION: Synthetic oligonucleotide sAd4310A Fiber-1 Knob

<400> SEQUENCE: 14
ctgtggaccg ctccgacctc gactggcaac tgcaccgtct acagcgaggg cgattcccta 60
cttagtctct gtttaaccaa atgcggagct cacgtcttag gaagtgtaag tttaaccggt 120
ttaacaggaa ccataaccca aatgactgat atttctgtca ccattcaatt tacatttgac 180
aacaatggta agctactaag ctctccgctt ataaacaacg cctttagtat tcgacagaat 240
gacagtacgg cctcaaaccc tacctacaac gccctggcgt ttatgcctaa cagtaccata 300
tatgcaagag ggggaggtgg tgaaccacga aacaactact acgtccaaac gtatcttagg 360
ggaaatgttc aaaaaccaat cattcttact gtaacctaca actcagccgc cacaggatat 420
tccttatctt ttaagtggac tgctcttgca cgtgaaaagt ttgcaacccc aacaacttcg 480
ttttgctac 489

<210> SEQ ID NO 15
<211> LENGTH: 489
<212> TYPE: DNA
<213> ORGANISM: Artificial Sequence
<220> FEATURE:
<223> OTHER INFORMATION: Synthetic oligonucleotide sAd4312 Fiber-1 Knob

<400> SEQUENCE: 15
ctatggacac ccccgacctc aaatcctaac tgcaccgttt acaccgaaag cgattcctta 60
cttagtctct gcttaactaa atgcggagct cacgttttag gaagtgtaag cttaaccggg 120
gtagcaggta ccatgataaa catggctgaa acttcgcttg ctattgaatt tacgtttgac 180
gacactggaa aactacttca ctcaccactt gttaacacca cttttagcat tcgtcagggc 240
gacagccccg cctcaaatcc tacctacaat gctctagcat ttatgccaaa cagtaccctc 300
tacgctagag gaggaagtgg tgaaccccga aacaattact acgtccaaac atacctcagg 360
ggaaatgttc agagaccgat taccctcact gttactttca actcagccgc cacgggatat 420
tccttatctt ttaagtggac tgctgttgca cgtgaaaaat ttgcagctcc tgcaacttca 480
ttttgctac 489

<210> SEQ ID NO 16
<211> LENGTH: 510
<212> TYPE: DNA
<213> ORGANISM: Artificial Sequence
<220> FEATURE:
<223> OTHER INFORMATION: Synthetic oligonucleotide sAd4287 Fiber-2 Knob

<400> SEQUENCE: 16
tggacaactg cagatccatc gcctaactgc tcagtgtacc aggacttgga cgccaggctg 60
tggctcgctc ttgttaaaag tggtgacatg gttcatggaa gcattgctct aaaagcccta 120
aaaggaacgt tgctaaatcc tacagcaagc tacatctcca ttgtgatata tttttacagc 180
aacggagtca ggcgtaccaa ctatcccacg tttgacaacg aaggcacctt agctaacagc 240
gctacctggg gataccgaga ggggcaatct gctaacacta atgtaaccaa tgccactgaa 300
tttatgccca gctcaaccag gtaccccgtg aataaaggag acaatattca gaatcaatct 360
ttttcataca cctgtatcaa aggagatttc gctatgcctg tcccgttccg tgtaacatat 420
aatcatgccc tggaaggata ctcccttaag ttcacctggc gcgttgtagc caaccaagct 480
tttgatattc cttgctgttc cttttcatac 510

<210> SEQ ID NO 17
<211> LENGTH: 513
<212> TYPE: DNA
<213> ORGANISM: Artificial Sequence
<220> FEATURE:
<223> OTHER INFORMATION: Synthetic oligonucleotide sAd4310A Fiber-2 Knob

<400> SEQUENCE: 17
ttatggacca ctgccgatcc atcccccaat tgttccatct acactgattt agatgccaaa 60
atgtggctct cgttggtaaa acaagggggt gtggttcacg gttctgttgc tttaaaagca 120
ttgaaaggaa ccctattgag tcctacggaa agtgccattg ttattatact acattttgac 180
aattatggag tgcgaattct caattatccc actttgggca ctcaaggcac gttgggaaat 240
aatgcaactt ggggttatag gcagggagaa tctgcagaca ctaatgtact caatgcacta 300
gcatttatgc ccagttcaaa aaggtaccca agagggcgtg gaagcgaagt tcagaatcaa 360
actgtgggct acacttgtat acagggtgac ctttctatgc ccgtaccgta ccaaatacag 420
tacaactatg gaccaactgg ctactccttt aaatttattt ggagaactgt ttcaagacaa 480
ccatttgaca tcccatgctg ttttttctct tac 513

<210> SEQ ID NO 18
<211> LENGTH: 516
<212> TYPE: DNA
<213> ORGANISM: Artificial Sequence
<220> FEATURE:
<223> OTHER INFORMATION: Synthetic oligonucleotide sAd4312 Fiber-2 Knob

<400> SEQUENCE: 18
ttatggacca cggccgatcc ttcgccaaac tgcactgtat atgaatcact tgactctaga 60
ctgtggctag cgcttgttaa atgtggggga atggtacacg gcagcatagc cctacaagct 120
gaaaaaggcc aattgctgcg tcctactgct agttttatct ccatcgtaat ttacttctac 180
agtgatgggg tccgtcgcac caactaccct acaattggca atgatgaggg tactctggcc 240
aacagcgcta cttggggcta cagacaaggg caatctgcag acaccaacgt caccaatgct 300
gttgaattca tgcctagttt acacagatat cctataaatc agggagacaa tattaaaaac 360
caaatgataa cttacacttg catacaaggc aacgtgaaca tgccagtacc cttgaaaatc 420
acgttcaatc atgctcttga aggctactcc ttaaagttta catggcgtgt ggtggctaat 480
gaaaagtttg atattccttg ctgttcgttt tcttac 516

<210> SEQ ID NO 19
<211> LENGTH: 364
<212> TYPE: PRT
<213> ORGANISM: Artificial Sequence
<220> FEATURE:
<223> OTHER INFORMATION: Synthetic polypeptide sAd4287 Fiber-1

<400> SEQUENCE: 19

Met Lys Arg Thr Arg Val Asp Glu Asp Phe Asn Pro Val Tyr Pro Tyr
1 5 10 15

Asp Ser Thr Ser Thr Pro Ala Val Pro Phe Ile Ser Pro Pro Phe Val
20 25 30

Asn Ser Asp Gly Leu Gln Glu Asn Pro Pro Gly Val Leu Ser Leu Arg
35 40 45

Ile Ala Lys Pro Leu Tyr Phe Asp Met Glu Arg Lys Leu Ala Leu Ser
50 55 60

Leu Gly Arg Gly Leu Ala Ile Thr Ser Thr Gly Gln Leu Glu Ser Thr
65 70 75 80

```
Gln Ser Val Gln Thr Thr Pro Pro Leu Val Val Asn Asn Ser Asn Thr
                85                  90                  95

Leu Val Leu Arg Tyr Ser Ser Pro Leu Gly Leu Ser Gly Asp Asn Leu
            100                 105                 110

Ile Leu Asn Cys Ser Asp Pro Leu Arg Val Val Asn Asn Ser Leu Thr
        115                 120                 125

Phe Ser Tyr Leu Ser Pro Leu Arg Phe Glu Gly Gly Ser Leu Thr Phe
    130                 135                 140

Asn Tyr Thr Ser Pro Leu Lys Leu Leu Asn Ser Ser Leu Ala Ile Gly
145                 150                 155                 160

Ile Asn Ser Asn Lys Gly Leu Gly Asn Asp Ser Asp Glu Leu Ser Val
                165                 170                 175

Lys Leu Thr Ser Asp Leu Lys Phe Asn Asn Asp Gly Lys Ile Ala Phe
            180                 185                 190

Gly Ile Gln Ser Leu Cys Thr Thr Pro Thr Ala Ala Ser Asn Cys Thr
        195                 200                 205

Val Phe Thr Asn Gly Asp Ser Leu Leu Cys Leu Cys Leu Thr Lys Cys
    210                 215                 220

Gly Ala His Val Leu Gly Ser Val Ser Leu Thr Gly Met Gln Gly Thr
225                 230                 235                 240

Ile Thr Ala Met Thr Gln Asn Tyr Ile Ser Ile Gln Phe Leu Phe Asp
                245                 250                 255

Asn Asn Gly Ala Leu Thr Ser Ser Pro Leu Leu Asn Asn Asn Thr Trp
            260                 265                 270

Gly Ile Arg Gln Asn Asp Thr Ser Ser Ala Asn Pro Ala Tyr Asn Ala
        275                 280                 285

Leu Ala Phe Met Pro Asn Ser Thr Val Tyr Val Arg Gly Gln Ser Gly
    290                 295                 300

Glu Pro Arg Asn Asn Tyr Tyr Thr Gln Thr Tyr Leu Arg Gly Asn Val
305                 310                 315                 320

Lys Lys Pro Ile Ile Leu Thr Val Thr Tyr Asn Ser Ala Ala Ser Gly
                325                 330                 335

Tyr Ser Leu Thr Phe Lys Trp Asp Ala Val Val Thr Glu Lys Phe Ala
            340                 345                 350

Thr Pro Thr Ser Ser Phe Cys Tyr Ile Thr Glu Gln
        355                 360
```

```
<210> SEQ ID NO 20
<211> LENGTH: 363
<212> TYPE: PRT
<213> ORGANISM: Artificial Sequence
<220> FEATURE:
<223> OTHER INFORMATION: Synthetic polypeptide sAd4310A Fiber-1

<400> SEQUENCE: 20

Met Lys Arg Thr Arg Val Asp Glu Asp Phe Asn Pro Val Tyr Pro Tyr
1               5                   10                  15

Asp Thr Thr Thr Thr Pro Ala Val Pro Phe Ile Ser Pro Pro Phe Val
            20                  25                  30

Asn Ser Asp Gly Leu Gln Glu Asn Pro Pro Gly Val Leu Ser Leu Arg
        35                  40                  45

Ile Ala Lys Pro Leu Tyr Phe Asp Met Glu Arg Lys Leu Ala Leu Ser
    50                  55                  60

Leu Gly Arg Gly Leu Thr Ile Thr Ala Ala Gly Gln Leu Glu Ser Thr
65                  70                  75                  80
```

Gln Ser Val Gln Thr Asn Pro Pro Leu Ile Ile Thr Asn Asn Asn Thr
85 90 95

Leu Thr Leu Arg His Ser Pro Pro Leu Asn Leu Thr Asp Asn Ser Leu
100 105 110

Val Leu Gly Tyr Ser Ser Pro Leu Arg Val Thr Asp Asn Lys Leu Thr
115 120 125

Phe Asn Phe Thr Ser Pro Leu Arg Tyr Glu Asn Glu Asn Leu Thr Phe
130 135 140

Asn Tyr Thr Glu Pro Leu Lys Leu Ile Asn Asn Ser Leu Ala Ile Asp
145 150 155 160

Ile Asn Ser Ser Lys Gly Leu Ser Ser Val Gly Gly Ser Leu Ala Val
165 170 175

Asn Leu Ser Ser Asp Leu Lys Phe Asp Ser Asn Gly Ser Ile Ala Phe
180 185 190

Gly Ile Gln Thr Leu Trp Thr Ala Pro Thr Ser Thr Gly Asn Cys Thr
195 200 205

Val Tyr Ser Glu Gly Asp Ser Leu Leu Ser Leu Cys Leu Thr Lys Cys
210 215 220

Gly Ala His Val Leu Gly Ser Val Ser Leu Thr Gly Leu Thr Gly Thr
225 230 235 240

Ile Thr Gln Met Thr Asp Ile Ser Val Thr Ile Gln Phe Thr Phe Asp
245 250 255

Asn Asn Gly Lys Leu Leu Ser Ser Pro Leu Ile Asn Asn Ala Phe Ser
260 265 270

Ile Arg Gln Asn Asp Ser Thr Ala Ser Asn Pro Thr Tyr Asn Ala Leu
275 280 285

Ala Phe Met Pro Asn Ser Thr Ile Tyr Ala Arg Gly Gly Gly Gly Glu
290 295 300

Pro Arg Asn Asn Tyr Tyr Val Gln Thr Tyr Leu Arg Gly Asn Val Gln
305 310 315 320

Lys Pro Ile Ile Leu Thr Val Thr Tyr Asn Ser Ala Ala Thr Gly Tyr
325 330 335

Ser Leu Ser Phe Lys Trp Thr Ala Leu Ala Arg Glu Lys Phe Ala Thr
340 345 350

Pro Thr Thr Ser Phe Cys Tyr Ile Thr Glu Gln
355 360

<210> SEQ ID NO 21
<211> LENGTH: 360
<212> TYPE: PRT
<213> ORGANISM: Artificial Sequence
<220> FEATURE:
<223> OTHER INFORMATION: Synthetic polypeptide sAd4312 Fiber-1

<400> SEQUENCE: 21

Met Lys Arg Thr Arg Val Asp Glu Asp Phe Asn Pro Val Tyr Pro Tyr
1 5 10 15

Asp Thr Thr Thr Thr Pro Ala Val Pro Phe Ile Ser Pro Pro Phe Val
20 25 30

Asn Ser Asp Gly Leu Gln Glu Asn Pro Pro Gly Val Leu Ser Leu Arg
35 40 45

Ile Ala Lys Pro Leu Tyr Phe Asp Met Glu Arg Lys Leu Ala Leu Ser
50 55 60

Leu Gly Arg Gly Leu Thr Ile Thr Ala Asn Gly Gln Leu Glu Ser Thr
65 70 75 80

```
Gln Ser Val Gln Thr Asn Pro Pro Leu Thr Val Thr Asn Asn Asn Thr
                85                  90                  95

Leu Ile Leu Arg His Ser Ser Pro Leu Ile Leu Thr Asp Asn Asn Leu
            100                 105                 110

Thr Val Gly Phe Ser Ser Pro Leu Arg Val Ile Asp Asn Lys Leu Thr
        115                 120                 125

Phe Thr Phe Thr Ser Pro Leu Arg Tyr Glu Asn Glu Thr Leu Thr Phe
    130                 135                 140

Asn Tyr Thr Glu Pro Leu Thr Leu Met Asn Ser Asn Leu Ala Leu Asn
145                 150                 155                 160

Val Asn Ser Ser Lys Gly Leu Arg Val Asp Gly Gly Ser Leu Gly Thr
                165                 170                 175

Asn Leu Ser Pro Asp Leu Arg Phe Asn Ser Ser Gly Ala Ile Ala Phe
            180                 185                 190

Gly Ile Gln Thr Leu Trp Thr Pro Pro Thr Ser Asn Pro Asn Cys Thr
        195                 200                 205

Val Tyr Thr Glu Ser Asp Ser Leu Leu Ser Leu Cys Leu Thr Lys Cys
    210                 215                 220

Gly Ala His Val Leu Gly Ser Val Ser Leu Thr Gly Val Ala Gly Thr
225                 230                 235                 240

Met Ile Asn Met Ala Glu Thr Ser Leu Ala Ile Glu Phe Thr Phe Asp
                245                 250                 255

Asp Thr Gly Lys Leu Leu His Ser Pro Leu Val Asn Thr Thr Phe Ser
            260                 265                 270

Ile Arg Gln Gly Asp Ser Pro Ala Ser Asn Pro Thr Tyr Asn Ala Leu
        275                 280                 285

Ala Phe Met Pro Asn Ser Thr Leu Tyr Ala Arg Gly Gly Ser Gly Glu
    290                 295                 300

Pro Arg Asn Asn Tyr Tyr Val Gln Thr Tyr Leu Arg Gly Asn Val Gln
305                 310                 315                 320

Arg Pro Ile Thr Leu Thr Val Thr Phe Asn Ser Ala Ala Thr Gly Tyr
                325                 330                 335

Ser Leu Ser Phe Lys Trp Thr Ala Val Ala Arg Glu Lys Phe Ala Ala
            340                 345                 350

Pro Ala Thr Ser Phe Cys Tyr Ile
        355                 360
```

<210> SEQ ID NO 22
<211> LENGTH: 559
<212> TYPE: PRT
<213> ORGANISM: Artificial Sequence
<220> FEATURE:
<223> OTHER INFORMATION: Synthetic polypeptide sAd4287 Fiber-2

<400> SEQUENCE: 22

```
Met Lys Arg Ala Arg Val Asp Glu Asp Phe Asn Pro Val Tyr Pro Tyr
1               5                   10                  15

Asp Pro Pro Tyr Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Lys Asp Pro Ile Thr Thr Gln Asn Gly Ser Leu Thr Leu Lys Ile
    50                  55                  60

Gly Asn Gly Leu Thr Leu Asp Asn Gln Gly Gln Leu Thr Ser Thr Ala
65                  70                  75                  80
```

-continued

```
Gly Glu Val Glu Pro Pro Leu Thr Asn Ala Asn Asn Lys Leu Ala Leu
                85                  90                  95

Ala Tyr Ser Glu Pro Leu Ala Val Lys Ser Asn Arg Leu Thr Leu Ser
            100                 105                 110

His Thr Ala Pro Leu Val Val Ala Asn Asn Ser Leu Ala Leu Gln Val
        115                 120                 125

Ser Glu Pro Ile Phe Ile Asn Asp Asp Asp Lys Leu Ala Leu Gln Thr
    130                 135                 140

Ala Ala Pro Leu Val Thr Asn Ala Gly Thr Leu Arg Leu Gln Ser Ala
145                 150                 155                 160

Ala Pro Leu Gly Leu Val Glu Asn Thr Leu Arg Leu Leu Phe Ser Lys
                165                 170                 175

Pro Leu Tyr Leu Gln Asn Asp Phe Leu Ala Leu Gly Ile Glu Arg Pro
            180                 185                 190

Leu Ala Ile Ala Ala Ala Gly Thr Leu Ala Leu Gln Leu Thr Pro Pro
        195                 200                 205

Leu Lys Thr Asn Asp Asp Gly Leu Thr Leu Ser Thr Val Glu Pro Leu
    210                 215                 220

Thr Val Lys Asn Gly Asn Leu Gly Leu Gln Ile Ser Arg Pro Leu Val
225                 230                 235                 240

Val Gln Asn Ser Ser Leu Ser Leu Ala Ile Thr Pro Pro Leu Arg Leu
                245                 250                 255

Phe Asn Ser Asp Pro Val Leu Gly Leu Gly Phe Thr Phe Pro Leu Ala
            260                 265                 270

Val Thr Asp Asn Leu Leu Ser Leu Asn Met Gly Asp Gly Val Lys Leu
        275                 280                 285

Thr Tyr Asn Lys Leu Thr Ala Asn Leu Gly Arg Asp Leu Gln Phe Glu
    290                 295                 300

Asn Gly Ala Ile Ala Val Thr Leu Thr Ala Glu Ser Pro Leu Gln Tyr
305                 310                 315                 320

Thr Asn Lys Leu Gln Leu Asn Ile Gly Ala Gly Leu Arg Tyr Asn Gly
                325                 330                 335

Ala Ser Arg Lys Leu Asp Val Asn Ile Asn Gln Asn Lys Gly Leu Thr
            340                 345                 350

Trp Asp Asn Asp Ala Val Ile Pro Lys Leu Gly Ser Gly Leu Gln Phe
        355                 360                 365

Asp Pro Asn Gly Asn Ile Ala Val Ile Pro Glu Thr Val Lys Pro Gln
    370                 375                 380

Thr Leu Trp Thr Thr Ala Asp Pro Ser Pro Asn Cys Ser Val Tyr Gln
385                 390                 395                 400

Asp Leu Asp Ala Arg Leu Trp Leu Ala Leu Val Lys Ser Gly Asp Met
                405                 410                 415

Val His Gly Ser Ile Ala Leu Lys Ala Leu Lys Gly Thr Leu Leu Asn
            420                 425                 430

Pro Thr Ala Ser Tyr Ile Ser Ile Val Ile Tyr Phe Tyr Ser Asn Gly
        435                 440                 445

Val Arg Arg Thr Asn Tyr Pro Thr Phe Asp Asn Glu Gly Thr Leu Ala
    450                 455                 460

Asn Ser Ala Thr Trp Gly Tyr Arg Glu Gly Gln Ser Ala Asn Thr Asn
465                 470                 475                 480

Val Thr Asn Ala Thr Glu Phe Met Pro Ser Ser Thr Arg Tyr Pro Val
                485                 490                 495
```

```
Asn Lys Gly Asp Asn Ile Gln Asn Gln Ser Phe Ser Tyr Thr Cys Ile
            500                 505                 510

Lys Gly Asp Phe Ala Met Pro Val Pro Phe Arg Val Thr Tyr Asn His
        515                 520                 525

Ala Leu Glu Gly Tyr Ser Leu Lys Phe Thr Trp Arg Val Val Ala Asn
    530                 535                 540

Gln Ala Phe Asp Ile Pro Cys Cys Ser Phe Ser Tyr Ile Thr Glu
545                 550                 555


<210> SEQ ID NO 23
<211> LENGTH: 560
<212> TYPE: PRT
<213> ORGANISM: Artificial Sequence
<220> FEATURE:
<223> OTHER INFORMATION: Synthetic polypeptide sAd4310A Fiber-2

<400> SEQUENCE: 23

Met Lys Arg Ala Arg Val Asp Glu Asp Phe Asn Pro Val Tyr Pro Tyr
1               5                   10                  15

Asp Pro Pro His Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Gly Ser Leu Thr Val Lys Leu
    50                  55                  60

Gly Asn Gly Leu Thr Leu Asp Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Val Tyr Ser Asp Pro Leu Ala Val Lys Arg Asn Ser Leu Thr Leu Ser
            100                 105                 110

His Thr Ala Pro Leu Val Ile Ala Asp Asn Ser Leu Ala Leu Gln Val
        115                 120                 125

Ser Glu Pro Ile Phe Ile Asn Asp Lys Asp Lys Leu Ala Leu Gln Thr
    130                 135                 140

Ala Ala Pro Leu Val Thr Asn Ala Gly Thr Leu Arg Leu Gln Ser Ala
145                 150                 155                 160

Ala Pro Leu Gly Ile Ala Asp Gln Thr Leu Lys Leu Leu Phe Thr Asn
                165                 170                 175

Pro Leu Tyr Leu Gln Asn Asn Phe Leu Thr Leu Ala Ile Glu Arg Pro
            180                 185                 190

Leu Ala Ile Thr Asn Ser Gly Lys Leu Ala Leu Gln Leu Ser Pro Pro
        195                 200                 205

Leu Gln Thr Ala Asp Thr Gly Leu Thr Leu Gln Thr Asn Val Pro Leu
    210                 215                 220

Thr Val Ser Asn Gly Thr Leu Gly Leu Ala Ile Lys Arg Pro Leu Ile
225                 230                 235                 240

Val Gln Asp Asn Asn Leu Phe Leu Asp Phe Arg Ala Pro Leu Arg Leu
                245                 250                 255

Phe Asn Ser Asp Pro Val Leu Gly Leu Asn Phe Tyr Thr Pro Leu Ala
            260                 265                 270

Val Arg Asp Glu Ala Leu Thr Val Asn Thr Gly Arg Gly Leu Thr Val
        275                 280                 285

Ser Tyr Asp Gly Leu Ile Leu Asn Leu Gly Lys Asp Leu Arg Phe Asp
    290                 295                 300
```

```
Asn Asn Thr Val Ser Val Ala Leu Ser Ala Ala Leu Pro Leu Gln Tyr
305                 310                 315                 320

Thr Asp Gln Leu Arg Leu Asn Val Gly Ala Gly Leu Arg Tyr Asn Pro
                325                 330                 335

Val Ser Lys Lys Leu Asp Val Asn Pro Asn Gln Asn Lys Gly Leu Thr
            340                 345                 350

Trp Glu Asn Asp Tyr Leu Ile Val Lys Leu Gly Asn Gly Leu Gly Phe
        355                 360                 365

Asp Gly Asn Gly Asn Ile Ala Val Ser Pro Gln Val Thr Ser Pro Asp
    370                 375                 380

Thr Leu Trp Thr Thr Ala Asp Pro Ser Pro Asn Cys Ser Ile Tyr Thr
385                 390                 395                 400

Asp Leu Asp Ala Lys Met Trp Leu Ser Leu Val Lys Gln Gly Gly Val
                405                 410                 415

Val His Gly Ser Val Ala Leu Lys Ala Leu Lys Gly Thr Leu Leu Ser
            420                 425                 430

Pro Thr Glu Ser Ala Ile Val Ile Ile Leu His Phe Asp Asn Tyr Gly
        435                 440                 445

Val Arg Ile Leu Asn Tyr Pro Thr Leu Gly Thr Gln Gly Thr Leu Gly
    450                 455                 460

Asn Asn Ala Thr Trp Gly Tyr Arg Gln Gly Glu Ser Ala Asp Thr Asn
465                 470                 475                 480

Val Leu Asn Ala Leu Ala Phe Met Pro Ser Ser Lys Arg Tyr Pro Arg
                485                 490                 495

Gly Arg Gly Ser Glu Val Gln Asn Gln Thr Val Gly Tyr Thr Cys Ile
            500                 505                 510

Gln Gly Asp Leu Ser Met Pro Val Pro Tyr Gln Ile Gln Tyr Asn Tyr
        515                 520                 525

Gly Pro Thr Gly Tyr Ser Phe Lys Phe Ile Trp Arg Thr Val Ser Arg
    530                 535                 540

Gln Pro Phe Asp Ile Pro Cys Cys Phe Phe Ser Tyr Ile Thr Glu Glu
545                 550                 555                 560


<210> SEQ ID NO 24
<211> LENGTH: 560
<212> TYPE: PRT
<213> ORGANISM: Artificial Sequence
<220> FEATURE:
<223> OTHER INFORMATION: Synthetic polypeptide sAd4312 Fiber-2

<400> SEQUENCE: 24

Met Lys Arg Ala Arg Val Asp Glu Asp Phe Asn Pro Val Tyr Pro Tyr
1               5                   10                  15

Asp Pro Pro Tyr Ala Pro Ile Met Pro Phe Ile Thr Pro Pro Phe Thr
            20                  25                  30

Ser Ser Asp Gly Leu Gln Glu Lys Pro Leu Gly Val Leu Ser Leu Lys
        35                  40                  45

Tyr Lys Asp Pro Ile Thr Thr Gln Asn Gly Ser Leu Thr Leu Lys Leu
    50                  55                  60

Gly Asn Gly Leu Asn Ile Asn Asn Gln Gly Gln Leu Thr Ser Ser Ala
65                  70                  75                  80

Gly Glu Val Glu Pro Pro Leu Thr Asn Ala Asp Asn Lys Leu Ala Leu
                85                  90                  95

Ala Tyr Ser Asp Pro Leu Thr Leu Lys Asn Ser Arg Leu Thr Leu Ser
            100                 105                 110
```

```
His Asn Ala Pro Leu Ala Ile Asn Asn Asn Ser Leu Ser Leu Glu Val
        115                 120                 125

Ser Glu Pro Ile Phe Ile Asn Asn Asp Asn Lys Leu Ser Leu Lys Ala
    130                 135                 140

Asp Ala Pro Leu Thr Thr Ser Ala Gly Thr Leu Arg Leu Gln Ser Ala
145                 150                 155                 160

Ala Pro Leu Gly Leu Ala Glu Gln Thr Leu Lys Leu Leu Phe Ser Asn
                165                 170                 175

Pro Leu Tyr Leu Arg Gly Asp Phe Leu Thr Leu Ala Ile Glu Arg Pro
            180                 185                 190

Leu Ala Val Thr Ala Asp Gly Leu Leu Ser Leu Ala Leu Asn Pro Pro
        195                 200                 205

Leu Thr Thr Thr Asn Thr Gly Leu Ala Leu Ser Thr Ala Val Pro Leu
    210                 215                 220

Thr Val Thr Asn Gly Asn Leu Ser Leu Asn Val Lys Arg Pro Phe Ile
225                 230                 235                 240

Ile Gln Asp Gly Ser Leu Tyr Met Asp Phe Arg Pro Pro Leu Tyr Leu
                245                 250                 255

Phe Asn Ser Glu Pro Gln Leu Gly Val Asn Phe Asn Ala Pro Leu Thr
            260                 265                 270

Val Arg Asp Asn Gly Leu Ala Ile Asn Thr Gly Asp Gly Leu Thr Val
        275                 280                 285

Thr Tyr Asn Lys Leu Thr Leu Asn Leu Gly Arg Asp Leu Gln Tyr Glu
    290                 295                 300

Asn Gly Ala Ala Ala Val Lys Leu Ser Thr Ala Pro Pro Leu Gln Tyr
305                 310                 315                 320

Thr Thr Gln Leu Gln Leu Asn Leu Gly Ala Gly Leu Arg Leu Gly Pro
                325                 330                 335

Thr Arg Asn Leu Asp Val Ala Ile Asn His Asn Lys Gly Leu Ala Trp
            340                 345                 350

Glu Asn Asn Glu Val Val Thr Lys Leu Gly Gln Gly Leu Tyr Phe Asp
        355                 360                 365

Ser Ser Gly Ser Ile Ala Leu Ser Pro Thr Asn Pro Arg Pro Asp Thr
    370                 375                 380

Leu Trp Thr Thr Ala Asp Pro Ser Pro Asn Cys Thr Val Tyr Glu Ser
385                 390                 395                 400

Leu Asp Ser Arg Leu Trp Leu Ala Leu Val Lys Cys Gly Gly Met Val
                405                 410                 415

His Gly Ser Ile Ala Leu Gln Ala Glu Lys Gly Gln Leu Leu Arg Pro
            420                 425                 430

Thr Ala Ser Phe Ile Ser Ile Val Ile Tyr Phe Tyr Ser Asp Gly Val
        435                 440                 445

Arg Arg Thr Asn Tyr Pro Thr Ile Gly Asn Asp Glu Gly Thr Leu Ala
    450                 455                 460

Asn Ser Ala Thr Trp Gly Tyr Arg Gln Gly Gln Ser Ala Asp Thr Asn
465                 470                 475                 480

Val Thr Asn Ala Val Glu Phe Met Pro Ser Leu His Arg Tyr Pro Ile
                485                 490                 495

Asn Gln Gly Asp Asn Ile Lys Asn Gln Met Ile Thr Tyr Thr Cys Ile
            500                 505                 510

Gln Gly Asn Val Asn Met Pro Val Pro Leu Lys Ile Thr Phe Asn His
        515                 520                 525

Ala Leu Glu Gly Tyr Ser Leu Lys Phe Thr Trp Arg Val Val Ala Asn
```

530 535 540

Glu Lys Phe Asp Ile Pro Cys Cys Ser Phe Ser Tyr Ile Thr Glu Gln
545 550 555 560

<210> SEQ ID NO 25
<211> LENGTH: 933
<212> TYPE: PRT
<213> ORGANISM: Artificial Sequence
<220> FEATURE:
<223> OTHER INFORMATION: Synthetic polypeptide sAd4287 Hexon

<400> SEQUENCE: 25

Met Ala Thr Pro Ser Met Met Pro Gln Trp Ser Tyr Met His Ile Ala
1 5 10 15

Gly Gln Asp Ala Ser Glu Tyr Leu Ser Pro Gly Leu Val Gln Phe Ala
20 25 30

Arg Ala Thr Asp Thr Tyr Phe Ser Leu Gly Asn Lys Phe Arg Asn Pro
35 40 45

Thr Val Ala Pro Thr His Asp Val Thr Thr Asp Arg Ser Gln Arg Leu
50 55 60

Thr Leu Arg Phe Val Pro Val Asp Arg Glu Asp Thr Ala Tyr Ser Tyr
65 70 75 80

Lys Val Arg Tyr Thr Leu Ala Val Gly Asp Asn Arg Val Leu Asp Met
85 90 95

Ala Ser Thr Tyr Phe Asp Ile Arg Gly Val Leu Asp Arg Gly Pro Ser
100 105 110

Phe Lys Pro Tyr Ser Gly Thr Ala Tyr Asn Ser Leu Ala Pro Lys Gly
115 120 125

Ala Pro Asn Pro Ala Glu Trp Ala Asp Thr Asn Asp Ser Asn Lys Leu
130 135 140

Lys Val Arg Gly Gln Ala Pro Phe Val Ser Thr Tyr Gly Ser Ala Thr
145 150 155 160

Ala Leu Thr Lys Asp Gly Ile Gln Val Gly Val Asp Thr Ser Glu Ala
165 170 175

Ser Gln Ala Val Tyr Ala Asp Arg Ser Tyr Gln Pro Glu Pro Gln Ile
180 185 190

Gly Glu Thr Glu Trp Asn Ser Glu Val Gly Asn Asp Asp Arg Val Ala
195 200 205

Gly Arg Val Leu Lys Lys Thr Thr Pro Met Phe Pro Cys Tyr Gly Ser
210 215 220

Tyr Ala Lys Pro Thr Asn Glu Lys Gly Gly Gln Ala Ile Gln Pro Thr
225 230 235 240

Ala Gly Asn Gly Asp Asn Gln Ala Val Glu Leu Gln Phe Phe Ala Thr
245 250 255

Thr Ser Thr Pro Thr Ala Pro Lys Ala Val Leu Tyr Ala Glu Asp Val
260 265 270

Ala Ile Glu Ala Pro Asp Thr His Leu Val Phe Lys Pro Thr Val Val
275 280 285

Ala Gly Thr Thr Ser Ser Glu Ala Leu Leu Thr Gln Gln Ala Ala Pro
290 295 300

Asn Arg Pro Asn Tyr Ile Ala Phe Arg Asp Asn Phe Ile Gly Leu Met
305 310 315 320

Tyr Tyr Asn Ser Thr Gly Asn Met Gly Val Leu Ala Gly Gln Ala Ser
325 330 335

Gln Leu Asn Ala Val Val Asp Leu Gln Asp Arg Asn Thr Glu Leu Ser

```
            340                 345                 350

Tyr Gln Leu Met Leu Asp Ala Leu Gly Asp Arg Ser Arg Tyr Phe Ser
        355                 360                 365

Met Trp Asn Gln Ala Val Asp Ser Tyr Asp Pro Asp Val Arg Ile Val
    370                 375                 380

Glu Asn His Gly Val Glu Asp Glu Leu Pro Asn Tyr Cys Phe Pro Leu
385                 390                 395                 400

Gly Gly Met Val Val Thr Asp Thr Tyr Lys Ala Ile Lys Val Asn Gly
                405                 410                 415

Ser Gly Trp Thr Ala Asn Thr Asp Val Phe Ser Glu Arg Val Glu Ile
            420                 425                 430

Gly Ser Gly Asn Leu Phe Ala Met Glu Ile Asn Leu Gln Ala Asn Leu
        435                 440                 445

Trp Arg Ser Phe Leu Tyr Ser Asn Ile Gly Leu Tyr Leu Pro Asp Ser
    450                 455                 460

Leu Lys Leu Thr Pro Asp Asn Ile Thr Leu Pro Glu Asn Lys Asn Thr
465                 470                 475                 480

Tyr Gln Tyr Met Asn Gly Arg Val Thr Pro Pro Gly Leu Val Asp Thr
                485                 490                 495

Tyr Val Asn Val Gly Ala Arg Trp Ser Pro Asp Val Met Asp Ser Ile
            500                 505                 510

Asn Pro Phe Asn His His Arg Asn Ala Gly Leu Arg Tyr Arg Ser Met
        515                 520                 525

Leu Leu Gly Asn Gly Arg Tyr Val Pro Phe His Ile Gln Val Pro Gln
    530                 535                 540

Lys Phe Phe Ala Ile Lys Asn Leu Leu Leu Leu Pro Gly Ser Tyr Thr
545                 550                 555                 560

Tyr Glu Trp Asn Phe Arg Lys Asp Val Asn Met Ile Leu Gln Ser Ser
                565                 570                 575

Leu Gly Asn Asp Leu Arg Val Asp Gly Ala Ser Ile Arg Phe Asp Ser
            580                 585                 590

Ile Asn Leu Tyr Ala Asn Phe Phe Pro Met Ala His Asn Thr Ala Ser
        595                 600                 605

Thr Leu Glu Ala Met Leu Arg Asn Asp Thr Asn Asp Gln Ser Phe Asn
    610                 615                 620

Asp Tyr Leu Cys Ala Ala Asn Met Leu Tyr Pro Ile Pro Ala Asn Ala
625                 630                 635                 640

Thr Ser Val Pro Ile Ser Ile Pro Ser Arg Asn Trp Ala Ala Phe Arg
                645                 650                 655

Gly Trp Ser Phe Thr Arg Leu Lys Thr Lys Glu Thr Pro Ser Leu Gly
            660                 665                 670

Ser Gly Phe Asp Pro Tyr Phe Val Tyr Ser Gly Ser Ile Pro Tyr Leu
        675                 680                 685

Asp Gly Thr Phe Tyr Leu Asn His Thr Phe Lys Lys Val Ser Ile Met
    690                 695                 700

Phe Asp Ser Ser Val Ser Trp Pro Gly Asn Asp Arg Leu Leu Thr Pro
705                 710                 715                 720

Asn Glu Phe Glu Ile Lys Arg Ser Val Asp Gly Glu Gly Tyr Asn Val
                725                 730                 735

Ala Gln Ser Asn Met Thr Lys Asp Trp Phe Leu Val Gln Met Leu Ser
            740                 745                 750

His Tyr Asn Ile Gly Tyr Gln Gly Phe Tyr Val Pro Glu Asn Tyr Lys
        755                 760                 765
```

```
Asp Arg Met Tyr Ser Phe Phe Arg Asn Phe Gln Pro Met Ser Arg Gln
    770                 775                 780

Val Val Asp Ser Val Ala Tyr Arg Asp Tyr Tyr Gln Asp Val Lys Leu
785                 790                 795                 800

Pro Tyr Gln His Asn Asn Ser Gly Phe Val Gly Tyr Met Gly Pro Thr
                805                 810                 815

Met Arg Glu Gly Gln Ala Tyr Pro Ala Asn Tyr Pro Tyr Pro Leu Ile
            820                 825                 830

Gly Glu Thr Ala Val Pro Ser Leu Thr Gln Lys Lys Phe Leu Cys Asp
        835                 840                 845

Arg Val Met Trp Arg Ile Pro Phe Ser Ser Asn Phe Met Ser Met Gly
    850                 855                 860

Ser Leu Thr Asp Leu Gly Gln Asn Met Leu Tyr Ala Asn Ser Ala His
865                 870                 875                 880

Ala Leu Asp Met Thr Phe Glu Val Asp Pro Met Asp Glu Pro Thr Leu
                885                 890                 895

Leu Tyr Val Leu Phe Glu Val Phe Asp Val Val Arg Ile His Gln Pro
            900                 905                 910

His Arg Gly Val Ile Glu Ala Val Tyr Leu Arg Thr Pro Phe Ser Ala
        915                 920                 925

Gly Asn Ala Thr Thr
    930


<210> SEQ ID NO 26
<211> LENGTH: 912
<212> TYPE: PRT
<213> ORGANISM: Artificial Sequence
<220> FEATURE:
<223> OTHER INFORMATION: Synthetic polypeptide sAd4310A Hexon

<400> SEQUENCE: 26

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Thr Gly Thr Ala Tyr Asn Ala Leu Ala Pro Lys Gly
        115                 120                 125

Ala Pro Asn Ala Cys Gln Trp Thr Thr Thr Asn Gly Gly Asn Lys Thr
    130                 135                 140

Asn Thr Phe Ala Gln Ala Pro Leu Ile Gly Thr Ala Ile Asp Gly Thr
145                 150                 155                 160

Asn Gly Leu Gln Ile Gly Gln Asp Asn Gly Gln Ala Val Tyr Ala Asp
                165                 170                 175

Lys Thr Phe Gln Pro Glu Pro Gln Val Gly Glu Ser Gln Trp Asn Thr
            180                 185                 190
```

```
Asn Pro Thr Thr Asn Ala Ala Gly Arg Val Leu Lys Thr Thr Thr Arg
        195                 200                 205

Met Leu Pro Cys Tyr Gly Ser Phe Ala Arg Pro Thr Asn Glu Lys Gly
    210                 215                 220

Gly Gln Ala Ser Gly Asp Val Thr Phe Gln Phe Phe Asp Thr Ala Ser
225                 230                 235                 240

Asp Asn Gly Asn Asn Pro Lys Val Val Leu Tyr Gly Glu Asp Val Asn
                245                 250                 255

Ile Glu Ser Pro Asp Thr His Leu Ile Tyr Lys Pro Thr Ala Asp Asn
            260                 265                 270

Thr Asn Ser Glu Asn Leu Leu Gly Gln Gln Ala Ala Pro Asn Arg Ala
        275                 280                 285

Asn Tyr Ile Ala Phe Arg Asp Asn Phe Ile Gly Leu Met Tyr Tyr Asn
    290                 295                 300

Ser Thr Gly Asn Met Gly Val Leu Ala Gly Gln Ala Ser Gln Leu Asn
305                 310                 315                 320

Ala Val Val Asp Leu Gln Asp Arg Asn Thr Glu Leu Ser Tyr Gln Leu
                325                 330                 335

Met Leu Asp Ala Ile Gly Asp Arg Ser Arg Tyr Phe Ser Met Trp Asn
            340                 345                 350

Gln Ala Val Asp Ser Tyr Asp Pro Asp Val Arg Ile Ile Glu Asn His
        355                 360                 365

Gly Val Glu Asp Glu Leu Pro Asn Tyr Cys Phe Pro Leu Asn Ala Gln
    370                 375                 380

Gly Ile Ala Asn Thr Tyr Lys Gly Val Lys Lys Asn Asn Gly Asn Trp
385                 390                 395                 400

Ala Lys Asp Asp Ala Val Val Glu Thr Asn Glu Ile Gly Ile Gly Asn
                405                 410                 415

Val Phe Ala Met Glu Ile Asn Leu Thr Ala Asn Leu Trp Arg Asn Phe
            420                 425                 430

Leu Tyr Ser Asn Ile Ala Leu Tyr Leu Pro Asp Ser Tyr Lys Tyr Ser
        435                 440                 445

Pro Gly Asn Ile Thr Leu Pro Glu Asn Lys Asn Ser Tyr Asn Tyr Ile
    450                 455                 460

Asn Gly Arg Val Thr Ala Pro Gly Leu Val Asp Thr Phe Val Asn Ile
465                 470                 475                 480

Gly Ala Arg Trp Ser Pro Asp Pro Met Asp Asn Val Asn Pro Phe Asn
                485                 490                 495

His His Arg Asn Ala Gly Leu Arg Tyr Arg Ser Met Leu Leu Gly Asn
            500                 505                 510

Gly Arg Tyr Val Pro Phe His Ile Gln Val Pro Gln Lys Phe Phe Ala
        515                 520                 525

Ile Lys Asn Leu Leu Leu Leu Pro Gly Ser Tyr Thr Tyr Glu Trp Asn
    530                 535                 540

Phe Arg Lys Asp Val Asn Met Ile Leu Gln Ser Thr Leu Gly Asn Asp
545                 550                 555                 560

Leu Arg Val Asp Gly Ala Ser Val Arg Phe Asp Ser Ile Asn Leu Tyr
                565                 570                 575

Ala Asn Phe Phe Pro Met Ala His Asn Thr Ala Ser Thr Leu Glu Ala
            580                 585                 590

Met Leu Arg Asn Asp Thr Asn Asp Gln Ser Phe Asn Asp Tyr Leu Cys
        595                 600                 605
```

```
Ala Ala Asn Met Leu Tyr Pro Ile Pro Ala Asn Ala Thr Ser Val Pro
    610                 615                 620

Ile Ser Ile Pro Ser Arg Asn Trp Ala Ala Phe Arg Gly Trp Ser Phe
625                 630                 635                 640

Thr Arg Leu Lys Thr Lys Glu Thr Pro Ser Leu Gly Ser Gly Phe Asp
                645                 650                 655

Pro Tyr Phe Val Tyr Ser Gly Ser Ile Pro Tyr Leu Asp Gly Thr Phe
            660                 665                 670

Tyr Leu Asn His Thr Phe Lys Lys Val Ser Ile Met Phe Asp Ser Ser
        675                 680                 685

Val Ser Trp Pro Gly Asn Asp Arg Leu Leu Thr Pro Asn Glu Phe Glu
    690                 695                 700

Ile Lys Arg Ser Val Asp Gly Glu Gly Tyr Asn Val Ala Gln Ser Asn
705                 710                 715                 720

Met Thr Lys Asp Trp Phe Leu Ile Gln Met Leu Ser His Tyr Asn Ile
                725                 730                 735

Gly Tyr Gln Gly Phe Tyr Val Pro Glu Ala Tyr Lys Asp Arg Met Tyr
            740                 745                 750

Ser Phe Phe Arg Asn Phe Gln Pro Met Ser Arg Gln Val Val Asp Ala
        755                 760                 765

Asp Arg Tyr Glu Gln Tyr Lys Lys Val Thr Val Glu Tyr Gln His Asn
    770                 775                 780

Asn Ser Gly Phe Val Gly Tyr Met Gly Pro Thr Met Arg Glu Gly Gln
785                 790                 795                 800

Ala Tyr Pro Ala Asn Tyr Pro Tyr Pro Leu Ile Gly Asp Thr Ala Val
                805                 810                 815

Pro Ser Leu Thr Gln Lys Lys Phe Leu Cys Asp Arg Thr Met Trp Arg
            820                 825                 830

Ile Pro Phe Ser Ser Asn Phe Met Ser Met Gly Ala Leu Thr Asp Leu
        835                 840                 845

Gly Gln Asn Met Leu Tyr Ala Asn Ser Ala His Ala Leu Asp Met Thr
    850                 855                 860

Phe Glu Val Asp Pro Met Asp Glu Pro Thr Leu Leu Tyr Val Leu Phe
865                 870                 875                 880

Glu Val Phe Asp Val Val Arg Ile His Gln Pro His Arg Gly Val Ile
                885                 890                 895

Glu Ala Val Tyr Leu Arg Thr Pro Phe Ser Ala Gly Asn Ala Thr Thr
            900                 905                 910


<210> SEQ ID NO 27
<211> LENGTH: 928
<212> TYPE: PRT
<213> ORGANISM: Artificial Sequence
<220> FEATURE:
<223> OTHER INFORMATION: Synthetic polypeptide sAd4312 Hexon

<400> SEQUENCE: 27

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Glu Ser Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60
```

-continued

```
Thr Leu Arg Phe Val Pro Val Asp Arg Glu Asp Thr Ala Tyr Ser Tyr
65                  70                  75                  80

Lys Val Arg Phe Thr Leu Ala Val Gly Asp Asn Arg Val Leu Asp Met
                85                  90                  95

Ala Ser Thr Tyr Phe Asp Ile Arg Gly Met Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Gln Trp Thr Thr Thr Asn Gly Gly Asn Lys Thr
    130                 135                 140

Asn Ser Phe Ala Gln Ala Ser Tyr Ile Gly Gln Ser Leu Ser Lys Asp
145                 150                 155                 160

Gly Val Gln Val Ala Val Asp Thr Ala Ala Gly Gly Ala Ala Val Tyr
                165                 170                 175

Ala Asp Lys Thr Phe Gln Pro Glu Pro Gln Val Gly Ile Ser Gln Trp
            180                 185                 190

Asn Glu Asn Pro Thr Thr Asn Ala Ala Gly Arg Ile Leu Lys Pro Thr
        195                 200                 205

Thr Ala Met Arg Pro Cys Tyr Gly Ser Tyr Ala Tyr Pro Thr Asn Glu
    210                 215                 220

Lys Gly Gly Gln Val Lys Ile Thr Asp Pro Asn Asn Asp Lys Thr Gly
225                 230                 235                 240

Ala Asn Asn Val Ser Leu Asn Phe Phe Asn Thr Ala Ala Asp Asn Gly
                245                 250                 255

Asn Asn Asn Pro Lys Val Val Leu Tyr Ser Glu Asp Val Asn Leu Glu
            260                 265                 270

Gly Pro Asp Thr His Leu Val Phe Lys Pro Asp Val Thr Gly Asp Ala
        275                 280                 285

Thr Ser Ala Glu Thr Leu Leu Gly Gln Gln Ala Ala Pro Asn Arg Pro
    290                 295                 300

Asn Tyr Ile Gly Phe Arg Asp Asn Phe Ile Gly Leu Met Tyr Tyr Asn
305                 310                 315                 320

Ser Thr Gly Asn Met Gly Val Leu Ala Gly Gln Ala Ser Gln Leu Asn
                325                 330                 335

Ala Val Val Asp Leu Gln Asp Arg Asn Thr Glu Leu Ser Tyr Gln Leu
            340                 345                 350

Met Leu Asp Ala Leu Gly Asp Arg Ser Arg Tyr Phe Ser Met Trp Asn
        355                 360                 365

Gln Ala Val Asp Ser Tyr Asp Pro Asp Val Arg Ile Ile Glu Asn His
    370                 375                 380

Gly Val Glu Asp Glu Leu Pro Asn Tyr Cys Phe Pro Leu Asn Gly Gln
385                 390                 395                 400

Gly Ile Ser Asn Thr Tyr Lys Gly Val Lys Tyr Asn Thr Asn Thr Trp
                405                 410                 415

Thr Gln Asp Thr Asp Val Val Thr Thr Asn Glu Ile Ser Ile Gly Asn
            420                 425                 430

Ile Phe Ala Met Glu Ile Asn Leu Ala Ala Asn Leu Trp Arg Ser Phe
        435                 440                 445

Leu Tyr Ser Asn Val Ala Leu Tyr Leu Pro Asp Ser Tyr Lys Tyr Thr
    450                 455                 460

Pro Asp Asn Ile Glu Leu Pro Thr Asn Lys Asn Ser Tyr Gly Tyr Ile
465                 470                 475                 480

Asn Gly Arg Val Thr Ala Pro Thr Ala Ile Asp Thr Tyr Val Asn Ile
```

-continued

```
                485                 490                 495

Gly Ala Arg Trp Ser Pro Asp Pro Met Asp Asn Val Asn Pro Phe Asn
            500                 505                 510

His His Arg Asn Ala Gly Leu Arg Tyr Arg Ser Met Leu Leu Gly Asn
        515                 520                 525

Gly Arg Tyr Val Pro Phe His Ile Gln Val Pro Gln Lys Phe Phe Ala
    530                 535                 540

Ile Lys Asn Leu Leu Leu Leu Pro Gly Ser Tyr Thr Tyr Glu Trp Asn
545                 550                 555                 560

Phe Arg Lys Asp Val Asn Met Ile Leu Gln Ser Thr Leu Gly Asn Asp
                565                 570                 575

Leu Arg Val Asp Gly Ala Ser Val Arg Phe Asp Ser Ile Asn Leu Tyr
            580                 585                 590

Ala Asn Phe Phe Pro Met Ala His Asn Thr Ala Ser Thr Leu Glu Ala
        595                 600                 605

Met Leu Arg Asn Asp Thr Asn Asp Gln Ser Phe Asn Asp Tyr Leu Cys
    610                 615                 620

Ala Ala Asn Met Leu Tyr Pro Ile Pro Ala Asn Ala Thr Ser Val Pro
625                 630                 635                 640

Ile Ser Ile Pro Ser Arg Asn Trp Ala Ala Phe Arg Gly Trp Ser Phe
                645                 650                 655

Thr Arg Leu Lys Thr Lys Glu Thr Pro Ser Leu Gly Ser Gly Phe Asp
            660                 665                 670

Pro Tyr Phe Val Tyr Ser Gly Ser Ile Pro Tyr Leu Asp Gly Thr Phe
        675                 680                 685

Tyr Leu Asn His Thr Phe Lys Lys Val Ser Ile Met Phe Asp Ser Ser
    690                 695                 700

Val Ser Trp Pro Gly Asn Asp Arg Leu Leu Thr Pro Asn Glu Phe Glu
705                 710                 715                 720

Ile Lys Arg Ser Val Asp Gly Glu Gly Tyr Asn Val Ala Gln Ser Asn
                725                 730                 735

Met Thr Lys Asp Trp Phe Leu Ile Gln Met Leu Ser His Tyr Asn Ile
            740                 745                 750

Gly Tyr Gln Gly Phe Tyr Val Pro Glu Ala Tyr Lys Asp Arg Met Tyr
        755                 760                 765

Ser Phe Phe Arg Asn Phe Gln Pro Met Ser Arg Gln Val Val Asp Thr
    770                 775                 780

Val Asn Tyr Ala Asn Tyr Lys Glu Val Thr Met Pro Phe Gln His Asn
785                 790                 795                 800

Asn Ser Gly Phe Val Gly Tyr Met Gly Pro Thr Met Arg Glu Gly Gln
                805                 810                 815

Ala Tyr Pro Ala Asn Tyr Pro Tyr Pro Leu Ile Gly Ala Thr Ala Val
            820                 825                 830

Pro Ser Leu Thr Gln Lys Lys Phe Leu Cys Asp Arg Thr Met Trp Arg
        835                 840                 845

Ile Pro Phe Ser Ser Asn Phe Met Ser Met Gly Ala Leu Thr Asp Leu
    850                 855                 860

Gly Gln Asn Met Leu Tyr Ala Asn Ser Ala His Ala Leu Asp Met Thr
865                 870                 875                 880

Phe Glu Val Asp Pro Met Asp Glu Pro Thr Leu Leu Tyr Val Leu Phe
                885                 890                 895

Glu Val Phe Asp Val Val Arg Ile His Gln Pro His Arg Gly Val Ile
            900                 905                 910
```

```
Glu Ala Val Tyr Leu Arg Thr Pro Phe Ser Ala Gly Asn Ala Thr Thr
        915                 920                 925


<210> SEQ ID NO 28
<211> LENGTH: 168
<212> TYPE: PRT
<213> ORGANISM: Artificial Sequence
<220> FEATURE:
<223> OTHER INFORMATION: Synthetic polypeptide sAd4287 Fiber-1 Knob

<400> SEQUENCE: 28

Leu Cys Thr Thr Pro Thr Ala Ala Ser Asn Cys Thr Val Phe Thr Asn
1               5                   10                  15

Gly Asp Ser Leu Leu Cys Leu Cys Leu Thr Lys Cys Gly Ala His Val
            20                  25                  30

Leu Gly Ser Val Ser Leu Thr Gly Met Gln Gly Thr Ile Thr Ala Met
        35                  40                  45

Thr Gln Asn Tyr Ile Ser Ile Gln Phe Leu Phe Asp Asn Asn Gly Ala
    50                  55                  60

Leu Thr Ser Ser Pro Leu Leu Asn Asn Asn Thr Trp Gly Ile Arg Gln
65                  70                  75                  80

Asn Asp Thr Ser Ser Ala Asn Pro Ala Tyr Asn Ala Leu Ala Phe Met
                85                  90                  95

Pro Asn Ser Thr Val Tyr Val Arg Gly Gln Ser Gly Glu Pro Arg Asn
            100                 105                 110

Asn Tyr Tyr Thr Gln Thr Tyr Leu Arg Gly Asn Val Lys Lys Pro Ile
        115                 120                 125

Ile Leu Thr Val Thr Tyr Asn Ser Ala Ala Ser Gly Tyr Ser Leu Thr
    130                 135                 140

Phe Lys Trp Asp Ala Val Val Thr Glu Lys Phe Ala Thr Pro Thr Ser
145                 150                 155                 160

Ser Phe Cys Tyr Ile Thr Glu Gln
                165


<210> SEQ ID NO 29
<211> LENGTH: 163
<212> TYPE: PRT
<213> ORGANISM: Artificial Sequence
<220> FEATURE:
<223> OTHER INFORMATION: Synthetic polypeptide sAd4310A Fiber-1 Knob

<400> SEQUENCE: 29

Leu Trp Thr Ala Pro Thr Ser Thr Gly Asn Cys Thr Val Tyr Ser Glu
1               5                   10                  15

Gly Asp Ser Leu Leu Ser Leu Cys Leu Thr Lys Cys Gly Ala His Val
            20                  25                  30

Leu Gly Ser Val Ser Leu Thr Gly Leu Thr Gly Thr Ile Thr Gln Met
        35                  40                  45

Thr Asp Ile Ser Val Thr Ile Gln Phe Thr Phe Asp Asn Asn Gly Lys
    50                  55                  60

Leu Leu Ser Ser Pro Leu Ile Asn Asn Ala Phe Ser Ile Arg Gln Asn
65                  70                  75                  80

Asp Ser Thr Ala Ser Asn Pro Thr Tyr Asn Ala Leu Ala Phe Met Pro
                85                  90                  95

Asn Ser Thr Ile Tyr Ala Arg Gly Gly Gly Gly Glu Pro Arg Asn Asn
            100                 105                 110

Tyr Tyr Val Gln Thr Tyr Leu Arg Gly Asn Val Gln Lys Pro Ile Ile
```

115 120 125

Leu Thr Val Thr Tyr Asn Ser Ala Ala Thr Gly Tyr Ser Leu Ser Phe
130 135 140

Lys Trp Thr Ala Leu Ala Arg Glu Lys Phe Ala Thr Pro Thr Thr Ser
145 150 155 160

Phe Cys Tyr

<210> SEQ ID NO 30
<211> LENGTH: 163
<212> TYPE: PRT
<213> ORGANISM: Artificial Sequence
<220> FEATURE:
<223> OTHER INFORMATION: Synthetic polypeptide sAd4312 Fiber-1 Knob

<400> SEQUENCE: 30

Leu Trp Thr Pro Pro Thr Ser Asn Pro Asn Cys Thr Val Tyr Thr Glu
1 5 10 15

Ser Asp Ser Leu Leu Ser Leu Cys Leu Thr Lys Cys Gly Ala His Val
20 25 30

Leu Gly Ser Val Ser Leu Thr Gly Val Ala Gly Thr Met Ile Asn Met
35 40 45

Ala Glu Thr Ser Leu Ala Ile Glu Phe Thr Phe Asp Asp Thr Gly Lys
50 55 60

Leu Leu His Ser Pro Leu Val Asn Thr Thr Phe Ser Ile Arg Gln Gly
65 70 75 80

Asp Ser Pro Ala Ser Asn Pro Thr Tyr Asn Ala Leu Ala Phe Met Pro
85 90 95

Asn Ser Thr Leu Tyr Ala Arg Gly Gly Ser Gly Glu Pro Arg Asn Asn
100 105 110

Tyr Tyr Val Gln Thr Tyr Leu Arg Gly Asn Val Gln Arg Pro Ile Thr
115 120 125

Leu Thr Val Thr Phe Asn Ser Ala Ala Thr Gly Tyr Ser Leu Ser Phe
130 135 140

Lys Trp Thr Ala Val Ala Arg Glu Lys Phe Ala Ala Pro Ala Thr Ser
145 150 155 160

Phe Cys Tyr

<210> SEQ ID NO 31
<211> LENGTH: 171
<212> TYPE: PRT
<213> ORGANISM: Artificial Sequence
<220> FEATURE:
<223> OTHER INFORMATION: Synthetic polypeptide sAd4287 Fiber-2 Knob

<400> SEQUENCE: 31

Leu Trp Thr Thr Ala Asp Pro Ser Pro Asn Cys Ser Val Tyr Gln Asp
1 5 10 15

Leu Asp Ala Arg Leu Trp Leu Ala Leu Val Lys Ser Gly Asp Met Val
20 25 30

His Gly Ser Ile Ala Leu Lys Ala Leu Lys Gly Thr Leu Leu Asn Pro
35 40 45

Thr Ala Ser Tyr Ile Ser Ile Val Ile Tyr Phe Tyr Ser Asn Gly Val
50 55 60

Arg Arg Thr Asn Tyr Pro Thr Phe Asp Asn Glu Gly Thr Leu Ala Asn
65 70 75 80

Ser Ala Thr Trp Gly Tyr Arg Glu Gly Gln Ser Ala Asn Thr Asn Val
85 90 95

Thr Asn Ala Thr Glu Phe Met Pro Ser Ser Thr Arg Tyr Pro Val Asn
100 105 110

Lys Gly Asp Asn Ile Gln Asn Gln Ser Phe Ser Tyr Thr Cys Ile Lys
115 120 125

Gly Asp Phe Ala Met Pro Val Pro Phe Arg Val Thr Tyr Asn His Ala
130 135 140

Leu Glu Gly Tyr Ser Leu Lys Phe Thr Trp Arg Val Val Ala Asn Gln
145 150 155 160

Ala Phe Asp Ile Pro Cys Cys Ser Phe Ser Tyr
165 170

<210> SEQ ID NO 32
<211> LENGTH: 171
<212> TYPE: PRT
<213> ORGANISM: Artificial Sequence
<220> FEATURE:
<223> OTHER INFORMATION: Synthetic polypeptide sAd4310A Fiber-2 Knob

<400> SEQUENCE: 32

Leu Trp Thr Thr Ala Asp Pro Ser Pro Asn Cys Ser Ile Tyr Thr Asp
1 5 10 15

Leu Asp Ala Lys Met Trp Leu Ser Leu Val Lys Gln Gly Gly Val Val
20 25 30

His Gly Ser Val Ala Leu Lys Ala Leu Lys Gly Thr Leu Leu Ser Pro
35 40 45

Thr Glu Ser Ala Ile Val Ile Ile Leu His Phe Asp Asn Tyr Gly Val
50 55 60

Arg Ile Leu Asn Tyr Pro Thr Leu Gly Thr Gln Gly Thr Leu Gly Asn
65 70 75 80

Asn Ala Thr Trp Gly Tyr Arg Gln Gly Glu Ser Ala Asp Thr Asn Val
85 90 95

Leu Asn Ala Leu Ala Phe Met Pro Ser Ser Lys Arg Tyr Pro Arg Gly
100 105 110

Arg Gly Ser Glu Val Gln Asn Gln Thr Val Gly Tyr Thr Cys Ile Gln
115 120 125

Gly Asp Leu Ser Met Pro Val Pro Tyr Gln Ile Gln Tyr Asn Tyr Gly
130 135 140

Pro Thr Gly Tyr Ser Phe Lys Phe Ile Trp Arg Thr Val Ser Arg Gln
145 150 155 160

Pro Phe Asp Ile Pro Cys Cys Phe Phe Ser Tyr
165 170

<210> SEQ ID NO 33
<211> LENGTH: 172
<212> TYPE: PRT
<213> ORGANISM: Artificial Sequence
<220> FEATURE:
<223> OTHER INFORMATION: Synthetic polypeptide sAd4312 Fiber-2 Knob

<400> SEQUENCE: 33

Leu Trp Thr Thr Ala Asp Pro Ser Pro Asn Cys Thr Val Tyr Glu Ser
1 5 10 15

Leu Asp Ser Arg Leu Trp Leu Ala Leu Val Lys Cys Gly Gly Met Val
20 25 30

His Gly Ser Ile Ala Leu Gln Ala Glu Lys Gly Gln Leu Leu Arg Pro
35 40 45

Thr Ala Ser Phe Ile Ser Ile Val Ile Tyr Phe Tyr Ser Asp Gly Val

```
    50                  55                  60

Arg Arg Thr Asn Tyr Pro Thr Ile Gly Asn Asp Glu Gly Thr Leu Ala
65                  70                  75                  80

Asn Ser Ala Thr Trp Gly Tyr Arg Gln Gly Gln Ser Ala Asp Thr Asn
                85                  90                  95

Val Thr Asn Ala Val Glu Phe Met Pro Ser Leu His Arg Tyr Pro Ile
            100                 105                 110

Asn Gln Gly Asp Asn Ile Lys Asn Gln Met Ile Thr Tyr Thr Cys Ile
        115                 120                 125

Gln Gly Asn Val Asn Met Pro Val Pro Leu Lys Ile Thr Phe Asn His
    130                 135                 140

Ala Leu Glu Gly Tyr Ser Leu Lys Phe Thr Trp Arg Val Val Ala Asn
145                 150                 155                 160

Glu Lys Phe Asp Ile Pro Cys Cys Ser Phe Ser Tyr
                165                 170


<210> SEQ ID NO 34
<211> LENGTH: 6109
<212> TYPE: DNA
<213> ORGANISM: Artificial Sequence
<220> FEATURE:
<223> OTHER INFORMATION: Synthetic oligonucleotide sAdApt4287.Empty

<400> SEQUENCE: 34

attaacatca tcaataatat accttattct ggaaacgtgc caatatgata atgagcgggg     60

aggagcgagg cggggccggg gtgacgtgcg gtgacgcggg gtgacgcggg gtggcgcgag    120

ggcggggcgg gagtggggag gcgcttagtt tttacgtatg cggaaggagg ttttataccg    180

gaagttgggt aatttgggcg tatatttgta agttttgtgt aatttggcgc gaaaaccggg    240

taatgaggaa gttgaggtta atatgtactt tttatgactg ggcggaattt ctgctgatca    300

gcagtgaact ttgggcgctg acggggaggt ttcgctacgt ggcagtacca cgagaaggct    360

caaaggtccc atttattgta ctcctcagcg ttttcgctgg gtatttaaac gctgtcagat    420

catcaagagg ccactcttga gtgccggcga gtagagtttt ctcctgtcga ctggtcaata    480

ttggccatta gccatattat tcattggtta tatagcataa atcaatattg gctattggcc    540

attgcatacg ttgtatccat atcataatat gtacatttat attggctcat gtccaacatt    600

accgccatgt tgacattgat tattgactag ttattaatag taatcaatta cggggtcatt    660

agttcatagc ccatatatgg agttccgcgt tacataactt acggtaaatg gcccgcctgg    720

ctgaccgccc aacgaccccc gcccattgac gtcaataatg acgtatgttc ccatagtaac    780

gccaataggg actttccatt gacgtcaatg ggtggagtat ttacggtaaa ctgcccactt    840

ggcagtacat caagtgtatc atatgccaag tacgccccct attgacgtca atgacggtaa    900

atggcccgcc tggcattatg cccagtacat gaccttatgg gactttccta cttggcagta    960

catctacgta ttagtcatcg ctattaccat ggtgatgcgg ttttggcagt acatcaatgg   1020

gcgtggatag cggtttgact cacggggatt tccaagtctc caccccattg acgtcaatgg   1080

gagtttgttt tggcaccaaa atcaacggga ctttccaaaa tgtcgtaaca actccgcccc   1140

attgacgcaa atgggcggta ggcgtgtacg gtgggaggtc tatataagca gagctcgttt   1200

agtgaaccgt cagatcgcct ggagacgcca tccacgctgt tttgacctcc atagaagaca   1260

ccgggaccga tccagcctcc gcggccggga acggtgcatt ggaagcttgg taccggtgaa   1320

ttcgctagcg ttaacggatc ctctagacga gatccgaact tgtttattgc agcttataat   1380
```

-continued

```
ggttacaaat aaagcaatag catcacaaat ttcacaaata aagcattttt ttcactgcat   1440
tctagttgtg gtttgtccaa actcatcaat gtatcttatc atgtctagat ccttaaggaa   1500
tgcggagcta atcatttgag gttgtatcct gtaaccctga acgtcaccga ggagctgagg   1560
acggaccacc acatgctgtc ttgcctgcgt accgactatg aatccagtga tgaggagtga   1620
ggtgaggggc ggagccacaa agggtataaa ggggcatgaa gggtggacgc ggtgtttcaa   1680
aatgagcggg acgacggacg gcaatgcgtt tgaggggga gtgttcagcc catatctgac   1740
atctcgtctt ccttcctggg caggagtgcg tcagaatgta gtgggctcca ccgtggacgg   1800
acggccggtc gcccctgcaa attccgccac cctcacctat gccaccgtgg gatcatcgtt   1860
ggacactgcc gcggcagctg ccgcttctgc tgccgcttct actgctcgcg gcatggcggc   1920
tgattttgga ctatataacc aactggccac tgcagctgtg gcgtctcggt ctctggttca   1980
agaagatgcc ctgaatgtga tcttgactcg cctggagatc atgtcacgtc gcctggacga   2040
actggctgcg cagatatccc aagctaaccc cgataccgct tcagaatctt aaataaagac   2100
aaacaaattt gttgaaaagt aaaatggctt tatttgtttt ttttggctcg gtaggctcgg   2160
gtccacctgt ctcggtcgtt aaggactttg tgtatgtttt ccaaaacacg gtacagatgg   2220
gcttggatgt tcaagtacat gggcatgagg ccatctttgg ggtggagata ggaccactga   2280
agagcgtcat gttccggggt ggtattgtaa atcacccagt cgtagcaggg tttttgagcg   2340
tggaactgga atatgtcctt caggagcagg ctaatggcca agggcagccc cttagtgtag   2400
gtgtttacaa agcggttgag ctgggaggga tgcatgcggg gggagatgat atgcatcttg   2460
gcttggattt tgaggttagc tatgttacca cccaggtctc tgcgggggtt catgttatga   2520
aggaccacca gcacggtgta gccggtgcac ttggggaact tgtcatgcag tttggagggg   2580
aaggcgtgga agaatttaga taccccttg tgcccccta ggttttccat gcactcatcc   2640
ataataatgg caatgggacc cctggcggcc gctttagcaa acacgttttg ggggttggaa   2700
acatcatagt tttgctctag agtgagctca tcataggcca tctttacaaa gcggggtagg   2760
agggtgcccg actgggggat gatagttcca tctgggcctg gagcgtagtt gccctcacag   2820
atctgcatct cccaggcctt aatttccgag gggggatca tgtccacctg gggggcgata   2880
aagaacacgg tttctggcgg gggattgatg agctgggtgg aaagcaagtt acgcaatagc   2940
tgggatttgc cgcaaccggt ggggccgtag atgaccccga tgacgggttg cagctggtag   3000
ttcagagagg aacagctgcc gtcggggcgc aggaggggg ccacatcgtt catcatgctt   3060
ctgacatgtt tattttcact cactaagttt tgcaagagcc tctccccacc cagggataag   3120
agttcttcca ggctgttgaa gtgtttcagc ggtttcaggc cgtcggccat gggcatcttt   3180
tcaagcgact gacgaagcaa gtacagtcgg tcccagagct cggtgacgtg ctctatggaa   3240
tctcgatcca gcagacttct tggttgcggg ggttgggccg actttcgctg tagggcacca   3300
gccggtgggc gtccagggcc gcgagggttc tgtccttcca gggtctcagc gttcgggtga   3360
gggtggtctc ggtgacggtg aagggatgag ccccgggctg ggcgcttgcg agggtgcgct   3420
tcaggctcat cctgctggtg ctgaagcggg cgtcgtctcc ctgtgagtcg gccagatagc   3480
aacgaagcat gaggtcgtag ctgagggact cggccgcgtg tcccttggcg cgcagctttc   3540
ccttggaaac gtgctgacat ttggtgcagt gcagacactt gagggcgtag agttttgggg   3600
ccaggaagac cgactcgggc gagtaggcgt cggctccgca ctgagcgcag acggtctcgc   3660
actccaccag ccacgtgagc tcgggtttag cgggatcaaa aaccaagttg cctccatttt   3720
ttttgatgcg tttcttacct tgcgtctcca tgagtctgtg tcccgcttcc gtgacaaaaa   3780
```

```
ggctgtcggt gtccccgtag accgacttga gggggcgatc ttccaaaggt gttccgaggt   3840
cttccgcgta caggaactgg gaccactccg agacaaaggc tcgggtccag gctaacacga   3900
aggaggcgat ctgcgagggg tatctgtcgt tttcaatgag gggtccacc ttttccaggg   3960
tgtgcagaca caggtcgtcc tcctccgcgt ccacgaagtt aattaattcg aacccataat   4020
acccataata gctgtttgcc atcgacgcga ggctggatgg ccttccccat tatgattctt   4080
ctcgcttccg gcggcatcgg gatgcccgcg ttgcaggcca tgctgtccag gcaggtagat   4140
gacgaccatc agggacagct tcaaggatcg ctcgcggctc ttaccagccc agcaaaaggc   4200
caggaaccgt aaaaaggccg cgttgctggc gtttttccat aggctccgcc cccctgacga   4260
gcatcacaaa aatcgacgct caagtcagag gtggcgaaac ccgacaggac tataaagata   4320
ccaggcgttt ccccctggaa gctccctcgt gcgctctcct gttccgaccc tgccgcttac   4380
cggatacctg tccgcctttc tcccttcggg aagcgtggcg ctttctcata gctcacgctg   4440
taggtatctc agttcggtgt aggtcgttcg ctccaagctg ggctgtgtgc acgaaccccc   4500
cgttcagccc gaccgctgcg ccttatccgg taactatcgt cttgagtcca acccggtaag   4560
acacgactta tcgccactgg cagcagccac tggtaacagg attagcagag cgaggtatgt   4620
aggcggtgct acagagttct tgaagtggtg gcctaactac ggctacacta gaaggacagt   4680
atttggtatc tgcgctctgc tgaagccagt taccttcgga aaaagagttg gtagctcttg   4740
atccggcaaa caaaccaccg ctggtagcgg tggttttttt gtttgcaagc agcagattac   4800
gcgcagaaaa aaaggatctc aagaagatcc tttgatcttt tctacggggt ctgacgctca   4860
gtggaacgaa aactcacgtt aagggatttt ggtcatgaga ttatcaaaaa ggatcttcac   4920
ctagatcctt ttaaattaaa aatgaagttt taaatcaatc taaagtatat atgagtaaac   4980
ttggtctgac agttaccaat gcttaatcag tgaggcacct atctcagcga tctgtctatt   5040
tcgttcatcc atagttgcct gactccccgt cgtgtagata actacgatac gggagggctt   5100
accatctggc cccagtgctg caatgatacc gcgagaccca cgctcaccgg ctccagattt   5160
atcagcaata aaccagccag ccggaagggc cgagcgcaga agtggtcctg caactttatc   5220
cgcctccatc cagtctatta attgttgccg ggaagctaga gtaagtagtt cgccagttaa   5280
tagtttgcgc aacgttgttg ccattgctgc aggcatcgtg gtgtcacgct cgtcgtttgg   5340
tatggcttca ttcagctccg gttcccaacg atcaaggcga gttacatgat cccccatgtt   5400
gtgcaaaaaa gcggttagct ccttcggtcc tccgatcgtt gtcagaagta agttggccgc   5460
agtgttatca ctcatggtta tggcagcact gcataattct cttactgtca tgccatccgt   5520
aagatgcttt tctgtgactg gtgagtactc aaccaagtca ttctgagaat agtgtatgcg   5580
gcgaccgagt tgctcttgcc cggcgtcaac acgggataat accgcgccac atagcagaac   5640
tttaaaagtg ctcatcattg gaaaacgttc ttcggggcga aaactctcaa ggatcttacc   5700
gctgttgaga tccagttcga tgtaacccac tcgtgcaccc aactgatctt cagcatcttt   5760
tactttcacc agcgtttctg ggtgagcaaa aacaggaagg caaaatgccg caaaaaaggg   5820
aataagggcg acacggaaat gttgaatact catactcttc ctttttcaat attattgaag   5880
catttatcag ggttattgtc tcatgagcgg atacatattt gaatgtattt agaaaaataa   5940
acaaataggg gttccgcgca catttccccg aaaagtgcca cctgacgtct aagaaaccat   6000
tattatcatg acattaacct ataaaaatag gcgtatcacg aggccctttc gtcttcaaga   6060
attggtcgat ggcaaacagc tattatgggt attatgggtt cgaattaat              6109
```

<210> SEQ ID NO 35
<211> LENGTH: 15808
<212> TYPE: DNA
<213> ORGANISM: Artificial Sequence
<220> FEATURE:
<223> OTHER INFORMATION: Synthetic oligonucleotide pBr/sAd4287.pIX-pV

<400> SEQUENCE: 35
attaagaatg cggagctaat catttgaggt tgtatcctgt aaccctgaac gtcaccgagg 60
agctgaggac ggaccaccac atgctgtctt gcctgcgtac cgactatgaa tccagtgatg 120
aggagtgagg tgaggggcgg agccacaaag ggtataaagg ggcatgaagg gtggacgcgg 180
tgtttcaaaa tgagcgggac gacggacggc aatgcgtttg aggggggagt gttcagccca 240
tatctgacat ctcgtcttcc ttcctgggca ggagtgcgtc agaatgtagt gggctccacc 300
gtggacggac ggccggtcgc cctgcaaat tccgccaccc tcacctatgc caccgtggga 360
tcatcgttgg acactgccgc ggcagctgcc gcttctgctg ccgcttctac tgctcgcggc 420
atggcggctg attttggact atataaccaa ctggccactg cagctgtggc gtctcggtct 480
ctggttcaag aagatgccct gaatgtgatc ttgactcgcc tggagatcat gtcacgtcgc 540
ctggacgaac tggctgcgca gatatcccaa gctaaccccg ataccgcttc agaatcttaa 600
ataaagacaa acaaatttgt tgaaaagtaa aatggcttta tttgtttttt ttggctcggt 660
aggctcgggt ccacctgtct cggtcgttaa ggactttgtg tatgttttcc aaaacacggt 720
acagatgggc ttggatgttc aagtacatgg gcatgaggcc atctttgggg tggagatagg 780
accactgaag agcgtcatgt tccggggtgg tattgtaaat cacccagtcg tagcagggtt 840
tttgagcgtg gaactggaat atgtccttca ggagcaggct aatggccaag ggcagcccct 900
tagtgtaggt gtttacaaag cggttgagct gggagggatg catgcggggg gagatgatat 960
gcatcttggc ttggattttg aggttagcta tgttaccacc caggtctctg cgggggttca 1020
tgttatgaag gaccaccagc acggtgtagc cggtgcactt ggggaacttg tcatgcagtt 1080
tggaggggaa ggcgtggaag aatttagata ccccccttgtg ccccccctagg ttttccatgc 1140 actcatccat aataatggca atgggacccc tggcggccgc tttagcaaac acgttttggg 1200
ggttggaaac atcatagttt tgctctagag tgagctcatc ataggccatc tttacaaagc 1260
ggggtaggag ggtgcccgac tgggggatga tagttccatc tggcctggga gcgtagttgc 1320
cctcacagat ctgcatctcc caggccttaa tttccgaggg ggggatcatg tccacctggg 1380
gggcgataaa gaacacggtt tctggcgggg gattgatgag ctgggtggaa agcaagttac 1440
gcaatagctg ggatttgccg caaccggtgg ggccgtagat gaccccgatg acgggttgca 1500
gctggtagtt cagagaggaa cagctgccgt cggggcgcag gaggggggcc acatcgttca 1560
tcatgcttct gacatgttta ttttcactca ctaagttttg caagagcctc tccccaccca 1620
gggataagag ttcttccagg ctgttgaagt gtttcagcgg tttcaggccg tcggccatgg 1680
gcatcttttc aagcgactga cgaagcaagt acagtcggtc ccagagctcg gtgacgtgct 1740
ctatggaatc tcgatccagc agacttcttg gttgcggggg ttgggccgac tttcgctgta 1800
gggcaccagc cggtgggcgt ccagggccgc gagggttctg tccttccagg gtctcagcgt 1860
tcgggtgagg gtggtctcgg tgacggtgaa gggatgagcc ccgggctggg cgcttgcgag 1920
ggtgcgcttc aggctcatcc tgctggtgct gaagcgggcg tcgtctccct gtgagtcggc 1980
cagatagcaa cgaagcatga ggtcgtagct gagggactcg gccgcgtgtc ccttggcgcg 2040
cagctttccc ttggaaacgt gctgacattt ggtgcagtgc agacacttga gggcgtagag 2100

-continued

```
ttttggggcc aggaagaccg actcgggcga gtaggcgtcg gctccgcact gagcgcagac   2160
ggtctcgcac tccaccagcc acgtgagctc gggtttagcg ggatcaaaaa ccaagttgcc   2220
tccatttttt ttgatgcgtt tcttaccttg cgtctccatg agtctgtgtc ccgcttccgt   2280
gacaaaaagg ctgtcggtgt ccccgtagac cgacttgagg gggcgatctt ccaaaggtgt   2340
tccgaggtct tccgcgtaca ggaactggga ccactccgag acaaaggctc gggtccaggc   2400
taacacgaag gaggcgatct gcgaggggta tctgtcgttt tcaatgaggg ggtccacctt   2460
ttccagggtg tgcagacaca ggtcgtcctc ctccgcgtcc acgaaggtga ttggcttgta   2520
agtgtaggtc acgtgacccg caccccccca aggggtataa aagggggcgt gcccactctc   2580
cccgtcactt tcttccgcat cgctgtggac cagagccagc tgttcgggtg agtaggccct   2640
ctcaaaagcc ggcatgattt cggcgctcaa gttgtcagtt tctacaaacg aggtggattt   2700
gatattcacg tgccccgcgg cgatgctttt gatggtggag gggtccatct gatcagaaaa   2760
cacgatcttt ttattgtcaa gtttggtggc gaaagacccg tagagggcgt tggaaagcaa   2820
cttggcgatg gagcgcaggg tctgattttt ctcccgatcg gccctctcct tggcagcgat   2880
gttgagttgc acgtactcgc gagccacgca ccgccactcg ggaacacgg cggtgcgctc   2940
gtcgggcagg atgcgcacgt gccagccgcg gttgtgcagg gtgatgaggt ccacgctggt   3000
ggccacctcc ccgcggaggg gctcgttggt ccaacacaat cgccccctt ttctggagca   3060
gaacggaggc aggggatcta gcaagttggc gggcgggggg tcggcgtcga tggtaaatat   3120
gccgggtagc agaattttat taaaataatc gatttcggtg tccgtgtctt gcaacgcgtc   3180
ttcccacttc ttcaccgcca gggccctttc gtagggattc aggggcggtc cccagggcat   3240
ggggtgggtc agggccgagg cgtacatgcc gcagatgtcg tacacgtaca ggggctccct   3300
caacaccccg atgtaagtgg ggtaacagcg ccccccgcgg atgctggctc gcacgtagtc   3360
gtacatctcg tgagagggag ccatgagccc gtctcccaag tgggtcttgt ggggtttctc   3420
ggcccggtag aggatctgcc tgaagatggc gtgggagttg gaagagatgg tggggcgttg   3480
gaagacatta aagttggctc cgggcagtcc cacggagtct tggatgaact gggcgtagga   3540
ttcccggagc ttgtccacca gggctgcggt taccagcacg tcgagagcgc agtagtccaa   3600
cgtctcgcgg accaggttgt aggccgtctc ttgtttttttc tcccacagtt cgcgattgag   3660
gaggtattcc tcgcggtctt tccagtactc ttcggcggga aatccttttt cgtccgctcg   3720
gtaagaacct aacatgtaaa attcgttcac ggctttgtat ggacaacagc ctttttctac   3780
cggcagggcg tacgcttgag cggcctttct gagagaggtg tgggtgaggg cgaaggtgtc   3840
ccgcaccatc actttcaggt actgatgttt gaagtccgtg tcgtcgcagg caccctgttc   3900
ccacagcgtg aagtcggtgc gctttttctg cctgggattg gggagggcga atgtgacgtc   3960
gttaaaaagg attttcccgg agcggggcat gaagttgcga gagatcctga agggtccggg   4020
cacgtccgag cggttgttga tgacttgtgc cgccaggacg atctcgtcga agccgttgat   4080
gttgtggccc acgatgtaaa gttcgataaa gcgcggctgt cccttgaggg ccggcgcttt   4140
tttcaactcc tcgtaggtga gacagtccgg cgaggagaga cccagctccg cccgggccca   4200
gtcggagagc tgagggttag ccgcgaggaa agagctccat aggtcaaggg ctagcagagt   4260
ttgcaagcgg tcgcggaact cgcgaaactt tttccccacg gccattttct ccggcgtcac   4320
cacgtagaaa gtgcaggggc ggtcgttcca gacgtcccat cggagctcta gggccagctc   4380
gcaggcttgg cgaacgaggg tctcctcgcc cgagacgtgc atgaccagca tgaagggtac   4440
```

caactgtttc ccgaacgagc ccatccatgt gtaggtttct acgtcgtagg tgacaaagag 4500
ccgctgggcg cgcgcgtggg agccgatcgg gaagaagctg atctcctgcc accagttgga 4560
ggaatgggtg ttgatgtggt gaaagtagaa gtcccgccgg cgcacagagc attcgtgctg 4620
atgtttgtaa aagcgaccgc agtagtcgca gcgctgcacg ctctgtatct cctgaatgag 4680
atgcgctttt cgcccgcgca ccagaaaccg gagggggaag ttgagacggg gggcttgtgg 4740
ggcggcatcc cattcgcctt ggcggtggga gtctgcgtct gcgtcctcct tctctgggtg 4800
gacgacggtg gggacgacaa cgccccgggt gccgcaagtc cagatctccg ccacggaggg 4860
gcgcaggcgc tgcaggaggg gacgcagctg cccgctgtcc agggagtcga gggcggccgc 4920
gctgaggtcg gcgggaagcg tttgcaagtt cactttcaga agaccggtaa gagcgtgagc 4980
caggtgcaga tggtacttga tttccagggg ggtgttggaa gaggcgtcca cggcgtagag 5040
gaggccgtgt ccgcgcgggg ccaccaccgt gccccgagga ggttttatct caatcgtcga 5100
gggcgagcgc cggggggtag aggcggctct gcgccggggg gcagcggagg cagcggcacg 5160
ttttcgtgag gatttggcag cggttgatga cgagcccgga gactgctggc gtgggcgacg 5220
acgcggcggt tgaggtcctg gatgtgccgt ctctgcgtga agaccaccgg cccccgggtc 5280
ctgaacctga aagagagttc cacagaatca atgtctgcat cgttaacggc ggcctgcctg 5340
aggatctcct gtacgtcgcc cgagttgtct tgataggcga tctcggccat gaactgctcc 5400
acttcttcct cgcggaggtc gccgtggccc gctcgctcca cggtggcggc caggtcgttg 5460
gagatgcgac gcatgagttg agagaaggcg ttgaggccgt tctcgttcca cacgcggctg 5520
tacaccacgt tgccgaagga gtcgcgcgct cgcatgacca cctgggccac gttgagttcc 5580
acgtggcggg cgaagacggc gtagtttctg aggcgctgga agaggtagtt gagcgtggtg 5640
gcgatgtgct cgcagacgaa gaagtacatg atccagcgcc gcagggtcat ctcgttgatg 5700
tctccgatgg cttcgagacg ctccatggcc tcgtagaagt cgacggcgaa gttgaaaaat 5760
tgggagttgc gggcggccac cgtgagttct tcttgcagga ggcggatgag atcggcgacc 5820
gtgtcgcgca cctcctgctc gaaagcgccc cgaggcgcct ctgcttcttc ctccggctcc 5880
tcctcttcca ggggcacggg ttcctccggc agctctgcga cggggacggg gcggcgacgt 5940
cgtcgtctga ccggcaggcg gtccacgaag cgctcgatca tttcgccgcg ccggcgacgc 6000
atggtctcgg tgacggcgcg tccgttttcg cgaggtcgca gttcgaagac gccgccgcgc 6060
agagcgcccc cgtgcaggga gggtaagtgg ttagggccgt cgggcaggga cacggcgctg 6120
acgatgcatt ttatcaattg ctgcgtaggc actccgtgca gggatctgag aacgtcgagg 6180
tcgacgggat ccgagaactt ctctaagaaa gcgtctatcc aatcgcagtc gcaaggtaag 6240
ctgaggacag tgggtcgctg gggggcgtcc gcgggcagtt gggaggtgat gctgctgatg 6300
atgtaattaa agtaggcggt cttcaggcgg cggatggtgg cgaggaggac cacgtctttg 6360
ggcccggcct gttgaatgcg caggcgctcg gccatgcccc aggcctcgct ctgacagcga 6420
cgcaggtctt tgtagtagtc ttgcatcagt ctctccaccg gaacctctgc ttctcccctg 6480
tctgccatgc gagtcgagcc gaacccccgc aggggctgca gcaacgctag gtcggccacg 6540 acccttttcgg ccagcacggc ctgttgaatc tgcgtgaggg tggtctggaa gtcgtccagg 6600
tccacgaagc ggtgataggc cccgtgttg atggtgtagg tgcagttggc catgacggac 6660
cagttgacga cttgcatacc gggttgggtg atctccgtgt acttgaggcg cgagtaggcg 6720
cgggactcga acacgtagtc gttgcatgtg cgcaccagat actggtagcc gaccaggaag 6780
tgaggaggcg gctctcggta caggggccag ccgacggtgg cgggggcgcc gggggacagg 6840

-continued

```
tcgtccagca tgaggcgatg gtagtggtag atgtagcggg agagccaggt gatgccggcc   6900
gaggtggtcg cggccctggt gaattcccgg acgcggttcc agatgttgcg caggggacgg   6960
aagcgttcca tggtgggcac gctctgcccc gtgaggcggg cgcagtcctg tacgctctag   7020
atggaaaaaa gacagggcgg tcatcgactc ccttccgtag cttgggggt aaagtcgcaa   7080
gggtgcggcg gcggggaacc ccggttcgag accggccgga tccgccgctc ccgatgcgcc   7140
tggccccgca tccacgacgt ccgcgccgag acccagccgc gacgctctgc cccaatacgg   7200
aggggagtct tttggtgttt tttcgtagat gcatccggtg ctgcggcaga tgcgacctca   7260
gacgcccacc accaccgccg cggcggcagt aaacctgagc ggaggcggtg acagggaggt   7320
ggaggagctg gctttagacc tggaagaggg agaggggctg gcccggctgg gagcgccgtc   7380
cccagagaga caccctaggg ttcagctcgt gagggacgcc aggcaggctt ttgtgccgaa   7440
gcagaacctg tttagggacc gcagcggtca ggaggcggag gagatgcgcg attgcaggtt   7500
tcgggcgggt agagagctga gggcgggctt cgatcgcgag cggctcctga gggcggagga   7560
tttcgagccc gacgagcgtt ctggggtgag cccggcccgc gctcacgtct cggcggccaa   7620
cctggtgagc gcgtacgagc agacggtgaa cgaggagcgc aacttccaaa agagctttaa   7680
caatcacgtg aggaccctga tcgcgaggga ggaggtgacc atcgggctga tgcatctgtg   7740
ggacttcgtg gaggcctacg tgcagaaccc ggccagcaaa cctctgacgg cccagctgtt   7800
cctgatcgtg cagcacagcc gcgacaacga gacgttccgc gacgccatgt tgaacatcgc   7860
ggagcccgag ggtcgctggc tcttggatct gattaacatc ctgcagagca tcgtggtgca   7920
ggagaggggt ctgagtttag cggacaaggt ggcggccatt aactattcga tgcagagcct   7980
ggggaagttc tacgctcgca agatctacaa gagcccttac gtgcccatag acaaggaggt   8040
gaagatagac agcttttaca tgcgcatggc gctaaaggtg ctgacgctga gcgacgacct   8100
cggcgtgtac cgtaacgaca agatccacaa ggcggtgagc gccagccgcc ggcgggagct   8160
gagcgacagg gagctgatgc acagcctgca gagggcgctg gcgggcgccg gggacgagga   8220
gcgtgaggct tactttgaca tgggagccga tctgcagtgg cgtcccagcg cgcgcgcctt   8280
ggaggcggcg ggttatcccg acgaggagga tcgggacgat ttggaggagg caggcgagta   8340
cgaggacgaa gcctgaccgg gcaggtgttg ttttagatgc agcggccggc ggacggggcc   8400
accgcggatc ccgcactttt ggcatccatg cagagtcaac cttcgggcgt gaccgcctcc   8460
gatgactggg cggcggccat ggaccgcatc atggcgctga ccacccgcaa ccccgaggct   8520
tttaggcagc aaccccaggc caaccgtttt tcggccatct tggaagcggt ggtgccctcc   8580
cgcaccaacc ccacacacga gaaagtcctg actatcgtga acgccctggt agacagcaag   8640
gccatccgcc gcgacgaggc gggcttgatt tacaacgctc tgctggaacg ggtggcgcgc   8700
tacaacagca ctaacgttca gaccaatctg gatcgcctca ccaccgacgt gaaggaggcg   8760
ctggctcaga aggagcggtt tctgagggac agcaatctgg gctctctggt ggcactcaac   8820
gccttcctga gcacgcagcc ggccaacgtg ccccgcgggc aggaggacta cgtgagcttc   8880
atcagcgctc tgaggctgct ggtgtccgag gtgccccaga gcgaggtgta tcagtctggg   8940
ccggattact tcttccagac gtcccgacag ggcttgcaaa cggtgaacct gactcaggcc   9000
tttaaaaact tgcaaggcat gtggggcgtt aaggccccgg tgggcgatcg agccaccatc   9060
tccagtctgc tgacccccaa cactcgcctg ctgctgctct tgatcgcgcc gttcaccaac   9120
agtagcacta tcagccgtga ctcgtacctg ggtcatctca tcactttgta ccgcgaggcc   9180
```

```
atcggtcagg ctcagattga cgagcataca tatcaggaga tcactaacgt gagccgggcc   9240
ctgggtcagg aagataccgg cagcctggaa gccacgttga actttttgct aaccaaccgg   9300
aggcaaaaaa taccctccca gtttacgtta agcgccgagg aggagaggat tctgcgatac   9360
gtgcagcagt ccgtgagtct gtacttgatg cgggagggcg ccaccgcttc cacggcttta   9420
gacatgacgg ctcggaacat ggaaccgtcc ttttactccg cccaccggcc gttcattaac   9480
cgtctgatgg actacttcca tcgcgcggcc gccatgaacg gggagtattt taccaatgcc   9540
atcctgaatc cgcattggat gcccccgtcc ggcttctaca ccggcgagtt tgacctgccc   9600
gaagccgacg acggctttct ttgggacgac gtgtccgaca gcattttcac gccgggcaat   9660
cgccgattcc agaagaagga gggcggagac gagctccccc tctccagcgt ggaggcggcc   9720
tctaggggag agagtccctt tcccagtctg tcttccgcca gcagtggtcg ggtaacgcgc   9780
ccgcggttgc cgggggagag cgactacctg aacgacccct tgctgcggcc ggctaggaag   9840
aaaaatttcc ccaacaacgg ggtggaaagc ttggtggata aaatgaatcg ttggaagacc   9900
tacgcccagg agcagcggga gtgggaggac agtcagccgc gaccgctggt tccgccgcac   9960
tggcgtcgtc agagagaaga cccggacgac tccgcagacg atagtagcgt gttggacctg  10020
ggagggagcg gagccaaccc ctttgctcac ttgcaaccca aggggcgttc gagccgcctc  10080
tactaataaa aaagaagcgg aaacttacca gagccatggc cacagcgtgt gtgctttctt  10140
cctctctttc ttcctcggcg cggcagaatg agaagagcgg tgagagtcac gccggcggcg  10200
tatgagggtc cgcccccttc ttacgaaagc gtgatgggat cagcgaacgt gccggccacg  10260
ctggaggcgc cttacgttcc tcccagatac ctgggaccta cggagggcag aaacagcatc  10320
cgttactccg agctggcacc cctgtacgat accaccaagg tgtacctggt ggacaacaag  10380
tcggcggaca tcgcctccct gaattatcaa aacgatcaca gcaactttct gactaccgtg  10440
gtgcagaaca atgacttcac cccgacggag gcgggcacgc agaccattaa ctttgacgag  10500
cgttcccgct ggggcggtca gctgaaaacc atcctgcaca ccaacatgcc caacatcaac  10560
gagttcatgt ccaccaacaa gttcagggct aagctgatgg tagaaaaaag taatgcggaa  10620
actcggcagc cccgatacga gtggttcgag tttaccattc cagagggcaa ctattccgaa  10680
actatgacta tcgatctcat gaataacgcg atcgtggaca attacctgca agtggggaga  10740
cagaacgggg tgctggaaag cgatatcggc gtgaaattcg ataccagaaa cttccgactg  10800
gggtgggatc ccgtgaccaa gctggtgatg ccaggcgtgt acaccaacga ggcttttcac  10860
cccgacatcg tgctgctgcc ggggtgcggt gtggacttca ctcagagccg tttgagtaac  10920
ctgttaggaa ttagaaagcg ccgccccttc caagagggct ttcaaatcat gtatgaggac  10980
ctggagggag gtaatatacc cgccttactg gacgtgtcga agtacgaagc tagcatacaa  11040
cgcgccaaag cggagggtag agagattcgg ggagacacct ttgcggtagc tccccaggac  11100
ctggaaatag tgcctttaac taaagacagc aaagacagaa gctacaatat tataaacaac  11160
acgacggaca ccctgtatcg gagctggttt ctggcttaca actacggaga ccccgagaaa  11220
ggagtgagat catggaccat actcaccacc acggacgtga cctgtggctc gcagcaagtg  11280
tactggtccc tgccggatat gatgcaagac ccggtcacct tccgcccctc cacccaagtc  11340
agcaacttcc cggtggtggg caccgagctg ctgcccgtcc atgccaagag cttctacaac  11400
gagcaggccg tctactcgca acttattcgc cagtccaccg cgcttaccca cgtgttcaat  11460
cgctttcccg agaaccagat tctggtgcgc cctcccgctc ctaccattac caccgtcagt  11520
gaaaacgttc ccgccctcac agatcacgga accctgccgc tgcgcagcag tatcagtgga  11580
```

gttcagcgcg tgaccatcac cgacgccaga cgtcgaacct gcccctacgt ttacaaagcg 11640
cttggcgtgg tggctcctaa agttctttct agtcgcacct tctaaaaaca tgtccatcct 11700
catctctccc gataacaaca ccggctgggg actgggctcc ggcaagatgt acggcggagc 11760
caaaaggcgc tccagtcagc acccagttcg agttcggggc cacttccgcg ctccttgggg 11820
agcttacaag cgaggactct cgggtcgaac ggctgtagac gataccatag atgccgtgat 11880
tgccgacgcc cgccggtaca accccggacc ggtcgctagc gccgcctcca ccgtggattc 11940
cgtgatcgac agcgtggtag ccggcgctcg ggcctatgct cgccgcaaga ggcggctgca 12000
tcggagacgt cgcccccaccg ccgccatgct ggcagccaga gccgtgctga gacgggcccg 12060
gagggtaggc aggagggcta tgcgccgcgc tgccgccaac gccgccgccg ggagggcccg 12120
ccgacaggct gcccgccagg ctgctgccgc catcgctagc atggccagac ccaggagagg 12180
gaacgtgtac tgggtgcgcg attctgtgac gggagtccga gtgccggtgc gcagccgacc 12240
tccccgaagt tagaagatcc aagctgcgaa gacggcggta ctgagtctcc ctgttgttat 12300
cagcccaaca tgagcaagcg caagtttaaa gaagaactgc tgcagacgct ggtgcctgag 12360
atctatggcc ctccggacgt gaagcctgac attaagcccc gcgatatcaa gcgtgttaaa 12420
aagcgggaaa agaaagagga actcgcggtg gtagacgatg gcggagtgga atttattagg 12480
agtttcgccc cgcggcgcag ggttcaatgg aaagggcgac gggtacaacg cgttttgagg 12540
ccgggcaccg cggtagtttt taccccggga gagcggtcgg ccgttagggg ttttaaaagg 12600
cagtacgacg aggtgtacgg cgacgaggac atattggaac aggcggctca acagatcgga 12660
gaatttgcct atggaaagcg ctcgcgtcgc gaagacctgg ccatcgcctt agacagcggc 12720
aaccccacgc ccagcctcaa acccgtgacg ctgcagcagg tgcttcccgt gagcgccagc 12780
acggacagca agaggggaat aaaaagagaa atggaagatc tgcagcctac catccagctc 12840
atggttccta aacggcagag gctggaagag gtcctggaga agatgaaagt ggaccccagc 12900
atagagccgg acgttaaagt caggccgatc aaagaagtgg cccctggact cggggtgcag 12960
acggtggata tccagatccc cgtcacgtca gcttcgaccg ccgtggaagc catggaaacg 13020
caaaccgaaa cccccgccgt ggttggtacc aaagaagtgg cgttgcaaac cgacccctgg 13080
tacgaatttg ccgccccccg gcgtcagagg cgacccgctc gttacggccc cgccaacgcc 13140
atcatgccag aatatgcgct gcatccgtct atcctgccca cccccggcta ccggggagtg 13200
acgtatcgcc cgtcaggaac ccgccgccga acccgtcgcc gccgccgctc ccgtcgcgct 13260
ctggcccccg tgtcggtgcg ccgcgtaaca cgccggggaa agacagtcac cattcccaac 13320
ccgcgctacc accctagcat cctttaatga ctctgccgtt ttgcagatgg ctctgacttg 13380
ccgcgtgcgc cttcccgttc cgcactatcg aggaagatct cgtcgtagga gaggcatggc 13440
gggcagtggt cgccggcggg ctttgcgcag gcgcatgaaa ggcggaattt tacccgcttt 13500
gatacccata atcgccgccg ccatcggtgc catacccggc gtcgcttcag tggccttgca 13560
agcagctcgt aataaataaa cgaaggcttt tgcacttatg tcctggtcct gactatttta 13620
tgcagaaaga gcatggaaga catcaatttt acgtcgctgg ctccgcggca cggctcgcgg 13680
ccgctcatgg gcacctggaa cgacatcggc accagtcagt taattaattc gaacccataa 13740
tacccataat agctgtttgc catcgacgcg aggctggatg gccttcccca ttatgattct 13800
tctcgcttcc ggcggcatcg ggatgcccgc gttgcaggcc atgctgtcca ggcaggtaga 13860
tgacgaccat cagggacagc ttcaaggcca gcaaaaggcc aggaaccgta aaaaggccgc 13920
gttgctggcg tttttccata ggctccgccc ccctgacgag catcacaaaa atcgacgctc 13980
aagtcagagg tggcgaaacc cgacaggact ataaagatac caggcgtttc cccctggaag 14040
ctccctcgtg cgctctcctg ttccgaccct gccgcttacc ggatacctgt ccgcctttct 14100
cccttcggga agcgtggcgc tttctcatag ctcacgctgt aggtatctca gttcggtgta 14160
ggtcgttcgc tccaagctgg gctgtgtgca cgaacccccc gttcagcccg accgctgcgc 14220
cttatccggt aactatcgtc ttgagtccaa cccggtaaga cacgacttat cgccactggc 14280
agcagccact ggtaacagga ttagcagagc gaggtatgta ggcggtgcta cagagttctt 14340
gaagtggtgg cctaactacg gctacactag aaggacagta tttggtatct gcgctctgct 14400
gaagccagtt accttcggaa aaagagttgg tagctcttga tccggcaaac aaaccaccgc 14460
tggtagcggt ggtttttttg tttgcaagca gcagattacg cgcagaaaaa aaggatctca 14520
agaagatcct ttgatctttt ctacggggtc tgacgctcag tggaacgaaa actcacgtta 14580
agggattttg gtcatgagat tatcaaaaag gatcttcacc tagatccttt taaattaaaa 14640
atgaagtttt aaatcaatct aaagtatata tgagtaaact tggtctgaca gttaccaatg 14700
cttaatcagt gaggcaccta tctcagcgat ctgtctattt cgttcatcca tagttgcctg 14760
actccccgtc gtgtagataa ctacgatacg ggagggctta ccatctggcc ccagtgctgc 14820
aatgataccg cgagacccac gctcaccggc tccagattta tcagcaataa accagccagc 14880
cggaagggcc gagcgcagaa gtggtcctgc aactttatcc gcctccatcc agtctattaa 14940
ttgttgccgg gaagctagag taagtagttc gccagttaat agtttgcgca acgttgttgc 15000
cattgctgca ggcatcgtgg tgtcacgctc gtcgtttggt atggcttcat tcagctccgg 15060
ttcccaacga tcaaggcgag ttacatgatc ccccatgttg tgcaaaaaag cggttagctc 15120
cttcggtcct ccgatcgttg tcagaagtaa gttggccgca gtgttatcac tcatggttat 15180
ggcagcactg cataattctc ttactgtcat gccatccgta agatgctttt ctgtgactgg 15240
tgagtactca accaagtcat tctgagaata gtgtatgcgg cgaccgagtt gctcttgccc 15300
ggcgtcaaca cgggataata ccgcgccaca tagcagaact ttaaaagtgc tcatcattgg 15360
aaaacgttct tcggggcgaa aactctcaag gatcttaccg ctgttgagat ccagttcgat 15420
gtaacccact cgtgcaccca actgatcttc agcatctttt actttcacca gcgtttctgg 15480
gtgagcaaaa acaggaaggc aaaatgccgc aaaaaaggga ataagggcga cacggaaatg 15540
ttgaatactc atactcttcc tttttcaata ttattgaagc atttatcagg gttattgtct 15600
catgagcgga tacatatttg aatgtattta gaaaaataaa caaatagggg ttccgcgcac 15660
atttccccga aaagtgccac ctgacgtcta agaaaccatt attatcatga cattaaccta 15720
taaaaatagg cgtatcacga ggccctttcg tcttcaagaa ttggtcgatg gcaaacagct 15780
attatgggta ttatgggttc gaattaat 15808

<210> SEQ ID NO 36
<211> LENGTH: 23168
<212> TYPE: DNA
<213> ORGANISM: Artificial Sequence
<220> FEATURE:
<223> OTHER INFORMATION: Synthetic oligonucleotide pBr/sAd4287.PsiI-rITR

<400> SEQUENCE: 36
attaacccag gacctggaaa tagtgccttt aactaaagac agcaaagaca gaagctacaa 60
tattataaac aacacgacgg acaccctgta tcggagctgg tttctggctt acaactacgg 120
agaccccgag aaaggagtga gatcatggac catactcacc accacggacg tgacctgtgg 180

```
ctcgcagcaa gtgtactggt ccctgccgga tatgatgcaa gacccggtca ccttccgccc    240
ctccacccaa gtcagcaact tcccggtggt gggcaccgag ctgctgcccg tccatgccaa    300
gagcttctac aacgagcagg ccgtctactc gcaacttatt cgccagtcca ccgcgcttac    360
ccacgtgttc aatcgctttc ccgagaacca gattctggtg cgccctcccg ctcctaccat    420
taccaccgtc agtgaaaacg ttcccgccct cacagatcac ggaaccctgc cgctgcgcag    480
cagtatcagt ggagttcagc gcgtgaccat caccgacgcc agacgtcgaa cctgccccta    540
cgtttacaaa gcgcttggcg tggtggctcc taaagttctt tctagtcgca ccttctaaaa    600
acatgtccat cctcatctct cccgataaca acaccggctg ggactgggc tccggcaaga     660
tgtacggcgg agccaaaagg cgctccagtc agcacccagt tcgagttcgg ggccacttcc    720
gcgctccttg gggagcttac aagcgaggac tctcgggtcg aacggctgta gacgatacca    780
tagatgccgt gattgccgac gcccgccggt acaaccccgg accggtcgct agcgccgcct    840
ccaccgtgga ttccgtgatc gacagcgtgg tagccggcgc tcgggcctat gctcgccgca    900
agaggcggct gcatcggaga cgtcgcccca ccgccgccat gctggcagcc agagccgtgc    960
tgagacgggc ccggagggta ggcaggaggg ctatgcgccg cgctgccgcc aacgccgccg   1020
ccgggagggc ccgccgacag gctgcccgcc aggctgctgc cgccatcgct agcatggcca   1080
gacccaggag agggaacgtg tactgggtgc gcgattctgt gacgggagtc cgagtgccgg   1140
tgcgcagccg acctccccga agttagaaga tccaagctgc gaagacggcg gtactgagtc   1200
tccctgttgt tatcagccca acatgagcaa gcgcaagttt aaagaagaac tgctgcagac   1260
gctggtgcct gagatctatg gccctccgga cgtgaagcct gacattaagc cccgcgatat   1320
caagcgtgtt aaaaagcggg aaaagaaaga ggaactcgcg gtggtagacg atggcggagt   1380
ggaatttatt aggagtttcg ccccgcggcg caggggttcaa tggaaagggc gacgggtaca  1440
acgcgttttg aggccgggca ccgcggtagt ttttaccccg ggagagcggt cggccgttag   1500
gggttttaaa aggcagtacg acgaggtgta cggcgacgag gacatattgg aacaggcggc   1560
tcaacagatc ggagaatttg cctatggaaa gcgctcgcgt cgcgaagacc tggccatcgc   1620
cttagacagc ggcaacccca cgcccagcct caaacccgtg acgctgcagc aggtgcttcc   1680
cgtgagcgcc agcacggaca gcaagagggg aataaaaaga gaaatggaag atctgcagcc   1740
taccatccag ctcatggttc ctaaacggca gaggctggaa gaggtcctgg agaagatgaa   1800
agtggacccc agcatagagc cggacgttaa agtcaggccg atcaaagaag tggcccctgg   1860
actcggggtg cagacggtgg atatccagat ccccgtcacg tcagcttcga ccgccgtgga   1920
agccatggaa acgcaaaccg aaaccccccgc cgtggttggt accaaagaag tggcgttgca  1980
aaccgacccc tggtacgaat ttgccgcccc ccggcgtcag aggcgacccg ctcgttacgg   2040
ccccgccaac gccatcatgc cagaatatgc gctgcatccg tctatcctgc ccacccccgg   2100
ctaccgggga gtgacgtatc gcccgtcagg aacccgccgc cgaacccgtc gccgccgccg   2160
ctcccgtcgc gctctggccc ccgtgtcggt gcgccgcgta acacgccggg gaaagacagt   2220
caccattccc aacccgcgct accaccctag catcctttaa tgactctgcc gttttgcaga   2280
tggctctgac ttgccgcgtg cgccttcccg ttccgcacta tcgaggaaga tctcgtcgta   2340
ggagaggcat ggcgggcagt ggtcgccggc gggctttgcg caggcgcatg aaaggcggaa   2400
ttttacccgc tttgataccc ataatcgccg ccgccatcgg tgccataccc ggcgtcgctt   2460
cagtggcctt gcaagcagct cgtaataaat aaacgaaggc ttttgcactt atgtcctggt   2520
```

```
cctgactatt ttatgcagaa agagcatgga agacatcaat tttacgtcgc tggctccgcg   2580
gcacggctcg cggccgctca tgggcacctg gaacgacatc ggcaccagtc agctcaacgg   2640
gggcgctttc aattggggga gcctttggag cggcattaaa aactttggct ccacgattaa   2700
atcctacggc agcaaagcct ggaacagtag tgctggtcag atgctccgag ataaactgaa   2760
ggacaccaac ttccaagaaa aagtggtcaa tggggtggtg accggcatcc acggtgcggt   2820
agatctcgcc aaccaagcgg tgcagaaaga gattgacagg cgtttggaaa actcgcgggt   2880
gccgccgcag aggggggatg aggtggaggt cgaggaagta gaagtagagg aaaagctgcc   2940
cccgctggag aaagttcccg gtgcacctcc gaggccgcag aagcggccca ggccagaact   3000
agaagaaact ctggtgacgg agagcaagga gcctccctcg tacgagcaag ccttgaaaga   3060
gggcgcctct ccaccctcct acccgatgac taagccgatc gcacccatgg ctcgaccggt   3120
gtacggcaag gattacaagc ccgtcacgct agagctgccc ccaccgcccc cttcgcgtcc   3180
gacggtgcct ccgctgcctg ccccgtcggc gggtcccgag tctgcaccat ccgctgtgcc   3240
tctgccagcc gcccgtcccg tggccgtggc cactgccagg aaccccagag gccagagagg   3300
agccaactgg caaagcacgc tgaacagcat cgtgggcctg ggggtgaaaa gcctgaaacg   3360
ccgccgttgc tattattaaa aagtgtagct aaaaaatttc ccgttgtata cgcctcctat   3420
gttaccgcca gagacgcgtg actgtcgccg cgagcgccgc ttccaagatg gccaccccat   3480
cgatgatgcc gcagtggtct tacatgcaca tcgccggcca ggacgcctcg gagtacctga   3540
gtcccggcct cgtgcagttt gcccgcgcca ccgacaccta cttcagcttg ggaaacaagt   3600
ttagaaaccc caccgtggcc cccacccacg atgtgaccac ggaccgctcg cagaggctga   3660
ccctgcgctt tgtgcccgta gaccgggagg acaccgcgta ctcttacaaa gtgcgctaca   3720
cgctggccgt aggggacaac cgagtgctgg acatggccag cacctacttt gacatccggg   3780
gggtgctgga tcggggtccc agcttcaagc cctactccgg caccgcttac aactccctgg   3840
ctcccaaggg cgcccccaat cctgcagaat gggccgatac caacgacagc aacaaactga   3900
aagtgagggg tcaggcgcct tttgtcagta cttacggttc tgctacggcg cttacaaaag   3960
atgggataca ggtgggagtg gatacttccg aagcatctca ggctgtttat gccgacagaa   4020
gttaccagcc agaaccccaa attggagaga cagagtggaa cagcgaagtg ggtaatgacg   4080
acagagtggc gggaagggtg ctaaagaaaa caactcccat gttcccttgt tacggttcat   4140
atgccaagcc caccaacgaa aaaggcggac aagcaataca gcccaccgcc ggcaacggcg   4200
ataatcaggc tgtagagtta caattctttg ccactactag cactcccact gcgccaaagg   4260
cagtattgta cgcggaggac gtggccattg aagctccaga tactcactta gtgtttaagc   4320
caacagtagt cgcgggaact acaagttcgg aagctctgct aacccaacaa gccgcaccta   4380
accgcccaaa ctacattgcc tttagagata actttattgg tctcatgtac tacaattcaa   4440
ccgggaatat gggagtactg gccggacaag catctcagct caatgcagtg gttgatcttc   4500
aggacagaaa caccgaactg tcatatcagc taatgctgga tgctctggga gatcgcagtc   4560
ggtacttttc tatgtggaat caagctgtag atagctatga tccagatgta agaattgtag   4620
aaaaccacgg tgtggaagac gaactgccta attattgctt cccactaggc gggatggtag   4680
taacggacac ttacaaagcc ataaaggtaa atggaagcgg atggacggct aatactgacg   4740
ttttcagcga gagagtagaa ataggctcag gtaacctgtt tgccatggaa attaacttgc   4800
aagctaatct gtggcgcagt ttcttgtatt ccaacatagg actgtacctc ccggactctt   4860
taaaattaac ccctgacaac atcacgctcc ctgagaacaa aaatacctac cagtatatga   4920
```

-continued acggtcgcgt aacaccaccc gggctcgtgg acacctacgt taacgtgggt gcgcgctggt 4980
cccccgatgt tatggacagc attaaccctt ttaaccacca ccgcaacgcc gggctccgct 5040
accgttccat gctcctggga aacggacgct acgtaccctt ccacattcag gtgccccaga 5100
aattctttgc aattaaaaac ctgctgctgc tccccggttc ctatacctac gagtggaatt 5160
tccgcaagga cgtgaacatg attttgcaaa gctcgctggg taacgacctg cgagttgacg 5220
gggccagcat acgcttcgac agcatcaacc tgtatgctaa ctttttcccc atggcccaca 5280
acacggcctc caccctggaa gccatgctgc gcaacgacac caatgaccag tccttcaacg 5340
actacctgtg cgcggccaac atgctgtatc ccatccccgc caacgccacc agcgtgccca 5400
tctccatccc gtctcgcaac tgggccgcct ttaggggttg gagtttcacc cgcctcaaaa 5460
ccaaggaaac cccctcgctg ggctctggct tcgaccccta cttcgtctac tcaggctcca 5520
ttccctacct ggacggcact ttctatctta accacacttt caaaaaggtg tctatcatgt 5580
tcgattcctc ggtcagctgg cccggcaacg accgcctgct gacgcccaac gagttcgaaa 5640
tcaagcgttc ggtggacggt gaagggtaca acgtggccca gagcaacatg accaaggact 5700
ggttcctggt tcaaatgctc agccattaca acatcggtta ccagggcttc tatgtgcccg 5760
agaactacaa ggaccgcatg tactccttct ttaggaactt ccaacccatg agtcgccaag 5820
tcgtggactc agtggcttac agggactact accaggacgt taagctcccc taccagcaca 5880
acaactcagg gttcgtgggc tacatgggtc ccaccatgcg agaggggcag gcctacccgg 5940
ccaactatcc ttatccccta atcggagaga ctgctgtacc cagcctgacg cagaaaaagt 6000
tcctctgcga ccgggtgatg tggaggatac ccttctctag caacttcatg tctatgggct 6060
ccctcaccga cctggggcag aacatgctgt acgccaactc cgctcacgcc ttggacatga 6120
cctttgaggt ggatcccatg gatgagccca cgcttctcta tgttctgttt gaagtcttcg 6180
acgtggtgcg catccaccag ccgcaccgcg gcgtcatcga ggccgtctac ctgcgcacac 6240
ctttctctgc cggtaacgcc accacctaaa gaagccgatg ggctccagcg aacaggagct 6300
gcaggccatt gttcgcgacc tgggctgcgg gccctacttt ttgggcacct tcgacaagcg 6360
gttccccggc ttcatgtccc ctcacaagcc ggcctgtgcc atcgttaaca cggccggacg 6420
ggaaaccggg ggggtccact ggctcgcctt cgcctggaac ccgcgtaacc gcacctgcta 6480
cctgttcgac ccttttggtt tctccgacga aaggctgaag cagatctacc agttcgagta 6540
cgaggggctc ctccagcgca gcgctctggc ctccacgccc gaccactgcg tcaccctgga 6600
aaagtccacc cagacggtcc aggggcccct ctcggccgcc tgcgggctct tctgttgcat 6660
gtttttgcac gccttcgtgc actggcctca cacccccatg gatcacaacc ccaccatgga 6720
tctgctcacc ggagtgccca acagcatgct tcacagcccc caggtcgccc ccaccctgcg 6780
ccgtaaccag gaacacctgt atcgctttct ggggaaacac tctgcctatt tccgccgcca 6840
tcggcagcgc atcgaacagg ccacggcctt cgaaagcatg agccaaagag tgtaatcaat 6900
aaaaaccatt tttatttgac atgatacgcg cttctggcgt tttattaaa aatcgaaggg 6960
ttcgagggag gggtcctcgt gcccgctggg gagggacacg ttgcgatact ggaatcgggc 7020
gctccaacga aactcgggga tcaccagtcg cggcaggggc acgtcttcca ggttctgctt 7080
ccaaaactgt cgcaccagct gcagggctcc catcacgtcg ggcgccgata tcttgaagtc 7140
gcagttaggg ccggagctcc cgcggctgtt ccggaacacg ggttggcac actggaacac 7200
catcacgctg ggttgtgaa tactagccag ggccgtcgga tcggtcacct ccgacgcatc 7260

-continued cagatcctcg gcgttgctca gggcgaacgg ggtcagcttg cacatctgcc gcccgatctg 7320
gggcaccagg tcgggtttgt tgaggcaatc gcagcgcaga gggatcagga tgcgtcgctg 7380
cccgcgttgc atgatagggt aactcgccgc caggaactcc tccatctgac ggaaggccat 7440
ctgggcctta acgccctcgg tgaaaaacag cccacaggac ttgctagaaa atacgttatt 7500
gccgcagtta atgtcttccg cgcagcagcg tgcatcttcg ttcttcagct gaaccacgtt 7560
acgcccccag cggttctgga ccaccttggc tttcgtagga tgctccttca gcgcccgctg 7620
cccgttctcg ctggtcacat ccatttccac cacgtgctcc ttgcagacca tctccactcc 7680
gtggaagcaa aacaggacgc cctcctgccg ggtattgcga tgctcccaaa cggcacaccc 7740
ggtgggctcc cagctcttgt gttttacccc cgcgtaggct tccatgtaag ccatgaggaa 7800
tctgcccatc agctcggtga aggtcttctg attggtgaag gttagcggca ggccgcggtg 7860
ctcctcgttc aaccaagttt gacagatctt gcggtacacc gttccctggt cgggcagaaa 7920
cttaaaagcc gctctgctgt cgttgtccac gtggaacttc tccattaaca tcatcatggt 7980
ttccataccc ttctcccacg ctgacaccag cggtttgctg tcggggttct tcaccaacac 8040
ggcggtagag ggccctcgc cggccccgac gtccttcatg gtcattcttt gaaactccac 8100
ggagccgtcc gcgcgacgta ctctgcgcac cggagggtag ctgaagccca cctccaccac 8160
ggtgccttcg ccctcgctgt cggaaacgat ctccggggat ggcggcggtg cgggtgtcgc 8220
cttgcgagcc ttcttcttgg gagggagctg aggcgcctcc tgctcgcgct cggggctcat 8280
ctcccgcaag taggggtta tggagctgcc tgcttggttc tgacggttgg ccattgtatc 8340
ctaggcagaa agacatggag cttatgcgcg aggaaacttt aaccgccccg tcccccgtca 8400
gcgacgaaga tgtcatcgtc gaacaggacc cgggctacgt tacgccgccc gaggatctgg 8460
aggggcctga ccggcgcgac gctagtgagc ggcaggaaaa tgagaaagag gaggcctgct 8520
acctcctgga aggcgacgtt ttgctaaagc atttcgccag gcagagcacc atagttaagg 8580
aggccttgca agaccgctcc gaggtgccct tggacgtcgc cgcgctctcc caggcctacg 8640
aggcgaacct tttctcgcct cgagtgcctc cgaagagaca gcccaacggc acctgcgagc 8700
ccaacccgcg actcaacttc taccccgtgt tcgccgtacc agaggcgctg gccacctatc 8760
acattttttt caaaaaccaa cgcatccccc tatcgtgccg ggccaaccgc accgcggccg 8820
ataggaatct caggcttaaa aacggagcca acatacctga tatcacgtcg ctggaggaag 8880
tgcccaagat tttcgagggt ctgggtcgag atgagaagcg ggcggcgaac gctctgcaga 8940
aagaacagaa agagagtcag aacgtgctgg tggagctgga gggggacaac gcgcgtctgg 9000
ccgtcctcaa acgctgcata gaagtctccc acttcgccta ccccgccctc aacttgccac 9060
ccaaagttat gaaatcggtc atggatcagc tgctcatcaa gagagctgag cccctggatc 9120
ccgaccaccc cgaggcggaa aactcagagg acggaaagcc cgtcgtcagc gacgaggagc 9180
tcgagcggtg gctggaaacc agggaccccc aacagttgca agagaggcgc aagatgatga 9240
tggcggccgt gctggtcacc gtggagctgg aatgcctgca acggtttttc agcgacgtgg 9300
agacgctacg caaaatcggg gaatccctgc actacacctt ccgccagggc tacgtccgcc 9360
aggcctgcaa gatctccaac gtggagctca gcaacctggt ctcctacatg ggcatcctcc 9420
acgagaaccg gctggggcag agcgtgctgc actgcacctt gcaaggcgag gcgcggcggg 9480
actacgtgcg agactgcatc tacctcttcc tcaccctcac ctggcagacc gccatgggcg 9540
tctggcagca gtgcttggaa gagagaaacc tcaaagagct agacaaactc ctctgccgcc 9600
agcggcgcgc cctgtggtcc ggtttcagcg agcgcacggt cgccagcgct ctggcggaca 9660
tcatcttccc ggagcgcctg atgaaaacct tgcaaaacgg cctgccggat ttcatcagtc 9720
aaagcatttt gcaaaacttc cgctcttttg tcctggaacg ctccgggatc ttgcccgcca 9780
tgagctgcgc gctaccttct gactttgtcc ccctctccta ccgcgagtgc cctccccca c 9840
tgtggagcca ctgctacctc ttccaactgg ccaactttct ggcctaccac tccgacctca 9900
tggaagacgt aagcggagag ggtttactgg agtgccactg ccgctgcaac ctgtgcaccc 9960
cccacagatc gctggcctgc aacaccgagc tactcagcga aacccaggtc ataggtacct 10020
tcgagatcca ggggccccag cagcaagagg gtgcttccgg cttgaagctc actccggcgc 10080
tgtggacctc ggcttactta cgcaaatttg tagccgagga ctaccacgcc cacaaaattc 10140
agttttacga agaccaatct caaccaccga aagccccccct cacggcctgc gtcatcaccc 10200
agagcaagat cctggcccaa ttgcaatcca tcaaccaagc gcgccgcgat ttcctttga 10260
aaaagggtcg gggggtgtat ctggaccccc agaccggcga ggaactcaac ccgtccacac 10320
tctccgtcga agcagccccc ccgagacatg ccgcccaagg gaaccgccaa gcagctgatc 10380
gctcggcaga gagcgaagaa gcaagagctg ctccagcagc aggtggagga cgaggaagag 10440
atgtgggaca gccaggcaga ggaggtgtca gaggacgagg aggagatgga aagctgggac 10500
agcctagacg aggaggagga cgagctttca gaggaagagg cgaccgaaga aaaaccacct 10560
gcatccagcg cgccttctct gagccgacag ccgaagcccc ggcccccgac gcccccggcc 10620
ggctcactca aagccagccg taggtgggac gccaccgaat ctccagcggc agcggcaacg 10680
gcagcgggta aggccaaacg cgagcggcgg gggtattgct cctggcgggc ccacaaaagc 10740
agtattgtga actgcttgca acactgcggg ggaaacatct cctttgcccg acgctacctc 10800
ctcttccatc acggtgtggc cttccctcgc aacgttctct attattaccg tcatctctac 10860
agcccctacg aaacgctcgg agaaaaaagc taaggcctcc tccgccgcga ggaaaaactc 10920
cgccgccgct gccgccgcca aggatccacc ggccaccgag gagctgagaa agcgcatctt 10980
tcccactctg tatgctatct ttcagcaaag ccgcgggcag caccctcagc gcgaactgaa 11040
aataaaaaac cgctccttcc gctcgctcac ccgcagctgt ctgtaccaca agagagaaga 11100
ccagctgcag cgcaccctgg acgacgccga agcactgttc agcaaatact gctcagcgtc 11160
tcttaaagac taaaagaccc gcgctttttc cccctcggcc gccaaaaccc acgtcatcgc 11220
cagcatgagc aaggagattc ccacccccta catgtggagc tatcagcccc agatgggcct 11280
ggccgcgggg gccgcccagg actactccag caagatgaac tggctcagcg ccggccccca 11340
catgatctca cgagttaacg gcatccgagc ccaccgaaac cagattctct tagaacaggc 11400
ggcaatcacc gccacacccc ggcgccaact caacccgcct agttggcccg ccgcccaggt 11460
gtatcaggaa aatccccgcc cgaccacagt cctcctgcca cgcgacgcgg aggccgaagt 11520
cctcatgact aactctgggg tacaattagc gggcgggtcc aggtacgcca ggtacagagg 11580
tcgggccgct ccttactctc ccgggagtat aaagagggtg atcattcgag gccgaggtat 11640
ccagctcaac gacgagacgg tgagctcctc aaccggtctc agacctgacg gagtcttcca 11700
gctcggagga gcgggccgct cttccttcac cactcgccag gcctacctga ccctgcagag 11760
ctcttcctcg cagccgcgct ccgggggaat cggcactctc cagttcgtgg aagagttcgt 11820
tccctccgtc tacttcaacc ccttctccgg ctcgcctgga cgctacccgg acgccttcat 11880
tcccaacttt gacgcagtga gtgaatccgt ggacggctac gactgatgac agatggtgcg 11940
gccgtgagag ctcggctgcg acatctgcat cactgccgtc agcctcgctg ctacgctcgg 12000

-continued

```
gaggcgatcg tcttcagcta ctttgagctg ccggacgagc accctcaggg tccggctcac  12060
gggttgaaac tcgagatcga gaacgcgctc gagtctcgcc tcatcgacac cttcaccgcc  12120
cgacctctcc tggtagaaat cgaacgcggg atcactacca tcaccctgtt ctgcatctgc  12180
cccacgcccg gattacatga agatctgtgc tgtcatcttt gcgctcagtt taataaaaac  12240
tgaacttttt gccgcacctt caacgccacg cgtcgtttct ccaaaagttg tcgacagctc  12300
ttcagtcaga ggtatacgag aaactgttta tttttacaac tctactactt ttctcaccct  12360
taactgctcc tgcactaacg aactaattca gtggttcgcg aacggctcac tctgccaagt  12420
ctttttttaat tctgctgttc ttcctgagtt tggctccttt gcgtgtggaa attctacccc  12480
ctccacctta accattgcgg cgccctttc ggaaatccag tatttttgta ttggggcggg  12540
aggtaaaccg ggttgtattc accgcttgtt tgtaaagcca tttgttgctt caattcccat  12600
taacacttca ctttcctcta atacatactt acctacctta cattctactc acccctcctg  12660
gcaacctctt attggcctca cggcttttat ttccgttgtt ttactaaact ttataattct  12720
taacaaactt tcttaaacat gcttgccatt ttgcttctgc tcgttacttt aacgtccgca  12780
gattaccaca atgtaattgt acgagaaaac agtttacaaa acccatcaca ggtatatgtt  12840
aaagcaggct ctaacttaac tttacaatcc ttctattcgc cttaccctga ggacatgcca  12900
cgtgttactt ggtacttaga agtttttgat tcgctatttg aaaggcatac gattcctcca  12960
tttttacag gcgttatact ttgtgacatt tctggtgaca tacagcatgt gtggaaccat  13020
tggcctttac aatttaattg cataaataaa agcttacata ttattaatct caaaccaagt  13080
gatgaaggcc tttacaatgt gaaggtttta aaggacagca ttcagcataa tacatacttt  13140
cgagtgcatg tagtaagttt tccaagacct gaatgtaaca tcaccactac atatctttca  13200
gatgactact gccttattaa cattgattgc tctcaattac catacctgc taaggtctat  13260
tataatggca atgaaagtaa gctgcattac tacttatctg aacgcggtgg ccagccaaac  13320
cttccaaatt actttactgt tgggtatcga tatagagatc tccgacaaaa ttatacagtt  13380
gaatatccat ttaatgaact atgtacagag ataattgctc ttgaaacagg gtctgatttt  13440
atgccaattt ttatagttac cctagtggtg agcattatag ttattgtgat gggcatcaca  13500
tatcttattt atcactgtag gactttaaag accaaaacca aaaccaaaac caagcctcct  13560
gaaatccgtt tgctttaatt ttttccagaa tggtagctgc tttcttcatt tttctctgta  13620
taccaatcat ctgcgcctcc acaacttttg ccgctgtttc ccacctggaa ccagactgtc  13680
taccaccttt tgttgtatac ctgatactga cttttgtggt ctgtacagcc attaccagca  13740
tagcctgctt ttttgtaaca attttccaag ccgccgatta tctctacgta cggtttgctt  13800
attttagaca tcaccccgag tatcggaatc aaaacgtagc ttctttactt tgtctagcat  13860
gattcgccta tttatactgc acactctgtt taccctcgca aaatgtcatt gcccttttac  13920
caaaccttgg tccttttaca cctgttacga tgtactgccc gaaaccccta ttgcctggct  13980
ttacgtagcc acagcggttt tagtttttgt agcaacctgc attggcgtta aactgtactt  14040
ctacttaaaa attggatggc ttcatccccc agaagattta ccccgatatc ctcttgttaa  14100
taactttcaa cagcctctgc cgcctcctga tcctcttccg cgagctccct ccgttgttag  14160
ctactttcaa ctcaccggtg gagatgactg actctcagga cattgatatt agtgtggaaa  14220
gaatagccgc tcagcgtcag cgagaaactc gggtgctgga gtactttgaa ctacagcagc  14280
ttaaagagtc ccactggtgt gagaaaggag tgctgtgtca tgttaagcag gcagcccttt  14340
cttacgatgt cagccttcag ggacatgaac tgtcttacac tttgccttcg caaaaacaaa  14400
```

ccttctgcac catgatgggc tctacctcca tcacaatcac ccaacaaacc ggacctgttg 14460
agggagctat cctgtgtcac tgtcacgcgc ctgattgtat gcccaaacta attagaactc 14520
tctgtgcctt aggtgatata tttaaaatgt aagtcagtat caataaactt accttaaatt 14580
tgacagcagt tttttggtaa catcattcag cagcaccact ttaccctctt cccaactctc 14640
gtatgggacg tgatggtggg cggcaaactt cctccaaacc ctaaaacaaa tattaatatc 14700
cacttccttg tccttaccca caattttcat cttttcatag atgaaaagaa ccagagttga 14760
tgaagacttc aaccccgtct acccttatga ctccacatcc actcctgcgg tcccctttat 14820
atccccccg tttgtaaaca gcgatggtct tcaggaaaac cctcctggag tcttaagttt 14880
acgaatagct aaacccttgt attttgacat ggaaaggaaa ctagcgcttt cacttggaag 14940
aggattggca attacctcca ccggacagct agaaagcaca cagagcgtgc aaaccacccc 15000
tccattagtt gtcaacaaca gcaacacgct tgtcctgcgt tattcctccc cgttaggctt 15060
atcgggtgac aatttaatac taaattgctc cgatcctctc cgcgtagtaa acaacagcct 15120
gacattcagc tacctatctc cacttcgttt tgaaggtggc agtcttacat tcaattacac 15180
atctcccctt aaactgttga acagcagcct tgcgatcgga ataaattcca acaaaggtct 15240
cggcaatgac agcgatgaac tttctgtcaa actaacatca gatctaaagt ttaacaacga 15300
tggaaaaata gcttttggta tacaaagcct gtgtaccacc cccacagccg cctctaactg 15360
taccgttttt accaacggtg attctttact ctgtttatgt ttaaccaaat gtggagctca 15420
cgtgttagga agtgtgagtt taaccggaat gcaaggaacc ataacagcca tgacacagaa 15480
ctacattagt attcaatttc tatttgacaa caatggtgcg ttgacttcat caccgctcct 15540
caacaacaac acttggggta tacggcaaaa cgacacttcg tccgctaacc ccgcctacaa 15600
tgctcttgca tttatgccta acagcactgt atatgtaaga ggtcaaagtg gtgagcccag 15660
aaataactat tacacccaaa catacettag gggaaacgtt aaaaagccaa ttatccttac 15720
cgttacctac aactcggctg cttcaggtta ttcactaact tttaaatggg atgctgtagt 15780
aacagaaaaa tttgccactc caacatcttc tttttgctat attacagaac aataaattcc 15840
tattacccca ccaattcgtt tttttcagat gaaacgggcc agagttgatg aagacttcaa 15900
cccagtgtac ccttatgacc ccccatacgc tcccgttatg ccctttcatta ctccaccttt 15960
tacctcctcg gatgggttgc aggaaaaacc acttggagtg ttaagtttaa actacaagga 16020
tcccattact acacaaaatg gatctctcac gttgaaaata ggaaacggcc tcactctaga 16080
caaccaggga caattaacat caactgctgg ggaagtagag cctccgctca ctaatgctaa 16140
caacaaactt gcactagcct atagcgaacc attagcagta aaaagcaacc gcttaacttt 16200
atcacacacc gcccccccttg tcgttgctaa taattcttta gcgttgcaag tttcagaacc 16260
tatttttata aatgacgatg acaagctagc cctgcagaca gccgccccccc ttgtaactaa 16320
cgctggcacc cttcgcttac agagcgccgc cccctttagga ttggttgaaa atactcttag 16380
actgctgttt tctaaaccct tgtatttgca aaatgatttt cttgcattag gcattgaacg 16440
ccccctggct atagcagccg caggtactct agcactacaa ctcactcctc cattaaagac 16500
taacgatgac gggctgacac tatccacagt cgagccatta actgtaaaaa acggaaactt 16560
aggcttgcaa atatctcgcc ctttggttgt tcaaaacagc agcctttcgc ttgctattac 16620
ccccccgctg cgtctattta acagcgaccc cgttcttggt ttgggcttta cttttcccct 16680
agccgtgaca gacaacctac tctccttaaa catgggagac ggtgttaaac taacctataa 16740

```
taaactaaca gccaatttgg gtagggattt acaatttgaa aacggtgcca ttgccgtaac  16800
gcttactgcc gaatcacctt tgcaatacac taacaaactt caactgaata ttggagctgg  16860
ccttcgttac aatggagcca gcagaaaact agatgtaaac attaaccaaa ataagggctt  16920
aacttgggac aacgatgcag ttattcccaa attaggatca ggtttacaat tcgaccctaa  16980
tggtaacatc gctgttatcc ctgaaaccgt aaagccgcaa acgttatgga caactgcaga  17040
tccatcgcct aactgctcag tgtaccagga cttggacgcc aggctgtggc tcgctcttgt  17100
taaaagtggt gacatggttc atggaagcat tgctctaaaa gccctaaaag gaacgttgct  17160
aaatcctaca gcaagctaca tctccattgt gatatatttt tacagcaacg gagtcaggcg  17220
taccaactat cccacgtttg acaacgaagg caccttagct aacagcgcta cctggggata  17280
ccgagagggg caatctgcta acactaatgt aaccaatgcc actgaattta tgcccagctc  17340
aaccaggtac cccgtgaata aaggagacaa tattcagaat caatcttttt catacacctg  17400
tatcaaagga gatttcgcta tgcctgtccc gttccgtgta acatataatc atgccctgga  17460
aggatactcc cttaagttca cctggcgcgt tgtagccaac caagcttttg atattccttg  17520
ctgttccttt tcatacatca cagaataaac cactttttaa aatttttctt tttattttac  17580
acgcacagta aggcttcctc cccccttcca tttgacagca tacaccagcc tctccccctt  17640
catggcagta aactgctgcg agccagtccg gtatttggga gttaaaatcc aaacagtctc  17700
tttggtgatg aaacgtcgat ccgtgatgga cacaaatccc tggggcaggt tttccagcgt  17760
ttcggtaaaa aactgcacac cgccctacaa aacaaacagg ttcaggctct ccatgggtta  17820
tctccccgat caaactcaga cagggtaaag gtgcggtgat gttccactaa accacgcagg  17880
tggcgctgtc tgaacctctc ggtgcgactc ctgtgaggct ggtaagaagt tagattgtcc  17940
agtagcctca cagcatggat gatcagttta cgtgtacgtc tggcgcaaca gcgcatctga  18000
atctcactga gattccggca agaatcgcac accatcacaa tcaggttgtt catgatccca  18060
tagctgaaca cgctccagcc aaagctcatt cgctccaaca gcgccaccgc gtgtccgtcc  18120
aaccttactt taacataaat caggtgtctg ccgcgtacaa acatactacc cgcatacaga  18180
acttcccggg gcaaacccct gttcaccacc tgcctgtacc agggaaacct cacatttatc  18240
agggagccat agatagccat tttaaaccaa ttagctaaca ccgcccccacc agctctacac  18300
tgaagagaac cgggagagtt acaatgacag tgaataatcc atctctcata acccctgatg  18360
gtctgatgga aatccagcac accgccctac aaaacaaaca ggttcaggct ctccatgggt  18420
tatctccccg atcaaactca gacagggtaa aggtgcggtg atgttccact aaaccacgca  18480
ggtggcgctg tctgaacctc tcggtgcgac tcctgtgagg ctggtaagaa gttagattgt  18540
ccagtagcct cacagcatgg atgatcagtt tacgtgtacg tctggcgcaa cagcgcatct  18600
gaatctcact gagattccgg caagaatcgc acaccatcac aatcaggttg ttcatgatcc  18660
catagctgaa cacgctccag ccaaagctca ttcgctccaa cagcgccacc gcgtgtccgt  18720
ccaaccttac tttaacataa atcaggtgtc tgccgcgtac aaacatacta cccgcataca  18780
gaacttcccg gggcaaaccc ctgttcacca cctgcctgta ccagggaaac ctcacattta  18840
tcagggagcc atagatagcc attttaaacc aattagctaa caccgcccca ccagctctac  18900
actgaagaga accgggagag ttacaatgac agtgaataat ccatctctca taacccctga  18960
tggtctgatg gaaatccaga tctaacgtgg cacagcagat acacactctc atatacattt  19020
tcatcacatg gttttcccag gccgttaaaa tacaatccca atacacgggc cactcctgca  19080
gtacaataaa gctaatacaa gatggtatac tcctcacctc actaacattg tgcatgttca  19140
```

```
tattttcaca ttctaagtac cgagagttct cctctacaac agcactgctg cggtcctcac  19200
aaggtggtag ctggtgacga tcgtaaggag ccagtctgca acgataccgt ctgtcgcgct  19260
gcatcgtaga ccagagaccg acgcacctcc tggtacttgt ggtagcagaa ccacgtccgc  19320
tgccaacagg tatccacgta acgccggtcc ctgcgtcgcg cgcgctctgt tctcaatgca  19380
aaatgcagcc actcttgtaa tccacacaga tccctctcgg cctccgggag gatacacact  19440
tcaaacctac aaatgtctcg gtacagttcc aaacacgaag tgagggcgag ttccaaccaa  19500
gacaggcagg ctggtctatc ccgacacact ggaggtggag gaagacacgg aagaggcatg  19560
ttattccaag cgattcacca acgggtcgaa atgaagatcc cgaagatgac aacggtcgcc  19620
tccggagccc tgatggaatt taacagccaa atcaaacatt atgcgatttt ccaggctatc  19680
gatcgcggcc tccaaaagag cctggacccg cacttccaca aacaccagca aagcaaaagc  19740
gttattatca aactcttcga tcatcaagct gcaagactgt acaatgccca agtaattttc  19800
atttctccac tcgcgaatga tgtcgcggca aatagtctga aggttcatgc cgtgcatatt  19860
aaaaagctcc gaaagggcgc cctctatagc catgcgtaga cacaccatca tgactgcaag  19920
atatcgggct cctgagacac ctgcagcaga tttaacagac ccaggtcagg ttgctctccg  19980
cgatcgcgaa tctccatccg caaggtcatt tgcaaataat taaatagatc tgcgccgact  20040
aaatctgtta actccgcgtt aggaactaaa tcaggtgtgg ctacgcagca caaaagttcc  20100
agggatggcg ccaaactcac tagaaccgct cccgagtagc aaaactgatg aatgggagta  20160
acacagtgta aaatgttcag ccaaaaatca ctaagccgct cctttaaaaa gtccagtact  20220
tctatattca gttcgtgcaa gtactgaagc aactgtgtgg gaatatgcac aacaaaaaaa  20280
atagggcggc tcagatacat gttgacctaa aataaaaaga atcattaaac taaagaagct  20340
tggcgaacgg tgggataaat gacacgttcc agcagcaggc aagcaaccgg ctgtccccgg  20400
gaaccgcggt aaaattcatc cgaatgatta aaaagaacaa cagaaacttc ccaccatgta  20460
ctcggttgga tctcctgagc acagagcaat acccccctca cattcatatc cgccacagaa  20520
aaaaagcgtc ccagataccc agcgggaata tccaacgaca gctgcaaaga cagcaaaaca  20580
atccctctgg gagcaatcac aaaatcctcc ggtgaaaaaa gcacatacat attagaataa  20640
ccctgctgct ggggcaaaaa ggcccgtcgt cccagcaaat gcacataaat atgttcatca  20700
gccattgccc cgtcttaccg cgtaaacagc cacgaaaaat tcgagctaaa atccacccaa  20760
cagcctatag ctatatatac actccgccca atgacgctaa taccgcacca cccaccgcca  20820
aagttcaccc acacccacga aacccgcgaa aatccagcgc cgtcagcact tccgcaattt  20880
cagtctcaca acgtcacttc cgcgcgcctt ttcacattcc cacacccgcc cacaaacccc  20940
gcgtcaccgc ccgtcacccc ggccccgcct cgctcctccc cgctcattat catattggca  21000
cgtttccaga ataaggtata ttattgatga tgttaattaa ttcgaaccca taatacccat  21060
aatagctgtt tgccatcgac caattctccc atattcccgg ttgaattgta gtacatgaga  21120
ccaataaagt tatttgaaga cgaaagggcc tcgtgatacg cctattttta taggttaatg  21180
tcatgataat aatggtttct tagacgtcag gtggcacttt tcggggaaat gtgcgcggaa  21240
cccctatttg tttatttttc taaatacatt caaatatgta tccgctcatg agacaataac  21300
cctgataaat gcttcaataa tattgaaaaa ggaagagtat gagtattcaa catttccgtg  21360
tcgcccttat tccctttttt gcggcatttt gccttcctgt ttttgctcac ccagaaacgc  21420
tggtgaaagt aaaagatgct gaagatcagt tgggtgcacg agtgggttac atcgaactgg  21480
```

atctcaacag cggtaagatc cttgagagtt ttcgccccga agaacgtttt ccaatgatga 21540
gcacttttaa agttctgcta tgtggcgcgg tattatcccg tgttgacgcc gggcaagagc 21600
aactcggtcg ccgcatacac tattctcaga atgacttggt tgagtactca ccagtcacag 21660
aaaagcatct tacggatggc atgacagtaa gagaattatg cagtgctgcc ataaccatga 21720
gtgataacac tgcggccaac ttacttctga caacgatcgg aggaccgaag gagctaaccg 21780
cttttttgca caacatgggg gatcatgtaa ctcgccttga tcgttgggaa ccggagctga 21840
atgaagccat accaaacgac gagcgtgaca ccacgatgcc tgcagcaatg gcaacaacgt 21900
tgcgcaaact attaactggc gaactactta ctctagcttc ccggcaacaa ttaatagact 21960
ggatggaggc ggataaagtt gcaggaccac ttctgcgctc ggcccttccg gctggctggt 22020
ttattgctga taaatctgga gccggtgagc gtgggtctcg cggtatcatt gcagcactgg 22080
ggccagatgg taagccctcc cgtatcgtag ttatctacac gacggggagt caggcaacta 22140
tggatgaacg aaatagacag atcgctgaga taggtgcctc actgattaag cattggtaac 22200
tgtcagacca agtttactca tatatacttt agattgattt aaaacttcat ttttaattta 22260
aaaggatcta ggtgaagatc ctttttgata atctcatgac caaaatccct taacgtgagt 22320
tttcgttcca ctgagcgtca gaccccgtag aaaagatcaa aggatcttct tgagatcctt 22380
tttttctgcg cgtaatctgc tgcttgcaaa caaaaaaacc accgctacca gcggtggttt 22440
gtttgccgga tcaagagcta ccaactcttt ttccgaaggt aactggcttc agcagagcgc 22500
agataccaaa tactgtcctt ctagtgtagc cgtagttagg ccaccacttc aagaactctg 22560
tagcaccgcc tacatacctc gctctgctaa tcctgttacc agtggctgct gccagtggcg 22620
ataagtcgtg tcttaccggg ttggactcaa gacgatagtt accggataag gcgcagcggt 22680
cgggctgaac ggggggttcg tgcacacagc ccagcttgga gcgaacgacc tacaccgaac 22740
tgagatacct acagcgtgag ctatgagaaa gcgccacgct tcccgaaggg agaaaggcgg 22800
acaggtatcc ggtaagcggc agggtcggaa caggagagcg cacgagggag cttccagggg 22860
gaaacgcctg gtatctttat agtcctgtcg ggtttcgcca cctctgactt gagcgtcgat 22920
ttttgtgatg ctcgtcaggg gggcggagcc tatggaaaaa cgccagcaac gcggcctttt 22980
tacggttcct ggccttttgc tggccttgaa gctgtccctg atggtcgtca tctacctgcc 23040
tggacagcat ggcctgcaac gcgggcatcc cgatgccgcc ggaagcgaga agaatcataa 23100
tggggaaggc catccagcct cgcgtcgatg gcaaacagct attatgggta ttatgggttc 23160
gaattaat 23168

<210> SEQ ID NO 37
<211> LENGTH: 21190
<212> TYPE: DNA
<213> ORGANISM: Artificial Sequence
<220> FEATURE:
<223> OTHER INFORMATION: Synthetic oligonucleotide pBr/sAd4287.PsiI-
rITR.dE3

<400> SEQUENCE: 37
attaacccag gacctggaaa tagtgccttt aactaaagac agcaaagaca gaagctacaa 60
tattataaac aacacgacgg acaccctgta tcggagctgg tttctggctt acaactacgg 120
agaccccgag aaaggagtga gatcatggac catactcacc accacggacg tgacctgtgg 180
ctcgcagcaa gtgtactggt ccctgccgga tatgatgcaa gacccggtca ccttccgccc 240
ctccacccaa gtcagcaact tcccggtggt gggcaccgag ctgctgcccg tccatgccaa 300

-continued

```
gagcttctac aacgagcagg ccgtctactc gcaacttatt cgccagtcca ccgcgcttac    360
ccacgtgttc aatcgctttc ccgagaacca gattctggtg cgccctcccg ctcctaccat    420
taccaccgtc agtgaaaacg ttcccgccct cacagatcac ggaaccctgc cgctgcgcag    480
cagtatcagt ggagttcagc gcgtgaccat caccgacgcc agacgtcgaa cctgccccta    540
cgtttacaaa gcgcttggcg tggtggctcc taaagttctt tctagtcgca ccttctaaaa    600
acatgtccat cctcatctct cccgataaca acaccggctg gggactgggc tccggcaaga    660
tgtacggcgg agccaaaagg cgctccagtc agcacccagt tcgagttcgg ggccacttcc    720
gcgctccttg gggagcttac aagcgaggac tctcgggtcg aacggctgta gacgatacca    780
tagatgccgt gattgccgac gcccgccggt acaaccccgg accggtcgct agcgccgcct    840
ccaccgtgga ttccgtgatc gacagcgtgg tagccggcgc tcgggcctat gctcgccgca    900
agaggcggct gcatcggaga cgtcgcccca ccgccgccat gctggcagcc agagccgtgc    960
tgagacgggc ccggagggta ggcaggaggg ctatgcgccg cgctgccgcc aacgccgccg   1020
ccgggagggc ccgccgacag gctgcccgcc aggctgctgc cgccatcgct agcatggcca   1080
gacccaggag agggaacgtg tactgggtgc gcgattctgt gacgggagtc cgagtgccgg   1140
tgcgcagccg acctccccga agttagaaga tccaagctgc gaagacggcg gtactgagtc   1200
tccctgttgt tatcagccca acatgagcaa gcgcaagttt aaagaagaac tgctgcagac   1260
gctggtgcct gagatctatg gccctccgga cgtgaagcct gacattaagc cccgcgatat   1320
caagcgtgtt aaaaagcggg aaaagaaaga ggaactcgcg gtggtagacg atggcggagt   1380
ggaatttatt aggagtttcg ccccgcggcg caggcttcaa tggaaagggc gacgggtaca   1440
acgcgttttg aggccgggca ccgcggtagt ttttaccccg ggagagcggt cggccgttag   1500
gggttttaaa aggcagtacg acgaggtgta cggcgacgag gacatattgg aacaggcggc   1560
tcaacagatc ggagaatttg cctatggaaa gcgctcgcgt cgcgaagacc tggccatcgc   1620
cttagacagc ggcaacccca cgcccagcct caaacccgtg acgctgcagc aggtgcttcc   1680
cgtgagcgcc agcacggaca gcaagagggg aataaaaaga gaaatggaag atctgcagcc   1740
taccatccag ctcatggttc ctaaacggca gaggctggaa gaggtcctgg agaagatgaa   1800
agtggacccc agcatagagc cggacgttaa agtcaggccg atcaaagaag tggcccctgg   1860
actcggggtg cagacggtgg atatccagat ccccgtcacg tcagcttcga ccgccgtgga   1920
agccatggaa acgcaaaccg aaacccccgc cgtggttggt accaaagaag tggcgttgca   1980
aaccgacccc tggtacgaat ttgccgcccc ccggcgtcag aggcgacccg ctcgttacgg   2040
ccccgccaac gccatcatgc cagaatatgc gctgcatccg tctatcctgc ccaccccccgg  2100
ctaccgggga gtgacgtatc gcccgtcagg aacccgccgc cgaacccgtc gccgccgccg   2160
ctcccgtcgc gctctggccc ccgtgtcggt gcgccgcgta acacgccggg gaaagacagt   2220
caccattccc aacccgcgct accaccctag catcctttaa tgactctgcc gttttgcaga   2280
tggctctgac ttgccgcgtg cgccttcccg ttccgcacta tcgaggaaga tctcgtcgta   2340
ggagaggcat ggcgggcagt ggtcgccggc gggctttgcg caggcgcatg aaaggcggaa   2400
ttttacccgc tttgataccc ataatcgccg ccgccatcgg tgccataccc ggcgtcgctt   2460
cagtggcctt gcaagcagct cgtaataaat aaacgaaggc ttttgcactt atgtcctggt   2520
cctgactatt ttatgcagaa agagcatgga agacatcaat tttacgtcgc tggctccgcg   2580
gcacggctcg cggccgctca tgggcacctg gaacgacatc ggcaccagtc agctcaacgg   2640
gggcgctttc aattggggga gcctttggag cggcattaaa aactttggct ccacgattaa   2700
```

atcctacggc agcaaagcct ggaacagtag tgctggtcag atgctccgag ataaactgaa 2760
ggacaccaac ttccaagaaa aagtggtcaa tggggtggtg accggcatcc acggtgcggt 2820
agatctcgcc aaccaagcgg tgcagaaaga gattgacagg cgtttggaaa actcgcgggt 2880
gccgccgcag aggggggatg aggtggaggt cgaggaagta gaagtagagg aaaagctgcc 2940
cccgctggag aaagttcccg gtgcacctcc gaggccgcag aagcggccca ggccagaact 3000
agaagaaact ctggtgacgg agagcaagga gcctccctcg tacgagcaag ccttgaaaga 3060
gggcgcctct ccaccctcct acccgatgac taagccgatc gcacccatgg ctcgaccggt 3120
gtacggcaag gattacaagc ccgtcacgct agagctgccc ccaccgcccc cttcgcgtcc 3180
gacggtgcct ccgctgcctg ccccgtcggc gggtcccgag tctgcaccat ccgctgtgcc 3240
tctgccagcc gcccgtcccg tggccgtggc cactgccagg aaccccagag gccagagagg 3300
agccaactgg caaagcacgc tgaacagcat cgtgggcctg gggggtgaaaa gcctgaaacg 3360
ccgccgttgc tattattaaa aagtgtagct aaaaaatttc ccgttgtata cgcctcctat 3420
gttaccgcca gagacgcgtg actgtcgccg cgagcgccgc ttccaagatg gccaccccat 3480
cgatgatgcc gcagtggtct tacatgcaca tcgccggcca ggacgcctcg gagtacctga 3540
gtcccggcct cgtgcagttt gcccgcgcca ccgacaccta cttcagcttg ggaaacaagt 3600
ttagaaaccc caccgtggcc cccacccacg atgtgaccac ggaccgctcg cagaggctga 3660
ccctgcgctt tgtgcccgta gaccgggagg acaccgcgta ctcttacaaa gtgcgctaca 3720
cgctggccgt aggggacaac cgagtgctgg acatggccag cacctacttt gacatccggg 3780
gggtgctgga tcggggtccc agcttcaagc cctactccgg caccgcttac aactccctgg 3840
ctcccaaggg cgcccccaat cctgcagaat gggccgatac caacgacagc aacaaactga 3900
aagtgagggg tcaggcgcct tttgtcagta cttacggttc tgctacggcg cttacaaaag 3960
atgggataca ggtgggagtg gatacttccg aagcatctca ggctgtttat gccgacagaa 4020
gttaccagcc agaaccccaa attggagaga cagagtggaa cagcgaagtg ggtaatgacg 4080
acagagtggc gggaagggtg ctaaagaaaa caactcccat gttcccttgt tacggttcat 4140
atgccaagcc caccaacgaa aaaggcggac aagcaataca gcccaccgcc ggcaacggcg 4200
ataatcaggc tgtagagtta caattctttg ccactactag cactcccact gcgccaaagg 4260
cagtattgta cgcggaggac gtggccattg aagctccaga tactcactta gtgtttaagc 4320
caacagtagt cgcgggaact acaagttcgg aagctctgct aacccaacaa gccgcaccta 4380
accgcccaaa ctacattgcc tttagagata actttattgg tctcatgtac tacaattcaa 4440
ccgggaatat gggagtactg gccggacaag catctcagct caatgcagtg gttgatcttc 4500
aggacagaaa caccgaactg tcatatcagc taatgctgga tgctctggga gatcgcagtc 4560
ggtacttttc tatgtggaat caagctgtag atagctatga tccagatgta agaattgtag 4620
aaaaccacgg tgtggaagac gaactgccta attattgctt cccactaggc gggatggtag 4680
taacggacac ttacaaagcc ataaaggtaa atggaagcgg atggacggct aatactgacg 4740
ttttcagcga gagagtagaa ataggctcag gtaacctgtt tgccatggaa attaacttgc 4800
aagctaatct gtggcgcagt ttcttgtatt ccaacatagg actgtacctc ccggactctt 4860
taaaattaac ccctgacaac atcacgctcc ctgagaacaa aaatacctac cagtatatga 4920
acggtcgcgt aacaccaccc gggctcgtgg acacctacgt taacgtgggt gcgcgctggt 4980
cccccgatgt tatggacagc attaaccctt ttaaccacca ccgcaacgcc gggctccgct 5040

-continued

```
accgttccat gctcctggga aacggacgct acgtaccctt ccacattcag gtgccccaga   5100
aattctttgc aattaaaaac ctgctgctgc tccccggttc ctatacctac gagtggaatt   5160
tccgcaagga cgtgaacatg attttgcaaa gctcgctggg taacgacctg cgagttgacg   5220
gggccagcat acgcttcgac agcatcaacc tgtatgctaa ctttttcccc atggcccaca   5280
acacggcctc caccctggaa gccatgctgc gcaacgacac caatgaccag tccttcaacg   5340
actacctgtg cgcggccaac atgctgtatc ccatccccgc caacgccacc agcgtgccca   5400
tctccatccc gtctcgcaac tgggccgcct ttaggggttg gagtttcacc cgcctcaaaa   5460
ccaaggaaac cccctcgctg ggctctggct tcgaccccta cttcgtctac tcaggctcca   5520
ttccctacct ggacggcact ttctatctta accacacttt caaaaaggtg tctatcatgt   5580
tcgattcctc ggtcagctgg cccggcaacg accgcctgct gacgcccaac gagttcgaaa   5640
tcaagcgttc ggtggacggt gaagggtaca acgtggccca gagcaacatg accaaggact   5700
ggttcctggt tcaaatgctc agccattaca acatcggtta ccagggcttc tatgtgcccg   5760
agaactacaa ggaccgcatg tactccttct ttaggaactt ccaacccatg agtcgccaag   5820
tcgtggactc agtggcttac agggactact accaggacgt taagctcccc taccagcaca   5880
acaactcagg gttcgtgggc tacatgggtc ccaccatgcg agaggggcag gcctacccgg   5940
ccaactatcc ttatccccta atcggagaga ctgctgtacc cagcctgacg cagaaaaagt   6000
tcctctgcga ccgggtgatg tggaggatac ccttctctag caacttcatg tctatgggct   6060
ccctcaccga cctggggcag aacatgctgt acgccaactc cgctcacgcc ttggacatga   6120
cctttgaggt ggatcccatg gatgagccca cgcttctcta tgttctgttt gaagtcttcg   6180
acgtggtgcg catccaccag ccgcaccgcg gcgtcatcga ggccgtctac ctgcgcacac   6240
ctttctctgc cggtaacgcc accacctaaa gaagccgatg ggctccagcg aacaggagct   6300
gcaggccatt gttcgcgacc tgggctgcgg gccctacttt ttgggcacct tcgacaagcg   6360
gttccccggc ttcatgtccc ctcacaagcc ggcctgtgcc atcgttaaca cggccggacg   6420
ggaaaccggg ggggtccact ggctcgcctt cgcctggaac ccgcgtaacc gcacctgcta   6480
cctgttcgac ccttttggtt tctccgacga aaggctgaag cagatctacc agttcgagta   6540
cgaggggctc ctccagcgca gcgctctggc ctccacgccc gaccactgcg tcaccctgga   6600
aaagtccacc cagacggtcc aggggcccct ctcggccgcc tgcgggctct tctgttgcat   6660
gtttttgcac gccttcgtgc actggcctca cacccccatg gatcacaacc ccaccatgga   6720
tctgctcacc ggagtgccca acagcatgct tcacagcccc caggtcgccc ccaccctgcg   6780
ccgtaaccag gaacacctgt atcgctttct ggggaaacac tctgcctatt tccgccgcca   6840
tcggcagcgc atcgaacagg ccacggcctt cgaaagcatg agccaaagag tgtaatcaat   6900
aaaaaccatt tttatttgac atgatacgcg cttctggcgt tttattaaa aatcgaaggg    6960
ttcgagggag gggtcctcgt gcccgctggg gagggacacg ttgcgatact ggaatcgggc   7020
gctccaacga aactcgggga tcaccagtcg cggcaggggc acgtcttcca ggttctgctt   7080
ccaaaactgt cgcaccagct gcagggctcc catcacgtcg ggcgccgata tcttgaagtc   7140
gcagttaggg ccggagctcc cgcggctgtt ccggaacacg gggttggcac actggaacac   7200
catcacgctg ggttgtgaa tactagccag ggccgtcgga tcggtcacct ccgacgcatc    7260
cagatcctcg gcgttgctca gggcgaacgg ggtcagcttg cacatctgcc gcccgatctg   7320
gggcaccagg tcgggtttgt tgaggcaatc gcagcgcaga gggatcagga tgcgtcgctg   7380
cccgcgttgc atgatagggt aactcgccgc caggaactcc tccatctgac ggaaggccat   7440
```

```
ctgggcctta acgccctcgg tgaaaaacag cccacaggac ttgctagaaa atacgttatt   7500
gccgcagtta atgtcttccg cgcagcagcg tgcatcttcg ttcttcagct gaaccacgtt   7560
acgcccccag cggttctgga ccaccttggc tttcgtagga tgctccttca gcgcccgctg   7620
cccgttctcg ctggtcacat ccatttccac cacgtgctcc ttgcagacca tctccactcc   7680
gtggaagcaa aacaggacgc cctcctgccg ggtattgcga tgctcccaaa cggcacaccc   7740
ggtgggctcc cagctcttgt gttttacccc cgcgtaggct tccatgtaag ccatgaggaa   7800
tctgcccatc agctcggtga aggtcttctg attggtgaag gttagcggca ggccgcggtg   7860
ctcctcgttc aaccaagttt gacagatctt gcggtacacc gttccctggt cgggcagaaa   7920
cttaaaagcc gctctgctgt cgttgtccac gtggaacttc tccattaaca tcatcatggt   7980
ttccataccc ttctcccacg ctgacaccag cggtttgctg tcggggttct tcaccaacac   8040
ggcggtagag ggccctcgc cggccccgac gtccttcatg gtcattcttt gaaactccac   8100
ggagccgtcc gcgcgacgta ctctgcgcac cggagggtag ctgaagccca cctccaccac   8160
ggtgccttcg ccctcgctgt cggaaacgat ctccggggat ggcggcggtg cgggtgtcgc   8220
cttgcgagcc ttcttcttgg gagggagctg aggcgcctcc tgctcgcgct cggggctcat   8280
ctcccgcaag taggggggtta tggagctgcc tgcttggttc tgacggttgg ccattgtatc   8340
ctaggcagaa agacatggag cttatgcgcg aggaaacttt aaccgccccg tcccccgtca   8400
gcgacgaaga tgtcatcgtc gaacaggacc cgggctacgt tacgccgccc gaggatctgg   8460
aggggcctga ccggcgcgac gctagtgagc ggcaggaaaa tgagaaagag gaggcctgct   8520
acctcctgga aggcgacgtt ttgctaaagc atttcgccag gcagagcacc atagttaagg   8580
aggccttgca agaccgctcc gaggtgccct tggacgtcgc cgcgctctcc caggcctacg   8640
aggcgaacct tttctcgcct cgagtgcctc cgaagagaca gcccaacggc acctgcgagc   8700
ccaacccgcg actcaacttc taccccgtgt tcgccgtacc agaggcgctg gccacctatc   8760
acattttttt caaaaaccaa cgcatccccc tatcgtgccg ggccaaccgc accgcggccg   8820
ataggaatct caggcttaaa aacggagcca acatacctga tatcacgtcg ctggaggaag   8880
tgcccaagat tttcgagggt ctgggtcgag atgagaagcg ggcggcgaac gctctgcaga   8940
aagaacagaa agagagtcag aacgtgctgg tggagctgga gggggacaac gcgcgtctgg   9000
ccgtcctcaa acgctgcata gaagtctccc acttcgccta ccccgccctc aacttgccac   9060
ccaaagttat gaaatcggtc atggatcagc tgctcatcaa gagagctgag cccctggatc   9120
ccgaccaccc cgaggcggaa aactcagagg acggaaagcc cgtcgtcagc gacgaggagc   9180
tcgagcggtg gctggaaacc agggaccccc aacagttgca agagaggcgc aagatgatga   9240
tggcggccgt gctggtcacc gtggagctgg aatgcctgca acggtttttc agcgacgtgg   9300
agacgctacg caaaatcggg gaatccctgc actacacctt ccgccagggc tacgtccgcc   9360
aggcctgcaa gatctccaac gtggagctca gcaacctggt ctcctacatg ggcatcctcc   9420
acgagaaccg gctggggcag agcgtgctgc actgcacctt gcaaggcgag gcgcggcggg   9480
actacgtgcg agactgcatc tacctcttcc tcaccctcac ctggcagacc gccatgggcg   9540
tctggcagca gtgcttggaa gagagaaacc tcaaagagct agacaaactc ctctgccgcc   9600
agcggcgcgc cctgtggtcc ggtttcagcg agcgcacggt cgccagcgct ctggcggaca   9660
tcatcttccc ggagcgcctg atgaaaacct tgcaaaacgg cctgccggat ttcatcagtc   9720
aaagcatttt gcaaaacttc cgctcttttg tcctggaacg ctccgggatc ttgcccgcca   9780
```

tgagctgcgc gctaccttct gactttgtcc ccctctccta ccgcgagtgc cctcccccac 9840
tgtggagcca ctgctacctc ttccaactgg ccaactttct ggcctaccac tccgacctca 9900
tggaagacgt aagcggagag ggtttactgg agtgccactg ccgctgcaac ctgtgcaccc 9960
cccacagatc gctggcctgc aacaccgagc tactcagcga aacccaggtc ataggtacct 10020
tcgagatcca ggggccccag cagcaagagg gtgcttccgg cttgaagctc actccggcgc 10080
tgtggacctc ggcttactta cgcaaatttg tagccgagga ctaccacgcc cacaaaattc 10140
agttttacga agaccaatct caaccaccga aagcccccct cacggcctgc gtcatcaccc 10200
agagcaagat cctggcccaa ttgcaatcca tcaaccaagc gcgccgcgat ttcctttga 10260 aaaagggtcg gggggtgtat ctggaccccc agaccggcga ggaactcaac ccgtccacac 10320
tctccgtcga agcagccccc ccgagacatg ccgcccaagg gaaccgccaa gcagctgatc 10380
gctcggcaga gagcgaagaa gcaagagctg ctccagcagc aggtggagga cgaggaagag 10440
atgtgggaca gccaggcaga ggaggtgtca gaggacgagg aggagatgga aagctgggac 10500
agcctagacg aggaggagga cgagctttca gaggaagagg cgaccgaaga aaaaccacct 10560
gcatccagcg cgccttctct gagccgacag ccgaagcccc ggcccccgac gcccccggcc 10620
ggctcactca aagccagccg taggtgggac gccaccgaat ctccagcggc agcggcaacg 10680
gcagcgggta aggccaaacg cgagcggcgg gggtattgct cctggcgggc ccacaaaagc 10740
agtattgtga actgcttgca acactgcggg ggaaacatct cctttgcccg acgctacctc 10800
ctcttccatc acggtgtggc cttccctcgc aacgttctct attattaccg tcatctctac 10860
agcccctacg aaacgctcgg agaaaaaagc taaggcctcc tccgccgcga ggaaaaactc 10920
cgccgccgct gccgccgcca aggatccacc ggccaccgag gagctgagaa agcgcatctt 10980
tcccactctg tatgctatct ttcagcaaag ccgcgggcag caccctcagc gcgaactgaa 11040
aataaaaaac cgctccttcc gctcgctcac ccgcagctgt ctgtaccaca agagagaaga 11100
ccagctgcag cgcaccctgg acgacgccga agcactgttc agcaaatact gctcagcgtc 11160
tcttaaagac taaaagaccc gcgctttttc cccctcggcc gccaaaaccc acgtcatcgc 11220
cagcatgagc aaggagattc ccacccccta catgtggagc tatcagcccc agatgggcct 11280
ggccgcgggg gccgcccagg actactccag caagatgaac tggctcagcg ccggccccca 11340
catgatctca cgagttaacg gcatccgagc ccaccgaaac cagattctct tagaacaggc 11400
ggcaatcacc gccacacccc ggcgccaact caacccgcct agttggcccg ccgcccaggt 11460
gtatcaggaa aatccccgcc cgaccacagt cctcctgcca cgcgacgcgg aggccgaagt 11520
cctcatgact aactctgggg tacaattagc gggcgggtcc aggtacgcca ggtacagagg 11580
tcgggccgct ccttactctc ccgggagtat aaagagggtg atcattcgag gccgaggtat 11640
ccagctcaac gacgagacgg tgagctcctc aaccggtctc agacctgacg gagtcttcca 11700
gctcggagga gcgggccgct cttccttcac cactcgccag gcctacctga ccctgcagag 11760
ctcttcctcg cagccgcgct ccgggggaat cggcactctc cagttcgtgg aagagttcgt 11820
tccctccgtc tacttcaacc ccttctccgg ctcgcctgga cgctacccgg acgccttcat 11880
tcccaacttt gacgcagtga gtgaatccgt ggacggctac gactgatgac agatggtgcg 11940
gccgtgagag ctcggctgcg acatctgcat cactgccgtc agcctcgctg ctacgctcgg 12000
gaggcgatcg tcttcagcta ctttgagctg ccggacgagc accctcaggg tccggctcac 12060
gggttgaaac tcgagatcga gaacgcgctc gagtctcgcc tcatcgacac cttcaccgcc 12120
cgacctctcc tggtagaaat cgaacgcggg atcactacca tcaccctgtt ctgcatctgc 12180

-continued

```
cccacgcccg gattacatga agatctgtgc tgtcatcttt gcgctcagtt taataaaaac  12240
tgaacttttt gccgcacctt caacgccacg cgtcgtttct ccaaaagttg tcgacagctc  12300
ttcagtcaga ggtatacgag aaactgttta tttttacaac tctactactt ttctcaccct  12360
taactgctcc tgcactaacg aactaattca gtggttcgcg aacggctcac tctgccaagt  12420
ctttttaat tctgctgttc ttcctgagtt tggctccttt gcgtgtggaa attctacact  12480
agtgggagct atcctgtgtc actgtcacgc gcctgattgt atgcccaaac taattagaac  12540
tctctgtgcc ttaggtgata tatttaaaat gtaagtcagt atcaataaac ttaccttaaa  12600
tttgacagca gtttttggt aacatcattc agcagcacca ctttaccctc ttcccaactc  12660
tcgtatggga cgtgatggtg ggcggcaaac ttcctccaaa ccctaaaaca aatattaata  12720
tccacttcct tgtccttacc cacaatttc atcttttcat agatgaaaag aaccagagtt  12780
gatgaagact tcaaccccgt ctacccttat gactccacat ccactcctgc ggtccccttt  12840
atatccccc cgtttgtaaa cagcgatggt cttcaggaaa accctcctgg agtcttaagt  12900
ttacgaatag ctaaaccctt gtattttgac atggaaagga aactagcgct ttcacttgga  12960
agaggattgg caattacctc caccggacag ctagaaagca cacagagcgt gcaaaccacc  13020
cctccattag ttgtcaacaa cagcaacacg cttgtcctgc gttattcctc cccgttaggc  13080
ttatcgggtg acaatttaat actaaattgc tccgatcctc tccgcgtagt aaacaacagc  13140
ctgacattca gctacctatc tccacttcgt tttgaaggtg gcagtcttac attcaattac  13200
acatctcccc ttaaactgtt gaacagcagc cttgcgatcg gaataaattc caacaaaggt  13260
ctcggcaatg acagcgatga actttctgtc aaactaacat cagatctaaa gtttaacaac  13320
gatggaaaaa tagcttttgg tatacaaagc ctgtgtacca cccccacagc cgcctctaac  13380
tgtaccgttt ttaccaacgg tgattcttta ctctgtttat gtttaaccaa atgtggagct  13440
cacgtgttag gaagtgtgag tttaaccgga atgcaaggaa ccataacagc catgacacag  13500
aactacatta gtattcaatt tctatttgac aacaatggtg cgttgacttc atcaccgctc  13560
ctcaacaaca acacttgggg tatacggcaa aacgacactt cgtccgctaa ccccgcctac  13620
aatgctcttg catttatgcc taacagcact gtatatgtaa gaggtcaaag tggtgagccc  13680
agaaataact attacaccca aacataccttt aggggaaacg ttaaaaagcc aattatcctt  13740
accgttacct acaactcggc tgcttcaggt tattcactaa cttttaaatg ggatgctgta  13800
gtaacagaaa aatttgccac tccaacatct tctttttgct atattacaga acaataaatt  13860
cctattaccc caccaattcg tttttttcag atgaaacggg ccagagttga tgaagacttc  13920
aacccagtgt acccttatga ccccccatac gctcccgtta tgcccttcat tactccacct  13980
tttacctcct cggatgggtt gcaggaaaaa ccacttggag tgttaagttt aaactacaag  14040
gatcccatta ctacacaaaa tggatctctc acgttgaaaa taggaaacgg cctcactcta  14100
gacaaccagg gacaattaac atcaactgct ggggaagtag agcctccgct cactaatgct  14160
aacaacaaac ttgcactagc ctatagcgaa ccattagcag taaaaagcaa ccgcttaact  14220
ttatcacaca ccgcccccct tgtcgttgct aataattctt tagcgttgca agtttcagaa  14280
cctattttta taaatgacga tgacaagcta gccctgcaga cagccgcccc ccttgtaact  14340
aacgctggca cccttcgctt acagagcgcc gccccttttag gattggttga aaatactctt  14400
agactgctgt tttctaaacc cttgtatttg caaaatgatt ttcttgcatt aggcattgaa  14460
cgccccctgg ctatagcagc cgcaggtact ctagcactac aactcactcc tccattaaag  14520
```

-continued actaacgatg acgggctgac actatccaca gtcgagccat taactgtaaa aaacggaaac 14580
ttaggcttgc aaatatctcg ccctttggtt gttcaaaaca gcagcctttc gcttgctatt 14640
acccccccgc tgcgtctatt taacagcgac cccgttcttg gtttgggctt tacttttccc 14700
ctagccgtga cagacaacct actctcctta aacatgggag acggtgttaa actaacctat 14760
aataaactaa cagccaattt gggtagggat ttacaatttg aaaacggtgc cattgccgta 14820
acgcttactg ccgaatcacc tttgcaatac actaacaaac ttcaactgaa tattggagct 14880
ggccttcgtt acaatggagc cagcagaaaa ctagatgtaa acattaacca aaataagggc 14940
ttaacttggg acaacgatgc agttattccc aaattaggat caggtttaca attcgaccct 15000
aatggtaaca tcgctgttat ccctgaaacc gtaaagccgc aaacgttatg gacaactgca 15060
gatccatcgc ctaactgctc agtgtaccag gacttggacg ccaggctgtg gctcgctctt 15120
gttaaaagtg gtgacatggt tcatggaagc attgctctaa aagccctaaa aggaacgttg 15180
ctaaatccta cagcaagcta catctccatt gtgatatatt tttacagcaa cggagtcagg 15240
cgtaccaact atcccacgtt tgacaacgaa ggcaccttag ctaacagcgc tacctgggga 15300
taccgagagg ggcaatctgc taacactaat gtaaccaatg ccactgaatt tatgcccagc 15360
tcaaccaggt accccgtgaa taaaggagac aatattcaga atcaatcttt ttcatacacc 15420
tgtatcaaag gagatttcgc tatgcctgtc ccgttccgtg taacatataa tcatgccctg 15480
gaaggatact cccttaagtt cacctggcgc gttgtagcca accaagcttt tgatattcct 15540
tgctgttcct tttcatacat cacagaataa accacttttt aaaatttttc tttttatttt 15600
acacgcacag taaggcttcc tccccccttc catttgacag catacaccag cctctccccc 15660
ttcatggcag taaactgctg cgagccagtc cggtatttgg gagttaaaat ccaaacagtc 15720
tctttggtga tgaaacgtcg atccgtgatg gacacaaatc cctggggcag gttttccagc 15780
gtttcggtaa aaaactgcac accgccctac aaaacaaaca ggttcaggct ctccatgggt 15840
tatctccccg atcaaactca gacagggtaa aggtgcggtg atgttccact aaaccacgca 15900
ggtggcgctg tctgaacctc tcggtgcgac tcctgtgagg ctggtaagaa gttagattgt 15960
ccagtagcct cacagcatgg atgatcagtt tacgtgtacg tctggcgcaa cagcgcatct 16020
gaatctcact gagattccgg caagaatcgc acaccatcac aatcaggttg ttcatgatcc 16080
catagctgaa cacgctccag ccaaagctca ttcgctccaa cagcgccacc gcgtgtccgt 16140
ccaaccttac tttaacataa atcaggtgtc tgccgcgtac aaacatacta cccgcataca 16200
gaacttcccg gggcaaaccc ctgttcacca cctgcctgta ccagggaaac ctcacattta 16260
tcagggagcc atagatagcc attttaaacc aattagctaa caccgcccca ccagctctac 16320
actgaagaga accgggagag ttacaatgac agtgaataat ccatctctca taacccctga 16380
tggtctgatg gaaatccagc acaccgccct acaaaacaaa caggttcagg ctctccatgg 16440
gttatctccc cgatcaaact cagacagggt aaaggtgcgg tgatgttcca ctaaaccacg 16500
caggtggcgc tgtctgaacc tctcggtgcg actcctgtga ggctggtaag aagttagatt 16560
gtccagtagc ctcacagcat ggatgatcag tttacgtgta cgtctggcgc aacagcgcat 16620
ctgaatctca ctgagattcc ggcaagaatc gcacaccatc acaatcaggt tgttcatgat 16680
cccatagctg aacacgctcc agccaaagct cattcgctcc aacagcgcca ccgcgtgtcc 16740
gtccaacctt actttaacat aaatcaggtg tctgccgcgt acaaacatac tacccgcata 16800
cagaacttcc cggggcaaac ccctgttcac cacctgcctg taccagggaa acctcacatt 16860
tatcagggag ccatagatag ccattttaaa ccaattagct aacaccgccc caccagctct 16920
acactgaaga gaaccgggag agttacaatg acagtgaata atccatctct cataacccct 16980
gatggtctga tggaaatcca gatctaacgt ggcacagcag atacacactc tcatatacat 17040
tttcatcaca tggttttccc aggccgttaa aatacaatcc caatacacgg gccactcctg 17100
cagtacaata aagctaatac aagatggtat actcctcacc tcactaacat tgtgcatgtt 17160
catattttca cattctaagt accgagagtt ctcctctaca acagcactgc tgcggtcctc 17220
acaaggtggt agctggtgac gatcgtaagg agccagtctg caacgatacc gtctgtcgcg 17280
ctgcatcgta gaccagagac cgacgcacct cctggtactt gtggtagcag aaccacgtcc 17340
gctgccaaca ggtatccacg taacgccggt ccctgcgtcg cgcgcgctct gttctcaatg 17400
caaaatgcag ccactcttgt aatccacaca gatccctctc ggcctccggg aggatacaca 17460
cttcaaacct acaaatgtct cggtacagtt ccaaacacga agtgagggcg agttccaacc 17520
aagacaggca ggctggtcta tcccgacaca ctggaggtgg aggaagacac ggaagaggca 17580
tgttattcca agcgattcac caacgggtcg aaatgaagat cccgaagatg acaacggtcg 17640
cctccggagc cctgatggaa tttaacagcc aaatcaaaca ttatgcgatt ttccaggcta 17700
tcgatcgcgg cctccaaaag agcctggacc cgcacttcca caaacaccag caaagcaaaa 17760
gcgttattat caaactcttc gatcatcaag ctgcaagact gtacaatgcc caagtaattt 17820
tcatttctcc actcgcgaat gatgtcgcgg caaatagtct gaaggttcat gccgtgcata 17880
ttaaaaagct ccgaaagggc gccctctata gccatgcgta gacacaccat catgactgca 17940
agatatcggg ctcctgagac acctgcagca gatttaacag acccaggtca ggttgctctc 18000
cgcgatcgcg aatctccatc cgcaaggtca tttgcaaata attaaataga tctgcgccga 18060
ctaaatctgt taactccgcg ttaggaacta aatcaggtgt ggctacgcag cacaaaagtt 18120
ccagggatgg cgccaaactc actagaaccg ctcccgagta gcaaaactga tgaatgggag 18180
taacacagtg taaaatgttc agccaaaaat cactaagccg ctcctttaaa aagtccagta 18240
cttctatatt cagttcgtgc aagtactgaa gcaactgtgt gggaatatgc acaacaaaaa 18300
aaatagggcg gctcagatac atgttgacct aaaataaaaa gaatcattaa actaaagaag 18360
cttggcgaac ggtgggataa atgacacgtt ccagcagcag gcaagcaacc ggctgtcccc 18420
gggaaccgcg gtaaaattca tccgaatgat taaaaagaac aacagaaact tcccaccatg 18480
tactcggttg gatctcctga gcacagagca atacccccct cacattcata tccgccacag 18540
aaaaaaagcg tcccagatac ccagcgggaa tatccaacga cagctgcaaa gacagcaaaa 18600
caatccctct gggagcaatc acaaaatcct ccggtgaaaa aagcacatac atattagaat 18660
aaccctgctg ctggggcaaa aaggcccgtc gtcccagcaa atgcacataa atatgttcat 18720
cagccattgc cccgtcttac cgcgtaaaca gccacgaaaa attcgagcta aaatccaccc 18780
aacagcctat agctatatat acactccgcc caatgacgct aataccgcac cacccaccgc 18840
caaagttcac ccacacccac gaaacccgcg aaaatccagc gccgtcagca cttccgcaat 18900
ttcagtctca caacgtcact tccgcgcgcc ttttcacatt ccccacacccg cccacaaacc 18960 ccgcgtcacc gcccgtcacc ccggccccgc ctcgctcctc cccgctcatt atcatattgg 19020
cacgtttcca gaataaggta tattattgat gatgttaatt aattcgaacc cataataccc 19080
ataatagctg tttgccatcg accaattctc ccatattccc ggttgaattg tagtacatga 19140
gaccaataaa gttatttgaa gacgaaaggg cctcgtgata cgcctatttt tataggttaa 19200
tgtcatgata ataatggttt cttagacgtc aggtggcact tttcggggaa atgtgcgcgg 19260 aaccccctatt tgtttatttt tctaaataca ttcaaatatg tatccgctca tgagacaata 19320
accctgataa atgcttcaat aatattgaaa aaggaagagt atgagtattc aacatttccg 19380
tgtcgccctt attccctttt ttgcggcatt ttgccttcct gtttttgctc acccagaaac 19440
gctggtgaaa gtaaaagatg ctgaagatca gttgggtgca cgagtgggtt acatcgaact 19500
ggatctcaac agcggtaaga tccttgagag ttttcgcccc gaagaacgtt ttccaatgat 19560
gagcactttt aaagttctgc tatgtggcgc ggtattatcc cgtgttgacg ccgggcaaga 19620
gcaactcggt cgccgcatac actattctca gaatgacttg gttgagtact caccagtcac 19680
agaaaagcat cttacggatg gcatgacagt aagagaatta tgcagtgctg ccataaccat 19740
gagtgataac actgcggcca acttacttct gacaacgatc ggaggaccga aggagctaac 19800
cgcttttttg cacaacatgg gggatcatgt aactcgcctt gatcgttggg aaccggagct 19860
gaatgaagcc ataccaaacg acgagcgtga caccacgatg cctgcagcaa tggcaacaac 19920
gttgcgcaaa ctattaactg gcgaactact tactctagct tcccggcaac aattaataga 19980
ctggatggag gcggataaag ttgcaggacc acttctgcgc tcggcccttc cggctggctg 20040
gtttattgct gataaatctg gagccggtga gcgtgggtct cgcggtatca ttgcagcact 20100
ggggccagat ggtaagccct cccgtatcgt agttatctac acgacgggga gtcaggcaac 20160
tatggatgaa cgaaatagac agatcgctga gataggtgcc tcactgatta agcattggta 20220
actgtcagac caagtttact catatatact ttagattgat ttaaaacttc atttttaatt 20280
taaaaggatc taggtgaaga tcctttttga taatctcatg accaaaatcc cttaacgtga 20340
gttttcgttc cactgagcgt cagaccccgt agaaaagatc aaaggatctt cttgagatcc 20400
tttttttctg cgcgtaatct gctgcttgca aacaaaaaaa ccaccgctac cagcggtggt 20460
ttgtttgccg gatcaagagc taccaactct ttttccgaag gtaactggct tcagcagagc 20520
gcagatacca aatactgtcc ttctagtgta gccgtagtta ggccaccact tcaagaactc 20580
tgtagcaccg cctacatacc tcgctctgct aatcctgtta ccagtggctg ctgccagtgg 20640
cgataagtcg tgtcttaccg ggttggactc aagacgatag ttaccggata aggcgcagcg 20700
gtcgggctga acggggggtt cgtgcacaca gcccagcttg gagcgaacga cctacaccga 20760
actgagatac ctacagcgtg agctatgaga aagcgccacg cttcccgaag ggagaaaggc 20820
ggacaggtat ccggtaagcg gcagggtcgg aacaggagag cgcacgaggg agcttccagg 20880
gggaaacgcc tggtatcttt atagtcctgt cgggtttcgc cacctctgac ttgagcgtcg 20940
atttttgtga tgctcgtcag gggggcggag cctatggaaa aacgccagca acgcggcctt 21000
tttacggttc ctggcctttt gctggccttg aagctgtccc tgatggtcgt catctacctg 21060
cctggacagc atggcctgca acgcgggcat cccgatgccg ccggaagcga gaagaatcat 21120
aatggggaag gccatccagc ctcgcgtcga tggcaaacag ctattatggg tattatgggt 21180
tcgaattaat 21190

<210> SEQ ID NO 38
<211> LENGTH: 19781
<212> TYPE: DNA
<213> ORGANISM: Artificial Sequence
<220> FEATURE:
<223> OTHER INFORMATION: Synthetic oligonucleotide pBr/sAd4287.PsiI-rITR.dE3.dE4

<400> SEQUENCE: 38
attaacccag gacctggaaa tagtgccttt aactaaagac agcaaagaca gaagctacaa 60

```
tattataaac aacacgacgg acaccctgta tcggagctgg tttctggctt acaactacgg    120
agaccccgag aaaggagtga gatcatggac catactcacc accacggacg tgacctgtgg    180
ctcgcagcaa gtgtactggt ccctgccgga tatgatgcaa gacccggtca ccttccgccc    240
ctccacccaa gtcagcaact tcccggtggt gggcaccgag ctgctgcccg tccatgccaa    300
gagcttctac aacgagcagg ccgtctactc gcaacttatt cgccagtcca ccgcgcttac    360
ccacgtgttc aatcgctttc ccgagaacca gattctggtg cgccctcccg ctcctaccat    420
taccaccgtc agtgaaaacg ttcccgccct cacagatcac ggaaccctgc cgctgcgcag    480
cagtatcagt ggagttcagc gcgtgaccat caccgacgcc agacgtcgaa cctgccccta    540
cgtttacaaa gcgcttggcg tggtggctcc taaagttctt tctagtcgca ccttctaaaa    600
acatgtccat cctcatctct cccgataaca acaccggctg ggactgggc tccggcaaga     660
tgtacggcgg agccaaaagg cgctccagtc agcacccagt tcgagttcgg ggccacttcc    720
gcgctccttg ggagcttac aagcgaggac tctcgggtcg aacggctgta gacgatacca     780
tagatgccgt gattgccgac gcccgccggt acaaccccgg accggtcgct agcgccgcct    840
ccaccgtgga ttccgtgatc gacagcgtgg tagccggcgc tcgggcctat gctcgccgca    900
agaggcggct gcatcggaga cgtcgcccca ccgccgccat gctggcagcc agagccgtgc    960
tgagacgggc ccggagggta ggcaggaggg ctatgcgccg cgctgccgcc aacgccgccg   1020
ccgggagggc ccgccgacag gctgcccgcc aggctgctgc cgccatcgct agcatggcca   1080
gacccaggag agggaacgtg tactgggtgc gcgattctgt gacgggagtc cgagtgccgg   1140
tgcgcagccg acctccccga agttagaaga tccaagctgc gaagacggcg gtactgagtc   1200
tccctgttgt tatcagccca acatgagcaa gcgcaagttt aaagaagaac tgctgcagac   1260
gctggtgcct gagatctatg gccctccgga cgtgaagcct gacattaagc cccgcgatat   1320
caagcgtgtt aaaaagcggg aaaagaaaga ggaactcgcg gtggtagacg atggcggagt   1380
ggaatttatt aggagtttcg ccccgcggcg cagggttcaa tggaaagggc gacgggtaca   1440
acgcgttttg aggccgggca ccgcggtagt tttaccccg ggagagcggt cggccgttag    1500
gggttttaaa aggcagtacg acgaggtgta cggcgacgag gacatattgg aacaggcggc   1560
tcaacagatc ggagaatttg cctatggaaa gcgctcgcgt cgcgaagacc tggccatcgc   1620
cttagacagc ggcaacccca cgcccagcct caaacccgtg acgctgcagc aggtgcttcc   1680
cgtgagcgcc agcacggaca gcaagagggg aataaaaaga gaaatggaag atctgcagcc   1740
taccatccag ctcatggttc ctaaacggca gaggctggaa gaggtcctgg agaagatgaa   1800
agtggacccc agcatagagc cggacgttaa agtcaggccg atcaaagaag tggcccctgg   1860
actcggggtg cagacggtgg atatccagat ccccgtcacg tcagcttcga ccgccgtgga   1920
agccatggaa acgcaaaccg aaacccccgc cgtggttggt accaaagaag tggcgttgca   1980
aaccgacccc tggtacgaat ttgccgcccc ccggcgtcag aggcgacccg ctcgttacgg   2040
ccccgccaac gccatcatgc cagaatatgc gctgcatccg tctatcctgc ccacccccgg   2100
ctaccgggga gtgacgtatc gcccgtcagg aacccgccgc cgaacccgtc gccgccgccg   2160
ctcccgtcgc gctctggccc ccgtgtcggt gcgccgcgta acacgccggg gaaagacagt   2220
caccattccc aacccgcgct accaccctag catcctttaa tgactctgcc gttttgcaga   2280
tggctctgac ttgccgcgtg cgccttcccg ttccgcacta tcgaggaaga tctcgtcgta   2340
ggagaggcat ggcgggcagt ggtcgccggc gggctttgcg caggcgcatg aaaggcggaa   2400
ttttacccgc tttgataccc ataatcgccg ccgccatcgg tgccataccc ggcgtcgctt   2460
```

cagtggcctt gcaagcagct cgtaataaat aaacgaaggc ttttgcactt atgtcctggt 2520
cctgactatt ttatgcagaa agagcatgga agacatcaat tttacgtcgc tggctccgcg 2580
gcacggctcg cggccgctca tgggcacctg gaacgacatc ggcaccagtc agctcaacgg 2640
gggcgctttc aattggggga gcctttggag cggcattaaa aactttggct ccacgattaa 2700
atcctacggc agcaaagcct ggaacagtag tgctggtcag atgctccgag ataaactgaa 2760
ggacaccaac ttccaagaaa aagtggtcaa tggggtggtg accggcatcc acggtgcggt 2820
agatctcgcc aaccaagcgg tgcagaaaga gattgacagg cgtttggaaa actcgcgggt 2880
gccgccgcag agggggggatg aggtggaggt cgaggaagta gaagtagagg aaaagctgcc 2940
cccgctggag aaagttcccg gtgcacctcc gaggccgcag aagcggccca ggccagaact 3000
agaagaaact ctggtgacgg agagcaagga gcctccctcg tacgagcaag ccttgaaaga 3060
gggcgcctct ccaccctcct acccgatgac taagccgatc gcacccatgg ctcgaccggt 3120
gtacggcaag gattacaagc ccgtcacgct agagctgccc ccaccgcccc cttcgcgtcc 3180
gacggtgcct ccgctgcctg ccccgtcggc gggtcccgag tctgcaccat ccgctgtgcc 3240
tctgccagcc gcccgtcccg tggccgtggc cactgccagg aaccccagag gccagagagg 3300
agccaactgg caaagcacgc tgaacagcat cgtgggcctg gggggtgaaaa gcctgaaacg 3360 ccgccgttgc tattattaaa aagtgtagct aaaaaatttc ccgttgtata cgcctcctat 3420
gttaccgcca gagacgcgtg actgtcgccg cgagcgccgc ttccaagatg gccaccccat 3480
cgatgatgcc gcagtggtct tacatgcaca tcgccggcca ggacgcctcg gagtacctga 3540
gtcccggcct cgtgcagttt gcccgcgcca ccgacaccta cttcagcttg ggaaacaagt 3600
ttagaaaccc caccgtggcc cccacccacg atgtgaccac ggaccgctcg cagaggctga 3660
ccctgcgctt tgtgcccgta gaccgggagg acaccgcgta ctcttacaaa gtgcgctaca 3720
cgctggccgt aggggacaac cgagtgctgg acatggccag cacctacttt gacatccggg 3780
gggtgctgga tcggggtccc agcttcaagc cctactccgg caccgcttac aactccctgg 3840
ctcccaaggg cgcccccaat cctgcagaat gggccgatac caacgacagc aacaaactga 3900
aagtgagggg tcaggcgcct tttgtcagta cttacggttc tgctacggcg cttacaaaag 3960
atgggataca ggtgggagtg gatacttccg aagcatctca ggctgtttat gccgacagaa 4020
gttaccagcc agaaccccaa attggagaga cagagtggaa cagcgaagtg ggtaatgacg 4080
acagagtggc gggaagggtg ctaaagaaaa caactcccat gttcccttgt tacggttcat 4140
atgccaagcc caccaacgaa aaaggcggac aagcaataca gcccaccgcc ggcaacggcg 4200
ataatcaggc tgtagagtta caattctttg ccactactag cactcccact gcgccaaagg 4260
cagtattgta cgcggaggac gtggccattg aagctccaga tactcactta gtgtttaagc 4320
caacagtagt cgcgggaact acaagttcgg aagctctgct aacccaacaa gccgcaccta 4380
accgcccaaa ctacattgcc tttagagata actttattgg tctcatgtac tacaattcaa 4440
ccgggaatat gggagtactg gccggacaag catctcagct caatgcagtg gttgatcttc 4500
aggacagaaa caccgaactg tcatatcagc taatgctgga tgctctggga gatcgcagtc 4560
ggtacttttc tatgtggaat caagctgtag atagctatga tccagatgta agaattgtag 4620
aaaaccacgg tgtggaagac gaactgccta attattgctt ccccactaggc gggatggtag 4680 taacggacac ttacaaagcc ataaaggtaa atggaagcgg atggacggct aatactgacg 4740
ttttcagcga gagagtagaa ataggctcag gtaacctgtt tgccatggaa attaacttgc 4800

-continued

```
aagctaatct gtggcgcagt ttcttgtatt ccaacatagg actgtacctc ccggactctt   4860
taaaattaac ccctgacaac atcacgctcc ctgagaacaa aaatacctac cagtatatga   4920
acggtcgcgt aacaccaccc gggctcgtgg acacctacgt taacgtgggt gcgcgctggt   4980
cccccgatgt tatggacagc attaaccctt ttaaccacca ccgcaacgcc gggctccgct   5040
accgttccat gctcctggga aacggacgct acgtaccctt ccacattcag gtgccccaga   5100
aattctttgc aattaaaaac ctgctgctgc tccccggttc ctatacctac gagtggaatt   5160
tccgcaagga cgtgaacatg attttgcaaa gctcgctggg taacgacctg cgagttgacg   5220
gggccagcat acgcttcgac agcatcaacc tgtatgctaa ctttttcccc atggcccaca   5280
acacggcctc caccctggaa gccatgctgc gcaacgacac caatgaccag tccttcaacg   5340
actacctgtg cgcggccaac atgctgtatc ccatccccgc caacgccacc agcgtgccca   5400
tctccatccc gtctcgcaac tgggccgcct ttaggggttg gagtttcacc cgcctcaaaa   5460
ccaaggaaac cccctcgctg ggctctggct tcgaccccta cttcgtctac tcaggctcca   5520
ttccctacct ggacggcact ttctatctta accacacttt caaaaaggtg tctatcatgt   5580
tcgattcctc ggtcagctgg cccggcaacg accgcctgct gacgcccaac gagttcgaaa   5640
tcaagcgttc ggtggacggt gaagggtaca acgtggccca gagcaacatg accaaggact   5700
ggttcctggt tcaaatgctc agccattaca acatcggtta ccagggcttc tatgtgcccg   5760
agaactacaa ggaccgcatg tactccttct ttaggaactt ccaacccatg agtcgccaag   5820
tcgtggactc agtggcttac agggactact accaggacgt taagctcccc taccagcaca   5880
acaactcagg gttcgtgggc tacatgggtc ccaccatgcg agaggggcag gcctacccgg   5940
ccaactatcc ttatccccta atcggagaga ctgctgtacc cagcctgacg cagaaaaagt   6000
tcctctgcga ccgggtgatg tggaggatac ccttctctag caacttcatg tctatgggct   6060
ccctcaccga cctggggcag aacatgctgt acgccaactc cgctcacgcc ttggacatga   6120
cctttgaggt ggatcccatg gatgagccca cgcttctcta tgttctgttt gaagtcttcg   6180
acgtggtgcg catccaccag ccgcaccgcg gcgtcatcga ggccgtctac ctgcgcacac   6240
ctttctctgc cggtaacgcc accacctaaa gaagccgatg ggctccagcg aacaggagct   6300
gcaggccatt gttcgcgacc tgggctgcgg gccctacttt ttgggcacct tcgacaagcg   6360
gttccccggc ttcatgtccc ctcacaagcc ggcctgtgcc atcgttaaca cggccggacg   6420
ggaaaccggg gggtccact ggctcgcctt cgcctggaac ccgcgtaacc gcacctgcta   6480
cctgttcgac ccttttggtt tctccgacga aaggctgaag cagatctacc agttcgagta   6540
cgaggggctc ctccagcgca gcgctctggc ctccacgccc gaccactgcg tcaccctgga   6600
aaagtccacc cagacggtcc aggggcccct ctcggccgcc tgcgggctct tctgttgcat   6660
gtttttgcac gccttcgtgc actggcctca cacccccatg gatcacaacc ccaccatgga   6720
tctgctcacc ggagtgccca acagcatgct tcacagcccc caggtcgccc ccaccctgcg   6780
ccgtaaccag gaacacctgt atcgctttct ggggaaacac tctgcctatt tccgccgcca   6840
tcggcagcgc atcgaacagg ccacggcctt cgaaagcatg agccaaagag tgtaatcaat   6900
aaaaaccatt tttatttgac atgatacgcg cttctggcgt tttattaaa aatcgaaggg   6960
ttcgagggag gggtcctcgt gcccgctggg gagggacacg ttgcgatact ggaatcgggc   7020
gctccaacga aactcgggga tcaccagtcg cggcaggggc acgtcttcca ggttctgctt   7080
ccaaaactgt cgcaccagct gcagggctcc catcacgtcg ggcgccgata tcttgaagtc   7140
gcagttaggg ccggagctcc cgcggctgtt ccggaacacg ggttggcac actggaacac   7200
```

```
catcacgctg gggttgtgaa tactagccag ggccgtcgga tcggtcacct ccgacgcatc   7260
cagatcctcg gcgttgctca gggcgaacgg ggtcagcttg cacatctgcc gcccgatctg   7320
gggcaccagg tcgggtttgt tgaggcaatc gcagcgcaga gggatcagga tgcgtcgctg   7380
cccgcgttgc atgatagggt aactcgccgc caggaactcc tccatctgac ggaaggccat   7440
ctgggcctta acgccctcgg tgaaaaacag cccacaggac ttgctagaaa atacgttatt   7500
gccgcagtta atgtcttccg cgcagcagcg tgcatcttcg ttcttcagct gaaccacgtt   7560
acgcccccag cggttctgga ccaccttggc tttcgtagga tgctccttca gcgcccgctg   7620
cccgttctcg ctggtcacat ccatttccac cacgtgctcc ttgcagacca tctccactcc   7680
gtggaagcaa aacaggacgc cctcctgccg ggtattgcga tgctcccaaa cggcacaccc   7740
ggtgggctcc cagctcttgt gttttacccc cgcgtaggct tccatgtaag ccatgaggaa   7800
tctgcccatc agctcggtga aggtcttctg attggtgaag gttagcggca ggccgcggtg   7860
ctcctcgttc aaccaagttt gacagatctt gcggtacacc gttccctggt cgggcagaaa   7920
cttaaaagcc gctctgctgt cgttgtccac gtggaacttc tccattaaca tcatcatggt   7980
ttccataccc ttctcccacg ctgacaccag cggtttgctg tcggggttct tcaccaacac   8040
ggcggtagag gggccctcgc cggccccgac gtccttcatg gtcattcttt gaaactccac   8100
ggagccgtcc gcgcgacgta ctctgcgcac cggagggtag ctgaagccca cctccaccac   8160
ggtgccttcg ccctcgctgt cggaaacgat ctccggggat ggcggcggtg cgggtgtcgc   8220
cttgcgagcc ttcttcttgg gagggagctg aggcgcctcc tgctcgcgct cggggctcat   8280
ctcccgcaag tagggggtta tggagctgcc tgcttggttc tgacggttgg ccattgtatc   8340
ctaggcagaa agacatggag cttatgcgcg aggaaacttt aaccgccccg tcccccgtca   8400
gcgacgaaga tgtcatcgtc gaacaggacc cgggctacgt tacgccgccc gaggatctgg   8460
aggggcctga ccggcgcgac gctagtgagc ggcaggaaaa tgagaaagag gaggcctgct   8520
acctcctgga aggcgacgtt ttgctaaagc atttcgccag gcagagcacc atagttaagg   8580
aggccttgca agaccgctcc gaggtgccct tggacgtcgc cgcgctctcc caggcctacg   8640
aggcgaacct tttctcgcct cgagtgcctc cgaagagaca gcccaacggc acctgcgagc   8700
ccaacccgcg actcaacttc taccccgtgt tcgccgtacc agaggcgctg gccacctatc   8760
acattttttt caaaaaccaa cgcatccccc tatcgtgccg ggccaaccgc accgcggccg   8820
ataggaatct caggcttaaa aacggagcca acatacctga tatcacgtcg ctggaggaag   8880
tgcccaagat tttcgagggt ctgggtcgag atgagaagcg ggcggcgaac gctctgcaga   8940
aagaacagaa agagagtcag aacgtgctgg tggagctgga gggggacaac gcgcgtctgg   9000
ccgtcctcaa acgctgcata gaagtctccc acttcgccta ccccgccctc aacttgccac   9060
ccaaagttat gaaatcggtc atggatcagc tgctcatcaa gagagctgag cccctggatc   9120
ccgaccaccc cgaggcggaa aactcagagg acggaaagcc cgtcgtcagc gacgaggagc   9180
tcgagcggtg gctggaaacc agggaccccc aacagttgca agagaggcgc aagatgatga   9240
tggcggccgt gctggtcacc gtggagctgg aatgcctgca acggtttttc agcgacgtgg   9300
agacgctacg caaaatcggg gaatccctgc actacacctt ccgccagggc tacgtccgcc   9360
aggcctgcaa gatctccaac gtggagctca gcaacctggt ctcctacatg ggcatcctcc   9420
acgagaaccg gctggggcag agcgtgctgc actgcacctt gcaaggcgag gcgcggcggg   9480
actacgtgcg agactgcatc tacctcttcc tcaccctcac ctggcagacc gccatgggcg   9540
```

```
tctggcagca gtgcttggaa gagagaaacc tcaaagagct agacaaactc ctctgccgcc    9600
agcggcgcgc cctgtggtcc ggtttcagcg agcgcacggt cgccagcgct ctggcggaca    9660
tcatcttccc ggagcgcctg atgaaaacct tgcaaaacgg cctgccggat ttcatcagtc    9720
aaagcatttt gcaaaacttc cgctcttttg tcctggaacg ctccgggatc ttgcccgcca    9780
tgagctgcgc gctaccttct gactttgtcc ccctctccta ccgcgagtgc cctcccccac    9840
tgtggagcca ctgctacctc ttccaactgg ccaactttct ggcctaccac tccgacctca    9900
tggaagacgt aagcggagag ggtttactgg agtgccactg ccgctgcaac ctgtgcaccc    9960
cccacagatc gctggcctgc aacaccgagc tactcagcga aacccaggtc ataggtacct   10020
tcgagatcca ggggccccag cagcaagagg gtgcttccgg cttgaagctc actccggcgc   10080
tgtggacctc ggcttactta cgcaaatttg tagccgagga ctaccacgcc cacaaaattc   10140
agttttacga agaccaatct caaccaccga aagccccct cacggcctgc gtcatcaccc   10200
agagcaagat cctggcccaa ttgcaatcca tcaaccaagc gcgccgcgat ttcctttga   10260
aaaagggtcg gggggtgtat ctggaccccc agaccggcga ggaactcaac ccgtccacac   10320
tctccgtcga agcagccccc ccgagacatg ccgcccaagg gaaccgccaa gcagctgatc   10380
gctcggcaga gagcgaagaa gcaagagctg ctccagcagc aggtggagga cgaggaagag   10440
atgtgggaca gccaggcaga ggaggtgtca gaggacgagg aggagatgga aagctgggac   10500
agcctagacg aggaggagga cgagctttca gaggaagagg cgaccgaaga aaaaccacct   10560
gcatccagcg cgccttctct gagccgacag ccgaagcccc ggcccccgac gcccccggcc   10620
ggctcactca aagccagccg taggtgggac gccaccgaat ctccagcggc agcggcaacg   10680
gcagcgggta aggccaaacg cgagcggcgg gggtattgct cctggcgggc ccacaaaagc   10740
agtattgtga actgcttgca acactgcggg ggaaacatct cctttgcccg acgctacctc   10800
ctcttccatc acggtgtggc cttccctcgc aacgttctct attattaccg tcatctctac   10860
agcccctacg aaacgctcgg agaaaaaagc taaggcctcc tccgccgcga ggaaaaactc   10920
cgccgccgct gccgccgcca aggatccacc ggccaccgag gagctgagaa agcgcatctt   10980
tcccactctg tatgctatct ttcagcaaag ccgcgggcag caccctcagc gcgaactgaa   11040
aataaaaaac cgctccttcc gctcgctcac ccgcagctgt ctgtaccaca agagagaaga   11100
ccagctgcag cgcaccctgg acgacgccga agcactgttc agcaaatact gctcagcgtc   11160
tcttaaagac taaaagaccc gcgctttttc cccctcggcc gccaaaaccc acgtcatcgc   11220
cagcatgagc aaggagattc ccacccccta catgtggagc tatcagcccc agatgggcct   11280
ggccgcgggg gccgcccagg actactccag caagatgaac tggctcagcg ccggccccca   11340
catgatctca cgagttaacg gcatccgagc ccaccgaaac cagattctct tagaacaggc   11400
ggcaatcacc gccacacccc ggcgccaact caacccgcct agttggcccg ccgcccaggt   11460
gtatcaggaa aatccccgcc cgaccacagt cctcctgcca cgcgacgcgg aggccgaagt   11520
cctcatgact aactctgggg tacaattagc gggcgggtcc aggtacgcca ggtacagagg   11580
tcgggccgct ccttactctc ccgggagtat aaagagggtg atcattcgag gccgaggtat   11640
ccagctcaac gacgagacgg tgagctcctc aaccggtctc agacctgacg gagtcttcca   11700
gctcggagga gcgggccgct cttccttcac cactcgccag gcctacctga ccctgcagag   11760
ctcttcctcg cagccgcgct ccgggggaat cggcactctc cagttcgtgg aagagttcgt   11820
tccctccgtc tacttcaacc ccttctccgg ctcgcctgga cgctacccgg acgccttcat   11880
tcccaacttt gacgcagtga gtgaatccgt ggacggctac gactgatgac agatggtgcg   11940
```

```
gccgtgagag ctcggctgcg acatctgcat cactgccgtc agcctcgctg ctacgctcgg  12000
gaggcgatcg tcttcagcta ctttgagctg ccggacgagc accctcaggg tccggctcac  12060
gggttgaaac tcgagatcga gaacgcgctc gagtctcgcc tcatcgacac cttcaccgcc  12120
cgacctctcc tggtagaaat cgaacgcggg atcactacca tcaccctgtt ctgcatctgc  12180
cccacgcccg gattacatga agatctgtgc tgtcatcttt gcgctcagtt taataaaaac  12240
tgaacttttt gccgcacctt caacgccacg cgtcgtttct ccaaaagttg tcgacagctc  12300
ttcagtcaga ggtatacgag aaactgttta tttttacaac tctactactt ttctcaccct  12360
taactgctcc tgcactaacg aactaattca gtggttcgcg aacggctcac tctgccaagt  12420
ctttttaat tctgctgttc ttcctgagtt tggctccttt gcgtgtggaa attctacact  12480
agtgggagct atcctgtgtc actgtcacgc gcctgattgt atgcccaaac taattagaac  12540
tctctgtgcc ttaggtgata tatttaaaat gtaagtcagt atcaataaac ttaccttaaa  12600
tttgacagca gtttttggt aacatcattc agcagcacca ctttaccctc ttcccaactc  12660
tcgtatggga cgtgatggtg ggcggcaaac ttcctccaaa ccctaaaaca aatattaata  12720
tccacttcct tgtccttacc cacaatttc atcttttcat agatgaaaag aaccagagtt  12780
gatgaagact tcaaccccgt ctacccttat gactccacat ccactcctgc ggtccccttt  12840
atatcccccc cgtttgtaaa cagcgatggt cttcaggaaa accctcctgg agtcttaagt  12900
ttacgaatag ctaaaccctt gtattttgac atggaaagga aactagcgct ttcacttgga  12960
agaggattgg caattacctc caccggacag ctagaaagca cacagagcgt gcaaaccacc  13020
cctccattag ttgtcaacaa cagcaacacg cttgtcctgc gttattcctc cccgttaggc  13080
ttatcgggtg acaatttaat actaaattgc tccgatcctc tccgcgtagt aaacaacagc  13140
ctgacattca gctacctatc tccacttcgt tttgaaggtg gcagtcttac attcaattac  13200
acatctcccc ttaaactgtt gaacagcagc cttgcgatcg gaataaattc caacaaaggt  13260
ctcggcaatg acagcgatga actttctgtc aaactaacat cagatctaaa gtttaacaac  13320
gatggaaaaa tagcttttgg tatacaaagc ctgtgtacca cccccacagc cgcctctaac  13380
tgtaccgttt ttaccaacgg tgattcttta ctctgtttat gtttaaccaa atgtggagct  13440
cacgtgttag gaagtgtgag tttaaccgga atgcaaggaa ccataacagc catgacacag  13500
aactacatta gtattcaatt tctatttgac aacaatggtg cgttgacttc atcaccgctc  13560
ctcaacaaca acacttgggg tatacggcaa aacgacactt cgtccgctaa ccccgcctac  13620
aatgctcttg catttatgcc taacagcact gtatatgtaa gaggtcaaag tggtgagccc  13680
agaaataact attacaccca aacatacctt aggggaaacg ttaaaaagcc aattatcctt  13740
accgttacct acaactcggc tgcttcaggt tattcactaa cttttaaatg ggatgctgta  13800
gtaacagaaa aatttgccac tccaacatct tctttttgct atattacaga acaataaatt  13860
cctattaccc caccaattcg tttttttcag atgaaacggg ccagagttga tgaagacttc  13920
aacccagtgt acccttatga ccccccatac gctcccgtta tgcccttcat tactccacct  13980
tttacctcct cggatgggtt gcaggaaaaa ccacttggag tgttaagttt aaactacaag  14040
gatcccatta ctacacaaaa tggatctctc acgttgaaaa taggaaacgg cctcactcta  14100
gacaaccagg gacaattaac atcaactgct ggggaagtag agcctccgct cactaatgct  14160
aacaacaaac ttgcactagc ctatagcgaa ccattagcag taaaaagcaa ccgcttaact  14220
ttatcacaca ccgcccccct tgtcgttgct aataattctt tagcgttgca agtttcagaa  14280
```

cctattttta taaatgacga tgacaagcta gccctgcaga cagccgcccc ccttgtaact 14340
aacgctggca cccttcgctt acagagcgcc gcccctttag gattggttga aaatactctt 14400
agactgctgt tttctaaacc cttgtatttg caaaatgatt ttcttgcatt aggcattgaa 14460
cgccccctgg ctatagcagc cgcaggtact ctagcactac aactcactcc tccattaaag 14520
actaacgatg acgggctgac actatccaca gtcgagccat taactgtaaa aaacggaaac 14580
ttaggcttgc aaatatctcg ccctttggtt gttcaaaaca gcagcctttc gcttgctatt 14640
acccccccgc tgcgtctatt taacagcgac cccgttcttg gtttgggctt tacttttccc 14700
ctagccgtga cagacaacct actctcctta aacatgggag acggtgttaa actaacctat 14760
aataaactaa cagccaattt gggtagggat ttacaatttg aaaacggtgc cattgccgta 14820
acgcttactg ccgaatcacc tttgcaatac actaacaaac ttcaactgaa tattggagct 14880
ggccttcgtt acaatggagc cagcagaaaa ctagatgtaa acattaacca aaataagggc 14940
ttaacttggg acaacgatgc agttattccc aaattaggat caggtttaca attcgaccct 15000
aatggtaaca tcgctgttat ccctgaaacc gtaaagccgc aaacgttatg gacaactgca 15060
gatccatcgc ctaactgctc agtgtaccag gacttggacg ccaggctgtg gctcgctctt 15120
gttaaaagtg gtgacatggt tcatggaagc attgctctaa aagccctaaa aggaacgttg 15180
ctaaatccta cagcaagcta catctccatt gtgatatatt tttacagcaa cggagtcagg 15240
cgtaccaact atcccacgtt tgacaacgaa ggcaccttag ctaacagcgc tacctgggga 15300
taccgagagg ggcaatctgc taacactaat gtaaccaatg ccactgaatt tatgcccagc 15360
tcaaccaggt accccgtgaa taaaggagac aatattcaga atcaatcttt ttcatacacc 15420
tgtatcaaag gagatttcgc tatgcctgtc ccgttccgtg taacatataa tcatgccctg 15480
gaaggatact cccttaagtt cacctggcgc gttgtagcca accaagcttt tgatattcct 15540
tgctgttcct tttcatacat cacagaataa accacttttt aaaatttttc tttttatttt 15600
acacgcacag taaggcttcc tcccccttc catttgacag catacaccag cctctccccc 15660
ttcatggcag taaactgctg cgagccagtc cggtatttgg gagttaaaat ccaaacagtc 15720
tctttggtga tgaaacgtcg atccgtgatg gacacaaatc cctggggcag gttttccagc 15780
gtttcggtaa aaaactgcac accgccctac aaaacaaaca ggttcaggct ctccatgggt 15840
tatctccccg atcaaactca gacagggtaa aggtgcggtg atgttccact aaaccacgca 15900
ggtggcgctg tctgaacctc tcggtgcgac tcctgtgagg ctggtaagaa gttagattgt 15960
ccagtagcct cacagcatgg atgatcagtt tacgtgtacg tctggcgcaa cagcgcatct 16020
gaatctcact gagattccgg caagaatcgc acaccatcac aatcaggttg ttcatgatcc 16080
catagctgaa cacgctccag ccaaagctca ttcgctccaa cagcgccacc gcgtgtccgt 16140
ccaaccttac tttaacataa atcaggtgtc tgccgcgtac aaacatacta cccgcataca 16200
gaacttcccg gggcaaaccc ctgttcacca cctgcctgta ccagggaaac ctcacattta 16260
tcagggagcc atagatagcc attttaaacc aattagctaa caccgcccca ccagctctac 16320
actgaagaga accgggagag ttacaatgac agtgaataat ccatctctca taacccctga 16380
tggtctgatg gaaatccagc acaccgccct acaaaacaaa caggttcagg ctctccatgg 16440
gttatctccc cgatcaaact cagacagggt aaaggtgcgg tgatgttcca ctaaaccacg 16500
caggtggcgc tgtctgaacc tctcggtgcg actcctgtga ggctggtaag aagttagatt 16560
gtccagtagc ctcacagcat ggatgatcag tttacgtgta cgtctggcgc aacagcgcat 16620
ctgaatctca ctgagattcc ggcaagaatc gcacaccatc acaatcaggt tgttcatgat 16680

```
cccatagctg aacacgctcc agccaaagct cattcgctcc aacagcgcca ccgcgtgtcc 16740
gtccaacctt actttaacat aaatcaggtg tctgccgcgt acaaacatac tacccgcata 16800
cagaacttcc cggggcaaac ccctgttcac cacctgcctg taccagggaa acctcacatt 16860
tatcagggag ccatagatag ccattttaaa ccaattagct aacaccgccc caccagctct 16920
acactgaaga gaaccgggag agttacaatg acagtgaata atccatctct cataacccct 16980
gatggtctga tggaaatcca gatctaacgt ggcacagcag atacacactc tcatatacat 17040
tttcatcaca tggttttccc aggccgttaa aatacaatcc caatacacgg gccactcctg 17100
cagtacaata aagctaatac aagatggtat actcctcacc tcactaacat tgtgcatgtt 17160
catattttca cattctaagt accgagagtt ctcctctaca acagcactgc tgcggtcctc 17220
acaaggtggt agctggtgac gatcgtaagg agccagtctg caacgatacc gtctgtcgcg 17280
ctgcatcgta gaccagagac cgacgcacct cctggtactg ccccgtctta ccgcgtaaac 17340
agccacgaaa aattcgagct aaaatccacc caacagccta tagctatata tacactccgc 17400
ccaatgacgc taataccgca ccacccaccg ccaaagttca cccacaccca cgaaacccgc 17460
gaaaatccag cgccgtcagc acttccgcaa tttcagtctc acaacgtcac ttccgcgcgc 17520
cttttcacat tcccacaccc gcccacaaac cccgcgtcac cgcccgtcac cccggccccg 17580
cctcgctcct ccccgctcat tatcatattg gcacgtttcc agaataaggt atattattga 17640
tgatgttaat taattcgaac ccataatacc cataatagct gtttgccatc gaccaattct 17700
cccatattcc cggttgaatt gtagtacatg agaccaataa agttatttga agacgaaagg 17760
gcctcgtgat acgcctattt ttataggtta atgtcatgat aataatggtt tcttagacgt 17820
caggtggcac ttttcgggga aatgtgcgcg gaacccctat ttgtttattt ttctaaatac 17880
attcaaatat gtatccgctc atgagacaat aaccctgata aatgcttcaa taatattgaa 17940
aaaggaagag tatgagtatt caacatttcc gtgtcgccct tattcccttt tttgcggcat 18000
tttgccttcc tgtttttgct cacccagaaa cgctggtgaa agtaaaagat gctgaagatc 18060
agttgggtgc acgagtgggt tacatcgaac tggatctcaa cagcggtaag atccttgaga 18120
gttttcgccc cgaagaacgt tttccaatga tgagcacttt taaagttctg ctatgtggcg 18180
cggtattatc ccgtgttgac gccgggcaag agcaactcgg tcgccgcata cactattctc 18240
agaatgactt ggttgagtac tcaccagtca cagaaaagca tcttacggat ggcatgacag 18300
taagagaatt atgcagtgct gccataacca tgagtgataa cactgcggcc aacttacttc 18360
tgacaacgat cggaggaccg aaggagctaa ccgctttttt gcacaacatg ggggatcatg 18420
taactcgcct tgatcgttgg gaaccggagc tgaatgaagc cataccaaac gacgagcgtg 18480
acaccacgat gcctgcagca atggcaacaa cgttgcgcaa actattaact ggcgaactac 18540
ttactctagc ttcccggcaa caattaatag actggatgga ggcggataaa gttgcaggac 18600
cacttctgcg ctcggccctt ccggctggct ggtttattgc tgataaatct ggagccggtg 18660
agcgtgggtc tcgcggtatc attgcagcac tggggccaga tggtaagccc tcccgtatcg 18720
tagttatcta cacgacgggg agtcaggcaa ctatggatga acgaaataga cagatcgctg 18780
agataggtgc ctcactgatt aagcattggt aactgtcaga ccaagtttac tcatatatac 18840
tttagattga tttaaaactt catttttaat ttaaaaggat ctaggtgaag atcctttttg 18900
ataatctcat gaccaaaatc ccttaacgtg agttttcgtt ccactgagcg tcagaccccg 18960
tagaaaagat caaaggatct tcttgagatc cttttttttct gcgcgtaatc tgctgcttgc 19020
```

aaacaaaaaa accaccgcta ccagcggtgg tttgtttgcc ggatcaagag ctaccaactc 19080
tttttccgaa ggtaactggc ttcagcagag cgcagatacc aaatactgtc cttctagtgt 19140
agccgtagtt aggccaccac ttcaagaact ctgtagcacc gcctacatac ctcgctctgc 19200
taatcctgtt accagtggct gctgccagtg gcgataagtc gtgtcttacc gggttggact 19260
caagacgata gttaccggat aaggcgcagc ggtcgggctg aacggggggt tcgtgcacac 19320
agcccagctt ggagcgaacg acctacaccg aactgagata cctacagcgt gagctatgag 19380
aaagcgccac gcttcccgaa gggagaaagg cggacaggta tccggtaagc ggcagggtcg 19440
gaacaggaga gcgcacgagg gagcttccag ggggaaacgc ctggtatctt tatagtcctg 19500
tcgggtttcg ccacctctga cttgagcgtc gatttttgtg atgctcgtca ggggggcgga 19560
gcctatggaa aaacgccagc aacgcggcct ttttacggtt cctggccttt tgctggcctt 19620
gaagctgtcc ctgatggtcg tcatctacct gcctggacag catggcctgc aacgcgggca 19680
tcccgatgcc gccggaagcg agaagaatca taatggggaa ggccatccag cctcgcgtcg 19740
atggcaaaca gctattatgg gtattatggg ttcgaattaa t 19781

<210> SEQ ID NO 39
<211> LENGTH: 8764
<212> TYPE: DNA
<213> ORGANISM: Artificial Sequence
<220> FEATURE:
<223> OTHER INFORMATION: Synthetic oligonucleotide
sAdApt4287.E1btg.Empty

<400> SEQUENCE: 39
attaattcga acccataata cccataatag ctgtttgcca tcgacgcgag gctggatggc 60
cttccccatt atgattcttc tcgcttccgg cggcatcggg atgcccgcgt tgcaggccat 120
gctgtccagg caggtagatg acgaccatca gggacagctt caaggccagc aaaaggccag 180
gaaccgtaaa aaggccgcgt tgctggcgtt tttccatagg ctccgccccc ctgacgagca 240
tcacaaaaat cgacgctcaa gtcagaggtg gcgaaacccg acaggactat aaagatacca 300
ggcgtttccc cctggaagct ccctcgtgcg ctctcctgtt ccgaccctgc cgcttaccgg 360
atacctgtcc gcctttctcc cttcgggaag cgtggcgctt tctcatagct cacgctgtag 420
gtatctcagt tcggtgtagg tcgttcgctc caagctgggc tgtgtgcacg aaccccccgt 480
tcagcccgac cgctgcgcct tatccggtaa ctatcgtctt gagtccaacc cggtaagaca 540
cgacttatcg ccactggcag cagccactgg taacaggatt agcagagcga ggtatgtagg 600
cggtgctaca gagttcttga agtggtggcc taactacggc tacactagaa ggacagtatt 660
tggtatctgc gctctgctga agccagttac cttcggaaaa agagttggta gctcttgatc 720
cggcaaacaa accaccgctg gtagcggtgg tttttttgtt tgcaagcagc agattacgcg 780
cagaaaaaaa ggatctcaag aagatccttt gatcttttct acggggtctg acgctcagtg 840
gaacgaaaac tcacgttaag ggattttggt catgagatta tcaaaaagga tcttcaccta 900
gatcctttta aattaaaaat gaagttttaa atcaatctaa agtatatatg agtaaacttg 960
gtctgacagt taccaatgct taatcagtga ggcacctatc tcagcgatct gtctatttcg 1020
ttcatccata gttgcctgac tccccgtcgt gtagataact acgatacggg agggcttacc 1080
atctggcccc agtgctgcaa tgataccgcg agacccacgc tcaccggctc cagatttatc 1140
agcaataaac cagccagccg gaagggccga gcgcagaagt ggtcctgcaa ctttatccgc 1200
ctccatccag tctattaatt gttgccggga agctagagta agtagttcgc cagttaatag 1260

-continued

```
tttgcgcaac gttgttgcca ttgctgcagg catcgtggtg tcacgctcgt cgtttggtat   1320
ggcttcattc agctccggtt cccaacgatc aaggcgagtt acatgatccc ccatgttgtg   1380
caaaaaagcg gttagctcct tcggtcctcc gatcgttgtc agaagtaagt tggccgcagt   1440
gttatcactc atggttatgg cagcactgca taattctctt actgtcatgc catccgtaag   1500
atgcttttct gtgactggtg agtactcaac caagtcattc tgagaatagt gtatgcggcg   1560
accgagttgc tcttgcccgg cgtcaacacg ggataatacc gcgccacata gcagaacttt   1620
aaaagtgctc atcattggaa aacgttcttc ggggcgaaaa ctctcaagga tcttaccgct   1680
gttgagatcc agttcgatgt aacccactcg tgcacccaac tgatcttcag catcttttac   1740
tttcaccagc gtttctgggt gagcaaaaac aggaaggcaa aatgccgcaa aaaagggaat   1800
aagggcgaca cggaaatgtt gaatactcat actcttcctt tttcaatatt attgaagcat   1860
ttatcagggt tattgtctca tgagcggata catatttgaa tgtatttaga aaaataaaca   1920
aataggggtt ccgcgcacat ttccccgaaa agtgccacct gacgtctaag aaaccattat   1980
tatcatgaca ttaacctata aaaataggcg tatcacgagg ccctttcgtc ttcaagaatt   2040
ggtcgatggc aaacagctat tatgggtatt atgggttcga attaattaac atcatcaata   2100
atatacctta ttctggaaac gtgccaatat gataatgagc ggggaggagc gaggcggggc   2160
cggggtgacg tgcggtgacg cggggtgacg cggggtggcg cgagggcggg gcgggagtgg   2220
ggaggcgctt agtttttacg tatgcggaag gaggttttat accggaagtt gggtaatttg   2280
ggcgtatatt tgtaagtttt gtgtaatttg gcgcgaaaac cgggtaatga ggaagttgag   2340
gttaatatgt actttttatg actgggcgga atttctgctg atcagcagtg aactttgggc   2400
gctgacgggg aggtttcgct acgtggcagt accacgagaa ggctcaaagg tcccatttat   2460
tgtactcctc agcgttttcg ctgggtattt aaacgctgtc agatcatcaa gaggccactc   2520
ttgagtgccg gcgagtagag ttttctcctc cgcgctgccg cgatgaggct ggttcccgag   2580
atgtacggtg ttttctgcag cgagacggcc cggaactcag atgagctgct taatacagat   2640
ctgctggatg ttcccaactc gcctgtggct tcgcctccgt cgcttcatga tcttttcgat   2700
gtggaagtgg atccaccgca agatcccaac gaggacgcgg taaacagtat gttccctgaa   2760
tgtctgtttg aggcggctga ggagggttct cacagcagtg aagagagcag acggggagag   2820
gaactggact tgaaatgcta cgaggaatgt ctgccttcta gcgattctga aacggaacag   2880
acagggggag acggctgtga gtcggcaatg aaaaatgaac ttgtattaga ctgtccagaa   2940
catcctggtc atggctgccg tgcctgtgct tttcatagaa atgccagcgg aaatcctgag   3000
actctatgtg ctctgtgtta tctgcgcctt accagcgatt ttgtatacag taagtaaagt   3060
gttttcattg gcgtacggta ggggattcgt tgaagtgctt tgtgacttat tatgtgtcat   3120
tatttctagg tgacgtgtcc gacgtggaag gggaaggaga tagatcaggg gctgctaatt   3180
ctccttgcac tttgggggct gtggttccag ctggcattat taaacccgtg gcggtcagag   3240
tctcaggcag acggtgcgca gttgaaaaaa ttgaagactt gctgcaggaa gaacagacgc   3300
aacctttgga cctgtccatg aaacgcccta agctgactta agtgtgttta ttgtatgcaa   3360
taaaagtgtt gatctttgaa ctgtgtttat gtgttgggtg tgtctgtggg tatataagca   3420
ggtggatggg aagtgagagc acagctgctt cagatggatc tgctaggaga cctaagagaa   3480
tttggcgtgg ttcggcgctt gttggagttg gcctctgaca gaacttccaa gttttggagg   3540
ttttgttttg gctcaacgct tagcaacgtg ctatataggg tcaagaagga gcaggagacg   3600
cagtttgcta ggctgttggc cgatactcct ggagtttttg tggctctgga tctaggccat   3660
```

cactctcttt tccaagagaa aattatcaaa aacctaactt ttacgtctcc tggccgcacg 3720
gttgcttccg ctgcctttat tacctatatt ttggatcaat ggagcaacag cggcagccac 3780
ctgtcgtggg agtacatgct ggattacatg tcgatggcgc tgtggagggc catgctgcgg 3840
aggagggttt gcatttactt gcgggcgcag cctccgcggc tgggccgagt ggaggaggag 3900
gacgagccgg gagagatgga gaacctgagg gccgggctgg accctccaac ggaggactag 3960
gtgctgagga tgatcctgaa gaggggacta gtgggggagc taggaaaaag caaaaaactg 4020
agcctgaacc tagaaacttt ttgaatgagt tgactgtaag cctgatgaat cggcagcgtc 4080
ctgagacggt gttttgggct gagttggagg atgagttcaa gaaggggga ttgaacctct 4140
tgtacaagta tgggtttgag cagttgaaaa ctcactggtt ggagccgtgg gaggacatgg 4200
aaatggctct agacaccttt gctaaagtgg ctctgcggcc ggataaagtt tacactattc 4260
gccgcactgt taatataaaa aagagtgttt atgttatcgg tcatggagct ctggtgcagg 4320
tgcagacccc agaccgggtg gctttcaatt gcggcatgca gagtttgggc cccggggtga 4380
taggtttgaa tggagttaca tttcaaaatg tcaggtttac tggtgatgat tttaatggct 4440
ctgtgtttgt gactagcacc cagctaaccc tccacggtgt ttactttttt aactttaaca 4500
atacatgtgt ggagtcatgg ggtagggtgt ctctgagggg ctgcagtttt catggttgct 4560
ggaaggcggt ggtgggaaga attaaaagtg tcatgtctgt gaagaaatgc atatttgaac 4620
gctgtgtgat agctctagca gtagaggggt acggacggat caggaataac gccgcatctg 4680
agaatggatg ttttcttttg ctgaaaggta cggccagcgt taagcataat atgatttgcg 4740
gcagcggcct gtgcccctcg cagctcttaa cttgcgcaga tggaaactgt cacaccttgc 4800
gcaccgtgca catagtgtcc cactcgcgcc gcacctggcc aacatttgag cacaatatgc 4860
tcatgcgttg cgccgttcac ctaggtgcta gacgcggcgt gtttatgcct tatcaatgta 4920
actttagtca tactaagatt ttgctggaaa ctgattcctt ccctcgagta tgtttcaatg 4980
gggtgtttga catgtcaatg gaacttttta aagtgataag atatgatgaa accaagtctc 5040
gttgtcgctc atgtgaatgc ggagctaatc atttgaggtt gtatcctgta accctgaacg 5100
tcaccgagga gctgaggacg gaccaccaca tgctgtcttg cctgcgtacc gactatgaat 5160
ccagtgatga ggagtgaggt gaggggcgga gccacaaagg gtataaaggg gcatgaaggg 5220
tggacggtcg actggtcaat attggccatt agccatatta ttcattggtt atatagcata 5280
aatcaatatt ggctattggc cattgcatac gttgtatcca tatcataata tgtacattta 5340
tattggctca tgtccaacat taccgccatg ttgacattga ttattgacta gttattaata 5400
gtaatcaatt acggggtcat tagttcatag cccatatatg gagttccgcg ttacataact 5460
tacggtaaat ggcccgcctg gctgaccgcc caacgacccc cgcccattga cgtcaataat 5520
gacgtatgtt cccatagtaa cgccaatagg gactttccat tgacgtcaat gggtggagta 5580
tttacggtaa actgcccact tggcagtaca tcaagtgtat catatgccaa gtacgccccc 5640
tattgacgtc aatgacggta aatggcccgc ctggcattat gcccagtaca tgaccttatg 5700
ggactttcct acttggcagt acatctacgt attagtcatc gctattacca tggtgatgcg 5760
gttttggcag tacatcaatg ggcgtggata gcggtttgac tcacggggat ttccaagtct 5820
ccaccccatt gacgtcaatg ggagtttgtt ttggcaccaa aatcaacggg actttccaaa 5880
atgtcgtaac aactccgccc cattgacgca aatgggcggt aggcgtgtac ggtgggaggt 5940
ctatataagc agagctcgtt tagtgaaccg tcagatcgcc tggagacgcc atccacgctg 6000

-continued

```
ttttgacctc catagaagac accgggaccg atccagcctc cgcggccggg aacggtgcat   6060

tggaagcttg gtaccggtga attcgctagc gttaacggat cctctagacg agatccgaac   6120

ttgtttattg cagcttataa tggttacaaa taaagcaata gcatcacaaa tttcacaaat   6180

aaagcatttt tttcactgca ttctagttgt ggtttgtcca aactcatcaa tgtatcttat   6240

catgtctaga tccttaagga atgcggagct aatcatttga ggttgtatcc tgtaaccctg   6300

aacgtcaccg aggagctgag gacggaccac cacatgctgt cttgcctgcg taccgactat   6360

gaatccagtg atgaggagtg aggtgagggg cggagccaca aagggtataa aggggcatga   6420

agggtggacg cggtgtttca aaatgagcgg gacgacggac ggcaatgcgt ttgagggggg   6480

agtgttcagc ccatatctga catctcgtct tccttcctgg gcaggagtgc gtcagaatgt   6540

agtgggctcc accgtggacg gacggccggt cgcccctgca aattccgcca ccctcaccta   6600

tgccaccgtg ggatcatcgt tggacactgc cgcggcagct gccgcttctg ctgccgcttc   6660

tactgctcgc ggcatggcgg ctgattttgg actatataac caactggcca ctgcagctgt   6720

ggcgtctcgg tctctggttc aagaagatgc cctgaatgtg atcttgactc gcctggagat   6780

catgtcacgt cgcctggacg aactggctgc gcagatatcc caagctaacc ccgataccgc   6840

ttcagaatct taaataaaga caaacaaatt tgttgaaaag taaaatggct ttatttgttt   6900

tttttggctc ggtaggctcg ggtccacctg tctcggtcgt taaggacttt gtgtatgttt   6960

tccaaaacac ggtacagatg ggcttggatg ttcaagtaca tgggcatgag gccatctttg   7020

gggtggagat aggaccactg aagagcgtca tgttccgggg tggtattgta aatcacccag   7080

tcgtagcagg gtttttgagc gtggaactgg aatatgtcct tcaggagcag gctaatggcc   7140

aagggcagcc ccttagtgta ggtgtttaca aagcggttga gctgggaggg atgcatgcgg   7200

ggggagatga tatgcatctt ggcttggatt ttgaggttag ctatgttacc acccaggtct   7260

ctgcgggggt tcatgttatg aaggaccacc agcacggtgt agccggtgca cttggggaac   7320

ttgtcatgca gtttggaggg gaaggcgtgg aagaatttag atacccccttt gtgccccccct   7380

aggttttcca tgcactcatc cataataatg gcaatgggac ccctggcggc cgctttagca   7440

aacacgtttt gggggttgga aacatcatag ttttgctcta gagtgagctc atcataggcc   7500

atctttacaa agcggggtag gagggtgccc gactgggggga tgatagttcc atctgggcct   7560

ggagcgtagt tgccctcaca gatctgcatc tcccaggcct taatttccga ggggggggatc   7620

atgtccacct ggggggcgat aaagaacacg gtttctggcg gggattgat gagctgggtg   7680

gaaagcaagt tacgcaatag ctgggatttg ccgcaaccgg tggggccgta gatgaccccg   7740

atgacgggtt gcagctggta gttcagagag gaacagctgc cgtcggggcg caggaggggg   7800

gccacatcgt tcatcatgct tctgacatgt ttattttcac tcactaagtt ttgcaagagc   7860

ctctccccac ccagggataa gagttcttcc aggctgttga agtgtttcag cggtttcagg   7920

ccgtcggcca tgggcatctt ttcaagcgac tgacgaagca agtacagtcg gtcccagagc   7980

tcggtgacgt gctctatgga atctcgatcc agcagacttc ttggttgcgg gggttgggcc   8040

gactttcgct gtagggcacc agccggtggg cgtccagggc cgcgagggtt ctgtccttcc   8100

agggtctcag cgttcgggtg agggtggtct cggtgacggt gaagggatga gccccgggct   8160

gggcgcttgc gagggtgcgc ttcaggctca tcctgctggt gctgaagcgg gcgtcgtctc   8220

cctgtgagtc ggccagatag caacgaagca tgaggtcgta gctgagggac tcggccgcgt   8280

gtcccttggc gcgcagcttt cccttggaaa cgtgctgaca tttggtgcag tgcagacact   8340

tgagggcgta gagttttggg gccaggaaga ccgactcggg cgagtaggcg tcggctccgc   8400
```

actgagcgca gacggtctcg cactccacca gccacgtgag ctcgggttta gcgggatcaa 8460
aaaccaagtt gcctccattt tttttgatgc gtttcttacc ttgcgtctcc atgagtctgt 8520
gtcccgcttc cgtgacaaaa aggctgtcgg tgtccccgta gaccgacttg agggggcgat 8580
cttccaaagg tgttccgagg tcttccgcgt acaggaactg ggaccactcc gagacaaagg 8640
ctcgggtcca ggctaacacg aaggaggcga tctgcgaggg gtatctgtcg ttttcaatga 8700
gggggtccac cttttccagg gtgtgcagac acaggtcgtc ctcctccgcg tccacgaagt 8760
taat 8764

<210> SEQ ID NO 40
<211> LENGTH: 6091
<212> TYPE: DNA
<213> ORGANISM: Artificial Sequence
<220> FEATURE:
<223> OTHER INFORMATION: Synthetic oligonucleotide sAdApt4310A.Empty

<400> SEQUENCE: 40
catcatcaat aatatacctt attctggaaa cgtgccaata tgataatgag cggggaggag 60
cgaggcgggg ccggggtgac gtgcggtgac gcggggtgac gcggggtggc gcgagggcgg 120
ggcgggtgtg cggaggcgct tagtttttac gtatgcggaa ggaggtttta taccggaagt 180
tgggtaattt gggcgtatac ttgtaagttt tgtgtagttt ggcgcgaaaa ccgggtaatg 240
aggaagttga ggttaatatg tactttttat gactgggcgg aatttctgct gatcagcagt 300
gaactttggg cgctgacggg gaggtttcgc tacgtggcag taccacgaga aggctcaaag 360
gtcccattta ttgtactcct cagcgttttc gctgggtatt taaacgctgt cagatcatca 420
agaggccact cttgagtgcc ggcgagtaga gttttctcct cgtcgactgg tcaatattgg 480
ccattagcca tattattcat tggttatata gcataaatca atattggcta ttggccattg 540
catacgttgt atccatatca taatatgtac atttatattg gctcatgtcc aacattaccg 600
ccatgttgac attgattatt gactagttat taatagtaat caattacggg gtcattagtt 660
catagcccat atatggagtt ccgcgttaca taacttacgg taaatggccc gcctggctga 720
ccgcccaacg acccccgccc attgacgtca ataatgacgt atgttcccat agtaacgcca 780
atagggactt tccattgacg tcaatgggtg gagtatttac ggtaaactgc ccacttggca 840
gtacatcaag tgtatcatat gccaagtacg ccccctattg acgtcaatga cggtaaatgg 900
cccgcctggc attatgccca gtacatgacc ttatgggact ttcctacttg gcagtacatc 960
tacgtattag tcatcgctat taccatggtg atgcggtttt ggcagtacat caatgggcgt 1020
ggatagcggt ttgactcacg gggatttcca agtctccacc ccattgacgt caatgggagt 1080
ttgttttggc accaaaatca acgggacttt ccaaaatgtc gtaacaactc cgccccattg 1140
acgcaaatgg gcggtaggcg tgtacggtgg gaggtctata taagcagagc tcgtttagtg 1200
aaccgtcaga tcgcctggag acgccatcca cgctgttttg acctccatag aagacaccgg 1260
gaccgatcca gcctccgcgg ccgggaacgg tgcattggaa gcttggtacc ggtgaattcg 1320
ctagcgttaa cggatcctct agacgagatc cgaacttgtt tattgcagct tataatggtt 1380
acaaataaag caatagcatc acaaatttca caaataaagc atttttttca ctgcattcta 1440
gttgtggttt gtccaaactc atcaatgtat cttatcatgt ctagatcctt aaggacatgt 1500
caatggaact gtttaaagtg ataagatatg atgaatccaa gtctcgttgt cgcccatgtg 1560
aatgcggagc taatcatttg aggttgtatc ctgtaactct gaacgtcacc gaggagctga 1620

-continued gaacggacca ccacatgctg tcttgcctgc gcactgacta tgaatccagc gacgaggagt 1680
gaggtgaggg gcggagccaa acgggtataa aggggcgtga ggggtcggtg cggtgtttca 1740
aaatgagcgg gacgacggac ggcaatgcgt ttgagggggg agtgttcagc ccatatctga 1800
catctcgtct tccttcctgg gcaggagtgc gtcagaatgt agtgggatcc accgtggacg 1860
gacgaccggt ggctcctgca aattccgcca ccctcaccta tgccaccgtg ggatcatcgt 1920
tggacactgc cgcggcagct gccgcttctg ctgccgcttc tactgctcgc ggcatggcgg 1980
ctgattttgg actgtataac caactggcca ctgcagctgt ggcgtctcgg tccctggttc 2040
aagaagatgc cctgaatgtg attctgactc gcctggagat catgtcacgc cgcctggacg 2100
aactggctgc gcagatatcc tcaactaacc ccgataccac ttcagaacct taaataaaga 2160
caaacaaatt tgttgaaaag taaaatggct ttatttgttt tttttggctc ggtaggctcg 2220
ggtccacctg tcccggtcgt taaggacctt gtgtatgttt tccaagaccc ggtacagatg 2280
ggcttggatg ttcaagtaca tgggcatgag gccatctcgg gggtggagat aggaccattg 2340
cagagcgtca tgctccgggg tggtgttgta aataacccag tcgtagcagg gtttctgagc 2400
gtggaactgg aagatgtcct ttaggagcag gctgatggcc aagggcagcc ccttagtgta 2460
ggtgttaaca aagcggttaa gctgggaggg atgcatgcgg ggggagatga tatgcatctt 2520
ggcttgaatt ttgaggttag ctatgttacc acctaggtcc ctgcgggggt tcatgttatg 2580
aaggaccacc agcacggtgt agccggtgca cttggggaac ttgtcatgca gtttggaggg 2640
gaaggcgtgg aagaatttag agaccccctt gtggcctcct aggttttcca tgcactcatc 2700
cataatgatg gcaatgggac ccctggcggc cgctttggca aacacgtttt gggggttgga 2760
aacatcatag ttttgctcta gagtgagctc atcataggcc atcttaacaa agcggggtag 2820
gagggtgccc gactggggga tgatagttcc atctgggcct ggggcgtagt tgccctcaca 2880
aatctgcatt tcccaggcct taatttccga ggggggtatc atgtccacct ggggggcgat 2940
aaagaacacg gtttctggcg gggggattgat gagctgggtg gaaagcaagt tacgcaacag 3000
ttgggatttg ccgcaaccgg tgggaccgta gatgaccccg atgacgggtt gcagctggta 3060
gttgagagag gaacagctgc cgtcggggcg caggaggggg gctacatcgt tcatcatgct 3120
tctgacatgt ttattttcac tcactaagtt ttgcaagagc ctctccccac ccagggataa 3180
gagttcttcc aggctgttga agtgtttcag cggtttcagg ccgtctgcca tgggcatctt 3240
ttcaagcgac tgacgaagca agtacagtcg gtcccagagc tcggtgacgt gctctatgga 3300
atctcgatcc agcagacttc ttggttgcgg gggttgggcc gactttcgct gtagggcacc 3360
agccggtggg cgtccagggc cgcgagggtt ctgtccttcc agggtctcag cgttcgggtg 3420
agggtggtct cggtgacggt gaagggatga gccccgggct gggcgcttgc gagggtgcgc 3480
ttcaggctca tcctgctggt gctgaagcgg gcgtcgtctc cctgtgagtc ggccagatag 3540
caacgaagca tgaggtcgta gctgagggac tcggccgcgt gtcccttggc gcgcagcttt 3600
cccttggaaa cgtgctgaca tttggtgcag tgcagacact tgagggcgta gagtttgggg 3660
gccaggaaga ccgactcgga cgagtaggcg tcggctccgc actgagcgca gacggtctcg 3720
cactccacca gccacgtgag ctcgggttta gcgggatcaa aaaccaagtt gcctccattt 3780
tttttgatgc gtttcttacc ttgcgtctcc atgagtctgt gtcccgcttc cgtgacaaaa 3840
aggctgtcgg tgtccccgta gaccgacttg agggggcgat cttccaaagg tgttccgaga 3900
tcttccgcgt acaggaactg ggaccactcc gagacaaagg ctcgggtcca ggctaacacg 3960
aaggaggcga tctgcgaggg gtatctgtcg ttttcaatga ggttaattaa ttcgaaccca 4020
taatacccat aatagctgtt tgccatcgac gcgaggctgg atggccttcc ccattatgat 4080
tcttctcgct tccggcggca tcgggatgcc cgcgttgcag gccatgctgt ccaggcaggt 4140
agatgacgac catcagggac agcttcaagg ccagcaaaag gccaggaacc gtaaaaaggc 4200
cgcgttgctg gcgtttttcc ataggctccg cccccctgac gagcatcaca aaaatcgacg 4260
ctcaagtcag aggtggcgaa acccgacagg actataaaga taccaggcgt ttccccctgg 4320
aagctccctc gtgcgctctc ctgttccgac cctgccgctt accggatacc tgtccgcctt 4380
tctcccttcg ggaagcgtgg cgctttctca tagctcacgc tgtaggtatc tcagttcggt 4440
gtaggtcgtt cgctccaagc tgggctgtgt gcacgaaccc cccgttcagc ccgaccgctg 4500
cgccttatcc ggtaactatc gtcttgagtc caacccggta agacacgact tatcgccact 4560
ggcagcagcc actggtaaca ggattagcag agcgaggtat gtaggcggtg ctacagagtt 4620
cttgaagtgg tggcctaact acggctacac tagaaggaca gtatttggta tctgcgctct 4680
gctgaagcca gttaccttcg gaaaaagagt tggtagctct tgatccggca aacaaaccac 4740
cgctggtagc ggtggttttt ttgtttgcaa gcagcagatt acgcgcagaa aaaaaggatc 4800
tcaagaagat cctttgatct tttctacggg gtctgacgct cagtggaacg aaaactcacg 4860
ttaagggatt ttggtcatga gattatcaaa aaggatcttc acctagatcc ttttaaatta 4920
aaaatgaagt tttaaatcaa tctaaagtat atatgagtaa acttggtctg acagttacca 4980
atgcttaatc agtgaggcac ctatctcagc gatctgtcta tttcgttcat ccatagttgc 5040
ctgactcccc gtcgtgtaga taactacgat acgggagggc ttaccatctg gccccagtgc 5100
tgcaatgata ccgcgagacc cacgctcacc ggctccagat ttatcagcaa taaaccagcc 5160
agccggaagg gccgagcgca gaagtggtcc tgcaacttta tccgcctcca tccagtctat 5220
taattgttgc cgggaagcta gagtaagtag ttcgccagtt aatagtttgc gcaacgttgt 5280
tgccattgct gcaggcatcg tggtgtcacg ctcgtcgttt ggtatggctt cattcagctc 5340
cggttcccaa cgatcaaggc gagttacatg atcccccatg ttgtgcaaaa aagcggttag 5400
ctccttcggt cctccgatcg ttgtcagaag taagttggcc gcagtgttat cactcatggt 5460
tatggcagca ctgcataatt ctcttactgt catgccatcc gtaagatgct tttctgtgac 5520
tggtgagtac tcaaccaagt cattctgaga atagtgtatg cggcgaccga gttgctcttg 5580
cccggcgtca acacgggata ataccgcgcc acatagcaga actttaaaag tgctcatcat 5640
tggaaaacgt tcttcggggc gaaaactctc aaggatctta ccgctgttga gatccagttc 5700
gatgtaaccc actcgtgcac ccaactgatc ttcagcatct tttactttca ccagcgtttc 5760
tgggtgagca aaaacaggaa ggcaaaatgc cgcaaaaaag ggaataaggg cgacacggaa 5820
atgttgaata ctcatactct tcctttttca atattattga agcatttatc agggttattg 5880
tctcatgagc ggatacatat ttgaatgtat ttagaaaaat aaacaaatag gggttccgcg 5940
cacatttccc cgaaaagtgc cacctgacgt ctaagaaacc attattatca tgacattaac 6000
ctataaaaat aggcgtatca cgaggccctt tcgtcttcaa gaattggtcg atggcaaaca 6060
gctattatgg gtattatggg ttcgaattaa t 6091

<210> SEQ ID NO 41
<211> LENGTH: 16580
<212> TYPE: DNA
<213> ORGANISM: Artificial Sequence
<220> FEATURE:
<223> OTHER INFORMATION: Synthetic oligonucleotide pBr/sAd4310A.pIX-pV -continued

<400> SEQUENCE: 41

```
attaagacat gtcaatggaa ctgtttaaag tgataagata tgatgaatcc aagtctcgtt     60
gtcgcccatg tgaatgcgga gctaatcatt tgaggttgta tcctgtaact ctgaacgtca    120
ccgaggagct gagaacggac caccacatgc tgtcttgcct gcgcactgac tatgaatcca    180
gcgacgagga gtgaggtgag gggcggagcc aaacgggtat aaaggggcgt gaggggtcgg    240
tgcggtgttt caaaatgagc gggacgacgg acggcaatgc gtttgagggg ggagtgttca    300
gcccatatct gacatctcgt cttccttcct gggcaggagt gcgtcagaat gtagtgggat    360
ccaccgtgga cggacgaccg gtggctcctg caaattccgc caccctcacc tatgccaccg    420
tgggatcatc gttggacact gccgcggcag ctgccgcttc tgctgccgct tctactgctc    480
gcggcatggc ggctgatttt ggactgtata accaactggc cactgcagct gtggcgtctc    540
ggtccctggt tcaagaagat gccctgaatg tgattctgac tcgcctggag atcatgtcac    600
gccgcctgga cgaactggct gcgcagatat cctcaactaa ccccgatacc acttcagaac    660
cttaaataaa gacaaacaaa tttgttgaaa agtaaaatgg ctttatttgt ttttttggc    720
tcggtaggct cgggtccacc tgtcccggtc gttaaggacc ttgtgtatgt tttccaagac    780
ccggtacaga tgggcttgga tgttcaagta catgggcatg aggccatctc gggggtggag    840
ataggaccat tgcagagcgt catgctccgg ggtggtgttg taaataaccc agtcgtagca    900
gggtttctga gcgtggaact ggaagatgtc ctttaggagc aggctgatgg ccaagggcag    960
ccccttagtg taggtgttaa caaagcggtt aagctgggag ggatgcatgc gggggggagat   1020
gatatgcatc ttggcttgaa ttttgaggtt agctatgtta ccacctaggt ccctgcgggg   1080
gttcatgtta tgaaggacca ccagcacggt gtagccggtg cacttgggga acttgtcatg   1140
cagtttggag gggaaggcgt ggaagaattt agagaccccc ttgtggcctc ctaggttttc   1200
catgcactca tccataatga tggcaatggg acccctggcg gccgctttgg caaacacgtt   1260
ttgggggttg gaaacatcat agttttgctc tagagtgagc tcatcatagg ccatcttaac   1320
aaagcggggt aggagggtgc ccgactgggg gatgatagtt ccatctgggc ctggggcgta   1380
gttgccctca caaatctgca tttcccaggc cttaatttcc gagggggggta tcatgtccac   1440
ctgggggggcg ataaagaaca cggtttctgg cgggggattg atgagctggg tggaaagcaa   1500
gttacgcaac agttgggatt tgccgcaacc ggtgggaccg tagatgaccc cgatgacggg   1560
ttgcagctgg tagttgagag aggaacagct gccgtcgggg cgcaggaggg gggctacatc   1620
gttcatcatg cttctgacat gtttattttc actcactaag ttttgcaaga gcctctcccc   1680
acccagggat aagagttctt ccaggctgtt gaagtgtttc agcggtttca ggccgtctgc   1740
catgggcatc ttttcaagcg actgacgaag caagtacagt cggtcccaga gctcggtgac   1800
gtgctctatg gaatctcgat ccagcagact tcttggttgc gggggttggg ccgactttcg   1860
ctgtagggca ccagccggtg ggcgtccagg gccgcgaggg ttctgtcctt ccagggtctc   1920
agcgttcggg tgagggtggt ctcggtgacg gtgaagggat gagccccggg ctgggcgctt   1980
gcgagggtgc gcttcaggct catcctgctg gtgctgaagc gggcgtcgtc tccctgtgag   2040
tcggccagat agcaacgaag catgaggtcg tagctgaggg actcggccgc gtgtcccttg   2100
gcgcgcagct ttcccttgga aacgtgctga catttggtgc agtgcagaca cttgagggcg   2160
tagagtttgg gggccaggaa gaccgactcg gacgagtagg cgtcggctcc gcactgagcg   2220
cagacggtct cgcactccac cagccacgtg agctcgggtt tagcgggatc aaaaaccaag   2280
ttgcctccat ttttttgat gcgtttctta ccttgcgtct ccatgagtct gtgtcccgct    2340
```

```
tccgtgacaa aaaggctgtc ggtgtccccg tagaccgact tgagggggcg atcttccaaa   2400
ggtgttccga gatcttccgc gtacaggaac tgggaccact ccgagacaaa ggctcgggtc   2460
caggctaaca cgaaggaggc gatctgcgag ggtatctgt cgttttcaat gagggggtcc    2520
accttttcca gggtgtgcag acacaggtcg tcctcctccg cgtccacgaa ggtgattggc   2580
ttgtaagtgt aggtcacgtg acccgcaccc ccccaagggg tataaaaggg ggcgtgccca   2640
ctctccccgt cactttcttc cgcatcgctg tggaccagag ccagctgttc gggtgagtag   2700
gccctctcaa aagccggcat gatttcggcg ctcaagttgt cagtttctac aaacgaggag   2760
gatttgatat tcacgtgccc cgcggcgatg cttttgatgg tggaggggtc catctgatca   2820
gaaaacacga tctttttatt gtcaagtttg gtggcgaaag acccgtagag ggcgttggaa   2880
agcaacttgg cgatggagcg cagggtctga tttttctccc gatcggccct ctccttggcg   2940
gcgatgttga gttgcacgta ctcgcgagcc acgcaccgcc actcggggaa cacggcggtg   3000
cgctcgtcgg gcaggatgcg cacgtgccag ccgcggttgt gcagggtgat gaggtccacg   3060
ctggtggcca cctccccgcg gaggggctcg ttggtccaac acaatcgccc ccccttttctg  3120
gagcagaacg gaggcagggg atctagcaag ttggcgggcg gggggtcggc gtcgatggta   3180
aatatgccgg gtagcagaat tttattaaaa taatcgattt cggtgtccgt gtcttgcaac   3240
gcgtcttccc acttcttcac cgccagggcc ctttcgtagg gatttagggg cggtccccag   3300
ggcatggggt gggtcagggc cgaggcgtac atgccgcaga tgtcgtacac gtacaggggc   3360
tccctcaaca ccccgatgta agtggggtaa cagcgccccc cgcggatgct ggctcgcacg   3420
tagtcgtaca tctcgtgaga gggagccatg agcccgtctc ccaagtgggt cttgtggggt   3480
ttctcggccc ggtagaggat ctgcctgaag atggcgtggg agttggaaga gatggtgggg   3540
cgttggaaga cgttaaagtt ggctccgggc agtcccacgg agtcttggat gaattgggcg   3600
taggattccc ggagcttgtc caccagggct gcggttacca gcacgtcgag agcgcagtag   3660
tccaacgtct cgcggaccag gttgtaggcc gtctcttgtt ttttctccca cagttcgcgg   3720
ttgaggaggt attcctcgcg gtctttccag tactcttcgg cgggaaatcc tttttcgtcc   3780
gctcggtaag aacctaacat gtaaaattcg ttcacggctt tgtatggaca acagcctttt   3840
tctaccggca gggcgtacgc ttgagcggcc tttctgagag aggtgtgggt gagggcgaag   3900
gtgtcccgca ccatcacttt caggtactga tgtttgaagt ccgtgtcgtc gcaggcaccc   3960
tgttcccaca gcgtgaagtc ggtgcgcttt ttctgcctgg gattggggag ggcgaaggtg   4020
acgtcgttaa agaggatttt cccggcgcgg ggcatgaagt tgcgagagat cctgaagggt   4080
ccgggcacgt ccgagcggtt gttgatgact tgcgccgcca ggacgatctc atcgaagccg   4140
ttgatgttgt ggcccacgat gtaaagttcg ataaagcgcg gctgtccctt gagggccggc   4200
gctttttca actcctcgta ggtgagacag tccggcgagg acagacccag ctcagcccgg    4260
gcccagtcgg agagttgagg attagccgcg aggaaggaac tccatagatc caaggccagg   4320
agagtttgca agcggtcgcg gaactcgcgg aactttttgc ccacggccat tttctccggc   4380
gttaccacgt aaaaggtgtc ggggcggttg ttccagacgt cccatcggag ctctagggcc   4440
agctcgcagg cttggcgaac gagggtctcc tcgcccgaga cgtgcatgac cagcatgaag   4500
ggtaccaact gtttcccgaa cgagcccatc catgtgtagg tttctacgtc gtaggtgaca   4560
aagagccgct gggtgcgcgc gtgggagccg atcgggaaga agctgatctc ctgccaccag   4620
ctggaggaat gggtgttgat gtggtgaaag tagaagtccc gccggcgcac agagcattcg   4680
```

-continued

```
tgctgatgtt tgtaaaagcg accgcagtag tcgcagcgtt gcacgctctg tatctcctga   4740
atgagatgcg cttttcgccc gcgcaccaga aaccggaggg ggaagttgag actggggctt   4800
ggtggggcgg catccccttc gccttggcgg tgggagtctg cgtctgcgcc cttcttctct   4860
gggtggacga cggtggggac gacgacgccc cgggtgccgc aagtccagat ctccgccacg   4920
gaggggcgca ggcgctgcag gagggggcgc agctgcccgc tgtccaggga gtcgagggcg   4980
gccgcgctga ggtcgacggg aagcgtttgc aagttcactt tcagaagacc ggtaagagcg   5040
tgagccaggt gcagatggta cttgatttcc aggggggtgt tggaagaggc gtccacggcg   5100
tagaggaggc cgtgtccgcg cggggtcacc accgtgcccc gaggaggttt tatctcactc   5160
gtcgagggcg agcgccgggt ggtagaggcg gctctgcgcc ggggggcagc ggaggcagag   5220
gcacgttttc gtgaggattc ggcagcggtt gatgacgagc ccggagactg ctggcgtggg   5280
cgacgacgcg gcggttgagg tcctggatgt gctgtctctg cgtgaagacc accggtcccc   5340
gggtcctgaa cctgaaagag agttccacag aatcaatgtc tgcatcgtta acggcggcct   5400
gcctgaggat ctcctgtacg tcgcccgagt tgtcttgata ggcgatctcg gccatgaact   5460
gctccacttc ttcctcgcgg aggtcgccgt ggcccgctcg ctccacggtg gcggccaggt   5520
cgttggagat gcgacgcatg agttgagaga aggcgttgag gccgttctcg ttccacacgc   5580
ggctgtacac cacgtttccg aaggagtcgc gcgctcgcat gaccacctgg gccacgttga   5640
gttccacgtg gcgggcgaag acggcgtagt ttctgaggcg ctggaagagg tagttgagcg   5700
tggtggcgat gtgctcgcag acgaagaagt acatgatcca gcgccgcagg gtcatctcgt   5760
tgatgtctcc gatggcttcg agacgctcca tggcctcgta gaagtcgacg gcgaagttga   5820
aaaattggga gttgcgggcg gccaccgtga gttcttcttg caggaggcgg atgagatcgg   5880
cgaccgtgtc gcgcacctcc tgctcgaaag cgccccgagg cgcctctgct tcttcctccg   5940
gctcctcctc ttccaggggc acgggttcct ccggcagctc tgcgacgggg acggggcggc   6000
gacgtcgtcg tctgaccggc aggcggtcca cgaagcgctc gatcatttcg ccgcgccggc   6060
gacgcatggt ctcggtgacg gcgcgtccgt tttcgcgagg tcgcagttcg aagacgccgc   6120
cgcgcagagc gccccgtgc agggagggta agtggttagg gccgtcgggc agggacacgg   6180
cgctgacgat gcattttatc aattgctgcg taggcactcc gtgcagggat ctgagaacgt   6240
cgaggtcgac gggatccgag aacttctcta ggaaagcgtc tatccaatcg caatcgcaag   6300
gtaagctgag gacggtgggc cgctgggggg cgtccgcggg cagttgggag gtgatgctgc   6360
tgatgatgta attaaagtag gcggtcttca ggcggcggat ggtggcgagg aggaccacgt   6420
ctttgggccc ggcctgttga atgcgcaggc gctcggccat gccccaggcc tcgctctgac   6480
agcgacgcag gtctttgtag tagtcttgca tcagtctctc caccggaacc tctgcttctc   6540
ccctgtctgc catgcgagtc gagccgaagc cccgcagggg ctgcagcaac gctaggtcgg   6600
ccacgaccct ctcggccagc acggcctgtt gaatctgcgt gagggtggtc tggaagtcgt   6660
ccaggtccac gaagcggtga taggcccccg tgttgatggt gtaggtgcag ttggccataa   6720
cggaccagtt gacgacttgc atgccgggtt gggtgatctc cgtgtacttg aggcgcgagt   6780
aggcgcggga ctcgaacacg tagtcgttgc atgtgcgcac cagatactgg tagccgacca   6840
ggaagtgagg aggcggttct cggtacaggg gccagccgac ggtggcgggg gcgccggggg   6900
acaggtcgtc cagcatgagg cggtggtagt ggtagatgta gcgggagagc caggtgatgc   6960
cggccgaggt ggtcgcggcc ctggtgaatt cgcggacgcg gttccagatg ttgcgcaggg   7020
ggcgaaagcg ctccatggtg ggcacgctct gccccgtgag gcgggcgcaa tcttgtacgc   7080
```

```
tctagatgga aaaaagacag ggcggtcatc gactcccttc cgtagctcgg ggggtaaagt   7140
cgcaagggtg cggcggcggg gaaccccggt tcgagaccgg ccggatccgc cgctcccgat   7200
gcgcctggcc ccgcatccac gacgtccgcg ccgagaccca gccgcgacgc tccgccccaa   7260
tacggagggg agtcttttgg tgtttttttcg tagatgcatc cggtgctgcg gcagatgcga   7320
cctcagacgc ccaccaccac cgccgcggcg gcagtaaacc tgagcggagg cggtgacagg   7380
gaggaggagg agctggcttt agacctggaa gagggagagg ggttggcccg gctgggagcg   7440
ccgtccccag agagacaccc tagggttcag ctcgtgaggg acgccaggca ggcttttgtg   7500
ccgaagcaga acctgtttag ggaccgcagc ggtcaggagg cggaggagat gcgcgattgc   7560
aggtttcgcg cgggcagaga gctgagggcg ggcttcgatc gcgagcggct cctgagggcg   7620
gaggatttcg agcccgacga gcgttctggg gtgagcccgg cccgcgctca cgtctcggcg   7680
gccaacctgg tgagcgcgta cgagcagacg gtgaacgagg agcgcaactt ccaaaagagc   7740
tttaacaatc acgtgaggac cctgatcgcg agggaggagg tgaccatcgg gctgatgcat   7800
ctgtgggact tcgtggaggc ctacgtgcag aacccggcca gcaaacctct gacggcccag   7860
ctgttcctga tcgtgcagca cagccgcgac aacgagacgt tccgcgacgc catgttgaac   7920
atcgcggagc ccgagggtcg ctggctcttg gatctgatta acatcctgca gagcatcgtg   7980
gtgcaggaga gggggctgag tttagcggac aaggtggcgg ccattaacta ttcgatgcag   8040
agcctgggga agttctacgc tcgcaagatc tacaagagcc cttacgtgcc catagacaag   8100
gaggtgaaga tagacagctt ttacatgcgc atggcgctga aggtgctgac gctgagcgac   8160
gatctcggcg tgtaccgtaa cgacaagatc cacaaggcgg tgagcgccag ccgccggcgg   8220
gagctgagcg acagggagct gatgcacagc ctgcagaggg cgctggcggg cgccggggac   8280
gaggagcgcg aggcttactt cgacatggga gccgatctgc agtggcgtcc cagcgcgcgc   8340
gccttggagg cggcgggcta ccccgacgag gaggaccggg atgatttgga ggaggcaggc   8400
gagtacgagg acgaagcctg accgggcagg tgttgtttta gatgcagcgg ccggcggacg   8460
gggccaccgc ggatcccgca cttttggcat ccatgcagag tcaaccttcg ggcgtgaccg   8520
cctccgatga ctgggcggcg gccatggacc gcatcatggc gctgaccacc cgcaaccccg   8580
aggcttttag gcagcaaccc caggccaacc gtttttcggc catattggaa gcggtggtac   8640
cgtcgcgcac caaccccaca cacgagaaag tcctgactat cgtgaacgcc ctggtagaca   8700
gcaaagctat ccgccgcgac gaggcggggc tgatctacaa cgctctgttg gaacgggtgg   8760
cgcgctacaa cagcactaac ttgcagacca atctggatcg cctcaccacg gacgtgaagg   8820
aggcgctggc tcagaaggag cggtttctga gggatagcaa tctgggttct ctggtggcac   8880
tgaacgcctt tctgagcacg cagccggcca acgtgccccg cgggcaggag gattacgtga   8940
gcttcatcag cgctctgaga ctgctggtgt ccgaggtgcc ccagagcgag gtgtaccagt   9000
ctgggccgga ttactttttt cagacgtccc gacagggctt gcaaacggtg aacctgactc   9060
aggcctttaa aaacttgcaa ggtatgtggg gcgtcaaggc cccggtgggc gatcgcgcca   9120
ctatctccag tctgctgacc cccaacactc gcctgctgct gctcttgatc gcaccgttca   9180
ccaacagtag cactatcagc cgtgactcgt acctgggtca tctcatcact ctgtaccgcg   9240
aggccatcgg ccaggctcag atcgacgagc atacgtatca ggagatcact aacgtgagcc   9300
gggccctggg tcaggaagat accggcagcc tggaagccac gttgaacttt ttgctaacca   9360
accggaggca aaaaataccc tcccagttca cgttaagcgc cgaggaggag aggattctgc   9420
```

```
gatacgtgca gcagtccgtg agcctgtact tgatgcgcga gggcgccacc gcttccacgg   9480
ctttagacat gacggctcgg aacatggaac cgtcctttta ctccgcccac cggccgttca   9540
ttaaccgtct gatggactac ttccatcgtg cggccgccat gaacggggag tacttcacca   9600
atgccatcct gaatccgcat tggatgcccc cgtccggctt ctacaccggg gagtttgacc   9660
tgcccgaagc cgacgacggc tttctgtggg acgacgtgtc cgatagcatt ttcacgccgg   9720
ggaatcgccg attccagaag aaggagggcg gagacgagct ccccctctcc agcgtggagg   9780
ctgcctctag gggagagagc ccctttccca gtctgtcttc cgccagtagc ggtcgggtaa   9840
cgcgcccgcg gttgccgggg gagagcgact acctgaacga ccccttgctg cgaccggcta   9900
gaaagaaaaa tttccccaac aacggggtgg aaagcttggt ggataaaatg aatcgttgga   9960
agacctacgc ccaggagcag cgggagtggg aggacagtca gccgcgaccg ctggttccgc  10020
cgcactggcg tcgccagaga gaagacccgg acgactccgc agacgatagt agcgtgttgg  10080
acctgggagg gagcggagcc aacccctttg ctcacttgca acccaagggg cgttcgagtc  10140
gcctctacta ataaaaaaga cgcggaaact taccagagcc atggccacag cgtgtgtcct  10200
ttcttcctct ctttcttcct cggcgcggca gaatgagaag agcggtgaga gtcacgccgg  10260
cggcgtatga gggtccgccc ccttcttacg aaagcgtgat gggatcagcg aacgtgccgg  10320
ccacgctgga ggcgccttac gttcctccca gatacctggg acctaccgag ggcagaaaca  10380
gcatccgtta ctccgagctg gcgcccctgt acgataccac caaggtgtac ctggtggaca  10440
acaagtcggc ggacatcgcc tccctgaatt accaaaacga ccacagcaac tttctgacca  10500
ccgtggtgca gaacaatgac ttcaccccga cggaggcggg cacgcagacc attaactttg  10560
acgagcgttc ccgctggggc ggtcagctga aaaccatcct gcacaccaac atgcccaaca  10620
tcaacgagtt catgtccacc aacaagttca gggccaggct gatggttaaa aaggtagaaa  10680
accagcctcc cgagtacgaa tggtttgagt tcaccatccc cgagggcaac tattccgaga  10740
ctatgactat cgatctgatg aacaatgcga tcgtggacaa ttacctgcaa gtggggaggc  10800
agaacggggt attggaaagc gatatcggtg tgaaatttga taccagaaac ttccgactgg  10860
ggtgggatcc cgtgaccaag ctggtaatgc caggcgtgta caccaacgag gcttttcacc  10920
ccgacatcgt gctgctgccg gggtgcggcg tggatttcac tcagagccgc ttgagtaacc  10980
tgttaggaat caggaagcgc cgtcccttcc aggagggctt tcagatcatg tatgaggacc  11040
tggagggagg taacattccc gctctactag atgtgacaaa gtacgaacaa agtgtacagc  11100
gagccaaggc ggaagggcga gagattcgcg gagacacttt tgccgtgtct ccccaggatt  11160
tggttataga gccgttagag catgacagca aaaatcgtag ttacaatctt ttgcccaaca  11220
aaaccgacac ggcctatcgc agctggtttt tggcttacaa ctacggagac cccgagaaag  11280
gagtgagatc atggaccata ctcaccacca cggacgtgac ctgcggctcg cagcaagtgt  11340
actggtccct gccggatatg atgcaagacc cggtcacctt ccgccccctcc acccaagtca  11400
gcaacttccc ggtggtgggc accgagctgc tgcccgtcca tgccaagagc ttctacaacg  11460
agcaggccgt ctactcgcaa ctcattcgcc agtccaccgc gcttacccac gtgttcaatc  11520
gttttcccga gaaccagatt ctggtgcgcc ctcccgctcc taccattacc accgtcagtg  11580
aaaacgttcc cgccctcaca gatcacggaa ccctaccgct gcgcagcagt atcagtggag  11640
ttcagcgcgt gaccatcacc gacgccagac gtcgaacctg cccctacgtt tacaaagcgc  11700
tcggcgtggt ggcccctaaa gttctctcta gtcgcacctt ttaaacatgt ccattctcat  11760
ctctcccgat aacaacaccg gctggggatt gggctccggc aagatgtacg gcggggctaa  11820
```

gcgacgctcc agtcagcatc ccgttcgcgt tcggggtcac ttccgcgctc cctggggagc 11880
ttacaagcga ggactctctg gccgaacggc tgtagacgat accatagatg ccgtgattgc 11940
cgacgcccgc cggtacaacc ccggaccggt cgctagcgcc gcctccaccg tggattccgt 12000
gatcgacagc gtggtggcca gcgccagggc ctatgctcgc cgcaagaggc ggctgcatcg 12060
gaaacgtcgc cccaccgccg ccatgctagc agccagggcc gtgctgaggc gggcccggag 12120
ggtaggcagg agggctatgc gccgcgctgc cgccaacgcc gccgggaggg cccgcagaca 12180
agccgcccgc caggccgccg ctgccatcgc tagcatggcc agacccagga gagggaacgt 12240
gtactgggtg cgcgattctg taacgggagt ccgagtgccg gtgcgcagcc gacctccccg 12300
aagttagaag atccaagctg cgaagacggc ggtactgagt ctccctgttg ttattagccc 12360
aacatgagca agcgcaagtt taaagaagaa ctgctgcaga cgctggtgcc tgagatctat 12420
ggccctccgg acgtgaagcc tgacattaag ccccgcgata tcaagcgtgt taaaaagcgg 12480
gaaaaaaaag aggaacttgc ggcggtagac gatggcggtg tagaatttat taggagtttc 12540
gccccacggc gcagggttca atggaaaggg cggcgtgtac aacgcgttct gaggccgggc 12600
accgcggtag tttttacccc gggagagcgg tcggccgtta ggggtttcaa gcggcagtac 12660
gatgaggtgt acggcgacga agacatactg gaacaggcgg ctcagcagat tggagaattc 12720
gcttatggca aacgttctcg gcgcgaagac ctggccatcg ccttggacag cggcaatccc 12780
acacccagcc tcaaacccgt gacgctgcaa caggtgcttc ccgtgagcgc cagtactgac 12840
agcaaaaggg ggattaaaag agagatggaa gagctgcaac ccaccatcca acttatggtc 12900
cctaaacgac agaggttgga agaggtcctg gagaagatga aagtggaccc cagcatagag 12960
ccggatgtga aagtgaggcc tattaaggaa gtggcccccg gtcttggggt gcaaacggtg 13020
gacattcaaa tccccgtcac gtccgcttca acagcggtgg aagccatgga aacgcaaacg 13080
gaagcccccg ccgtcacggt cggtaccagg gaagtggcgt tgcaaacgga accctggtac 13140
gaatacgcca cccctaggcg tcagaggcgg tccgcccgtt acggacccgt caacgccatc 13200
atgcccgagt acgcgctaca tccgtctatc cggcccactc ccggctaccg gggagtgacg 13260
tatcgcccgt caggaactcg ccgccgttac cgtcgccgcc gtcgctctcg ccgcgctctg 13320
gccccagtgt cggtgcggcg cgtgacccgc caggggaaaa cagtcaccat ccccaacccg 13380
cgctaccacc ctagcattct ttaatgactc tgccgttttg cagatggctc tgacttgccg 13440
cgtgcgcctt cccgttctgc actatcgagg aagatctcgt cgtaggagag gcatggcggg 13500
cagtggtcgc cggcgggctt tgcgcaggcg catgaaaggc ggaattttac ccgccctaat 13560
acctataatc gccgccgcca taggcgccat acccggcgtc gcttcagtgg ccttgcaagc 13620
agctcgtaat aaataaacga aggcttttgc acttatgtcc tggtcctgac tattttatgc 13680
agaaaaagca tggaagacat caattttacg tcgctggctc cgcggcaagg ctcgcggccg 13740
ctcatgggca cctggaacga catcggcacc agtcagctca acgggggcgc tttcaattgg 13800
gggagccttt ggagcggcat taaaaacttt ggctccacga ttaaatccta cggcagcaaa 13860
gcctggaaca gtagtgctgg tcaaatgctc cgagataaac tgaaggacac caacttccaa 13920
gagaaagtgg tcaacggggt ggtgaccggc atacacggcg cggtagatct tgccaaccaa 13980
gcggtgcaga aagagattga caggcgattg gaaaactcgc gggtgccgcc gcagagaggg 14040
gatgaggtgg aggtcgagga agtagaagta gaggaaaagc tgcccccctt ggagaaagtt 14100
cccggtgcga ttccaaggcc gcagaagcgg ccaaggccag aactagaaga aactctggtg 14160

```
acggagagca aggagcctcc ctcgtacgag caagccttaa aagagggcgc ttcaccctac  14220
ccgatgacca aaccgatcgc gcctatggct cggccggtgt acgggaagga ctacaaacct  14280
gtcacgctag aacttcctcc gccactccct tcgcgtccta cggtgcctcc catgccagcg  14340
ccgtcggccg gtcccgtgtc tgcaccttcc gcagcgcctc tgccagccgc ccgcccagtg  14400
gccgtggcca ctgccagaaa ccccagaggc cagagaggag ccaactggca aaacacgctg  14460
aacagcatct taattaattc gaacccataa tacccataat agctgtttgc catcgacgcg  14520
aggctggatg gccttcccca ttatgattct tctcgcttcc ggcggcatcg ggatgcccgc  14580
gttgcaggcc atgctgtcca ggcaggtaga tgacgaccat cagggacagc ttcaaggatc  14640
gctcgcggct cttaccagcc cagcaaaagg ccaggaaccg taaaaaggcc gcgttgctgg  14700
cgtttttcca taggctccgc ccccctgacg agcatcacaa aaatcgacgc tcaagtcaga  14760
ggtggcgaaa cccgacagga ctataaagat accaggcgtt tccccctgga agctccctcg  14820
tgcgctctcc tgttccgacc ctgccgctta ccggatacct gtccgccttt ctcccttcgg  14880
gaagcgtggc gctttctcat agctcacgct gtaggtatct cagttcggtg taggtcgttc  14940
gctccaagct gggctgtgtg cacgaacccc ccgttcagcc cgaccgctgc gccttatccg  15000
gtaactatcg tcttgagtcc aacccggtaa gacacgactt atcgccactg gcagcagcca  15060
ctggtaacag gattagcaga gcgaggtatg taggcggtgc tacagagttc ttgaagtggt  15120
ggcctaacta cggctacact agaaggacag tatttggtat ctgcgctctg ctgaagccag  15180
ttaccttcgg aaaaagagtt ggtagctctt gatccggcaa acaaaccacc gctggtagcg  15240
gtggtttttt tgtttgcaag cagcagatta cgcgcagaaa aaaaggatct caagaagatc  15300
ctttgatctt ttctacgggg tctgacgctc agtggaacga aaactcacgt taagggattt  15360
tggtcatgag attatcaaaa aggatcttca cctagatcct tttaaattaa aaatgaagtt  15420
ttaaatcaat ctaaagtata tatgagtaaa cttggtctga cagttaccaa tgcttaatca  15480
gtgaggcacc tatctcagcg atctgtctat ttcgttcatc catagttgcc tgactccccg  15540
tcgtgtagat aactacgata cgggagggct taccatctgg ccccagtgct gcaatgatac  15600
cgcgagaccc acgctcaccg gctccagatt tatcagcaat aaaccagcca gccggaaggg  15660
ccgagcgcag aagtggtcct gcaactttat ccgcctccat ccagtctatt aattgttgcc  15720
gggaagctag agtaagtagt tcgccagtta atagtttgcg caacgttgtt gccattgctg  15780
caggcatcgt ggtgtcacgc tcgtcgtttg gtatggcttc attcagctcc ggttcccaac  15840
gatcaaggcg agttacatga tcccccatgt tgtgcaaaaa agcggttagc tccttcggtc  15900
ctccgatcgt tgtcagaagt aagttggccg cagtgttatc actcatggtt atggcagcac  15960
tgcataattc tcttactgtc atgccatccg taagatgctt ttctgtgact ggtgagtact  16020
caaccaagtc attctgagaa tagtgtatgc ggcgaccgag ttgctcttgc ccggcgtcaa  16080
cacgggataa taccgcgcca catagcagaa ctttaaaagt gctcatcatt ggaaaacgtt  16140
cttcggggcg aaaactctca aggatcttac cgctgttgag atccagttcg atgtaaccca  16200
ctcgtgcacc caactgatct tcagcatctt ttactttcac cagcgtttct gggtgagcaa  16260
aaacaggaag gcaaaatgcc gcaaaaaagg gaataagggc gacacggaaa tgttgaatac  16320
tcatactctt cctttttcaa tattattgaa gcatttatca gggttattgt ctcatgagcg  16380
gatacatatt tgaatgtatt tagaaaaata aacaaatagg ggttccgcgc acatttcccc  16440
gaaaagtgcc acctgacgtc taagaaacca ttattatcat gacattaacc tataaaaata  16500
ggcgtatcac gaggcccttt cgtcttcaag aattggtcga tggcaaacag ctattatggg  16560
```

tattatgggt tcgaattaat 16580

<210> SEQ ID NO 42
<211> LENGTH: 21626
<212> TYPE: DNA
<213> ORGANISM: Artificial Sequence
<220> FEATURE:
<223> OTHER INFORMATION: Synthetic oligonucleotide pBr/sAd4310A.RsrII-rITR

<400> SEQUENCE: 42
attaacaccg tggattccgt gatcgacagc gtggtggcca gcgccagggc ctatgctcgc 60
cgcaagaggc ggctgcatcg gaaacgtcgc cccaccgccg ccatgctagc agccagggcc 120
gtgctgaggc gggcccggag ggtaggcagg agggctatgc gccgcgctgc cgccaacgcc 180
gccgggaggg cccgcagaca agccgcccgc caggccgccg ctgccatcgc tagcatggcc 240
agacccagga gagggaacgt gtactgggtg cgcgattctg taacgggagt ccgagtgccg 300
gtgcgcagcc gacctccccg aagttagaag atccaagctg cgaagacggc ggtactgagt 360
ctccctgttg ttattagccc aacatgagca agcgcaagtt taaagaagaa ctgctgcaga 420
cgctggtgcc tgagatctat ggccctccgg acgtgaagcc tgacattaag ccccgcgata 480
tcaagcgtgt taaaaagcgg gaaaaaaaag aggaacttgc ggcggtagac gatggcggtg 540
tagaatttat taggagtttc gccccacggc gcagggttca atggaaaggg cggcgtgtac 600
aacgcgttct gaggccgggc accgcggtag tttttacccc gggagagcgg tcggccgtta 660
ggggtttcaa gcggcagtac gatgaggtgt acggcgacga agacatactg gaacaggcgg 720
ctcagcagat tggagaattc gcttatggca aacgttctcg gcgcgaagac ctggccatcg 780
ccttggacag cggcaatccc acacccagcc tcaaacccgt gacgctgcaa caggtgcttc 840
ccgtgagcgc cagtactgac agcaaaaggg ggattaaaag agagatggaa gagctgcaac 900
ccaccatcca acttatggtc cctaaacgac agaggttgga agaggtcctg gagaagatga 960
aagtggaccc cagcatagag ccggatgtga aagtgaggcc tattaaggaa gtggcccccg 1020
gtcttggggt gcaaacggtg gacattcaaa tccccgtcac gtccgcttca acagcggtgg 1080
aagccatgga aacgcaaacg gaagccccccg ccgtcacggt cggtaccagg gaagtggcgt 1140
tgcaaacgga accctggtac gaatacgcca cccctaggcg tcagaggcgg tccgcccgtt 1200
acggacccgt caacgccatc atgcccgagt acgcgctaca tccgtctatc cggcccactc 1260
ccggctaccg gggagtgacg tatcgcccgt caggaactcg ccgccgttac cgtcgccgcc 1320
gtcgctctcg ccgcgctctg gccccagtgt cggtgcggcg cgtgacccgc caggggaaaa 1380
cagtcaccat ccccaacccg cgctaccacc ctagcattct ttaatgactc tgccgttttg 1440
cagatggctc tgacttgccg cgtgcgcctt cccgttctgc actatcgagg aagatctcgt 1500
cgtaggagag gcatggcggg cagtggtcgc cggcgggctt tgcgcaggcg catgaaaggc 1560
ggaattttac ccgccctaat acctataatc gccgccgcca taggcgccat acccggcgtc 1620
gcttcagtgg ccttgcaagc agctcgtaat aaataaacga aggcttttgc acttatgtcc 1680
tggtcctgac tattttatgc agaaaaagca tggaagacat caattttacg tcgctggctc 1740
cgcggcaagg ctcgcggccg ctcatgggca cctggaacga catcggcacc agtcagctca 1800
acgggggcgc tttcaattgg gggagccttt ggagcggcat taaaaacttt ggctccacga 1860
ttaaatccta cggcagcaaa gcctggaaca gtagtgctgg tcaaatgctc cgagataaac 1920
tgaaggacac caacttccaa gagaaagtgg tcaacggggt ggtgaccggc atacacggcg 1980

```
cggtagatct tgccaaccaa gcggtgcaga aagagattga caggcgattg gaaaactcgc   2040
gggtgccgcc gcagagaggg gatgaggtgg aggtcgagga agtagaagta gaggaaaagc   2100
tgccccccctt ggagaaagtt cccggtgcga ttccaaggcc gcagaagcgg ccaaggccag   2160
aactagaaga aactctggtg acggagagca aggagcctcc ctcgtacgag caagccttaa   2220
aagagggcgc ttcaccctac ccgatgacca aaccgatcgc gcctatggct cggccggtgt   2280
acgggaagga ctacaaacct gtcacgctag aacttcctcc gccactccct tcgcgtccta   2340
cggtgcctcc catgccagcg ccgtcggccg gtcccgtgtc tgcaccttcc gcagcgcctc   2400
tgccagccgc ccgcccagtg gccgtggcca ctgccagaaa ccccagaggc cagagaggag   2460
ccaactggca aaacacgctg aacagcatcg tgggcctggg agttaaaagc ctgaaacgcc   2520
gccgttgcta ttattaaaaa agtgtagcta aaaaatctcc cgttgtatac gcctcctatg   2580
ttaccgccag agacgtgtga ctgtcgtcgc gagcagcgct ttcaagatgg ccaccccatc   2640
gatgatgccg cagtggtctt acatgcacat cgccgggcag gacgcctcgg agtatctgag   2700
ccccggtctt gtgcagtttg cccgcgccac cgacacctac ttcagcttgg gaaacaagtt   2760
tagaaatccc accgtggccc ccacgcacga tgtgaccacg gatcgttcgc agaggctgac   2820
tctgcgcttt gtaccggtag accgtgagga tactgcctat tcttacaaag ttcggtatac   2880
gttagccgta ggagacaaca gggtgctgga catggccagt acttactttg acatccgcgg   2940
tgttcttgac cgcggtccaa gctttaaacc gtataccgga acggcataca atgccttggc   3000
tccaaagggc gctccaaatg cttgccagtg gacaacgacc aacgggggca ataaaacgaa   3060
cacttttgcc caagcccctt taataggcac ggctattgac ggaaccaacg gactgcagat   3120
tgggcaagat aatggacaag ctgtttatgc tgacaaaacc tttcaacccg aaccacaagt   3180
gggagaatct cagtggaata ctaatccaac cacaaacgca gcaggacgcg tgttaaaaac   3240
aactactcgc atgctgcctt gctatggttc ttttgcaagg cccaccaatg agaaaggggg   3300
tcaagcttca ggagacgtta ccttccaatt tttcgacact gcctcggaca atggcaacaa   3360
ccctaaggtg gtgctatatg gagaagacgt caacattgaa tcgcctgaca cacacttaat   3420
ctacaaaccc accgctgaca acacaaactc tgaaaacctt ttgggtcaac aggccgctcc   3480
aaacagagcc aattacattg cctttcggga caacttcatt ggactaatgt actataattc   3540
aacaggaaac atgggagtgt tggcagggca ggcttcccaa ctaaatgctg tggtagactt   3600
gcaagacaga aacactgagc tttcctacca actcatgtta gatgcaatag gagaccggag   3660
tcgttacttt tcaatgtgga accaagcagt ggacagctat gatccagatg tgcgaattat   3720
tgaaaatcat ggcgttgagg acgaactgcc aaattactgc ttccctctta acgctcaagg   3780
aattgctaac acctataaag gcgttaagaa aaacaacggc aattgggcga aagacgacgc   3840
agtagtagaa actaacgaaa ttggcatagg aaatgttttt gccatggaga taaatttaac   3900
tgctaacttg tggcgaaact ttctgtattc caatattgct ttgtacctgc cagactccta   3960
caagtattca ccgggaaaca taaccttacc cgaaaacaaa aacagttaca attacattaa   4020
tggtcgagta acagctcctg gtctggtaga cacctttgta aacattggcg cgcgatggtc   4080
tcccgacccc atggacaacg tgaatccttt taatcaccat cgcaatgctg gtctgcgtta   4140
tcgctccatg cttctaggca acggccgcta cgtgcccttc cacattcagg tgcctcaaaa   4200
attctttgcc attaagaacc tgcttctgct gcctgggtcc tacacctacg agtggaactt   4260
cagaaaagat gtaaacatga tcttgcagag cacgctgggc aacgacctcc gtgtcgacgg   4320
```

-continued

```
ggccagcgtc agattcgaca gcattaacct ctacgctaat ttcttcccca tggcacataa   4380
caccgcttcc accctggagg ctatgttacg caacgacacc aacgaccagt cctttaatga   4440
ctacctctgc gcggccaaca tgctataccc cattcctgcc aatgccacca gtgtgcccat   4500
ctccatcccc tctcgcaact gggcagcttt cagagggtgg agtttcaccc gcctcaaaac   4560
aaaagaaacc ccctcgctgg gttccggatt tgatccatac tttgtttact caggctccat   4620
tccctacctg gatggtacct tctacctgaa ccacaccttc aaaaaggtgt ctattatgtt   4680
cgactcttct gtgagctggc ccggcaacga ccgcctgctg acccctaatg agtttgaaat   4740
taagcgctcg gtggacggag aaggatacaa tgtagcccag agcaacatga ccaaagactg   4800
gttcttaatt caaatgctca gccactacaa cattggttac caagggtttt acgtgcccga   4860
ggcttacaaa gacagaatgt actccttttt tagaaacttc caacctatga gtagacaggt   4920
agtggatgca gatcggtatg aacaatacaa aaaagtcacc gttgagtatc aacataataa   4980
ttctggtttt gtgggataca tggacccaac catgagggaa gggcaggctt atccagcgaa   5040
ttacccttat cctcttattg gagacaccgc cgtgcccagc ctgacccaga aaaagttcct   5100
ctgtgaccgc accatgtgga gaatcccctt ctctagcaac ttcatgtcta tgggggccct   5160
caccgacctg ggcagaaca tgctgtacgc caattccgct cacgccttgg atatgacctt   5220
tgaggtggac cccatggatg agcccacgct tctctatgtt ctgtttgaag tcttcgacgt   5280
ggtgcgcatc caccagccgc accgcggcgt catcgaggcc gtctacctgc gcacaccttt   5340
ctctgccggt aacgccacca cataagaagc aaatgggctc cagcgaacag gagctgcggg   5400
ccattattcg cgacctgggc tgcggaccct actttttggg caccttcgac aagcgtttcc   5460
ccggattcat gtcccccag aagccggcct gtgccatagt caacacggcc gggcgggaga   5520
ccgggggggt tcactggctc gccttcgcct ggaacccgcg caaccgcacc tgctacctgt   5580
tcgacccttt tggtttttcc gacgaaaggc tgaagcaaat ctaccagttc gaatacgaag   5640
gactcctcaa gcgcagcgct ctggcctcca cgcccgacca ctgcgtcacc ctggaaaaat   5700
ccacccaaac ggtgcagggg cccctctcgg ccgcctgcgg gcttttctgt tgcatgtttt   5760
tgcacgcctt cgtgcactgg cctcacaacc ccatggagcg caaccccacc atggatctgc   5820
tcaccggagt gcccaacagc atgcttcaca gcccccaggt cgccccccacc ctgcgccgta   5880
accaggaaca cctgtatcgc tttctgggga aacactctgc ctatttccgc cgccaccggc   5940
agcgcatcga gcaggccacg gcctttgaaa gcatgagcca aagagtgtaa tcaataaaaa   6000
ccatttttat ttaacatgat acgcgcttct ggcgttttta ttaaaaatcg aacggttcga   6060
gggaggggtc ctcgtgcccg ctgggaaggg acacgttgcg gtactggaaa cgggcgctcc   6120
aacgaaactc ggggatcacc agccgcggca ggggcacgtc ttctaggttc tgcttccaga   6180
actgccgcac cagctgcagg gctcccatga cgtcgggcgc cgagatcttg aagtcgcagt   6240
tagggccgga gcccccgcgg ctgttgcgga acacggggtt ggcacactgg aacaccagca   6300
cgctggggtt gtaaatactg gccagggccg ttgggtcggt cacctccgac gcatccagat   6360
cctcggcatt gctcagggcg aacggagtca gcttgcacat ctgccgtccg atctggggca   6420
ccaggtcggg tttgttgagg caatcgcagc gcagagggat taggatgcga cgctgcccgc   6480
gttgcatgat agggtaactc gccgccagga actcctccat ctgacggaag gccatctggg   6540
ccttggtacc ctcggtgaaa aatagcccac aggacttgct agaaaatacg ttattgccgc   6600
agttgatgtc ttccgcgcag cagcgtgcat cttcgttctt cagctgaacc acgttacgcc   6660
cccagcggtt ctggaccacc ttggctttcg taggatgctc cttcaacgcc cgctgaccgt   6720
```

```
tctcgctggt cacatccatt tccaccacgt gctccttgca gaccatctcc actccgtgga   6780
agcagaacag gacgccctcc tgctgggtat tgcgatgctc ccaaacggca catccggtgg   6840
gctcccagct cttgcgtttc acccccgcgt atgcttccat gtaagccatg aggaatctgc   6900
ccatcagctc ggtgaaggtc ttctggttgg tgaaggttag cggcaggccg cggtgctcct   6960
cgttcaacca agtttgacag attttgcggt acacggctcc ctggtcgggc agaaacttaa   7020
aagccgctct gctctcgttg tccacgtgga acttctccat caacatcgtc atgacttcca   7080
tgcccttctc ccacgccgtc accaacggtt cggtcccggg gttcttcacc aacacggcgg   7140
tggaggggcc ctcgccggcc ccgacgtcct tcatggtcat tctttggaac tccacggtgc   7200
cgtccgcgcg gcgtactctg cgcatcggag ggtagctgaa gcccacctcc accacggtgc   7260
cttcgccctc gctgtcggaa acgatctccg gggatggcgg cggcgcgggt gtcgccttgc   7320
gagccttctt cttgggaggg agcggaggca cctcctgctc gcgctcgggg ctcatctccc   7380
gcaagtaggg ggtaatggag cttccgggtt ggttctgacg gttggccatt gtatcctagg   7440
cagaaagaca tggatcttat gcgcgaggaa actttaaccg ccccgtcccc cgtcagcgac   7500
gaagaggtca tcgtcgaaca ggacccgggc tacgttacgc cgcccgagga tctggagtcc   7560
cccttagacg accgacgcga cgctagtgag cggcaggaaa atgagaaaga ggaggaggag   7620
ggctgctacc tcctggaagg cgacgtcttg ctaaagcatt tcgccaggca gagcaccata   7680
ctcaaggagg ccttgcaaga ccgctccgag gtgcccttgg acgtcgccgc gctctcccag   7740
gcctacgagg cgaacctttt ctcgccccga gtgcctccga agagacagcc caacggcacc   7800
tgcgagccca acccgcgact caacttctac cccgtgttcg ccgtgcccga ggcgctggcc   7860
acctaccaca tctttttcaa aaaccagcgc attccccttt cctgccgggc caaccgcacc   7920
gcagccgata ggaagctaac actcagaaac ggagccagca tacctgatat cacgtcactg   7980
gaggaagtgc ctaagatctt cgagggtctg ggtcgagatg agaagcgggc ggcgaacgct   8040
ctgcagaaag aacagaaaga gagtcagaac gtgctggtgg agctggaggg ggacaacgcg   8100
cgtctggccg tcctcaaacg ctgcatagaa gtctcccact tcgcctaccc cgccctcaac   8160
ttgccaccca aagttatgaa atcggtcatg gatcagctgc tcatcaagag agctgagccc   8220
ctggatcccg accaccccga ggcggaaaac tcagaggacg gaaagcccgt cgtcagcgac   8280
gaggagctcg agcggtggct ggaaaccggg gacccccaac agttgcaaga gaggcgcaag   8340
atgatgatgg cggccgtgct ggtcaccgtg gagctggaat gcctgcaacg gtttttcagc   8400
gacgtggaga cgctacgcaa aatcggggag tccctgcact acaccttccg ccagggctac   8460
gtccgccagg cctgcaagat ctccaacgtg gagctcagca acctggtctc ctacatgggc   8520
atcctccacg agaaccggct ggggcagagc gtgctgcact gcaccttgca aggcgaggcg   8580
cggcgggact acgtccgcga ctgcatctac ctcttcctca ccctcacctg gcagaccgcc   8640
atgggcgtct ggcagcagtg cttggaagag agaaacctca aagagctaga caaactcctc   8700
tgccgccagc ggcgggccct ctggaccggt ttcagcgagc gcacggtcgc ctgcgccctg   8760
gcagacatta tcttcccgga gcgcctgatg aaaaccttgc agaacggcct gccggatttt   8820
atcagtcaaa gtattttgca aaacttccgc tccttcgttc tggagcgctc cgggatcttg   8880
cccgccatga gctgcgcgct gccttctgac tttgtccccc tttcctaccg cgagtgtcct   8940
ccccccctgt ggagccactg ctacctcttc caactggcca actttctggc ctaccactcc   9000
gacctcatgg aagacgtgag cggagagggg ctgctcgagt gccactgccg ctgcaacctc   9060
```

-continued

```
tgcaccccccc acagatcgct ggcctgcaac accgagctgc tcagcgaaac ccaggtcata   9120
ggtaccttcg agatccaggg gccccagcag caagagggtg cttccggctt gaagctcact   9180
ccggcgctgt ggacctcggc ttacttacgc aaatttgtag ccgaggacta ccacgcccac   9240
aaaattcagt tctatgaaga ccaatctcga ccacccaaag ccccccctcac ggcctgcgtc   9300
atcactcaga gcaaaatcct ggcccaattg caatccatca accaagcgcg ccgagatttc   9360
cttttgaaaa agggtcgggg ggtgtaccta gacccccaga ccggcgagga actcaacccg   9420
tccacactct ccgtcgaagc agcccccccg agacatgccg cccaagggaa ccgccaagca   9480
gctgatcgct cggcagagag cgaagaagca agagctgctc cagcagcagc agcaggtgga   9540
ggacgaggaa gagctgtggg acagccaggc agaggaggtg tcagaggacg aggaggagat   9600
ggaaagctgg gacagcctag acgaggagga ggacgagctt tcagaggaag aggcgaccga   9660
agaaaaacca cctgcatcca gcgcgccttc tctgagccga cagccgaagc cccggccccc   9720
gacgcccccg gccggctcac tcaaagccag ccgtaggtgg gacgccaccg gatctccagc   9780
ggcagcggca acggcagcgg gtaaggccaa acgcgagcgg cgggggtatt gctcctggcg   9840
ggcccacaaa agcagtatcg tgaactgctt gcaacactgc gggggaaaca tctcctttgc   9900
ccgacgctac ctcctcttcc atcacggtgt ggccttccct cgcaacgttc tctattatta   9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttcccccctcg ggcgccaaaa  10320
cccacgtcat tgccagcatg agcaaggaga ttcccaccccc ttacatgtgg agctatcagc  10380
cccagatggg cctggccgcg ggggccgccc aggactactc cagcaagatg aactggctca  10440
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
acggagtctt ccagctcgga ggagcgggcc gctcttcctt caccactcgc caggcctacc  10860
tgaccctgca gagctcttcc tcgcagccgc gctccggggg aatcggcact ctccagttcg  10920
tggaagagtt cgtcccctcc gtctacttca acccgttttc cggctcacct ggacgctacc  10980
cggacgcctt cattcccaac tttgacgcag tgagtgaatc cgtggacggc tacgactgat  11040
gacagatggt gcggccgtga gagctcggct gcgacatctg catcactgcc gccagcctcg  11100
ctgctacgct cgggaggcga tcgtgttcag ctactttgag ctgccggacg agcaccctca  11160
ggggccggct cacgggttga aactcgagat cgagaacgcg ctcgagtctc gcctcatcga  11220
cgccttcacc gcccggcctc tcctggtaga aaccgaacgc gggatcacta ccatcaccct  11280
gttctgcatc tgccccacgc ccggattaca tgaagatctg tgttgtcatc tttgcgctca  11340
gtttaataaa aactgaactg tttgccgcac cttcaacgcc atctgtgatt tctacaacaa  11400
aaagttcttc tggcaaaggt acacaaactg tattttattc taattctacc tcatctattg  11460
```

```
tgctgaactg cgcctgcact aacgaactta tccagtggat tgcaaacggt agtgtgtgca  11520
agtacttttg ggggaacgag atagttagta gaaataacag cctttgcaag cactgcaact  11580
cctccacact aatcctttat cccccatttg ttactggatg gtatatgtgc gttggctccg  11640
gtttaaatcc tagttgcttt cataagtggt ttctacaaaa agagaccctt cccaacaatt  11700
ctgtttcttt tttcaccctg tcctactgct gttctccctc tggttactct ttcaaacctc  11760
taattggtat tttagctttg atactgataa tctttattaa ctttataata attaacaact  11820
tacagtaaac atgcttgtta tcctcctgct cgccacattt ttcgctctct ctcacgccag  11880
aacaagtatt gttggcgcag gttacaatgc aactcttcaa tctgcttaca tgccagattc  11940
cgaccagata ccccatatta cgtggtactt acaaacctcc aaacctaatt cttcatttta  12000
tgaaggaaac aaactctgcg atgactccga caacaggacg cacacatttc cccacccttc  12060
actacaattc gaatgcgtaa acaaaagctt gaagctttac aacttaaagc cttcagattc  12120
tggcttgtat catgctgtag ttgaaaaaag taatttagaa gtccacagtg attacattga  12180
attgatggtt gtggacctgc cacctccaaa atgtgaggtt tcctcctctt accttgaagt  12240
tcaaggcgtg gatgcctact gcctcataca cattaactgc agcaactcta aatatccagc  12300
tagaatttac tataatggac aggaaagtaa tcttttttat tatttaacaa caagcgctgg  12360
taacggtaaa cagttacctg attattttac tgctgttgtt gaattttcca cctacagaga  12420
aacgtatgcc aagcggcctt acaatttctc atacccgttt aacgaccttt gcaatgaaat  12480
acaagcgctc gaaactggaa ctgattttac tccaattttc attgctgcca ttgttgtgag  12540
cttaattacc attattgtca gcctagcatt ttactgcttt tgcaagccca aaaaacctaa  12600
gtttgaaaaa cttaaactaa aacctgtcat tcaacaagtg tgattttgtt ttccagcatg  12660
gtagctgcat ttctacttct cctctgtcta cccatcattt tcgtctcttc aactttcgcc  12720
gcagtttccc acctggaacc agagtgccta ccgccttttg acgtgtatct gattctcacc  12780
tttgtttgtt gtatatccat ttgcagtata gcctgctttt ttataacaat ctttcaagcc  12840
gccgactatc tttacgtgcg aattgcttac tttagacacc atcctgaata cagaaatcaa  12900
aacgttgcct ccttactttg tttggcatga ttaagctatt gctaatactt aattatttac  12960
ccctaatcaa ctgtaattgt ccattcacca aaccctggtc attctacacc tgttatgata  13020
aaatccccga cactcctgtt gcttggcttt acgcagccac cgccgctttg gtatttgtat  13080
ctacttgcct tggagtaaaa ttgtatttta ttctacacac tgggtggcta catcccagag  13140
aagatttacc tagacatcct cttgtaaacg cttttcaatt acagcctctg cctcctcctg  13200
atcttcttcc tcgagctccc tctattgtga gctactttca actcaccggt ggagatgact  13260
gactctcagg acattaatat tagtgtggaa agaatagctg ctcagcgtca gcgagaaacg  13320
cgagtgttgg aatacctgga actacaacag cttaaggagt cccactggtg tgagaaagga  13380
gtgctgtgtc atgttaagca ggcagccctt tcctacgatg tcagcgttca gggacatgaa  13440
ctgtcttaca ctttgccttt gcagaaacaa accttctgca ccatgatggg ctctacctcc  13500
atcacaatca cccaacaagc cgggcctgta gagggggcta tcctctgtca ctgtcacgca  13560
cctgattgca tgtccaaact aatcaaaact ctctgtgctt taggtgatat ttttaaaatg  13620
taaatcataa taaacttacc ttaaatttga caacaatttt ctggtgacat cattcagcag  13680
caccacttta ccctcttccc agctctcgta tgggatgcga tagtgggtgg caaacttcct  13740
ccaaacccta aaagaaatat tggtatccac ttccttgtcc tcacccacaa ttttcatctt  13800
```

-continued

```
ttcatagatg aaaagaacca gagttgatga agacttcaac cccgtctacc cctatgacac  13860
cacaaccact cctgcagttc cctttatatc acccccettt gtaaacagcg atggtcttca  13920
ggaaaacccc ccaggtgttt taagtctgcg aatagctaaa cccctatatt tcgacatgga  13980
gagaaaacta gccctttcac ttggaagagg gttgacaatt accgccgccg gacaattaga  14040
aagtacgcag agcgtacaaa ccaacccacc gttgataatt accaacaaca acacactgac  14100
cctacgtcat tctcccccct taaacctaac tgacaatagc ttagtgctag gctactcgag  14160
tccgctccgc gtcacagaca acaaacttac atttaacttc acatcaccac tccgttatga  14220
aaatgaaaac cttactttta actatacaga gcctcttaaa cttataaata acagccttgc  14280
cattgacatc aattcctcaa aaggccttag tagcgtcgga ggctcactag ctgtaaacct  14340
gagttcagac ttaaagtttg acagcaacgg atccatagct tttggcatac aaaccctgtg  14400
gaccgctccg acctcgactg gcaactgcac cgtctacagc gagggcgatt ccctacttag  14460
tctctgttta accaaatgcg gagctcacgt cttaggaagt gtaagtttaa ccggtttaac  14520
aggaaccata acccaaatga ctgatatttc tgtcaccatt caatttacat ttgacaacaa  14580
tggtaagcta ctaagctctc cgcttataaa caacgccttt agtattcgac agaatgacag  14640
tacggcctca aaccctacct acaacgccct ggcgtttatg cctaacagta ccatatatgc  14700
aagaggggga ggtggtgaac cacgaaacaa ctactacgtc caaacgtatc ttaggggaaa  14760
tgttcaaaaa ccaatcattc ttactgtaac ctacaactca gccgccacag gatattcctt  14820
atcttttaag tggactgctc ttgcacgtga aaagtttgca accccaacaa cttcgttttg  14880
ctacattaca gaacaataaa accgtgtacc ccaccgtttc gtttttttca gatgaaacgg  14940
gcgagagttg atgaagactt caacccagtg taccettatg acccccccaca tgctcccgtt  15000
atgcccttca ttactccacc ttttacctcc tcggatgggt tgcaggaaaa accacttgga  15060
gtgttaagtt taaactacag agatcccatt actacgcaaa atgggtctct tacagttaaa  15120
ctaggaaacg gcctcactct agacaaccag ggacaactaa catcaaccgc tggggaagta  15180
gaacctccac tcactaacgc taacaacaaa cttgcactgg tctatagcga tcctttagca  15240
gtaaagcgca acagcctaac cttatcgcac accgctcccc ttgttattgc tgataactct  15300
ttagcattgc aagtttcaga gcctattttt ataaatgaca aggacaaact agccctgcaa  15360
acagccgcgc cccttgtaac taacgctggc acccttcgct tacaaagcgc cgccccttta  15420
ggcattgcag accaaaccct aaaactcctg tttaccaacc ctttgtactt gcagaataac  15480
tttctcacgt tagccattga acgacccctt gccattacca atagtggaaa gctggctcta  15540
cagctctccc caccgctaca aacagcagac acaggcttga ctttgcaaac caacgtgcca  15600
ttaactgtaa gcaacgggac cctaggctta gccataaagc gcccacttat tgttcaggac  15660
aacaacttgt ttttggactt cagagctccc ctgcgtcttt tcaacagcga ccccgtacta  15720
gggcttaact tttacacccc tcttgcagtg cgcgatgagg cgctcactgt taacacaggc  15780
cgcggcctca cagtgagtta cgatggttta attttaaatc ttggtaagga tcttcgcttt  15840
gacaacaaca ccgtttctgt cgctcttagt gctgctttgc ctttacaata cactgatcag  15900
cttcgcctta acgtgggcgc tgggctgcgt tacaatccag tgagtaaaaa attggacgtg  15960
aaccccaatc aaaacaaggg tttaacctgg gaaaatgact acctcattgt aaagctagga  16020
aatggattag gttttgatgg caatggaaac atagctgttt ctcctcaagt tacatcgcct  16080
gacaccttat ggaccactgc cgatccatcc cccaattgtt ccatctacac tgatttagat  16140
gccaaaatgt ggctctcgtt ggtaaaacaa gggggtgtgg ttcacggttc tgttgcttta  16200
```

aaagcattga aaggaaccct attgagtcct acggaaagtg ccattgttat tatactacat 16260
tttgacaatt atggagtgcg aattctcaat tatcccactt tgggcactca aggcacgttg 16320
ggaaataatg caacttgggg ttataggcag ggagaatctg cagacactaa tgtactcaat 16380
gcactagcat ttatgcccag ttcaaaaagg tacccaagag ggcgtggaag cgaagttcag 16440
aatcaaactg tgggctacac ttgtatacag ggtgaccttt ctatgcccgt accgtaccaa 16500
atacagtaca actatggacc aactggctac tcctttaaat ttatttggag aactgtttca 16560
agacaaccat ttgacatccc atgctgtttt ttctcttaca ttacggaaga ataaaacaac 16620
ttttcctttt tattttcttt ttattttaca cgcacagtaa ggcttcctcc acccttccat 16680
ttgacagcat acaccagcct ctccccccttc atggcagtaa actgctgcga gccagtccgg 16740
tatttgggag ttaagatcca aacagtctct ttggtaatca gatgtcgatc cgtgatggac 16800
acaaatccct ggggcaggtt ctccaacgtt tcggtgaaaa actgcatgcc gccctacaaa 16860
acaaacaggt tcaggctctc cacgggttat ctccccgatc aaactcagac agggtaaagg 16920
tgcgatgatg ttccactaaa ccacgcaggt ggcgctgtct gaacctctcg gtgcgactcc 16980
tgtgaggctg gtaagaagtt agattgtcca gcagcctcac agcatggatc atcagtctac 17040
gagtgcgtct ggcgcagcag cgcatctgaa tctcactgag attccggcaa gaatcgcaca 17100
ccatcacaat caggttgttc atgatcccat agctgaacac gctccagcca aagctcattc 17160
gctccaacag cgccaccgcg tgtccgtcca accttacttt aacataaatc aggtgtctgc 17220
cgcgtacaaa catgctaccc gcatacagaa cctcccgggg cagtcccctg ttcaccacct 17280
gcctgtacca gggaaacctc acatttatca gggagccata gatagccatc ttaaaccaat 17340
tagctaacac cgccccacca gctctacact gaagagaacc gggagagtta caatgacagt 17400
gaataatcca tctctcataa cccctaatgg tctgatggaa atccagatct aacgtggcac 17460
agcagataca cactttcata tacattttca tcacatgttt ttcccaggcc gttaaaatac 17520
aatcccaata cacgggccac tcctgcagta caataaagct aatacaagat ggtatactcc 17580
tcacctcact aacattgtgc atgttcatat tttcacattc taagtaccga gagctctcct 17640
ctacaacagc actgccgcgg tcctcacaag gtggtagctg gtgacaattg tagggagcca 17700
gtctgcagcg ataccgtctg tcgcgttgca tcgtagacca gggaccgacg cacttcctcg 17760
tacttgtagt agcagaacca cgtccgctgc cagcacgtct ccaagtaacg ccggtccctg 17820
cgtcgctcac gctccctcct caacgcaaag tgcaaccact cttgtaatcc acacagatcc 17880
ctctcggcct ccggggcgat gcacacctca aacctacaga tgtctcggta cagttccaaa 17940
cacgtagtga gggcgagttc caaccaagac agacagcctg atctatcccg acacactgga 18000
ggtggaggaa gacacggaag aggcatgtta ttccaagcga ttcaccaacg ggtcgaaatg 18060
aagatcccga agatgacaac ggtcgcctcc ggagccctga tggaatttaa cagccagatc 18120
aaacattatg cgattttcca ggctatcaat cgcggcctcc aaaagagcct ggacccgcac 18180
ttccacaaac accagcaaag caaaagcgtt attatcaaac tcttcgatca tcaagctgca 18240
ggactgtaca atgcccaagt aattttcatt tctccactcg cgaatgatgt cgcggcaaat 18300
agtctgaagg ttcatgccgt gcatattaaa aagctccgaa agggcgccct ctatagccat 18360
gcgtagacac accatcatga ctgcaagata tcgggctcct gagacacctg cagcagattt 18420
aacagaccca ggtcaggttg ctctccgcga tcgcgaatct ccatccgcaa ggtcatttgc 18480
aaataattaa atagatctgc gccgactaaa tctgttaact ccgcgctagg aactaaatca 18540

```
ggtgtggcta tgcagcacaa aagttccagg gatggcgcca aactcactag aaccgctccc  18600
gagtagcaaa actgatgaat gggagtaaca cagtgtaaaa tgttcagcca aaaatcacta  18660
agctgctcct ttaaaaagtc cagtacttct atattcagtc cgtgcaagta ctgaagcaac  18720
tgtgcgggaa tatgcacagc aaaaaaaata gggcggctca gatacatgtt gacctaaaat  18780
aaaaataaac attaaactaa agaagcttgg cgaacggtgg gatatatgac acgctccagc  18840
agcaggcaag caaccggctg tccccgggaa ccgcggtaaa attcatccga atgattaaaa  18900
agaacaacag aaacttccca ccatgtactc ggttggatct cctgagcaca cagcaatacc  18960
cccctcacat tcatatccgc cacagaaaaa aaacgtccca gatacccagt gggaatatcc  19020
aacgacagct gcaaagacag caaaataatc cctctgggag caagcacaaa atcctccggt  19080
gaaaaaagaa catacatatt agaataaccc tgttgctggg gcaaaaaggc ccgacgtccc  19140
agcaaatgca catatatgtg ttgatcagcc attgccccgt cttaccgcgt ataaagccac  19200
gaaaaagtcg agctaaaatc cacccaacag cctatagcta tatatacact ccgcccaatg  19260
acgctaacac cgtaccaccc acgaccaaag ttcacccaca cccacaaaac ccgcgaaaat  19320
ccagcgccgt cagcacttcc gcaatttcag tctcacaacg tcacttccgc gcgccttttt  19380
tcactattcc cacacccgcc ctcgcgccac cccgcgtcac cccgcgtcac cgcacgtcac  19440
cccggccccg cctcgctcct ccccgctcat tatcatattg gcacgtttcc agaataaggt  19500
atattattga tgatgttaat taattcgaac ccataatacc cataatagct gtttgccatc  19560
gacgcgaggc tggatggcct tccccattat gattcttctc gcttccggcg gcatcgggat  19620
gcccgcgttg caggccatgc tgtccaggca ggtagatgac gaccatcagg gacagcttca  19680
aggatcgctc gcggctctta ccagcccagc aaaaggccag gaaccgtaaa aaggccgcgt  19740
tgctggcgtt tttccatagg ctccgccccc ctgacgagca tcacaaaaat cgacgctcaa  19800
gtcagaggtg gcgaaacccg acaggactat aaagatacca ggcgtttccc cctggaagct  19860
ccctcgtgcg ctctcctgtt ccgaccctgc cgcttaccgg atacctgtcc gcctttctcc  19920
cttcgggaag cgtggcgctt tctcatagct cacgctgtag gtatctcagt tcggtgtagg  19980
tcgttcgctc caagctgggc tgtgtgcacg aaccccccgt tcagcccgac cgctgcgcct  20040
tatccggtaa ctatcgtctt gagtccaacc cggtaagaca cgacttatcg ccactggcag  20100
cagccactgg taacaggatt agcagagcga ggtatgtagg cggtgctaca gagttcttga  20160
agtggtggcc taactacggc tacactagaa ggacagtatt tggtatctgc gctctgctga  20220
agccagttac cttcggaaaa agagttggta gctcttgatc cggcaaacaa accaccgctg  20280
gtagcggtgg tttttttgtt tgcaagcagc agattacgcg cagaaaaaaa ggatctcaag  20340
aagatccttt gatcttttct acggggtctg acgctcagtg gaacgaaaac tcacgttaag  20400
ggattttggt catgagatta tcaaaaagga tcttcaccta gatcctttta aattaaaaat  20460
gaagttttaa atcaatctaa agtatatatg agtaaacttg gtctgacagt taccaatgct  20520
taatcagtga ggcacctatc tcagcgatct gtctatttcg ttcatccata gttgcctgac  20580
tccccgtcgt gtagataact acgatacggg agggcttacc atctggcccc agtgctgcaa  20640
tgataccgcg agacccacgc tcaccggctc cagatttatc agcaataaac cagccagccg  20700
gaagggccga gcgcagaagt ggtcctgcaa ctttatccgc ctccatccag tctattaatt  20760
gttgccggga agctagagta agtagttcgc cagttaatag tttgcgcaac gttgttgcca  20820
ttgctgcagg catcgtggtg tcacgctcgt cgtttggtat ggcttcattc agctccggtt  20880
cccaacgatc aaggcgagtt acatgatccc ccatgttgtg caaaaaagcg gttagctcct  20940
```

tcggtcctcc gatcgttgtc agaagtaagt tggccgcagt gttatcactc atggttatgg 21000
cagcactgca taattctctt actgtcatgc catccgtaag atgcttttct gtgactggtg 21060
agtactcaac caagtcattc tgagaatagt gtatgcggcg accgagttgc tcttgcccgg 21120
cgtcaacacg ggataatacc gcgccacata gcagaacttt aaaagtgctc atcattggaa 21180
aacgttcttc ggggcgaaaa ctctcaagga tcttaccgct gttgagatcc agttcgatgt 21240
aacccactcg tgcacccaac tgatcttcag catcttttac tttcaccagc gtttctgggt 21300
gagcaaaaac aggaaggcaa aatgccgcaa aaaagggaat aagggcgaca cggaaatgtt 21360
gaatactcat actcttcctt tttcaatatt attgaagcat ttatcagggt tattgtctca 21420
tgagcggata catatttgaa tgtatttaga aaaataaaca aataggggtt ccgcgcacat 21480
ttccccgaaa agtgccacct gacgtctaag aaaccattat tatcatgaca ttaacctata 21540
aaaataggcg tatcacgagg ccctttcgtc ttcaagaatt ggtcgatggc aaacagctat 21600
tatgggtatt atgggttcga attaat 21626

<210> SEQ ID NO 43
<211> LENGTH: 19593
<212> TYPE: DNA
<213> ORGANISM: Artificial Sequence
<220> FEATURE:
<223> OTHER INFORMATION: Synthetic oligonucleotide pBr/sAd4310A.RsrII-
rITR.dE3

<400> SEQUENCE: 43
attaacaccg tggattccgt gatcgacagc gtggtggcca gcgccagggc ctatgctcgc 60
cgcaagaggc ggctgcatcg gaaacgtcgc cccaccgccg ccatgctagc agccagggcc 120
gtgctgaggc gggcccggag ggtaggcagg agggctatgc gccgcgctgc cgccaacgcc 180
gccgggaggg cccgcagaca agccgcccgc caggccgccg ctgccatcgc tagcatggcc 240
agacccagga gagggaacgt gtactgggtg cgcgattctg taacgggagt ccgagtgccg 300
gtgcgcagcc gacctccccg aagttagaag atccaagctg cgaagacggc ggtactgagt 360
ctccctgttg ttattagccc aacatgagca agcgcaagtt taaagaagaa ctgctgcaga 420
cgctggtgcc tgagatctat ggccctccgg acgtgaagcc tgacattaag ccccgcgata 480
tcaagcgtgt taaaaagcgg gaaaaaaaag aggaacttgc ggcggtagac gatggcggtg 540
tagaatttat taggagtttc gccccacggc gcagggttca atggaaaggg cggcgtgtac 600
aacgcgttct gaggccgggc accgcggtag tttttacccc gggagagcgg tcggccgtta 660
ggggtttcaa gcggcagtac gatgaggtgt acggcgacga agacatactg gaacaggcgg 720
ctcagcagat tggagaattc gcttatggca aacgttctcg gcgcgaagac ctggccatcg 780
ccttggacag cggcaatccc acacccagcc tcaaacccgt gacgctgcaa caggtgcttc 840
ccgtgagcgc cagtactgac agcaaaaggg ggattaaaag agagatggaa gagctgcaac 900
ccaccatcca acttatggtc cctaaacgac agaggttgga agaggtcctg gagaagatga 960
aagtggaccc cagcatagag ccggatgtga aagtgaggcc tattaaggaa gtggcccccg 1020
gtcttggggt gcaaacggtg gacattcaaa tccccgtcac gtccgcttca acagcggtgg 1080
aagccatgga aacgcaaacg gaagcccccg ccgtcacggt cggtaccagg gaagtggcgt 1140
tgcaaacgga accctggtac gaatacgcca cccctaggcg tcagaggcgg tccgcccgtt 1200
acggacccgt caacgccatc atgcccgagt acgcgctaca tccgtctatc cggcccactc 1260
ccggctaccg ggagtgacgc tatcgcccgt caggaactcg ccgccgttac cgtcgccgcc 1320

```
gtcgctctcg ccgcgctctg gccccagtgt cggtgcggcg cgtgacccgc caggggaaaa   1380
cagtcaccat ccccaacccg cgctaccacc ctagcattct ttaatgactc tgccgttttg   1440
cagatggctc tgacttgccg cgtgcgcctt cccgttctgc actatcgagg aagatctcgt   1500
cgtaggagag gcatggcggg cagtggtcgc cggcgggctt tgcgcaggcg catgaaaggc   1560
ggaattttac ccgccctaat acctataatc gccgccgcca taggcgccat acccggcgtc   1620
gcttcagtgg ccttgcaagc agctcgtaat aaataaacga aggcttttgc acttatgtcc   1680
tggtcctgac tattttatgc agaaaaagca tggaagacat caattttacg tcgctggctc   1740
cgcggcaagg ctcgcggccg ctcatgggca cctggaacga catcggcacc agtcagctca   1800
acgggggcgc tttcaattgg gggagccttt ggagcggcat taaaaacttt ggctccacga   1860
ttaaatccta cggcagcaaa gcctggaaca gtagtgctgg tcaaatgctc cgagataaac   1920
tgaaggacac caacttccaa gagaaagtgg tcaacggggt ggtgaccggc atacacggcg   1980
cggtagatct tgccaaccaa gcggtgcaga aagagattga caggcgattg gaaaactcgc   2040
gggtgccgcc gcagagaggg gatgaggtgg aggtcgagga agtagaagta gaggaaaagc   2100
tgcccccctt ggagaaagtt cccggtgcga ttccaaggcc gcagaagcgg ccaaggccag   2160
aactagaaga aactctggtg acggagagca aggagcctcc ctcgtacgag caagccttaa   2220
aagagggcgc ttcaccctac ccgatgacca aaccgatcgc gcctatggct cggccggtgt   2280
acgggaagga ctacaaacct gtcacgctag aacttcctcc gccactccct tcgcgtccta   2340
cggtgcctcc catgccagcg ccgtcggccg gtcccgtgtc tgcaccttcc gcagcgcctc   2400
tgccagccgc ccgcccagtg gccgtggcca ctgccagaaa ccccagaggc cagagaggag   2460
ccaactggca aaacacgctg aacagcatcg tgggcctggg agttaaaagc ctgaaacgcc   2520
gccgttgcta ttattaaaaa agtgtagcta aaaaatctcc cgttgtatac gcctcctatg   2580
ttaccgccag agacgtgtga ctgtcgtcgc gagcagcgct ttcaagatgg ccaccccatc   2640
gatgatgccg cagtggtctt acatgcacat cgccgggcag gacgcctcgg agtatctgag   2700
ccccggtctt gtgcagtttg cccgcgccac cgacacctac ttcagcttgg gaaacaagtt   2760
tagaaatccc accgtggccc ccacgcacga tgtgaccacg gatcgttcgc agaggctgac   2820
tctgcgcttt gtaccggtag accgtgagga tactgcctat tcttacaaag ttcggtatac   2880
gttagccgta ggagacaaca gggtgctgga catggccagt acttactttg acatccgcgg   2940
tgttcttgac cgcggtccaa gctttaaacc gtataccgga acggcataca atgccttggc   3000
tccaaagggc gctccaaatg cttgccagtg gacaacgacc aacgggggca ataaaacgaa   3060
cacttttgcc caagcccctt taataggcac ggctattgac ggaaccaacg gactgcagat   3120
tgggcaagat aatggacaag ctgtttatgc tgacaaaacc tttcaacccg aaccacaagt   3180
gggagaatct cagtggaata ctaatccaac cacaaacgca gcaggacgcg tgttaaaaac   3240
aactactcgc atgctgcctt gctatggttc ttttgcaagg cccaccaatg agaaaggggg   3300
tcaagcttca ggagacgtta ccttccaatt tttcgacact gcctcggaca atggcaacaa   3360
ccctaaggtg gtgctatatg gagaagacgt caacattgaa tcgcctgaca cacacttaat   3420
ctacaaaccc accgctgaca acacaaactc tgaaaacctt ttgggtcaac aggccgctcc   3480
aaacagagcc aattacattg cctttcggga caacttcatt ggactaatgt actataattc   3540
aacaggaaac atgggagtgt tggcagggca ggcttcccaa ctaaatgctg tggtagactt   3600
gcaagacaga aacactgagc tttcctacca actcatgtta gatgcaatag gagaccggag   3660
```

-continued

```
tcgttacttt tcaatgtgga accaagcagt ggacagctat gatccagatg tgcgaattat   3720
tgaaaatcat ggcgttgagg acgaactgcc aaattactgc ttccctctta acgctcaagg   3780
aattgctaac acctataaag gcgttaagaa aaacaacggc aattgggcga aagacgacgc   3840
agtagtagaa actaacgaaa ttggcatagg aaatgttttt gccatggaga taaatttaac   3900
tgctaacttg tggcgaaact ttctgtattc caatattgct ttgtacctgc cagactccta   3960
caagtattca ccgggaaaca taaccttacc cgaaaacaaa aacagttaca attacattaa   4020
tggtcgagta acagctcctg gtctggtaga cacctttgta aacattggcg cgcgatggtc   4080
tcccgacccc atggacaacg tgaatccttt taatcaccat cgcaatgctg gtctgcgtta   4140
tcgctccatg cttctaggca acggccgcta cgtgcccttc cacattcagg tgcctcaaaa   4200
attctttgcc attaagaacc tgcttctgct gcctgggtcc tacacctacg agtggaactt   4260
cagaaaagat gtaaacatga tcttgcagag cacgctgggc aacgacctcc gtgtcgacgg   4320
ggccagcgtc agattcgaca gcattaacct ctacgctaat ttcttcccca tggcacataa   4380
caccgcttcc accctggagg ctatgttacg caacgacacc aacgaccagt cctttaatga   4440
ctacctctgc gcggccaaca tgctataccc cattcctgcc aatgccacca gtgtgcccat   4500
ctccatcccc tctcgcaact gggcagcttt cagagggtgg agtttcaccc gcctcaaaac   4560
aaaagaaacc ccctcgctgg gttccggatt tgatccatac tttgtttact caggctccat   4620
tccctacctg gatggtacct tctacctgaa ccacaccttc aaaaaggtgt ctattatgtt   4680
cgactcttct gtgagctggc ccggcaacga ccgcctgctg acccctaatg agtttgaaat   4740
taagcgctcg gtggacggag aaggatacaa tgtagcccag agcaacatga ccaaagactg   4800
gttcttaatt caaatgctca gccactacaa cattggttac caagggtttt acgtgcccga   4860
ggcttacaaa gacagaatgt actccttttt tagaaacttc caacctatga gtagacaggt   4920
agtggatgca gatcggtatg aacaatacaa aaaagtcacc gttgagtatc aacataataa   4980
ttctggtttt gtgggataca tgggacccac catgagggaa gggcaggctt atccagcgaa   5040
ttacccttat cctcttattg gagacaccgc cgtgcccagc ctgacccaga aaaagttcct   5100
ctgtgaccgc accatgtgga gaatcccctt ctctagcaac ttcatgtcta tgggggccct   5160
caccgacctg gggcagaaca tgctgtacgc caattccgct cacgccttgg atatgacctt   5220
tgaggtggac cccatggatg agcccacgct tctctatgtt ctgtttgaag tcttcgacgt   5280
ggtgcgcatc caccagccgc accgcggcgt catcgaggcc gtctacctgc gcacaccttt   5340
ctctgccggt aacgccacca cataagaagc aaatgggctc cagcgaacag gagctgcggg   5400
ccattattcg cgacctgggc tgcggaccct actttttggg caccttcgac aagcgtttcc   5460
ccggattcat gtcccccag aagccggcct gtgccatagt caacacggcc gggcgggaga   5520
ccgggggggt tcactggctc gccttcgcct ggaacccgcg caaccgcacc tgctacctgt   5580
tcgacccttt tggtttttcc gacgaaaggc tgaagcaaat ctaccagttc gaatacgaag   5640
gactcctcaa gcgcagcgct ctggcctcca cgcccgacca ctgcgtcacc ctggaaaaat   5700
ccacccaaac ggtgcagggg cccctctcgg ccgcctgcgg gcttttctgt tgcatgtttt   5760
tgcacgcctt cgtgcactgg cctcacaacc ccatggagcg caaccccacc atggatctgc   5820
tcaccggagt gcccaacagc atgcttcaca gcccccaggt cgcccccacc ctgcgccgta   5880
accaggaaca cctgtatcgc tttctgggga aacactctgc ctatttccgc cgccaccggc   5940
agcgcatcga gcaggccacg gcctttgaaa gcatgagcca aagagtgtaa tcaataaaaa   6000
ccatttttat ttaacatgat acgcgcttct ggcgttttta ttaaaaatcg aacggttcga   6060
```

gggaggggtc ctcgtgcccg ctgggaaggg acacgttgcg gtactggaaa cgggcgctcc 6120
aacgaaactc ggggatcacc agccgcggca ggggcacgtc ttctaggttc tgcttccaga 6180
actgccgcac cagctgcagg gctcccatga cgtcgggcgc cgagatcttg aagtcgcagt 6240
tagggccgga gcccccgcgg ctgttgcgga acacggggtt ggcacactgg aacaccagca 6300
cgctggggtt gtaaatactg gccagggccg ttgggtcggt cacctccgac gcatccagat 6360
cctcggcatt gctcagggcg aacggagtca gcttgcacat ctgccgtccg atctggggca 6420
ccaggtcggg tttgttgagg caatcgcagc gcagagggat taggatgcga cgctgcccgc 6480
gttgcatgat agggtaactc gccgccagga actcctccat ctgacggaag gccatctggg 6540
ccttggtacc ctcggtgaaa aatagcccac aggacttgct agaaaatacg ttattgccgc 6600
agttgatgtc ttccgcgcag cagcgtgcat cttcgttctt cagctgaacc acgttacgcc 6660
cccagcggtt ctggaccacc ttggctttcg taggatgctc cttcaacgcc cgctgaccgt 6720
tctcgctggt cacatccatt tccaccacgt gctccttgca gaccatctcc actccgtgga 6780
agcagaacag gacgccctcc tgctgggtat tgcgatgctc ccaaacggca catccggtgg 6840
gctcccagct cttgcgtttc acccccgcgt atgcttccat gtaagccatg aggaatctgc 6900
ccatcagctc ggtgaaggtc ttctggttgg tgaaggttag cggcaggccg cggtgctcct 6960
cgttcaacca agtttgacag attttgcggt acacggctcc ctggtcgggc agaaacttaa 7020
aagccgctct gctctcgttg tccacgtgga acttctccat caacatcgtc atgacttcca 7080
tgcccttctc ccacgccgtc accaacggtt cggtcccggg gttcttcacc aacacggcgg 7140
tggaggggcc ctcgccggcc ccgacgtcct tcatggtcat tctttggaac tccacggtgc 7200
cgtccgcgcg gcgtactctg cgcatcggag ggtagctgaa gcccacctcc accacggtgc 7260
cttcgccctc gctgtcggaa acgatctccg gggatggcgg cggcgcgggt gtcgccttgc 7320
gagccttctt cttgggaggg agcggaggca cctcctgctc gcgctcgggg ctcatctccc 7380
gcaagtaggg ggtaatggag cttccgggtt ggttctgacg gttggccatt gtatcctagg 7440
cagaaagaca tggatcttat gcgcgaggaa actttaaccg ccccgtcccc cgtcagcgac 7500
gaagaggtca tcgtcgaaca ggacccgggc tacgttacgc cgcccgagga tctggagtcc 7560
cccttagacg accgacgcga cgctagtgag cggcaggaaa atgagaaaga ggaggaggag 7620
ggctgctacc tcctggaagg cgacgtcttg ctaaagcatt tcgccaggca gagcaccata 7680
ctcaaggagg ccttgcaaga ccgctccgag gtgcccttgg acgtcgccgc gctctcccag 7740
gcctacgagg cgaacctttt ctcgccccga gtgcctccga agagacagcc caacggcacc 7800
tgcgagccca acccgcgact caacttctac cccgtgttcg ccgtgcccga ggcgctggcc 7860
acctaccaca tctttttcaa aaaccagcgc attccccttt cctgccgggc caaccgcacc 7920
gcagccgata ggaagctaac actcagaaac ggagccagca tacctgatat cacgtcactg 7980
gaggaagtgc ctaagatctt cgagggtctg ggtcgagatg agaagcgggc ggcgaacgct 8040
ctgcagaaag aacagaaaga gagtcagaac gtgctggtgg agctggaggg ggacaacgcg 8100
cgtctggccg tcctcaaacg ctgcatagaa gtctcccact tcgcctaccc cgccctcaac 8160
ttgccaccca aagttatgaa atcggtcatg gatcagctgc tcatcaagag agctgagccc 8220
ctggatcccg accaccccga ggcggaaaac tcagaggacg gaaagcccgt cgtcagcgac 8280
gaggagctcg agcggtggct ggaaaccggg gacccccaac agttgcaaga gaggcgcaag 8340
atgatgatgg cggccgtgct ggtcaccgtg gagctggaat gcctgcaacg gtttttcagc 8400

-continued

```
gacgtggaga cgctacgcaa aatcggggag tccctgcact acaccttccg ccagggctac   8460
gtccgccagg cctgcaagat ctccaacgtg gagctcagca acctggtctc ctacatgggc   8520
atcctccacg agaaccggct ggggcagagc gtgctgcact gcaccttgca aggcgaggcg   8580
cggcgggact acgtccgcga ctgcatctac ctcttcctca ccctcacctg gcagaccgcc   8640
atgggcgtct ggcagcagtg cttggaagag agaaacctca aagagctaga caaactcctc   8700
tgccgccagc ggcgggccct ctggaccggt ttcagcgagc gcacggtcgc ctgcgccctg   8760
gcagacatta tcttcccgga gcgcctgatg aaaaccttgc agaacggcct gccggatttt   8820
atcagtcaaa gtattttgca aaacttccgc tccttcgttc tggagcgctc cgggatcttg   8880
cccgccatga gctgcgcgct gccttctgac tttgtccccc tttcctaccg cgagtgtcct   8940
ccccccctgt ggagccactg ctacctcttc caactggcca actttctggc ctaccactcc   9000
gacctcatgg aagacgtgag cggagagggg ctgctcgagt gccactgccg ctgcaacctc   9060
tgcacccccc acagatcgct ggcctgcaac accgagctgc tcagcgaaac ccaggtcata   9120
ggtaccttcg agatccaggg gccccagcag caagagggtg cttccggctt gaagctcact   9180
ccggcgctgt ggacctcggc ttacttacgc aaatttgtag ccgaggacta ccacgcccac   9240
aaaattcagt tctatgaaga ccaatctcga ccacccaaag ccccccctcac ggcctgcgtc   9300
atcactcaga gcaaaatcct ggcccaattg caatccatca accaagcgcg ccgagatttc   9360
cttttgaaaa agggtcgggg ggtgtaccta gaccccccaga ccggcgagga actcaacccg   9420
tccacactct ccgtcgaagc agcccccccg agacatgccg cccaagggaa ccgccaagca   9480
gctgatcgct cggcagagag cgaagaagca agagctgctc cagcagcagc agcaggtgga   9540
ggacgaggaa gagctgtggg acagccaggc agaggaggtg tcagaggacg aggaggagat   9600
ggaaagctgg gacagcctag acgaggagga ggacgagctt tcagaggaag aggcgaccga   9660
agaaaaacca cctgcatcca gcgcgccttc tctgagccga cagccgaagc cccggccccc   9720
gacgcccccg gccggctcac tcaaagccag ccgtaggtgg gacgccaccg gatctccagc   9780
ggcagcggca acggcagcgg gtaaggccaa acgcgagcgg cgggggtatt gctcctggcg   9840
ggcccacaaa agcagtatcg tgaactgctt gcaacactgc gggggaaaca tctcctttgc   9900
ccgacgctac ctcctcttcc atcacggtgt ggccttccct cgcaacgttc tctattatta   9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttccccctcg ggcgccaaaa  10320
cccacgtcat tgccagcatg agcaaggaga ttcccacccc ttacatgtgg agctatcagc  10380
cccagatggg cctggccgcg ggggccgccc aggactactc cagcaagatg aactggctca  10440
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
```

acggagtctt ccagctcgga ggagcgggcc gctcttcctt caccactcgc caggcctacc 10860
tgaccctgca gagctcttcc tcgcagccgc gctccggggg aatcggcact ctccagttcg 10920
tggaagagtt cgtcccctcc gtctacttca acccgttttc cggctcacct ggacgctacc 10980
cggacgcctt cattcccaac tttgacgcag tgagtgaatc cgtggacggc tacgactgat 11040
gacagatggt gcggccgtga gagctcggct gcgacatctg catcactgcc gccagcctcg 11100
ctgctacgct cgggaggcga tcgtgttcag ctactttgag ctgccggacg agcaccctca 11160
ggggccggct cacgggttga aactcgagat cgagaacgcg ctcgagtctc gcctcatcga 11220
cgccttcacc gcccggcctc tcctggtaga aaccgaacgc gggatcacta ccatcaccct 11280
gttctgcatc tgccccacgc ccggattaca tgaagatctg tgttgtcatc tttgcgctca 11340
gtttaataaa aactgaactg tttgccgcac cttcaacgcc atctgtgatt tctacaacaa 11400
aaagttcttc tggcaaaggt acacaaactg tattttattc taattctacc tcatctattg 11460
tgctgaactg cgcctgcact aacgaactta tcctgtagag gggctatcc tctgtcactg 11520
tcacgcacct gattgcatgt ccaaactaat caaaactctc tgtgctttag gtgatatttt 11580
taaaatgtaa atcataataa acttacctta aatttgacaa caattttctg gtgacatcat 11640
tcagcagcac cactttaccc tcttcccagc tctcgtatgg gatgcgatag tgggtggcaa 11700
acttcctcca aaccctaaaa gaaatattgg tatccacttc cttgtcctca cccacaattt 11760
tcatcttttc atagatgaaa agaaccagag ttgatgaaga cttcaacccc gtctacccct 11820
atgacaccac aaccactcct gcagttccct ttatatcacc cccctttgta aacagcgatg 11880
gtcttcagga aaaccccca ggtgttttaa gtctgcgaat agctaaaccc ctatatttcg 11940
acatggagag aaaactagcc ctttcacttg gaagagggtt gacaattacc gccgccggac 12000
aattagaaag tacgcagagc gtacaaacca acccaccgtt gataattacc aacaacaaca 12060
cactgaccct acgtcattct cccccttaa acctaactga caatagctta gtgctaggct 12120
actcgagtcc gctccgcgtc acagacaaca aacttacatt taacttcaca tcaccactcc 12180
gttatgaaaa tgaaaacctt acttttaact atacagagcc tcttaaactt ataaataaca 12240
gccttgccat tgacatcaat tcctcaaaag gccttagtag cgtcggaggc tcactagctg 12300
taaacctgag ttcagactta aagtttgaca gcaacggatc catagctttt ggcatacaaa 12360
ccctgtggac cgctccgacc tcgactggca actgcaccgt ctacagcgag ggcgattccc 12420
tacttagtct ctgtttaacc aaatgcggag ctcacgtctt aggaagtgta agtttaaccg 12480
gtttaacagg aaccataacc caaatgactg atatttctgt caccattcaa tttacatttg 12540
acaacaatgg taagctacta agctctccgc ttataaacaa cgcctttagt attcgacaga 12600
atgacagtac ggcctcaaac cctacctaca acgccctggc gtttatgcct aacagtacca 12660
tatatgcaag agggggaggt ggtgaaccac gaaacaacta ctacgtccaa acgtatctta 12720
ggggaaatgt tcaaaaacca atcattctta ctgtaaccta caactcagcc gccacaggat 12780
attccttatc ttttaagtgg actgctcttg cacgtgaaaa gtttgcaacc ccaacaactt 12840
cgttttgcta cattacagaa caataaaacc gtgtacccca ccgtttcgtt tttttcagat 12900
gaaacgggcg agagttgatg aagacttcaa cccagtgtac ccttatgacc ccccacatgc 12960
tcccgttatg cccttcatta ctccaccttt tacctcctcg gatgggttgc aggaaaaacc 13020
acttggagtg ttaagtttaa actacagaga tcccattact acgcaaaatg ggtctcttac 13080
agttaaacta ggaaacggcc tcactctaga caaccaggga caactaacat caaccgctgg 13140

-continued

```
ggaagtagaa cctccactca ctaacgctaa caacaaactt gcactggtct atagcgatcc  13200
tttagcagta aagcgcaaca gcctaacctt atcgcacacc gctccccttg ttattgctga  13260
taactcttta gcattgcaag tttcagagcc tatttttata aatgacaagg acaaactagc  13320
cctgcaaaca gccgcgcccc ttgtaactaa cgctggcacc cttcgcttac aaagcgccgc  13380
ccctttaggc attgcagacc aaaccctaaa actcctgttt accaaccctt tgtacttgca  13440
gaataacttt ctcacgttag ccattgaacg acccccttgcc attaccaata gtggaaagct  13500
ggctctacag ctctccccac cgctacaaac agcagacaca ggcttgactt tgcaaaccaa  13560
cgtgccatta actgtaagca acgggaccct aggcttagcc ataaagcgcc cacttattgt  13620
tcaggacaac aacttgtttt tggacttcag agctcccctg cgtcttttca acagcgaccc  13680
cgtactaggg cttaactttt acacccctct tgcagtgcgc gatgaggcgc tcactgttaa  13740
cacaggccgc ggcctcacag tgagttacga tggtttaatt ttaaatcttg gtaaggatct  13800
tcgctttgac aacaacaccg tttctgtcgc tcttagtgct gctttgcctt tacaatacac  13860
tgatcagctt cgccttaacg tgggcgctgg gctgcgttac aatccagtga gtaaaaaatt  13920
ggacgtgaac cccaatcaaa acaagggttt aacctgggaa aatgactacc tcattgtaaa  13980
gctaggaaat ggattaggtt ttgatggcaa tggaaacata gctgtttctc ctcaagttac  14040
atcgcctgac accttatgga ccactgccga tccatccccc aattgttcca tctacactga  14100
tttagatgcc aaaatgtggc tctcgttggt aaaacaaggg ggtgtggttc acggttctgt  14160
tgctttaaaa gcattgaaag gaaccctatt gagtcctacg gaaagtgcca ttgttattat  14220
actacatttt gacaattatg gagtgcgaat tctcaattat cccactttgg gcactcaagg  14280
cacgttggga aataatgcaa cttggggtta taggcaggga gaatctgcag acactaatgt  14340
actcaatgca ctagcattta tgcccagttc aaaaaggtac ccaagagggc gtggaagcga  14400
agttcagaat caaactgtgg gctacacttg tatacagggt gacctttcta tgcccgtacc  14460
gtaccaaata cagtacaact atggaccaac tggctactcc tttaaattta tttggagaac  14520
tgtttcaaga caaccatttg acatcccatg ctgtttttc tcttacatta cggaagaata  14580
aaacaacttt tcctttttat tttcttttta ttttacacgc acagtaaggc ttcctccacc  14640
cttccatttg acagcataca ccagcctctc cccttcatg gcagtaaact gctgcgagcc  14700
agtccggtat ttgggagtta agatccaaac agtctctttg gtaatcagat gtcgatccgt  14760
gatggacaca aatccctggg gcaggttctc caacgtttcg gtgaaaaact gcatgccgcc  14820
ctacaaaaca aacaggttca ggctctccac gggttatctc cccgatcaaa ctcagacagg  14880
gtaaaggtgc gatgatgttc cactaaacca cgcaggtggc gctgtctgaa cctctcggtg  14940
cgactcctgt gaggctggta agaagttaga ttgtccagca gcctcacagc atggatcatc  15000
agtctacgag tgcgtctggc gcagcagcgc atctgaatct cactgagatt ccggcaagaa  15060
tcgcacacca tcacaatcag gttgttcatg atcccatagc tgaacacgct ccagccaaag  15120
ctcattcgct ccaacagcgc caccgcgtgt ccgtccaacc ttactttaac ataaatcagg  15180
tgtctgccgc gtacaaacat gctacccgca tacagaacct cccggggcag tcccctgttc  15240
accacctgcc tgtaccaggg aaacctcaca tttatcaggg agccatagat agccatctta  15300
aaccaattag ctaacaccgc ccccaccagct ctacactgaa gagaaccggg agagttacaa  15360
tgacagtgaa taatccatct ctcataaccc ctaatggtct gatggaaatc cagatctaac  15420
gtggcacagc agatacacac tttcatatac attttcatca catgtttttc ccaggccgtt  15480
aaaatacaat cccaatacac gggccactcc tgcagtacaa taaagctaat acaagatggt  15540
```

atactcctca cctcactaac attgtgcatg ttcatatttt cacattctaa gtaccgagag 15600
ctctcctcta caacagcact gccgcggtcc tcacaaggtg gtagctggtg acaattgtag 15660
ggagccagtc tgcagcgata ccgtctgtcg cgttgcatcg tagaccaggg accgacgcac 15720
ttcctcgtac ttgtagtagc agaaccacgt ccgctgccag cacgtctcca agtaacgccg 15780
gtccctgcgt cgctcacgct ccctcctcaa cgcaaagtgc aaccactctt gtaatccaca 15840
cagatccctc tcggcctccg gggcgatgca cacctcaaac ctacagatgt ctcggtacag 15900
ttccaaacac gtagtgaggg cgagttccaa ccaagacaga cagcctgatc tatcccgaca 15960
cactggaggt ggaggaagac acggaagagg catgttattc caagcgattc accaacgggt 16020
cgaaatgaag atcccgaaga tgacaacggt cgcctccgga gccctgatgg aatttaacag 16080
ccagatcaaa cattatgcga ttttccaggc tatcaatcgc ggcctccaaa agagcctgga 16140
cccgcacttc cacaaacacc agcaaagcaa aagcgttatt atcaaactct tcgatcatca 16200
agctgcagga ctgtacaatg cccaagtaat tttcatttct ccactcgcga atgatgtcgc 16260
ggcaaatagt ctgaaggttc atgccgtgca tattaaaaag ctccgaaagg gcgccctcta 16320
tagccatgcg tagacacacc atcatgactg caagatatcg ggctcctgag acacctgcag 16380
cagatttaac agacccaggt caggttgctc tccgcgatcg cgaatctcca tccgcaaggt 16440
catttgcaaa taattaaata gatctgcgcc gactaaatct gttaactccg cgctaggaac 16500
taaatcaggt gtggctatgc agcacaaaag ttccagggat ggcgccaaac tcactagaac 16560
cgctcccgag tagcaaaact gatgaatggg agtaacacag tgtaaaatgt tcagccaaaa 16620
atcactaagc tgctccttta aaaagtccag tacttctata ttcagtccgt gcaagtactg 16680
aagcaactgt gcgggaatat gcacagcaaa aaaaataggg cggctcagat acatgttgac 16740
ctaaaataaa aataaacatt aaactaaaga agcttggcga acggtgggat atatgacacg 16800
ctccagcagc aggcaagcaa ccggctgtcc ccgggaaccg cggtaaaatt catccgaatg 16860
attaaaaaga acaacagaaa cttcccacca tgtactcggt tggatctcct gagcacacag 16920
caataccccc ctcacattca tatccgccac agaaaaaaaa cgtcccagat acccagtggg 16980
aatatccaac gacagctgca aagacagcaa aataatccct ctgggagcaa gcacaaaatc 17040
ctccggtgaa aaaagaacat acatattaga ataaccctgt tgctggggca aaaaggcccg 17100
acgtcccagc aaatgcacat atatgtgttg atcagccatt gccccgtctt accgcgtata 17160
aagccacgaa aaagtcgagc taaaatccac ccaacagcct atagctatat atacactccg 17220
cccaatgacg ctaacaccgt accacccacg accaaagttc acccacaccc acaaaacccg 17280
cgaaaatcca gcgccgtcag cacttccgca atttcagtct cacaacgtca cttccgcgcg 17340 cctttttca ctattcccac acccgccctc gcgccacccc gcgtcacccc gcgtcaccgc 17400
acgtcacccc ggccccgcct cgctcctccc cgctcattat catattggca cgtttccaga 17460
ataaggtata ttattgatga tgttaattaa ttcgaaccca taatacccat aatagctgtt 17520
tgccatcgac gcgaggctgg atggccttcc ccattatgat tcttctcgct tccggcggca 17580
tcgggatgcc cgcgttgcag gccatgctgt ccaggcaggt agatgacgac catcagggac 17640
agcttcaagg atcgctcgcg gctcttacca gcccagcaaa aggccaggaa ccgtaaaaag 17700
gccgcgttgc tggcgttttt ccataggctc cgcccccctg acgagcatca caaaaatcga 17760
cgctcaagtc agaggtggcg aaacccgaca ggactataaa gataccaggc gtttccccct 17820
ggaagctccc tcgtgcgctc tcctgttccg accctgccgc ttaccggata cctgtccgcc 17880

-continued

```
tttctccctt cgggaagcgt ggcgctttct catagctcac gctgtaggta tctcagttcg  17940

gtgtaggtcg ttcgctccaa gctgggctgt gtgcacgaac cccccgttca gcccgaccgc  18000

tgcgccttat ccggtaacta tcgtcttgag tccaacccgg taagacacga cttatcgcca  18060

ctggcagcag ccactggtaa caggattagc agagcgaggt atgtaggcgg tgctacagag  18120

ttcttgaagt ggtggcctaa ctacggctac actagaagga cagtatttgg tatctgcgct  18180

ctgctgaagc cagttacctt cggaaaaaga gttggtagct cttgatccgg caaacaaacc  18240

accgctggta gcggtggttt ttttgtttgc aagcagcaga ttacgcgcag aaaaaaagga  18300

tctcaagaag atcctttgat cttttctacg gggtctgacg ctcagtggaa cgaaaactca  18360

cgttaaggga ttttggtcat gagattatca aaaaggatct tcacctagat ccttttaaat  18420

taaaaatgaa gttttaaatc aatctaaagt atatatgagt aaacttggtc tgacagttac  18480

caatgcttaa tcagtgaggc acctatctca gcgatctgtc tatttcgttc atccatagtt  18540

gcctgactcc ccgtcgtgta gataactacg atacgggagg gcttaccatc tggccccagt  18600

gctgcaatga taccgcgaga cccacgctca ccggctccag atttatcagc aataaaccag  18660

ccagccggaa gggccgagcg cagaagtggt cctgcaactt tatccgcctc catccagtct  18720

attaattgtt gccgggaagc tagagtaagt agttcgccag ttaatagttt gcgcaacgtt  18780

gttgccattg ctgcaggcat cgtggtgtca cgctcgtcgt ttggtatggc ttcattcagc  18840

tccggttccc aacgatcaag gcgagttaca tgatccccca tgttgtgcaa aaaagcggtt  18900

agctccttcg gtcctccgat cgttgtcaga agtaagttgg ccgcagtgtt atcactcatg  18960

gttatggcag cactgcataa ttctcttact gtcatgccat ccgtaagatg cttttctgtg  19020

actggtgagt actcaaccaa gtcattctga gaatagtgta tgcggcgacc gagttgctct  19080

tgcccggcgt caacacggga taataccgcg ccacatagca gaactttaaa agtgctcatc  19140

attggaaaac gttcttcggg gcgaaaactc tcaaggatct taccgctgtt gagatccagt  19200

tcgatgtaac ccactcgtgc acccaactga tcttcagcat cttttacttt caccagcgtt  19260

tctgggtgag caaaaacagg aaggcaaaat gccgcaaaaa agggaataag ggcgacacgg  19320

aaatgttgaa tactcatact cttccttttt caatattatt gaagcattta tcagggttat  19380

tgtctcatga gcggatacat atttgaatgt atttagaaaa ataaacaaat aggggttccg  19440

cgcacatttc cccgaaaagt gccacctgac gtctaagaaa ccattattat catgacatta  19500

acctataaaa ataggcgtat cacgaggccc tttcgtcttc aagaattggt cgatggcaaa  19560

cagctattat gggtattatg ggttcgaatt aat                               19593
```

```
<210> SEQ ID NO 44
<211> LENGTH: 18199
<212> TYPE: DNA
<213> ORGANISM: Artificial Sequence
<220> FEATURE:
<223> OTHER INFORMATION: Synthetic oligonucleotide pBr/sAd4310A.RsrII-
      rITR.dE3.dE4

<400> SEQUENCE: 44
```

```
attaacaccg tggattccgt gatcgacagc gtggtggcca gcgccagggc ctatgctcgc     60

cgcaagaggc ggctgcatcg gaaacgtcgc cccaccgccg ccatgctagc agccagggcc    120

gtgctgaggc gggcccggag ggtaggcagg agggctatgc gccgcgctgc cgccaacgcc    180

gccgggaggg cccgcagaca agccgcccgc caggccgccg ctgccatcgc tagcatggcc    240

agacccagga gagggaacgt gtactgggtg cgcgattctg taacgggagt ccgagtgccg    300
```

-continued

```
gtgcgcagcc gacctccccg aagttagaag atccaagctg cgaagacggc ggtactgagt    360
ctccctgttg ttattagccc aacatgagca agcgcaagtt taaagaagaa ctgctgcaga    420
cgctggtgcc tgagatctat ggccctccgg acgtgaagcc tgacattaag ccccgcgata    480
tcaagcgtgt taaaaagcgg gaaaaaaaag aggaacttgc ggcggtagac gatggcggtg    540
tagaatttat taggagtttc gccccacggc gcagggttca atggaaaggg cggcgtgtac    600
aacgcgttct gaggccgggc accgcggtag tttttacccc gggagagcgg tcggccgtta    660
ggggtttcaa gcggcagtac gatgaggtgt acggcgacga agacatactg gaacaggcgg    720
ctcagcagat tggagaattc gcttatggca aacgttctcg gcgcgaagac ctggccatcg    780
ccttggacag cggcaatccc acacccagcc tcaaacccgt gacgctgcaa caggtgcttc    840
ccgtgagcgc cagtactgac agcaaaaggg ggattaaaag agagatggaa gagctgcaac    900
ccaccatcca acttatggtc cctaaacgac agaggttgga agaggtcctg gagaagatga    960
aagtggaccc cagcatagag ccggatgtga aagtgaggcc tattaaggaa gtggcccccg   1020
gtcttggggt gcaaacggtg gacattcaaa tccccgtcac gtccgcttca acagcggtgg   1080
aagccatgga aacgcaaacg gaagccccccg ccgtcacggt cggtaccagg gaagtggcgt   1140
tgcaaacgga accctggtac gaatacgcca cccctaggcg tcagaggcgg tccgcccgtt   1200
acggacccgt caacgccatc atgcccgagt acgcgctaca tccgtctatc cggcccactc   1260
ccggctaccg gggagtgacg tatcgcccgt caggaactcg ccgccgttac cgtcgccgcc   1320
gtcgctctcg ccgcgctctg gccccagtgt cggtgcggcg cgtgacccgc caggggaaaa   1380
cagtcaccat ccccaacccg cgctaccacc ctagcattct ttaatgactc tgccgttttg   1440
cagatggctc tgacttgccg cgtgcgcctt cccgttctgc actatcgagg aagatctcgt   1500
cgtaggagag gcatggcggg cagtggtcgc cggcgggctt tgcgcaggcg catgaaaggc   1560
ggaattttac ccgccctaat acctataatc gccgccgcca taggcgccat acccggcgtc   1620
gcttcagtgg ccttgcaagc agctcgtaat aaataaacga aggcttttgc acttatgtcc   1680
tggtcctgac tattttatgc agaaaaagca tggaagacat caattttacg tcgctggctc   1740
cgcggcaagg ctcgcggccg ctcatgggca cctggaacga catcggcacc agtcagctca   1800
acgggggcgc tttcaattgg gggagccttt ggagcggcat taaaaacttt ggctccacga   1860
ttaaatccta cggcagcaaa gcctggaaca gtagtgctgg tcaaatgctc cgagataaac   1920
tgaaggacac caacttccaa gagaaagtgg tcaacggggt ggtgaccggc atacacggcg   1980
cggtagatct tgccaaccaa gcggtgcaga aagagattga caggcgattg gaaaactcgc   2040
gggtgccgcc gcagagaggg gatgaggtgg aggtcgagga agtagaagta gaggaaaagc   2100
tgcccccctt ggagaaagtt cccggtgcga ttccaaggcc gcagaagcgg ccaaggccag   2160
aactagaaga aactctggtg acggagagca aggagcctcc ctcgtacgag caagccttaa   2220
aagagggcgc ttcaccctac ccgatgacca aaccgatcgc gcctatggct cggccggtgt   2280
acgggaagga ctacaaacct gtcacgctag aacttcctcc gccactccct tcgcgtccta   2340
cggtgcctcc catgccagcg ccgtcggccg gtcccgtgtc tgcaccttcc gcagcgcctc   2400
tgccagccgc ccgcccagtg gccgtggcca ctgccagaaa ccccagaggc cagagaggag   2460
ccaactggca aaacacgctg aacagcatcg tgggcctggg agttaaaagc ctgaaacgcc   2520
gccgttgcta ttattaaaaa agtgtagcta aaaaatctcc cgttgtatac gcctcctatg   2580
ttaccgccag agacgtgtga ctgtcgtcgc gagcagcgct ttcaagatgg ccaccccatc   2640
gatgatgccg cagtggtctt acatgcacat cgccgggcag gacgcctcgg agtatctgag   2700
```

-continued

```
ccccggtctt gtgcagtttg cccgcgccac cgacacctac ttcagcttgg gaaacaagtt   2760
tagaaatccc accgtggccc ccacgcacga tgtgaccacg gatcgttcgc agaggctgac   2820
tctgcgcttt gtaccggtag accgtgagga tactgcctat tcttacaaag ttcggtatac   2880
gttagccgta ggagacaaca gggtgctgga catggccagt acttactttg acatccgcgg   2940
tgttcttgac cgcggtccaa gctttaaacc gtataccgga acggcataca atgccttggc   3000
tccaaagggc gctccaaatg cttgccagtg gacaacgacc aacgggggca ataaaacgaa   3060
cacttttgcc caagcccctt taataggcac ggctattgac ggaaccaacg gactgcagat   3120
tgggcaagat aatggacaag ctgtttatgc tgacaaaacc tttcaacccg aaccacaagt   3180
gggagaatct cagtggaata ctaatccaac cacaaacgca gcaggacgcg tgttaaaaac   3240
aactactcgc atgctgcctt gctatggttc ttttgcaagg cccaccaatg agaaaggggg   3300
tcaagcttca ggagacgtta ccttccaatt tttcgacact gcctcggaca atggcaacaa   3360
ccctaaggtg gtgctatatg gagaagacgt caacattgaa tcgcctgaca cacacttaat   3420
ctacaaaccc accgctgaca acacaaactc tgaaaacctt ttgggtcaac aggccgctcc   3480
aaacagagcc aattacattg cctttcggga caacttcatt ggactaatgt actataattc   3540
aacaggaaac atgggagtgt tggcagggca ggcttcccaa ctaaatgctg tggtagactt   3600
gcaagacaga aacactgagc tttcctacca actcatgtta gatgcaatag gagaccggag   3660
tcgttacttt tcaatgtgga accaagcagt ggacagctat gatccagatg tgcgaattat   3720
tgaaaatcat ggcgttgagg acgaactgcc aaattactgc ttccctctta acgctcaagg   3780
aattgctaac acctataaag gcgttaagaa aaacaacggc aattgggcga aagacgacgc   3840
agtagtagaa actaacgaaa ttggcatagg aaatgttttt gccatggaga taaatttaac   3900
tgctaacttg tggcgaaact ttctgtattc caatattgct ttgtacctgc cagactccta   3960
caagtattca ccgggaaaca taaccttacc cgaaaacaaa aacagttaca attacattaa   4020
tggtcgagta acagctcctg gtctggtaga cacctttgta aacattggcg cgcgatggtc   4080
tcccgacccc atggacaacg tgaatccttt taatcaccat cgcaatgctg gtctgcgtta   4140
tcgctccatg cttctaggca acggccgcta cgtgcccttc cacattcagg tgcctcaaaa   4200
attctttgcc attaagaacc tgcttctgct gcctgggtcc tacacctacg agtggaactt   4260
cagaaaagat gtaaacatga tcttgcagag cacgctgggc aacgacctcc gtgtcgacgg   4320
ggccagcgtc agattcgaca gcattaacct ctacgctaat ttcttcccca tggcacataa   4380
caccgcttcc accctggagg ctatgttacg caacgacacc aacgaccagt cctttaatga   4440
ctacctctgc gcggccaaca tgctataccc cattcctgcc aatgccacca gtgtgcccat   4500
ctccatcccc tctcgcaact gggcagcttt cagagggtgg agtttcaccc gcctcaaaac   4560
aaaagaaacc ccctcgctgg gttccggatt tgatccatac tttgtttact caggctccat   4620
tccctacctg gatggtacct tctacctgaa ccacaccttc aaaaaggtgt ctattatgtt   4680
cgactcttct gtgagctggc ccggcaacga ccgcctgctg acccctaatg agtttgaaat   4740
taagcgctcg gtggacggag aaggatacaa tgtagcccag agcaacatga ccaaagactg   4800
gttcttaatt caaatgctca gccactacaa cattggttac caagggtttt acgtgcccga   4860
ggcttacaaa gacagaatgt actccttttt tagaaacttc caacctatga gtagacaggt   4920
agtggatgca gatcggtatg aacaatacaa aaaagtcacc gttgagtatc aacataataa   4980
ttctggtttt gtgggataca tggacccac catgagggaa gggcaggctt atccagcgaa   5040
```

ttacccttat cctcttattg gagacaccgc cgtgcccagc ctgacccaga aaaagttcct 5100
ctgtgaccgc accatgtgga gaatcccctt ctctagcaac ttcatgtcta tgggggccct 5160
caccgacctg ggcagaaca tgctgtacgc caattccgct cacgccttgg atatgacctt 5220
tgaggtggac cccatggatg agcccacgct tctctatgtt ctgtttgaag tcttcgacgt 5280
ggtgcgcatc caccagccgc accgcggcgt catcgaggcc gtctacctgc gcacaccttt 5340
ctctgccggt aacgccacca cataagaagc aaatgggctc cagcgaacag gagctgcggg 5400
ccattattcg cgacctgggc tgcggaccct actttttggg caccttcgac aagcgtttcc 5460
ccggattcat gtccccccag aagccggcct gtgccatagt caacacggcc gggcgggaga 5520
ccggggggt tcactggctc gccttcgcct ggaacccgcg caaccgcacc tgctacctgt 5580
tcgacccttt tggtttttcc gacgaaaggc tgaagcaaat ctaccagttc gaatacgaag 5640
gactcctcaa gcgcagcgct ctggcctcca cgcccgacca ctgcgtcacc ctggaaaaat 5700
ccacccaaac ggtgcagggg cccctctcgg ccgcctgcgg gcttttctgt tgcatgtttt 5760
tgcacgcctt cgtgcactgg cctcacaacc ccatggagcg caaccccacc atggatctgc 5820
tcaccggagt gcccaacagc atgcttcaca gcccccaggt cgcccccacc ctgcgccgta 5880
accaggaaca cctgtatcgc tttctgggga aacactctgc ctatttccgc cgccaccggc 5940
agcgcatcga gcaggccacg gcctttgaaa gcatgagcca aagagtgtaa tcaataaaaa 6000
ccatttttat ttaacatgat acgcgcttct ggcgttttta ttaaaaatcg aacggttcga 6060
gggaggggtc ctcgtgcccg ctgggaaggg acacgttgcg gtactggaaa cgggcgctcc 6120
aacgaaactc ggggatcacc agccgcggca ggggcacgtc ttctaggttc tgcttccaga 6180
actgccgcac cagctgcagg gctcccatga cgtcgggcgc cgagatcttg aagtcgcagt 6240
tagggccgga gcccccgcgg ctgttgcgga acacggggtt ggcacactgg aacaccagca 6300
cgctggggtt gtaaatactg gccagggccg ttgggtcggt cacctccgac gcatccagat 6360
cctcggcatt gctcagggcg aacggagtca gcttgcacat ctgccgtccg atctggggca 6420
ccaggtcggg tttgttgagg caatcgcagc gcagagggat taggatgcga cgctgcccgc 6480
gttgcatgat agggtaactc gccgccagga actcctccat ctgacggaag gccatctggg 6540
ccttggtacc ctcggtgaaa aatagcccac aggacttgct agaaaatacg ttattgccgc 6600
agttgatgtc ttccgcgcag cagcgtgcat cttcgttctt cagctgaacc acgttacgcc 6660
cccagcggtt ctggaccacc ttggctttcg taggatgctc cttcaacgcc cgctgaccgt 6720
tctcgctggt cacatccatt tccaccacgt gctccttgca gaccatctcc actccgtgga 6780
agcagaacag gacgccctcc tgctgggtat tgcgatgctc ccaaacggca catccggtgg 6840
gctcccagct cttgcgtttc acccccgcgt atgcttccat gtaagccatg aggaatctgc 6900
ccatcagctc ggtgaaggtc ttctggttgg tgaaggttag cggcaggccg cggtgctcct 6960
cgttcaacca agtttgacag attttgcggt acacggctcc ctggtcgggc agaaacttaa 7020
aagccgctct gctctcgttg tccacgtgga acttctccat caacatcgtc atgacttcca 7080
tgcccttctc ccacgccgtc accaacggtt cggtcccggg gttcttcacc aacacggcgg 7140
tggaggggcc ctcgccggcc ccgacgtcct tcatggtcat tctttggaac tccacggtgc 7200
cgtccgcgcg gcgtactctg cgcatcggag ggtagctgaa gcccacctcc accacggtgc 7260
cttcgccctc gctgtcggaa acgatctccg gggatggcgg cggcgcgggt gtcgccttgc 7320
gagccttctt cttgggaggg agcggaggca cctcctgctc gcgctcgggg ctcatctccc 7380
gcaagtaggg ggtaatggag cttccgggtt ggttctgacg gttggccatt gtatcctagg 7440
cagaaagaca tggatcttat gcgcgaggaa actttaaccg ccccgtcccc cgtcagcgac 7500
gaagaggtca tcgtcgaaca ggacccgggc tacgttacgc cgcccgagga tctggagtcc 7560
cccttagacg accgacgcga cgctagtgag cggcaggaaa atgagaaaga ggaggaggag 7620
ggctgctacc tcctggaagg cgacgtcttg ctaaagcatt tcgccaggca gagcaccata 7680
ctcaaggagg ccttgcaaga ccgctccgag gtgcccttgg acgtcgccgc gctctcccag 7740
gcctacgagg cgaacctttt ctcgccccga gtgcctccga agagacagcc caacggcacc 7800
tgcgagccca acccgcgact caacttctac cccgtgttcg ccgtgcccga ggcgctggcc 7860
acctaccaca tctttttcaa aaaccagcgc attccccttt cctgccgggc caaccgcacc 7920
gcagccgata ggaagctaac actcagaaac ggagccagca tacctgatat cacgtcactg 7980
gaggaagtgc ctaagatctt cgagggtctg ggtcgagatg agaagcgggc ggcgaacgct 8040
ctgcagaaag aacagaaaga gagtcagaac gtgctggtgg agctggaggg ggacaacgcg 8100
cgtctggccg tcctcaaacg ctgcatagaa gtctcccact tcgcctaccc cgccctcaac 8160
ttgccaccca aagttatgaa atcggtcatg gatcagctgc tcatcaagag agctgagccc 8220
ctggatcccg accaccccga ggcggaaaac tcagaggacg gaaagcccgt cgtcagcgac 8280
gaggagctcg agcggtggct ggaaaccggg gacccccaac agttgcaaga gaggcgcaag 8340
atgatgatgg cggccgtgct ggtcaccgtg gagctggaat gcctgcaacg gtttttcagc 8400
gacgtggaga cgctacgcaa aatcggggag tccctgcact acaccttccg ccagggctac 8460
gtccgccagg cctgcaagat ctccaacgtg gagctcagca acctggtctc ctacatgggc 8520
atcctccacg agaaccggct ggggcagagc gtgctgcact gcaccttgca aggcgaggcg 8580
cggcgggact acgtccgcga ctgcatctac ctcttcctca ccctcacctg gcagaccgcc 8640
atgggcgtct ggcagcagtg cttggaagag agaaacctca aagagctaga caaactcctc 8700
tgccgccagc ggcgggccct ctggaccggt ttcagcgagc gcacggtcgc ctgcgccctg 8760
gcagacatta tcttcccgga gcgcctgatg aaaaccttgc agaacggcct gccggatttt 8820
atcagtcaaa gtattttgca aaacttccgc tccttcgttc tggagcgctc cgggatcttg 8880
cccgccatga gctgcgcgct gccttctgac tttgtccccc tttcctaccg cgagtgtcct 8940
ccccccctgt ggagccactg ctacctcttc caactggcca actttctggc ctaccactcc 9000
gacctcatgg aagacgtgag cggagagggg ctgctcgagt gccactgccg ctgcaacctc 9060
tgcacccccc acagatcgct ggcctgcaac accgagctgc tcagcgaaac ccaggtcata 9120
ggtaccttcg agatccaggg gccccagcag caagagggtg cttccggctt gaagctcact 9180
ccggcgctgt ggacctcggc ttacttacgc aaatttgtag ccgaggacta ccacgcccac 9240
aaaattcagt tctatgaaga ccaatctcga ccacccaaag ccccccctcac ggcctgcgtc 9300
atcactcaga gcaaaatcct ggcccaattg caatccatca accaagcgcg ccgagatttc 9360
cttttgaaaa agggtcgggg ggtgtaccta gacccccaga ccggcgagga actcaacccg 9420
tccacactct ccgtcgaagc agcccccccg agacatgccg cccaagggaa ccgccaagca 9480
gctgatcgct cggcagagag cgaagaagca agagctgctc cagcagcagc agcaggtgga 9540
ggacgaggaa gagctgtggg acagccaggc agaggaggtg tcagaggacg aggaggagat 9600
ggaaagctgg gacagcctag acgaggagga ggacgagctt tcagaggaag aggcgaccga 9660
agaaaaacca cctgcatcca gcgcgccttc tctgagccga cagccgaagc cccggccccc 9720
gacgcccccg gccggctcac tcaaagccag ccgtaggtgg gacgccaccg gatctccagc 9780

-continued

```
ggcagcggca acggcagcgg gtaaggccaa acgcgagcgg cgggggtatt gctcctggcg   9840
ggcccacaaa agcagtatcg tgaactgctt gcaacactgc gggggaaaca tctcctttgc   9900
ccgacgctac ctcctcttcc atcacggtgt ggccttccct cgcaacgttc tctattatta   9960
ccgtcatctc tacagcccct acgaaacgct cggagaaaaa agctaaggcc tcctctgccg  10020
cgaggaaaaa ctccgccgcc gctgccgccg ccaaggatcc gccggccacc gaggagctga  10080
gaaagcgcat ctttcccact ctgtatgcta tctttcagca aagccgcggg cagcaccctc  10140
agcgcgaact gaaaataaaa aaccgctcct tccgctcact cacccgcagc tgtctgtacc  10200
acaagagaga agaccagctg cagcgcaccc tggacgacgc cgaagcactg ttcagcaaat  10260
actgctcagc gtctcttaaa gactaaaaga cccgcgcttt ttccccctcg ggcgccaaaa  10320
cccacgtcat tgccagcatg agcaaggaga ttcccacccc ttacatgtgg agctatcagc  10380
cccagatggg cctggccgcg ggggccgccc aggactactc cagcaagatg aactggctca  10440
gcgccggccc ccacatgatc tcacgagtta acggcatccg agcccaccga aaccagatcc  10500
tcttagaaca ggcggcaatc accgccacac cccggcgcca actcaacccg cccagttggc  10560
ccgccgccca ggtgtatcag gaaactcccc gcccgaccac agtcctcctg ccacgcgacg  10620
cggaggccga agtcctcatg actaactctg gggtacaatt agcgggcggg tccaggtacg  10680
ccaggtacag aggtcgggcc gctccttact ctcccgggag tataaagagg gtgatcattc  10740
gaggccgagg tatccagctc aacgacgagg cggtgagctc ctcaaccggt ctcagacctg  10800
acggagtctt ccagctcgga ggagcgggcc gctcttcctt caccactcgc caggcctacc  10860
tgaccctgca gagctcttcc tcgcagccgc gctccggggg aatcggcact ctccagttcg  10920
tggaagagtt cgtcccctcc gtctacttca acccgttttc cggctcacct ggacgctacc  10980
cggacgcctt cattcccaac tttgacgcag tgagtgaatc cgtggacggc tacgactgat  11040
gacagatggt gcggccgtga gagctcggct gcgacatctg catcactgcc gccagcctcg  11100
ctgctacgct cgggaggcga tcgtgttcag ctactttgag ctgccggacg agcaccctca  11160
ggggccggct cacgggttga aactcgagat cgagaacgcg ctcgagtctc gcctcatcga  11220
cgccttcacc gcccggcctc tcctggtaga aaccgaacgc gggatcacta ccatcaccct  11280
gttctgcatc tgccccacgc ccggattaca tgaagatctg tgttgtcatc tttgcgctca  11340
gtttaataaa aactgaactg tttgccgcac cttcaacgcc atctgtgatt tctacaacaa  11400
aaagttcttc tggcaaaggt acacaaactg tattttattc taattctacc tcatctattg  11460
tgctgaactg cgcctgcact aacgaactta tcctgtagag gggctatcc tctgtcactg  11520
tcacgcacct gattgcatgt ccaaactaat caaaactctc tgtgctttag gtgatatttt  11580
taaaatgtaa atcataataa acttacctta aatttgacaa caattttctg gtgacatcat  11640
tcagcagcac cactttaccc tcttcccagc tctcgtatgg gatgcgatag tgggtggcaa  11700
acttcctcca aaccctaaaa gaaatattgg tatccacttc cttgtcctca cccacaattt  11760
tcatcttttc atagatgaaa agaaccagag ttgatgaaga cttcaacccc gtctacccct  11820
atgacaccac aaccactcct gcagttccct ttatatcacc cccctttgta aacagcgatg  11880
gtcttcagga aaaccccccca ggtgttttaa gtctgcgaat agctaaaccc ctatatttcg  11940
acatggagag aaaactagcc ctttcacttg gaagagggtt gacaattacc gccgccggac  12000
aattagaaag tacgcagagc gtacaaacca acccaccgtt gataattacc aacaacaaca  12060
cactgaccct acgtcattct cccccttaa acctaactga caatagctta gtgctaggct  12120
actcgagtcc gctccgcgtc acagacaaca aacttacatt taacttcaca tcaccactcc  12180
```

gttatgaaaa tgaaaacctt acttttaact atacagagcc tcttaaactt ataaataaca 12240
gccttgccat tgacatcaat tcctcaaaag gccttagtag cgtcggaggc tcactagctg 12300
taaacctgag ttcagactta aagtttgaca gcaacggatc catagctttt ggcatacaaa 12360
ccctgtggac cgctccgacc tcgactggca actgcaccgt ctacagcgag ggcgattccc 12420
tacttagtct ctgtttaacc aaatgcggag ctcacgtctt aggaagtgta agtttaaccg 12480
gtttaacagg aaccataacc caaatgactg atatttctgt caccattcaa tttacatttg 12540
acaacaatgg taagctacta agctctccgc ttataaacaa cgcctttagt attcgacaga 12600
atgacagtac ggcctcaaac cctacctaca acgccctggc gtttatgcct aacagtacca 12660
tatatgcaag agggggaggt ggtgaaccac gaaacaacta ctacgtccaa acgtatctta 12720
ggggaaatgt tcaaaaacca atcattctta ctgtaaccta caactcagcc gccacaggat 12780
attccttatc ttttaagtgg actgctcttg cacgtgaaaa gtttgcaacc ccaacaactt 12840
cgttttgcta cattacagaa caataaaacc gtgtacccca ccgtttcgtt tttttcagat 12900
gaaacgggcg agagttgatg aagacttcaa cccagtgtac ccttatgacc ccccacatgc 12960
tcccgttatg cccttcatta ctccaccttt tacctcctcg gatgggttgc aggaaaaacc 13020
acttggagtg ttaagtttaa actacagaga tcccattact acgcaaaatg ggtctcttac 13080
agttaaacta ggaaacggcc tcactctaga caaccaggga caactaacat caaccgctgg 13140
ggaagtagaa cctccactca ctaacgctaa caacaaactt gcactggtct atagcgatcc 13200
tttagcagta aagcgcaaca gcctaacctt atcgcacacc gctccccttg ttattgctga 13260
taactcttta gcattgcaag tttcagagcc tatttttata aatgacaagg acaaactagc 13320
cctgcaaaca gccgcgcccc ttgtaactaa cgctggcacc cttcgcttac aaagcgccgc 13380
ccctttaggc attgcagacc aaaccctaaa actcctgttt accaaccctt tgtacttgca 13440
gaataacttt ctcacgttag ccattgaacg accccttgcc attaccaata gtggaaagct 13500
ggctctacag ctctccccac cgctacaaac agcagacaca ggcttgactt tgcaaaccaa 13560
cgtgccatta actgtaagca acgggaccct aggcttagcc ataaagcgcc cacttattgt 13620
tcaggacaac aacttgtttt tggacttcag agctcccctg cgtcttttca acagcgaccc 13680
cgtactaggg cttaactttt acacccctct tgcagtgcgc gatgaggcgc tcactgttaa 13740
cacaggccgc ggcctcacag tgagttacga tggtttaatt ttaaatcttg gtaaggatct 13800
tcgctttgac aacaacaccg tttctgtcgc tcttagtgct gctttgcctt tacaatacac 13860
tgatcagctt cgccttaacg tgggcgctgg gctgcgttac aatccagtga gtaaaaaatt 13920
ggacgtgaac cccaatcaaa acaagggttt aacctgggaa aatgactacc tcattgtaaa 13980
gctaggaaat ggattaggtt ttgatggcaa tggaaacata gctgtttctc ctcaagttac 14040
atcgcctgac accttatgga ccactgccga tccatccccc aattgttcca tctacactga 14100
tttagatgcc aaaatgtggc tctcgttggt aaaacaaggg ggtgtggttc acggttctgt 14160
tgctttaaaa gcattgaaag gaaccctatt gagtcctacg gaaagtgcca ttgttattat 14220
actacatttt gacaattatg gagtgcgaat tctcaattat ccccactttgg gcactcaagg 14280
cacgttggga aataatgcaa cttggggtta taggcaggga gaatctgcag acactaatgt 14340
actcaatgca ctagcattta tgcccagttc aaaaaggtac ccaagagggc gtggaagcga 14400
agttcagaat caaactgtgg gctacacttg tatacagggt gacctttcta tgcccgtacc 14460
gtaccaaata cagtacaact atggaccaac tggctactcc tttaaattta tttggagaac 14520
tgtttcaaga caaccatttg acatcccatg ctgtttttc tcttacatta cggaagaata 14580
aaacaacttt tcctttttat tttcttttta ttttacacgc acagtaaggc ttcctccacc 14640
cttccatttg acagcataca ccagcctctc ccccttcatg gcagtaaact gctgcgagcc 14700
agtccggtat ttgggagtta agatccaaac agtctctttg gtaatcagat gtcgatccgt 14760
gatggacaca aatccctggg gcaggttctc caacgtttcg gtgaaaaact gcatgccgcc 14820
ctacaaaaca aacaggttca ggctctccac gggttatctc cccgatcaaa ctcagacagg 14880
gtaaaggtgc gatgatgttc cactaaacca cgcaggtggc gctgtctgaa cctctcggtg 14940
cgactcctgt gaggctggta agaagttaga ttgtccagca gcctcacagc atggatcatc 15000
agtctacgag tgcgtctggc gcagcagcgc atctgaatct cactgagatt ccggcaagaa 15060
tcgcacacca tcacaatcag gttgttcatg atcccatagc tgaacacgct ccagccaaag 15120
ctcattcgct ccaacagcgc caccgcgtgt ccgtccaacc ttactttaac ataaatcagg 15180
tgtctgccgc gtacaaacat gctacccgca tacagaacct cccggggcag tcccctgttc 15240
accacctgcc tgtaccaggg aaacctcaca tttatcaggg agccatagat agccatctta 15300
aaccaattag ctaacaccgc cccaccagct ctacactgaa gagaaccggg agagttacaa 15360
tgacagtgaa taatccatct ctcataaccc ctaatggtct gatggaaatc cagatctaac 15420
gtggcacagc agatacacac tttcatatac attttcatca catgtttttc ccaggccgtt 15480
aaaatacaat cccaatacac gggccactcc tgcagtacaa taaagctaat acaagatggt 15540
atactcctca cctcactaac attgtgcatg ttcatatttt cacattctaa gtaccgagag 15600
ctctcctcta caacagcact gccgcggtcc tcacaaggtg gtagctggtg acaattgtag 15660
ggagccagtc tgcagcgata ccgtctgtcg cgttgcatcg tagaccaggg accgacgcac 15720
ttcctcgtac ttgtagtagc agaactgccc cgtcttaccg cgtataaagc cacgaaaaag 15780
tcgagctaaa atccacccaa cagcctatag ctatatatac actccgccca atgacgctaa 15840
caccgtacca cccacgacca aagttcaccc acacccacaa aacccgcgaa aatccagcgc 15900
cgtcagcact tccgcaattt cagtctcaca acgtcacttc cgcgcgcctt ttttcactat 15960
tcccacaccc gccctcgcgc caccccgcgt caccccgcgt caccgcacgt caccccggcc 16020
ccgcctcgct cctccccgct cattatcata ttggcacgtt tccagaataa ggtatattat 16080
tgatgatgtt aattaattcg aacccataat acccataata gctgtttgcc atcgacgcga 16140
ggctggatgg ccttccccat tatgattctt ctcgcttccg gcggcatcgg gatgcccgcg 16200
ttgcaggcca tgctgtccag gcaggtagat gacgaccatc agggacagct tcaaggatcg 16260
ctcgcggctc ttaccagccc agcaaaaggc caggaaccgt aaaaaggccg cgttgctggc 16320
gtttttccat aggctccgcc cccctgacga gcatcacaaa aatcgacgct caagtcagag 16380
gtggcgaaac ccgacaggac tataaagata ccaggcgttt ccccctggaa gctccctcgt 16440
gcgctctcct gttccgaccc tgccgcttac cggatacctg tccgcctttc tcccttcggg 16500
aagcgtggcg ctttctcata gctcacgctg taggtatctc agttcggtgt aggtcgttcg 16560
ctccaagctg ggctgtgtgc acgaaccccc cgttcagccc gaccgctgcg ccttatccgg 16620
taactatcgt cttgagtcca acccggtaag acacgactta tcgccactgg cagcagccac 16680
tggtaacagg attagcagag cgaggtatgt aggcggtgct acagagttct tgaagtggtg 16740
gcctaactac ggctacacta gaaggacagt atttggtatc tgcgctctgc tgaagccagt 16800
taccttcgga aaaagagttg gtagctcttg atccggcaaa caaaccaccg ctggtagcgg 16860
tggttttttt gtttgcaagc agcagattac gcgcagaaaa aaaggatctc aagaagatcc 16920
tttgatcttt tctacggggt ctgacgctca gtggaacgaa aactcacgtt aagggatttt 16980
ggtcatgaga ttatcaaaaa ggatcttcac ctagatcctt ttaaattaaa aatgaagttt 17040
taaatcaatc taaagtatat atgagtaaac ttggtctgac agttaccaat gcttaatcag 17100
tgaggcacct atctcagcga tctgtctatt tcgttcatcc atagttgcct gactccccgt 17160
cgtgtagata actacgatac gggagggctt accatctggc cccagtgctg caatgatacc 17220
gcgagaccca cgctcaccgg ctccagattt atcagcaata aaccagccag ccggaagggc 17280
cgagcgcaga agtggtcctg caactttatc cgcctccatc cagtctatta attgttgccg 17340
ggaagctaga gtaagtagtt cgccagttaa tagtttgcgc aacgttgttg ccattgctgc 17400
aggcatcgtg gtgtcacgct cgtcgtttgg tatggcttca ttcagctccg gttcccaacg 17460
atcaaggcga gttacatgat cccccatgtt gtgcaaaaaa gcggttagct ccttcggtcc 17520
tccgatcgtt gtcagaagta agttggccgc agtgttatca ctcatggtta tggcagcact 17580
gcataattct cttactgtca tgccatccgt aagatgcttt tctgtgactg gtgagtactc 17640
aaccaagtca ttctgagaat agtgtatgcg gcgaccgagt tgctcttgcc cggcgtcaac 17700
acgggataat accgcgccac atagcagaac tttaaaagtg ctcatcattg gaaaacgttc 17760
ttcggggcga aaactctcaa ggatcttacc gctgttgaga tccagttcga tgtaacccac 17820
tcgtgcaccc aactgatctt cagcatcttt tactttcacc agcgtttctg ggtgagcaaa 17880
aacaggaagg caaaatgccg caaaaaaggg aataagggcg acacggaaat gttgaatact 17940
catactcttc ctttttcaat attattgaag catttatcag ggttattgtc tcatgagcgg 18000
atacatattt gaatgtattt agaaaaataa acaaataggg gttccgcgca catttccccg 18060
aaaagtgcca cctgacgtct aagaaaccat tattatcatg acattaacct ataaaaatag 18120
gcgtatcacg aggccctttc gtcttcaaga attggtcgat ggcaaacagc tattatgggt 18180
attatgggtt cgaattaat 18199

<210> SEQ ID NO 45
<211> LENGTH: 8765
<212> TYPE: DNA
<213> ORGANISM: Artificial Sequence
<220> FEATURE:
<223> OTHER INFORMATION: Synthetic oligonucleotide
sAdApt4310A.E1btg.Empty

<400> SEQUENCE: 45
attaacatca tcaataatat accttattct ggaaacgtgc caatatgata atgagcgggg 60
aggagcgagg cggggccggg gtgacgtgcg gtgacgcggg gtgacgcggg gtggcgcgag 120
ggcggggcgg gtgtgcggag gcgcttagtt tttacgtatg cggaaggagg ttttataccg 180
gaagttgggt aatttgggcg tatacttgta agttttgtgt agtttggcgc gaaaaccggg 240
taatgaggaa gttgaggtta atatgtactt tttatgactg ggcggaattt ctgctgatca 300
gcagtgaact ttgggcgctg acggggaggt ttcgctacgt ggcagtacca cgagaaggct 360
caaaggtccc atttattgta ctcctcagcg ttttcgctgg gtatttaaac gctgtcagat 420
catcaagagg ccactcttga gtgccggcga gtagagtttt ctcctccgcg ctgccgcgat 480
gaggctggtt cccgagatgt acggtgtttt ctgcagcgag acggcccgga actcagatga 540
gctgctgaat tcagacctgc tggaaatttc gaattcgcct gtgcttttgc cgccgtcact 600
tcacgacctg tttgatgtgg aagtggaccc tccggaagat cccaacgagg acgcggtaaa 660
tactatgttt ccagaatgtc tgtttgaggc ggctgaggag ggttcttaca gcggtgaaga 720

```
cggcgggcag ggagaggaag tggacctgaa gtgctacgag gaatgtctac cttctagcga    780
ttctgaaacg gaacagacag ggggagatgg ctgtgctgaa cctgttgtga aaaatgaact    840
tgtattagac tgtcctgata atcctggtca cggttgccgc gcctgtgatt ttcatagaaa    900
tgccagtgga aatcctgaga ctctatgtgc tctgtgttac ctgcgcctta ccagccattg    960
tgtatacagt aagtagaaac tttttcgctt tgtgcatgct ggtgggattt ttaaagtgcg   1020
ttgggcttat tgttgcgtaa tgttttacag gcgacgtgtc tgacgcggaa ggggatggag   1080
atagatcagg ctctgctggt tctccttgca ctttgggggc tgtggttcca gatggcatta   1140
ttaaacccgt ggcggtaaga gtttcaggca gacggtgtgc ggtcgaaaaa attgaagact   1200
tgctgcagga ggaacagatg caacctttgg acctgtccct gaaacgccct aagctgacct   1260
aagagtgttt attgtatgca ataaaaagtg ttgatctttg aactgtgttt atgtgttggg   1320
tgtgtctgtg ggtatataag caggtggatg ggaagtgaga gcacagctgc ttcagatgga   1380
tctgctagga gacctgaggg aatttggcgt ggttcggcgc ttgctggagt tggcctctga   1440
cagaacttcc aagttttgga ggttttgttt tggctcaacg cttagcaacg tgctatatag   1500
ggtcaagaag gagcaggaga cgcagtttgc taggctgttg gccgatactc ctggagtttt   1560
tgtggctctg gatctaggcc atcactctct tttccaagag aaaattatca aaaacttaac   1620
ttttacgtct cctggtcgca cggttgcttc cgctgccttt attacctata ttttggatca   1680
atggagcaac agcggcagtc acctgtcgtg ggagtacatg ctggattaca tgtcgatggc   1740
gctgtggagg gccatgctgc ggaggagggt ttgcatttac ttgcgggcgc agcctccgcg   1800
gctggaccga gtggaggagg aggacgagcc gggggagacc gagaacctga gggccgggct   1860
ggaccctcca acggaggact aggtgctgag gatgatcccg aagaggggac tagtggggct   1920
aggaagaagc aaaagactga gtctgaacct cgaaactttt tgaatgagtt gactgtgagt   1980
ttgatgaatc gtcagcgtcc ggagacaatt ttctggtctg aattggagga ggaattcagg   2040
aggggggaac tgaacctgct atacaagtat gggtttgaac agttgaaaac tcactggttg   2100
gagccgtggg aggattttga aaccgccttg gacacttttg ctaaagtggc tctgcgaccg   2160
gataaggttt acactatccg ccgcactgtt aacataaaga agagtgttta tgttataggc   2220
catggagctc tggtgcaggt gcaaaccgcc gaccgggtgg cctttagttg cggcatgcaa   2280
aatctgggcc ccggggtgat aggcttaaat ggtgtaacat ttcacaatgt aaggtttact   2340
ggtgaaagtt ttaacggctc tgtgtttgca aataacacac agctgacgct ccacggcgtt   2400
tacttttttta actttaataa cacatgtgtg gagtcgtggg gcagggtgtc tttgaggggc   2460
tgctgttttc acggctgctg gaaggcggtg gtgggaagac ttaaaagtgt aacatctgta   2520
aaaaaatgcg tgtttgagcg ctgtgtgttg gctttaaccg tggagggctg tggacgcatt   2580
aggaataatg cagcgtctga gaatggatgt ttccttttgc taaaaggcac ggctagcgtt   2640
aagcataaca tgatatgcgg cagcggtttg tacccttcgc agctgttaac ttgcgcggat   2700
ggaaactgtc agaccctgcg caccgtgcac atagcgtccc accagcgacg cgcctggcca   2760
acattcgagc acaatatgct tatgcgctgt gccgttcacc tgggccctag gcgaggcgtg   2820
tttgtgcctt accagtgtaa ctttagccat accaagtttt tactagaacc tgacaccttc   2880
tctcgagtgt gtttcaacgg ggtttttgac atgtcaatgg aactgtttaa agtgataaga   2940
tatgatgaat ccaagtctcg ttgtcgccca tgtgaatgcg gagctaatca tttgaggttg   3000
tatcctgtaa ctctgaacgt caccgaggag ctgagaacgg accaccacat gctgtcttgc   3060
```

-continued

```
ctgcgcactg actatgaatc cagcgacgag gagtgaggtg aggggcggag ccaaacgggt   3120
ataaaggggc gtgaggtcga ctggtcaata ttggccatta gccatattat tcattggtta   3180
tatagcataa atcaatattg gctattggcc attgcatacg ttgtatccat atcataatat   3240
gtacatttat attggctcat gtccaacatt accgccatgt tgacattgat tattgactag   3300
ttattaatag taatcaatta cggggtcatt agttcatagc ccatatatgg agttccgcgt   3360
tacataactt acggtaaatg gcccgcctgg ctgaccgccc aacgaccccc gcccattgac   3420
gtcaataatg acgtatgttc ccatagtaac gccaataggg actttccatt gacgtcaatg   3480
ggtggagtat ttacggtaaa ctgcccactt ggcagtacat caagtgtatc atatgccaag   3540
tacgccccct attgacgtca atgacggtaa atggcccgcc tggcattatg cccagtacat   3600
gaccttatgg gactttccta cttggcagta catctacgta ttagtcatcg ctattaccat   3660
ggtgatgcgg ttttggcagt acatcaatgg gcgtggatag cggtttgact cacggggatt   3720
tccaagtctc caccccattg acgtcaatgg gagtttgttt tggcaccaaa atcaacggga   3780
ctttccaaaa tgtcgtaaca actccgcccc attgacgcaa atgggcggta ggcgtgtacg   3840
gtgggaggtc tatataagca gagctcgttt agtgaaccgt cagatcgcct ggagacgcca   3900
tccacgctgt tttgacctcc atagaagaca ccgggaccga tccagcctcc gcggccggga   3960
acggtgcatt ggaagcttgg taccggtgaa ttcgctagcg ttaacggatc ctctagacga   4020
gatccgaact tgtttattgc agcttataat ggttacaaat aaagcaatag catcacaaat   4080
ttcacaaata aagcattttt ttcactgcat tctagttgtg gtttgtccaa actcatcaat   4140
gtatcttatc atgtctagat ccttaaggac atgtcaatgg aactgtttaa agtgataaga   4200
tatgatgaat ccaagtctcg ttgtcgccca tgtgaatgcg gagctaatca tttgaggttg   4260
tatcctgtaa ctctgaacgt caccgaggag ctgagaacgg accaccacat gctgtcttgc   4320
ctgcgcactg actatgaatc cagcgacgag gagtgaggtg aggggcggag ccaaacgggt   4380
ataaaggggc gtgaggggtc ggtgcggtgt ttcaaaatga gcgggacgac ggacggcaat   4440
gcgtttgagg ggggagtgtt cagcccatat ctgacatctc gtcttccttc ctgggcagga   4500
gtgcgtcaga atgtagtggg atccaccgtg gacggacgac cggtggctcc tgcaaattcc   4560
gccaccctca cctatgccac cgtgggatca tcgttggaca ctgccgcggc agctgccgct   4620
tctgctgccg cttctactgc tcgcggcatg gcggctgatt ttggactgta taaccaactg   4680
gccactgcag ctgtggcgtc tcggtccctg gttcaagaag atgccctgaa tgtgattctg   4740
actcgcctgg agatcatgtc acgccgcctg gacgaactgg ctgcgcagat atcctcaact   4800
aaccccgata ccacttcaga accttaaata aagacaaaca aatttgttga aaagtaaaat   4860
ggctttattt gtttttttg gctcggtagg ctcgggtcca cctgtcccgg tcgttaagga   4920
ccttgtgtat gttttccaag acccggtaca gatgggcttg gatgttcaag tacatgggca   4980
tgaggccatc tcgggggtgg agataggacc attgcagagc gtcatgctcc ggggtggtgt   5040
tgtaaataac ccagtcgtag cagggtttct gagcgtggaa ctggaagatg tcctttagga   5100
gcaggctgat ggccaagggc agccccttag tgtaggtgtt aacaaagcgg ttaagctggg   5160
agggatgcat gcggggggag atgatatgca tcttggcttg aattttgagg ttagctatgt   5220
taccacctag gtccctgcgg gggttcatgt tatgaaggac caccagcacg gtgtagccgg   5280
tgcacttggg gaacttgtca tgcagtttgg aggggaaggc gtggaagaat ttagagaccc   5340
ccttgtggcc tcctaggttt tccatgcact catccataat gatggcaatg ggacccctgg   5400
cggccgcttt ggcaaacacg ttttgggggt tggaaacatc atagttttgc tctagagtga   5460
```

-continued gctcatcata ggccatctta acaaagcggg gtaggagggt gcccgactgg gggatgatag 5520
ttccatctgg gcctggggcg tagttgccct cacaaatctg catttcccag gccttaattt 5580
ccgagggggg tatcatgtcc acctgggggg cgataaagaa cacggtttct ggcgggggat 5640
tgatgagctg ggtggaaagc aagttacgca acagttggga tttgccgcaa ccggtgggac 5700
cgtagatgac cccgatgacg ggttgcagct ggtagttgag agaggaacag ctgccgtcgg 5760
ggcgcaggag gggggctaca tcgttcatca tgcttctgac atgtttattt tcactcacta 5820
agttttgcaa gagcctctcc ccacccaggg ataagagttc ttccaggctg ttgaagtgtt 5880
tcagcggttt caggccgtct gccatgggca tcttttcaag cgactgacga agcaagtaca 5940
gtcggtccca gagctcggtg acgtgctcta tggaatctcg atccagcaga cttcttggtt 6000
gcgggggttg ggccgacttt cgctgtaggg caccagccgg tgggcgtcca gggccgcgag 6060
ggttctgtcc ttccagggtc tcagcgttcg ggtgagggtg gtctcggtga cggtgaaggg 6120
atgagccccg ggctgggcgc ttgcgagggt gcgcttcagg ctcatcctgc tggtgctgaa 6180
gcgggcgtcg tctccctgtg agtcggccag atagcaacga agcatgaggt cgtagctgag 6240
ggactcggcc gcgtgtccct tggcgcgcag ctttcccttg gaaacgtgct gacatttggt 6300
gcagtgcaga cacttgaggg cgtagagttt gggggccagg aagaccgact cggacgagta 6360
ggcgtcggct ccgcactgag cgcagacggt ctcgcactcc accagccacg tgagctcggg 6420
tttagcggga tcaaaaacca agttgcctcc atttttttg atgcgtttct taccttgcgt 6480
ctccatgagt ctgtgtcccg cttccgtgac aaaaaggctg tcggtgtccc cgtagaccga 6540
cttgaggggg cgatcttcca aaggtgttcc gagatcttcc gcgtacagga actgggacca 6600
ctccgagaca aaggctcggg tccaggctaa cacgaaggag gcgatctgcg aggggtatct 6660
gtcgttttca atgaggttaa ttaattcgaa cccataatac ccataatagc tgtttgccat 6720
cgacgcgagg ctggatggcc ttccccatta tgattcttct cgcttccggc ggcatcggga 6780
tgcccgcgtt gcaggccatg ctgtccaggc aggtagatga cgaccatcag ggacagcttc 6840
aaggccagca aaaggccagg aaccgtaaaa aggccgcgtt gctggcgttt ttccataggc 6900
tccgcccccc tgacgagcat cacaaaaatc gacgctcaag tcagaggtgg cgaaacccga 6960
caggactata aagataccag gcgtttcccc ctggaagctc cctcgtgcgc tctcctgttc 7020
cgaccctgcc gcttaccgga tacctgtccg cctttctccc ttcgggaagc gtggcgcttt 7080
ctcatagctc acgctgtagg tatctcagtt cggtgtaggt cgttcgctcc aagctgggct 7140
gtgtgcacga acccccgtt cagcccgacc gctgcgcctt atccggtaac tatcgtcttg 7200
agtccaaccc ggtaagacac gacttatcgc cactggcagc agccactggt aacaggatta 7260
gcagagcgag gtatgtaggc ggtgctacag agttcttgaa gtggtggcct aactacggct 7320
acactagaag gacagtattt ggtatctgcg ctctgctgaa gccagttacc ttcggaaaaa 7380
gagttggtag ctcttgatcc ggcaaacaaa ccaccgctgg tagcggtggt ttttttgttt 7440
gcaagcagca gattacgcgc agaaaaaaag gatctcaaga agatcctttg atcttttcta 7500
cggggtctga cgctcagtgg aacgaaaact cacgttaagg gattttggtc atgagattat 7560
caaaaaggat cttcacctag atccttttaa attaaaaatg aagttttaaa tcaatctaaa 7620
gtatatatga gtaaacttgg tctgacagtt accaatgctt aatcagtgag gcacctatct 7680
cagcgatctg tctatttcgt tcatccatag ttgcctgact ccccgtcgtg tagataacta 7740
cgatacggga gggcttacca tctggcccca gtgctgcaat gataccgcga gacccacgct 7800
caccggctcc agatttatca gcaataaacc agccagccgg aagggccgag cgcagaagtg 7860
gtcctgcaac tttatccgcc tccatccagt ctattaattg ttgccgggaa gctagagtaa 7920
gtagttcgcc agttaatagt ttgcgcaacg ttgttgccat tgctgcaggc atcgtggtgt 7980
cacgctcgtc gtttggtatg gcttcattca gctccggttc ccaacgatca aggcgagtta 8040
catgatcccc catgttgtgc aaaaaagcgg ttagctcctt cggtcctccg atcgttgtca 8100
gaagtaagtt ggccgcagtg ttatcactca tggttatggc agcactgcat aattctctta 8160
ctgtcatgcc atccgtaaga tgcttttctg tgactggtga gtactcaacc aagtcattct 8220
gagaatagtg tatgcggcga ccgagttgct cttgcccggc gtcaacacgg gataataccg 8280
cgccacatag cagaacttta aaagtgctca tcattggaaa acgttcttcg gggcgaaaac 8340
tctcaaggat cttaccgctg ttgagatcca gttcgatgta acccactcgt gcacccaact 8400
gatcttcagc atcttttact ttcaccagcg tttctgggtg agcaaaaaca ggaaggcaaa 8460
atgccgcaaa aaagggaata agggcgacac ggaaatgttg aatactcata ctcttccttt 8520
ttcaatatta ttgaagcatt tatcagggtt attgtctcat gagcggatac atatttgaat 8580
gtatttagaa aaataaacaa ataggggttc cgcgcacatt tccccgaaaa gtgccacctg 8640
acgtctaaga aaccattatt atcatgacat taacctataa aaataggcgt atcacgaggc 8700
cctttcgtct tcaagaattg gtcgatggca aacagctatt atgggtatta tgggttcgaa 8760
ttaat 8765

<210> SEQ ID NO 46
<211> LENGTH: 6174
<212> TYPE: DNA
<213> ORGANISM: Artificial Sequence
<220> FEATURE:
<223> OTHER INFORMATION: Synthetic oligonucleotide sAdApt4312.Empty

<400> SEQUENCE: 46
attaacatca tcaataatat accttattct ggaaacgtgc caatatgata atgagtgggg 60
aggagcgagg cggggccggg gtggggtgag gcggggccgg ggtggggtga gggtgacgtc 120
ggggcgggcg gggcggccga cgtgtgtggg gaggcgcgta gtgtttacgt atgcggaagg 180
aggttttata ccggaagatg ggtaatttgg gcgtatactt gtaagttttg tgtaatttgg 240
cgcgaaaact gggtaatgag gaagttgagg ttaatatgta ctttttatga ctgggcggaa 300
tttctgctgt tcagcagtga actttgggcg ctgacgggga ggtttcgcta cgtggcagta 360
ccacgagaag gctcaaaggt cccatttatt gtactcctca gcgttttcgc cgggtattta 420
aacgctgtca gatcatcaag aggccactct tgagtgctgg cgagtagagt tttctcctcc 480
ggtcgactgg tcaatattgg ccattagcca tattattcat tggttatata gcataaatca 540
atattggcta ttggccattg catacgttgt atccatatca taatatgtac atttatattg 600
gctcatgtcc aacattaccg ccatgttgac attgattatt gactagttat taatagtaat 660
caattacggg gtcattagtt catagcccat atatggagtt ccgcgttaca taacttacgg 720
taaatggccc gcctggctga ccgcccaacg acccccgccc attgacgtca ataatgacgt 780
atgttcccat agtaacgcca atagggactt tccattgacg tcaatgggtg gagtatttac 840
ggtaaactgc ccacttggca gtacatcaag tgtatcatat gccaagtacg ccccctattg 900
acgtcaatga cggtaaatgg cccgcctggc attatgccca gtacatgacc ttatgggact 960
ttcctacttg gcagtacatc tacgtattag tcatcgctat taccatggtg atgcggtttt 1020
ggcagtacat caatgggcgt ggatagcggt ttgactcacg gggatttcca agtctccacc 1080

```
ccattgacgt caatgggagt ttgttttggc accaaaatca acgggacttt ccaaaatgtc   1140
gtaacaactc cgccccattg acgcaaatgg gcggtaggcg tgtacggtgg gaggtctata   1200
taagcagagc tcgtttagtg aaccgtcaga tcgcctggag acgccatcca cgctgttttg   1260
acctccatag aagacaccgg gaccgatcca gcctccgcgg ccgggaacgg tgcattggaa   1320
gcttggtacc ggtgaattcg ctagcgttaa cggatcctct agacgagatc cgaacttgtt   1380
tattgcagct tataatggtt acaaataaag caatagcatc acaaatttca caaataaagc   1440
atttttttca ctgcattcta gttgtggttt gtccaaactc atcaatgtat cttatcatgt   1500
ctagatcctt aaggtgataa gatatgatga atccaagtct cgttgtcgcc cctgtgaatg   1560
cggagctaat catttgaggt tgtatcccgc gaccctgaac gtaaccgagg agctgagggc   1620
cgaccaccac atgttgtcct gcttgcgcac cgactatgag tccagcgacg aagagtgagg   1680
tgaggggcgg agccacaaag ggtataaagg gtcaggatgg gtgggcacag gtattcaaaa   1740
tgagcgggac gacggacggc aacgcgtttg aggggggagt gttcagccca tatctgacat   1800
ctcgtcttcc ttcctgggca ggagtgcgtc agaatgtagt gggctccacc gtggacggac   1860
ggccggtcgc ccctgcgaat tccgccaccc ttacctatgc caccgtggga tcaccgttgg   1920
acactgccgc ggcagccgca gcttctgctg ccgcttctac tgctcgcggt atggcggctg   1980
actttggact ttataaccaa ctggctaccg cggctgtggc atctcgcact ctggttcaag   2040
aagatgccct gagcgtggtt ctgcttcgac tggaagatct gtctcgtcgc ttggatcagc   2100
tggctgcgca gatatcccca cctaaccccg atactactca agaatcttaa ataaagacaa   2160
acagatttgt tgaaaataaa tggctttatt tgtttttttt ggctcgatag gctcgggtcc   2220
acctgtcccg gtcgttaagg actttgtgta tgctttccaa gacccggtac agatgggctt   2280
ggatgtttag atacatgggc atgaggccat cccgggggtg gagataggac cattgcagag   2340
cgtcatgctc cggggtggtg ttgtagatga cccagtcgta gcagggtttt tgggcgtgga   2400
actgaaaaat gtccttgaga agcaggctga tggccagggg cagaccctta gtgtaggtgt   2460
tcacaaagcg gttgagctgg gagggatgca tgcggggaga gatgatatgc atcttagcct   2520
ggattttcag gttagctatg ttgcccccca ggtcccttcg agggttcata ttgtggagga   2580
ccaccagaac ggtgtagccg gtacacttgg gaaacttatc gtgcagtttg gaggggaagg   2640
cgtgaaagaa tttggaaacc cctttgtgac cacctaagtt ttccatgcac tcgtccatga   2700
taatggcgat gggccccttg gcggcagctt tagcgaacac gttgtggggg ttggaaacat   2760
catagttttg ctctagagtt agctcgtcat aggccatttt tacgaagcgg ggtaggaggg   2820
tgccagactg agggacgata gttccatctg gccccggtgc gtaattaccc tcgcagatct   2880
gcatctccca agctttaatt tccgagggag ggatcatgtc cacctggggg gcgataaaga   2940
acacggtttc tggcggggga ttaatgagct gggtggaaag caggttgcgc aagagctgag   3000
acttgccgca accggtggga ccgtagatga ccccgatgac gggctgcagc tggtagttga   3060
gagaggagca gctgccgtcg gggcgtagga ggggagccac ctcgttcatc atgcttctta   3120
catgtttatt ttcactgact aagctttgca agagcctctc cccacccagg gacaagagtt   3180
cttccaggct gttgaagtgt ttcagcggtt tcaggccgtc ggccatgggc atcttttcaa   3240
gcgactgacg aagcaagtac agccggtccc agagctcggt gacgtgctct atggaatctc   3300
gatccagcag acttcttggt tgcgggggtt gggccgactt tcgctgtagg gtacgagccg   3360
gtgggcgtcc agggccgcga gggttttgtc cttccagggt ctcagcgtcc gggtgagggt   3420
```

-continued

```
ggtctcggtg acggtgaacg gatgagcccc gggctgggcg cttgccaggg tgcgcttcag   3480
gctcatccgg ctggtgctga agcgggcgtc gtctccctgg gaatcggcca gatagcaacg   3540
gagcatgagg tcgtagctaa gggattcggc cgcgtgtccc ttggcgcgca gttttccctt   3600
ggaaacatgc tggcatctgg tgcagtgtaa acacttgagg gcgtacagct tgggggcgag   3660
gaagacggac tcgggcgagt aggcgtcggc cccgcactcg gcgcagacgg tttcacactc   3720
caccagccac gtgagctcgg gtttgtcggg gtcaaaaacc aggttgcctc catttttttt   3780
gatgcgtttc ttaccttgcg tctccatgag cctgtgaccc gcttcggtga caaaaaggct   3840
gtctgtgtct ccgtagaccg acttgagggg gcgttcttcc aagggcgtgc cgcggtcttc   3900
tgcgtacaaa aactgggacc actccgaaac gaaggccctg gtccacgcta acacgaagga   3960
tgcgatctgc gaggggtatc tgtcgttctc aatgagggga tccacctttt ccagggtatg   4020
cagacacagg tcgtcctcct ccgcgtccac aaaggtgatt ggcttgtaag tgtaggtcac   4080
gtgacttaat taattcgaac ccataatacc cataatagct gtttgccatc gacgcgaggc   4140
tggatggcct tccccattat gattcttctc gcttccggcg gcatcgggat gcccgcgttg   4200
caggccatgc tgtccaggca ggtagatgac gaccatcagg gacagcttca aggccagcaa   4260
aaggccagga accgtaaaaa ggccgcgttg ctggcgtttt tccataggct ccgcccccct   4320
gacgagcatc acaaaaatcg acgctcaagt cagaggtggc gaaacccgac aggactataa   4380
agataccagg cgtttccccc tggaagctcc ctcgtgcgct ctcctgttcc gaccctgccg   4440
cttaccggat acctgtccgc ctttctccct tcgggaagcg tggcgctttc tcatagctca   4500
cgctgtaggt atctcagttc ggtgtaggtc gttcgctcca agctgggctg tgtgcacgaa   4560
ccccccgttc agcccgaccg ctgcgcctta tccggtaact atcgtcttga gtccaacccg   4620
gtaagacacg acttatcgcc actggcagca gccactggta acaggattag cagagcgagg   4680
tatgtaggcg gtgctacaga gttcttgaag tggtggccta actacggcta cactagaagg   4740
acagtatttg gtatctgcgc tctgctgaag ccagttacct tcggaaaaag agttggtagc   4800
tcttgatccg gcaaacaaac caccgctggt agcggtggtt tttttgtttg caagcagcag   4860
attacgcgca gaaaaaaagg atctcaagaa gatcctttga tcttttctac ggggtctgac   4920
gctcagtgga acgaaaactc acgttaaggg attttggtca tgagattatc aaaaaggatc   4980
ttcacctaga tccttttaaa ttaaaaatga agttttaaat caatctaaag tatatatgag   5040
taaacttggt ctgacagtta ccaatgctta atcagtgagg cacctatctc agcgatctgt   5100
ctatttcgtt catccatagt tgcctgactc cccgtcgtgt agataactac gatacgggag   5160
ggcttaccat ctggccccag tgctgcaatg ataccgcgag acccacgctc accggctcca   5220
gatttatcag caataaacca gccagccgga agggccgagc gcagaagtgg tcctgcaact   5280
ttatccgcct ccatccagtc tattaattgt tgccgggaag ctagagtaag tagttcgcca   5340
gttaatagtt tgcgcaacgt tgttgccatt gctgcaggca tcgtggtgtc acgctcgtcg   5400
tttggtatgg cttcattcag ctccggttcc caacgatcaa ggcgagttac atgatccccc   5460
atgttgtgca aaaaagcggt tagctccttc ggtcctccga tcgttgtcag aagtaagttg   5520
gccgcagtgt tatcactcat ggttatggca gcactgcata attctcttac tgtcatgcca   5580
tccgtaagat gcttttctgt gactggtgag tactcaacca agtcattctg agaatagtgt   5640
atgcggcgac cgagttgctc ttgcccggcg tcaacacggg ataataccgc gccacatagc   5700
agaactttaa aagtgctcat cattggaaaa cgttcttcgg ggcgaaaact ctcaaggatc   5760
ttaccgctgt tgagatccag ttcgatgtaa cccactcgtg cacccaactg atcttcagca   5820
```

-continued tcttttactt tcaccagcgt ttctgggtga gcaaaaacag gaaggcaaaa tgccgcaaaa 5880
aagggaataa gggcgacacg gaaatgttga atactcatac tcttcctttt tcaatattat 5940
tgaagcattt atcagggtta ttgtctcatg agcggataca tatttgaatg tatttagaaa 6000
aataaacaaa taggggttcc gcgcacattt ccccgaaaag tgccacctga cgtctaagaa 6060
accattatta tcatgacatt aacctataaa aataggcgta tcacgaggcc ctttcgtctt 6120
caagaattgg tcgatggcaa acagctatta tgggtattat gggttcgaat taat 6174

<210> SEQ ID NO 47
<211> LENGTH: 16854
<212> TYPE: DNA
<213> ORGANISM: Artificial Sequence
<220> FEATURE:
<223> OTHER INFORMATION: Synthetic oligonucleotide pBr/sAd4312.pIX-pV

<400> SEQUENCE: 47
attaagtgat aagatatgat gaatccaagt ctcgttgtcg cccctgtgaa tgcggagcta 60
atcatttgag gttgtatccc gcgaccctga acgtaaccga ggagctgagg gccgaccacc 120
acatgttgtc ctgcttgcgc accgactatg agtccagcga cgaagagtga ggtgaggggc 180
ggagccacaa agggtataaa gggtcaggat gggtgggcac aggtattcaa aatgagcggg 240
acgacggacg gcaacgcgtt tgaggggga gtgttcagcc catatctgac atctcgtctt 300
ccttcctggg caggagtgcg tcagaatgta gtgggctcca ccgtggacgg acggccggtc 360
gcccctgcga attccgccac ccttacctat gccaccgtgg gatcaccgtt ggacactgcc 420
gcggcagccg cagcttctgc tgccgcttct actgctcgcg gtatggcggc tgactttgga 480
ctttataacc aactggctac cgcggctgtg gcatctcgca ctctggttca agaagatgcc 540
ctgagcgtgg ttctgcttcg actggaagat ctgtctcgtc gcttggatca gctggctgcg 600
cagatatccc cacctaaccc cgatactact caagaatctt aaataaagac aaacagattt 660
gttgaaaata aatggcttta tttgtttttt ttggctcgat aggctcgggt ccacctgtcc 720
cggtcgttaa ggactttgtg tatgctttcc aagacccggt acagatgggc ttggatgttt 780
agatacatgg gcatgaggcc atcccggggg tggagatagg accattgcag agcgtcatgc 840
tccggggtgg tgttgtagat gacccagtcg tagcagggtt tttgggcgtg gaactgaaaa 900
atgtccttga gaagcaggct gatggccagg ggcagaccct tagtgtaggt gttcacaaag 960
cggttgagct gggagggatg catgcgggga gagatgatat gcatcttagc ctggattttc 1020
aggttagcta tgttgccccc caggtccctt cgagggttca tattgtggag gaccaccaga 1080
acggtgtagc cggtacactt gggaaactta tcgtgcagtt tggaggggaa ggcgtgaaag 1140
aatttggaaa ccccctttgtg accacctaag ttttccatgc actcgtccat gataatggcg 1200
atgggcccct tggcggcagc tttagcgaac acgttgtggg ggttggaaac atcatagttt 1260
tgctctagag ttagctcgtc ataggccatt tttacgaagc ggggtaggag ggtgccagac 1320
tgagggacga tagttccatc tggccccggt gcgtaattac cctcgcagat ctgcatctcc 1380
caagctttaa tttccgaggg agggatcatg tccacctggg gggcgataaa gaacacggtt 1440
tctggcgggg gattaatgag ctgggtggaa agcaggttgc gcaagagctg agacttgccg 1500
caaccggtgg gaccgtagat gaccccgatg acgggctgca gctggtagtt gagagaggag 1560
cagctgccgt cggggcgtag gaggggagcc acctcgttca tcatgcttct tacatgttta 1620
ttttcactga ctaagctttg caagagcctc tccccaccca gggacaagag ttcttccagg 1680

-continued

```
ctgttgaagt gtttcagcgg tttcaggccg tcggccatgg gcatcttttc aagcgactga   1740
cgaagcaagt acagccggtc ccagagctcg gtgacgtgct ctatggaatc tcgatccagc   1800
agacttcttg gttgcggggg ttgggccgac tttcgctgta gggtacgagc cggtgggcgt   1860
ccagggccgc gagggttttg tccttccagg gtctcagcgt ccgggtgagg gtggtctcgg   1920
tgacggtgaa cggatgagcc ccgggctggg cgcttgccag ggtgcgcttc aggctcatcc   1980
ggctggtgct gaagcgggcg tcgtctccct gggaatcggc cagatagcaa cggagcatga   2040
ggtcgtagct aagggattcg gccgcgtgtc ccttggcgcg cagttttccc ttggaaacat   2100
gctggcatct ggtgcagtgt aaacacttga gggcgtacag cttgggggcg aggaagacgg   2160
actcgggcga gtaggcgtcg gccccgcact cggcgcagac ggtttcacac tccaccagcc   2220
acgtgagctc gggtttgtcg gggtcaaaaa ccaggttgcc tccatttttt ttgatgcgtt   2280
tcttaccttg cgtctccatg agcctgtgac ccgcttcggt gacaaaaagg ctgtctgtgt   2340
ctccgtagac cgacttgagg gggcgttctt ccaagggcgt gccgcggtct tctgcgtaca   2400
aaaactggga ccactccgaa acgaaggccc tggtccacgc taacacgaag gatgcgatct   2460
gcgaggggta tctgtcgttc tcaatgaggg gatccacctt ttccagggta tgcagacaca   2520
ggtcgtcctc ctccgcgtcc acaaaggtga ttggcttgta agtgtaggtc acgtgaccgg   2580
cgcccccggg aggggtataa aagggggcgt gcccaccctc cccgtcactt tcttccgcat   2640
cgctgtggac cagagccagc tgttcgggtg agtaggccct ctcaaaggcc ggcatgactt   2700
cggcactcaa gttgtcagtt tctacaaacg aggaggattt gatgttcacg tgccccgcgg   2760
cgatgctttt gatggtggag tggtccatct ggtcagaaaa cacgatcttt ttgttgtcaa   2820
gtttggtggc aaaagaccca tagagggcgt tggaaagcaa cttggcgatg gagcgcaggg   2880
tctgattttt ttcccgatcg gccctttcct tcgcggcgat gtttaattgc acgtactcgc   2940
gggccacgca tcgccattcc gggaacacgg cggtgcgctc gtcgggcagg atgcgcacgc   3000
gccagccgcg attgtgcagg gtgatcatgt ccacgctggt ggccacctcc ccccggaggg   3060
gctcgttggt ccaacacaat ctccctcctt ttctggagca gaacggaggg aggggatcta   3120
ggaggttggc gtgcgggggg tcggcgtcga tggtgaagat gccaggcagg agaactttat   3180
taaagtaatc gatctcggtt tccacgtctt gcaacgcctc ctcccatctc tttaccgcca   3240
gggccctctc gtaggggttc aggggcgccc cccagggcat ggggtgggtg agagccgagg   3300
cgtacatgcc acagatgtca tagacgtaga ggggctcccg taggaccccg atgtaagtgg   3360
gataacagcg ccccccgcgg atgctggccc gcacgtagtc gtacatctcg tgagatgggg   3420
ccaggagacc ctctcccaag tgggtcttgt ggggcttctc cgcccggtag aggatctgcc   3480
tgaagatggc gtgggagttg gaagagatgg tgggccgttg gaagacgtta aagttggccc   3540
gcggcagccc caccgagtct tcgatgaact gggcgtagga ttcctggagt ttgttcacga   3600
gggcggcggt gaccagcacg tccagggcgc agtaatccag ggtctcgcgg accaggttgt   3660
aggagctctc ttgttttttc tcccacagtt cgcggttgag gaggtattcc tcgcggtctt   3720
tccagtactc ttcggcggga aatccttttt cgtccgctcg gtaagaacct aacatgtaaa   3780
actcgttcac cgctttgtat ggacaacagc ctttctctac cggcagggcg tacgcctgag   3840
cggcctttct gagagaagtg tgggtgaggg cgaaggtgtc ccgcaccatg actttcaggt   3900
actgatgttt gaagtccgtg tcgtcgcagc ttccttgttc ccacaggctg aagtcggtgc   3960
gctttttctg cctcgggttg ggagggcga aagtgacatc gttaaacaag attttcccgg   4020
cgcggggcat aaagttgcga gagattctga agggccctgg cacgtccgag cggttgttga   4080
```

tgacctgcgc cgccaggacg atctcgtcga agccgttgat gttatgcccc acgatgtaca 4140
gttctatgaa gcgcggctgt cccttgaggg cgggcgcttt tttcagttcc tcgtaggtga 4200
gggactcggg agaggcgagc cccagctccg cgcgggccca gtcggccagt tgagggttag 4260
ccgcgaggaa ggaattccag agctccgagg ccagaagagt ttgcaagcga tcgcgaaact 4320
cgcggaactt tttccccacg gccatttttt ctggcgtgac cacgtagaaa gtggcggagc 4380
gatcgttcca gacgtcccac ttgagctccc gggccagctc gcaggcctga cgcacgagag 4440
tttcctcgcc cgagacgtgc atgaccaaca tgaaaggcac taactgtttt ccgaacgcgc 4500
ccatccacgt gtaggtctct acatcgtagg tgacaaagag ccgttgggtg cgtgcgtggg 4560
agccgatcgg aaagaagctg atctcctgcc accagctgga ggaatgggtg ttgatgtggt 4620
gaaagtagaa gtcccgccgg cgcacagagc attcgtgctg gtgtttgtaa aagcgaccgc 4680
agtagtcgca gcgctgcacg ctctgtattt cttgaatgag atgcactttt cgcccgcgaa 4740
ccagaaatcg gaggggaaag ttgagcccgg gggatggtgg agtcgcgtcc ccttcgcctt 4800
ggcggtgggc gtctgcgtct gcgtcctgtt tttctgggtg gacgacggtg gggacgacga 4860
cgccccgggt tccgcaagtc cagatttcag cgacggaggg gcgcagacgc agaaggaggg 4920
ggcgcagttg cccgctgtcc agagagtcga ggaaagcgac gctgaggtca gcggggagcg 4980
tttgcaaatt cactttcaag agaccggtaa gagcgtgagc caggtggaga tgatacttga 5040
tttccagggg ggtgttggaa gaggcgtcca cgccgtacaa gaggccgtgt ccgcgcggag 5100
ccaccacggt tccccgcgga ggttttatct cactcgccga gggcgagcgc cggggggtag 5160
aggcggctct gcgccgggtg gtagcggagg cagaggcacg ttttcgtgag gattcggcag 5220
cggctgatga cgcgctcgga gactgctggc gtgggcgacg acgcggcggt tgaggtcctg 5280
gatgtgctgc ctctgcgtga agaccaccgg tcccctggtc ctgaacctga aagagagttc 5340
cacagagtca atgtctgcat cgttaacggc cgcctgcctg aggatctcct gcacgtcgcc 5400
cgagttgtct tggtaggcga tctcggccat gaactgttcg acttcttctt cgcggaggtc 5460
gccgtggccc gcgcgttcta cggtggcggc caggtcgtta gagatgcgac gcatgagctg 5520
ggagaaggcg ttgaggccgt tctcgttcca cacgcggctg tacaccacgt taccgaagga 5580
gtcgcgcgct cgcatgacca cctgcgccac gttgagttcc acgtggcggg cgaagacggc 5640
gtagtttctg aggcgctgga agaggtagtt gagcgtggtg gcgatgtgct cgcagacgaa 5700
gaagtacatg atccagcgcc tcagagtctg ctcgttgatg tctccgatgg cttcgaggcg 5760
ttccatggcc tcgtagaagt cgacggcgaa gttgaaaaat tgggagttgc gggcggccac 5820
cgtgagttct tcttgcagga ggcggatgag atcggcgacg gtgtcgcgca cctcctgttc 5880
gaaagcgccc cgaggcgcct ctgcttcttc ctccagctcc tcctcttcca ggggcacagg 5940
ttcctccggc acctctgcgg cggggacggg gcggcgacgt cgtcgtctga ccggcagtcg 6000
gtccacgaag cgttcgatca tttcaccgcg ccggcgacgc atggtctcgg tgacggcgcg 6060
tccgttttcg cggggacgca gttcgaagac gccgccgcgc agagcgcccc cgtgcaggga 6120
gggtaagtgg ttagggccgt cgggcagaga cacggcgctg acgatgcatt ttatcaattg 6180
ttgcgtaggc actccgtgca gggatctgag aacgtcgagg tcgacgggat ccgaaaactt 6240
ctctaggaaa gcgtctatcc aatcgcaatc gcaaggtaag ctgaggacgg tgggccgctg 6300
gggggcgtcc gcgggtagtt gggaggtgat gctgctgatg atgtaattaa agtaggcggt 6360
tttcaggcgg cggatggtgg cgaggaggac cacgtctttg ggcccggcct gttgaatgcg 6420

-continued

```
caggcgctcg gccatccccc aggcctcgct ctgacagcga cgcaggtctt tgtagtagtc   6480
ttgcatcagt ctctccaccg gaatctctgc ttctcccctg tctgccatgc gagtcgagcc   6540
gtacccccgc aagggctgca gcaacgctag gtctgccact actctttcgg ccagcacggc   6600
ctgttgaatc tgcgtgaggg tggcctggaa gtcgtccagg tccacgaagc ggtggtaggc   6660
tcccgtgttg atggtgtagg tgcagttggc catgacggac cagttgacga cttggatgcc   6720
gggttgggtg atctccgtgt acttgaggcg cgagtaggcc ctggactcga acacgtagtc   6780
gttgcatgcg cgcaccagat actggtagcc gacgagaaag tgcggaggcg gttcccgata   6840
caggggccag cccacggtgg cgggggctcc gggggccagg tcttccagca tgaggcggtg   6900
gtagtggtac acgtatcgag agagccaggt gatgccggct gaggtggtgg cggccctggt   6960
gaactcgcgg acgcggttcc agatgttgcg caggggggcgg aagcgttcca tggtgggcac   7020
gctctgtccc gtcaggcgcg cgcaatcctg tacgctctag atggagaaaa gacagggcgg   7080
tcatcgactc ccgtccgtag ctgggaggta aagtcgcaag ggtgcggcgg cggggaaccc   7140
cggttcgaga ccggctggat ccgccgttcc cgatgcgcct ggccccgcat ccacgacgtt   7200
cgcgccgaga cccagccgcg gcacaccgcc ccaatacgga ggggagtctt ttggtgtttt   7260
ttcatagatg catccggtgc tgcgacagat gcgaccccag acgcccactg ctactaccgc   7320
cgcggcggca gtaaacctga gcggaggcgg tgacagggag gacgaagagc tggctttaga   7380
cctggaagag ggagagggtc tggcgcgact gggcgccccc tcccccgaga gacaccccag   7440
ggtccagctc gtgagggatg cgagacaggc ttttgtaccg cggcagaacc tgtttaggga   7500
ccgcagcggc caggaggcgg aggagatgcg cgattgtcgg tttcgggcgg gcagagagct   7560
gagggcgggg ttcgaccggg agcggttgct gcgggcggag gatttcgaac ccgacgagcg   7620
gtcgggggtg agtccggccc gagcccacgt gtcggccgcc aacctggtga gtgcgtatga   7680
gcagacggtg aacgaggagc gtaactttca aaagagcttt aataatcacg ttcggaccct   7740
catcgcgagg gaggaggtgg ccatcgggct gatgcatctg tgggacttcg tggaggccta   7800
cgtgcagaac ccggcgagca agcccctgac ggctcagctg ttcctgatcg tgcagcacag   7860
ccgcgacaac gagacgtttc gcgacgccat gctcaacatc gccgagcccg agggccgctg   7920
gctcttggat cttatcaaca tcttgcagag catcgtggtt caggagaggg gtctcagctt   7980
agcggacaag gtggcggcca ttaactactc catgcagagt ctgggaaaat tctacgctcg   8040
caagatctac aagagcccct acgtgcccat agacaaggag gtgaagatag acagctttta   8100
catgcgcatg gcgctgaagg tgctgacgct gagcgacgat ctcggcgtgt accgtaacga   8160
caagatccac aaggcggtga gcgccagccg ccggcgggag ctgagcgata gggagctgat   8220
gcacagcctg cagagggcgc tggcgggtgc cggggacgag gagcgcgaga cttacttcga   8280
tatgggagcg gacttacagt ggaaacccag cgcccgagcg ttggaggcgg cgggctaccg   8340
tggcgacgag gatcgggatg actttgagga ggcaggcgag tacgaggacg aagcctgacc   8400
gggcaggtgt tgttttagat gcagcgtccg gcggacgggg ccaccgtgga tcccgcgctt   8460
ttggcatcca tgcagagtca acctacgggc gtgaccgcct ccgatgactg ggcggcggcc   8520
atggaccgca tcatggcact gaccacccgc aaccccgagg cttttaggca gcaaccccag   8580
gccaaccgtt tttcggccat cttggaagcg gtagtgccgt ctcgcactaa tccgacccac   8640
gaaaaggttt taactatcgt gaacgcgctg gtagacagca aggccatccg ccgcgacgag   8700
gcggggctga tttacaacgc tctgctggaa cgcgtggcgc gctacaacag cactaacgtg   8760
cagaccaatc tggaccgcct caccacggac gtgaaggaag cgttggctca gaaggagcgg   8820
```

```
ttcttaaggg acagcaatct gggttctctg gtggcgctga acgcttttct gagcacgcag   8880
ccggcgaacg taccccgcgg gcaggaggac tacgtgagct tcatcagcgc tctgagactg   8940
ctcgtttccg aggtgccgca gagcgaggtg taccagtcgg gacctgacta cttcttccag   9000
acgtcccgac agggcttgca aacggtgaac ctgactcagg cttttaaaaa cttgcaaggc   9060
atgtggggcg tgaaggcgcc ggttggcgat cgcgcgacca tttccagcct gctgaccccc   9120
aacacgagac tgctgttgct tttaatcgcc ccgttcacca acagcagcac catcagccgc   9180
gactcgtacc tgggccatct catcactctg taccgagagg ccataggtca ggctcagatt   9240
gacgagcata cgtatcaaga gatcaccaat gtgagccgag ccctgggtca ggaagacacc   9300
ggcagtttgg aagccacgct aaactttctg ctgaccaatc ggagacaaaa gattccctcg   9360
cagtacacgt taagcgccga ggaggagagg attctgcgct acgtgcagca gtccgtgagc   9420
ctgtacttga tgcgggaggg tgctaccgct tccacggcct tggacatgac ggctcgaaac   9480
atggaaccgt ctttttactc agcccaccgt ccgttcatca atcgcctgat ggactacttc   9540
catcgcgcgg ccgccatgaa cggggagtat ttcaccaatg ccatcttgaa tccgcattgg   9600
atgcctccgt ccggtttcta caccggggag ttcgacctgc ccgaggccga cgacggcttt   9660
ctgtgggacg atgtgtccga cagcattttt acgccaggta acagtcgttt ccataaaaag   9720
gaagggggag acgaacttcc cctttcgagt gtggaggcgg cctccagggg ggagagcccc   9780
ttttccagct tgtcttccgt gagtagcggt cgggtgacgc gcccacgctt gccgggggag   9840
agcgactacc taaacgaccc tttgctgcga ccggctaaaa agaaaaattt tcccaacaac   9900
ggggtggaaa gcttggtgga taaaatgaat cgttggaaga cctacgctca ggagcagcgg   9960
gagtgggagg acagtcagcc ccgaccgctg gtcccgccgc actggcgccg ccagagagaa  10020
gacccggacg actccgcaga cgatagtagc gtgttggact tgggagggag cggagccaac  10080
ccctttgctc acttgcaacc caaggggcgc ttgagtcgcc tgtactaata aaaagaaagc  10140
ggaaacgtac cagagccatg gccacagcgt gtgtcctttc ttcctctctt tcctcctcgg  10200
cgcggcagaa tgagaagagc ggtgagagtc acgccggcgg tgtatgccga gggtccgccc  10260
ccttcttacg aaagcgtgat gggatcagcg aacgtgccgg ccacgctgga ggcgccttac  10320
gttcctccca gatacctggg acctaccgag ggcagaaaca gcatccgtta ctccgagctg  10380
gcccccctgt acgataccac caaggtgtac ctggtggaca acaagtcggc ggacatcgcc  10440
tccctgaatt accaaaacga ccacagcaac ttcctgacca ccgtggtgca gaacaatgac  10500
ttcaccccga cggaggcggg cacgcaaacc attaactttg acgagcgttc ccgctggggc  10560
ggtcagctga aaaccatcct gcacaccaac atgcccaaca tcaacgagtt tatgtccacc  10620
aacaagttta gggccaggtt gatggtagag aagactagcg gccagccgcc caaatacgag  10680
tggttcgagt tcaccattcc cgagggtaac tactccgaga ccatgactat cgatctcatg  10740
aataacgcga tcgtggacaa ttacctgcaa gttggaaggc aaaacggggt attggagagc  10800
gacataggag taaaatttga taccaggaac ttccgactgg ggtgggatcc ggtgaccaag  10860
ctggtgatgc ctggcgtgta caccaacgag gcttttcacc ccgatatcgt gctgcttccg  10920
gggtgcggag tggactttac gcagagccgc ttgagtaacc tgttaggaat caggaagcgc  10980
cgtccctttc aggagggctt tcagattatg tatgaggact tggagggagg taatattcca  11040
ggcctgctag acgtgccggc ctatgaacaa agcttacaac aggcccaaga ggagggaaga  11100
gtcactcgcg gagacacctt tgccacggct cccaacgagg tagtgattaa gcccttattg  11160
```

-continued

```
aaagacagta aggatagaag ttataatatt ataaccgaca ccacggacac tttgtaccgg  11220
agttggtttc tggcttacaa ctacggggac cccgaaaacg gagtgagatc atggaccata  11280
ctcaccacca cggacgtgac ctgcggctcg cagcaagtgt actggtccct gccggatatg  11340
atgcaagacc cagtcacctt ccgcccctcc acccaagtca gcaactttcc ggtggtgggc  11400
actgagctgt tgcccgttca cgccaagagc ttctacaacg agcaggctgt ttattcgcaa  11460
ctcattcgcc agtctaccgc gcttacccac gtattcaacc gtttccccga gaaccagatt  11520
ctcgtgcgcc ctcccgctcc taccattacc accgtgagtg aaaacgttcc cgccctcaca  11580
gatcacggaa ccctgccgct gcgcagcagt atcagtggag ttcagcgcgt gaccatcacc  11640
gacgccagac gtcgaacctg cccttacgtt tacaaagcgc tcggcgtagt ggccccaaaa  11700
gtgctctcta gtcgcacctt ctaaaacatg tccattctca tctctcccga taacaacacc  11760
ggctggggac tgggctccgg caagatgtat ggcggggcga agcggcgctc cagtcagcac  11820
cctgttcgcg ttcggggtca tttccgcgct ccctggggag cttacaaacg aggactctcg  11880
ggccgaacgg cggtagacga caccattgac gccgtcattg ccgatgcccg ccggtataac  11940
cccggaacgg tcgctagcgc cgcctccacc gtggattccg tgatcgacag cgtggtggcc  12000
ggcgccaggg cctacgctcg ccgcaaaagg cggctgcacc gcaggcgtcg acccacggcc  12060
gccatgctgg ccgccagggc cgtgctgaga cgggcccgca gggtaggcag gagggccatg  12120
cgccgcgcgg ccgccaacgc tgccgccggg agggcccgca ggcaagccgc cagccgggcc  12180
gccgccgcca tcgctaacat ggccagaccc aggagaggga acgtttactg ggtgcgcgat  12240
tctgtgacgg gagtcagagt gccggtgcgc agccgacctc cccgaagtta gaagaccaaa  12300
ggtgcgaaga cggcgtactg agtctccctg ttgttatcag cccaacatga gcaagcgcaa  12360
gtttaaagaa gaactcctgc agaccctggc tcctgaaatc tatggccctc cggacgtgaa  12420
gcccgacatt aagccccgcg atatcaagcg tgttaaaaag cgggaaaaaa aagaggaact  12480
cgcggtggta gacgatggcg gggtagaatt tattagaagt ttcgccccgc gacgcagggt  12540
gcagtggaaa gggcggcgcg tgcaacgcgt tctcaggcca ggcaccgcgg tagtttttac  12600
tccgggagag cggtcggctg tcaggggttt caagcggcaa tatgacgagg tgtacggcga  12660
cgaagacatc ctggaacagg cggctcagca gattggagaa ttcgcctacg gaaagcggtc  12720
tcgccgcgaa gacctggcca ttgccttgga cagtggcaac ccccaccccca gcctcaaacc  12780
cgtcacgctg cagcaggtgc tccccgtgag cgcgagcacg gagagcaaaa ggggaatcaa  12840
gagagagatg gaagatctga agcccaccat ccaacttatg gtccctaaac gacagaagct  12900
ggaggaggtt ctggaaaaca tgaaagtgga ccccagcata gagccggatg taaaagtgag  12960
gcctattaag gaagtggctc cgggtctcgg ggtgcaaacg gtggacattc agatcccagt  13020
cagatccgct tcgaccgccg tggaagccat ggaaacgcaa accgaaactc cggtcgcggc  13080
cggtaccaga gaagtggctt tgcaaacgga gccctggtac gaatacaccg ctcctcggcg  13140
ccagaggcgg cgttacggcc cggcaaatgc catcatgcca gagtatgcgc tgcacccgtc  13200
tatccgaccc acccccggct accgggggggt aacgtatcgc ccgtcgccaa cccgacgccg  13260
ttatcgtcgc cgccgccgtt ctcgtcgcgc tctggcgccc gtgtccgtgc gacgcgtaac  13320
gcgccgggga agaacagtca ccatccctaa cccgcgctac caccctagca ttctttaatg  13380
actctgccgt tttgcagatg gctctgactt gccgcgtgcg ccttcccgtt ctgcactatc  13440
gaggaagatc tcgtcgtagg agaggcatgg cggggagcgg ccgccgtcgg gctttacgca  13500
ggcgcatgaa aggcggaatt ttgcccgcac tgattcccat aattgccgcc gccattgggg  13560
```

cgatacccgg cgttgcttca gtggccttgc aagcagctcg taataaataa acgaaggctt 13620
ttcaacttat gacctggtcc tgactatttt atgcagaaaa agcatggaag acatcaattt 13680
tacgtcgctg gctccgcggc aaggctcacg cccgctcatg ggcacctgga acgacatcgg 13740
cagcagccag ctcaacgggg gcgctttcaa ttgggggagc ctttggagcg gcattaaaaa 13800
ctttggctcc gcgattaaat cctacggcag caaagcctgg aacagtagta ctggtcagat 13860
gctccgggat aaactgaagg acacaaactt tcaagagaaa gtggtcaacg gggtggtgac 13920
cggcatccac ggcgcggtgg atctcgctaa tcaagcggtg caaaaagaga tagacagacg 13980
atgggaaaac tcgcgggtgc ctccgcagag aggggacgaa gtggaggtgg aggaagtaga 14040
agtcgaggag aaactgcccc cgctagagaa agttcccggg gcgccgccca ggccacagaa 14100
gcgtccccgg ccggatctgg aagaaacttt agtgacggaa accatcgaac ctccctcgta 14160
cgaacaagct ttaaaggagg gcgcctctcc ttaccccatg actaagccca tcgcgcccat 14220
ggcgcgtccg gtgtacggaa aagatcacaa gccagtaacg ttagagctac cccccaccacc 14280
cccttcccgt cctacggtgc ctccgttacc cgccccgtcg gcaggtccca gctctgcacc 14340
atccgcagct cctgcaccaa ccgctcgccc ggtggccgtg gcaaccgcca gagcccccag 14400
aggatccaac tggcaaagca cgctgaacag catcgtgggc ttgggagtga aaaccctaaa 14460
acgccgccgc tgctattatt aaagagtgta gctaaaaatt tcccgttgta tacgcctcct 14520
atgttaccgc cagagacgcg tgactggtcg ccgctccgcc gctttcaaga tggccacccc 14580
atcgatgatg ccgcagtggt cttacatgca catcgccggc caggacgcct cggagtacct 14640
gagtcccggc ctggtgcagt ttgcccgcgc caccgaaagc tacttcagct tgggaaacaa 14700
gtttagaaac cccaccgtgg cccccacgca cgatgtaacc acggaccgct cgcagaggct 14760
gacacttaat taattcgaac ccataatacc cataatagct gtttgccatc gacgcgaggc 14820
tggatggcct tccccattat gattcttctc gcttccggcg gcatcgggat gcccgcgttg 14880
caggccatgc tgtccaggca ggtagatgac gaccatcagg gacagcttca aggccagcaa 14940
aaggccagga accgtaaaaa ggccgcgttg ctggcgtttt tccataggct ccgcccccct 15000
gacgagcatc acaaaaatcg acgctcaagt cagaggtggc gaaacccgac aggactataa 15060
agataccagg cgtttccccc tggaagctcc ctcgtgcgct ctcctgttcc gaccctgccg 15120
cttaccggat acctgtccgc ctttctccct tcgggaagcg tggcgctttc tcatagctca 15180
cgctgtaggt atctcagttc ggtgtaggtc gttcgctcca agctgggctg tgtgcacgaa 15240
ccccccgttc agcccgaccg ctgcgcctta tccggtaact atcgtcttga gtccaacccg 15300
gtaagacacg acttatcgcc actggcagca gccactggta acaggattag cagagcgagg 15360
tatgtaggcg gtgctacaga gttcttgaag tggtggccta actacggcta cactagaagg 15420
acagtatttg gtatctgcgc tctgctgaag ccagttacct tcggaaaaag agttggtagc 15480
tcttgatccg gcaaacaaac caccgctggt agcggtggtt tttttgtttg caagcagcag 15540
attacgcgca gaaaaaaagg atctcaagaa gatcctttga tcttttctac ggggtctgac 15600
gctcagtgga acgaaaactc acgttaaggg attttggtca tgagattatc aaaaaggatc 15660
ttcacctaga tccttttaaa ttaaaaatga agttttaaat caatctaaag tatatatgag 15720
taaacttggt ctgacagtta ccaatgctta atcagtgagg cacctatctc agcgatctgt 15780
ctatttcgtt catccatagt tgcctgactc cccgtcgtgt agataactac gatacgggag 15840
ggcttaccat ctggccccag tgctgcaatg ataccgcgag acccacgctc accggctcca 15900
gatttatcag caataaacca gccagccgga agggccgagc gcagaagtgg tcctgcaact 15960
ttatccgcct ccatccagtc tattaattgt tgccgggaag ctagagtaag tagttcgcca 16020
gttaatagtt tgcgcaacgt tgttgccatt gctgcaggca tcgtggtgtc acgctcgtcg 16080
tttggtatgg cttcattcag ctccggttcc caacgatcaa ggcgagttac atgatccccc 16140
atgttgtgca aaaaagcggt tagctccttc ggtcctccga tcgttgtcag aagtaagttg 16200
gccgcagtgt tatcactcat ggttatggca gcactgcata attctcttac tgtcatgcca 16260
tccgtaagat gcttttctgt gactggtgag tactcaacca agtcattctg agaatagtgt 16320
atgcggcgac cgagttgctc ttgcccggcg tcaacacggg ataataccgc gccacatagc 16380
agaactttaa aagtgctcat cattggaaaa cgttcttcgg ggcgaaaact ctcaaggatc 16440
ttaccgctgt tgagatccag ttcgatgtaa cccactcgtg cacccaactg atcttcagca 16500
tcttttactt tcaccagcgt ttctgggtga gcaaaaacag gaaggcaaaa tgccgcaaaa 16560
aagggaataa gggcgacacg gaaatgttga atactcatac tcttcctttt tcaatattat 16620
tgaagcattt atcagggtta ttgtctcatg agcggataca tatttgaatg tatttagaaa 16680
aataaacaaa taggggttcc gcgcacattt ccccgaaaag tgccacctga cgtctaagaa 16740
accattatta tcatgacatt aacctataaa aataggcgta tcacgaggcc ctttcgtctt 16800
caagaattgg tcgatggcaa acagctatta tgggtattat gggttcgaat taat 16854

<210> SEQ ID NO 48
<211> LENGTH: 21377
<212> TYPE: DNA
<213> ORGANISM: Artificial Sequence
<220> FEATURE:
<223> OTHER INFORMATION: Synthetic oligonucleotide pBr/sAd4312.pV-rITR

<400> SEQUENCE: 48
attaaccgaa gttagaagac caaaggtgcg aagacggcgt actgagtctc cctgttgtta 60
tcagcccaac atgagcaagc gcaagtttaa agaagaactc ctgcagaccc tggctcctga 120
aatctatggc cctccggacg tgaagcccga cattaagccc cgcgatatca agcgtgttaa 180
aaagcgggaa aaaaaagagg aactcgcggt ggtagacgat ggcggggtag aatttattag 240
aagtttcgcc ccgcgacgca gggtgcagtg gaaagggcgg cgcgtgcaac gcgttctcag 300
gccaggcacc gcggtagttt ttactccggg agagcggtcg gctgtcaggg gtttcaagcg 360
gcaatatgac gaggtgtacg gcgacgaaga catcctggaa caggcggctc agcagattgg 420
agaattcgcc tacggaaagc ggtctcgccg cgaagacctg gccattgcct tggacagtgg 480
caaccccacc cccagcctca aacccgtcac gctgcagcag gtgctccccg tgagcgcgag 540
cacggagagc aaaaggggaa tcaagagaga gatggaagat ctgaagccca ccatccaact 600
tatggtccct aaacgacaga agctggagga ggttctggaa aacatgaaag tggaccccag 660
catagagccg gatgtaaaag tgaggcctat taaggaagtg gctccgggtc tcggggtgca 720
aacggtggac attcagatcc cagtcagatc cgcttcgacc gccgtggaag ccatggaaac 780
gcaaaccgaa actccggtcg cggccggtac cagagaagtg gctttgcaaa cggagccctg 840
gtacgaatac accgctcctc ggcgccagag gcggcgttac ggcccggcaa atgccatcat 900
gccagagtat gcgctgcacc cgtctatccg acccaccccc ggctaccggg ggtaacgta 960 tcgcccgtcg ccaacccgac gccgttatcg tcgccgccgc cgttctcgtc gcgctctggc 1020
gcccgtgtcc gtgcgacgcg taacgcgccg gggaagaaca gtcaccatcc ctaacccgcg 1080
ctaccaccct agcattcttt aatgactctg ccgttttgca gatggctctg acttgccgcg 1140
tgcgccttcc cgttctgcac tatcgaggaa gatctcgtcg taggagaggc atggcgggga 1200
gcggccgccg tcgggcttta cgcaggcgca tgaaaggcgg aattttgccc gcactgattc 1260
ccataattgc cgccgccatt ggggcgatac ccggcgttgc ttcagtggcc ttgcaagcag 1320
ctcgtaataa ataaacgaag gcttttcaac ttatgacctg gtcctgacta ttttatgcag 1380
aaaaagcatg gaagacatca attttacgtc gctggctccg cggcaaggct cacgcccgct 1440
catgggcacc tggaacgaca tcggcagcag ccagctcaac gggggcgctt tcaattgggg 1500
gagcctttgg agcggcatta aaaactttgg ctccgcgatt aaatcctacg gcagcaaagc 1560
ctggaacagt agtactggtc agatgctccg ggataaactg aaggacacaa actttcaaga 1620
gaaagtggtc aacggggtgg tgaccggcat ccacggcgcg gtggatctcg ctaatcaagc 1680
ggtgcaaaaa gagatagaca gacgatggga aaactcgcgg gtgcctccgc agagagggga 1740
cgaagtggag gtggaggaag tagaagtcga ggagaaactg cccccgctag agaaagttcc 1800
cggggcgccg cccaggccac agaagcgtcc ccggccggat ctggaagaaa ctttagtgac 1860
ggaaaccatc gaacctccct cgtacgaaca agctttaaag gagggcgcct ctccttaccc 1920
catgactaag cccatcgcgc ccatggcgcg tccggtgtac ggaaaagatc acaagccagt 1980
aacgttagag ctacccccac cacccccttc ccgtcctacg gtgcctccgt tacccgcccc 2040
gtcggcaggt cccagctctg caccatccgc agctcctgca ccaaccgctc gcccggtggc 2100
cgtggcaacc gccagagccc ccagaggatc caactggcaa agcacgctga acagcatcgt 2160
gggcttggga gtgaaaaccc taaaacgccg ccgctgctat tattaaagag tgtagctaaa 2220
aatttcccgt tgtatacgcc tcctatgtta ccgccagaga cgcgtgactg gtcgccgctc 2280
cgccgctttc aagatggcca ccccatcgat gatgccgcag tggtcttaca tgcacatcgc 2340
cggccaggac gcctcggagt acctgagtcc cggcctggtg cagtttgccc gcgccaccga 2400
aagctacttc agcttgggaa acaagtttag aaaccccacc gtggccccca cgcacgatgt 2460
aaccacggac cgctcgcaga ggctgacact gcgcttcgtg cccgtagacc gggaggacac 2520
cgcgtactcc tacaaagtgc gcttcaccct cgccgtaggg gacaacaggg tgctggacat 2580
ggccagcacg tactttgaca tccggggaat gctggaccga gggcccagct ttaaacccta 2640
ctcgggaact gcctacaatt cgctggcacc taagggcgct cccaacccta gtcaatggac 2700
tactaccaac ggagggaata aaacaaattc atttgcccaa gcatcctaca taggtcaaag 2760
cctgtcgaaa gacggggtgc aagtagcagt agatacagcc gctggggggg ctgcagtata 2820
tgctgacaaa acgtttcaac cagaacccca agtaggaata tcacaatgga atgaaaatcc 2880
tactacaaat gctgcaggaa gaattttaaa gcctactacc gcaatgcgtc catgctacgg 2940
ttcatacgct taccccacca acgaaaaagg tgggcaggta aaaatcactg accctaacaa 3000
tgacaaaacc ggcgctaata acgttagctt aaattttttc aacactgccg ctgacaatgg 3060
gaataacaat ccaaaagtag tactctacag cgaagatgta aatttagaag ggccagatac 3120
ccaccttgtt tttaagccag atgtaactgg cgacgcaacc agtgcagaaa ccctgttagg 3180
tcaacaagca gctcccaatc gtccaaacta cattgggttc agggacaact ttattggcct 3240
gatgtactac aattcaactg gaaacatggg agtgctagca ggtcaggctt ctcagctaaa 3300
cgccgtagtg gatcttcaag acagaaatac cgaattgtca tatcagctaa tgcttgacgc 3360
tttgggtgac agaagtcggt acttttctat gtggaatcaa gcagtggaca gctacgatcc 3420
tgacgttaga atcatagaaa atcatggagt agaagacgaa cttccaaatt attgttttcc 3480
gttaaatgga caggggattt cgaatacata caaaggtgtg aaatataaca caaacacttg 3540
gacgcaagac actgatgtag tcacaaccaa tgaaatttcc attggcaaca tttttgccat 3600
ggaaataaac ctggcggcta acttgtggcg cagctttctg tactccaatg tcgccctgta 3660
cttgccagat tcctacaaat acactcccga caatattgaa cttcctacaa acaagaacag 3720
ctacggctac attaacggaa gggtaaccgc ccccactgcc atcgacactt acgttaacat 3780
cggcgcccgg tggtctccgg accccatgga caacgttaac cctttcaacc accaccgcaa 3840
cgccggcttg cgataccgct ccatgctgct gggcaacggt cgctacgtac ccttccacat 3900
tcaggtgccc cagaaatttt ttgccattaa aaacctgctt ctgcttcccg ggtcctacac 3960
ctacgagtgg aacttcagga aagatgtaaa catgatcttg cagagcacct tgggcaacga 4020
cctccgcgtt gacggagcta gcgtgaggtt tgacagcatt aacctctacg ctaacttctt 4080
ccccatggcc cacaacacgg cctccacctt ggaagccatg ctgcgcaacg acaccaacga 4140
ccagtccttt aatgattacc tgtgcgcggc caacatgctg taccccatcc ccgccaatgc 4200
caccagcgtg ccgatctcca ttccctcacg caactgggcc gccttcagag gttggagttt 4260
cactcgcctg aaaaccaagg agacccccctc gctgggctcc ggtttcgacc catactttgt 4320
ttactccggg agcattccct acctggacgg aactttctac ctgaaccaca ccttcaaaaa 4380
ggtgtctatt atgtttgact cctccgtgag ctggcccggt aacgaccgct tgctaacccc 4440
caacgagttc gaaatcaaac gctcggtgga cggagagggt tacaatgtag cccagagcaa 4500
catgaccaaa gactggtttt taattcaaat gctaagccac tataacattg gctaccaagg 4560
attctacgtg cctgaagcct acaaggacag aatgtactcc ttctttagaa acttccaacc 4620
catgagccgc caggtagtag acacggtaaa ctatgctaac tacaaggaag taacaatgcc 4680
attccagcac aacaactcag gcttcgtggg gtacatggga cctaccatga gagaggggca 4740
ggcctacccg gctaattatc cctacccccct aatcggagcc actgccgtgc ccagcctgac 4800
acagaaaaag tttctctgcg atcgaacaat gtggaggatt cccttctcta gcaacttcat 4860
gtccatgggg gctctcaccg acctggggca gaacatgctg tacgctaact ccgctcacgc 4920
cttggacatg acctttgagg tggaccccat ggatgagccc acgcttctct atgttctgtt 4980
tgaagtcttc gacgtggtgc gcattcacca gccgcaccgc ggcgtcatcg aggccgtcta 5040
cctgcgcaca cctttctctg ccggtaacgc caccacctaa gaagctgatg ggctccagcg 5100
aacaggagct gcgggccatt gttcgcgacc tgggctgcgg gccctacttt ttgggcacct 5160
tcgacaagcg cttccccggc ttcatgtccc cccacaagcc ggcctgcgcc atcgtcaaca 5220
cggccggacg cgagaccggg ggggttcact ggctcgcctt tgcctggaac ccgcgtaacc 5280
acacctgcta cctgttcgac ccttttggtt tttctgacga aaggcttaaa cagatttacc 5340
agttcgagta cgaggggctc cttaaacgca gcgctctggc ctccacgccc gaccactgcg 5400
tcaccctgga gaagtccacc caaacggttc agggtcccct ctcggcggcc tgcggactct 5460
tttgttgcat gtttttgcat gctttcgtcc actggccgaa cacccccatg gaccgcaacc 5520
ccactatgga tctgctcacg ggagtgccta acagcatgct tcacagccct caggtcgcac 5580
ccaccctgcg tcgcaatcag gaacagctgt atgcttttct gggaaaacat tctgcctact 5640
ttcgccgcca ccggcagcgc atagaacagg ccacggcctt tgaaagcatg agtcaaagag 5700
tgtaatcaat aaaatcaact tttattttac atcacacgcg cttctggcgt ttcttaaaa 5760 atcaaagggt tcgggggagg ggtcgtcgtg cccgctgggc agggacacgt tgcgatactg 5820
gaagcggggg ctccagcgga actcggggat cgccagccgg ggcagaggca cttcttccag 5880

-continued

```
gttctgcttc caaaactgcc gcaccagctg gagggctccc attacgtcgg gcgccgagat   5940
cttgaagtcg cagttggggc ccgagcttcc gcggctgttg cgaaacacgg ggttggcaca   6000
ctggaacacc agcacgctcg ggtagttgat actggccagg gccgttgcgt cggtcaccgc   6060
cgttacatcc agatcctccg cgttggtcag ggcgaaggga gtcagcttgc acatctgccg   6120
cccgatgtgg ggcacgccgt catgcttgtt gaggcagtcg caacgcaggg gaatcagaat   6180
gcgatgctgg ccgcgttgca tctgagggta gttggcccgc aagaacgctt ccatctgacg   6240
gaaggccgtc tgggctttca ttccctcggt gtagaaaaga ccgcaggact tgctagaaaa   6300
tacattattg ccgcaggtga cgtcttccgc gcagcagcgg gcgtcttcgt tctttagctg   6360
caccacgttg cgaccccacc ggttctgtac caccttggcc ctcgtgggct gctccttcag   6420
cgcccgctgg ccgttttcgc tggtcacatc catttccaac acgtgctcct tacacaccat   6480
ttccactccg tggaagcaga acaggacgcc ctcctgctgg gtattgcgat gctcccacac   6540
ggcgcagcct gtggcctccc agctcttatg cttcaccccc gcgtagtttt ccatgtaagc   6600
catcaggaat ctgcccatca tctcggtaaa ggttttctga ctggtgaagg tcaaaggcaa   6660
gccgcggtgc tcttcgttca gccacgtttg acagatcttg cggtacgtgg cgccctgatc   6720
cggcagaaac ttaaacgccc ccttgctctc gttgtccacg tggaactttt ccatcagcat   6780
tagcataact tccataccct tctcccacgc cgtcaccagc ggtgtgctgt cggggttctt   6840
caccaacatg gtagaagggc cctcgccggc cctgaagtcg ctcatactca tttttgaaa    6900
ctccacagtg ccgtccgcac gacggacccg gcgcatcgga gggtagctga agccaacctc   6960
caccagggtg ccttcgctct cgctgtcgga gacgatctcc ggggagggcg gcggcgcggg   7020
tgtcgacttg cgagccttct tcttgggagg aagcggtggc gcctcttggt cgcgctcggg   7080
actcatctcc ctcaagtagg gggtgatgga gcttcctgct tggttctgac ggttggccat   7140
tgtatcctag gcagaaacac atggagctta tgcgcgagga aactttaacc gccccgtccc   7200
ccgtcaacga cgaagaggtc atcatcgaac aggacccggg ctacgttact ccgcccgagg   7260
atctggaggg gcctttagac gaccggcgcg acgctagtga gcagcaggaa aatgagaaag   7320
aggaagcctg ctacctcctg gaaggcgacg tgttgctaaa acatttcgcc aggcagagca   7380
ccatagtgaa ggaggctttg caagaccgct cggaggtgcc cttggacgtc gccgcgctct   7440
cccaggccta cgaggcgaac ctcttctcgc cccgagtgcc tccgaagaga cagcccaacg   7500
gcacctgcga gcccaacccg cgccttaact tctaccccgt gttcgccgtg cccgaggcgc   7560
tggccaccta ccacattttt ttcaagaacc agcgcatccc gctctcgtgc cgggccaacc   7620
gcaccgcggc cgatagaaag ctgagactca aaaacggagc tagcatacct gatatcacgt   7680
ccctggagga agtgcctaag atcttcgaag gtctgggtcg agacgagaaa cgggcggcaa   7740
acgctctgca gaaagaacag aaggacagtc agaacgtgct ggtggaactg gagggggaca   7800
atgcgcgtct ggccgttctc aagcgctgca tagaagtttc ccacttcgcc taccctgccc   7860
tgaacctgcc gcccaaagtc atgcgctcgg tcatggacca gctgctcatc aagagagctg   7920
agcccctgaa ccccgagcac cccgaggcgg agaactcgga ggacggaaag cccgtcgtca   7980
gcgacgagga gctcgagcgg tggctggaca gcacggaccc cgagcagttg caagagcggc   8040
gcaaaatgat gatggcggcc gtcctggtca ccgttgagct ggagtgcctg cagcggtttt   8100
ttagcgacgt ggaaacgctg cgtaaaatcg gagagtccct gcactacacc ttccgccagg   8160
gctacgtccg ccaggcctgc aagatctcca acgtggagct cagcaacctg gtctcctaca   8220
```

-continued

```
tgggcatcct ccacgagaac cggctgggac agagcgtgct gcactgcacc ttgcaaggcg   8280
aggcgcggcg ggactacgtg cgagactgcg tctacctctt cctcactctc acctggcaga   8340
ccgccatggg agtgtggcag cagtgcttgg aagacagaaa cctcaaagag ctagacaaac   8400
tcctctgccg ccagcggcgc gccctgtggt ccggtttcag cgagcgcacg gtcgccagcg   8460
ctctggcgga catcatcttc ccggagcgcc tgatgaaaac cttgcaaaac ggcctgccgg   8520
atttcatcag tcaaagcatt ttgcaaaact tccgctcttt tgtcctggaa cgctccggga   8580
tattgcccgc catgagctgc gcgctacctt ctgactttgt ccccctctcc taccgcgagt   8640
gccctccccc actgtggagc cactgctacc tcttccaact ggccaacttt ctggcctacc   8700
actccgacct catggaagac gtaagcggag agggtttact ggagtgccac tgccgctgca   8760
acctgtgcac cccccacaga tcgctggcct gcaacaccga gctactcagc gaaacccagg   8820
tcataggtac cttcgagatc caggggcccc agcagcaaga gggtgcttcc ggcttgaagc   8880
tcactccggc gctgtggacc tcggcttact tacgcaaatt tgtagccgag gactaccacg   8940
cccacaaaat tcagttttac gaagaccaat ctcgaccacc gaaagccccc ctcacggcct   9000
gcgtcatcac ccagagcaag atcctggccc aattgcaatc catcaaccaa gcgcgccgcg   9060
atttcctttt gaaaaagggt cggggggtgt acctggaccc ccagaccggc gaggaactca   9120
acccgtccac actctccgtc gaagcagccc ccccgagaca tgccgcccaa gggaaccgcc   9180
aagcagctga tcgctcggca gagagcgaag aagcaagagc tgctccagca gcaggtggag   9240
gacgaggaag agatgtggga cagccaggca gaggaggtgt cagaggacga ggaggagatg   9300
gaaagctggg acagcctaga cgaggaggag gacgagcttt cagaggaaga ggcgaccgaa   9360
gaaaaaccac ctgcatccag cgcgccttct ctgagccgac agccgaagcc ccggcccccg   9420
acgcccccgg ccggctcact caaagccagc cgtaggtggg acgccaccga atctccagcg   9480
gcagcggcaa cggcagcggg taaggccaaa cgcgagcggc gggggtattg ctcctggcgg   9540
gcccacaaaa gcagtattgt gaactgcttg caacactgcg gggggaaacat ctcctttgcc   9600
cgacgctacc tcctcttcca tcacggtgtg gccttccctc gcaacgttct ctattattac   9660
cgtcatctct acagccccta cgaaacgctc ggagaaaaaa gctaaggcct cctccgccgc   9720
gaggaaaaac tccgccgccg ctgccgccgc caaggatcca ccggccaccg aagagctgag   9780
aaagcgcatc tttcccactc tgtatgctat ctttcagcaa agccgcgggc agcaccctca   9840
gcgcgaactg aaaataaaaa accgctcctt ccgctcgctc acccgcagct gtctgtacca   9900
caagagagaa gaccagctgc agcgcaccct ggacgacgcc gaagcactgt tcagcaaata   9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
cttagaacag gcggcaatca ccgccacacc ccggcgccaa ctcaacccgc ctagttggcc  10260
cgccgcccag gtgtatcagg aaaatccccg cccgaccaca gtcctcctgc cacgcgacgc  10320
ggaggccgaa gtcctcatga ctaactctgg ggtacaatta gcgggcgggt ccaggtacgc  10380
caggtacaga ggtcgggccg ctccttactc tcccgggagt ataaagaggg tgatcattcg  10440
aggccgaggt atccagctca acgacgagac ggtgagctcc tcaaccggtc tcagacctga  10500
cggagtcttc cagctcggag gagcaggccg ctcttccttc accactcgcc aggcctacct  10560
gaccctgcag agctcttcct cgcagccgcg ctccgggggga atcggcactc tccagttcgt  10620
```

ggaagagttc gttccctccg tctacttcaa ccccttctcc ggctcgcctg gacgctaccc 10680
ggacgccttc attcccaact ttgacgcagt gagtgaatcc gtggacggct acgactgatg 10740
acagatggtg cggccgtgag agctcggctg cgacatctgc atcactgccg tcagcctcgc 10800
tgctacgctc gggaggcgat cgtgttcagc tactttgagc tgccggacga gcaccctcag 10860
ggtccggctc acgggttgaa actcgagatc gagaacgcgc tcgagtctcg cctcatcgac 10920
accttcaccg cccgacctct cctggtagaa atccaacggg ggatcactac catcaccctg 10980
ttctgcatct gccccacgcc cggattacat gaagatctgt gttgtcatct ttgcgctcag 11040
tttaataaaa actgaacttt ttgccgcacc ttcaacgcca cgcgttgttt ctccaacagt 11100
cgacgatagc tcttcaatta aaggtacccg agaaactgtt tattttgaca attctactac 11160
ttctcttatc cttaactgtt cttgcactaa cgaactaatt cagtggttcg ccaacggttc 11220
actctgcaaa gttttccttg actctgcgat acttcccgga tttagcagct ctgcgtgtga 11280
taattctacc ccctccacct taaccatcac aaagccattt tcagaagtcc agtatttttg 11340
tattggagcg gggggtaaac cgggctgtat tcaccgcttc tttctggaga catttgttgc 11400
ttcgattccc attaacactt cactttcctc taatacatac ttaactacct tacattctac 11460
tcacccctcc tggaaacctc ttattggcct cacagctttt atttccgttg ttttactaaa 11520
ctttataatt cttaacaaac tttcttaaac atgcttgcca ttttgcttct gctcgttact 11580
ttaacctccg cagattacca caatgcaatt gtacgagaaa acagtttaca aaacccatca 11640
caggtatatg ttaaagcagg ttctaactta actctacaat ccttctattc gccttaccct 11700
gaggacatgc cacgtgtcac ctggtactta gaagtttttg attcgctatt tgaaagacat 11760
acaattcctc cattttttac aggcgttata ctttgtgaca tttctggtga catacagcat 11820
gtgtggaacc attggccttt acaatttaat tgcataaata aaagcttaca tattatcaat 11880
ctcaaaccaa gtgatgaagg cctttacaat gtgaaggttt taaagggcag cattcagcat 11940
aatacatact ttcgtgtgca tgtagtaagt tttccaaaac ctgaatgtaa catcaccact 12000
acatatcttt cagatgacta ctgccttatt aacattgatt gctctcaatt accataccct 12060
gctaaggtct attataatgg caatgaaagt aagctgcatt actacttatc tgaacgcggt 12120
ggccaaccaa accttccaaa ttactttact gttgggtatc gatatagaga tctccgacag 12180
aattatacag ttgaatatcc atttaatgaa ctctgtacag atataattgc tcttgaaaca 12240
gggtctgatt ttacgccaat ttttatagtt accctagtgg tgagcattat agttattgtg 12300
atgggcatca catatcttat ttatcactgt aggactttaa aaaccaaaac caaaaccaag 12360
cctcctgaaa tccgtctgct ttaatttttt ccagaatggt agctgctttc ttcattctcc 12420
tctgtatacc aatcatctgc gcctccacaa cttttgccgc tgtttcccac ctggaaccag 12480
actgtctacc accttttgtt gtatacctaa tactgacttt tgtggtctgt acagccatta 12540
ccagtatagc ctgctttttt gtaacaattt tccaagccgc cgattacctc tacgtacggt 12600
ttgcttactt tagacatcac cccgagtatc ggaatcaaaa cgtagcctct ctgctttgtt 12660
tagcatgatt cgcattttta tactttgtaa gctctttacc accacaatat gtcaatgccc 12720
ttttaccaaa ccctggtcct tttacacttg ttataatgta ttacccgaaa cccccattgc 12780
ctggctttac gtagccacag cggctttagt ttttgtagca acctgcattg gcgttaaact 12840
gtacttttac ttaaaaattg gatggcttca tcccccagaa gatttacccc gatatcctct 12900
tgttaataac tttcaacagc ctctaccgcc tcctgatctt ccgcgagctc cctccgttgt 12960

```
tagctacttt caactcaccg gtggagatga ctgacactca ggacattaac attactgtgg  13020
aaagaatagc tgctcagcgt cagcgagaga cgcgggtgat ggagtacgtg gaactacagc  13080
agcttaaaga gtcccactgg tgtgaaaaag gagtgctttg ccatgttaag caagcagccc  13140
tttcttacga tgtcagcact cagggacatg aactgtccta cactttgcct ttacagaaac  13200
aaaccttctg caccatgatg ggctctacct ccattacaat cagccaacaa accggacctg  13260
tcgagggggc tatcctgtgt cactgtcacg cgcctgattg tatgcccaaa ctaatcagaa  13320
ctctttgtgc tttaggtgat atatttaaaa tatagatagt atcaataaac ttaccttaaa  13380
tttgacagca atttttggt atcatcattc agcagcacca ctttaccctc ttcccaactc  13440
tcatatggga tatgatggtg ggcggcaaac ttcctccaaa ccctgaaaga aatatcggta  13500
tccacttcct tgtcctcacc cacaattttc atcttttcat agatgaaaag aacccgagtt  13560
gatgaagact tcaaccccgt ctacccttat gacaccacaa ccactccagc cgttcctttc  13620
atatcacccc cgtttgtaaa cagtgacggt cttcaggaaa accccccccgg agttttaagc  13680
ctgcgaatag ctaaacccct gtattttgac atggagagaa aactagccct ttcacttgga  13740
agagggttaa caattaccgc gaacggacaa ttagaaagca cccagagcgt gcagactaac  13800
ccgccgttaa ctgtcaccaa taacaacaca cttatcctac gccactcctc ccctttaatc  13860
ctaactgaca ataatttaac cgtaggcttc tcaagtcctc tccgtgttat agacaacaaa  13920
ctgacattca cttttacctc acctctccgt tatgaaaacg aaacccttac cttcaattac  13980
acagagcccc ttacacttat gaacagcaac cttgcgctta acgtaaactc ctctaaaggc  14040
cttagggttg acgggggctc actaggtaca aacttaagtc cggacttaag gtttaacagc  14100
agtggagcca tagcttttgg tatacaaacc ctatggacac ccccgacctc aaatcctaac  14160
tgcaccgttt acaccgaaag cgattcctta cttagtctct gcttaactaa atgcggagct  14220
cacgttttag gaagtgtaag cttaaccggg gtagcaggta ccatgataaa catggctgaa  14280
acttcgcttg ctattgaatt tacgtttgac gacactggaa aactacttca ctcaccactt  14340
gttaacacca cttttagcat tcgtcagggc gacagccccg cctcaaatcc tacctacaat  14400
gctctagcat ttatgccaaa cagtaccctc tacgctagag gaggaagtgg tgaaccccga  14460
aacaattact acgtccaaac atacctcagg ggaaatgttc agagaccgat taccctcact  14520
gttactttca actcagccgc cacgggatat tccttatctt ttaagtggac tgctgttgca  14580
cgtgaaaaat ttgcagctcc tgcaacttca ttttgctaca ttaccgaaca ataaaaccct  14640
gtgttcccac cgtttcgttt tttccagatg aaacgggcca gagttgatga agacttcaat  14700
cccgtgtacc cttacgatcc cccttacgcc cccattatgc cgtttattac cccgccgttt  14760
acatcttcag atgggttaca ggaaaaacca cttggtgttt taagtttaaa atacaaggat  14820
cctatcacta cacaaaatgg ttctctaacc cttaaattag gaaacgggct gaacattaac  14880
aaccagggcc aacttacatc atctgctggg gaagtcgagc ctcccctcac caatgctgac  14940
aacaagctgg ccttagccta cagcgaccct ctgacattaa aaaacagccg tctaacactg  15000
tctcacaatg ccccacttgc aattaacaat aattctctaa gtttggaagt atcagagcct  15060
atatttataa ataacgacaa caaactgtct ctgaaagctg acgccccccct gacaaccagc  15120
gctggaaccc tccgcctgca aagcgctgct ccattaggac ttgctgaaca gacactaaag  15180
ctgctgtttt ctaacccttt gtacttgcga ggtgacttcc ttacattagc cattgaacgc  15240
ccattggctg taacagcaga cgggctatta tcacttgccc tcaaccctcc gctcacaaca  15300
actaacacag gcttagctct ctctaccgcg gttccattaa ctgttaccaa cgggaacctt  15360
```

agcctaaacg taaaacggcc gtttattata caggacggca gcctttacat ggattttaga 15420
cccccactat atctgtttaa cagcgagcca caacttggtg ttaattttaa tgcccctcta 15480
actgttagag ataacggcct agctataaac accggagacg ggctaacagt aacgtataat 15540
aaactaacat taaacctcgg tagagacttg caatatgaaa atggagctgc agctgttaag 15600
ctaagtaccg cccctcctct acagtatact actcaactgc agctgaattt gggagcgggc 15660
ttacgtctag gtcctactag gaacttagac gtggccatta accacaataa agggttagcg 15720
tgggaaaaca atgaagtggt tactaaatta ggacaaggcc tttactttga ttcctccgga 15780
agcatagctt tatcgcctac aaaccccaga ccagatactt tatggaccac ggccgatcct 15840
tcgccaaact gcactgtata tgaatcactt gactctagac tgtggctagc gcttgttaaa 15900
tgtgggggaa tggtacacgg cagcatagcc ctacaagctg aaaaaggcca attgctgcgt 15960
cctactgcta gttttatctc catcgtaatt tacttctaca gtgatggggt ccgtcgcacc 16020
aactacccta caattggcaa tgatgagggt actctggcca acagcgctac ttggggctac 16080
agacaagggc aatctgcaga caccaacgtc accaatgctg ttgaattcat gcctagttta 16140
cacagatatc ctataaatca gggagacaat attaaaaacc aaatgataac ttacacttgc 16200
atacaaggca acgtgaacat gccagtaccc ttgaaaatca cgttcaatca tgctcttgaa 16260
ggctactcct taaagtttac atggcgtgtg gtggctaatg aaaagtttga tattccttgc 16320
tgttcgtttt cttacattac agaacaataa aacaactttt ttatttttca tttcttttat 16380
tttacacgca cagtaagact tcctcccccc ttccatttaa cagcgtacac cagcctttcc 16440
cccttcatgg cggtaaactt ctgtgagtta gtccggtatt tgggagttaa aatccaaaca 16500
ggctctttgg tgattaaacg ttgatccgtg atggacacaa atccctgaga caggtcctcc 16560
aacgttgcgg taaaaaactg aacgccgccc tacaaaacaa acagttcagg ctctccacgg 16620
gttatcaccc cgatcaaact cagacagagt aaaggtgcgg tgatgttcca caagaccgcg 16680
caagtggcgc tgtctaaagc tctcagtgcg acttctatgc ggctggtagg atgttacatt 16740
atccaacagc ctcacagcgc ggattattag tctacgagtg cgcctggcgc agcagcgcat 16800
ctgaatttca gtcaagtctt gacaagaagc gcataccata acaatcaggt tgttcatgat 16860
cccatagcta aacgcgctcc agccaaaact cattcgctcc aacagcacca ccgcgtgtcc 16920
gtcaagtctt acttttacat aaacaaggtg tctgccacgt acatacatgc tacccgcata 16980
caaaacttcc cggggcaaac ctctattcac cacctgtctg taccagggaa acctgatgtt 17040
tatcagggaa ccatagatgg ccattttaaa ccagttagcc agcaccaccc cgccagctct 17100
acactgaagg gaaccgggag agttacaatg acagtggatc atccacctct cgtaacccct 17160
aattacctga ttaaaatcca aatctaacgt ggcacaacag atacacactc tcataaacat 17220
tttcatgaca tgtttttccc aggatgttaa aatacaatcc caatacacgg gccactcctg 17280
taatacaata aagctaatgc atgatggaac gctcctcacc tcactaacat tgtgcatgtt 17340
tacattttca cactctaagt accgagtcct ctcctcaaca gccgcagtgt cgcgctcctc 17400
acacggtggt agctgatgac aattgtaagg ggccagtctg cagcgatatc gtctgtcgcg 17460
ctgcatcgta aaacagggac cgtctcactt cctcgtactt ccaatagcag aaccacgtcc 17520
gctgccagca ggtttccacg aaccgccgat cccttcgtcg ttcacgctcc ctcctcaacg 17580
caaaatgcag ccactcctgc aatccacaca aatccctctc ggcctccgga gtcatgcaca 17640
cctcatacct atatatgtct cggtacagtt ccaaacacga agtaagggcg agctccaacc 17700

-continued aacacaaaca ggctgattta tcccgacaca ctggaggtgg aggaagacac ggaagaggca 17760
tgttattcca agcgatccgg caaaggatca aagtgcagat cccgaagatg gcaacgctcg 17820
cctccggagc cctggtgaaa tttaacggcc aaatcaaaca ttatgcggtt ttccaaacta 17880
tcaatcgccg cctccaaaag ggcctgaacc cgcacttcca caatcaccag caaagcaaaa 17940
gcgtgattat caaagtcttc aatcatcaga tggcatgact gtacaatgcc caaataattc 18000
tcatttctcc actcgcgaat agtgtcgcgg cagatcgtct gaaggtccat gccatgcatg 18060
ttaaaaagct cccagagggc gccctctacc gacatgcgta gacacaccat catgactgca 18120
aaatatcagg ctcctgagac acctgcagca gatttaacag atcaaagtca ggttgctgtc 18180
cgcggtcacg aatctccatg cgcaaagcca tttgcaaaaa attatatagg tctgtgccaa 18240
ctagctctgt taattccgcg ttaggaagca aatcaggtga ggctatgcag cacaaaagtt 18300
gcagggaagg cgccaaactc agtaaaaccg ctccagaata acaaaattga tgaagcggag 18360
tcacacagtg taaaatgtgc aaccaaaaat cattcagctg ctcttttaaa tagtccagta 18420
cttctatatt caatccgtgc aagtactgaa gcaactgcgc gggaacagtc acattaaaaa 18480
aaatggggcg gctcaaatac atgtcgacct aaaataaaaa taatcattaa accagagaag 18540
cttgacgaat ggaaggataa aatacacgct ccagcaaaag gcaggcaacc ggctgtcccc 18600
gagaaccgta aaaaaattca tccgaatgat taaaaagaac cacagaaatt tcccaccatg 18660
tactcggttg taactcctga gcacacagca acaccccccct aacgttcatg tccgccactg 18720
aaaaaagacg tcccaaatac ccaggtggaa tgtcaagaga caactgcaga gacagcaaaa 18780
caacccctct gggagcgatc ataaactcct ccggtgagaa aagcgcatac aaattagaat 18840
aaccctgttg ctggggcaaa atagcccggc ggcccagcaa atggacataa atatgttcag 18900
cagccatcgc cccgtcttac cgcgtaaaaa gccagaaaaa tccagctaac tacactctac 18960
agcctattac tatatatact ctcctcccac tgacgctata ccaccccgcc cacgtccaaa 19020
gttcacccac gcccaaaaaa cccgcgaaaa tccagcgccg tcagcacttc cgcaattgta 19080
gtctctcaac gtcacttccg cgcgcctttt ccctattccc acacacgccc gcggacttcg 19140
ccccgcccgc cctcgcgcca ccccgcgtca ccccgcgtca ccgcacgtca ccccggcccc 19200
gcctcgctcc tccccactca ttatcatatt ggcacgtttc cagaataagg tatattattg 19260
atgatgttaa ttaattcgaa cccataatac ccataatagc tgtttgccat cgacgcgagg 19320
ctggatggcc ttccccatta tgattcttct cgcttccggc ggcatcggga tgcccgcgtt 19380
gcaggccatg ctgtccaggc aggtagatga cgaccatcag ggacagcttc aaggatcgct 19440
cgcggctctt accagcccag caaaaggcca ggaaccgtaa aaaggccgcg ttgctggcgt 19500
ttttccatag gctccgcccc cctgacgagc atcacaaaaa tcgacgctca agtcagaggt 19560
ggcgaaaccc gacaggacta taaagatacc aggcgtttcc ccctggaagc tccctcgtgc 19620
gctctcctgt tccgaccctg ccgcttaccg gatacctgtc cgcctttctc ccttcgggaa 19680
gcgtggcgct ttctcatagc tcacgctgta ggtatctcag ttcggtgtag gtcgttcgct 19740
ccaagctggg ctgtgtgcac gaaccccccg ttcagcccga ccgctgcgcc ttatccggta 19800
actatcgtct tgagtccaac ccggtaagac acgacttatc gccactggca gcagccactg 19860
gtaacaggat tagcagagcg aggtatgtag gcggtgctac agagttcttg aagtggtggc 19920
ctaactacgg ctacactaga aggacagtat ttggtatctg cgctctgctg aagccagtta 19980
ccttcggaaa aagagttggt agctcttgat ccggcaaaca aaccaccgct ggtagcggtg 20040
gtttttttgt ttgcaagcag cagattacgc gcagaaaaaa aggatctcaa gaagatcctt 20100
tgatcttttc tacggggtct gacgctcagt ggaacgaaaa ctcacgttaa gggattttgg 20160
tcatgagatt atcaaaaagg atcttcacct agatcctttt aaattaaaaa tgaagtttta 20220
aatcaatcta aagtatatat gagtaaactt ggtctgacag ttaccaatgc ttaatcagtg 20280
aggcacctat ctcagcgatc tgtctatttc gttcatccat agttgcctga ctccccgtcg 20340
tgtagataac tacgatacgg gagggcttac catctggccc cagtgctgca atgataccgc 20400
gagacccacg ctcaccggct ccagatttat cagcaataaa ccagccagcc ggaagggccg 20460
agcgcagaag tggtcctgca actttatccg cctccatcca gtctattaat tgttgccggg 20520
aagctagagt aagtagttcg ccagttaata gtttgcgcaa cgttgttgcc attgctgcag 20580
gcatcgtggt gtcacgctcg tcgtttggta tggcttcatt cagctccggt tcccaacgat 20640
caaggcgagt tacatgatcc cccatgttgt gcaaaaaagc ggttagctcc ttcggtcctc 20700
cgatcgttgt cagaagtaag ttggccgcag tgttatcact catggttatg gcagcactgc 20760
ataattctct tactgtcatg ccatccgtaa gatgcttttc tgtgactggt gagtactcaa 20820
ccaagtcatt ctgagaatag tgtatgcggc gaccgagttg ctcttgcccg gcgtcaacac 20880
gggataatac cgcgccacat agcagaactt taaaagtgct catcattgga aaacgttctt 20940
cggggcgaaa actctcaagg atcttaccgc tgttgagatc cagttcgatg taacccactc 21000
gtgcacccaa ctgatcttca gcatctttta ctttcaccag cgtttctggg tgagcaaaaa 21060
caggaaggca aaatgccgca aaaaagggaa taagggcgac acggaaatgt tgaatactca 21120
tactcttcct ttttcaatat tattgaagca tttatcaggg ttattgtctc atgagcggat 21180
acatatttga atgtatttag aaaaataaac aaataggggt tccgcgcaca tttccccgaa 21240
aagtgccacc tgacgtctaa gaaaccatta ttatcatgac attaacctat aaaaataggc 21300
gtatcacgag gccctttcgt cttcaagaat tggtcgatgg caaacagcta ttatgggtat 21360
tatgggttcg aattaat 21377

<210> SEQ ID NO 49
<211> LENGTH: 19308
<212> TYPE: DNA
<213> ORGANISM: Artificial Sequence
<220> FEATURE:
<223> OTHER INFORMATION: Synthetic oligonucleotide pBr/sAd4312.pV-rITR.dE3

<400> SEQUENCE: 49
attaaccgaa gttagaagac caaaggtgcg aagacggcgt actgagtctc cctgttgtta 60
tcagcccaac atgagcaagc gcaagtttaa agaagaactc ctgcagaccc tggctcctga 120
aatctatggc cctccggacg tgaagcccga cattaagccc cgcgatatca agcgtgttaa 180
aaagcgggaa aaaaaagagg aactcgcggt ggtagacgat ggcggggtag aatttattag 240
aagtttcgcc ccgcgacgca gggtgcagtg gaaagggcgg cgcgtgcaac gcgttctcag 300
gccaggcacc gcggtagttt ttactccggg agagcggtcg gctgtcaggg gtttcaagcg 360
gcaatatgac gaggtgtacg gcgacgaaga catcctggaa caggcggctc agcagattgg 420
agaattcgcc tacggaaagc ggtctcgccg cgaagacctg gccattgcct tggacagtgg 480
caaccccacc cccagcctca aacccgtcac gctgcagcag gtgctccccg tgagcgcgag 540
cacggagagc aaaaggggaa tcaagagaga gatggaagat ctgaagccca ccatccaact 600
tatggtccct aaacgacaga agctggagga ggttctggaa aacatgaaag tggaccccag 660
catagagccg gatgtaaaag tgaggcctat taaggaagtg gctccgggtc tcggggtgca 720

```
aacggtggac attcagatcc cagtcagatc cgcttcgacc gccgtggaag ccatggaaac    780
gcaaaccgaa actccggtcg cggccggtac cagagaagtg gctttgcaaa cggagccctg    840
gtacgaatac accgctcctc ggcgccagag gcggcgttac ggcccggcaa atgccatcat    900
gccagagtat gcgctgcacc cgtctatccg acccaccccc ggctaccggg gggtaacgta    960
tcgcccgtcg ccaacccgac gccgttatcg tcgccgccgc cgttctcgtc gcgctctggc   1020
gcccgtgtcc gtgcgacgcg taacgcgccg gggaagaaca gtcaccatcc ctaacccgcg   1080
ctaccaccct agcattcttt aatgactctg ccgttttgca gatggctctg acttgccgcg   1140
tgcgccttcc cgttctgcac tatcgaggaa gatctcgtcg taggagaggc atggcgggga   1200
gcggccgccg tcgggcttta cgcaggcgca tgaaaggcgg aattttgccc gcactgattc   1260
ccataattgc cgccgccatt ggggcgatac ccggcgttgc ttcagtggcc ttgcaagcag   1320
ctcgtaataa ataaacgaag gcttttcaac ttatgacctg gtcctgacta ttttatgcag   1380
aaaaagcatg gaagacatca attttacgtc gctggctccg cggcaaggct cacgcccgct   1440
catgggcacc tggaacgaca tcggcagcag ccagctcaac gggggcgctt tcaattgggg   1500
gagcctttgg agcggcatta aaaactttgg ctccgcgatt aaatcctacg gcagcaaagc   1560
ctggaacagt agtactggtc agatgctccg ggataaactg aaggacacaa actttcaaga   1620
gaaagtggtc aacggggtgg tgaccggcat ccacggcgcg gtggatctcg ctaatcaagc   1680
ggtgcaaaaa gagatagaca gacgatggga aaactcgcgg gtgcctccgc agagagggga   1740
cgaagtggag gtggaggaag tagaagtcga ggagaaactg cccccgctag agaaagttcc   1800
cggggcgccg cccaggccac agaagcgtcc ccggccggat ctggaagaaa ctttagtgac   1860
ggaaaccatc gaacctccct cgtacgaaca agctttaaag gagggcgcct ctccttaccc   1920
catgactaag cccatcgcgc ccatggcgcg tccggtgtac ggaaaagatc acaagccagt   1980
aacgttagag ctacccccac cacccccttc ccgtcctacg gtgcctccgt tacccgcccc   2040
gtcggcaggt cccagctctg caccatccgc agctcctgca ccaaccgctc gcccggtggc   2100
cgtggcaacc gccagagccc ccagaggatc caactggcaa agcacgctga acagcatcgt   2160
gggcttggga gtgaaaaccc taaaacgccg ccgctgctat tattaaagag tgtagctaaa   2220
aatttcccgt tgtatacgcc tcctatgtta ccgccagaga cgcgtgactg gtcgccgctc   2280
cgccgctttc aagatggcca ccccatcgat gatgccgcag tggtcttaca tgcacatcgc   2340
cggccaggac gcctcggagt acctgagtcc cggcctggtg cagtttgccc gcgccaccga   2400
aagctacttc agcttgggaa acaagtttag aaaccccacc gtggccccca cgcacgatgt   2460
aaccacggac cgctcgcaga ggctgacact gcgcttcgtg cccgtagacc gggaggacac   2520
cgcgtactcc tacaaagtgc gcttcaccct cgccgtaggg gacaacaggg tgctggacat   2580
ggccagcacg tactttgaca tccgggggaat gctggaccga gggcccagct ttaaacccta   2640
ctcgggaact gcctacaatt cgctggcacc taagggcgct cccaacccta gtcaatggac   2700
tactaccaac ggagggaata aaacaaattc atttgcccaa gcatcctaca taggtcaaag   2760
cctgtcgaaa gacggggtgc aagtagcagt agatacagcc gctggggggg ctgcagtata   2820
tgctgacaaa acgtttcaac cagaacccca agtaggaata tcacaatgga atgaaaatcc   2880
tactacaaat gctgcaggaa gaattttaaa gcctactacc gcaatgcgtc catgctacgg   2940
ttcatacgct taccccacca acgaaaaagg tgggcaggta aaaatcactg accctaacaa   3000
tgacaaaacc ggcgctaata acgttagctt aaattttttc aacactgccg ctgacaatgg   3060
```

```
gaataacaat ccaaaagtag tactctacag cgaagatgta aatttagaag ggccagatac   3120
ccaccttgtt tttaagccag atgtaactgg cgacgcaacc agtgcagaaa ccctgttagg   3180
tcaacaagca gctcccaatc gtccaaacta cattgggttc agggacaact ttattggcct   3240
gatgtactac aattcaactg gaaacatggg agtgctagca ggtcaggctt ctcagctaaa   3300
cgccgtagtg gatcttcaag acagaaatac cgaattgtca tatcagctaa tgcttgacgc   3360
tttgggtgac agaagtcggt acttttctat gtggaatcaa gcagtggaca gctacgatcc   3420
tgacgttaga atcatagaaa atcatggagt agaagacgaa cttccaaatt attgttttcc   3480
gttaaatgga caggggattt cgaatacata caaaggtgtg aaatataaca caaacacttg   3540
gacgcaagac actgatgtag tcacaaccaa tgaaatttcc attggcaaca tttttgccat   3600
ggaaataaac ctggcggcta acttgtggcg cagctttctg tactccaatg tcgccctgta   3660
cttgccagat tcctacaaat acactcccga caatattgaa cttcctacaa acaagaacag   3720
ctacggctac attaacggaa gggtaaccgc ccccactgcc atcgacactt acgttaacat   3780
cggcgcccgg tggtctccgg accccatgga caacgttaac cctttcaacc accaccgcaa   3840
cgccggcttg cgataccgct ccatgctgct gggcaacggt cgctacgtac ccttccacat   3900
tcaggtgccc cagaaatttt ttgccattaa aaacctgctt ctgcttcccg ggtcctacac   3960
ctacgagtgg aacttcagga aagatgtaaa catgatcttg cagagcacct tgggcaacga   4020
cctccgcgtt gacggagcta gcgtgaggtt tgacagcatt aacctctacg ctaacttctt   4080
ccccatggcc cacaacacgg cctccacctt ggaagccatg ctgcgcaacg acaccaacga   4140
ccagtccttt aatgattacc tgtgcgcggc caacatgctg taccccatcc ccgccaatgc   4200
caccagcgtg ccgatctcca ttccctcacg caactgggcc gccttcagag gttggagttt   4260
cactcgcctg aaaaccaagg agacccccte gctgggctcc ggtttcgacc catactttgt   4320
ttactccggg agcattccct acctggacgg aactttctac ctgaaccaca ccttcaaaaa   4380
ggtgtctatt atgtttgact cctccgtgag ctggcccggt aacgaccgct tgctaacccc   4440
caacgagttc gaaatcaaac gctcggtgga cggagagggt tacaatgtag cccagagcaa   4500
catgaccaaa gactggtttt taattcaaat gctaagccac tataacattg gctaccaagg   4560
attctacgtg cctgaagcct acaaggacag aatgtactcc ttctttagaa acttccaacc   4620
catgagccgc caggtagtag acacggtaaa ctatgctaac tacaaggaag taacaatgcc   4680
attccagcac aacaactcag gcttcgtggg gtacatggga cctaccatga gagaggggca   4740
ggcctacccg gctaattatc cctacccccct aatcggagcc actgccgtgc ccagcctgac   4800
acagaaaaag tttctctgcg atcgaacaat gtggaggatt cccttctcta gcaacttcat   4860
gtccatgggg gctctcaccg acctggggca gaacatgctg tacgctaact ccgctcacgc   4920
cttggacatg acctttgagg tggaccccat ggatgagccc acgcttctct atgttctgtt   4980
tgaagtcttc gacgtggtgc gcattcacca gccgcaccgc ggcgtcatcg aggccgtcta   5040
cctgcgcaca cctttctctg ccggtaacgc caccacctaa gaagctgatg ggctccagcg   5100
aacaggagct gcgggccatt gttcgcgacc tgggctgcgg gccctacttt ttgggcacct   5160
tcgacaagcg cttccccggc ttcatgtccc cccacaagcc ggcctgcgcc atcgtcaaca   5220
cggccggacg cgagaccggg ggggttcact ggctcgcctt tgcctggaac ccgcgtaacc   5280
acacctgcta cctgttcgac ccttttggtt tttctgacga aaggcttaaa cagatttacc   5340
agttcgagta cgaggggctc cttaaacgca gcgctctggc ctccacgccc gaccactgcg   5400
tcaccctgga gaagtccacc caaacggttc agggtcccct ctcggcggcc tgcggactct   5460
```

```
tttgttgcat gtttttgcat gctttcgtcc actggccgaa cacccccatg gaccgcaacc   5520
ccactatgga tctgctcacg ggagtgccta acagcatgct tcacagccct caggtcgcac   5580
ccaccctgcg tcgcaatcag gaacagctgt atgctttttct gggaaaacat tctgcctact   5640
ttcgccgcca ccggcagcgc atagaacagg ccacggcctt tgaaagcatg agtcaaagag   5700
tgtaatcaat aaaatcaact tttattttac atcacacgcg cttctggcgt tttcttaaaa   5760
atcaaagggt tcgggggagg ggtcgtcgtg cccgctgggc agggacacgt tgcgatactg   5820
gaagcggggg ctccagcgga actcggggat cgccagccgg ggcagaggca cttcttccag   5880
gttctgcttc caaaactgcc gcaccagctg gagggctccc attacgtcgg gcgccgagat   5940
cttgaagtcg cagttggggc ccgagcttcc gcggctgttg cgaaacacgg ggttggcaca   6000
ctggaacacc agcacgctcg ggtagttgat actggccagg gccgttgcgt cggtcaccgc   6060
cgttacatcc agatcctccg cgttggtcag ggcgaaggga gtcagcttgc acatctgccg   6120
cccgatgtgg ggcacgccgt catgcttgtt gaggcagtcg caacgcaggg gaatcagaat   6180
gcgatgctgg ccgcgttgca tctgagggta gttggcccgc aagaacgctt ccatctgacg   6240
gaaggccgtc tgggctttca ttccctcggt gtagaaaaga ccgcaggact tgctagaaaa   6300
tacattattg ccgcaggtga cgtcttccgc gcagcagcgg gcgtcttcgt tctttagctg   6360
caccacgttg cgaccccacc ggttctgtac caccttggcc ctcgtgggct gctccttcag   6420
cgcccgctgg ccgttttcgc tggtcacatc catttccaac acgtgctcct tacacaccat   6480
ttccactccg tggaagcaga acaggacgcc ctcctgctgg gtattgcgat gctcccacac   6540
ggcgcagcct gtggcctccc agctcttatg cttcaccccc gcgtagtttt ccatgtaagc   6600
catcaggaat ctgcccatca tctcggtaaa ggttttctga ctggtgaagg tcaaaggcaa   6660
gccgcggtgc tcttcgttca gccacgtttg acagatcttg cggtacgtgg cgccctgatc   6720
cggcagaaac ttaaacgccc ccttgctctc gttgtccacg tggaactttt ccatcagcat   6780
tagcataact tccataccct tctcccacgc cgtcaccagc ggtgtgctgt cggggttctt   6840
caccaacatg gtagaagggc cctcgccggc cctgaagtcg ctcatactca ttttttgaaa   6900
ctccacagtg ccgtccgcac gacggacccg gcgcatcgga gggtagctga agccaacctc   6960
caccagggtg ccttcgctct cgctgtcgga gacgatctcc ggggagggcg gcggcgcggg   7020
tgtcgacttg cgagccttct tcttgggagg aagcggtggc gcctcttggt cgcgctcggg   7080
actcatctcc ctcaagtagg gggtgatgga gcttcctgct tggttctgac ggttggccat   7140
tgtatcctag gcagaaacac atggagctta tgcgcgagga aactttaacc gccccgtccc   7200
ccgtcaacga cgaagaggtc atcatcgaac aggacccggg ctacgttact ccgcccgagg   7260
atctggaggg gcctttagac gaccggcgcg acgctagtga gcagcaggaa aatgagaaag   7320
aggaagcctg ctacctcctg gaaggcgacg tgttgctaaa acatttcgcc aggcagagca   7380
ccatagtgaa ggaggctttg caagaccgct cggaggtgcc cttggacgtc gccgcgctct   7440
cccaggccta cgaggcgaac ctcttctcgc cccgagtgcc tccgaagaga cagcccaacg   7500
gcacctgcga gcccaacccg cgccttaact tctaccccgt gttcgccgtg cccgaggcgc   7560
tggccaccta ccacattttt ttcaagaacc agcgcatccc gctctcgtgc cgggccaacc   7620
gcaccgcggc cgatagaaag ctgagactca aaaacggagc tagcatacct gatatcacgt   7680
ccctggagga agtgcctaag atcttcgaag gtctgggtcg agacgagaaa cgggcggcaa   7740
acgctctgca gaaagaacag aaggacagtc agaacgtgct ggtggaactg gagggggaca   7800
```

```
atgcgcgtct ggccgttctc aagcgctgca tagaagtttc ccacttcgcc taccctgccc   7860
tgaacctgcc gcccaaagtc atgcgctcgg tcatggacca gctgctcatc aagagagctg   7920
agcccctgaa ccccgagcac cccgaggcgg agaactcgga ggacggaaag cccgtcgtca   7980
gcgacgagga gctcgagcgg tggctggaca gcacggaccc cgagcagttg caagagcggc   8040
gcaaaatgat gatggcggcc gtcctggtca ccgttgagct ggagtgcctg cagcggtttt   8100
ttagcgacgt ggaaacgctg cgtaaaatcg gagagtccct gcactacacc ttccgccagg   8160
gctacgtccg ccaggcctgc aagatctcca acgtggagct cagcaacctg gtctcctaca   8220
tgggcatcct ccacgagaac cggctgggac agagcgtgct gcactgcacc ttgcaaggcg   8280
aggcgcggcg ggactacgtg cgagactgcg tctacctctt cctcactctc acctggcaga   8340
ccgccatggg agtgtggcag cagtgcttgg aagacagaaa cctcaaagag ctagacaaac   8400
tcctctgccg ccagcggcgc gccctgtggt ccggtttcag cgagcgcacg gtcgccagcg   8460
ctctggcgga catcatcttc ccggagcgcc tgatgaaaac cttgcaaaac ggcctgccgg   8520
atttcatcag tcaaagcatt ttgcaaaact tccgctcttt tgtcctggaa cgctccggga   8580
tattgcccgc catgagctgc gcgctacctt ctgactttgt ccccctctcc taccgcgagt   8640
gccctccccc actgtggagc cactgctacc tcttccaact ggccaacttt ctggcctacc   8700
actccgacct catggaagac gtaagcggag agggtttact ggagtgccac tgccgctgca   8760
acctgtgcac cccccacaga tcgctggcct gcaacaccga gctactcagc gaaacccagg   8820
tcataggtac cttcgagatc caggggcccc agcagcaaga gggtgcttcc ggcttgaagc   8880
tcactccggc gctgtggacc tcggcttact tacgcaaatt tgtagccgag gactaccacg   8940
cccacaaaat tcagttttac gaagaccaat ctcgaccacc gaaagccccc ctcacggcct   9000
gcgtcatcac ccagagcaag atcctggccc aattgcaatc catcaaccaa gcgcgccgcg   9060
atttcctttt gaaaaagggt cggggggtgt acctggaccc ccagaccggc gaggaactca   9120
acccgtccac actctccgtc gaagcagccc ccccgagaca tgccgcccaa gggaaccgcc   9180
aagcagctga tcgctcggca gagagcgaag aagcaagagc tgctccagca gcaggtggag   9240
gacgaggaag agatgtggga cagccaggca gaggaggtgt cagaggacga ggaggagatg   9300
gaaagctggg acagcctaga cgaggaggag gacgagcttt cagaggaaga ggcgaccgaa   9360
gaaaaaccac ctgcatccag cgcgccttct ctgagccgac agccgaagcc ccggcccccg   9420
acgcccccgg ccggctcact caaagccagc cgtaggtggg acgccaccga atctccagcg   9480
gcagcggcaa cggcagcggg taaggccaaa cgcgagcggc gggggtattg ctcctggcgg   9540
gcccacaaaa gcagtattgt gaactgcttg caacactgcg ggggaaacat ctcctttgcc   9600
cgacgctacc tcctcttcca tcacggtgtg gccttccctc gcaacgttct ctattattac   9660
cgtcatctct acagccccta cgaaacgctc ggagaaaaaa gctaaggcct cctccgccgc   9720
gaggaaaaac tccgccgccg ctgccgccgc caaggatcca ccggccaccg aagagctgag   9780
aaagcgcatc tttcccactc tgtatgctat ctttcagcaa agccgcgggc agcaccctca   9840
gcgcgaactg aaaataaaaa accgctcctt ccgctcgctc acccgcagct gtctgtacca   9900
caagagagaa gaccagctgc agcgcaccct ggacgacgcc gaagcactgt tcagcaaata   9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
```

cttagaacag gcggcaatca ccgccacacc ccggcgccaa ctcaacccgc ctagttggcc 10260
cgccgcccag gtgtatcagg aaaatccccg cccgaccaca gtcctcctgc cacgcgacgc 10320
ggaggccgaa gtcctcatga ctaactctgg ggtacaatta gcgggcgggt ccaggtacgc 10380
caggtacaga ggtcgggccg ctccttactc tcccgggagt ataaagaggg tgatcattcg 10440
aggccgaggt atccagctca acgacgagac ggtgagctcc tcaaccggtc tcagacctga 10500
cggagtcttc cagctcggag gagcaggccg ctcttccttc accactcgcc aggcctacct 10560
gaccctgcag agctcttcct cgcagccgcg ctccgggggga atcggcactc tccagttcgt 10620
ggaagagttc gttccctccg tctacttcaa ccccttctcc ggctcgcctg gacgctaccc 10680
ggacgccttc attcccaact ttgacgcagt gagtgaatcc gtggacggct acgactgatg 10740
acagatggtg cggccgtgag agctcggctg cgacatctgc atcactgccg tcagcctcgc 10800
tgctacgctc gggaggcgat cgtgttcagc tactttgagc tgccggacga gcaccctcag 10860
ggtccggctc acgggttgaa actcgagatc gagaacgcgc tcgagtctcg cctcatcgac 10920
accttcaccg cccgacctct cctggtagaa atccaacggg ggatcactac catcaccctg 10980
ttctgcatct gccccacgcc cggattacat gaagatctgt gttgtcatct ttgcgctcag 11040
tttaataaaa actgaacttt ttgccgcacc ttcaacgcca cgcgttgttt ctccaacagt 11100
cgacgatagc tcttcaatta aaggtacccg agaaactgtt tattttgaca attctactac 11160
ttctcttatc cttaactgtt cttgcacact agtgaggggg ctatcctgtg tcactgtcac 11220
gcgcctgatt gtatgcccaa actaatcaga actctttgtg ctttaggtga tatatttaaa 11280
atatagatag tatcaataaa cttaccttaa atttgacagc aattttttgg tatcatcatt 11340
cagcagcacc actttaccct cttcccaact ctcatatggg atatgatggt gggcggcaaa 11400
cttcctccaa accctgaaag aaatatcggt atccacttcc ttgtcctcac ccacaatttt 11460
catcttttca tagatgaaaa gaacccgagt tgatgaagac ttcaaccccg tctaccctta 11520
tgacaccaca accactccag ccgttccttt catatcaccc ccgtttgtaa acagtgacgg 11580
tcttcaggaa aaccccccccg gagttttaag cctgcgaata gctaaacccc tgtattttga 11640
catggagaga aaactagccc tttcacttgg aagagggtta acaattaccg cgaacggaca 11700
attagaaagc acccagagcg tgcagactaa cccgccgtta actgtcacca ataacaacac 11760
acttatccta cgccactcct cccctttaat cctaactgac aataatttaa ccgtaggctt 11820
ctcaagtcct ctccgtgtta tagacaacaa actgacattc acttttacct cacctctccg 11880
ttatgaaaac gaaaccctta ccttcaatta cacagagccc cttacactta tgaacagcaa 11940
ccttgcgctt aacgtaaact cctctaaagg ccttagggtt gacgggggct cactaggtac 12000
aaacttaagt ccggacttaa ggtttaacag cagtggagcc atagcttttg gtatacaaac 12060
cctatggaca cccccgacct caaatcctaa ctgcaccgtt tacaccgaaa gcgattcctt 12120
acttagtctc tgcttaacta aatgcggagc tcacgtttta ggaagtgtaa gcttaaccgg 12180
ggtagcaggt accatgataa acatggctga aacttcgctt gctattgaat ttacgtttga 12240
cgacactgga aaactacttc actcaccact tgttaacacc acttttagca ttcgtcaggg 12300
cgacagcccc gcctcaaatc ctacctacaa tgctctagca tttatgccaa acagtaccct 12360
ctacgctaga ggaggaagtg gtgaaccccg aaacaattac tacgtccaaa catacctcag 12420
gggaaatgtt cagagaccga ttaccctcac tgttactttc aactcagccg ccacgggata 12480
ttccttatct tttaagtgga ctgctgttgc acgtgaaaaa tttgcagctc ctgcaacttc 12540

```
attttgctac attaccgaac aataaaaccc tgtgttccca ccgtttcgtt ttttccagat  12600
gaaacgggcc agagttgatg aagacttcaa tcccgtgtac ccttacgatc cccccttacgc  12660
ccccattatg ccgtttatta ccccgccgtt tacatcttca gatgggttac aggaaaaacc  12720
acttggtgtt ttaagtttaa aatacaagga tcctatcact acacaaaatg gttctctaac  12780
ccttaaatta ggaaacgggc tgaacattaa caaccagggc caacttacat catctgctgg  12840
ggaagtcgag cctcccctca ccaatgctga caacaagctg gccttagcct acagcgaccc  12900
tctgacatta aaaaacagcc gtctaacact gtctcacaat gccccacttg caattaacaa  12960
taattctcta agtttggaag tatcagagcc tatatttata aataacgaca acaaactgtc  13020
tctgaaagct gacgcccccc tgacaaccag cgctggaacc ctccgcctgc aaagcgctgc  13080
tccattagga cttgctgaac agacactaaa gctgctgttt tctaaccctt tgtacttgcg  13140
aggtgacttc cttacattag ccattgaacg cccattggct gtaacagcag acgggctatt  13200
atcacttgcc ctcaaccctc cgctcacaac aactaacaca ggcttagctc tctctaccgc  13260
ggttccatta actgttacca acgggaacct tagcctaaac gtaaaacggc cgtttattat  13320
acaggacggc agcctttaca tggattttag acccccacta tatctgttta acagcgagcc  13380
acaacttggt gttaatttta atgcccctct aactgttaga gataacggcc tagctataaa  13440
caccggagac gggctaacag taacgtataa taaactaaca ttaaacctcg gtagagactt  13500
gcaatatgaa aatggagctg cagctgttaa gctaagtacc gcccctcctc tacagtatac  13560
tactcaactg cagctgaatt tgggagcggg cttacgtcta ggtcctacta ggaacttaga  13620
cgtggccatt aaccacaata aagggttagc gtgggaaaac aatgaagtgg ttactaaatt  13680
aggacaaggc ctttactttg attcctccgg aagcatagct ttatcgccta caaaccccag  13740
accagatact ttatggacca cggccgatcc ttcgccaaac tgcactgtat atgaatcact  13800
tgactctaga ctgtggctag cgcttgttaa atgtgggggga atggtacacg gcagcatagc  13860
cctacaagct gaaaaaggcc aattgctgcg tcctactgct agttttatct ccatcgtaat  13920
ttacttctac agtgatgggg tccgtcgcac caactaccct acaattggca atgatgaggg  13980
tactctggcc aacagcgcta cttggggcta cagacaaggg caatctgcag acaccaacgt  14040
caccaatgct gttgaattca tgcctagttt acacagatat cctataaatc agggagacaa  14100
tattaaaaac caaatgataa cttacacttg catacaaggc aacgtgaaca tgccagtacc  14160
cttgaaaatc acgttcaatc atgctcttga aggctactcc ttaaagttta catggcgtgt  14220
ggtggctaat gaaaagtttg atattccttg ctgttcgttt tcttacatta cagaacaata  14280
aaacaacttt tttattttc atttctttta ttttacacgc acagtaagac ttcctccccc  14340
cttccattta acagcgtaca ccagcctttc cccccttcatg gcggtaaact tctgtgagtt  14400
agtccggtat ttgggagtta aaatccaaac aggctctttg gtgattaaac gttgatccgt  14460
gatggacaca aatccctgag acaggtcctc caacgttgcg gtaaaaaact gaacgccgcc  14520
ctacaaaaca aacagttcag gctctccacg ggttatcacc ccgatcaaac tcagacagag  14580
taaaggtgcg gtgatgttcc acaagaccgc gcaagtggcg ctgtctaaag ctctcagtgc  14640
gacttctatg cggctggtag gatgttacat tatccaacag cctcacagcg cggattatta  14700
gtctacgagt gcgcctggcg cagcagcgca tctgaatttc agtcaagtct tgacaagaag  14760
cgcataccat aacaatcagg ttgttcatga tcccatagct aaacgcgctc cagccaaaac  14820
tcattcgctc caacagcacc accgcgtgtc cgtcaagtct tacttttaca taaacaaggt  14880
gtctgccacg tacatacatg ctacccgcat acaaaacttc ccggggcaaa cctctattca  14940
```

```
ccacctgtct gtaccaggga aacctgatgt ttatcaggga accatagatg gccattttaa  15000
accagttagc cagcaccacc ccgccagctc tacactgaag ggaaccggga gagttacaat  15060
gacagtggat catccacctc tcgtaacccc taattacctg attaaaatcc aaatctaacg  15120
tggcacaaca gatacacact ctcataaaca ttttcatgac atgtttttcc caggatgtta  15180
aaatacaatc ccaatacacg ggccactcct gtaatacaat aaagctaatg catgatggaa  15240
cgctcctcac ctcactaaca ttgtgcatgt ttacattttc acactctaag taccgagtcc  15300
tctcctcaac agccgcagtg tcgcgctcct cacacggtgg tagctgatga caattgtaag  15360
gggccagtct gcagcgatat cgtctgtcgc gctgcatcgt aaaacaggga ccgtctcact  15420
tcctcgtact tccaatagca gaaccacgtc cgctgccagc aggtttccac gaaccgccga  15480
tcccttcgtc gttcacgctc cctcctcaac gcaaaatgca gccactcctg caatccacac  15540
aaatccctct cggcctccgg agtcatgcac acctcatacc tatatatgtc tcggtacagt  15600
tccaaacacg aagtaagggc gagctccaac caacacaaac aggctgattt atcccgacac  15660
actggaggtg gaggaagaca cggaagaggc atgttattcc aagcgatccg gcaaaggatc  15720
aaagtgcaga tcccgaagat ggcaacgctc gcctccggag ccctggtgaa atttaacggc  15780
caaatcaaac attatgcggt tttccaaact atcaatcgcc gcctccaaaa gggcctgaac  15840
ccgcacttcc acaatcacca gcaaagcaaa agcgtgatta tcaaagtctt caatcatcag  15900
atggcatgac tgtacaatgc ccaaataatt ctcatttctc cactcgcgaa tagtgtcgcg  15960
gcagatcgtc tgaaggtcca tgccatgcat gttaaaaagc tcccagaggg cgccctctac  16020
cgacatgcgt agacacacca tcatgactgc aaaatatcag gctcctgaga cacctgcagc  16080
agatttaaca gatcaaagtc aggttgctgt ccgcggtcac gaatctccat gcgcaaagcc  16140
atttgcaaaa aattatatag gtctgtgcca actagctctg ttaattccgc gttaggaagc  16200
aaatcaggtg aggctatgca gcacaaaagt tgcagggaag gcgccaaact cagtaaaacc  16260
gctccagaat aacaaaattg atgaagcgga gtcacacagt gtaaaatgtg caaccaaaaa  16320
tcattcagct gctcttttaa atagtccagt acttctatat tcaatccgtg caagtactga  16380
agcaactgcg cgggaacagt cacattaaaa aaaatggggc ggctcaaata catgtcgacc  16440
taaaataaaa ataatcatta aaccagagaa gcttgacgaa tggaaggata aaatacacgc  16500
tccagcaaaa ggcaggcaac cggctgtccc cgagaaccgt aaaaaaattc atccgaatga  16560
ttaaaaagaa ccacagaaat ttcccaccat gtactcggtt gtaactcctg agcacacagc  16620
aacacccccc taacgttcat gtccgccact gaaaaaagac gtcccaaata cccaggtgga  16680
atgtcaagag acaactgcag agacagcaaa acaacccctc tgggagcgat cataaactcc  16740
tccggtgaga aaagcgcata caaattagaa taaccctgtt gctggggcaa aatagcccgg  16800
cggcccagca aatggacata aatatgttca gcagccatcg ccccgtctta ccgcgtaaaa  16860
agccagaaaa atccagctaa ctacactcta cagcctatta ctatatatac tctcctccca  16920
ctgacgctat accaccccgc ccacgtccaa agttcaccca cgcccaaaaa acccgcgaaa  16980
atccagcgcc gtcagcactt ccgcaattgt agtctctcaa cgtcacttcc gcgcgccttt  17040
tccctattcc cacacacgcc cgcggacttc gccccgcccg ccctcgcgcc accccgcgtc  17100
accccgcgtc accgcacgtc accccggccc cgcctcgctc ctccccactc attatcatat  17160
tggcacgttt ccagaataag gtatattatt gatgatgtta attaattcga acccataata  17220
cccataatag ctgtttgcca tcgacgcgag gctggatggc cttccccatt atgattcttc  17280
```

-continued

```
tcgcttccgg cggcatcggg atgcccgcgt tgcaggccat gctgtccagg caggtagatg  17340

acgaccatca gggacagctt caaggatcgc tcgcggctct taccagccca gcaaaaggcc  17400

aggaaccgta aaaaggccgc gttgctggcg tttttccata ggctccgccc ccctgacgag  17460

catcacaaaa atcgacgctc aagtcagagg tggcgaaacc cgacaggact ataaagatac  17520

caggcgtttc cccctggaag ctccctcgtg cgctctcctg ttccgaccct gccgcttacc  17580

ggatacctgt ccgcctttct cccttcggga agcgtggcgc tttctcatag ctcacgctgt  17640

aggtatctca gttcggtgta ggtcgttcgc tccaagctgg gctgtgtgca cgaacccccc  17700

gttcagcccg accgctgcgc cttatccggt aactatcgtc ttgagtccaa cccggtaaga  17760

cacgacttat cgccactggc agcagccact ggtaacagga ttagcagagc gaggtatgta  17820

ggcggtgcta cagagttctt gaagtggtgg cctaactacg gctacactag aaggacagta  17880

tttggtatct gcgctctgct gaagccagtt accttcggaa aaagagttgg tagctcttga  17940

tccggcaaac aaaccaccgc tggtagcggt ggtttttttg tttgcaagca gcagattacg  18000

cgcagaaaaa aaggatctca agaagatcct ttgatctttt ctacggggtc tgacgctcag  18060

tggaacgaaa actcacgtta agggattttg gtcatgagat tatcaaaaag gatcttcacc  18120

tagatccttt taaattaaaa atgaagtttt aaatcaatct aaagtatata tgagtaaact  18180

tggtctgaca gttaccaatg cttaatcagt gaggcaccta tctcagcgat ctgtctattt  18240

cgttcatcca tagttgcctg actccccgtc gtgtagataa ctacgatacg ggagggctta  18300

ccatctggcc ccagtgctgc aatgataccg cgagacccac gctcaccggc tccagattta  18360

tcagcaataa accagccagc cggaagggcc gagcgcagaa gtggtcctgc aactttatcc  18420

gcctccatcc agtctattaa ttgttgccgg gaagctagag taagtagttc gccagttaat  18480

agtttgcgca acgttgttgc cattgctgca ggcatcgtgg tgtcacgctc gtcgtttggt  18540

atggcttcat tcagctccgg ttcccaacga tcaaggcgag ttacatgatc ccccatgttg  18600

tgcaaaaaag cggttagctc cttcggtcct ccgatcgttg tcagaagtaa gttggccgca  18660

gtgttatcac tcatggttat ggcagcactg cataattctc ttactgtcat gccatccgta  18720

agatgctttt ctgtgactgg tgagtactca accaagtcat tctgagaata gtgtatgcgg  18780

cgaccgagtt gctcttgccc ggcgtcaaca cgggataata ccgcgccaca tagcagaact  18840

ttaaaagtgc tcatcattgg aaaacgttct tcggggcgaa aactctcaag gatcttaccg  18900

ctgttgagat ccagttcgat gtaacccact cgtgcaccca actgatcttc agcatctttt  18960

actttcacca gcgtttctgg gtgagcaaaa acaggaaggc aaaatgccgc aaaaaaggga  19020

ataagggcga cacggaaatg ttgaatactc atactcttcc tttttcaata ttattgaagc  19080

atttatcagg gttattgtct catgagcgga tacatatttg aatgtattta gaaaaataaa  19140

caaatagggg ttccgcgcac atttccccga aaagtgccac ctgacgtcta agaaaccatt  19200

attatcatga cattaaccta taaaaatagg cgtatcacga ggccctttcg tcttcaagaa  19260

ttggtcgatg gcaaacagct attatgggta ttatgggttc gaattaat              19308
```

<210> SEQ ID NO 50
<211> LENGTH: 17915
<212> TYPE: DNA
<213> ORGANISM: Artificial Sequence
<220> FEATURE:
<223> OTHER INFORMATION: Synthetic oligonucleotide
      pBr/sAd4312.pV-rITR.dE3.dE4

<400> SEQUENCE: 50
attaaccgaa gttagaagac caaaggtgcg aagacggcgt actgagtctc cctgttgtta 60
tcagcccaac atgagcaagc gcaagtttaa agaagaactc ctgcagaccc tggctcctga 120
aatctatggc cctccggacg tgaagcccga cattaagccc cgcgatatca agcgtgttaa 180
aaagcgggaa aaaaaagagg aactcgcggt ggtagacgat ggcggggtag aatttattag 240
aagtttcgcc ccgcgacgca gggtgcagtg gaaagggcgg cgcgtgcaac gcgttctcag 300
gccaggcacc gcggtagttt ttactccggg agagcggtcg gctgtcaggg gtttcaagcg 360
gcaatatgac gaggtgtacg gcgacgaaga catcctggaa caggcggctc agcagattgg 420
agaattcgcc tacggaaagc ggtctcgccg cgaagacctg gccattgcct tggacagtgg 480
caaccccacc cccagcctca aacccgtcac gctgcagcag gtgctccccg tgagcgcgag 540
cacggagagc aaaaggggaa tcaagagaga gatggaagat ctgaagccca ccatccaact 600
tatggtccct aaacgacaga agctggagga ggttctggaa aacatgaaag tggaccccag 660
catagagccg gatgtaaaag tgaggcctat taaggaagtg gctccgggtc tcggggtgca 720
aacggtggac attcagatcc cagtcagatc cgcttcgacc gccgtggaag ccatggaaac 780
gcaaaccgaa actccggtcg cggccggtac cagagaagtg gctttgcaaa cggagccctg 840
gtacgaatac accgctcctc ggcgccagag gcggcgttac ggcccggcaa atgccatcat 900
gccagagtat gcgctgcacc cgtctatccg acccaccccc ggctaccggg ggtaacgta 960
tcgcccgtcg ccaacccgac gccgttatcg tcgccgccgc cgttctcgtc gcgctctggc 1020
gcccgtgtcc gtgcgacgcg taacgcgccg gggaagaaca gtcaccatcc ctaacccgcg 1080
ctaccaccct agcattcttt aatgactctg ccgttttgca gatggctctg acttgccgcg 1140
tgcgccttcc cgttctgcac tatcgaggaa gatctcgtcg taggagaggc atggcgggga 1200
gcggccgccg tcgggcttta cgcaggcgca tgaaaggcgg aattttgccc gcactgattc 1260
ccataattgc cgccgccatt ggggcgatac ccggcgttgc ttcagtggcc ttgcaagcag 1320
ctcgtaataa ataaacgaag gcttttcaac ttatgacctg gtcctgacta ttttatgcag 1380
aaaaagcatg gaagacatca attttacgtc gctggctccg cggcaaggct cacgcccgct 1440
catgggcacc tggaacgaca tcggcagcag ccagctcaac gggggcgctt tcaattgggg 1500
gagcctttgg agcggcatta aaaactttgg ctccgcgatt aaatcctacg gcagcaaagc 1560
ctggaacagt agtactggtc agatgctccg ggataaactg aaggacacaa actttcaaga 1620
gaaagtggtc aacggggtgg tgaccggcat ccacggcgcg gtggatctcg ctaatcaagc 1680
ggtgcaaaaa gagatagaca gacgatggga aaactcgcgg gtgcctccgc agagagggga 1740
cgaagtggag gtggaggaag tagaagtcga ggagaaactg cccccgctag agaaagttcc 1800
cggggcgccg cccaggccac agaagcgtcc ccggccggat ctggaagaaa ctttagtgac 1860
ggaaaccatc gaacctccct cgtacgaaca agctttaaag gagggcgcct ctccttaccc 1920
catgactaag cccatcgcgc ccatggcgcg tccggtgtac ggaaaagatc acaagccagt 1980
aacgttagag ctacccccac cacccccttc ccgtcctacg gtgcctccgt tacccgcccc 2040
gtcggcaggt cccagctctg caccatccgc agctcctgca ccaaccgctc gcccggtggc 2100
cgtggcaacc gccagagccc ccagaggatc caactggcaa agcacgctga acagcatcgt 2160
gggcttggga gtgaaaaccc taaaacgccg ccgctgctat tattaaagag tgtagctaaa 2220
aatttcccgt tgtatacgcc tcctatgtta ccgccagaga cgcgtgactg gtcgccgctc 2280
cgccgctttc aagatggcca ccccatcgat gatgccgcag tggtcttaca tgcacatcgc 2340
cggccaggac gcctcggagt acctgagtcc cggcctggtg cagtttgccc gcgccaccga 2400

-continued

```
aagctacttc agcttgggaa acaagtttag aaaccccacc gtggccccca cgcacgatgt   2460
aaccacggac cgctcgcaga ggctgacact gcgcttcgtg cccgtagacc gggaggacac   2520
cgcgtactcc tacaaagtgc gcttcaccct cgccgtaggg gacaacaggg tgctggacat   2580
ggccagcacg tactttgaca tccggggaat gctggaccga gggcccagct ttaaacccta   2640
ctcgggaact gcctacaatt cgctggcacc taagggcgct cccaacccta gtcaatggac   2700
tactaccaac ggagggaata aaacaaattc atttgcccaa gcatcctaca taggtcaaag   2760
cctgtcgaaa gacggggtgc aagtagcagt agatacagcc gctgggggg ctgcagtata   2820
tgctgacaaa acgtttcaac cagaacccca agtaggaata tcacaatgga atgaaaatcc   2880
tactacaaat gctgcaggaa gaattttaaa gcctactacc gcaatgcgtc catgctacgg   2940
ttcatacgct taccccacca acgaaaaagg tgggcaggta aaaatcactg accctaacaa   3000
tgacaaaacc ggcgctaata acgttagctt aaatttttc aacactgccg ctgacaatgg   3060
gaataacaat ccaaaagtag tactctacag cgaagatgta aatttagaag ggccagatac   3120
ccaccttgtt tttaagccag atgtaactgg cgacgcaacc agtgcagaaa ccctgttagg   3180
tcaacaagca gctcccaatc gtccaaacta cattgggttc agggacaact ttattggcct   3240
gatgtactac aattcaactg gaaacatggg agtgctagca ggtcaggctt ctcagctaaa   3300
cgccgtagtg gatcttcaag acagaaatac cgaattgtca tatcagctaa tgcttgacgc   3360
tttgggtgac agaagtcggt acttttctat gtggaatcaa gcagtggaca gctacgatcc   3420
tgacgttaga atcatagaaa atcatggagt agaagacgaa cttccaaatt attgttttcc   3480
gttaaatgga caggggattt cgaatacata caaaggtgtg aaatataaca caaacacttg   3540
gacgcaagac actgatgtag tcacaaccaa tgaaatttcc attggcaaca tttttgccat   3600
ggaaataaac ctggcggcta acttgtggcg cagctttctg tactccaatg tcgccctgta   3660
cttgccagat tcctacaaat acactcccga caatattgaa cttcctacaa acaagaacag   3720
ctacggctac attaacggaa gggtaaccgc ccccactgcc atcgacactt acgttaacat   3780
cggcgcccgg tggtctccgg accccatgga caacgttaac cctttcaacc accaccgcaa   3840
cgccggcttg cgataccgct ccatgctgct gggcaacggt cgctacgtac ccttccacat   3900
tcaggtgccc cagaaatttt ttgccattaa aaacctgctt ctgcttcccg ggtcctacac   3960
ctacgagtgg aacttcagga aagatgtaaa catgatcttg cagagcacct tgggcaacga   4020
cctccgcgtt gacggagcta gcgtgaggtt tgacagcatt aacctctacg ctaacttctt   4080
ccccatggcc cacaacacgg cctccacctt ggaagccatg ctgcgcaacg acaccaacga   4140
ccagtccttt aatgattacc tgtgcgcggc caacatgctg taccccatcc ccgccaatgc   4200
caccagcgtg ccgatctcca ttccctcacg caactgggcc gccttcagag gttggagttt   4260
cactcgcctg aaaaccaagg agacccccctc gctgggctcc ggtttcgacc catactttgt   4320
ttactccggg agcattccct acctggacgg aactttctac ctgaaccaca ccttcaaaaa   4380
ggtgtctatt atgtttgact cctccgtgag ctggcccggt aacgaccgct tgctaacccc   4440
caacgagttc gaaatcaaac gctcggtgga cggagagggt tacaatgtag cccagagcaa   4500
catgaccaaa gactggtttt taattcaaat gctaagccac tataacattg gctaccaagg   4560
attctacgtg cctgaagcct acaaggacag aatgtactcc ttctttagaa acttccaacc   4620
catgagccgc caggtagtag acacggtaaa ctatgctaac tacaaggaag taacaatgcc   4680
attccagcac aacaactcag gcttcgtggg gtacatggga cctaccatga gagaggggca   4740
```

ggcctacccg gctaattatc cctacccccct aatcggagcc actgccgtgc ccagcctgac 4800
acagaaaaag tttctctgcg atcgaacaat gtggaggatt cccttctcta gcaacttcat 4860
gtccatgggg gctctcaccg acctggggca gaacatgctg tacgctaact ccgctcacgc 4920
cttggacatg acctttgagg tggaccccat ggatgagccc acgcttctct atgttctgtt 4980
tgaagtcttc gacgtggtgc gcattcacca gccgcaccgc ggcgtcatcg aggccgtcta 5040
cctgcgcaca cctttctctg ccggtaacgc caccacctaa gaagctgatg ggctccagcg 5100
aacaggagct gcgggccatt gttcgcgacc tgggctgcgg gccctacttt ttgggcacct 5160
tcgacaagcg cttccccggc ttcatgtccc cccacaagcc ggcctgcgcc atcgtcaaca 5220
cggccggacg cgagaccggg ggggttcact ggctcgcctt tgcctggaac ccgcgtaacc 5280
acacctgcta cctgttcgac cctttttggtt tttctgacga aaggcttaaa cagatttacc 5340
agttcgagta cgaggggctc cttaaacgca gcgctctggc ctccacgccc gaccactgcg 5400
tcaccctgga gaagtccacc caaacggttc agggtcccct ctcggcggcc tgcggactct 5460
tttgttgcat gtttttgcat gctttcgtcc actggccgaa cacccccatg gaccgcaacc 5520
ccactatgga tctgctcacg ggagtgccta acagcatgct tcacagccct caggtcgcac 5580
ccaccctgcg tcgcaatcag gaacagctgt atgcttttct gggaaaacat tctgcctact 5640
ttcgccgcca ccggcagcgc atagaacagg ccacggcctt tgaaagcatg agtcaaagag 5700
tgtaatcaat aaaatcaact tttattttac atcacacgcg cttctggcgt tttcttaaaa 5760
atcaaagggt tcgggggagg ggtcgtcgtg cccgctgggc agggacacgt tgcgatactg 5820
gaagcggggg ctccagcgga actcggggat cgccagccgg ggcagaggca cttcttccag 5880
gttctgcttc caaaactgcc gcaccagctg gagggctccc attacgtcgg gcgccgagat 5940
cttgaagtcg cagttggggc ccgagcttcc gcggctgttg cgaaacacgg ggttggcaca 6000
ctggaacacc agcacgctcg ggtagttgat actggccagg gccgttgcgt cggtcaccgc 6060
cgttacatcc agatcctccg cgttggtcag ggcgaaggga gtcagcttgc acatctgccg 6120
cccgatgtgg ggcacgccgt catgcttgtt gaggcagtcg caacgcaggg gaatcagaat 6180
gcgatgctgg ccgcgttgca tctgagggta gttggcccgc aagaacgctt ccatctgacg 6240
gaaggccgtc tgggctttca ttccctcggt gtagaaaaga ccgcaggact tgctagaaaa 6300
tacattattg ccgcaggtga cgtcttccgc gcagcagcgg gcgtcttcgt tctttagctg 6360
caccacgttg cgaccccacc ggttctgtac caccttggcc ctcgtgggct gctccttcag 6420
cgcccgctgg ccgttttcgc tggtcacatc catttccaac acgtgctcct tacacaccat 6480
ttccactccg tggaagcaga acaggacgcc ctcctgctgg gtattgcgat gctcccacac 6540
ggcgcagcct gtggcctccc agctcttatg cttcaccccc gcgtagtttt ccatgtaagc 6600
catcaggaat ctgcccatca tctcggtaaa ggttttctga ctggtgaagg tcaaaggcaa 6660
gccgcggtgc tcttcgttca gccacgtttg acagatcttg cggtacgtgg cgccctgatc 6720
cggcagaaac ttaaacgccc ccttgctctc gttgtccacg tggaactttt ccatcagcat 6780
tagcataact tccataccct tctcccacgc cgtcaccagc ggtgtgctgt cggggttctt 6840
caccaacatg gtagaagggc cctcgccggc cctgaagtcg ctcatactca ttttttgaaa 6900
ctccacagtg ccgtccgcac gacggacccg gcgcatcgga gggtagctga agccaacctc 6960
caccagggtg ccttcgctct cgctgtcgga gacgatctcc ggggagggcg gcggcgcggg 7020
tgtcgacttg cgagccttct tcttgggagg aagcggtggc gcctcttggt cgcgctcggg 7080
actcatctcc ctcaagtagg gggtgatgga gcttcctgct tggttctgac ggttggccat 7140
tgtatcctag gcagaaacac atggagctta tgcgcgagga aactttaacc gccccgtccc 7200
ccgtcaacga cgaagaggtc atcatcgaac aggacccggg ctacgttact ccgcccgagg 7260
atctggaggg gcctttagac gaccggcgcg acgctagtga gcagcaggaa aatgagaaag 7320
aggaagcctg ctacctcctg gaaggcgacg tgttgctaaa acatttcgcc aggcagagca 7380
ccatagtgaa ggaggctttg caagaccgct cggaggtgcc cttggacgtc gccgcgctct 7440
cccaggccta cgaggcgaac ctcttctcgc cccgagtgcc tccgaagaga cagcccaacg 7500
gcacctgcga gcccaacccg cgccttaact tctaccccgt gttcgccgtg cccgaggcgc 7560
tggccaccta ccacattttt ttcaagaacc agcgcatccc gctctcgtgc cgggccaacc 7620
gcaccgcggc cgatagaaag ctgagactca aaaacggagc tagcatacct gatatcacgt 7680
ccctggagga agtgcctaag atcttcgaag gtctgggtcg agacgagaaa cgggcggcaa 7740
acgctctgca gaaagaacag aaggacagtc agaacgtgct ggtggaactg gagggggaca 7800
atgcgcgtct ggccgttctc aagcgctgca tagaagtttc ccacttcgcc taccctgccc 7860
tgaacctgcc gcccaaagtc atgcgctcgg tcatggacca gctgctcatc aagagagctg 7920
agcccctgaa ccccgagcac cccgaggcgg agaactcgga ggacggaaag cccgtcgtca 7980
gcgacgagga gctcgagcgg tggctggaca gcacggaccc cgagcagttg caagagcggc 8040
gcaaaatgat gatggcggcc gtcctggtca ccgttgagct ggagtgcctg cagcggtttt 8100
ttagcgacgt ggaaacgctg cgtaaaatcg gagagtccct gcactacacc ttccgccagg 8160
gctacgtccg ccaggcctgc aagatctcca acgtggagct cagcaacctg gtctcctaca 8220
tgggcatcct ccacgagaac cggctgggac agagcgtgct gcactgcacc ttgcaaggcg 8280
aggcgcggcg ggactacgtg cgagactgcg tctacctctt cctcactctc acctggcaga 8340
ccgccatggg agtgtggcag cagtgcttgg aagacagaaa cctcaaagag ctagacaaac 8400
tcctctgccg ccagcggcgc gccctgtggt ccggtttcag cgagcgcacg gtcgccagcg 8460
ctctggcgga catcatcttc ccggagcgcc tgatgaaaac cttgcaaaac ggcctgccgg 8520
atttcatcag tcaaagcatt ttgcaaaact tccgctcttt tgtcctggaa cgctccggga 8580
tattgcccgc catgagctgc gcgctacctt ctgactttgt cccccctctcc taccgcgagt 8640 gccctccccc actgtggagc cactgctacc tcttccaact ggccaacttt ctggcctacc 8700
actccgacct catggaagac gtaagcggag agggtttact ggagtgccac tgccgctgca 8760
acctgtgcac cccccacaga tcgctggcct gcaacaccga gctactcagc gaaacccagg 8820
tcataggtac cttcgagatc caggggcccc agcagcaaga gggtgcttcc ggcttgaagc 8880
tcactccggc gctgtggacc tcggcttact tacgcaaatt tgtagccgag gactaccacg 8940
cccacaaaat tcagttttac gaagaccaat ctcgaccacc gaaagccccc ctcacggcct 9000
gcgtcatcac ccagagcaag atcctggccc aattgcaatc catcaaccaa gcgcgccgcg 9060
atttcctttt gaaaaagggt cggggggtgt acctggaccc ccagaccggc gaggaactca 9120
acccgtccac actctccgtc gaagcagccc ccccgagaca tgccgcccaa gggaaccgcc 9180
aagcagctga tcgctcggca gagagcgaag aagcaagagc tgctccagca gcaggtggag 9240
gacgaggaag agatgtggga cagccaggca gaggaggtgt cagaggacga ggaggagatg 9300
gaaagctggg acagcctaga cgaggaggag gacgagcttt cagaggaaga ggcgaccgaa 9360
gaaaaaccac ctgcatccag cgcgccttct ctgagccgac agccgaagcc ccggccccccg 9420 acgcccccgg ccggctcact caaagccagc cgtaggtggg acgccaccga atctccagcg 9480

```
gcagcggcaa cggcagcggg taaggccaaa cgcgagcggc gggggtattg ctcctggcgg   9540
gcccacaaaa gcagtattgt gaactgcttg caacactgcg ggggaaacat ctcctttgcc   9600
cgacgctacc tcctcttcca tcacggtgtg gccttccctc gcaacgttct ctattattac   9660
cgtcatctct acagccccta cgaaacgctc ggagaaaaaa gctaaggcct cctccgccgc   9720
gaggaaaaac tccgccgccg ctgccgccgc caaggatcca ccggccaccg aagagctgag   9780
aaagcgcatc tttcccactc tgtatgctat ctttcagcaa agccgcgggc agcaccctca   9840
gcgcgaactg aaaataaaaa accgctcctt ccgctcgctc acccgcagct gtctgtacca   9900
caagagagaa gaccagctgc agcgcaccct ggacgacgcc gaagcactgt tcagcaaata   9960
ctgctcagcg tctcttaaag actaaaagac ccgcgctttt tccccctcgg ccgccaaaac  10020
ccacgtcatc gccagcatga gcaaggagat tcccaccccc tacatgtgga gctatcagcc  10080
ccagatgggc ctggccgcgg gggccgccca ggactactcc agcaagatga actggctcag  10140
cgccggcccc cacatgatct cacgagttaa cggcatccga gcccaccgaa accagattct  10200
cttagaacag gcggcaatca ccgccacacc ccggcgccaa ctcaacccgc ctagttggcc  10260
cgccgcccag gtgtatcagg aaaatccccg cccgaccaca gtcctcctgc cacgcgacgc  10320
ggaggccgaa gtcctcatga ctaactctgg ggtacaatta gcgggcgggt ccaggtacgc  10380
caggtacaga ggtcgggccg ctccttactc tcccgggagt ataaagaggg tgatcattcg  10440
aggccgaggt atccagctca acgacgagac ggtgagctcc tcaaccggtc tcagacctga  10500
cggagtcttc cagctcggag gagcaggccg ctcttccttc accactcgcc aggcctacct  10560
gaccctgcag agctcttcct cgcagccgcg ctccgggggga atcggcactc tccagttcgt  10620
ggaagagttc gttccctccg tctacttcaa cccctctcc ggctcgcctg gacgctaccc  10680
ggacgccttc attcccaact ttgacgcagt gagtgaatcc gtggacggct acgactgatg  10740
acagatggtg cggccgtgag agctcggctg cgacatctgc atcactgccg tcagcctcgc  10800
tgctacgctc gggaggcgat cgtgttcagc tactttgagc tgccggacga gcaccctcag  10860
ggtccggctc acgggttgaa actcgagatc gagaacgcgc tcgagtctcg cctcatcgac  10920
accttcaccg cccgacctct cctggtagaa atccaacggg ggatcactac catcaccctg  10980
ttctgcatct gccccacgcc cggattacat gaagatctgt gttgtcatct ttgcgctcag  11040
tttaataaaa actgaacttt ttgccgcacc ttcaacgcca cgcgttgttt ctccaacagt  11100
cgacgatagc tcttcaatta aaggtacccg agaaactgtt tattttgaca attctactac  11160
ttctcttatc cttaactgtt cttgcacact agtgaggggg ctatcctgtg tcactgtcac  11220
gcgcctgatt gtatgcccaa actaatcaga actctttgtg ctttaggtga tatatttaaa  11280
atatagatag tatcaataaa cttaccttaa atttgacagc aattttttgg tatcatcatt  11340
cagcagcacc actttaccct cttcccaact ctcatatggg atatgatggt gggcggcaaa  11400
cttcctccaa accctgaaag aaatatcggt atccacttcc ttgtcctcac ccacaatttt  11460
catcttttca tagatgaaaa gaacccgagt tgatgaagac ttcaaccccg tctaccctta  11520
tgacaccaca accactccag ccgttccttt catatcaccc ccgtttgtaa acagtgacgg  11580
tcttcaggaa aacccccccg gagttttaag cctgcgaata gctaaacccc tgtattttga  11640
catggagaga aaactagccc tttcacttgg aagagggtta acaattaccg cgaacggaca  11700
attagaaagc acccagagcg tgcagactaa cccgccgtta actgtcacca ataacaacac  11760
acttatccta cgccactcct cccctttaat cctaactgac aataatttaa ccgtaggctt  11820
ctcaagtcct ctccgtgtta tagacaacaa actgacattc acttttacct cacctctccg  11880
```

-continued

```
ttatgaaaac gaaaccctta ccttcaatta cacagagccc cttacactta tgaacagcaa  11940
ccttgcgctt aacgtaaact cctctaaagg ccttagggtt gacgggggct cactaggtac  12000
aaacttaagt ccggacttaa ggtttaacag cagtggagcc atagcttttg gtatacaaac  12060
cctatggaca cccccgacct caaatcctaa ctgcaccgtt tacaccgaaa gcgattcctt  12120
acttagtctc tgcttaacta aatgcggagc tcacgtttta ggaagtgtaa gcttaaccgg  12180
ggtagcaggt accatgataa acatggctga aacttcgctt gctattgaat ttacgtttga  12240
cgacactgga aaactacttc actcaccact tgttaacacc acttttagca ttcgtcaggg  12300
cgacagcccc gcctcaaatc ctacctacaa tgctctagca tttatgccaa acagtaccct  12360
ctacgctaga ggaggaagtg gtgaaccccg aaacaattac tacgtccaaa catacctcag  12420
gggaaatgtt cagagaccga ttaccctcac tgttactttc aactcagccg ccacgggata  12480
ttccttatct tttaagtgga ctgctgttgc acgtgaaaaa tttgcagctc ctgcaacttc  12540
attttgctac attaccgaac aataaaaccc tgtgttccca ccgtttcgtt ttttccagat  12600
gaaacgggcc agagttgatg aagacttcaa tcccgtgtac ccttacgatc cccccttacgc  12660
ccccattatg ccgtttatta ccccgccgtt tacatcttca gatgggttac aggaaaaacc  12720
acttggtgtt ttaagtttaa aatacaagga tcctatcact acacaaaatg gttctctaac  12780
ccttaaatta ggaaacgggc tgaacattaa caaccagggc caacttacat catctgctgg  12840
ggaagtcgag cctcccctca ccaatgctga caacaagctg gccttagcct acagcgaccc  12900
tctgacatta aaaaacagcc gtctaacact gtctcacaat gccccacttg caattaacaa  12960
taattctcta agtttggaag tatcagagcc tatatttata aataacgaca acaaactgtc  13020
tctgaaagct gacgcccccc tgacaaccag cgctggaacc ctccgcctgc aaagcgctgc  13080
tccattagga cttgctgaac agacactaaa gctgctgttt tctaaccctt tgtacttgcg  13140
aggtgacttc cttacattag ccattgaacg cccattggct gtaacagcag acgggctatt  13200
atcacttgcc ctcaaccctc cgctcacaac aactaacaca ggcttagctc tctctaccgc  13260
ggttccatta actgttacca acgggaacct tagcctaaac gtaaaacggc cgtttattat  13320
acaggacggc agcctttaca tggattttag acccccacta tatctgttta acagcgagcc  13380
acaacttggt gttaatttta atgcccctct aactgttaga gataacggcc tagctataaa  13440
caccggagac gggctaacag taacgtataa taaactaaca ttaaacctcg gtagagactt  13500
gcaatatgaa aatggagctg cagctgttaa gctaagtacc gcccctcctc tacagtatac  13560
tactcaactg cagctgaatt tgggagcggg cttacgtcta ggtcctacta ggaacttaga  13620
cgtggccatt aaccacaata aagggttagc gtgggaaaac aatgaagtgg ttactaaatt  13680
aggacaaggc ctttactttg attcctccgg aagcatagct ttatcgccta caaaccccag  13740
accagatact ttatggacca cggccgatcc ttcgccaaac tgcactgtat atgaatcact  13800
tgactctaga ctgtggctag cgcttgttaa atgtgggga atggtacacg gcagcatagc  13860
cctacaagct gaaaaaggcc aattgctgcg tcctactgct agttttatct ccatcgtaat  13920
ttacttctac agtgatgggg tccgtcgcac caactaccct acaattggca atgatgaggg  13980
tactctggcc aacagcgcta cttggggcta cagacaaggg caatctgcag acaccaacgt  14040
caccaatgct gttgaattca tgcctagttt acacagatat cctataaatc agggagacaa  14100
tattaaaaac caaatgataa cttacacttg catacaaggc aacgtgaaca tgccagtacc  14160
cttgaaaatc acgttcaatc atgctcttga aggctactcc ttaaagttta catggcgtgt  14220
```

```
ggtggctaat gaaaagtttg atattccttg ctgttcgttt tcttacatta cagaacaata  14280
aaacaacttt tttatttttc atttctttta ttttacacgc acagtaagac ttcctccccc  14340
cttccattta acagcgtaca ccagcctttc cccccttcatg gcggtaaact tctgtgagtt  14400
agtccggtat ttgggagtta aaatccaaac aggctctttg gtgattaaac gttgatccgt  14460
gatggacaca aatccctgag acaggtcctc caacgttgcg gtaaaaaact gaacgccgcc  14520
ctacaaaaca aacagttcag gctctccacg ggttatcacc ccgatcaaac tcagacagag  14580
taaaggtgcg gtgatgttcc acaagaccgc gcaagtggcg ctgtctaaag ctctcagtgc  14640
gacttctatg cggctggtag gatgttacat tatccaacag cctcacagcg cggattatta  14700
gtctacgagt gcgcctggcg cagcagcgca tctgaatttc agtcaagtct tgacaagaag  14760
cgcataccat aacaatcagg ttgttcatga tcccatagct aaacgcgctc cagccaaaac  14820
tcattcgctc caacagcacc accgcgtgtc cgtcaagtct tacttttaca taaacaaggt  14880
gtctgccacg tacatacatg ctacccgcat acaaaacttc ccggggcaaa cctctattca  14940
ccacctgtct gtaccaggga aacctgatgt ttatcaggga accatagatg gccattttaa  15000
accagttagc cagcaccacc ccgccagctc tacactgaag ggaaccggga gagttacaat  15060
gacagtggat catccacctc tcgtaacccc taattacctg attaaaatcc aaatctaacg  15120
tggcacaaca gatacacact ctcataaaca ttttcatgac atgtttttcc caggatgtta  15180
aaatacaatc ccaatacacg ggccactcct gtaatacaat aaagctaatg catgatggaa  15240
cgctcctcac ctcactaaca ttgtgcatgt ttacattttc acactctaag taccgagtcc  15300
tctcctcaac agccgcagtg tcgcgctcct cacacggtgg tagctgatga caattgtaag  15360
gggccagtct gcagcgatat cgtctgtcgc gctgcatcgt aaaacaggga ccgtctcact  15420
tcctcgtact tccaatagca gaacccgccc cgtcttaccg cgtaaaaagc cagaaaaatc  15480
cagctaacta cactctacag cctattacta tatatactct cctcccactg acgctatacc  15540
accccgccca cgtccaaagt tcacccacgc ccaaaaaacc cgcgaaaatc cagcgccgtc  15600
agcacttccg caattgtagt ctctcaacgt cacttccgcg cgccttttcc ctattcccac  15660
acacgcccgc ggacttcgcc ccgcccgccc tcgcgccacc ccgcgtcacc ccgcgtcacc  15720
gcacgtcacc ccggccccgc ctcgctcctc cccactcatt atcatattgg cacgtttcca  15780
gaataaggta tattattgat gatgttaatt aattcgaacc cataataccc ataatagctg  15840
tttgccatcg acgcgaggct ggatggcctt ccccattatg attcttctcg cttccggcgg  15900
catcgggatg cccgcgttgc aggccatgct gtccaggcag gtagatgacg accatcaggg  15960
acagcttcaa ggatcgctcg cggctcttac cagcccagca aaaggccagg aaccgtaaaa  16020
aggccgcgtt gctggcgttt ttccataggc tccgcccccc tgacgagcat cacaaaaatc  16080
gacgctcaag tcagaggtgg cgaaacccga caggactata aagataccag gcgtttcccc  16140
ctggaagctc cctcgtgcgc tctcctgttc cgaccctgcc gcttaccgga tacctgtccg  16200
cctttctccc ttcgggaagc gtggcgcttt ctcatagctc acgctgtagg tatctcagtt  16260
cggtgtaggt cgttcgctcc aagctgggct gtgtgcacga accccccgtt cagcccgacc  16320
gctgcgcctt atccggtaac tatcgtcttg agtccaaccc ggtaagacac gacttatcgc  16380
cactggcagc agccactggt aacaggatta gcagagcgag gtatgtaggc ggtgctacag  16440
agttcttgaa gtggtggcct aactacggct acactagaag gacagtattt ggtatctgcg  16500
ctctgctgaa gccagttacc ttcggaaaaa gagttggtag ctcttgatcc ggcaaacaaa  16560
ccaccgctgg tagcggtggt ttttttgttt gcaagcagca gattacgcgc agaaaaaaag  16620
```

```
gatctcaaga agatcctttg atcttttcta cggggtctga cgctcagtgg aacgaaaact  16680
cacgttaagg gattttggtc atgagattat caaaaaggat cttcacctag atccttttaa  16740
attaaaaatg aagttttaaa tcaatctaaa gtatatatga gtaaacttgg tctgacagtt  16800
accaatgctt aatcagtgag gcacctatct cagcgatctg tctatttcgt tcatccatag  16860
ttgcctgact ccccgtcgtg tagataacta cgatacggga gggcttacca tctggcccca  16920
gtgctgcaat gataccgcga gacccacgct caccggctcc agatttatca gcaataaacc  16980
agccagccgg aagggccgag cgcagaagtg gtcctgcaac tttatccgcc tccatccagt  17040
ctattaattg ttgccgggaa gctagagtaa gtagttcgcc agttaatagt ttgcgcaacg  17100
ttgttgccat tgctgcaggc atcgtggtgt cacgctcgtc gtttggtatg gcttcattca  17160
gctccggttc ccaacgatca aggcgagtta catgatcccc catgttgtgc aaaaaagcgg  17220
ttagctcctt cggtcctccg atcgttgtca gaagtaagtt ggccgcagtg ttatcactca  17280
tggttatggc agcactgcat aattctctta ctgtcatgcc atccgtaaga tgcttttctg  17340
tgactggtga gtactcaacc aagtcattct gagaatagtg tatgcggcga ccgagttgct  17400
cttgcccggc gtcaacacgg gataataccg cgccacatag cagaacttta aaagtgctca  17460
tcattggaaa acgttcttcg gggcgaaaac tctcaaggat cttaccgctg ttgagatcca  17520
gttcgatgta acccactcgt gcacccaact gatcttcagc atcttttact ttcaccagcg  17580
tttctgggtg agcaaaaaca ggaaggcaaa atgccgcaaa aaagggaata agggcgacac  17640
ggaaatgttg aatactcata ctcttccttt ttcaatatta ttgaagcatt tatcagggtt  17700
attgtctcat gagcggatac atatttgaat gtatttagaa aaataaacaa ataggggttc  17760
cgcgcacatt tccccgaaaa gtgccacctg acgtctaaga aaccattatt atcatgacat  17820
taacctataa aaataggcgt atcacgaggc cctttcgtct tcaagaattg gtcgatggca  17880
aacagctatt atgggtatta tgggttcgaa ttaat                             17915
```

<210> SEQ ID NO 51
<211> LENGTH: 8865
<212> TYPE: DNA
<213> ORGANISM: Artificial Sequence
<220> FEATURE:
<223> OTHER INFORMATION: Synthetic oligonucleotide
sAdApt4312.E1btg.Empty

<400> SEQUENCE: 51

```
attaacatca tcaataaagg gtcaggatgg gtgggcacag gtattgtcga ctggtcaata     60
ttggccattg agcgaggcgg ggccggggtg gggtgaggcg gggccggggt ggggtgaggg    120
tgacgtcggg gcgggcgggg cggccgacgt gtgtggggag gcgcgtagtg tttacgtatg    180
cggaaggagg ttttataccg gaagatgggt aatttgggcg tatacttgta agttttgtgt    240
aatttggcgc gaaaactggg taatgaggaa gttgaggtta atatgtactt tttatgactg    300
ggcggaattt ctgctgttca gcagtgaact ttgggcgctg acggggaggt ttcgctacgt    360
ggcagtacca cgagaaggct caaaggtccc atttattgta ctcctcagcg ttttcgccgg    420
gtatttaaac gctgtcagat catcaagagg ccactcttga gtgctggcga gtagagtttt    480
ctcctccgcg ctgccacaat gaggctggtc cccgagatgt ttggtgtttt ttgcgacgag    540
gcggcgcgga actcagatga cctgctgaat tcagatttgc tggaaattcc caattcgcct    600
gtggcttcgc ctccgtcact tcacgacctt ttcgatgtgg aagtggatcc tccggcagat    660
cccaacgagg acgcggtaaa tagtatgttt cccgaatgtc tgttcgaggc ggctgacgag    720
```

ggtagcgaca gcggtggaga gagtggacag ggtgaggaac tggacttaaa atgctacgag 780
gaatgcatac cgtctagcga ttctgaaacg gaacaaacag ggggagatgg ctgcgctgag 840
ccaactgaga aaaatgaact tatattagac tgtcctgaac atcctggtca tggctgccgt 900
gcctgtgctt ttcatagaga tgccagtgga aatcctgaaa ctctatgtgc tctgtgttac 960
ctgcgtctta ccggcaattt tgtatacagt aagtaggttt tttactttgt gtacggtagg 1020
gaagtttttg taaagtgtgt tatgacttat tgcttgtgta atgttttaca ggtgacgtgt 1080
ctgatgtgga ggagggagat aagtcagtcc atactagttc tccttgcact ttgggggctg 1140
tggttccaga taatgttatt aaacccgtgg cggtcagagt atcaggcagg cggtgtgcag 1200
tcgaaaaaat tgaagacttg ctgcaggaag agcagatgca acctttggac ctgtccctca 1260
aacgccctaa gatgacctaa gcctgtttat tgagtgcaat aaaactgttg atctttgaac 1320
tgtgtttatg tgttgggtgt gtctgtggat atataagcag gtggatggga agtgagagca 1380
catctgcctt gatggatctg ttggggaact tgcgggaatt tgacgtggtt cgtcgcttgc 1440
tggagttggc ctccgacaaa acttccaggc tttggaggtt ttggtttggc tcaacgctta 1500
gcagcgtagt gtacagggtc aagaaggagc aggaggggca attttctagg ctgttggctg 1560
atattcctgg agtttttgtg gctctggatt taggccatca cagtcttttt caagagaaaa 1620
ttgtcaaaag cttaactttc tcgtctcctg gccgcacggt tgtttcagca gcctttatta 1680
cctatatttt ggatcaatgg agcagcagcg gcagccacct gtcgtgggat tacatgctgg 1740
attacctggc aatggccctg tggagggcca tgctgcggag gagggtttgc atttactcgc 1800
gggcgcagcc tccgcggctg gatcgagtgg tggaggagga cgagccggac gagaccgaga 1860
acctgagagc cggcctggac cctccaatgg aagactaggt gcagaggata atcctgaaga 1920
gggaactagt gggggtgcta gaaaaaagca aaaaaccgag actgagccta gaaacttttt 1980
gaatgagctg actgtgagtt tgatgaatcg ccatcgtccc gagacaattt tctggtctga 2040
gttggaggaa gagtttagga agggggattt gaacctgctg tacaagtatg ggttcgaaca 2100
gttgaagact cactggttgg agccgtggga ggattttgaa accgctctgg acactttgc 2160
taaagtggct ttgcggccgg ataaagttta tactatccgc tgcactgtta atataaggaa 2220
aagtgtttat gttataggcc atggagcact ggtgcaggtg gagaccgccg atcgggtggc 2280
tttcaactgc ggcatgcaga atctgggccc tggggtgata ggtgttaatg gtgtcacgtt 2340
tcagaacgtg aggttcgcgg gtgaaagctt tagcggctcc gtgtttgcaa ataacacaca 2400
gctcactctc cacggcgttt actttttaa ctttaacaat acatgtgtgg agtcgtgggg 2460
cagggcgtcc ttgaggggct gcacttttca cggttgctgg aaggcggtgg tgggaagact 2520
gaaaagtgta acgtctgtga aaaaatgcat attcgagcgg tgtgtgctag ctgtaaccgt 2580
ggaagggcat ggacgcatta gaaacaacgc agcgtctgag aatgggtgtt ttcttttact 2640
gaaaggcacg gccagcgtta agcataacat gatctgtggc agtgggctgt acccgtcgca 2700
gttgttaacc tgcgcggatg gaaactgcca gacattgcgc accgtgcaca tagtgtctca 2760
cccgcgtcgc cactggccaa cgtttgagca caacttgctt atgcgttgta cggtccatct 2820
ggggcctaga cggggcatgt ttgtgccttt tcagtgtaac tttagccaca ctaagatctt 2880
actagaagca gatgccttca ctcgagtgtg tttcaatggg gtgtttgaca tgtcggtgga 2940
aatttttaaa gtgataagat atgatgaatc caagtctcgt tgtcgcccct gtgaatgcgg 3000
agctaatcat ttgaggttgt atcccgcgac cctgaacgta accgaggagc tgagggccga 3060

-continued

```
ccaccacatg ttgtcctgct tgcgcaccga ctatgagtcc agcgacgaag agtgaggtga   3120
ggggcggagc cacaaagggt ataaagggtc aggatgggtg ggcacaggta ttgtcgactg   3180
gtcaatattg gccattagcc atattattca ttggttatat agcataaatc aatattggct   3240
attggccatt gcatacgttg tatccatatc ataatatgta catttatatt ggctcatgtc   3300
caacattacc gccatgttga cattgattat tgactagtta ttaatagtaa tcaattacgg   3360
ggtcattagt tcatagccca tatatggagt tccgcgttac ataacttacg gtaaatggcc   3420
cgcctggctg accgcccaac gacccccgcc cattgacgtc aataatgacg tatgttccca   3480
tagtaacgcc aatagggact ttccattgac gtcaatgggt ggagtattta cggtaaactg   3540
cccacttggc agtacatcaa gtgtatcata tgccaagtac gccccctatt gacgtcaatg   3600
acggtaaatg gcccgcctgg cattatgccc agtacatgac cttatgggac tttcctactt   3660
ggcagtacat ctacgtatta gtcatcgcta ttaccatggt gatgcggttt tggcagtaca   3720
tcaatgggcg tggatagcgg tttgactcac ggggatttcc aagtctccac cccattgacg   3780
tcaatgggag tttgttttgg caccaaaatc aacgggactt tccaaaatgt cgtaacaact   3840
ccgccccatt gacgcaaatg ggcggtaggc gtgtacggtg ggaggtctat ataagcagag   3900
ctcgtttagt gaaccgtcag atcgcctgga gacgccatcc acgctgtttt gacctccata   3960
gaagacaccg ggaccgatcc agcctccgcg gccgggaacg gtgcattgga agcttggtac   4020
cggtgaattc gctagcgtta acggatcctc tagacgagat ccgaacttgt ttattgcagc   4080
ttataatggt tacaaataaa gcaatagcat cacaaatttc acaaataaag catttttttc   4140
actgcattct agttgtggtt tgtccaaact catcaatgta tcttatcatg tctagatcct   4200
taaggtgata agatatgatg aatccaagtc tcgttgtcgc ccctgtgaat gcggagctaa   4260
tcatttgagg ttgtatcccg cgaccctgaa cgtaaccgag gagctgaggg ccgaccacca   4320
catgttgtcc tgcttgcgca ccgactatga gtccagcgac gaagagtgag gtgaggggcg   4380
gagccacaaa gggtataaag ggtcaggatg ggtgggcaca ggtattcaaa atgagcggga   4440
cgacggacgg caacgcgttt gaggggggag tgttcagccc atatctgaca tctcgtcttc   4500
cttcctgggc aggagtgcgt cagaatgtag tgggctccac cgtggacgga cggccggtcg   4560
cccctgcgaa ttccgccacc cttacctatg ccaccgtggg atcaccgttg gacactgccg   4620
cggcagccgc agcttctgct gccgcttcta ctgctcgcgg tatggcggct gactttggac   4680
tttataacca actggctacc gcggctgtgg catctcgcac tctggttcaa gaagatgccc   4740
tgagcgtggt tctgcttcga ctggaagatc tgtctcgtcg cttggatcag ctggctgcgc   4800
agatatcccc acctaacccc gatactactc aagaatctta aataaagaca aacagatttg   4860
ttgaaaataa atggctttat ttgttttttt tggctcgata ggctcgggtc cacctgtccc   4920
ggtcgttaag gactttgtgt atgctttcca agacccggta cagatgggct tggatgttta   4980
gatacatggg catgaggcca tcccgggggt ggagatagga ccattgcaga gcgtcatgct   5040
ccggggtggt gttgtagatg acccagtcgt agcagggttt ttgggcgtgg aactgaaaaa   5100
tgtccttgag aagcaggctg atggccaggg gcagaccctt agtgtaggtg ttcacaaagc   5160
ggttgagctg ggagggatgc atgcggggag agatgatatg catcttagcc tggattttca   5220
ggttagctat gttgcccccc aggtcccttc gagggttcat attgtggagg accaccagaa   5280
cggtgtagcc ggtacacttg ggaaacttat cgtgcagttt ggaggggaag gcgtgaaaga   5340
atttggaaac ccctttgtga ccacctaagt tttccatgca ctcgtccatg ataatggcga   5400
tgggcccctt ggcggcagct ttagcgaaca cgttgtgggg gttggaaaca tcatagtttt   5460
```

```
gctctagagt tagctcgtca taggccattt ttacgaagcg gggtaggagg gtgccagact   5520
gagggacgat agttccatct ggccccggtg cgtaattacc ctcgcagatc tgcatctccc   5580
aagctttaat ttccgaggga gggatcatgt ccacctgggg ggcgataaag aacacggttt   5640
ctggcggggg attaatgagc tgggtggaaa gcaggttgcg caagagctga gacttgccgc   5700
aaccggtggg accgtagatg accccgatga cgggctgcag ctggtagttg agagaggagc   5760
agctgccgtc ggggcgtagg aggggagcca cctcgttcat catgcttctt acatgtttat   5820
tttcactgac taagctttgc aagagcctct ccccacccag ggacaagagt tcttccaggc   5880
tgttgaagtg tttcagcggt ttcaggccgt cggccatggg catcttttca agcgactgac   5940
gaagcaagta cagccggtcc cagagctcgg tgacgtgctc tatggaatct cgatccagca   6000
gacttcttgg ttgcgggggt tgggccgact ttcgctgtag ggtacgagcc ggtgggcgtc   6060
cagggccgcg agggttttgt ccttccaggg tctcagcgtc cgggtgaggg tggtctcggt   6120
gacggtgaac ggatgagccc cgggctgggc gcttgccagg gtgcgcttca ggctcatccg   6180
gctggtgctg aagcgggcgt cgtctccctg ggaatcggcc agatagcaac ggagcatgag   6240
gtcgtagcta agggattcgg ccgcgtgtcc cttggcgcgc agttttccct tggaaacatg   6300
ctggcatctg gtgcagtgta aacacttgag ggcgtacagc ttgggggcga ggaagacgga   6360
ctcgggcgag taggcgtcgg ccccgcactc ggcgcagacg gtttcacact ccaccagcca   6420
cgtgagctcg ggtttgtcgg ggtcaaaaac caggttgcct ccattttttt tgatgcgttt   6480
cttaccttgc gtctccatga gcctgtgacc cgcttcggtg acaaaaaggc tgtctgtgtc   6540
tccgtagacc gacttgaggg ggcgttcttc caagggcgtg ccgcggtctt ctgcgtacaa   6600
aaactgggac cactccgaaa cgaaggccct ggtccacgct aacacgaagg atgcgatctg   6660
cgaggggtat ctgtcgttct caatgagggg atccaccttt tccagggtat gcagacacag   6720
gtcgtcctcc tccgcgtcca caaaggtgat tggcttgtaa gtgtaggtca cgtgacttaa   6780
ttaattcgaa cccataatac ccataatagc tgtttgccat cgacgcgagg ctggatggcc   6840
ttccccatta tgattcttct cgcttccggc ggcatcggga tgcccgcgtt gcaggccatg   6900
ctgtccaggc aggtagatga cgaccatcag ggacagcttc aaggccagca aaaggccagg   6960
aaccgtaaaa aggccgcgtt gctggcgttt ttccataggc tccgcccccc tgacgagcat   7020
cacaaaaatc gacgctcaag tcagaggtgg cgaaacccga caggactata aagataccag   7080
gcgtttcccc ctggaagctc cctcgtgcgc tctcctgttc cgaccctgcc gcttaccgga   7140
tacctgtccg cctttctccc ttcgggaagc gtggcgcttt ctcatagctc acgctgtagg   7200
tatctcagtt cggtgtaggt cgttcgctcc aagctgggct gtgtgcacga accccccgtt   7260
cagcccgacc gctgcgcctt atccggtaac tatcgtcttg agtccaaccc ggtaagacac   7320
gacttatcgc cactggcagc agccactggt aacaggatta gcagagcgag gtatgtaggc   7380
ggtgctacag agttcttgaa gtggtggcct aactacggct acactagaag gacagtattt   7440
ggtatctgcg ctctgctgaa gccagttacc ttcggaaaaa gagttggtag ctcttgatcc   7500
ggcaaacaaa ccaccgctgg tagcggtggt ttttttgttt gcaagcagca gattacgcgc   7560
agaaaaaaag gatctcaaga agatcctttg atcttttcta cggggtctga cgctcagtgg   7620
aacgaaaact cacgttaagg gattttggtc atgagattat caaaaaggat cttcacctag   7680
atccttttaa attaaaaatg aagttttaaa tcaatctaaa gtatatatga gtaaacttgg   7740
tctgacagtt accaatgctt aatcagtgag gcacctatct cagcgatctg tctatttcgt   7800
```

tcatccatag ttgcctgact ccccgtcgtg tagataacta cgatacggga gggcttacca 7860
tctggcccca gtgctgcaat gataccgcga gacccacgct caccggctcc agatttatca 7920
gcaataaacc agccagccgg aagggccgag cgcagaagtg gtcctgcaac tttatccgcc 7980
tccatccagt ctattaattg ttgccgggaa gctagagtaa gtagttcgcc agttaatagt 8040
ttgcgcaacg ttgttgccat tgctgcaggc atcgtggtgt cacgctcgtc gtttggtatg 8100
gcttcattca gctccggttc ccaacgatca aggcgagtta catgatcccc catgttgtgc 8160
aaaaaagcgg ttagctcctt cggtcctccg atcgttgtca gaagtaagtt ggccgcagtg 8220
ttatcactca tggttatggc agcactgcat aattctctta ctgtcatgcc atccgtaaga 8280
tgcttttctg tgactggtga gtactcaacc aagtcattct gagaatagtg tatgcggcga 8340
ccgagttgct cttgcccggc gtcaacacgg gataataccg cgccacatag cagaacttta 8400
aaagtgctca tcattggaaa acgttcttcg gggcgaaaac tctcaaggat cttaccgctg 8460
ttgagatcca gttcgatgta acccactcgt gcacccaact gatcttcagc atcttttact 8520
ttcaccagcg tttctgggtg agcaaaaaca ggaaggcaaa atgccgcaaa aaagggaata 8580
agggcgacac ggaaatgttg aatactcata ctcttccttt ttcaatatta ttgaagcatt 8640
tatcagggtt attgtctcat gagcggatac atatttgaat gtatttagaa aaataaacaa 8700
ataggggttc cgcgcacatt tccccgaaaa gtgccacctg acgtctaaga aaccattatt 8760
atcatgacat taacctataa aaataggcgt atcacgaggc cctttcgtct tcaagaattg 8820
gtcgatggca aacagctatt atgggtatta tgggttcgaa ttaat 8865

<210> SEQ ID NO 52
<211> LENGTH: 40
<212> TYPE: DNA
<213> ORGANISM: Artificial Sequence
<220> FEATURE:
<223> OTHER INFORMATION: Synthetic oligonucleotide sAd4287.1A.fwd

<400> SEQUENCE: 52
tctcacttaa ttaacatcat caataatata ccttattctg 40

<210> SEQ ID NO 53
<211> LENGTH: 35
<212> TYPE: DNA
<213> ORGANISM: Artificial Sequence
<220> FEATURE:
<223> OTHER INFORMATION: Synthetic oligonucleotide sAd4287.1A.rev

<400> SEQUENCE: 53
ttatgagtcg acaggagaaa actctactcg ccggc 35

<210> SEQ ID NO 54
<211> LENGTH: 36
<212> TYPE: DNA
<213> ORGANISM: Artificial Sequence
<220> FEATURE:
<223> OTHER INFORMATION: Synthetic oligonucleotide sAd4287.1B.fwd

<400> SEQUENCE: 54
tatactctta aggaatgcgg agctaatcat ttgagg 36

<210> SEQ ID NO 55
<211> LENGTH: 36
<212> TYPE: DNA
<213> ORGANISM: Artificial Sequence
<220> FEATURE:
<223> OTHER INFORMATION: Synthetic oligonucleotide sAd4287.1B.rev

<400> SEQUENCE: 55
tctcacttaa ttaacttcgt ggacgcggag gaggac 36

<210> SEQ ID NO 56
<211> LENGTH: 36
<212> TYPE: DNA
<213> ORGANISM: Artificial Sequence
<220> FEATURE:
<223> OTHER INFORMATION: Synthetic oligonucleotide sAd4287.TGC.fwd

<400> SEQUENCE: 56
ttatgagtcg actggtcaat attggccatt agccat 36

<210> SEQ ID NO 57
<211> LENGTH: 37
<212> TYPE: DNA
<213> ORGANISM: Artificial Sequence
<220> FEATURE:
<223> OTHER INFORMATION: Synthetic oligonucleotide sAd4287.TGC.rev

<400> SEQUENCE: 57
tatactctta aggatctaga catgataaga tacattg 37

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide sAd4287.2A.rev

<400> SEQUENCE: 58
tctcaccctg caggcaggag atcctcaggc aggccg 36

<210> SEQ ID NO 59
<211> LENGTH: 37
<212> TYPE: DNA
<213> ORGANISM: Artificial Sequence
<220> FEATURE:
<223> OTHER INFORMATION: Synthetic oligonucleotide sAd4287.2A.fwd

<400> SEQUENCE: 59
tctcaccctg caggcgacta cctgaacgac cccttgc 37

<210> SEQ ID NO 60
<211> LENGTH: 35
<212> TYPE: DNA
<213> ORGANISM: Artificial Sequence
<220> FEATURE:
<223> OTHER INFORMATION: Synthetic oligonucleotide sAd4287.2B.fwd

<400> SEQUENCE: 60
tctcacatta atcgactacc tgaacgaccc cttgc 35

<210> SEQ ID NO 61
<211> LENGTH: 37
<212> TYPE: DNA
<213> ORGANISM: Artificial Sequence
<220> FEATURE:
<223> OTHER INFORMATION: Synthetic oligonucleotide sAd4287.2B.rev

<400> SEQUENCE: 61
tctcacttaa ttaactgact ggtgccgatg tcgttcc 37

<210> SEQ ID NO 62

<211> LENGTH: 37
<212> TYPE: DNA
<213> ORGANISM: Artificial Sequence
<220> FEATURE:
<223> OTHER INFORMATION: Synthetic oligonucleotide sAd4287.3A.fwd

<400> SEQUENCE: 62
tctcacttaa ttaacccagg acctggaaat agtgcct 37

<210> SEQ ID NO 63
<211> LENGTH: 37
<212> TYPE: DNA
<213> ORGANISM: Artificial Sequence
<220> FEATURE:
<223> OTHER INFORMATION: Synthetic oligonucleotide sAd4287.3A.rev

<400> SEQUENCE: 63
tctcaccctg caggggtggg ctgtattgct tgtccgc 37

<210> SEQ ID NO 64
<211> LENGTH: 38
<212> TYPE: DNA
<213> ORGANISM: Artificial Sequence
<220> FEATURE:
<223> OTHER INFORMATION: Synthetic oligonucleotide sAd4287.3B.fwd

<400> SEQUENCE: 64
tctcaccctg caggggttgc aggaaaaacc acttggag 38

<210> SEQ ID NO 65
<211> LENGTH: 40
<212> TYPE: DNA
<213> ORGANISM: Artificial Sequence
<220> FEATURE:
<223> OTHER INFORMATION: Synthetic oligonucleotide sAd4287.3B.rev

<400> SEQUENCE: 65
tctcacttaa ttaacatcat caataatata ccttattctg 40

<210> SEQ ID NO 66
<211> LENGTH: 23
<212> TYPE: DNA
<213> ORGANISM: Artificial Sequence
<220> FEATURE:
<223> OTHER INFORMATION: Synthetic oligonucleotide sAd4287.dE3A.fwd

<400> SEQUENCE: 66
gagctagaca aactcctctg ccg 23

<210> SEQ ID NO 67
<211> LENGTH: 36
<212> TYPE: DNA
<213> ORGANISM: Artificial Sequence
<220> FEATURE:
<223> OTHER INFORMATION: Synthetic oligonucleotide sAd4287.dE3A.rev

<400> SEQUENCE: 67
ttcctaacta gtgtagaatt tccacacgca aaggag 36

<210> SEQ ID NO 68
<211> LENGTH: 35
<212> TYPE: DNA
<213> ORGANISM: Artificial Sequence
<220> FEATURE:
<223> OTHER INFORMATION: Synthetic oligonucleotide sAd4287.dE3B.fwd

<400> SEQUENCE: 68
ttcctaacta gtgggagcta tcctgtgtca ctgtc 35

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide sAd4287.dE3B.rev

<400> SEQUENCE: 69
cagcagttga tgttaattgt ccct 24

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide sAd4287.E1.fwd

<400> SEQUENCE: 70
cgctgtcaga tcatcaagag gcca 24

<210> SEQ ID NO 71
<211> LENGTH: 54
<212> TYPE: DNA
<213> ORGANISM: Artificial Sequence
<220> FEATURE:
<223> OTHER INFORMATION: Synthetic oligonucleotide sAd4287.E1.rev

<400> SEQUENCE: 71
atggctaatg gccaatattg accagtcgac cgtccaccct tcatgcccct ttat 54

<210> SEQ ID NO 72
<211> LENGTH: 55
<212> TYPE: DNA
<213> ORGANISM: Artificial Sequence
<220> FEATURE:
<223> OTHER INFORMATION: Synthetic oligonucleotide sAd4287.dE4A.fwd

<400> SEQUENCE: 72
ctcacgttga aaataggaaa cggcctcact ctagacaacc agggacaatt aacat 55

<210> SEQ ID NO 73
<211> LENGTH: 38
<212> TYPE: DNA
<213> ORGANISM: Artificial Sequence
<220> FEATURE:
<223> OTHER INFORMATION: Synthetic oligonucleotide sAd4287.dE4A.rev

<400> SEQUENCE: 73
cggtaagacg gggcagtacc aggaggtgcg tcggtctc 38

<210> SEQ ID NO 74
<211> LENGTH: 38
<212> TYPE: DNA
<213> ORGANISM: Artificial Sequence
<220> FEATURE:
<223> OTHER INFORMATION: Synthetic oligonucleotide sAd4287.dE4B.fwd

<400> SEQUENCE: 74
cgcacctcct ggtactgccc cgtcttaccg cgtaaaca 38

<210> SEQ ID NO 75
<211> LENGTH: 53
<212> TYPE: DNA

<213> ORGANISM: Artificial Sequence
<220> FEATURE:
<223> OTHER INFORMATION: Synthetic oligonucleotide sAd4287.dE4B.rev

<400> SEQUENCE: 75
tgccgatgtc gttccaggtg cccatgagcg gccgcgagcc gtgccgcgga gcc 53

<210> SEQ ID NO 76
<211> LENGTH: 40
<212> TYPE: DNA
<213> ORGANISM: Artificial Sequence
<220> FEATURE:
<223> OTHER INFORMATION: Synthetic oligonucleotide sAd4310A.1A.fwd

<400> SEQUENCE: 76
tctcacttaa ttaacatcat caataatata ccttattctg 40

<210> SEQ ID NO 77
<211> LENGTH: 35
<212> TYPE: DNA
<213> ORGANISM: Artificial Sequence
<220> FEATURE:
<223> OTHER INFORMATION: Synthetic oligonucleotide sAd4310A.1A.rev

<400> SEQUENCE: 77
ttatgagtcg acgaggagaa aactctactc gccgg 35

<210> SEQ ID NO 78
<211> LENGTH: 37
<212> TYPE: DNA
<213> ORGANISM: Artificial Sequence
<220> FEATURE:
<223> OTHER INFORMATION: Synthetic oligonucleotide sAd4310A.1B.fwd

<400> SEQUENCE: 78
tatactctta aggacatgtc aatggaactg tttaaag 37

<210> SEQ ID NO 79
<211> LENGTH: 38
<212> TYPE: DNA
<213> ORGANISM: Artificial Sequence
<220> FEATURE:
<223> OTHER INFORMATION: Synthetic oligonucleotide sAd4310A.1B.rev

<400> SEQUENCE: 79
tctcacttaa ttaacctcat tgaaaacgac agataccc 38

<210> SEQ ID NO 80
<211> LENGTH: 36
<212> TYPE: DNA
<213> ORGANISM: Artificial Sequence
<220> FEATURE:
<223> OTHER INFORMATION: Synthetic oligonucleotide sAd4310A.TGC.fwd

<400> SEQUENCE: 80
ttatgagtcg actggtcaat attggccatt agccat 36

<210> SEQ ID NO 81
<211> LENGTH: 37
<212> TYPE: DNA
<213> ORGANISM: Artificial Sequence
<220> FEATURE:
<223> OTHER INFORMATION: Synthetic oligonucleotide sAd4310A.TGC.rev

<400> SEQUENCE: 81
tatactctta aggatctaga catgataaga tacattg 37

<210> SEQ ID NO 82
<211> LENGTH: 39
<212> TYPE: DNA
<213> ORGANISM: Artificial Sequence
<220> FEATURE:
<223> OTHER INFORMATION: Synthetic oligonucleotide sAd4310A.2A.fwd

<400> SEQUENCE: 82
tctcacttaa ttaagacatg tcaatggaac tgtttaaag 39

<210> SEQ ID NO 83
<211> LENGTH: 38
<212> TYPE: DNA
<213> ORGANISM: Artificial Sequence
<220> FEATURE:
<223> OTHER INFORMATION: Synthetic oligonucleotide sAd4310A.2A.rev

<400> SEQUENCE: 83
tctcaccctg caggcaaact ctcctggcct tggatcta 38

<210> SEQ ID NO 84
<211> LENGTH: 37
<212> TYPE: DNA
<213> ORGANISM: Artificial Sequence
<220> FEATURE:
<223> OTHER INFORMATION: Synthetic oligonucleotide sAd4310A.2B.fwd

<400> SEQUENCE: 84
tctcaccctg cagggtgact cgtacctggg tcatctc 37

<210> SEQ ID NO 85
<211> LENGTH: 38
<212> TYPE: DNA
<213> ORGANISM: Artificial Sequence
<220> FEATURE:
<223> OTHER INFORMATION: Synthetic oligonucleotide sAd4310A.2B.rev

<400> SEQUENCE: 85
tctcacttaa ttaagatgct gttcagcgtg ttttgcca 38

<210> SEQ ID NO 86
<211> LENGTH: 37
<212> TYPE: DNA
<213> ORGANISM: Artificial Sequence
<220> FEATURE:
<223> OTHER INFORMATION: Synthetic oligonucleotide sAd4310A.3A.fwd

<400> SEQUENCE: 86
tctcacttaa ttaacaccgt ggattccgtg atcgaca 37

<210> SEQ ID NO 87
<211> LENGTH: 38
<212> TYPE: DNA
<213> ORGANISM: Artificial Sequence
<220> FEATURE:
<223> OTHER INFORMATION: Synthetic oligonucleotide sAd4310A.3A.rev

<400> SEQUENCE: 87
tctcaccctg cagggttaat gctgtcgaat ctgacgct 38

<210> SEQ ID NO 88
<211> LENGTH: 38
<212> TYPE: DNA
<213> ORGANISM: Artificial Sequence
<220> FEATURE:

<223> OTHER INFORMATION: Synthetic oligonucleotide sAd4310A.3B.fwd

<400> SEQUENCE: 88
tctcaccctg cagggaagac ttcaacccag tgtaccct 38

<210> SEQ ID NO 89
<211> LENGTH: 40
<212> TYPE: DNA
<213> ORGANISM: Artificial Sequence
<220> FEATURE:
<223> OTHER INFORMATION: Synthetic oligonucleotide sAd4310A.3B.rev

<400> SEQUENCE: 89
tctcacttaa ttaacatcat caataatata ccttattctg 40

<210> SEQ ID NO 90
<211> LENGTH: 23
<212> TYPE: DNA
<213> ORGANISM: Artificial Sequence
<220> FEATURE:
<223> OTHER INFORMATION: Synthetic oligonucleotide sAd4310A.dE3A.fwd.G

<400> SEQUENCE: 90
gttgcatgat agggtaactc gcc 23

<210> SEQ ID NO 91
<211> LENGTH: 47
<212> TYPE: DNA
<213> ORGANISM: Artificial Sequence
<220> FEATURE:
<223> OTHER INFORMATION: Synthetic oligonucleotide sAd4310A.dE3A.rev.G

<400> SEQUENCE: 91
agagaggata gccccctcta caggataagt tcgttagtgc aggcgca 47

<210> SEQ ID NO 92
<211> LENGTH: 47
<212> TYPE: DNA
<213> ORGANISM: Artificial Sequence
<220> FEATURE:
<223> OTHER INFORMATION: Synthetic oligonucleotide sAd4310A.dE3B.fwd.G

<400> SEQUENCE: 92
tgcgcctgca ctaacgaact tatcctgtag agggggctat cctctgt 47

<210> SEQ ID NO 93
<211> LENGTH: 23
<212> TYPE: DNA
<213> ORGANISM: Artificial Sequence
<220> FEATURE:
<223> OTHER INFORMATION: Synthetic oligonucleotide sAd4310A.dE3B.rev.G

<400> SEQUENCE: 93
gttctacttc cccagcggtt gat 23

<210> SEQ ID NO 94
<211> LENGTH: 24
<212> TYPE: DNA
<213> ORGANISM: Artificial Sequence
<220> FEATURE:
<223> OTHER INFORMATION: Synthetic oligonucleotide sAd4310A.E1.fwd

<400> SEQUENCE: 94
cgtatgcgga aggaggtttt atac 24

<210> SEQ ID NO 95
<211> LENGTH: 54
<212> TYPE: DNA
<213> ORGANISM: Artificial Sequence
<220> FEATURE:
<223> OTHER INFORMATION: Synthetic oligonucleotide sAd4310A.E1.rev

<400> SEQUENCE: 95
atggctaatg gccaatattg accagtcgac ctcacgcccc tttatacccg tttg 54

<210> SEQ ID NO 96
<211> LENGTH: 53
<212> TYPE: DNA
<213> ORGANISM: Artificial Sequence
<220> FEATURE:
<223> OTHER INFORMATION: Synthetic oligonucleotide sAd4310A.dE4A.fwd

<400> SEQUENCE: 96
ttacagttaa actaggaaac ggcctcactc tagacaacca gggacaacta aca 53

<210> SEQ ID NO 97
<211> LENGTH: 43
<212> TYPE: DNA
<213> ORGANISM: Artificial Sequence
<220> FEATURE:
<223> OTHER INFORMATION: Synthetic oligonucleotide sAd4310A.dE4A.rev

<400> SEQUENCE: 97
gcggtaagac ggggcagttc tgctactaca agtacgagga agt 43

<210> SEQ ID NO 98
<211> LENGTH: 39
<212> TYPE: DNA
<213> ORGANISM: Artificial Sequence
<220> FEATURE:
<223> OTHER INFORMATION: Synthetic oligonucleotide sAd4310A.dE4B.fwd

<400> SEQUENCE: 98
ttgtagtagc agaactgccc cgtcttaccg cgtataaag 39

<210> SEQ ID NO 99
<211> LENGTH: 51
<212> TYPE: DNA
<213> ORGANISM: Artificial Sequence
<220> FEATURE:
<223> OTHER INFORMATION: Synthetic oligonucleotide sAd4310A.dE4B.rev

<400> SEQUENCE: 99
gtgccgatgt cgttccaggt gcccatgagc ggccgcgagc cttgccgcgg a 51

<210> SEQ ID NO 100
<211> LENGTH: 40
<212> TYPE: DNA
<213> ORGANISM: Artificial Sequence
<220> FEATURE:
<223> OTHER INFORMATION: Synthetic oligonucleotide sAd4312.1A.fwd

<400> SEQUENCE: 100
tctcacttaa ttaacatcat caataatata ccttattctg 40

<210> SEQ ID NO 101
<211> LENGTH: 35
<212> TYPE: DNA
<213> ORGANISM: Artificial Sequence
<220> FEATURE:
<223> OTHER INFORMATION: Synthetic oligonucleotide sAd4312.1A.rev

<400> SEQUENCE: 101
ttatgagtcg accggaggag aaaactctac tcgcc 35

<210> SEQ ID NO 102
<211> LENGTH: 38
<212> TYPE: DNA
<213> ORGANISM: Artificial Sequence
<220> FEATURE:
<223> OTHER INFORMATION: Synthetic oligonucleotide sAd4312.1B.fwd

<400> SEQUENCE: 102
tatactctta aggtgataag atatgatgaa tccaagtc 38

<210> SEQ ID NO 103
<211> LENGTH: 38
<212> TYPE: DNA
<213> ORGANISM: Artificial Sequence
<220> FEATURE:
<223> OTHER INFORMATION: Synthetic oligonucleotide sAd4312.1B.rev

<400> SEQUENCE: 103
tctcacttaa ttaagtcacg tgacctacac ttacaagc 38

<210> SEQ ID NO 104
<211> LENGTH: 36
<212> TYPE: DNA
<213> ORGANISM: Artificial Sequence
<220> FEATURE:
<223> OTHER INFORMATION: Synthetic oligonucleotide sAd4312.TGC.fwd

<400> SEQUENCE: 104
ttatgagtcg actggtcaat attggccatt agccat 36

<210> SEQ ID NO 105
<211> LENGTH: 37
<212> TYPE: DNA
<213> ORGANISM: Artificial Sequence
<220> FEATURE:
<223> OTHER INFORMATION: Synthetic oligonucleotide sAd4312.TGC.rev

<400> SEQUENCE: 105
tatactctta aggatctaga catgataaga tacattg 37

<210> SEQ ID NO 106
<211> LENGTH: 40
<212> TYPE: DNA
<213> ORGANISM: Artificial Sequence
<220> FEATURE:
<223> OTHER INFORMATION: Synthetic oligonucleotide sAd4312.2A.fwd

<400> SEQUENCE: 106
tctcacttaa ttaagtgata agatatgatg aatccaagtc 40

<210> SEQ ID NO 107
<211> LENGTH: 35
<212> TYPE: DNA
<213> ORGANISM: Artificial Sequence
<220> FEATURE:
<223> OTHER INFORMATION: Synthetic oligonucleotide sAd4312.2A.rev

<400> SEQUENCE: 107
tctcaccata tgcttctctc agaaaggccg ctcag 35

<210> SEQ ID NO 108
<211> LENGTH: 36

<212> TYPE: DNA
<213> ORGANISM: Artificial Sequence
<220> FEATURE:
<223> OTHER INFORMATION: Synthetic oligonucleotide sAd4312.2B.fwd

<400> SEQUENCE: 108
tctcaccata tgcaagcggc aatatgacga ggtgta 36

<210> SEQ ID NO 109
<211> LENGTH: 36
<212> TYPE: DNA
<213> ORGANISM: Artificial Sequence
<220> FEATURE:
<223> OTHER INFORMATION: Synthetic oligonucleotide sAd4312.2B.rev

<400> SEQUENCE: 109
tctcacttaa ttaagtgtca gcctctgcga gcggtc 36

<210> SEQ ID NO 110
<211> LENGTH: 38
<212> TYPE: DNA
<213> ORGANISM: Artificial Sequence
<220> FEATURE:
<223> OTHER INFORMATION: Synthetic oligonucleotide sAd4312.3A.fwd

<400> SEQUENCE: 110
tctcacttaa ttaaccgaag ttagaagacc aaaggtgc 38

<210> SEQ ID NO 111
<211> LENGTH: 36
<212> TYPE: DNA
<213> ORGANISM: Artificial Sequence
<220> FEATURE:
<223> OTHER INFORMATION: Synthetic oligonucleotide sAd4312.3A.rev

<400> SEQUENCE: 111
tctcaccctg cagggtgtca gcctctgcga gcggtc 36

<210> SEQ ID NO 112
<211> LENGTH: 38
<212> TYPE: DNA
<213> ORGANISM: Artificial Sequence
<220> FEATURE:
<223> OTHER INFORMATION: Synthetic oligonucleotide sAd4312.3B.fwd

<400> SEQUENCE: 112
tctcaccctg caggccagac cagatacttt atggacca 38

<210> SEQ ID NO 113
<211> LENGTH: 40
<212> TYPE: DNA
<213> ORGANISM: Artificial Sequence
<220> FEATURE:
<223> OTHER INFORMATION: Synthetic oligonucleotide sAd4312.3B.rev

<400> SEQUENCE: 113
tctcacttaa ttaacatcat caataatata ccttattctg 40

<210> SEQ ID NO 114
<211> LENGTH: 24
<212> TYPE: DNA
<213> ORGANISM: Artificial Sequence
<220> FEATURE:
<223> OTHER INFORMATION: Synthetic oligonucleotide sAd4312.dE3A.fwd

<400> SEQUENCE: 114

```
ggaagacaga aacctcaaag agct                                            24


<210> SEQ ID NO 115
<211> LENGTH: 37
<212> TYPE: DNA
<213> ORGANISM: Artificial Sequence
<220> FEATURE:
<223> OTHER INFORMATION: Synthetic oligonucleotide sAd4312.dE3A.rev

<400> SEQUENCE: 115

ttcctaacta gtgtgcaaga acagttaagg ataagag                              37


<210> SEQ ID NO 116
<211> LENGTH: 35
<212> TYPE: DNA
<213> ORGANISM: Artificial Sequence
<220> FEATURE:
<223> OTHER INFORMATION: Synthetic oligonucleotide sAd4312.dE3B.fwd

<400> SEQUENCE: 116

ttcctaacta gtgagggggc tatcctgtgt cactg                                35


<210> SEQ ID NO 117
<211> LENGTH: 24
<212> TYPE: DNA
<213> ORGANISM: Artificial Sequence
<220> FEATURE:
<223> OTHER INFORMATION: Synthetic oligonucleotide sAd4312.dE3B.rev

<400> SEQUENCE: 117

ccacatttaa caagcgctag ccac                                            24


<210> SEQ ID NO 118
<211> LENGTH: 24
<212> TYPE: DNA
<213> ORGANISM: Artificial Sequence
<220> FEATURE:
<223> OTHER INFORMATION: Synthetic oligonucleotide sAd4312.E1.fwd

<400> SEQUENCE: 118

gaaggaggtt ttataccgga agat                                            24


<210> SEQ ID NO 119
<211> LENGTH: 53
<212> TYPE: DNA
<213> ORGANISM: Artificial Sequence
<220> FEATURE:
<223> OTHER INFORMATION: Synthetic oligonucleotide sAd4312.E1.rev

<400> SEQUENCE: 119

atggctaatg gccaatattg accagtcgac aatacctgtg cccacccatc ctg            53


<210> SEQ ID NO 120
<211> LENGTH: 53
<212> TYPE: DNA
<213> ORGANISM: Artificial Sequence
<220> FEATURE:
<223> OTHER INFORMATION: Synthetic oligonucleotide sAd4312.dE4A.fwd

<400> SEQUENCE: 120

agcaccactt taccctcttc ccaactctca tatgggatat gatggtgggc ggc            53


<210> SEQ ID NO 121
<211> LENGTH: 40
<212> TYPE: DNA
<213> ORGANISM: Artificial Sequence
```

-continued

```
<220> FEATURE:
<223> OTHER INFORMATION: Synthetic oligonucleotide sAd4312.dE4A.rev

<400> SEQUENCE: 121

gcggtaagac ggggcgggtt ctgctattgg aagtacgagg                          40


<210> SEQ ID NO 122
<211> LENGTH: 38
<212> TYPE: DNA
<213> ORGANISM: Artificial Sequence
<220> FEATURE:
<223> OTHER INFORMATION: Synthetic oligonucleotide sAd4312.dE4B.fwd

<400> SEQUENCE: 122

tccaatagca gaacccgccc cgtcttaccg cgtaaaaa                            38


<210> SEQ ID NO 123
<211> LENGTH: 50
<212> TYPE: DNA
<213> ORGANISM: Artificial Sequence
<220> FEATURE:
<223> OTHER INFORMATION: Synthetic oligonucleotide sAd4312.dE4B.rev

<400> SEQUENCE: 123

ctttcatgcg cctgcgtaaa gcccgacggc ggccgctccc cgccatgcct                50


<210> SEQ ID NO 124
<211> LENGTH: 11
<212> TYPE: PRT
<213> ORGANISM: SIVmac239

<400> SEQUENCE: 124

Ala Ala Val Lys Asn Trp Met Thr Gln Thr Leu
1               5                   10


<210> SEQ ID NO 125
<211> LENGTH: 9
<212> TYPE: PRT
<213> ORGANISM: SIVmac239

<400> SEQUENCE: 125

Lys Ser Leu Tyr Asn Thr Val Cys Val
1               5


<210> SEQ ID NO 126
<211> LENGTH: 13
<212> TYPE: PRT
<213> ORGANISM: SIVmac239

<400> SEQUENCE: 126

Asp Arg Phe Tyr Lys Ser Leu Arg Ala Glu Gln Thr Asp
1               5                   10
```